(12) United States Patent
Lançois et al.

(10) Patent No.: US 11,339,165 B2
(45) Date of Patent: May 24, 2022

(54) PYRAZOLOPYRIMIDINES HAVING ACTIVITY AGAINST THE RESPIRATORY SYNCYTIAL VIRUS (RSV)

(71) Applicant: Janssen Sciences Ireland Unlimited Company, County Cork (IE)

(72) Inventors: David Francis Alain Lançois, Louviers (FR); Jérôme Émile Georges Guillemont, Andé (FR); Pierre Jean-Marie Bernard Raboisson, Wavre (BE); Dirk André Emmy Roymans, Turnhout (BE); Peter Rigaux, Overijse (BE); Antoine Benjamin Michaut, Le Vaudreuil (FR); Guillaume Jean Maurice Mercey, Montaure (FR)

(73) Assignee: Janssen Sciences Ireland Unlimited Company, County Cork (IE)

( * ) Notice: Subject to any disclaimer, the term of this patent is extended or adjusted under 35 U.S.C. 154(b) by 43 days.

(21) Appl. No.: 16/768,049

(22) PCT Filed: Nov. 28, 2018

(86) PCT No.: PCT/EP2018/082828
§ 371 (c)(1),
(2) Date: May 28, 2020

(87) PCT Pub. No.: WO2019/106004
PCT Pub. Date: Jun. 6, 2019

(65) Prior Publication Data
US 2020/0361942 A1 Nov. 19, 2020

(30) Foreign Application Priority Data

Nov. 29, 2017 (EP) .................................... 17204280

(51) Int. Cl.
*C07D 487/00* (2006.01)
*A61K 31/519* (2006.01)
(Continued)

(52) U.S. Cl.
CPC ............ *C07D 487/04* (2013.01); *A61P 31/16* (2018.01); *A61K 31/519* (2013.01); *A61K 45/06* (2013.01); *A61P 31/14* (2018.01)

(58) Field of Classification Search
CPC ...... C07D 487/04; A61P 31/14; A61K 31/519
(Continued)

(56) References Cited

U.S. PATENT DOCUMENTS 5,972,966 A 10/1999 deSolms
5,977,134 A 11/1999 Ciccarone et al.
(Continued)

FOREIGN PATENT DOCUMENTS

CN 105777632 A 7/2016
WO 199619483 A1 6/1996
(Continued)

OTHER PUBLICATIONS

Herr "5-substituted -1H-tetrazoles as carboxylic acid isosteres: Medicinal Chemistry and synthetic methods," Bioorganic & Medicinal Chemistry, 2002, vol. 10, pp. 3379-3393. (Year: 2002).*
(Continued)

*Primary Examiner* — Shengjun Wang

(57) ABSTRACT

The invention concerns compounds having antiviral activity, in particular, having an inhibitory activity on the replication of the respiratory syncytial virus (RSV). The invention further concerns pharmaceutical compositions comprising these compounds and the compounds for use in the treatment of respiratory syncytial virus infection. Formula (Ia).
(Continued)

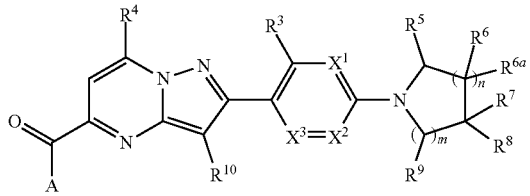

(51) Int. Cl.
*C07D 487/04* (2006.01)
*A61P 31/16* (2006.01)
*A61K 45/06* (2006.01)
*A61P 31/14* (2006.01)

(58) Field of Classification Search
USPC .................................. 544/281; 514/259.31
See application file for complete search history.

(56) References Cited

U.S. PATENT DOCUMENTS

| | | |
|---|---|---|
| 6,177,443 B1 | 1/2001 | Madsen et al. |
| 6,218,404 B1 | 4/2001 | Bigge et al. |
| 6,608,203 B2 | 8/2003 | Cameron et al. |
| 6,765,096 B1 | 7/2004 | Aono et al. |
| 6,919,376 B2 | 7/2005 | Llompart et al. |
| 7,507,842 B2 | 3/2009 | Oehler et al. |
| 7,642,272 B2 | 1/2010 | Shankar et al. |
| 7,662,826 B2 | 2/2010 | Seno et al. |
| 7,893,096 B2 | 2/2011 | Valiante, Jr. |
| 8,450,343 B2 | 5/2013 | Huang et al. |
| 8,691,938 B2 | 4/2014 | DeGoey et al. |
| 8,829,027 B2 | 9/2014 | Eckhardt et al. |
| 10,208,048 B2 | 2/2019 | Lançois et al. |
| 10,611,769 B2 | 4/2020 | Lançois |
| 2003/0073681 A1 | 4/2003 | Hauske et al. |
| 2010/0063047 A1 | 3/2010 | Borchardt et al. |
| 2010/0204265 A1 | 8/2010 | Baskaran et al. |

FOREIGN PATENT DOCUMENTS

| | | |
|---|---|---|
| WO | 199701275 A1 | 1/1997 |
| WO | 2004029042 A1 | 4/2004 |
| WO | 2004037817 A1 | 6/2004 |
| WO | 2005000315 A1 | 1/2005 |
| WO | 2005035516 A1 | 4/2005 |
| WO | 2005042530 A1 | 5/2005 |
| WO | 2005058871 A1 | 6/2005 |
| WO | 2005061513 A1 | 7/2005 |
| WO | 2006030925 A1 | 3/2006 |
| WO | 2006034341 A2 | 3/2006 |
| WO | 2006136561 A1 | 12/2006 |
| WO | 2007/044085 A2 | 4/2007 |
| WO | 2007060409 A1 | 5/2007 |
| WO | 2008063671 A2 | 5/2008 |
| WO | 2009/023179 A2 | 2/2009 |
| WO | 2010104306 A2 | 9/2010 |
| WO | 2010111058 A1 | 9/2010 |
| WO | 2011163518 A1 | 12/2011 |
| WO | 2012051361 A1 | 4/2012 |
| WO | 2015042297 A1 | 3/2015 |
| WO | 2015106025 A1 | 7/2015 |
| WO | 2016017980 A1 | 2/2016 |
| WO | 2016071293 A2 | 5/2016 |
| WO | 2016/091774 | 6/2016 |
| WO | 2016/174079 A1 | 11/2016 |

OTHER PUBLICATIONS

Hallack, et al., "Glycosaminoglycan Sulfation Requirements for Respiratory Syncytial Virus Infection", Journal of Virology, vol. 74(22):pp. 10508-10513 (Nov. 2000).
Wyde, et al., "CL387626 exhibits marked and unusual antiviral activity against respiratory syncytial virus in tissue culture and in cotton rats", Antiviral Research, vol. 38: pp. 31-42 (1998).
International Search Report and Written Opinion dated Jan. 30, 2019 for PCT/EP2018/082828 filed on Nov. 28, 2020.

\* cited by examiner

Figure 1 : plasma concentration profile of Compound (102) - dog (1 mg/kg iv)
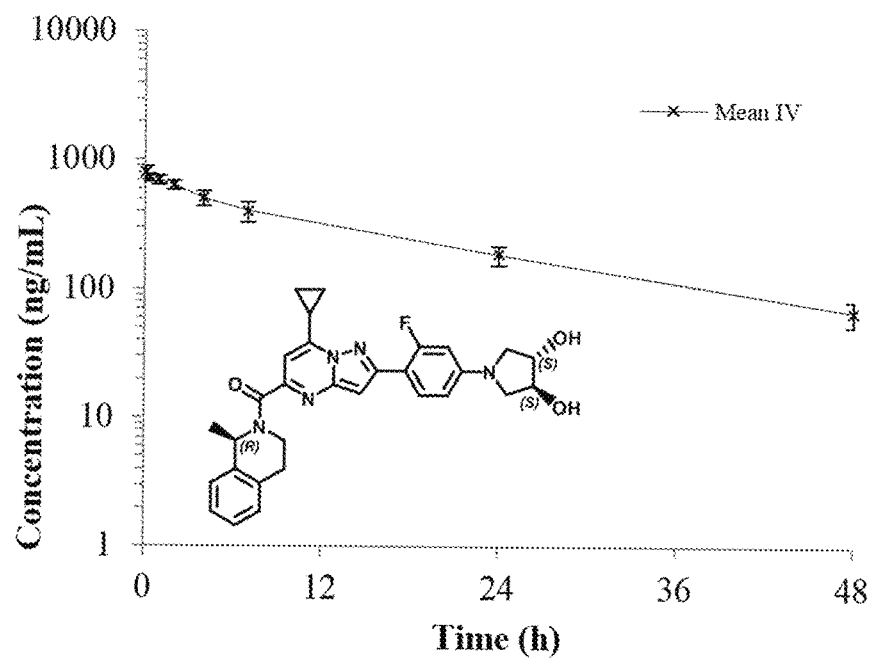
Figure 2 : plasma concentration profile of Compound (37) - dog (1 mg/kg iv)
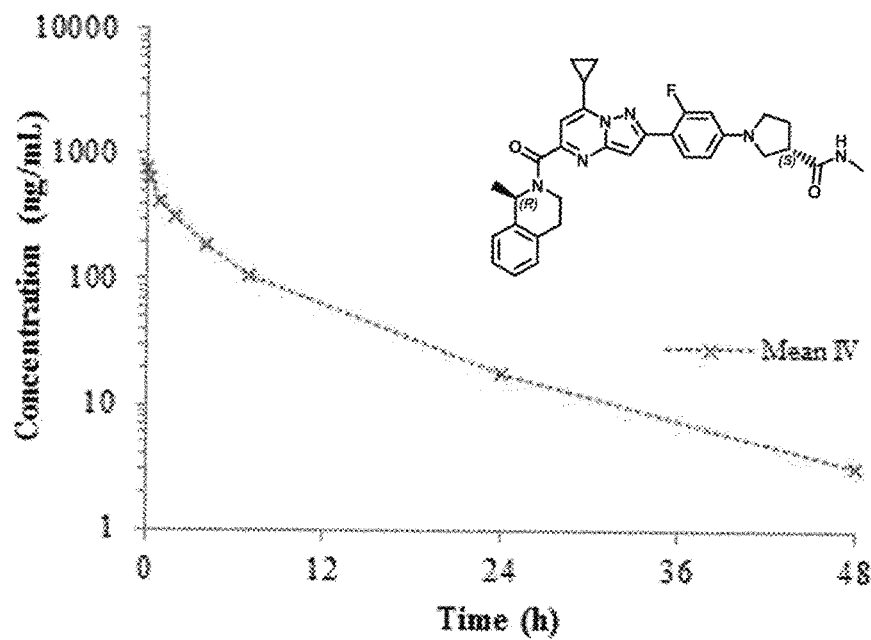

Figure 3 : plasma concentration profile of compound (W37) of WO-2016/174079
dog (1 mg/kg iv)
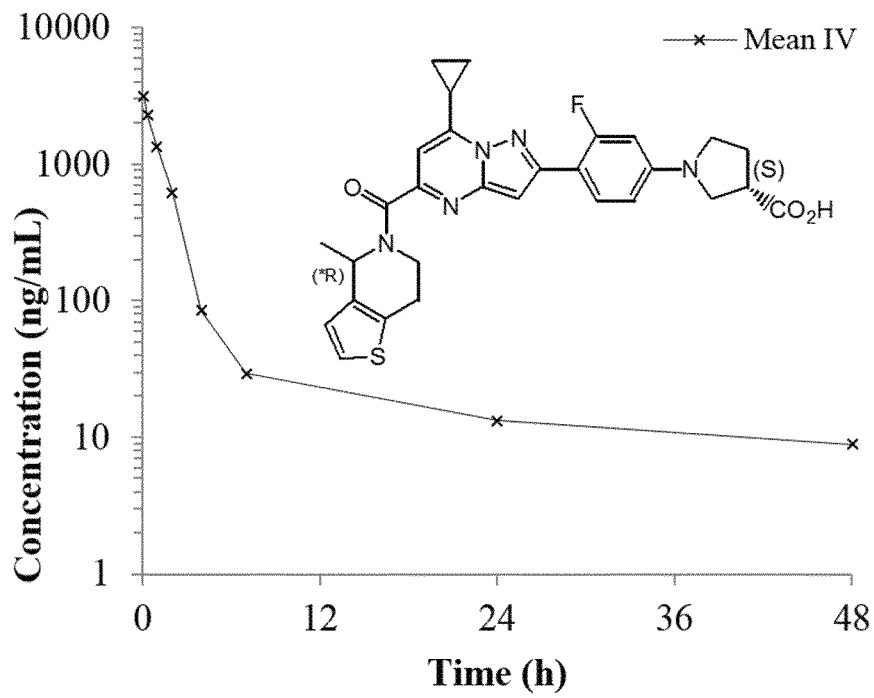
Figure 4 : plasma concentration profile of compound (W38) of WO-2016/174079
dog (1 mg/kg iv)
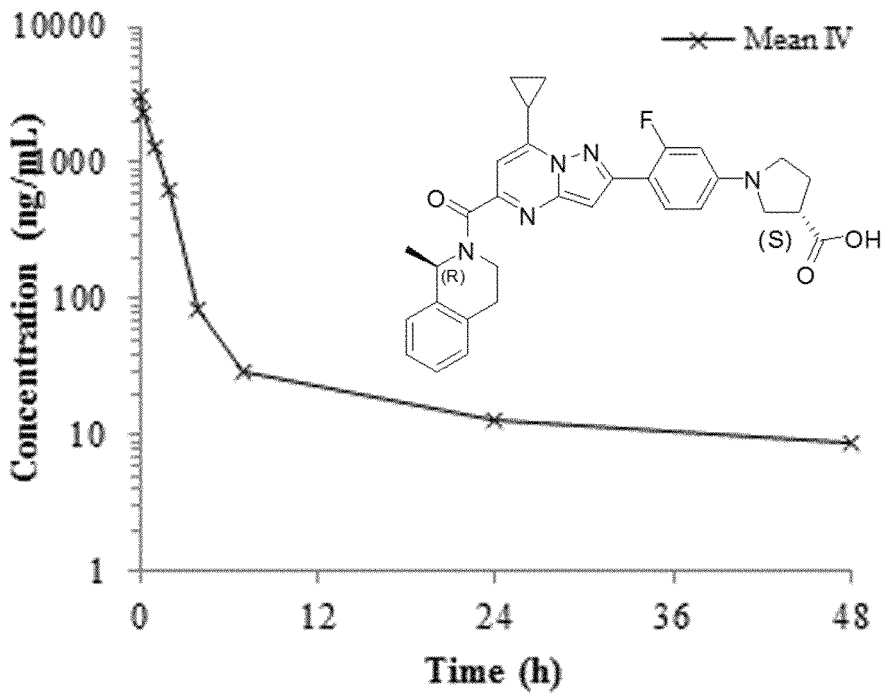

PYRAZOLOPYRIMIDINES HAVING ACTIVITY AGAINST THE RESPIRATORY SYNCYTIAL VIRUS (RSV)

CROSS-REFERENCE TO RELATED APPLICATIONS

This application is a national phase entry of International Application No. PCT/EP2018/082828, filed on Nov. 28, 2018, which claims priority to EP Patent Application No. 17204280.6, filed on Nov. 29, 2017, each of which is incorporated herein in its entirety.

FIELD OF THE INVENTION

The invention concerns compounds having antiviral activity, in particular, having an inhibitory activity on the replication of the respiratory syncytial virus (RSV). The invention further concerns pharmaceutical compositions comprising these compounds and the compounds for use in the treatment of respiratory syncytial virus infection.

BACKGROUND

Human RSV or Respiratory Syncytial Virus is a large RNA virus, member of the family of Pneumoviridae, genus *Orthopneumovirus* together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue that provides an aerosol treatment for serious RSV infection in hospitalized children. The aerosol route of administration, the toxicity (risk of teratogenicity), the cost and the highly variable efficacy limit its use. The other two drugs, RespiGam® (RSV-IG) and Synagis® (palivizumab), polyclonal and monoclonal antibody immunostimulants, are intended to be used in a preventive way. Both are very expensive, and require parenteral administration.

Clearly there is a need for an efficacious non-toxic and easy to administer drug against RSV replication. It would be particularly preferred to provide drugs against RSV replication that could be administered perorally.

Compounds that exhibit anti-RSV activity are disclosed in WO-2016/174079 and WO-2016/091774.

The compounds of the present invention have unexpected better plasma concentration profiles than the pyrazolopyrimidine compounds of WO-2016/174079 bearing a substituted pyrrolidine moiety as demonstrated in Pharmacological Example E.2.

DETAILED DESCRIPTION OF THE INVENTION

The present invention relates to compounds of formula (I)

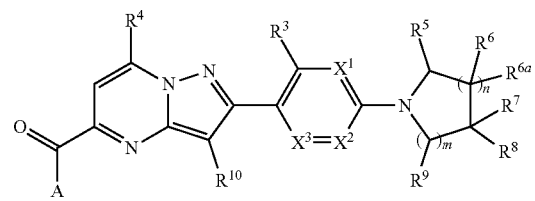

(I)

including any stereochemically isomeric form thereof, wherein
A is

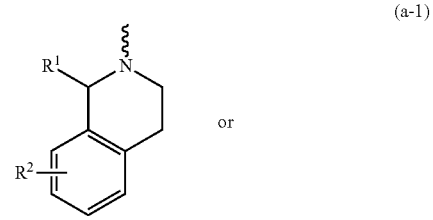

(a-1)

or

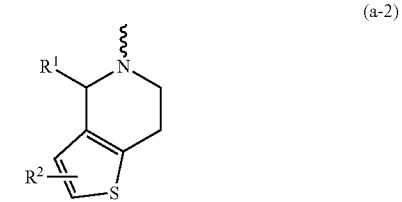

(a-2)

n is 0, 1, or 2;
m is 1 or 2;
$X^1$, $X^2$ and $X^3$ are selected from $X^1$ is $CR^{11}$ and $X^2$ is $CR^{11}$ and $X^3$ is $CR^{11}$,
 or $X^1$ is N and $X^2$ is $CR^{11}$ and $X^3$ is $CR^{11}$,
 or $X^1$ is $CR^{11}$ and $X^2$ is N and $X^3$ is $CR^{11}$,
 or $X^1$ is $CR^{11}$ and $X^2$ is $CR^{11}$ and $X^3$ is N,
 or $X^1$ is N and $X^2$ is $CR^{11}$ and $X^3$ is N,
 wherein each $R^{11}$ is independently selected from the group consisting of hydrogen, halo, hydroxy, $C_{1-4}$alkyl, $C_{1-4}$alkyloxy, $C_{1-4}$alkyloxy$C_{1-4}$alkyloxy, hydroxy$C_{1-4}$alkyl and hydroxy$C_{1-4}$alkyloxy;
$R^1$ is $CH_3$ or $CH_2CH_3$;
$R^2$ is hydrogen, halo or $C_{1-4}$alkyl;
$R^3$ is halo or $CH_3O$;
$R^4$ is $C_{3-6}$cycloalkyl; phenyl; phenyl substituted with 1, 2 or 3 substituents each individually selected from halo, hydroxy, cyano, $C_{1-4}$alkyl, polyhalo$C_{1-4}$alkyl, and $C_{1-4}$alkyloxy; Heteroaryl; or $C_{1-4}$alkyl substituted with Heteroaryl;
$R^5$ is hydrogen, $C_{1-4}$alkyl or hydroxy$C_{1-4}$alkyl;
each $R^6$ is independently selected from the group consisting of hydrogen, $C_{1-4}$alkyl, hydroxy, halo and $C_{1-4}$alkyloxy;
each $R^{6a}$ is independently selected from the group consisting of hydrogen and halo;
$R^7$ is hydrogen, $C_{1-4}$alkyl, or hydroxy$C_{1-4}$alkyl;
$R^8$ is —OH,
—CN, O—(CO)—NR$^{12}$R$^{13}$,
—C$_{1-4}$alkyl-(CO)—NR$^{12}$R$^{13}$,
(CO)—NR$^{12}$R$^{13}$,
(CS)—NR$^{12}$R$^{13}$,
(CO)—NR$^{12}$—CN,
(CO)—NR$^{12}$—SO$_2$—R$^{14}$,
—NR$^{12}$—(CO)—R$^{14}$,
—NR$^{12}$—(CO)—O—R$^{14}$,
—NR$^{12}$—SO$_2$—R$^{14}$,
—NH$_2$,
—NR$^{12}$—R$^{15}$;
SO$_2$—R$^{14}$,
—SO$_2$—NR$^{12}$R$^{13}$,
—SO$_2$—NR$^{12}$—(CO)—R$^{14}$, or
SO(=NH)(—R$^{14}$), or
Heteroaryl$^1$;
  wherein
    R$^{12}$ and R$^{13}$ are each independently selected from hydrogen and C$_{1-4}$alkyl, and;
    R$^{14}$ is C$_{1-4}$alkyl or polyhaloC$_{1-4}$alkyl;
    R$^{15}$ is di(C$_{1-4}$alkyl)-(P=O)— or polyhaloC$_{1-4}$alkyl;
or R$^7$ and R$^8$ may be taken together to form —CH$_2$—(SO$_2$)—CH$_2$— or —CH$_2$—O—CH$_2$—;
each R$^9$ is independently selected from the group consisting of hydrogen and C$_{1-4}$alkyl;
R$^{10}$ is hydrogen, halo or C$_{1-6}$alkyl;
when n=1 and m=1, R$^8$ and R$^9$ may be taken together to form —CH$_2$—;
when n=1 and m=1, R$^5$ and R$^9$ may be taken together to form —CH$_2$CH$_2$—;
when n=1 and m=1, R$^8$ and R$^9$ may be taken together to form —CH$_2$—(CO)—O—;
Heteroaryl is pyridinyl or pyrimidinyl, wherein each Heteroaryl is optionally substituted with one or two substituents each independently selected from C$_{1-4}$alkyl, halo, amino, and aminocarbonyl;
Heteroaryl$^1$ is tetrazolyl, oxadiazolyl or 5-oxo-4,5-dihydro-1,2,4-oxadiazolyl;
or a pharmaceutically acceptable acid addition salt thereof.
  As used in the foregoing definitions:
  halo is generic to fluoro, chloro, bromo and iodo;
  C$_{1-4}$alkyl defines straight and branched chain saturated hydrocarbon radicals having from 1 to 4 carbon atoms such as, for example, methyl, ethyl, propyl, butyl, 1-methylethyl, 2-methylpropyl and the like;
  C$_{1-6}$alkyl is meant to include C$_{1-4}$alkyl and the higher homologues thereof having 5 or 6 carbon atoms, such as, for example, 2 methylbutyl, pentyl, hexyl and the like;
  C$_{3-6}$cycloalkyl is generic to cyclopropyl, cyclobutyl, cyclopentyl, and cyclohexyl;
  polyhaloC$_{1-4}$alkyl is defined as polyhalosubstituted C$_{1-4}$alkyl, in particular C$_{1-4}$alkyl (as hereinabove defined) substituted with 2 to 6 halogen atoms such as difluoromethyl, trifluoromethyl, trifluoroethyl, and the like;
  —(CO)— or (CO) means carbonyl.
  —(CS)— or (CS) means thiocarbonyl.
  The term "compounds of the invention" as used herein, is meant to include the compounds of formula (I), and the salts and solvates thereof.
  As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the terms "compound of formula (I)" and "intermediates of synthesis of formula (I)" are meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers. Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration.

The term "stereoisomers" also includes any rotamers, also called conformational isomers, the compounds of formula (I) may form.

Therefore, the invention includes enantiomers, diastereomers, racemates, E isomers, Z isomers, cis isomers, trans isomers, rotamers, and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

Some of the compounds according to formula (I) may also exist in their tautomeric form. Such forms in so far as they may exist, although not explicitly indicated in the above formula (I) are intended to be included within the scope of the present invention.

It follows that a single compound may exist in both stereoisomeric and tautomeric form.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butane-dioic acid), maleic, fumaric, malic, tartaric, citric, methanesulfonic, ethanesulfonic, benzenesulfonic, p toluenesulfonic, cyclamic, salicylic, p aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

For the avoidance of doubt, compounds of formula (I) may contain the stated atoms in any of their natural or non-natural isotopic forms. In this respect, embodiments of the invention that may be mentioned include those in which (a) the compound of formula (I) is not isotopically enriched or labelled with respect to any atoms of the compound; and (b) the compound of formula (I) is isotopically enriched or labelled with respect to one or more atoms of the compound. Compounds of formula (I) that are isotopically enriched or labelled (with respect to one or more atoms of the compound) with one or more stable isotopes include, for example, compounds of formula (I) that are isotopically enriched or labelled with one or more atoms such as deuterium, $^{13}C$, $^{14}C$, $^{14}N$, $^{15}O$ or the like.

The present invention also relates to compounds of formula (I)

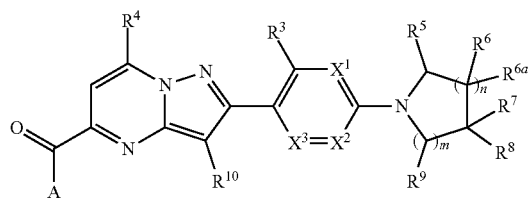

(I)

including any stereochemically isomeric form thereof, wherein
A is

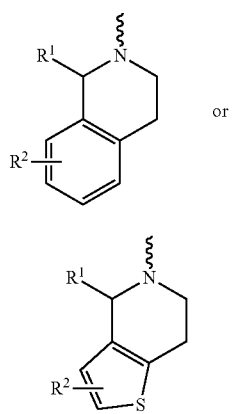

(a-1)

or (a-2)

n is 0, 1, or 2;
m is 1 or 2;
$X^1$, $X^2$ and $X^3$ are selected from $X^1$ is $CR^{11}$ and $X^2$ is $CR^{11}$ and $X^3$ is $CR^{11}$,
or $X^1$ is N and $X^2$ is $CR^{11}$ and $X^3$ is $CR^{11}$,
or $X^1$ is $CR^{11}$ and $X^2$ is N and $X^3$ is $CR^{11}$,
or $X^1$ is $CR^{11}$ and $X^2$ is $CR^{11}$ and $X^3$ is N,
or $X^1$ is N and $X^2$ is $CR^{11}$ and $X^3$ is N,
wherein each $R^{11}$ is independently selected from the group consisting of hydrogen, halo, hydroxy, $C_{1-4}$alkyl, $C_{1-4}$alkyloxy, $C_{1-4}$alkyloxy$C_{1-4}$alkyloxy and hydroxy$C_{1-4}$alkyl;
$R^1$ is $CH_3$ or $CH_2CH_3$;
$R^2$ is hydrogen, halo or $C_{1-4}$alkyl;
$R^3$ is halo or $CH_3O$;
$R^4$ is $C_{3-6}$cycloalkyl; phenyl; phenyl substituted with 1, 2 or 3 substituents each individually selected from halo, hydroxy, cyano, $C_{1-4}$alkyl, polyhalo$C_{1-4}$alkyl, and $C_{1-4}$alkyloxy; Heteroaryl; or $C_{1-4}$alkyl substituted with Heteroaryl;
$R^5$ is hydrogen or $C_{1-4}$alkyl;
each $R^6$ is independently selected from the group consisting of hydrogen, $C_{1-4}$alkyl and hydroxy;
each $R^{6a}$ is hydrogen;
$R^8$ is —OH,
—CN,
—O—(CO)—$NR^{12}R^{13}$,
—$C_{1-4}$alkyl-(CO)—$NR^{12}R^{13}$,
—(CO)—$NR^{12}R^{13}$,
—(CO)—$NR^{12}$—CN,
—(CO)—$NR^{12}$—$SO_2$—$R^{14}$,
—$NR^{12}$—(CO)—$R^{14}$,
—$NR^{12}$—(CO)—O—$R^{14}$,
—$NR^{12}$—$SO_2$—$R^{14}$,
—$NR^{12}$—$R^{15}$;
—$SO_2$—$R^{14}$,
—$SO_2$—$NR^{12}R^{13}$,
—$SO_2$—$NR^{12}$—(CO)—$R^{14}$, or
—SO(=NH)(—$R^{14}$), or
Heteroaryl$^1$;
wherein
$R^{12}$ and $R^{13}$ are each independently selected from hydrogen and $C_{1-4}$alkyl;
$R^{14}$ is $C_{1-4}$alkyl, or polyhalo$C_{1-4}$alkyl;
$R^{15}$ is di($C_{1-4}$alkyl)-(P=O)—;
or $R^7$ and $R^8$ may be taken together to form —$CH_2$—($SO_2$)—$CH_2$— or —$CH_2$—O—$CH_2$—;
each $R^9$ is independently selected from the group consisting of hydrogen and $C_{1-4}$alkyl;
$R^{10}$ is hydrogen, halo or $C_{1-6}$alkyl;
when n=1 and m=1, $R^8$ and $R^9$ may be taken together to form —$CH_2$—;
when n=1 and m=1, $R^5$ and $R^9$ may be taken together to form —$CH_2CH_2$—;
when n=1 and m=1, $R^8$ and $R^9$ may be taken together to form —$CH_2$—(CO)—O—;
Heteroaryl is pyridinyl or pyrimidinyl, wherein each Heteroaryl is optionally substituted with one or two substituents each independently selected from $C_{1-4}$alkyl, halo, amino, and aminocarbonyl;
Heteroaryl$^1$ is tetrazolyl or oxadiazolyl;
or a pharmaceutically acceptable acid addition salt thereof.

In a first embodiment the invention concerns compounds of formula (I), including any stereochemically isomeric form thereof, wherein
n is 0, 1, or 2;
m is 1 or 2;
$X^1$, $X^2$ and $X^3$ are selected from $X^1$ is $CR^{11}$ and $X^2$ is $CR^{11}$ and $X^3$ is $CR^{11}$,
  or $X^1$ is N and $X^2$ is $CR^{11}$ and $X^3$ is $CR^{11}$,
  or $X^1$ is $CR^{11}$ and $X^2$ is N and $X^3$ is $CR^{11}$,
  or $X^1$ is N and $X^2$ is $CR^{11}$ and $X^3$ is N,
  wherein each $R^{11}$ is independently selected from the group consisting of hydrogen, halo, $C_{1-4}$alkyl, $C_{1-4}$alkyloxy, and $C_{1-4}$alkyloxy$C_{1-4}$alkyloxy;
$R^1$ is $CH_3$;
$R^2$ is hydrogen, or halo;
$R^3$ is halo;
$R^4$ is $C_{3-6}$cycloalkyl; phenyl; phenyl substituted with 1 substituent selected from halo, cyano, $C_{1-4}$alkyl, polyhalo$C_{1-4}$alkyl, and $C_{1-4}$alkyloxy; or Heteroaryl;
$R^5$ is hydrogen or $C_{1-4}$alkyl;
each $R^6$ is independently selected from the group consisting of hydrogen, $C_{1-4}$alkyl and hydroxy;
each $R^{6a}$ is hydrogen;
$R^7$ is hydrogen or $C_{1-4}$alkyl;
$R^8$ is —OH,
  —CN,
  —O—(CO)—$NR^{12}R^{13}$,
  —$C_{1-4}$alkyl-(CO)—$NR^{12}R^{13}$,
  —(CO)—$NR^{12}R^{13}$,
  —(CO)—$NR^{12}$—CN,
  —(CO)—$NR^{12}$—$SO_2$—$R^{14}$,
  —$NR^{12}$—(CO)—$R^{14}$,
  —$NR^{12}$—(CO)—O—$R^{14}$,
  —$NR^{12}$—$SO_2$—$R^{14}$,
  —$NR^{12}$—$R^{15}$;
  —$SO_2$—$R^{14}$,
  —$SO_2$—$NR^{12}R^{13}$,
  —$SO_2$—$NR^{12}$—(CO)—$R^{14}$, or
  —SO(=NH)(—$R^{14}$), or
  Heteroaryl$^1$;
  wherein
    $R^{12}$ and $R^{13}$ are each independently selected from hydrogen and $C_{1-4}$alkyl;
    $R^{14}$ is $C_{1-4}$alkyl;
    $R^{15}$ is di($C_{1-4}$alkyl)-(P=O)—;
or $R^7$ and $R^8$ may be taken together to form —$CH_2$—($SO_2$)—$CH_2$— or —$CH_2$—O—$CH_2$—;
each $R^9$ is independently selected from the group consisting of hydrogen and $C_{1-4}$alkyl;
$R^{10}$ is hydrogen, halo or $C_{1-6}$alkyl;
when n=1 and m=1, $R^8$ and $R^9$ may be taken together to form —$CH_2$—(CO)—O—;
Heteroaryl is pyridinyl or pyrimidinyl, wherein each Heteroaryl is optionally substituted with one substituent selected from halo;
Heteroaryl$^1$ is tetrazolyl or oxadiazolyl;
or a pharmaceutically acceptable acid addition salt thereof.

In a second embodiment the invention concerns compounds of formula (I), (I)

including any stereochemically isomeric form thereof,
wherein
A is (a-1)

or (a-2)

wherein
n is 0, 1, or 2;
m is 1 or 2;
$X^1$, $X^2$ and $X^3$ are selected from $X^1$ is $CR^{11}$ and $X^2$ is $CR^{11}$ and $X^3$ is $CR^{11}$,
  or $X^1$ is N and $X^2$ is $CR^{11}$ and $X^3$ is $CR^{11}$,
  or $X^1$ is $CR^{11}$ and $X^2$ is N and $X^3$ is $CR^{11}$,
  or $X^1$ is N and $X^2$ is $CR^{11}$ and $X^3$ is N,
  wherein each $R^{11}$ is independently selected from the group consisting of hydrogen, halo, hydroxy, $C_{1-4}$alkyl, $C_{1-4}$alkyloxy, $C_{1-4}$alkyloxy$C_{1-4}$alkyloxy, and hydroxy$C_{1-4}$alkyloxy;
$R^1$ is $CH_3$;
$R^2$ is hydrogen, or halo;
$R^3$ is halo;
$R^4$ is $C_{3-6}$cycloalkyl; phenyl; phenyl substituted with 1 substituent selected from halo, cyano, $C_{1-4}$alkyl, polyhalo$C_{1-4}$alkyl, and $C_{1-4}$alkyloxy; or Heteroaryl;
$R^5$ is hydrogen, $C_{1-4}$alkyl or hydroxy$C_{1-4}$alkyl;
each $R^6$ is independently selected from the group consisting of hydrogen, $C_{1-4}$alkyl, hydroxy, halo and $C_{1-4}$alkyloxy;
each $R^{6a}$ is independently selected from the group consisting of hydrogen and halo;
$R^7$ is hydrogen, $C_{1-4}$alkyl, or hydroxy$C_{1-4}$alkyl;
$R^8$ is —OH,
  —CN,
  —O—(CO)—$NR^{12}R^{13}$,
  —$C_{1-4}$alkyl-(CO)—$NR^{12}R^{13}$,
  —(CO)—$NR^{12}R^{13}$,
  —(CS)—$NR^{12}R^{13}$,
  —(CO)—$NR^{12}$—CN,
  —(CO)—$NR^{12}$—$SO_2$—$R^{14}$,
  —$NR^{12}$—(CO)—$R^{14}$,
  —$NR^{12}$—(CO)—O—$R^{14}$,
  —$NR^{12}$—$SO_2$—$R^{14}$,
  —$NH_2$,
  —$NR^{12}$—$R^{15}$;
  —$SO_2$—$R^{14}$,
  —$SO_2$—$NR^{12}R^{13}$,
  —$SO_2$—$NR^{12}$—(CO)—$R^{14}$, or
  SO(=NH)(—$R^{14}$), or
  Heteroaryl$^1$;

wherein
R$^{12}$ and R$^{13}$ are each independently selected from hydrogen and C$_{1-4}$alkyl, and;
R$^{14}$ is C$_{1-4}$alkyl or polyhaloC$_{1-4}$alkyl;
R$^{15}$ is di(C$_{1-4}$alkyl)-(P=O)— or polyhaloC$_{1-4}$alkyl;
or R$^7$ and R$^8$ may be taken together to form —CH$_2$—(SO$_2$)—CH$_2$— or —CH$_2$—O—CH$_2$—;
each R$^9$ is independently selected from the group consisting of hydrogen and C$_{1-4}$alkyl; R$^{10}$ is hydrogen;
when n=1 and m=1, R$^8$ and R$^9$ may be taken together to form —CH$_2$—(CO)—O—;
Heteroaryl is pyridinyl or pyrimidinyl, wherein each Heteroaryl is optionally substituted with one substituent selected from halo;
Heteroaryl$^1$ is tetrazolyl or 5-oxo-4,5-dihydro-1,2,4-oxadiazolyl;
or a pharmaceutically acceptable acid addition salt thereof.

A first group of compounds are compounds of formula (I) wherein X$^1$ is CR$^{11}$ and X$^2$ is CR$^{11}$ and X$^3$ is CR$^{11}$.

A second group of compounds are compounds of formula (I) wherein X$^1$ is N and X$^2$ is CR$^{11}$ and X$^3$ is CR$^{11}$; or X$^1$ is CR$^{11}$ and X$^2$ is N and X$^3$ is CR$^{11}$; or X$^1$ is CR$^{11}$ and X$^2$ is CR$^{11}$ and X$^3$ is N; or X$^1$ is N and X$^2$ is CR$^{11}$ and X$^3$ is N.

A third group of compounds are compounds of formula (I) wherein X$^1$ is N and X$^2$ is CR$^{11}$ and X$^3$ is CR$^{11}$.

A third group of compounds are compounds of formula (I) X$^1$ is CR$^{11}$ and X$^2$ is N and X$^3$ is CR$^{11}$.

A fourth group of compounds are compounds of formula (I) wherein X$^1$ is CR$^{11}$ and X$^2$ is CR$^{11}$ and X$^3$ is N.

A fifth group of compounds are compounds of formula (I) wherein X$^1$ is N and X$^2$ is CR$^{11}$ and X$^3$ is N.

In a further embodiment the invention concerns compounds of formula (I),

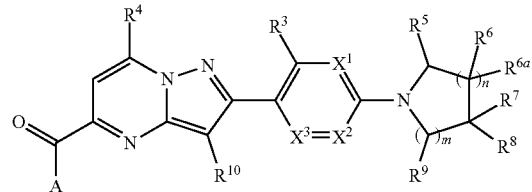

(I)

including any stereochemically isomeric form thereof,
wherein
A is

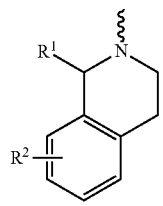

wherein
n is 0 or 1;
m is 1;
X$^1$, X$^2$ and X$^3$ are selected from X$^1$ is CR$^{11}$ and X$^2$ is CR$^{11}$ and X$^3$ is CR$^{11}$, wherein each R$^{11}$ is hydrogen;
R$^1$ is CH$_3$;
R$^2$ is hydrogen;
R$^3$ is halo;
R$^4$ is C$_{3-6}$cycloalkyl or Heteroaryl;
R$^5$ is hydrogen;
each R$^6$ is independently selected from the group consisting of hydrogen, hydroxy, and halo;
each R$^{6a}$ is hydrogen;
R$^7$ is hydrogen or hydroxyC$_{1-4}$alkyl;
R$^8$ is —OH,
—C$_{1-4}$alkyl-(CO)—NR$^{12}$R$^{13}$, or
—(CO)—NR$^{12}$R$^{13}$,
wherein
R$^{12}$ and R$^{13}$ are each independently selected from hydrogen and C$_{1-4}$alkyl,
R$^{10}$ is hydrogen;
Heteroaryl is pyridinyl;
or a pharmaceutically acceptable acid addition salt thereof.

In another further embodiment the invention concerns compounds of formula (I),

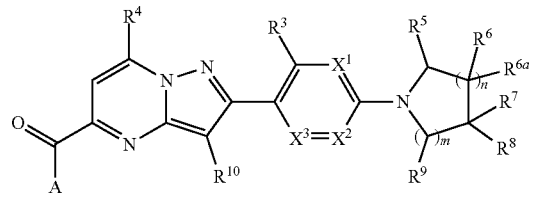

(I)

including any stereochemically isomeric form thereof,
wherein
A is

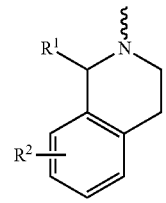

wherein
n is 1;
m is 1;
X$^1$, X$^2$ and X$^3$ are selected from X$^1$ is CR$^{11}$ and X$^2$ is CR$^{11}$ and X$^3$ is CR$^{11}$, wherein each R$^{11}$ is hydrogen;
R$^1$ is CH$_3$;
R$^2$ is hydrogen;
R$^3$ is halo;
R$^4$ is C$_{3-6}$cycloalkyl;
R$^5$ is hydrogen;
each R$^6$ is independently selected from the group consisting of hydrogen, hydroxy, and halo;
each R$^{6a}$ is hydrogen;
R$^7$ is hydrogen or hydroxyC$_{1-4}$alkyl;
R$^8$ is —OH, or
—(CO)—NR$^{12}$R$^{13}$,
wherein
R$^{12}$ and R$^{13}$ are each independently selected from hydrogen and C$_{1-4}$alkyl,
R$^{10}$ is hydrogen;
or a pharmaceutically acceptable acid addition salt thereof.

In yet another further embodiment the invention concerns compounds of formula (I), (I)

including any stereochemically isomeric form thereof, wherein
A is wherein
n is 1;
m is 1;
$X^1$, $X^2$ and $X^3$ are selected from $X^1$ is $CR^{11}$ and $X^2$ is $CR^{11}$ and $X^3$ is $CR^{11}$, wherein each $R^{11}$ is hydrogen;
$R^1$ is $CH_3$;
$R^2$ is hydrogen;
$R^3$ is halo;
$R^4$ is $C_{3-6}$cycloalkyl;
$R^5$ is hydrogen;
each $R^6$ is independently selected from the group consisting of hydrogen and hydroxy;
each $R^{6a}$ is hydrogen;
$R^7$ is hydrogen;
$R^8$ is —OH, or
—(CO)—$NR^{12}R^{13}$,
wherein
$R^{12}$ and $R^{13}$ are each independently selected from hydrogen and $C_{1-4}$alkyl,
$R^{10}$ is hydrogen;
or a pharmaceutically acceptable acid addition salt thereof.

Interesting compounds of formula (I) are those compounds of formula (I) wherein one or more of the following restrictions apply:
a) A is a radical of formula (a-1); or
b) A is a radical of formula (a-2); or
c) $R^1$ is methyl; or
d) $R^2$ is hydrogen; or
e) $R^3$ is fluoro; or
f) $R^4$ is cyclopropyl; or
g) $R^4$ is phenyl; or
h) $R^4$ is pyridinyl; or
i) n is 0 and m is 1; or
j) n is 0 and m is 2; or
k) n is 1 and m is 1; or
l) n is 1 and m is 2; and
m) n is 2 and m is 1.

Specific examples of compounds of formula (I) are:

Co. No. 13

Co. No. 14

Co. No. 36

Co. No. 37

-continued
Co. No. 66
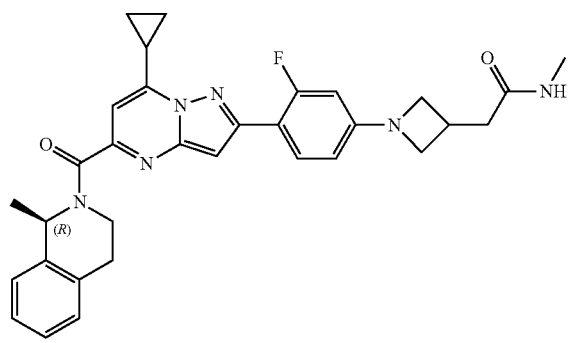
Co. No. 84
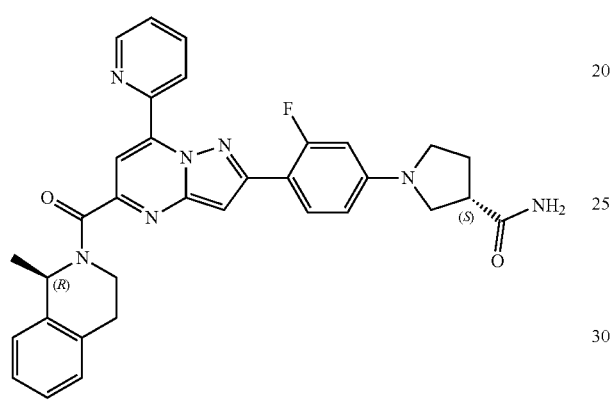
Co. No. 95
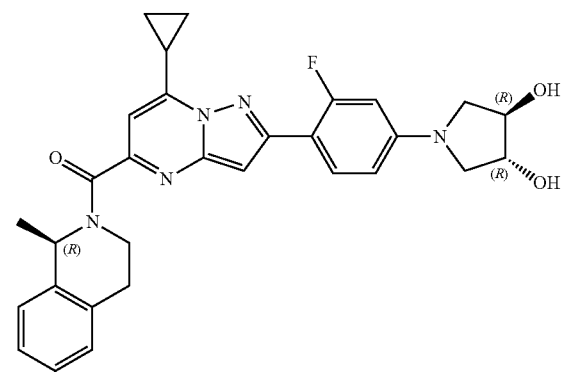
Co. No. 100
-continued
Co. No. 102
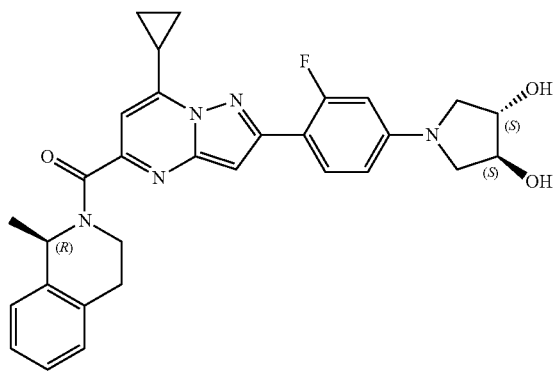
Co. No. 103
(-)
Co. No. 104
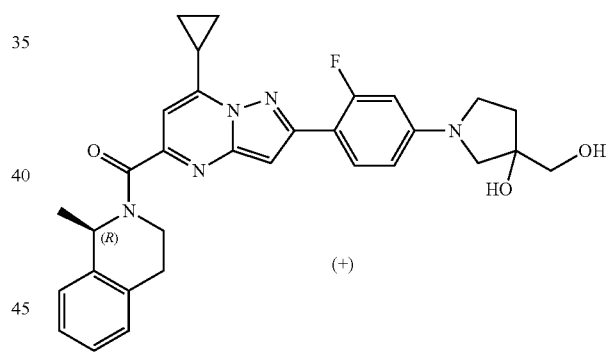
(+)
Co. No. 107
Compounds of formula (I) can generally be prepared by reacting an intermediate of formula (II) with an intermediate of formula (III) in a reaction-inert solvent.

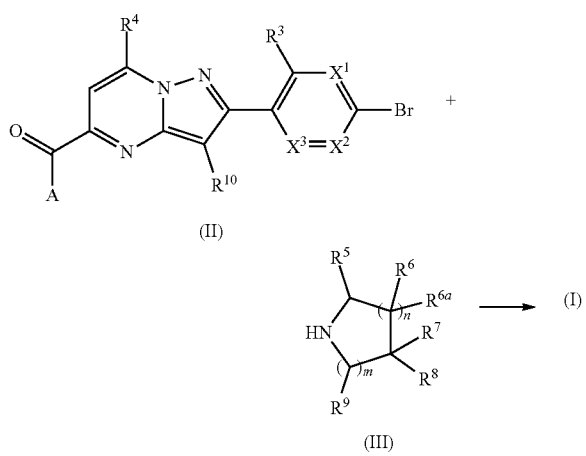

(II)

(III)

Compounds of formula (I) can also be prepared by reacting an intermediate of formula (IV) with an intermediate of formula (V) in a reaction-inert solvent.

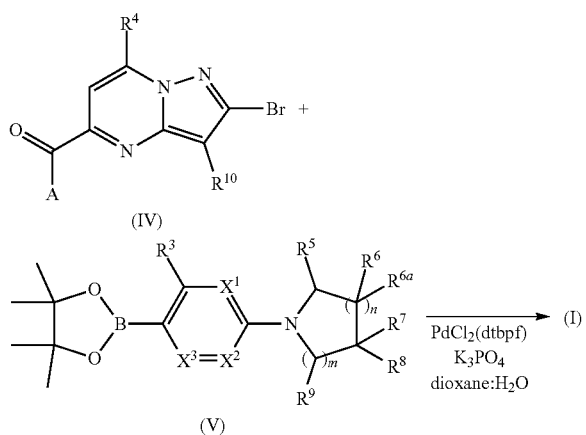

(IV)

(V)

Other synthetic pathways for preparing compounds of formula (I) have been described in the experimental party as general methods of preparation and specific working examples.

The compounds of formula (I) may further be prepared by converting compounds of formula (I) into each other according to art-known group transformation reactions.

The starting materials and some of the intermediates are known compounds and are commercially available or may be prepared according to conventional reaction procedures generally known in the art.

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I) show antiviral properties. Viral infections treatable using the compounds and methods of the present invention include those infections brought on by Pneumoviridae and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailabilty, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. in Antiviral Research, 38, p. 31-42(1998).

Additionally the present invention provides pharmaceutical compositions comprising at least one pharmaceutically acceptable carrier and a therapeutically effective amount of a compound of formula (I). Also provided are pharmaceutical compositions comprising a pharmaceutically acceptable carrier, a therapeutically active amount of a compound of formula (I), and another antiviral agent, in particular a RSV inhibiting compound.

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1', 6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen free water, before use.

The compounds of formula (I) may also be formulated in rectal compositions such as suppositories or retention enemas, e.g. containing conventional suppository bases such as cocoa butter and/or other glycerides.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections. Other antiviral compounds (b) to be combined with a compound of formula (I) for use in the treatment of RSV are RSV fusion inhibitors or RSV polymerase inhibitors. Specific antiviral compounds for combination with any of the compounds of formula (I) that are useful in the treatment of RSV are the RSV inhibiting compounds selected from ribavirin, lumicitabine, presatovir, ALX-0171, MDT-637, BTA-9881, BMS-433771, YM-543403, A-60444, TMC-353121, RFI-641, CL-387626, MBX-300, 3-({5-chloro-1-[3-(methyl-sulfonyl)propyl]-1H-benzimidazol-2-yl}methyl)-1-cyclopropyl-1,3-dihydro-2H-imidazo[4,5-c]pyridin-2-one, 3-[[7-chloro-3-(2-ethylsulfonyl-ethyl)imidazo[1,2-a]pyridin-2-yl]methyl]-1-cyclopropyl-imidazo[4,5-c]pyridin-2-one, and 3-({5-chloro-1-[3-(methyl-sulfonyl)propyl]-1H-indol-2-yl}methyl)-1-(2,2,2-trifluoroethyl)-1,3-dihydro-2H-imidazo[4,5-c]pyridin-2-one.

The invention will hereinafter be illustrated with reference to the following, non-limiting examples.

Experimental Part

A. ABBREVIATIONS

| (±)-BINAP | (±)-2,2'-bis(diphenylphosphino)-1,1'-binaphthalene CAS [98327-87-8] |
| μw | microwave |
| AcOH | acetic acid |
| aq. | aqueous |
| Boc₂O | di-tert-butyl dicarbonate - CAS [24424-99-5] |
| br | broad |
| CDI | 1,1'-carbonyldiimidazole - CAS [530-62-1] |
| CPME | cyclopentyl methyl ether - CAS [5614-37-9] |
| d | doublet |
| DBU | 1,8-diazabicyclo[5.4.0]undec-7-ene - CAS [6674-22-2] |
| DCM | dichloromethane |
| DIPE | diisopropyl ether |
| DIPEA | N,N-diisopropylethylamine |
| DMAP | 4-(dimethylamino)pyridine |
| DMF | dimethylformamide |
| DMSO | dimethyl sulfoxide |
| Et₂O | diethyl ether |
| Et₃N | triethylamine |
| EtOAc | ethyl acetate |
| EtOH | ethanol |
| H₂ | hydrogen |
| H | hour |
| HATU | 2-(7-aza-1H-benzotriazole-1-yl)-1,1,3,3-tetramethyluronium hexafluorophosphate - CAS [148893-10-1] |
| HMDS | hexamethyldisilazane - CAS [999-97-3] |
| i-PrOH | isopropyl alcohol |
| KOAc | potassium actate |
| LiHMDS | lithium bis(trimethylsilyl)amide - CAS [4039-32-1] |
| m | multiplet |
| m/z | mass-to-charge ratio |
| m-CPBA | 3-chloroperbenzoic acid - CAS [937-14-4] |
| MeCN | acetonitrile |
| MeOH | methanol |
| min | minute(s) |
| N₂ | nitrogen |
| NaOt-Bu | sodium tert-butoxide |
| NBS | N-bromosuccinimide - CAS [128-08-5] |
| NMP | methylpyrrolidone - CAS [872-50-4] |
| NMR | Nuclear Magnetic Resonance |
| o/n | overnight |
| Pd(OAc)₂ | palladium (II) acetate - CAS [3375-31-3] |
| Pd(PPh₃)₄ | tetrakis(triphenylphosphine)palladium (0) - CAS [1422-01-3] |
| Pd₂(dba)₃ | tris(dibenzylideneacetone)dipalladium (0) - CAS [51364-51-3] |
| PdCl₂(dtbpf) | [1,1'-bis(di-tert-butylphosphino)ferrocene]dichloropalladium(II) CAS [95408-45-0] |
| PPACA | propylphosphonic anhydride - CAS [68957-94-8] |
| ppm | parts per million |
| Pt/C | platinum on activated charcoal |
| q | quartet |
| quin | quintuplet |
| rt | room temperature |
| s | singulet |
| t | triplet |
| t-BuOK | potassium tert-butoxide |
| TFA | trifluoroacetic acid - CAS [76-05-1] |
| THF | tetrahydrofuran |
| TMSCl | chlorotrimethylsilane - CAS [75-77-4] |
| TTBP.HBF₄ | tri-tert-butylphosphonium tetrafluoroborate - CAS [13274-22-1] |
| wt | weight |
| XantPhos | 4,5-bis(diphenylphosphino)-9,9-dimethylxanthene CAS [161265-03-8] |
| XPhos | 2-dicyclohexylphosphino-2',4',6'-triisopropylbiphenyl CAS [564483-18-7] |
| Δ | heat |

The stereochemical configuration for some compounds has been designated as R* or S* (or *R or *S) when the absolute stereochemistry is undetermined although the compound itself has been isolated as a single stereoisomer and is enantiomerically pure.

B. COMPOUND SYNTHESIS

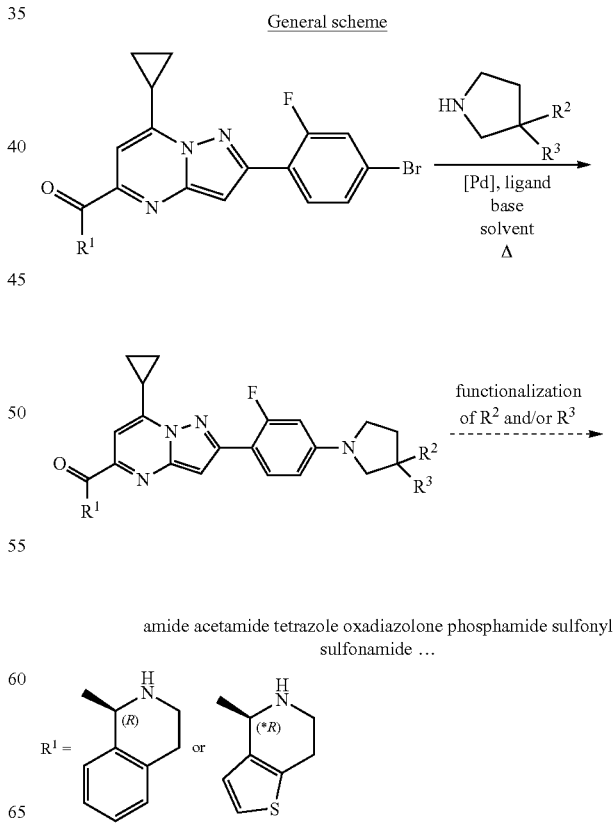

Compound 1

1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)pyrrolidine-3-carbonitrile

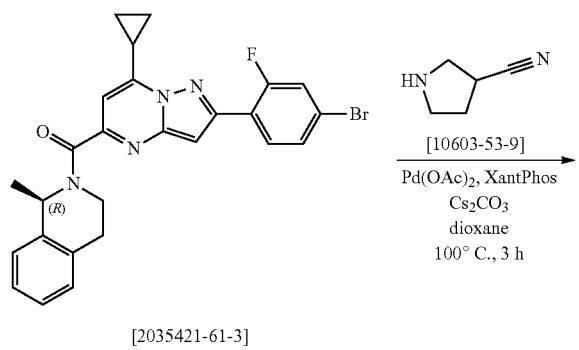

[2035421-61-3]

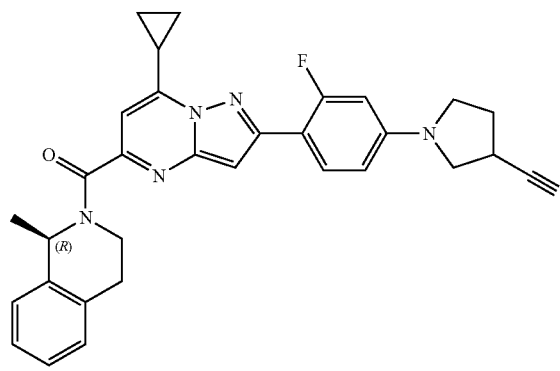

1

A mixture of (1R)-2-[2-(4-bromo-2-fluorophenyl)-7-cyclopropylpyrazolo[1,5-a]pyrimidine-5-carbonyl]-1-methyl-1,2,3,4-tetrahydroisoquinoline [2035421-61-3] (0.20 g, 0.39 mmol), pyrrolidine-3-carbonitrile [10603-53-9] (45.7 mg, 475 μmol) and cesium carbonate (387 mg, 1.19 mmol) was purged with nitrogen. 1,4-Dioxane (2 mL) was added and the mixture was degassed with nitrogen. Palladium acetate (17.8 mg, 79.1 μmol) and XantPhos (45.8 mg, 79.1 μmol) were added. The reaction mixture was purged with nitrogen and stirred at 100° C. for 3 h. The reaction mixture was poured out into water and the aqueous phase was extracted with EtOAc. The mixture was filtered through a pad of Celite® and rinsed with EtOAc. The layers were separated and the aqueous phase was extracted with EtOAc. The combined organic extracts were washed with brine, dried over MgSO₄, filtered and the solvent was removed under reduced pressure. The crude mixture was purified by flash chromatography over silica gel (cartridge 24 g, 15-40 μm, mobile phase gradient: heptane/EtOAc from 70:30 to 50:50). The pure fractions were collected and evaporated to dryness. The residue (0.16 g) was taken up in DIPE. The solid was filtered off and dried under vacuum to give compound 1 (127 mg, 62%).

Compound 2 and Compound 3

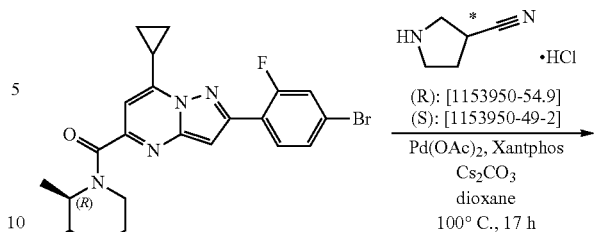

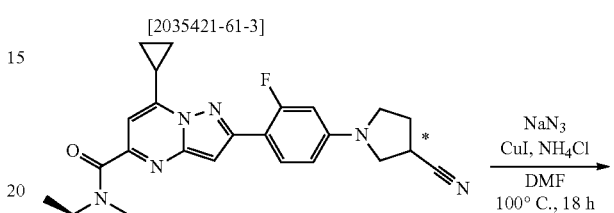

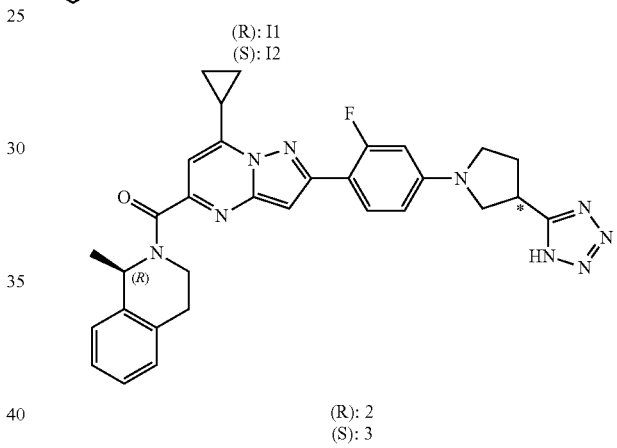

(R): 2
(S): 3

Intermediate I1

(3R)-1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)pyrrolidine-3-carbonitrile

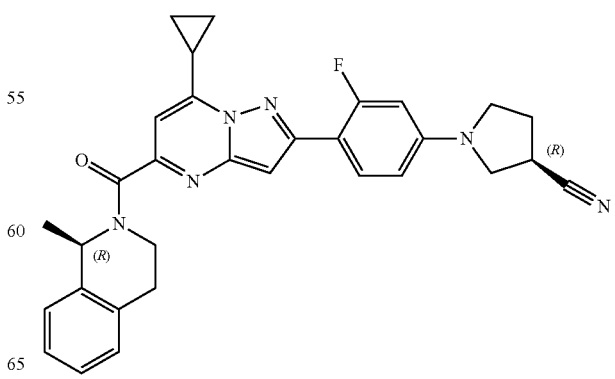

I1

A Schlenk tube was charged with (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (1.00 g, 1.91 mmol), (R)-pyrrolidine-3-carbonitrile hydrochloride [1153950-54-9] (304 mg, 2.29 mmol), cesium carbonate (1.87 g, 5.73 mmol) and XantPhos (111 mg, 191 μmol) and purged with nitrogen. 1,4-Dioxane (20 mL) was added and the mixture was purged again with nitrogen. Palladium acetate (42.9 mg, 191 μmol) was added. The reaction mixture was purged with nitrogen and stirred at 100° C. for 17 h. The mixture was diluted with EtOAc and H₂O. The layers were separated and the aqueous phase was extracted with EtOAc (twice). The combined organic extracts were washed with brine, dried over MgSO₄, filtered and the solvent was removed under reduced pressure. The crude mixture was purified by preparative LC (irregular SiOH, 15-40 μm, 12 g Grace®, liquid injection (DCM), mobile phase gradient: heptane/EtOAc from 90:10 to 50:50) to afford intermediate I1 (879 mg, 88%) as a pale yellow solid.

Intermediate I2

(3S)-1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)pyrrolidine-3-carbonitrile

I2

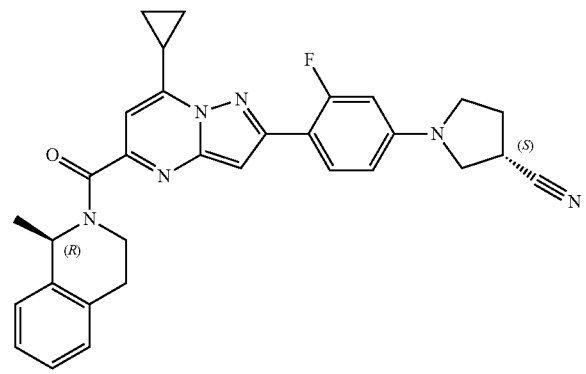

Intermediate I2 was synthesized from (S)-pyrrolidine-3-carbonitrile hydrochloride [1153950-49-2] and (1R)-2-[2-(4-bromo-2-fluorophenyl)-7-cyclopropylpyrazolo[1,5-a]pyrimidine-5-carbonyl]-1-methyl-1,2,3,4-tetrahydroisoquinoline [2035421-61-3] according to the procedure reported for the synthesis of intermediate I1. The purification was carried out by preparative LC (irregular SiOH, 15-40 μm, 40 g Grace®, liquid injection (DCM), mobile phase gradient: heptane/EtOAc from 90:10 to 40:60). The residue (997 mg) was taken up in MeCN and concentrated under reduced pressure to afford intermediate I2 (840 mg, 84%) as a yellow solid.

Compound 2

(1R)-2-(7-Cyclopropyl-2-{2-fluoro-4-[(3R)-3-(1H-1,2,3,4-tetrazol-5-yl)pyrrolidin-1-yl]phenyl}pyrazolo[1,5-a]pyrimidine-5-carbonyl)-1-methyl-1,2,3,4-tetrahydroisoquinoline

2

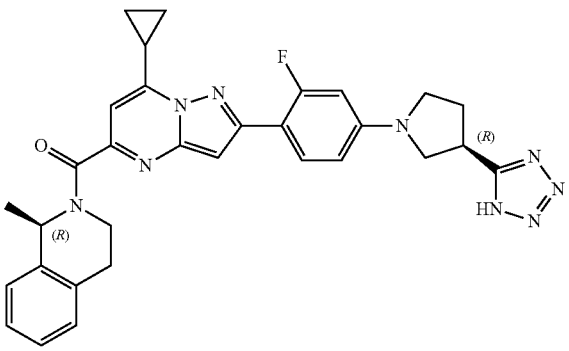

In a sealed tube, sodium azide (212 mg, 3.27 mmol) was added to a mixture of intermediate I1 (170 mg, 327 μmol), copper iodide (93.3 mg, 0.49 mmol) and ammonium chloride (52.4 mg, 0.98 mmol) in DMF (5 mL). The reaction mixture was stirred at 100° C. for 18 h. EtOAc, 1N aqueous solution of HCl and brine were added. The layers were separated and the aqueous phase was extracted with EtOAc (3 times). The combined organic extracts were dried over MgSO₄, filtered and the solvent was removed under reduced pressure. The crude mixture was purified by preparative LC (irregular SiOH, 15-40 μm, 12 g GraceResolv™, dry loading (Celite®), mobile phase gradient: DCM/(MeOH/AcOH 9:1) from 100:0 to 94:6). The product was taken up in EtOAc and a 1N aqueous solution of HCl was added. The layers were separated and the organic phase was washed with 1N aqueous solution of HCl (twice), dried over MgSO₄, filtered and the solvent was removed under reduced pressure. The residue (88 mg) was triturated with MeOH. The solid was filtered off and dried under high vacuum at 50° C. for 18 h to afford compound 2 (76 mg, 41%) as an orange solid.

Compound 3

(1R)-2-(7-Cyclopropyl-2-{2-fluoro-4-[(3S)-3-(1H-1,2,3,4-tetrazol-5-yl)pyrrolidin-1-yl]phenyl}pyrazolo[1,5-a]pyrimidine-5-carbonyl)-1-methyl-1,2,3,4-tetrahydroisoquinoline

3

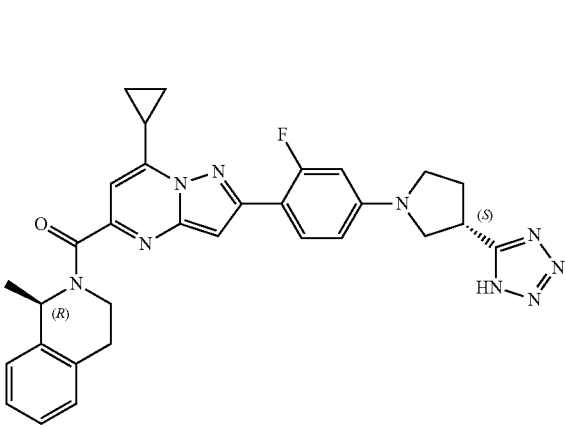

Compound 3 was synthesized from intermediate I2 according to the procedure reported for the synthesis of compound 2. The purification was carried out by preparative LC (irregular SiOH, 15-40 μm, 12 g GraceResolv™, dry loading (Celite®), mobile phase gradient: DCM/(MeOH/ AcOH 9:1) from 100:0 to 94:6). The residue was triturated with MeOH. The solid was filtered off and dried under high vacuum at 50° C. for 18 h to afford compound 3 (126 mg, 68%) as an orange solid.

Compound 4

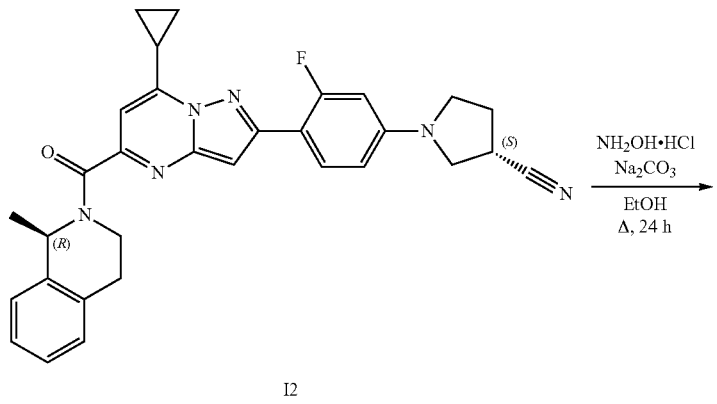

I2

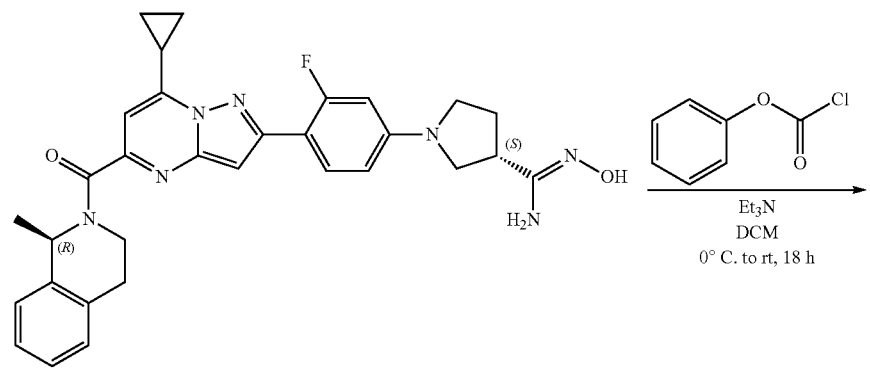

I3

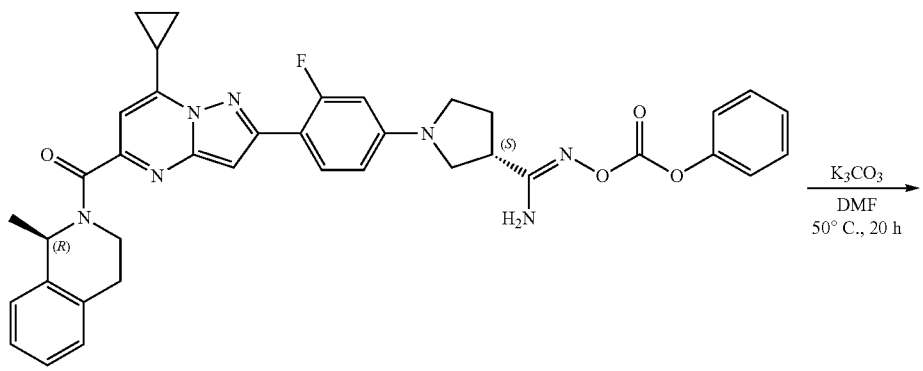

I4

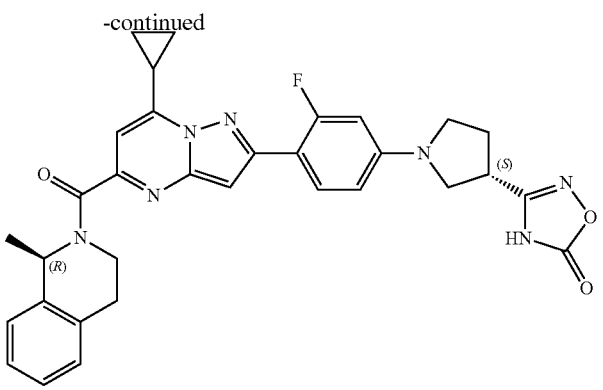

4

Intermediate I3

(Z,3S)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-N'-hydroxypyrrolidine-3-carboximidamide

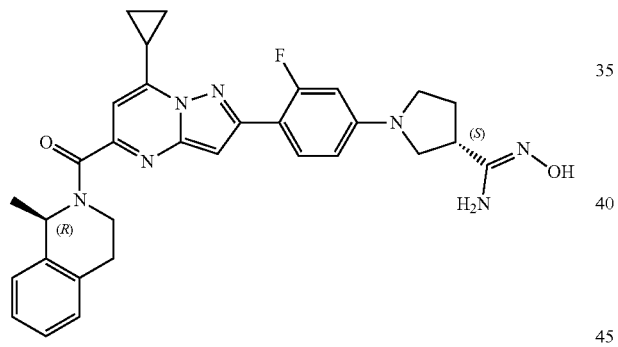

I3

Hydroxylamine hydrochloride (120 mg, 1.73 mmol) was added to a suspension intermediate I2 (300 mg, 0.58 mmol) and sodium carbonate (244 mg, 2.31 mmol) in EtOH (8 mL). The reaction mixture was stirred under reflux for 24 h and the solvent was evaporated under reduced pressure. DCM and H₂O were added to the residue. The layers were separated and the aqueous phase was extracted with DCM (twice). The combined organic extracts were dried over MgSO₄, filtered and evaporated under reduced pressure to afford intermediate I3 (331 mg, 90%, 87% purity) as a yellow gum.

Intermediate I4

(Z)-{Amino[(3S)-1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-yl]methylidene}-amino phenyl carbonate

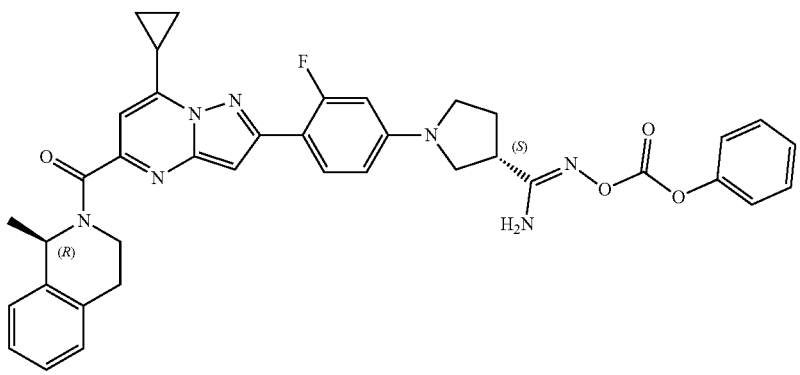

I4

Phenyl chloroformate (98.0 µL, 0.78 mmol) was added to a mixture of intermediate I3 (331 mg, 0.52 mmol, 87% purity) and triethylamine (220 µL, 1.58 mmol) in DCM (7 mL) at 0° C. The reaction mixture was stirred at rt for 18 h. The reaction mixture was diluted with DCM and H₂O. The layers were separated and the aqueous phase was extracted with DCM (twice). The combined organic extracts were dried over MgSO₄, filtered and evaporated under reduced pressure. The crude mixture was purified by preparative LC (irregular SiOH, 15-40 µm, 24 g GraceResolv™, liquid injection (DCM), mobile phase gradient: DCM/EtOAc from 100:0 to 90:10). The residue (210 mg) was taken up in MeCN and concentrated under reduced pressure (twice) to give intermediate I4 (189 mg, 52%) as a yellow gum.

Compound 4

3-[(3S)-1-(4-{7-Cyclopropyl-5-[(1R)-1-methyl-1,2, 3,4-tetrahydroisoquinoline-2-carbonyl]pyrazolo[1,5-a]pyrimidin-2-yl}-3-fluorophenyl)pyrrolidin-3-yl]-4, 5-dihydro-1,2,4-oxadiazol-5-one In a sealed tube, potassium carbonate (41.1 mg, 0.30 mmol) was added to a solution of intermediate I4 (172 mg, 0.25 mmol) in DMF (1 mL). The reaction mixture was stirred at 50° C. for 20 h. Brine, a 1N aqueous solution of HCl and EtOAc were added. The layers were separated and the aqueous phase was extracted with EtOAc (twice). The combined organic extracts were washed with brine (4 times), dried over MgSO₄, filtered and evaporated under reduced pressure. The crude mixture was crystallized from MeOH, and the solid was filtered off and dried under high vacuum at 50° C. for 3 h. The solid (110 mg) was purified by preparative LC (irregular SiOH, 15-40 µm, 24 g GraceResolv™, liquid injection (DCM), mobile phase gradient: DCM/MeOH from 100:0 to 97:3). The residue was re-crystallized from MeOH, filtered off and dried under high vacuum at 50° C. for 3 h to afford compound 4 (81 mg, 56%) as a pale yellowish solid.

Compound 5

(1R)-2-[7-Cyclopropyl-2-(2-fluoro-4-{2-oxa-6-azaspiro[3.4]octan-6-yl}phenyl)pyrazolo[1,5-a]pyrimidine-5-carbonyl]-1-methyl-1,2,3,4-tetrahydroisoquinoline

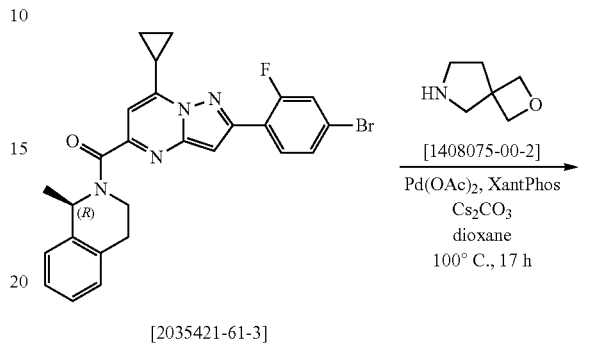

A sealed tube was charged with (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (150 mg, 0.28 mmol), 2-oxa-6-azaspiro[3.4]octane hemioxalate [1408075-00-2] (89.2 mg, 0.28 mmol), cesium carbonate (276 mg, 0.85 mmol) and XantPhos (16.3 mg, 28.2 µmol) and purged with nitrogen. 1,4-Dioxane (4.5 mL) was added and the mixture was purged again with nitrogen. Palladium acetate (6.33 mg, 28.2 µmol) was added. The reaction mixture was purged with nitrogen and stirred at 100° C. for 17 h. The reaction mixture was diluted with EtOAc and H₂O. The layers were separated and the aqueous phase was extracted with EtOAc (twice). The combined organic extracts were washed with brine, dried over MgSO₄, filtered and the solvent was removed under reduced pressure. The crude mixture was purified by preparative LC (irregular SiOH, 15-40 µm, 12 g Grace®, liquid injection (DCM), mobile phase gradient: heptane/EtOAc from 90:10 to 50:50). The residue was crystallized from MeOH, filtered off and dried under high vacuum at 50° C. for 20 h to afford compound 5 (112 mg, 74%) as a yellow solid.

Compound 6

6-[4-(7-Cyclopropyl-5-{[(1R)-1-methyl-1,2,3,4-tetrahydroisoquinoline-2-carbonyl]-pyrazolo[1,5-a]pyrimidin-2-yl]-3-fluorophenyl)-2$\lambda^6$-thia-6-azaspiro[3.4]octane-2,2-dione

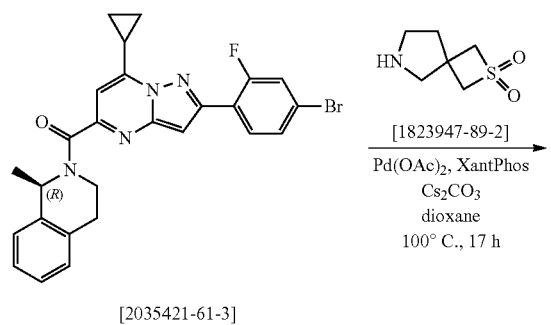

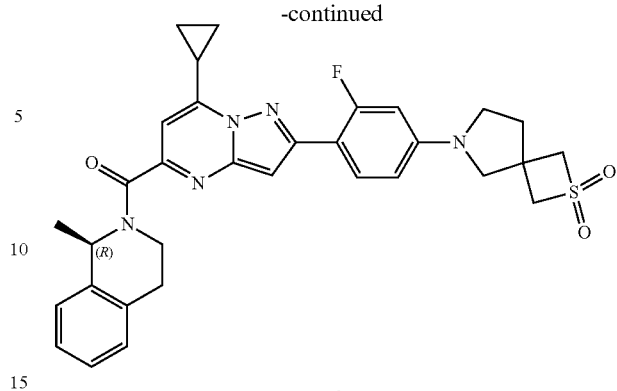

6

Compound 6 was synthesized from (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] and 2-thia-6-azaspiro[3.4]octane 2,2-dioxide [1823947-89-2] according to the procedure reported for the synthesis of compound 5. Compound 6 (86 mg, 58%) was obtained as a yellow solid.

Compound 7 and Compound 8

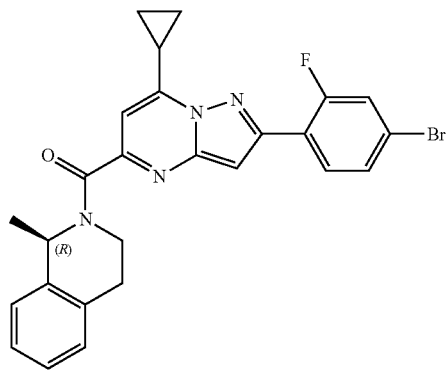

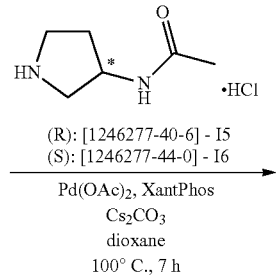

(R): [1246277-40-6] - I5
(S): [1246277-44-0] - I6

Pd(OAc)$_2$, XantPhos
Cs$_2$CO$_3$
dioxane
100° C., 7 h

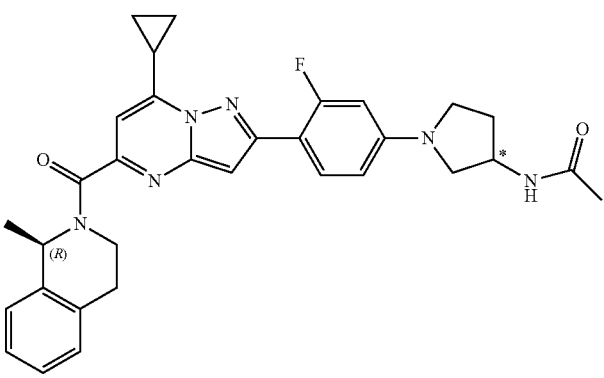

(R): 7
(S): 8

Synthesis of Intermediates I5 and I6

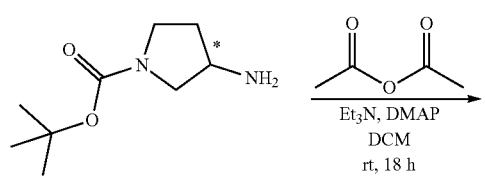

(R): [147081-49-0]
(S): [147081-44-5]

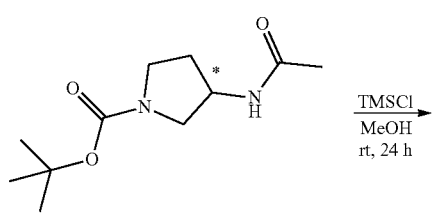

(R): [550371-67-0] - I7
(S): [114636-37-2] - I8

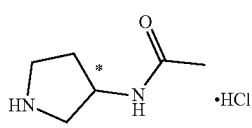

(R): [1246277-40-6] - I5
(S): [1246277-44-0] - I6

Intermediate I7

Tert-butyl (3R)-3-acetamidopyrrolidine-1-carboxylate

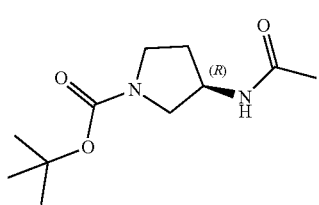

Acetic anhydride (0.56 mL, 5.91 mmol) was added dropwise to a mixture of (R)-(+)-1-boc-3-aminopyrrolidine [147081-49-0] (1.00 g, 5.37 mmol), triethylamine (1.12 mL, 8.05 mmol) and DMAP (32.8 mg, 0.27 mmol) in DCM (20 mL). The reaction mixture was stirred at rt for 18 h. The reaction mixture was diluted with DCM and H₂O. The layers were separated and the aqueous phase was extracted with DCM (twice). The combined organic extracts were dried over MgSO₄, filtered and evaporated under reduced pressure to afford intermediate I7 (1.64 g) as an oil.

Intermediate I8

Tert-butyl (3S)-3-acetamidopyrrolidine-1-carboxylate

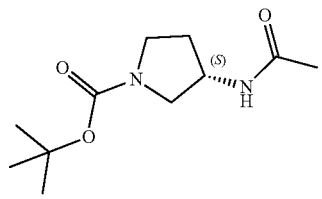

Intermediate I8 (1.97 g) was synthesized from (S)-(−)-1-boc-3-aminopyrrolidine [147081-44-5] according to the procedure reported for the synthesis of intermediate I7.

Intermediate I5

N-[(3R)-Pyrrolidin-3-yl]acetamide hydrochloride

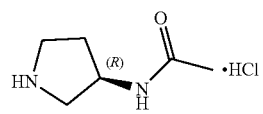

A mixture of intermediate I7 (1.64 g, 4.53 mmol, 63% purity) and chlorotrimethylsilane (2.30 mL, 18.1 mmol) in MeOH (20 mL) was stirred at rt for 24 h. The mixture was evaporated under reduced pressure to afford intermediate I5 (1.12 g).

Intermediate I6

N-[(3S)-Pyrrolidin-3-yl]acetamide hydrochloride

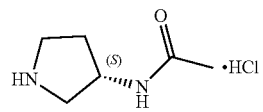

Intermediate I6 (1.34 g) was synthesized from intermediate I8 according to the procedure reported for the synthesis of intermediate I5.

Synthesis of Compounds 7 and 8

Compound 7

N-[(3R)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-yl]acetamide

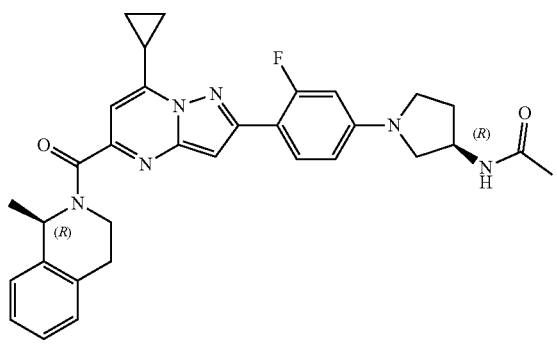

7

A sealed tube was charged with (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (250 mg, 0.48 mmol), intermediate I5 (180 mg, 0.72 mmol, 66% purity) and cesium carbonate (782 mg, 2.40 mmol) and purged with nitrogen. 1,4-Dioxane (10 mL) was added and the mixture was degassed with nitrogen. Palladium acetate (16.2 mg, 72.0 µmol) and XantPhos (41.6 mg, 72.0 µmol) were added. The reaction mixture was stirred at 100° C. for 7 h. The reaction mixture was poured out into water and the aqueous phase was extracted with EtOAc (twice). The combined organic extracts were dried over MgSO$_4$, filtered and evaporated to dryness. The crude mixture was purified by preparative LC (irregular SiOH, 15-40 µm, 40 g GraceResolv™, liquid injection (DCM), mobile phase gradient: DCM/MeOH/aq.NH$_3$ from 100:0:0 to 98:2:0.2). The residue (191 mg) was co-evaporated with EtOH (5 times) and triturated with EtOH/Et$_2$O (1:9). The solid was filtered off and dried under high vacuum at 50° C. for 2 h to give compound 7 (140 mg, 53%) as a yellow solid.

Compound 8

N-[(3S)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-yl]acetamide

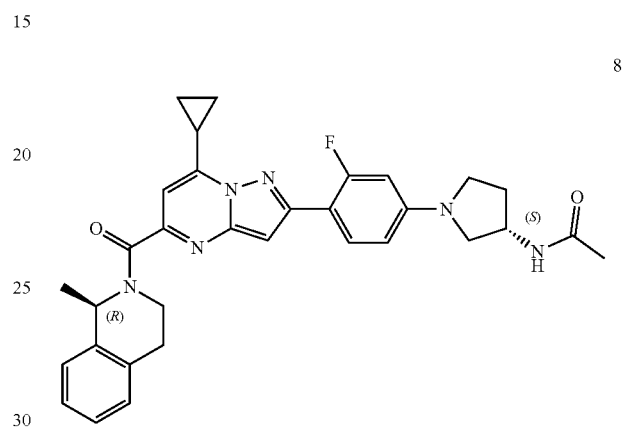

8

Compound 8 (107 mg, 40%) was synthesized from (1R)-2-[2-(4-bromo-2-fluorophenyl)-7-cyclopropylpyrazolo[1,5-a]pyrimidine-5-carbonyl]-1-methyl-1,2,3,4-tetrahydroisoquinoline [2035421-61-3] and intermediate I6 according to the procedure reported for the synthesis of compound 7.

Compound 9 and Compound 10

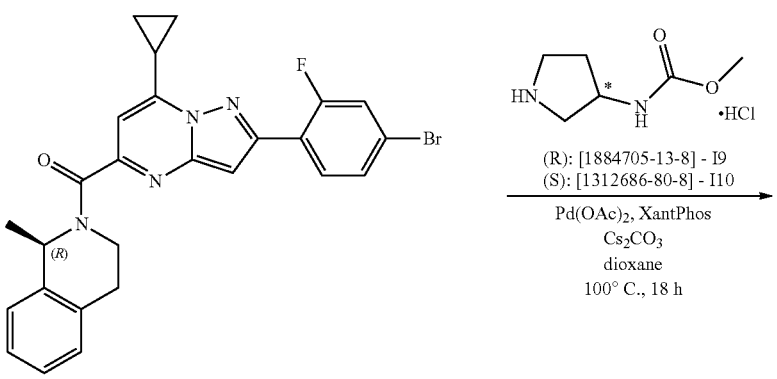

[2035421-61-3]

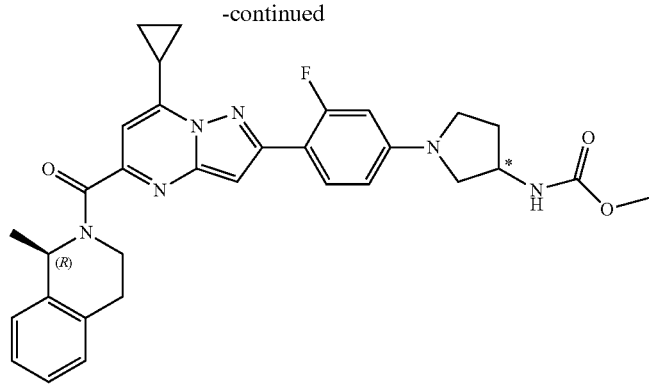

(R): 9
(S): 10

Synthesis of intermediates I9 and I10

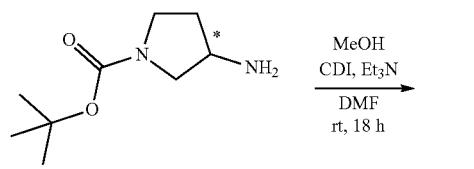

(R): [147081-49-0]
(S): [147081-44-5]

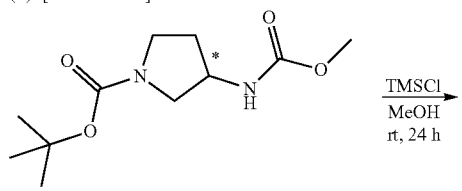

(R): [1884705-14-9] - I11
(S): [1334550-71-8] - I12

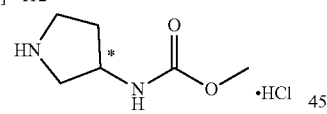

(R): [1884705-13-8] - I9
(S): [1312686-80-8] - I10

Intermediate I11

Tert-butyl (3R)-3-[(methoxycarbonyl)amino]pyrrolidine-1-carboxylate

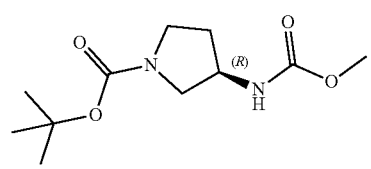

In a sealed tube, CDI (653 mg, 4.03 mmol) was added to a mixture of (R)-(+)-1-boc-3-aminopyrrolidine [147081-49-0] (500 mg, 2.69 mmol) and triethylamine (1.49 mL, 10.7 mmol) in DMF (10 mL). The reaction mixture was stirred at rt. MeOH (10 mL, 247 mmol) was added and the reaction mixture was stirred at rt for 18 h. H₂O, brine and EtOAc were added and the aqueous phase was extracted with EtOAc (twice). The combined organic extracts were dried over MgSO₄, filtered and concentrated under reduced pressure. The crude mixture was purified by preparative LC (irregular SiOH, 15-40 μm, 24 g GraceResolv™, liquid injection (DCM), mobile phase gradient: heptane/EtOAc from 90:10 to 70:30) to afford intermediate I11 (344 mg, 52%).

Intermediate I12

Tert-butyl (3S)-3-[(methoxycarbonyl)amino]pyrrolidine-1-carboxylate

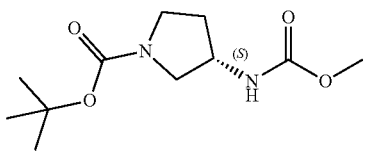

Intermediate I12 (444 mg, 68%) was synthesized from (S)-(−)-1-boc-3-aminopyrrolidine [147081-44-5] according to the procedure reported for the synthesis of intermediate I11.

Intermediate I9

Methyl N-[(3R)-pyrrolidin-3-yl]carbamate hydrochloride

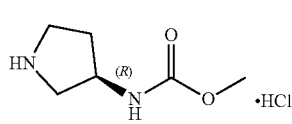

A mixture of intermediate I11 (344 mg, 1.41 mmol) and chlorotrimethylsilane (0.72 mL, 5.63 mmol) in MeOH (10 mL) was stirred at rt for 24 h. The mixture was evaporated under reduced pressure to afford intermediate I9 (225 mg, quant.).

Intermediate I10

Methyl N-[(3S)-pyrrolidin-3-yl]carbamate hydrochloride

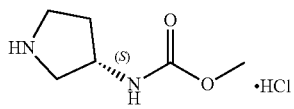

Intermediate I10 (310 mg, 92%) was synthesized from intermediate I12 according to the procedure reported for the synthesis of intermediate I9.

Synthesis of compounds 9 and 10

Compound 9

Methyl N-[(3R)-1-[4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-yl]carbamate

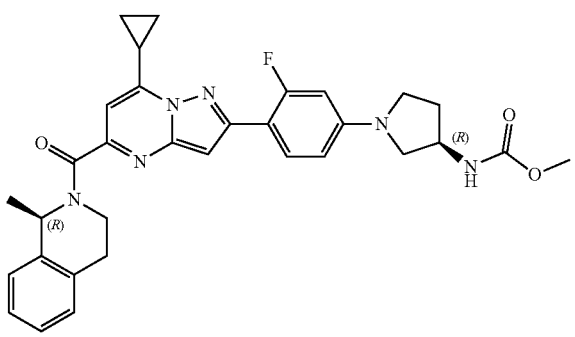

A sealed tube was charged with (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (250 mg, 0.48 mmol), intermediate I9 (130 mg, 0.72 mmol) and cesium carbonate (782 mg, 2.40 mmol) and purged with nitrogen. 1,4-Dioxane (10 mL) was added and the mixture was degassed with nitrogen. Palladium acetate (10.7 mg, 48.0 µmol) and XantPhos (27.8 mg, 48.0 µmol) were added. The reaction mixture was stirred at 100° C. for 18 h. The reaction mixture was poured out into water and the aqueous phase was extracted with EtOAc (twice). The combined organic extracts were dried over MgSO$_4$, filtered and evaporated to dryness. The crude mixture was purified by preparative LC (irregular SiOH, 15-40 µm, 40 g GraceResolv™, liquid injection (DCM), mobile phase gradient: DCM/MeOH/aq.NH$_3$ from 100:0:0 to 98:2:0.2). The residue (221 mg) was co-evaporated with EtOH (5 times) and triturated with Et$_2$O. The solid was filtered off and dried under high vacuum at 50° C. for 18 h to afford compound 9 (102 mg, 37%) as a yellow solid.

Compound 10

Methyl N-[(3S)-1-[4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-yl]carbamate

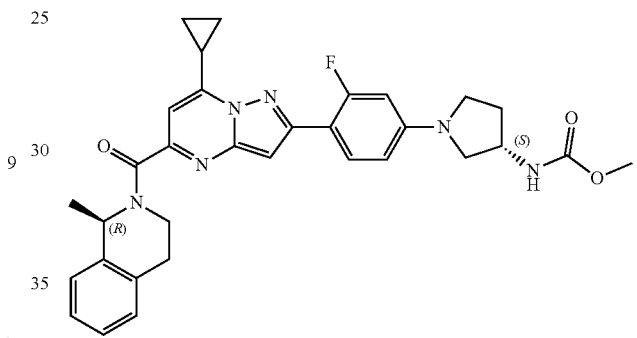

Compound 10 (145 mg, 53%) was synthesized from (1R)-2-[2-(4-bromo-2-fluorophenyl)-7-cyclopropylpyrazolo[1,5-a]pyrimidine-5-carbonyl]-1-methyl-1,2,3,4-tetrahydroisoquinoline [2035421-61-3] and intermediate I10 according to the procedure reported for the synthesis of compound 9.

Compound 11 and Compound 12

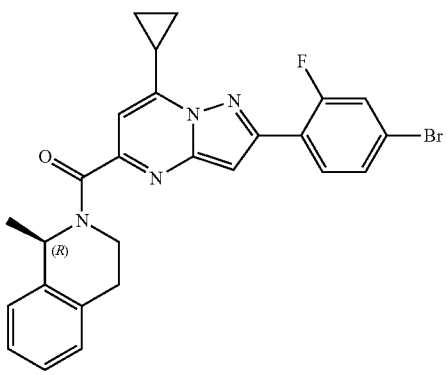

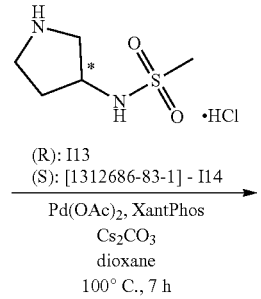

(R): I13
(S): [1312686-83-1] - I14

Pd(OAc)$_2$, XantPhos
Cs$_2$CO$_3$
dioxane
100° C., 7 h

[2035421-61-3]

-continued

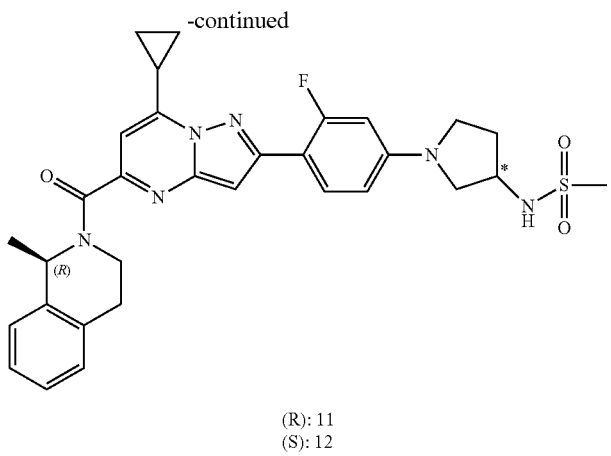

(R): 11
(S): 12

Synthesis of Intermediates I13 and I14

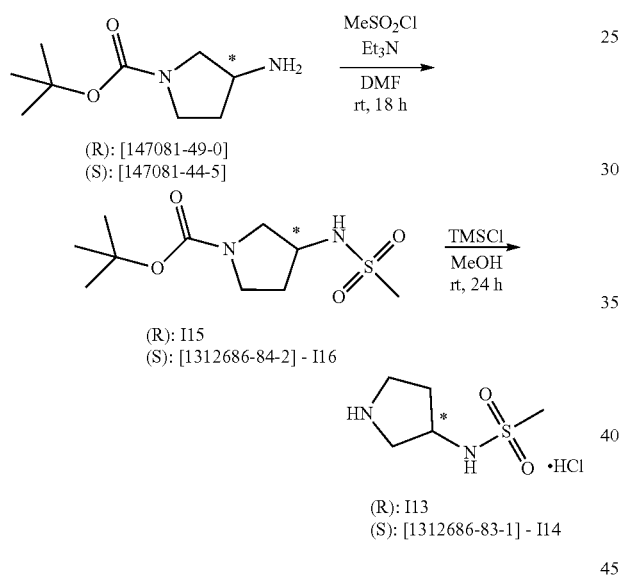

Intermediate I15

Tert-butyl (3R)-3-methanesulfonamidopyrrolidine-1-carboxylate

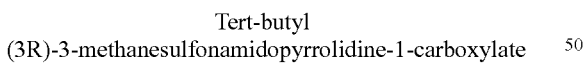

Methanesulfonyl chloride (0.50 mL, 6.44 mmol) was added dropwise to a solution of (R)-(+)-1-boc-3-aminopyrrolidine [147081-49-0] (1.00 g, 5.37 mmol) and triethylamine (1.50 mL, 10.7 mmol) in DCM (20 mL). The reaction mixture was stirred at rt for 18 h. The reaction mixture was diluted with DCM and H$_2$O. The layers were separated and the aqueous phase was extracted with DCM (twice). The combined organic extracts were dried over MgSO$_4$, filtered and evaporated under reduced pressure to afford intermediate I15 (2.00 g) as an oil.

Intermediate I16

Tert-butyl (3S)-3-methanesulfonamidopyrrolidine-1-carboxylate

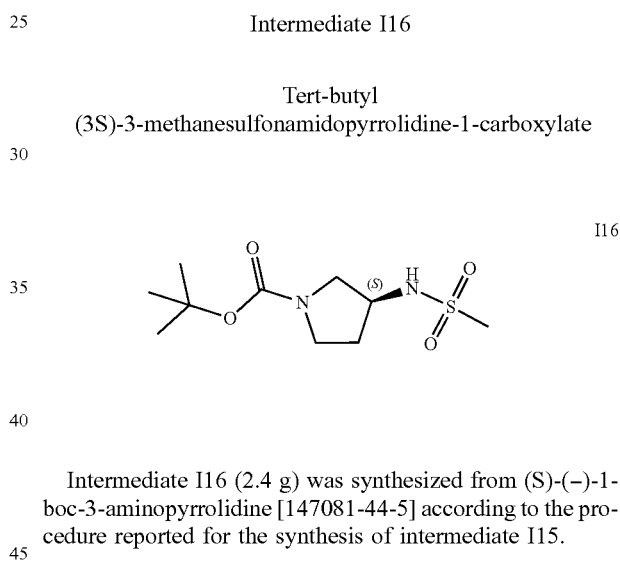

Intermediate I16 (2.4 g) was synthesized from (S)-(−)-1-boc-3-aminopyrrolidine [147081-44-5] according to the procedure reported for the synthesis of intermediate I15.

Intermediate I13

N-[(3R)-pyrrolidin-3-yl]methanesulfonamide hydrochloride

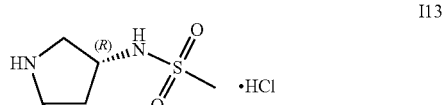

A mixture of intermediate I15 (2.00 g, 5.37 mmol, 71% purity) and chlorotrimethylsilane (2.73 mL, 21.5 mmol) in DCM (20 mL) was stirred at rt for 24 h. The mixture was evaporated under reduced pressure to give intermediate I13 (1.20 g).

Intermediate I14

N-[(3S)-pyrrolidin-3-yl]methanesulfonamide hydrochloride

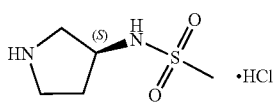

Intermediate I14 (1.68 g) was synthesized from intermediate I16 according to the procedure reported for the synthesis of intermediate I13.

Synthesis of Compounds 11 and 12

Compound 11

N-[(3R)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-yl]methane-sulfonamide

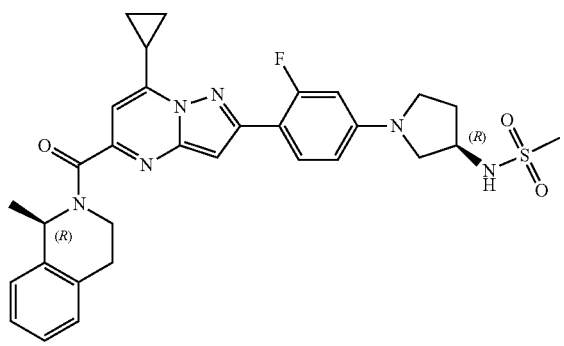

A sealed tube was charged with (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (250 mg, 0.48 mmol), intermediate I13 (181 mg, 0.72 mmol, 80% purity) and cesium carbonate (782 mg, 2.40 mmol) and purged with nitrogen. 1,4-Dioxane (10 mL) was added and the mixture was degassed with nitrogen. Palladium acetate (16.2 mg, 72.0 µmol) and XantPhos (41.6 mg, 72.0 µmol) were added. The reaction mixture was stirred at 100° C. for 7 h. The reaction mixture was poured out into water and the aqueous phase was extracted with EtOAc (twice). The combined organic extracts were dried over MgSO$_4$, filtered and concentrated to dryness. The crude mixture was purified by preparative LC (irregular SiOH, 15-40 µm, 40 g GraceResolv™, liquid injection (DCM), mobile phase gradient: DCM/MeOH/aq.NH$_3$ from 100:0:0 to 98:2:0.2). The residue (256 mg) was co-evaporated with EtOH (5 times) and triturated with EtOH/Et$_2$O (1:9). The solid was filtered off and dried under high vacuum at 50° C. for 2 h to afford compound 11 (148 mg, 52%) as a yellow solid.

Compound 12

N-[(3S)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-yl]methane-sulfonamide

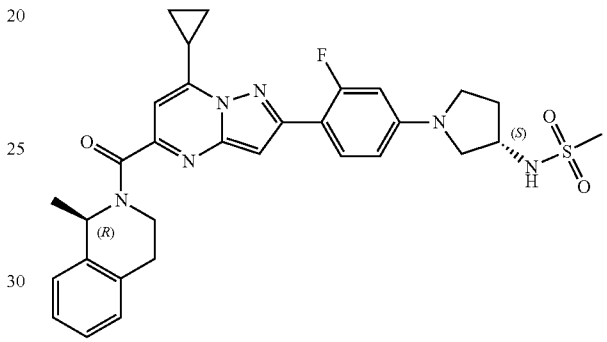

A sealed tube was charged with (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (250 mg, 0.48 mmol), intermediate I14 (226 mg, 0.72 mmol, 64% purity) and cesium carbonate (782 mg, 2.40 mmol) and purged with nitrogen. 1,4-Dioxane (10 mL) was added and the mixture was degassed with nitrogen. Palladium acetate (10.8 mg, 48.0 µmol) and XantPhos (27.8 mg, 48.0 µmol) were added. The reaction mixture was stirred at 100° C. for 7 h. The reaction mixture was poured out into water and the aqueous phase was extracted with EtOAc (twice). The combined organic extracts were dried over MgSO$_4$, filtered and concentrated to dryness. The crude mixture was purified by preparative LC (irregular SiOH, 15-40 µm, 40 g GraceResolv™, liquid injection (DCM), mobile phase gradient: DCM/MeOH/aq.NH$_3$ from 100:0:0 to 98:2:0.2). The residue (158 mg) was co-evaporated with EtOH (5 times) and triturated with EtOH/Et$_2$O (1:9). The solid was filtered off and dried under high vacuum at 50° C. for 2 h. The purification sequence was repeated: purification by preparative LC (irregular SiOH, 15-40 µm, 40 g GraceResolv™, liquid injection (DCM), mobile phase gradient: DCM/MeOH/aq.NH$_3$ from 100:0:0 to 98:2:0.2). The residue was co-evaporated with EtOH (3 times) and triturated with Et$_2$O. The solid was filtered off and dried under high vacuum at 50° C. to afford compound 12 (99 mg, 35%) as a yellow solid.

Compound 13

(3R)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-ol

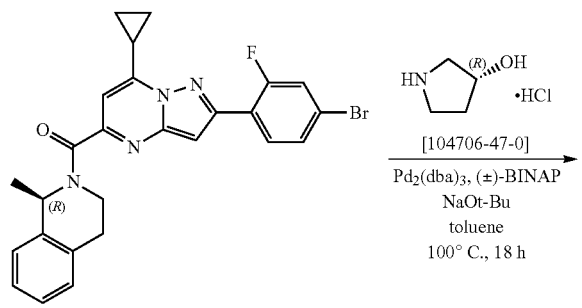

[2035421-61-3]

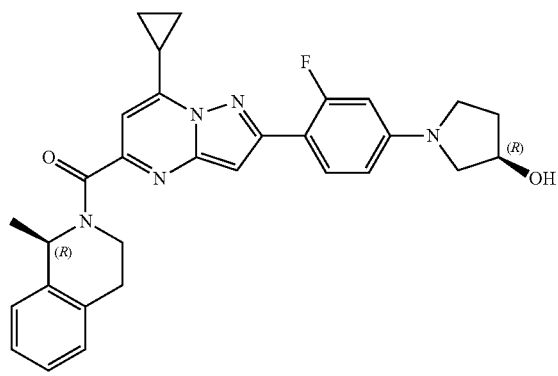

13

A sealed tube was charged with (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (250 mg, 0.48 mmol), (R)-3-pyrrolidinol hydrochloride [104706-47-0] (77.6 µL, 0.96 mmol) and sodium tert-butoxide (138 mg, 1.44 mmol) and purged with nitrogen. Toluene (10 mL) was added and the mixture was degassed with nitrogen. Tris(dibenzylideneacetone)dipalladium (43.9 mg, 48.0 µmol) and (±)-BINAP (59.7 mg, 96.0 µmol) were added. The reaction mixture was stirred at 100° C. for 18 h. The reaction mixture was poured out into water and the aqueous phase was extracted with DCM. The combined organic extracts were washed with brine, dried over MgSO$_4$, filtered and concentrated to dryness. The crude mixture was purified by preparative LC (regular SiOH, 30 µm, 25 g Interchim®, liquid injection (DCM), mobile phase gradient: heptane/EtOAc from 80:20 to 0:100). The residue (65 mg) was taken up in MeCN and DIPE and partially evaporated. The solid was filtered off and dried under high vacuum at 50° C. for 16 h and then at 60° C. for 24 h to afford compound 13 (45 mg, 18%).

Compound 14

(3S)-1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)pyrrolidin-3-ol

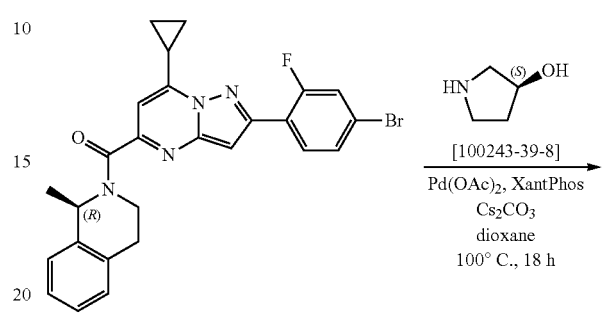

[2035421-61-3]

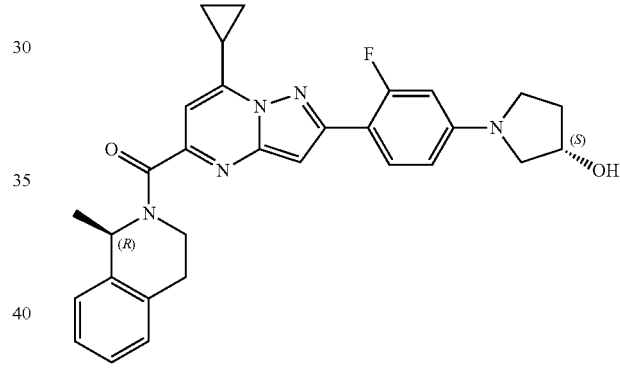

14

A sealed tube was charged with (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (200 mg, 0.38 mmol), (S)-3-pyrrolidinol [100243-39-8] (167 mg, 1.92 mmol) and cesium carbonate (625 mg, 1.92 mmol) and purged with nitrogen. 1,4-Dioxane (8 mL) was added and the mixture was degassed with nitrogen. Palladium acetate (8.61 mg, 38.4 µmol) and Xant-Phos (22.2 mg, 38.4 µmol) were added. The reaction mixture was stirred at 100° C. for 18 h. The reaction mixture was diluted with H$_2$O and the aqueous phase was extracted with EtOAc (twice). The combined organic extracts were washed with brine, dried over MgSO$_4$, filtered and the solvent was removed under reduced pressure. The crude mixture was purified by preparative LC (regular SiOH, 30 µm, 25 g Interchim®, liquid injection (DCM), mobile phase gradient: heptane/EtOAc from 80:20 to 0:100). The residue was taken up in MeCN and Et$_2$O and evaporated to dryness. The solid was triturated with Et$_2$O, filtered off and dried under high vacuum at 60° C. for 18 h to afford compound 14 (64 mg, 33%) as a yellow solid.

47
Compound 77

(3R)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-yl carbamate

48
Compound 78

(3S)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-yl carbamate

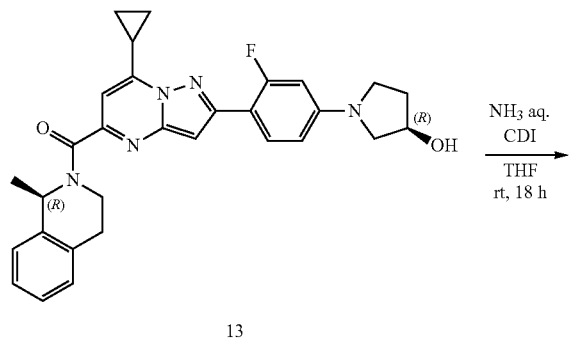

13

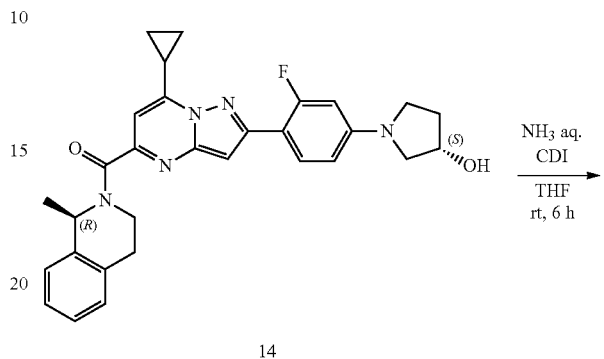

14

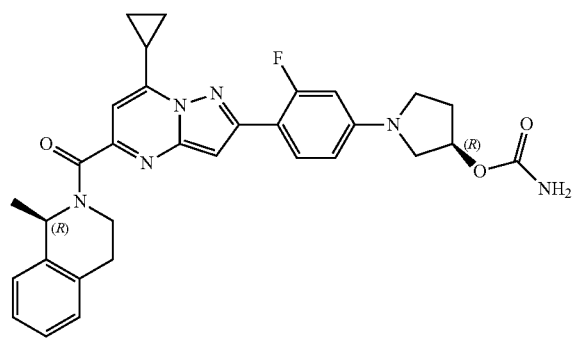

77

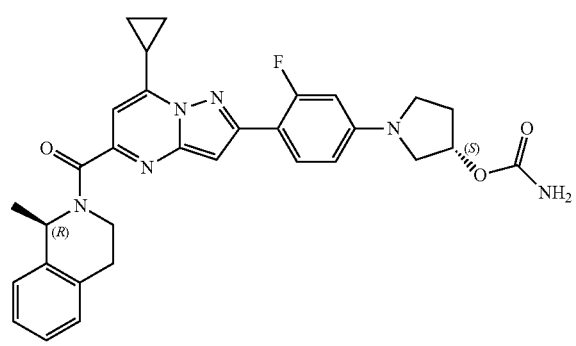

78

CDI (2.15 g, 13.3 mmol) was added to a solution of compound 13 (3.39 g, 6.63 mmol) in THF (25 mL). The reaction mixture was stirred at rt for 1 h. Ammonia (28% in H$_2$O, 24.8 mL, 367 mmol) was added and the reaction mixture was stirred at rt for 18 h. The reaction mixture was diluted with H$_2$O, brine and EtOAc. The layers were separated and the aqueous phase was extracted with EtOAc (twice). The combined organic extracts were dried over MgSO$_4$, filtered and concentrated in vacuo. The crude mixture was purified by preparative LC (irregular SiOH, 15-40 μm, 330 g GraceResolv™, liquid injection (DCM), mobile phase gradient: DCM/EtOAc from 100:0 to 80:20). The residue (2.8 g) was triturated with MeCN. The solid was filtered off and dried under high vacuum at 50° C. for 2 h. The solid (1.87 g) was triturated again with MeCN, filtered off and dried under high vacuum at 50° C. overnight. The product (1.32 g) was suspended in MeOH (20 mL) and the solution was stirred at rt for 18 h. The solid was filtered off and dried under high vacuum at 50° C. to give compound 77 (951 mg, 26%) as a pale yellow solid.

CDI (1.97 g, 12.1 mmol) was added to a solution of compound 14 (3.11 g, 6.07 mmol) in THF (23 mL). The reaction mixture was stirred at rt for 1 h. Ammonia (28% in H$_2$O, 22.7 mL, 336 mmol) was added and the reaction mixture was stirred at rt for 6 h. The reaction mixture was diluted with H$_2$O, brine and EtOAc. The layers were separated and the aqueous phase was extracted with EtOAc (twice). The combined organic extracts were dried over MgSO$_4$, filtered and concentrated in vacuo. The crude mixture was purified by preparative LC (irregular SiOH, 15-40 μm, 330 g GraceResolv™, liquid injection (DCM), mobile phase gradient: DCM/EtOAc from 100:0 to 80:20). The residue (2.4 g) was triturated with MeCN. The solid was filtered off and dried under high vacuum at 50° C. The solid was triturated again with MeCN, filtered off and dried under high vacuum at 50° C. overnight. The product (1.03 g) was suspended in MeOH (25 mL) and stirred at rt for 18 h. The solid was filtered off and dried under high vacuum at 50° C. to give compound 78 (825 mg, 25%) as a yellow solid.

Compound 15 and Compound 16

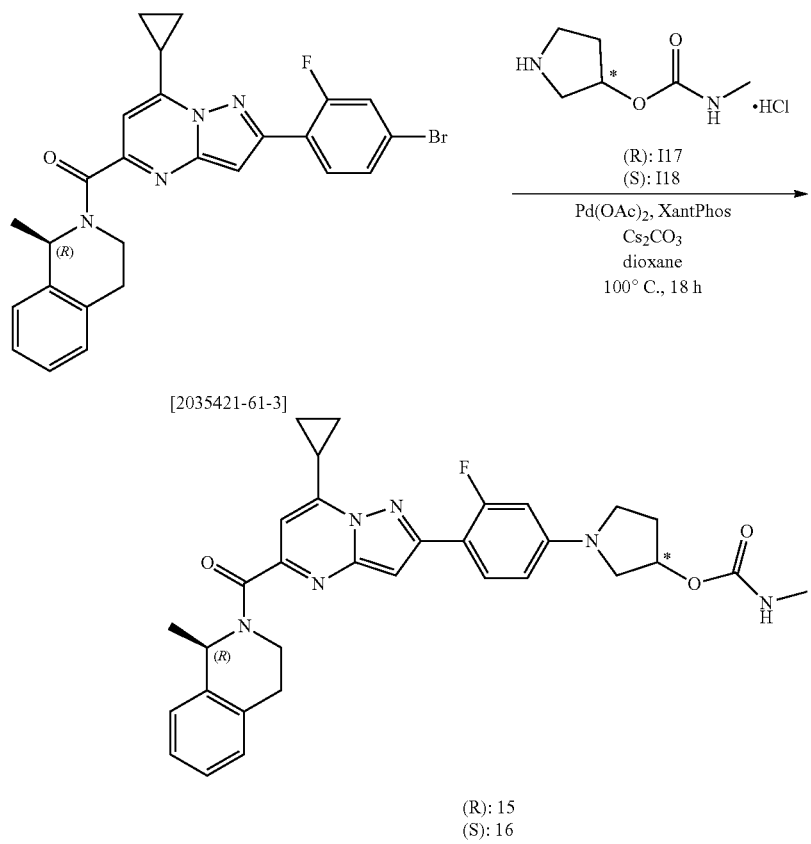

(R): 15
(S): 16

Synthesis of Intermediates I17 and I18

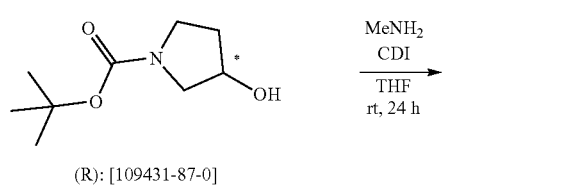

(R): [109431-87-0]
(S): [101469-92-5]

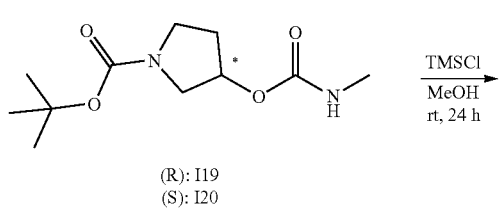

(R): I19
(S): I20

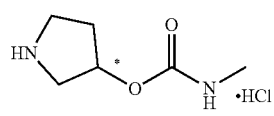

(R): I17
(S): I18

Intermediate I19

Tert-butyl (3R)-3-[(methylcarbamoyl)oxy]pyrrolidine-1-carboxylate

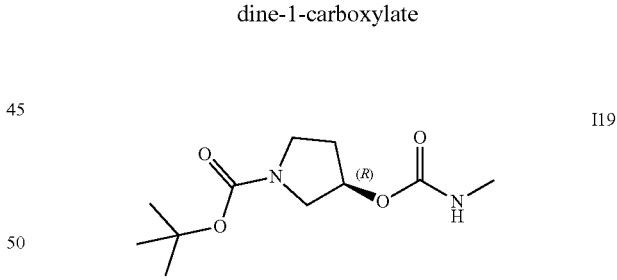

In a sealed tube CDI (871 mg, 5.37 mmol) was added to a solution of (R)-(−)-N-boc-3-pyrrolidinol [109431-87-0] (503 mg, 2.69 mmol) in THF (10 mL). The reaction mixture was stirred at rt for 1 h. Methylamine (40% in H₂O, 10 mL, 116 mmol) was added and the reaction mixture was stirred at rt for 2 h. H₂O, brine and EtOAc were added. The layers were separated and the aqueous phase was extracted with EtOAc (twice). The combined organic extracts were dried over MgSO₄, filtered and concentrated under reduced pressure. The crude mixture was purified by preparative LC (irregular SiOH, 15-40 μm, 24 g GraceResolv™, liquid injection (DCM), mobile phase gradient: heptane/EtOAc from 90:10 to 70:30) to give intermediate I19 (700 mg, quant., 94% purity).

Intermediate I20

Tert-butyl (3S)-3-[(methylcarbamoyl)oxy]pyrrolidine-1-carboxylate

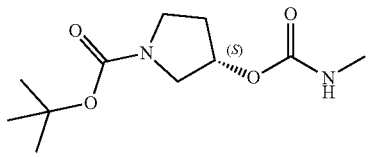

Intermediate I20 (610 mg, 93%) was synthesized from (S)-(+)—N-boc-3-pyrrolidinol [101469-92-5] according to the procedure reported for the synthesis of intermediate I19.

Intermediate I17

(3R)-Pyrrolidin-3-yl N-methylcarbamate hydrochloride

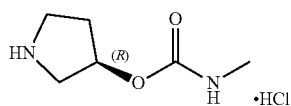

A mixture of intermediate I19 (700 mg, 2.67 mmol, 93% purity) and chlorotrimethylsilane (1.35 mL, 10.7 mmol) in MeOH (10 mL) was stirred at rt for 24 h. The mixture was evaporated under reduced pressure to afford intermediate I17 (525 mg).

Intermediate I18

(3S)-Pyrrolidin-3-yl N-methylcarbamate hydrochloride

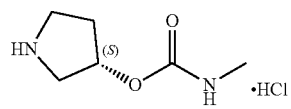

Intermediate I18 (475 mg) was synthesized from intermediate I20 according to the procedure reported for the synthesis of intermediate I17.

Synthesis of Compounds 15 and 16

Compound 15

(3R)-1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)pyrrolidin-3-yl N-methylcarbamate

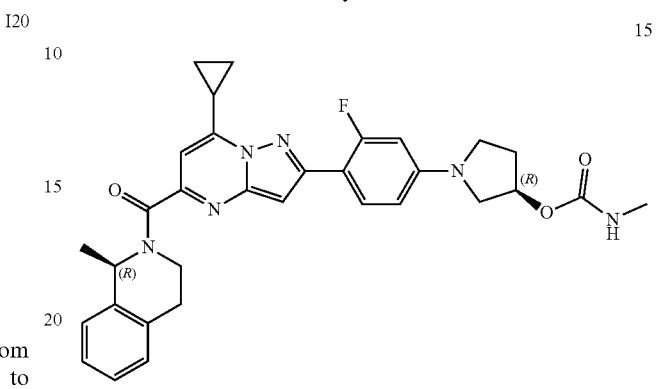

A sealed tube was charged with (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (250 mg, 0.48 mmol), intermediate I17 (143 mg, 0.72 mmol, 91% purity) and cesium carbonate (782 mg, 2.40 mmol) and purged with nitrogen. 1,4-Dioxane (10 mL) was added and the mixture was degassed with nitrogen. Palladium acetate (10.8 mg, 48.0 µmol) and XantPhos (27.8 mg, 48.0 µmol) were added. The reaction mixture was stirred at 100° C. for 18 h. The reaction mixture was poured out into water and the aqueous phase was extracted with EtOAc (twice). The combined organic extracts were dried over MgSO$_4$, filtered and concentrated to dryness. The crude mixture was purified by preparative LC (irregular SiOH, 15-40 µm, 40 g GraceResolv™, liquid injection (DCM), mobile phase gradient: DCM/MeOH/aq.NH$_3$ from 100:0:0 to 98:2:0.2). A second purification was performed by reverse phase (spherical C18, 25 µm, 40 g YMC-ODS-25, dry loading (Celite®), mobile phase gradient: (0.2% aq.NH$_4$HCO$_3$)/MeCN from 40:60 to 0:100). The residue was co-evaporated with EtOH (3 times) and triturated with EtOH. The solid was filtered off and dried under high vacuum at 50° C. for 18 h to afford compound 15 (75 mg, 27%) as a yellow solid.

Compound 16

(3S)-1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)pyrrolidin-3-yl N-methylcarbamate

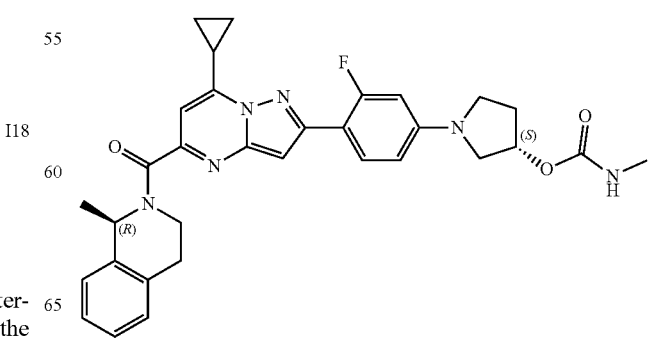

Compound 16 was synthesized from (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] and intermediate I18 according to the procedure reported for the synthesis of compound 15. The crude mixture was purified by preparative LC (irregular SiOH, 15-40 μm, 40 g GraceResolv™, liquid injection (DCM), mobile phase gradient: DCM/MeOH/aq.NH₃ from 100:0:0 to 98:2:0.2). A second purification was performed by reverse phase (spherical C18, 25 μm, 40 g YMC-ODS-25, dry loading (Celite®), mobile phase gradient: (0.2% aq.NH₄HCO₃)/MeCN from 40:60 to 0:100). The residue was co-evaporated with EtOH (5 times) and triturated with EtOH/Et₂O (1:9). The solid was filtered off and dried under high vacuum at 50° C. for 2 h to give compound 16 (54 mg, 20%) as a white solid.

Compound 17 and Compound 18

Compound 17

(1R)-2-(7-Cyclopropyl-2-{2-fluoro-4-[(3R)-3-methanesulfonylpyrrolidin-1-yl]phenyl}-pyrazolo[1,5-a]pyrimidine-5-carbonyl)-1-methyl-1,2,3,4-tetrahydroisoquinoline

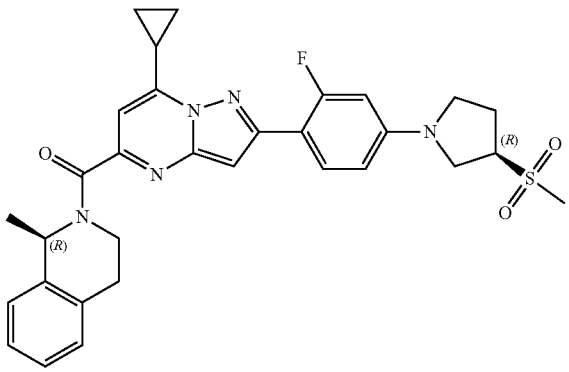

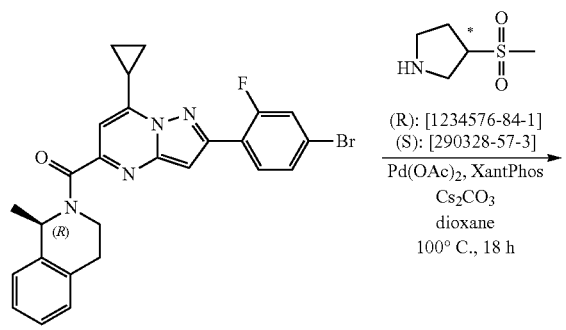

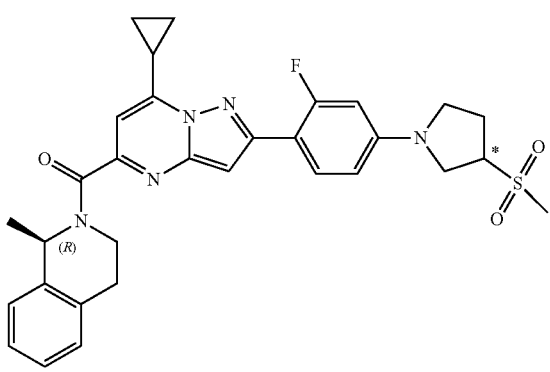

(R): 17
(S): 18

A sealed tube was charged with (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (150 mg, 288 μmol), (R)-3-(methylsulfonyl)pyrrolidine [1234576-84-1] (53.4 mg, 288 μmol), cesium carbonate (276 mg, 846 μmol) and XantPhos (19.7 mg, 34.0 μmol) and purged with nitrogen. 1,4-Dioxane (6 mL) was added and the mixture was purged with nitrogen. Palladium acetate (7.88 mg, 35.1 μmol) was added. The reaction mixture was purged with nitrogen and stirred at 100° C. for 18 h. The reaction mixture was diluted with EtOAc and brine. The layers were separated and the aqueous phase was extracted. The combined organic extracts were washed with H₂O, dried over MgSO₄, filtered and evaporated under reduced pressure. The crude mixture was purified by preparative LC (irregular SiOH, 15-40 μm, 40 g GraceResolv™, liquid injection (DCM), mobile phase gradient: heptane/EtOAc from 50:50 to 0:100). A second purification was performed by preparative LC (spherical C18 25 μm, 40 g YMC-ODS-25, loading (MeCN, H₂O), mobile phase gradient: (0.2% aq. NH₄HCO₃)/MeCN from 50:50 to 0:100). The fractions containing the product were combined and a 10% aqueous solution of KHSO₄ was added. The layers were separated and the aqueous phase was extracted with EtOAc. The combined organic extracts were washed with H₂O, dried over MgSO₄, filtered and evaporated under reduced pressure. The residue (105 mg) was purified by preparative LC (irregular SiOH, 15-40 μm, 40 g GraceResolv™, liquid injection (DCM), mobile phase gradient: heptane/EtOAc from 50:50 to 0:100). The residue was triturated and co-evaporated with Et₂O (twice) and dried under high vacuum at 50° C. for 18 h to give compound 17 (54 mg, 32%) as a yellow solid.

Compound 18

(1R)-2-(7-Cyclopropyl-2-{2-fluoro-4-[(3S)-3-methanesulfonylpyrrolidin-1-yl]phenyl}-pyrazolo[1,5-a]pyrimidine-5-carbonyl)-1-methyl-1,2,3,4-tetrahydroisoquinoline

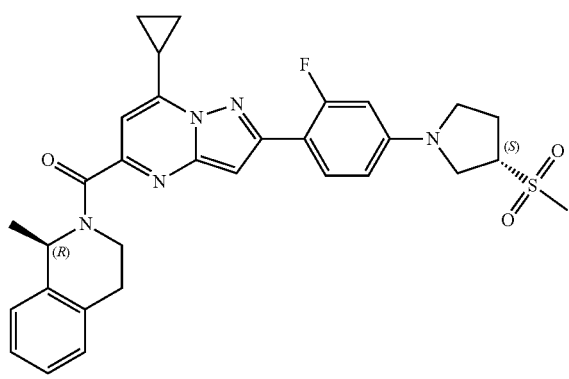

18

Compound 18 was synthesized from (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] and (S)-3-(methylsulfonyl)pyrrolidine [290328-57-3] according to the procedure reported for the synthesis of compound 17. The crude mixture was purified by preparative LC (irregular SiOH, 15-40 µm, 40 g GraceResolv™, liquid injection (DCM), mobile phase gradient: heptane/EtOAc from 50:50 to 0:100). A second purification was performed by preparative LC (spherical C18 25 µm, 40 g YMC-ODS-25, loading (MeCN, H₂O), mobile phase gradient (0.2% aq.NH₄HCO₃)/MeCN from 50:50 to 0:100). The fractions containing the product were combined and a 10% aqueous solution of KHSO₄ was added. The layers were separated and the aqueous phase was extracted with EtOAc. The organic phase was washed with H₂O, dried over MgSO₄, filtered and evaporated under reduced pressure. The residue was triturated and co-evaporated with Et₂O (twice) and dried under high vacuum at 50° C. for 18 h to give compound 18 (67 mg, 40%) as a pale red solid.

Compound 19

1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)pyrrolidine-3-sulfonamide

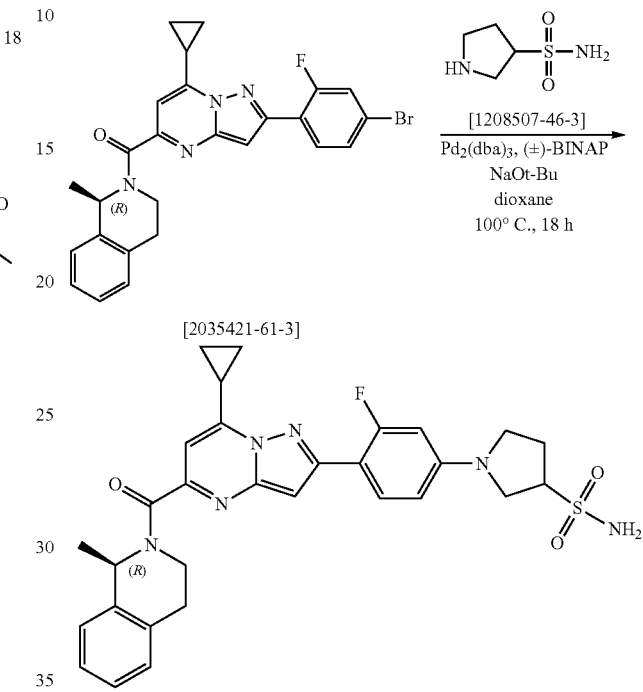

19

A sealed tube was charged with (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (400 mg, 768 µmol), pyrrolidine-3-sulfonamide [1208507-46-3] (115 mg, 768 µmol), sodium tert-butoxide (105 mg, 1.09 mmol) and (±)-BINAP (100 mg, 161 µmol) and purged with nitrogen. 1,4-Dioxane (10 mL) was added and the mixture was purged again with nitrogen. Tris(dibenzylideneacetone)dipalladium (140 mg, 153 µmol) was added. The reaction mixture was purged with nitrogen and stirred at 100° C. for 18 h. A 10% aqueous solution of KHSO₄ was added until pH 6. The aqueous phase was extracted with EtOAc. The combined organic extracts were washed with H₂O, dried over MgSO₄, filtered and evaporated under reduced pressure. The crude mixture was purified by preparative LC (irregular SiOH, 15-40 µm, 80 g GraceResolv™, liquid injection (DCM), mobile phase gradient: DCM/MeOH from 100:0 to 95:5). A second purification was performed by preparative LC (spherical C18 25 µm, 40 g YMC-ODS-25, loading (MeCN, H₂O), mobile phase gradient: (0.2% aq.NH₄HCO₃)/MeCN from 50:50 to 0:100). The product was freeze-dried to give compound 19 (48 mg, 11%) as a yellow solid.

Compound 20

N-{[1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)pyrrolidin-3-yl]sulfonyl}acetamide

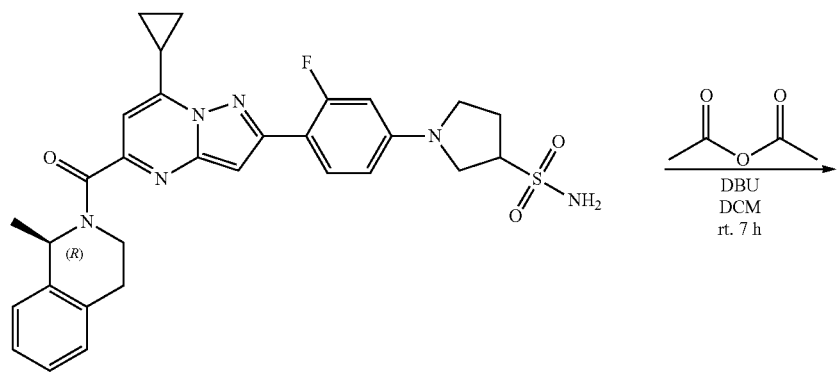

19

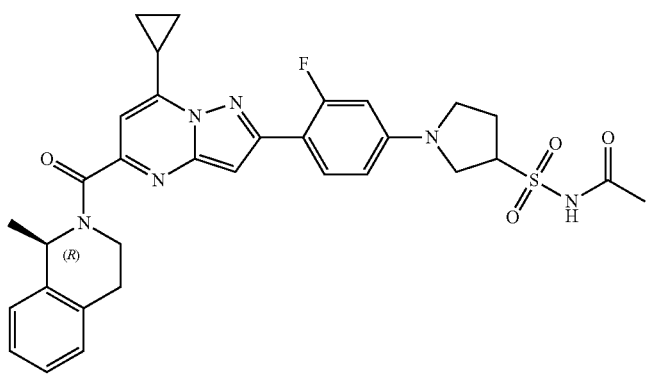

20

A mixture of compound 19 (215 mg, 0.37 mmol), acetic anhydride (53.0 μL, 0.56 mmol) and DBU (83.8 μL, 0.56 mmol) in DCM (2 mL) was stirred at rt for 7 h. The reaction mixture was diluted with EtOAc and brine. The layers were separated and the aqueous phase was extracted. The combined organic extracts were washed with $H_2O$, dried over $MgSO_4$, filtered and evaporated under reduced pressure. The crude mixture was purified by preparative LC (spherical C18 25 μm, 40 g YMC-ODS-25, loading (MeCN, $H_2O$), mobile phase gradient: (0.2% aq. $NH_4HCO_3$)/MeCN from 15:85 to 65:35). The product was freeze-dried to give compound 20 (40 mg, 17%) as a yellow solid.

Compound 21

1-(4-{7-Cyclopropyl-5-[(1R)-1-methyl-1,2,3,4-tetra-hydroisoquinoline-2-carbonyl]-pyrazolo[1,5-a]pyrimidin-2-yl}-3-fluorophenyl)-N-methylpyrrolidine-3-sulfonamide

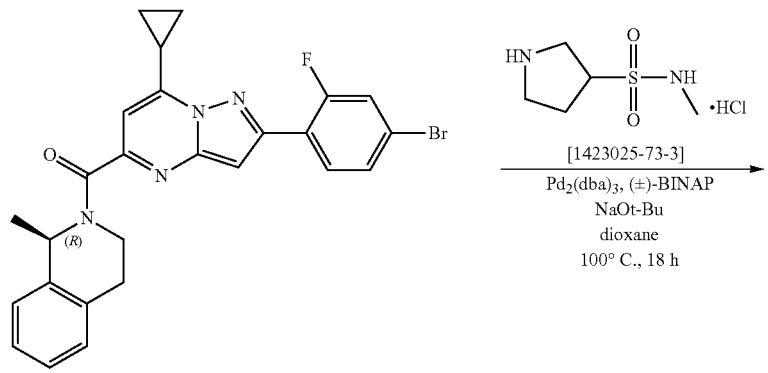

[2035421-61-3]

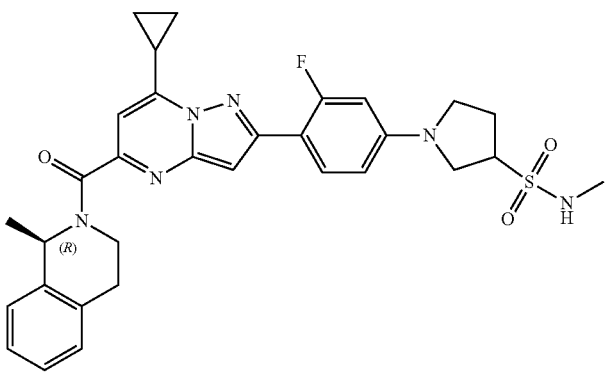

21

A sealed tube was charged with (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (200 mg, 384 μmol), N-methylpyrrolidine-3-sulfonamide hydrochloride [1423025-73-3] (77.0 mg, 384 μmol), sodium tert-butoxide (50.0 mg, 0.52 mmol) and (±)-BINAP (47.8 mg, 76.8 μmol) and purged with nitrogen. 1,4-Dioxane (9 mL) was added and the mixture was purged again with nitrogen. Tris(dibenzylideneacetone)dipalladium (70.3 mg, 76.8 μmol) was added. The reaction mixture was purged with nitrogen and stirred at 100° C. for 18 h. The reaction mixture was diluted with EtOAc and brine. The layers were separated and the aqueous phase was extracted. The combined organic extracts were washed with H₂O, dried over MgSO₄, filtered and evaporated under reduced pressure. The crude mixture was purified by preparative LC (irregular SiOH, 15-40 μm, 40 g GraceResolv™, liquid injection (DCM), mobile phase gradient: heptane/EtOAc from 50:50 to 0:100). A second purification was performed by preparative LC (spherical C18 25 μm, 40 g YMC-ODS-25, loading (MeCN, H₂O), mobile phase gradient (0.2% aq.NH₄HCO₃)/MeCN from 50:50 to 0:100). The fractions containing the product were combined and a 10% aqueous solution of KHSO₄ was added. The layers were separated and the aqueous phase was extracted with EtOAc. The organic phase was washed with H₂O, dried over MgSO₄, filtered and evaporated under reduced pressure. The residue was triturated and co-evaporated with Et₂O (twice) and dried under high vacuum at 50° C. for 18 h to give compound 21 (109 mg, 48%) as a pale red solid.

Compound 22

1-(4-{7-Cyclopropyl-5-[(1R)-1-methyl-1,2,3,4-tetra-hydroisoquinoline-2-carbonyl]-pyrazolo[1,5-a]pyrimidin-2-yl}-3-fluorophenyl)-N,N-dimethylpyrrolidine-3-sulfonamide

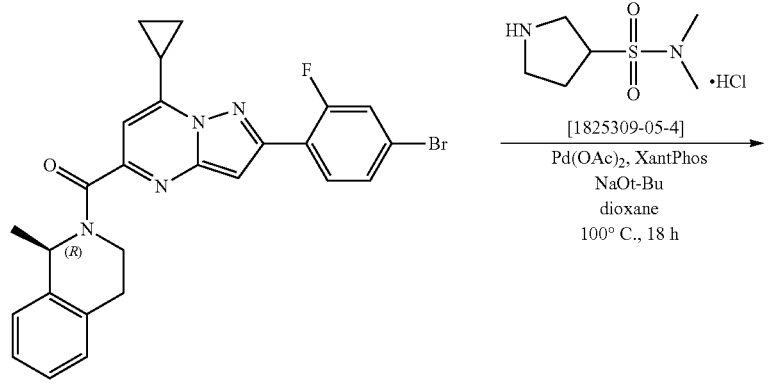

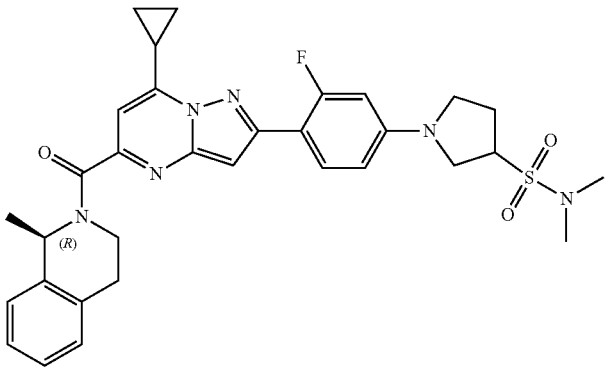

In a sealed tube a mixture of (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (250 mg, 480 µmol), N,N-dimethyl-3-pyrrolidinesulfonamide hydrochloride [1825309-05-4] (155 mg, 720 µmol) and sodium tert-butoxide (231 mg, 2.40 mmol) in 1,4-dioxane (10 mL) was degassed with nitrogen. Palladium acetate (11.0 mg, 72.0 µmol) and XantPhos (27.8 mg, 48.0 µmol) were added. The reaction mixture was stirred at 100° C. for 18 h. The reaction mixture was poured out into water and the aqueous phase was extracted with EtOAc (twice). The combined organic extracts were dried over MgSO4, filtered and concentrated to dryness. The crude mixture was purified by preparative LC (irregular SiOH, 15-40 µm, 40 g GraceResolv™, liquid injection (DCM), mobile phase gradient: DCM/MeOH from 100:0 to 96:4). The residue was co-evaporated (5 times) and triturated with EtOH. The solid was filtered off and dried under high vacuum at 50° C. for 18 h to give compound 22 (150 mg, 52%) as a yellow solid.

Compound 79
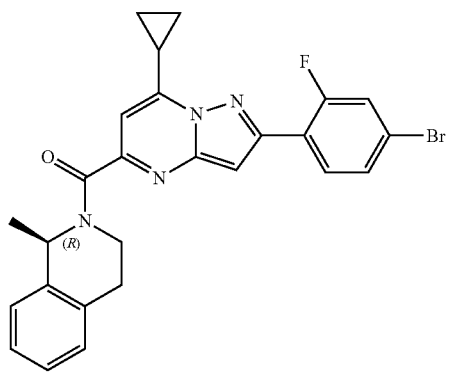
[2035421-61-3]
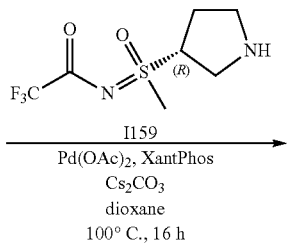
I159
Pd(OAc)₂, XantPhos
Cs₂CO₃
dioxane
100° C., 16 h
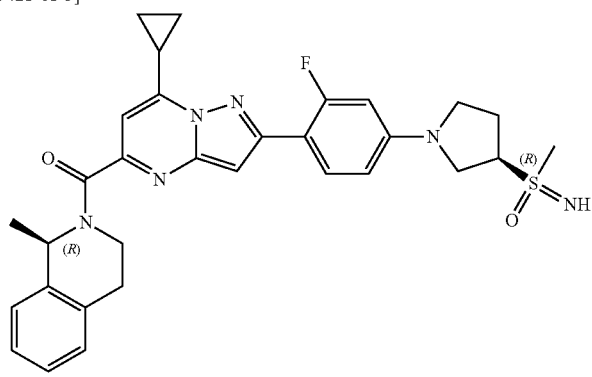
79
Synthesis of Intermediate I159
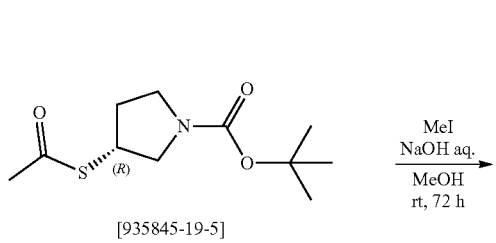
[935845-19-5]
MeI
NaOH aq.
MeOH
rt, 72 h
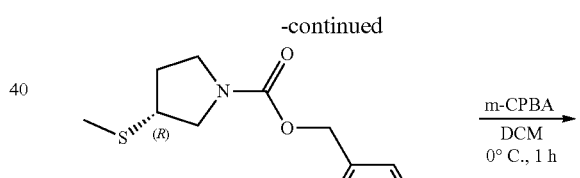
I162
m-CPBA
DCM
0° C., 1 h
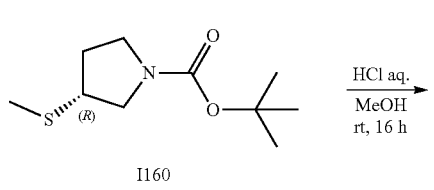
I160
HCl aq.
MeOH
rt, 16 h
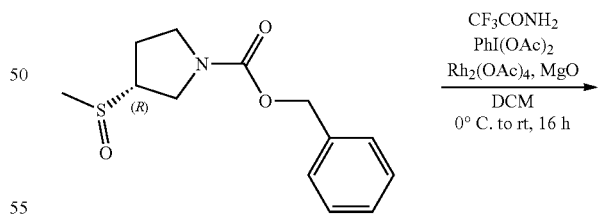
I163
CF₃CONH₂
PhI(OAc)₂
Rh₂(OAc)₄, MgO
DCM
0° C. to rt, 16 h
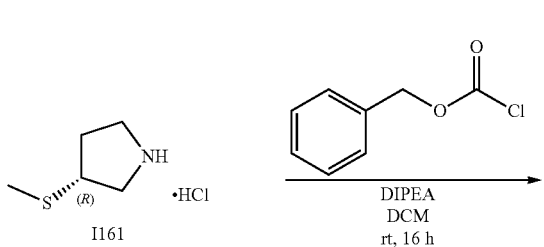
I161
DIPEA
DCM
rt, 16 h
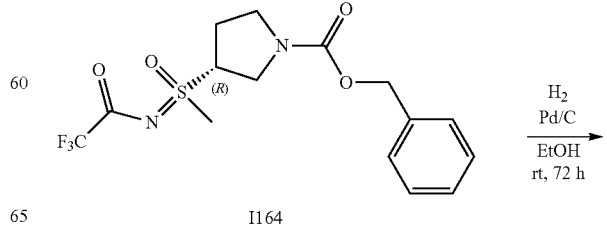
I164
H₂
Pd/C
EtOH
rt, 72 h

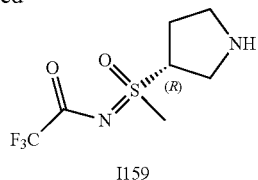

Intermediate I160

Tert-butyl
(3R)-3-(methylsulfanyl)pyrrolidine-1-carboxylate

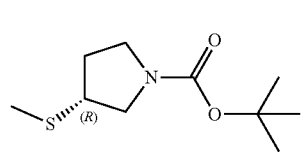

Methyl iodide (3.9 mL, 62.8 mmol) was added to a mixture of (R)-tert-butyl 3-(acethylthio)pyrrolidine-1-carboxylate [935845-19-5] (7.00 g, 28.5 mmol) and sodium hydroxide (1.0 M in H₂O, 31 mL, 31.0 mmol) in MeOH (140 mL). The reaction mixture was stirred at rt for 72 h. The reaction mixture was diluted with H₂O and EtOAc. The layers were separated and the aqueous phase was extracted with EtOAc. The combined organic extracts were washed with brine, dried over MgSO₄, filtered and the solvent was evaporated in vacuo to afford intermediate I160 (5.2 g, 84%).

Intermediate I161

(3R)-3-(Methylsulfanyl)pyrrolidine hydrochloride

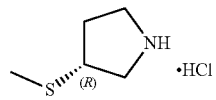

A mixture of intermediate I160 (5.20 g, 23.9 mmol) and hydrogen chloride (3.0 M in H₂O, 80 mL, 239 mmol) in MeOH (185 mL) was stirred at rt for 16 h. The mixture was evaporated to dryness and co-evaporated with MeOH to afford intermediate I161 (3.7 g, quant.).

Intermediate I162

Benzyl
(3R)-3-(methylsulfanyl)pyrrolidine-1-carboxylate

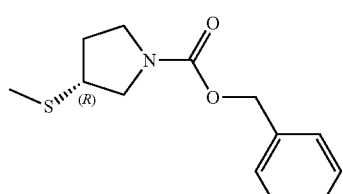

Benzyl chloroformate (3.8 mL, 26.5 mmol) was added to a mixture of intermediate I161 (3.70 g, 24.1 mmol) and DIPEA (10.3 mL, 60.2 mmol) in DCM (122 mL) at 0° C. The reaction mixture was stirred at rt for 16 h. An aqueous solution of NaHCO₃, brine and DCM were added. The layers were separated and the aqueous phase was extracted with DCM (twice). The combined organic extracts were washed with brine, dried over MgSO₄, filtered and the solvent was evaporated in vacuo. The crude mixture was purified by preparative LC (regular SiOH, 30 μm, 220 g Interchim®, liquid injection (DCM/heptane), mobile phase gradient: heptane/EtOAc from 100:0 to 50:50) to afford intermediate I162 (3.22 g, 53%).

Intermediate I163

Benzyl
(3R)-3-methanesulfinylpyrrolidine-1-carboxylate

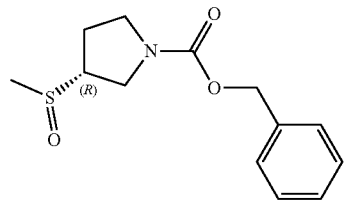

m-CPBA (3.16 g, 14.1 mmol, 77% purity) was added portionwise to a solution of intermediate I162 (3.22 g, 12.8 mmol) in DCM (128 mL) at 0° C. The reaction mixture was stirred at 0° C. for 1 h. A 10% aqueous solution of NaHCO₃ and H₂O were added. The layers were separated and the aqueous phase was extracted with DCM. The combined organic extracts were dried over MgSO₄, filtered and the solvent was evaporated in vacuo. The crude mixture was purified by preparative LC (regular SiOH, 30 μm, 120 g Interchim®, liquid injection (DCM), mobile phase gradient: DCM/MeOH from 99.8:0.2 to 95:5) to afford intermediate I163 (1.63 g, 48%).

Intermediate I164

Benzyl (3R)-3-[methyl(oxo)[(trifluoroacetyl)imino]-λ⁶-sulfanyl]pyrrolidine-1-carboxylate

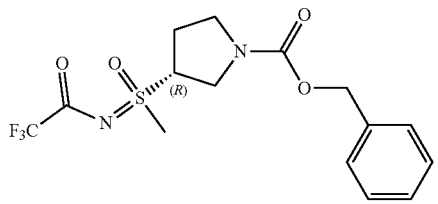

To a mixture of intermediate I163 (1.63 g, 6.10 mmol), trifluoroacetamide (1.03 g, 9.15 mmol) and magnesium oxide (983 mg, 24.4 mmol) in DCM (85 mL) at 0° C. was added rhodium acetate dimer (90.0 mg, 0.41 mmol) and (diacetoxyiodo)benzene (2.95 g, 9.15 mmol). The reaction mixture was stirred at 0° C. for 1 h and at rt for 16 h. Celite® was added and the mixture was evaporated to dryness. The crude mixture was purified by preparative LC (regular SiOH, 30 μm, 80 g Interchim®, dry loading (Celite®), mobile phase gradient: DCM/MeOH from 100:0 to 95:5) to afford intermediate I164 (1.47 g, 64%).

Intermediate I159

2,2,2-Trifluoro-N-[methyl(oxo)(3R)-pyrrolidin-3-yl-λ⁶-sulfanylidene]acetamide

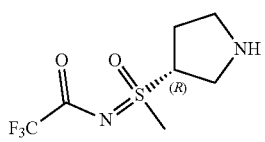

I159

A mixture of intermediate I164 (1.47 g, 3.89 mmol) and Pd/C (10% wt and in 50% H₂O, 4.13 g, 1.94 mmol) in EtOH (50 mL) was stirred under H₂ atmosphere (20 bars) at rt for 72 h. The reaction mixture was filtered over a pad of Celite® and rinsed with EtOH (twice). The filtrate was evaporated to dryness to give intermediate I159 (838 mg, 88%).

Compound 79

[(3R)-1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)pyrrolidin-3-yl](imino)methyl-λ⁶-sulfanone

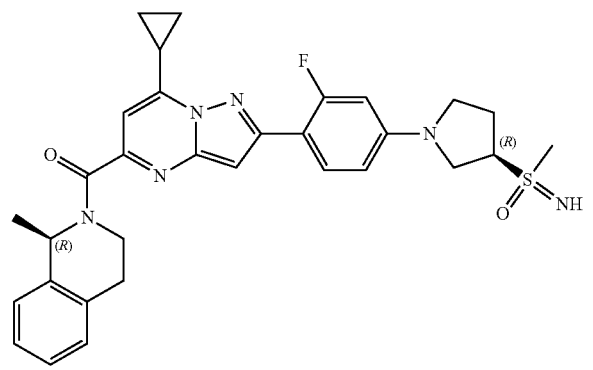

79

In a Schlenk tube were added (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (300 mg, 0.59 mmol), intermediate I159 (217 mg, 0.89 mmol), cesium carbonate (580 mg, 1.78 mmol) and 1,4-dioxane (9.5 mL). The mixture was degassed with nitrogen and palladium acetate (13.3 mg, 5.94 µmol) and XantPhos (34.3 mg, 5.94 µmol) were added successively. The reaction mixture was stirred at 100° C. for 16 h. H₂O (3.8 mL) was added and the reaction mixture was stirred at rt for 1 h. The reaction mixture was diluted with H₂O and EtOAc. The layers were separated and the aqueous phase was extracted with EtOAc. The combined organic extracts were washed with brine, dried over MgSO₄, filtered and the solvent was evaporated in vacuo. The crude mixture was purified by preparative LC (regular SiOH, 30 µm, 25 g Interchim®, liquid injection (DCM), mobile phase gradient: DCM/MeOH from 99.8:0.2 to 90:10). The residue was solubilized in EtOAc and the mixture was evaporated under vacuum (twice). The residue was dissolved in EtOAc and a precipitate was observed upon the addition of heptane. The solid was filtered off and dried under high vacuum at 40° C. for 16 h to give compound 79 (143 mg, 42%).

Compound 23 and Compound 24

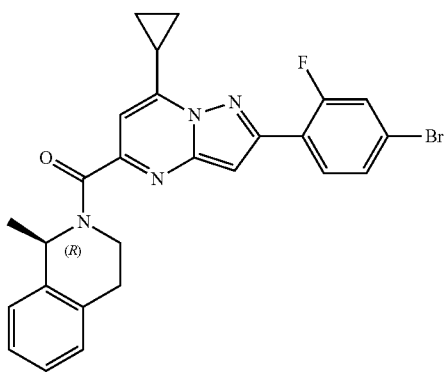 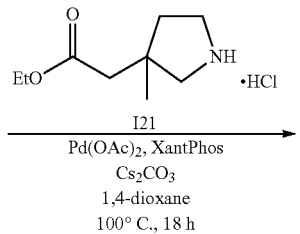

[2035421-61-3]

I21
Pd(OAc)₂, XantPhos
Cs₂CO₃
1,4-dioxane
100° C., 18 h

-continued
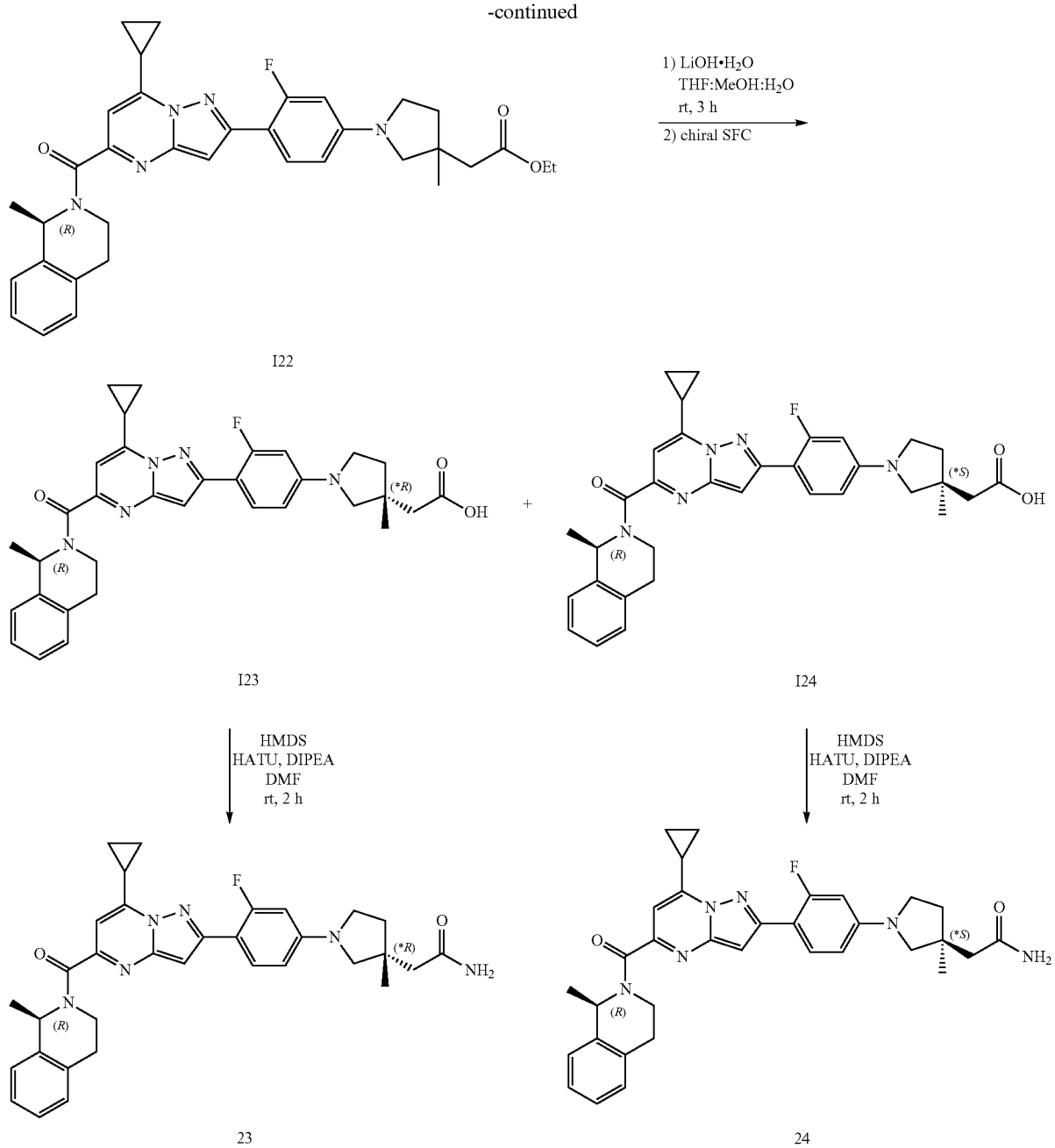
Synthesis of intermediate I21
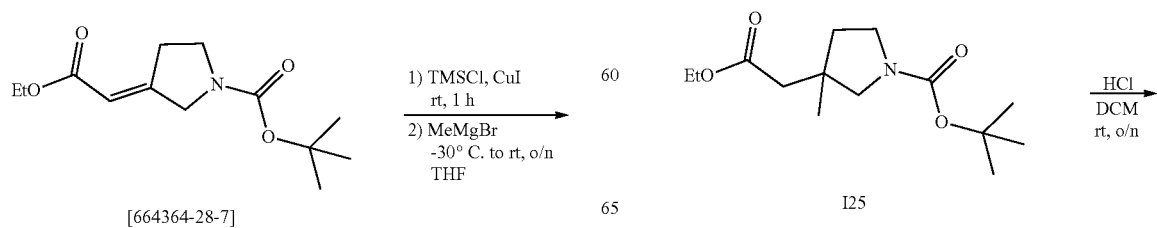

Intermediate I25

Tert-butyl 3-(2-ethoxy-2-oxoethyl)-3-methylpyrrolidine-1-carboxylate

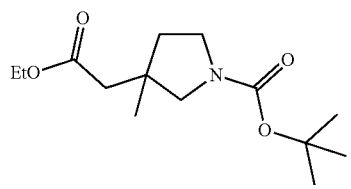

A mixture of tert-butyl (3E)-3-(2-ethoxy-2-oxoethylidene)pyrrolidine-1-carboxylate [664364-28-7] (3.50 g, 13.7 mmol), chlorotrimethylsilane (63.8 mL, 54.8 mmol) and cuprous iodide (3.02 g, 15.8 mmol) in THF (150 mL) was stirred at rt for 1 h. The reaction mixture was cooled down to −30° C. and methylmagnesium bromide (3.0 M in Et$_2$O, 27.4 mL, 82.3 mmol) was added dropwise. The reaction mixture was slowly warmed to rt and stirred overnight. EtOAc and 1N aqueous solution of HCl were added. The layers were separated and the organic phase was washed with brine, dried over MgSO$_4$, filtered and the solvent was removed under reduced pressure. The crude mixture was purified by preparative LC (irregular SiOH, 15-40 µm, 80 g Grace®, liquid injection (DCM), mobile phase gradient: heptane/EtOAc from 90:10 to 70:30) to afford intermediate I25 (2.0 g, 54%).

Intermediate I21

Ethyl 2-(3-methylpyrrolidin-3-yl)acetate hydrochloride

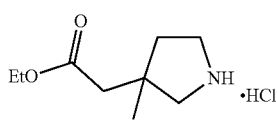

HCl (4.0 M in dioxane, 2.53 mL, 10.1 mmol) was added to a solution of intermediate I25 (550 mg, 2.03 mmol) in DCM (10 mL). The reaction mixture was stirred at rt overnight and the solvent was evaporated under reduced pressure. The product I21 was used in the next step without further purification.

Synthesis of Compounds 23 and 24

Intermediate I22

Ethyl-2-[1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)-3-methylpyrrolidin-3-yl]acetate

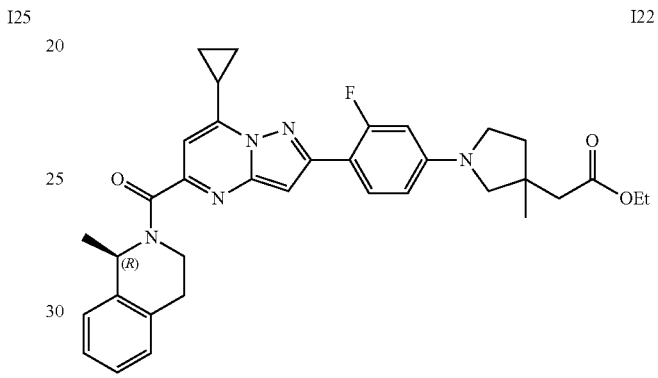

A mixture of (1R)-2-[2-(4-bromo-2-fluorophenyl)-7-cyclopropylpyrazolo[1,5-a]pyrimidine-5-carbonyl]-1-methyl-1,2,3,4-tetrahydroisoquinoline [2035421-61-3] (474 mg, 0.94 mmol), intermediate I21 (390 mg, 1.88 mmol), cesium carbonate (0.92 g, 2.82 mmol) and XantPhos (54.3 mg, 93.9 µmol) was purged with nitrogen. 1,4-Dioxane (15 mL) was added and the mixture was purged again with nitrogen. Palladium acetate (21.1 mg, 93.9 µmol) was added. The reaction mixture was purged with nitrogen and stirred at 100° C. for 18 h. The reaction mixture was diluted with EtOAc and H$_2$O. The layers were separated and the aqueous phase was extracted with EtOAc (twice). The combined organic extracts were washed with brine, dried over MgSO$_4$, filtered and the solvent was removed under reduced pressure. The crude mixture was purified by preparative LC (irregular SiOH, 15-40 µm, 40 g Grace®, liquid injection (DCM), mobile phase gradient: heptane/EtOAc from 100:0 to 70:30) to afford intermediate I22 (490 mg, 88%).

Intermediates I23 and I24

2-[(3*R)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-3-methylpyrrolidin-3-yl]acetic acid 2-[(3*S)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-3-methylpyrrolidin-3-yl]acetic acid

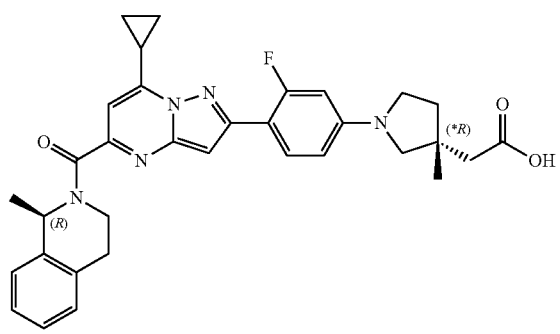

I23

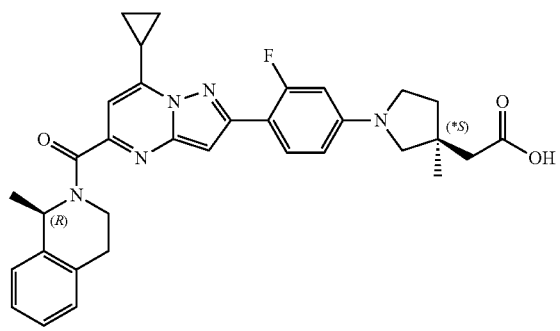

I24

Lithium hydroxide monohydrate (104 mg, 2.45 mmol) was added to a solution of intermediate I22 (490 mg, 823 µmol) in THF (10 mL), MeOH (3 mL) and H$_2$O (1.2 mL). The reaction mixture was stirred at rt for 3 h. Few drops of H$_2$O were added followed by the addition of a 3N aqueous solution of HCl. The layers were separated and the aqueous phase was extracted with DCM (twice). The combined organic extracts were washed with H$_2$O, dried over MgSO$_4$, filtered and evaporated under reduced pressure. The crude mixture was purified by preparative LC (irregular SiOH, 15-40 µm, 12 g Grace®, liquid injection (DCM), mobile phase gradient: DCM/MeOH from 100:0 to 97:3) to deliver a mixture of diastereomers (250 mg, 53%). A purification was performed via chiral SFC (Stationary phase: Chiralpak AS-H 5 µm 250*20 mm, Mobile phase: 65% CO$_2$, 35% i-PrOH) to afford the diastereomers I23 (120 mg, 26%) and I24 (122 mg, 26%). The diastereomers were purified separately by preparative LC (irregular SiOH, 15-40 µm, 12 g Grace®, liquid injection (DCM), mobile phase gradient: DCM/MeOH from 100:0 to 97:3) to give I23 (95 mg, 20%) and I24 (92 mg, 20%).

Compound 23

2-[(3*R)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-3-methylpyrrolidin-3-yl]acetamide

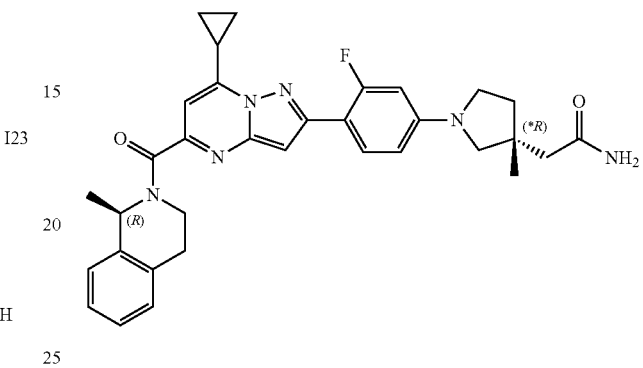

23

A mixture of intermediate I23 (80.0 mg, 0.14 mmol), HMDS (35.9 µL, 0.17 mmol), HATU (80.4 mg, 0.21 mmol) and DIPEA (36.4 µL, 0.21 mmol) in DMF (2 mL) was stirred at rt for 2 h. H$_2$O was added and the aqueous phase was extracted with EtOAc. The combined organic extracts were washed with H$_2$O, brine, dried over MgSO$_4$ and concentrated to dryness. The crude mixture was purified by flash chromatography over silica gel (15-40 µm, 12 g Grace®, mobile phase gradient: DCM/MeOH from 100:0 to 97:3). The pure fractions were collected and evaporated to dryness. The residue (53 mg) was crystallized from DIPE to give compound 23 (35.6 mg, 44%).

Compound 24

2-[(3*S)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-3-methylpyrrolidin-3-yl]acetamide

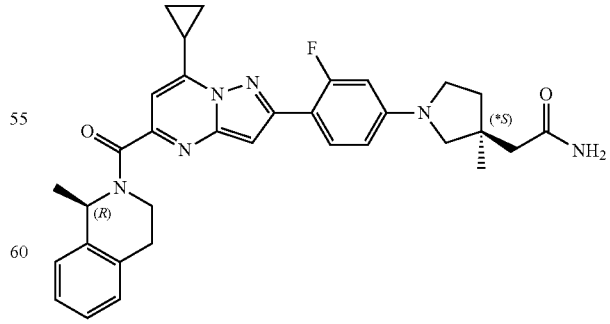

24

Compound 24 (29 mg, 32%) was synthesized from intermediate I24 according to the procedure reported for the synthesis of compound 23.

Compound 25 and Compound 26
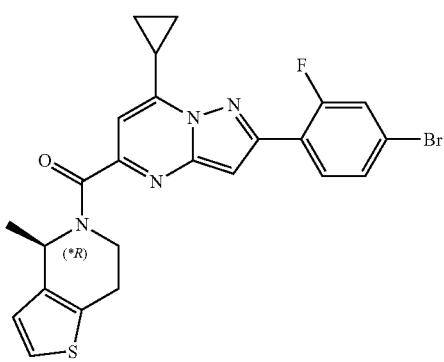 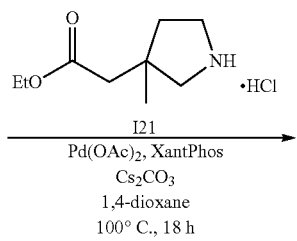
[2035419-01-1]
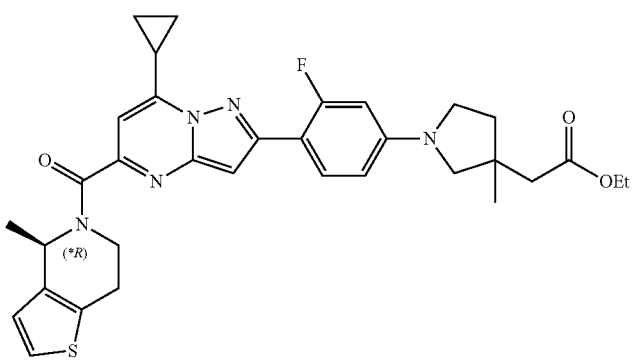
I26
1) LiOH·H₂O
THF:MeOH:H₂O
rt, 3 h
2) chiral SFC
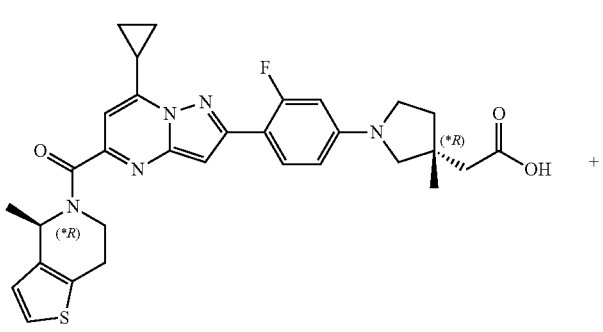 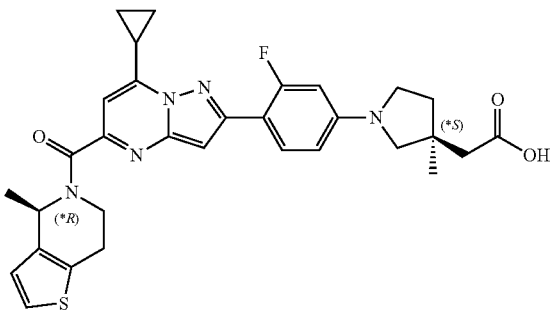
I127    I28
I27    I28
HMDS
HATU, DIPEA
DMF
rt, 5 h
HMDS
HATU, DIPEA
DMF
rt, 5 h

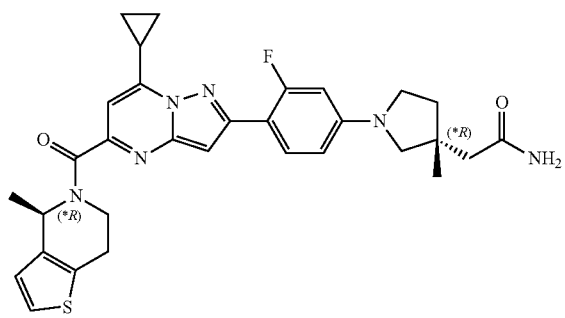

25

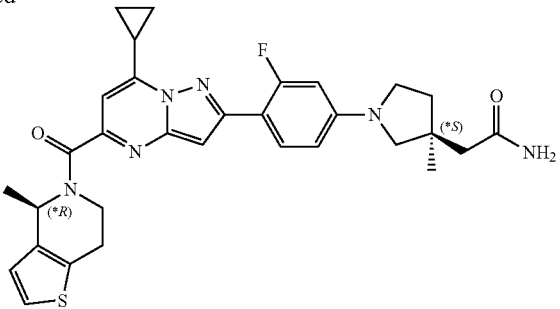

26

Intermediate I26

Ethyl 2-[1-(4-{7-cyclopropyl-5-[(4*R)-4-methyl-4,5,6,7-tetrahydro-thieno[3,2-c]pyridine-5-carbonyl]pyrazolo[1,5-a]pyrimidin-2-yl}-3-fluorophenyl)-3-methylpyrrolidin-3-yl]acetate

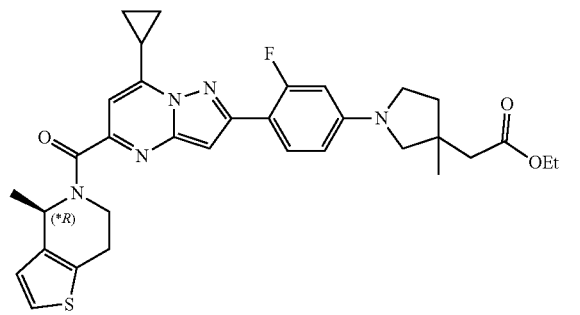

I26

A mixture of 2-(4-bromo-2-fluorophenyl)-7-cyclopropyl-5-[(4R)-4-methyl-4,5,6,7-tetrahydro-thieno[3,2-c]pyridine-5-carbonyl]pyrazolo[1,5-a]pyrimidine [2035419-01-1] (517 mg, 1.01 mmol), intermediate I21 (420 mg, 2.02 mmol), cesium carbonate (0.99 g, 3.03 mmol) and XantPhos (80.1 mg, 0.14 mmol) was purged with nitrogen. 1,4-Dioxane (12 mL) was added and the mixture was degassed with nitrogen. Palladium acetate (22.7 mg, 0.10 mmol) was added. The reaction mixture was purged with nitrogen and stirred at 100° C. for 18 h. The reaction mixture was diluted with EtOAc and H₂O. The layers were separated and the aqueous phase was extracted with EtOAc (twice). The combined organic extracts were washed with brine, dried over MgSO₄, filtered and the solvent was removed under reduced pressure. The crude mixture was purified by preparative LC (irregular SiOH, 15-40 µm, 40 g Grace®, liquid injection (DCM), mobile phase gradient: heptane/EtOAc from 100:0 to 70:30) to afford intermediate I26 (440 mg, 72%).

Intermediates I27 and I28

2-[(3*R)-1-(4-{7-Cyclopropyl-5-[(4*R)-4-methyl-4,5,6,7-tetrahydro-thieno[3,2-c]pyridine-5-carbonyl]pyrazolo[1,5-a]pyrimidin-2-yl}-3-fluorophenyl)-3-methylpyrrolidin-3-yl]acetic acid 2-[(3*S)-1-(4-{7-Cyclopropyl-5-[(4*R)-4-methyl-4,5,6,7-tetrahydro-thieno[3,2-c]pyridine-5-carbonyl]pyrazolo[1,5-a]pyrimidin-2-yl}-3-fluorophenyl)-3-methylpyrrolidin-3-yl]acetic acid

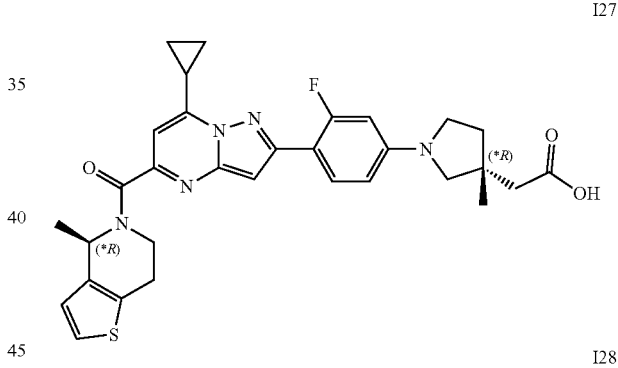

I27

I28

Lithium hydroxide monohydrate (92.1 mg, 2.19 mmol) was added to a solution of intermediate I26 (440 mg, 0.73 mmol) in THF (10 mL), MeOH (3 mL) and H₂O (1.2 mL). The reaction mixture was stirred at rt for 18 h. Few drops of H₂O were added followed by the addition of a 3N aqueous solution of HCl. The layers were separated and the aqueous phase was extracted with DCM (twice). The combined organic extracts were washed with H₂O, dried over MgSO₄, filtered and evaporated under reduced pressure. The crude mixture was purified by preparative LC (irregular SiOH, 15-40 μm, 12 g Grace®, liquid injection (DCM), mobile phase gradient: DCM/MeOH from 100:0 to 97:3). The diastereoisomers (220 mg) were separated via chiral SFC (Stationary phase: Chiralpak AS-H 5 μm 250*20 mm, Mobile phase: 65% CO$_2$, 35% i-PrOH) to give I27 (94 mg) and I28 (94 mg). The two separated diastereoisomers were taken up in DIPE and the solids were filtered off and dried under vacuum at 50° C. The diastereoisomers were purified separately by preparative LC (irregular SiOH, 15-40 μm, 12 g Grace®, liquid injection (DCM), mobile phase gradient: DCM/MeOH from 100:0 to 97:3) to afford intermediates I27 (78 mg, 18%) and I28 (70 mg, 17%).

Compound 25

2-[(3*R)-1-(4-{7-Cyclopropyl-5-[(4*R)-4-methyl-4,5,6,7-tetrahydro-thieno[3,2-c]pyridine-5-carbonyl]pyrazolo[1,5-a]pyrimidin-2-yl}-3-fluorophenyl)-3-methylpyrrolidin-3-yl]acetamide A solution of intermediate I27 (78.0 mg, 0.14 mmol), HMDS (34.6 μL, 0.16 mmol), HATU (77.5 mg, 0.20 mmol) and DIPEA (46.9 μL, 0.27 mmol) in DMF (2 mL) was stirred at rt for 5 h. The reaction mixture was diluted with H$_2$O and the aqueous phase was extracted with EtOAc. The combined organic extracts were washed with H$_2$O, brine, dried over MgSO$_4$ and concentrated to dryness. The crude mixture was purified by flash chromatography over silica gel (15-40 μm, 12 g Grace®, mobile phase gradient: DCM/MeOH from 100:0 to 97:3). The pure fractions were collected and evaporated to dryness. The residue (32 mg) was crystallized from DIPE to give compound 25 (18 mg, 23%).

Compound 26

2-[(3*S)-1-(4-{7-Cyclopropyl-5-[(4*R)-4-methyl-4,5,6,7-tetrahydro-thieno[3,2-c]pyridine-5-carbonyl]pyrazolo[1,5-a]pyrimidin-2-yl}-3-fluorophenyl)-3-methylpyrrolidin-3-yl]acetamide

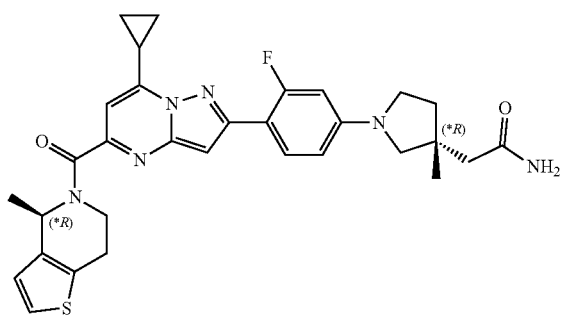

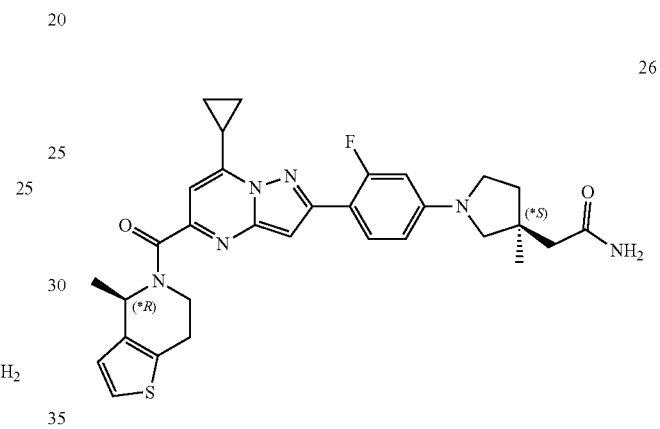

Compound 26 (28 mg, 40%) was synthesized from intermediate I28 according to the procedure reported for the synthesis of compound 25.

Compound 27 and Compound 28

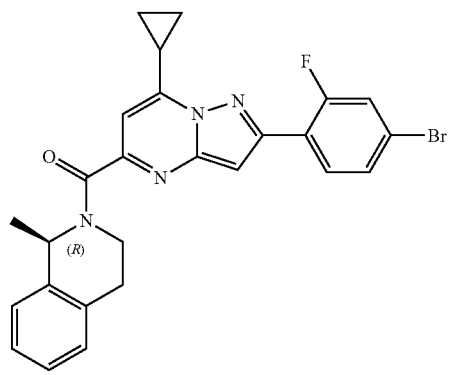 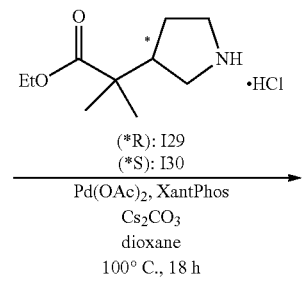

[2035421-61-3]

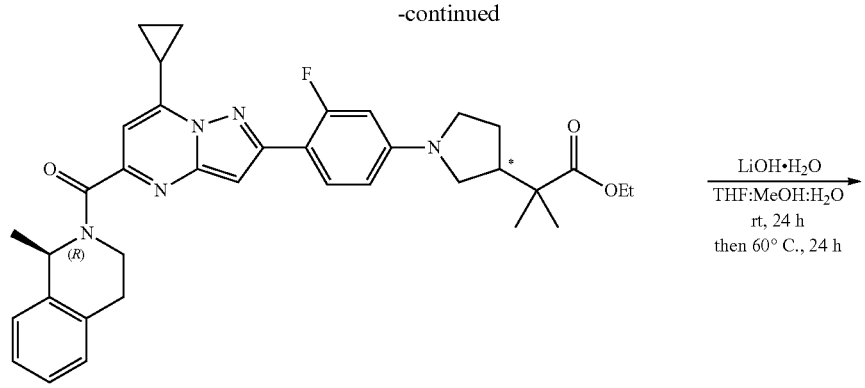
(R,*R): I31
(R,*S): I32
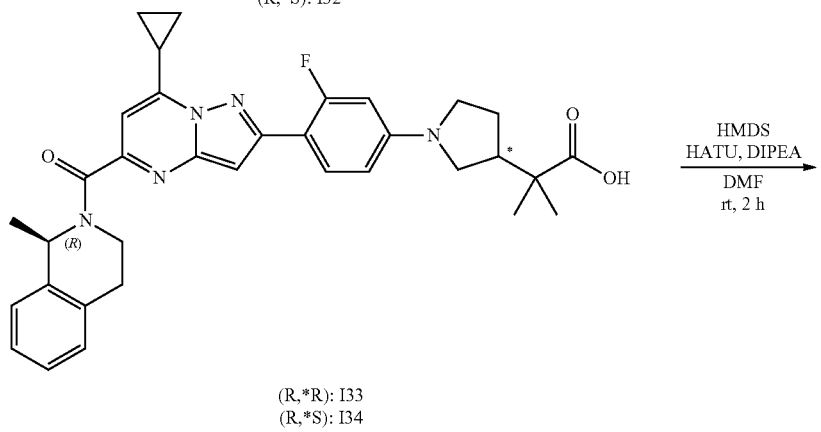
(R,*R): I33
(R,*S): I34
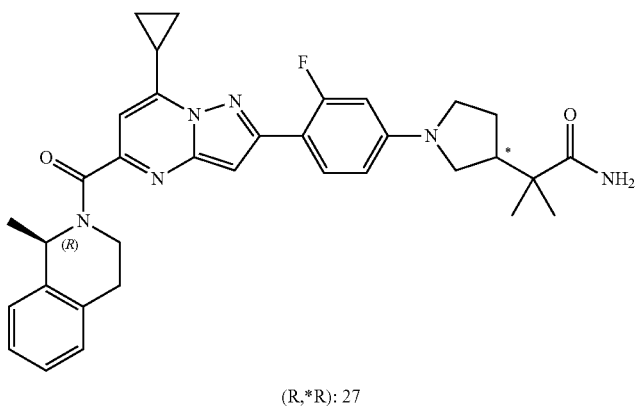
(R,*R): 27
(R,*S): 28
Synthesis of Intermediates I29 and I30
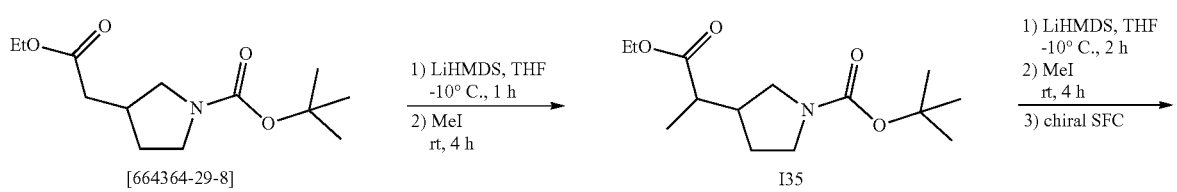

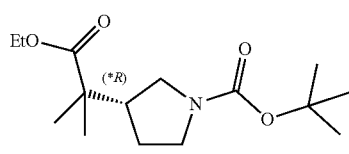
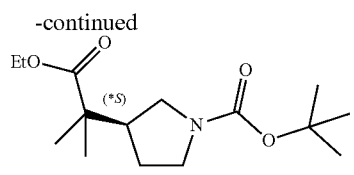

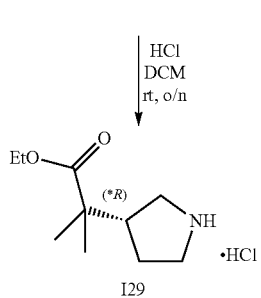
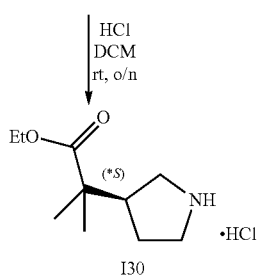

Intermediate I35

Tert-butyl 3-(1-ethoxy-1-oxopropan-2-yl)pyrrolidine-1-carboxylate

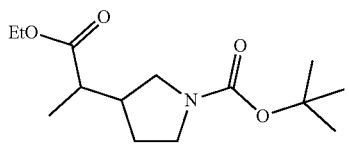

Lithium bis(trimethylsilyl)amide (1.5 M in THF, 10.6 mL, 15.9 mmol) was added to a solution of tert-butyl 3-(2-ethoxy-2-oxoethyl)pyrrolidine-1-carboxylate [664364-29-8] (1.7 g, 6.61 mmol) in THF (60 mL) at −10° C. for 1 h. Iodomethane (0.98 mL, 15.9 mmol) was added and the reaction mixture was stirred at rt for 4 h. H$_2$O was added and the aqueous phase was extracted with EtOAc (twice). The combined organic extracts were dried over MgSO$_4$, filtered and evaporated under reduced pressure. Intermediate I35 was used in the next step without further purification.

Intermediates I36 and I37

Tert-butyl (3*R)-3-(1-ethoxy-2-methyl-1-oxopropan-2-yl)pyrrolidine-1-carboxylate Tert-butyl (3*S)-3-(1-ethoxy-2-methyl-1-oxopropan-2-yl)pyrrolidine-1-carboxylate

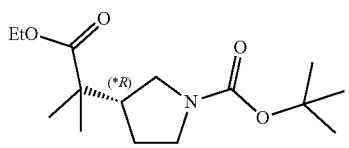

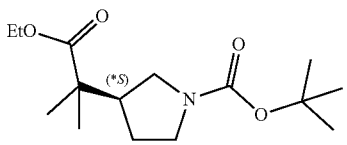

Lithium bis(trimethylsilyl)amide (1.5 M in THF, 18.4 mL, 27.6 mmol) was added to a solution of intermediate I35 (2.50 g, 9.21 mmol) in THF (37.5 mL) at −10° C. under nitrogen. The reaction mixture was stirred at −10° C. for 2 h. Iodomethane (1.37 mL, 22.1 mmol) was added and the reaction mixture was stirred at rt for 4 h. The reaction mixture was diluted with EtOAc and the organic phase was washed with H$_2$O, brine, dried over MgSO$_4$ and the solvent was evaporated under reduced pressure. The crude mixture was purified by preparative LC (irregular SiOH, 15-40 μm, 24 g Grace®, liquid injection (DCM), mobile phase gradient: heptane/EtOAc from 100:0 to 70:30). The enantiomers were separated via chiral SFC (Stationary phase: Lux amylose 2 5 μm 250*21.2 mm, Mobile phase: 90% CO$_2$, 10% i-PrOH) to afford intermediates I36 (850 mg, 32%) and I37 (850 mg, 32%).

Intermediate I29

Ethyl 2-methyl-2-[(3*R)-pyrrolidin-3-yl]propanoate hydrochloride

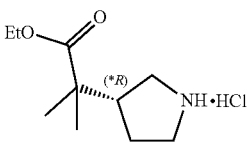

HCl (4.0 M in dioxane, 1.1 mL, 4.40 mmol) was added to a solution of intermediate I36 (250 mg, 876 μmol) in DCM (5 mL). The reaction mixture was stirred at rt overnight. The solvent was evaporated under reduced pressure and the product I29 was used in the next step as soon as possible without further purification.

Intermediate I30

Ethyl 2-methyl-2-[(3*S)-pyrrolidin-3-yl]propanoate hydrochloride

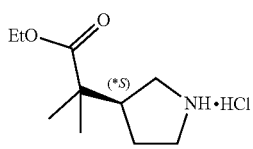

I30

Intermediate I30 was synthesized from intermediate I37 according to the procedure reported for the synthesis of intermediate I29. The product was used in the next step without further purification.

Synthesis of Compounds 27 and 28

Intermediate I31

Ethyl 2-[(3*R)-1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-yl]-2-methylpropanoate

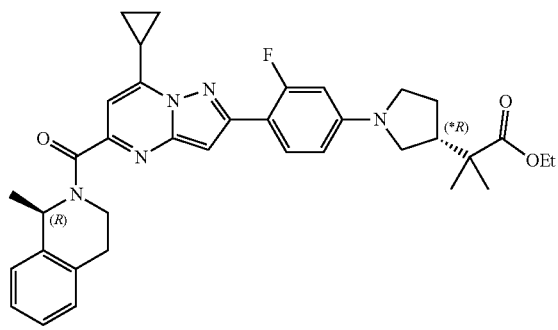

I31

A mixture of (1R)-2-[2-(4-bromo-2-fluorophenyl)-7-cyclopropylpyrazolo[1,5-a]pyrimidine-5-carbonyl]-1-methyl-1,2,3,4-tetrahydroisoquinoline [2035421-61-3] (228 mg, 0.45 mmol), intermediate I29 (150 mg, 0.68 mmol), cesium carbonate (441 mg, 1.35 mmol) and XantPhos (26.1 mg, 45.1 µmol) was purged with nitrogen. 1,4-Dioxane (7 mL) was added and the mixture was purged again with nitrogen. Palladium acetate (10.1 mg, 45.1 µmol) was added. The reaction mixture was purged with nitrogen and stirred at 100° C. for 18 h. The reaction mixture was diluted with EtOAc and H₂O. The layers were separated and the aqueous phase was extracted with EtOAc (twice). The combined organic extracts were washed with brine, dried over MgSO₄, filtered and the solvent was evaporated under reduced pressure. The crude mixture was purified by preparative LC (irregular SiOH, 15-40 µm, 12 g Grace®, liquid injection (DCM), mobile phase gradient: heptane/EtOAc from 100:0 to 75:25) to afford intermediate I31 (190 mg, 69%).

Intermediate I32

Ethyl 2-[(3*S)-1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-yl]-2-methylpropanoate

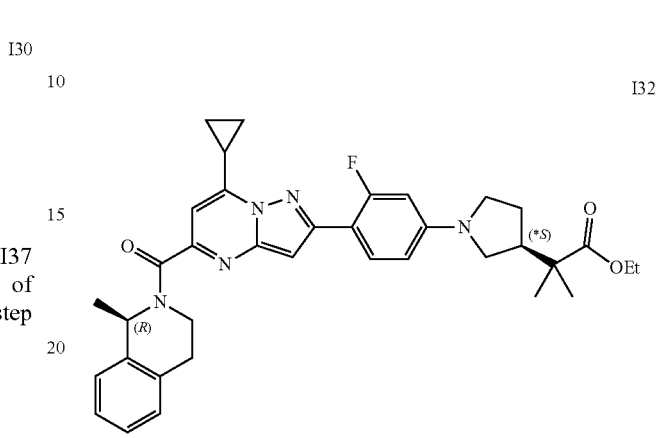

I32

Intermediate I32 (125 mg, 57%) was synthesized from (1R)-2-[2-(4-bromo-2-fluorophenyl)-7-cyclopropylpyrazolo[1,5-a]pyrimidine-5-carbonyl]-1-methyl-1,2,3,4-tetrahydroisoquinoline [2035421-61-3] and intermediate I30 according to the procedure reported for the synthesis of compound I31 with a shorter reaction time of 3 h.

Intermediate I33

2-[(3*R)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-yl]-2-methylpropanoic acid

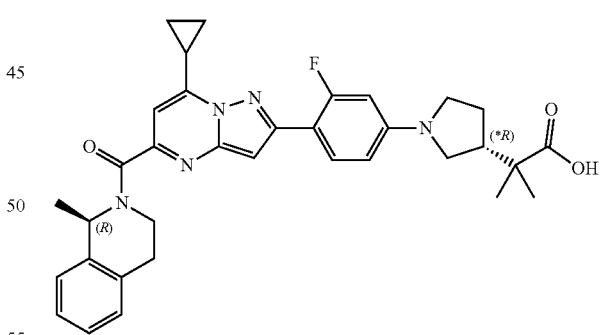

I33

Lithium hydroxide monohydrate (65.4 mg, 1.56 mmol) was added to a solution of intermediate I31 (0.19 g, 0.31 mmol) in THF (5 mL), MeOH (2 mL) and H₂O (0.4 mL). The reaction mixture was stirred at rt for 24 h and at 60° C. for 24 h. Few drops of H₂O were added followed by the addition of a 3N aqueous solution of HCl. The layers were separated and the aqueous phase was extracted with DCM (twice). The combined organic extracts were washed with H₂O, dried over MgSO₄, filtered and evaporated under reduced pressure. The product I33 (210 mg) was used in the next step without further purification.

Intermediate I34

2-[(3*S)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-yl]-2-methylpropanoic acid

I34

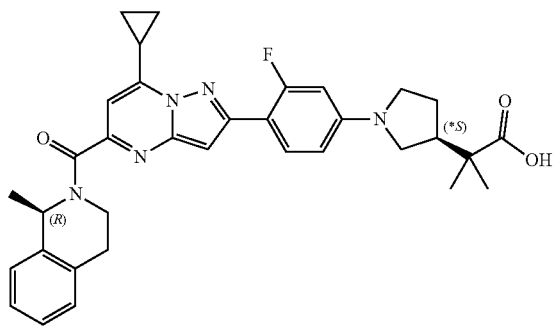

Intermediate I34 was synthesized from intermediate I32 according to the procedure reported for the synthesis of intermediate I33. The reaction mixture was stirred at 60° C. for 24 h. The product I34 (155 mg) was used in the next step without further purification.

Compound 27

2-[(3*R)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-yl]-2-methylpropanamide

27

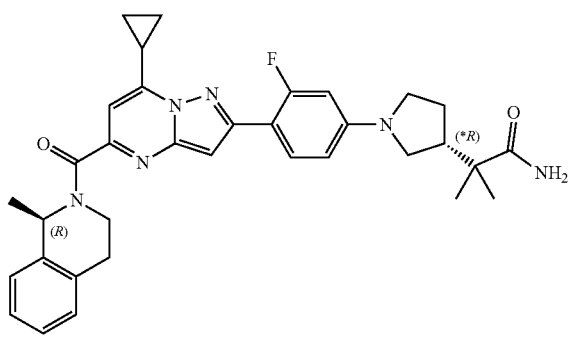

A mixture of intermediate I33 (190 mg, 327 μmol), HMDS (83.2 μL, 392 μmol), HATU (186 mg, 0.49 mmol) and DIPEA (112 μL, 0.65 mmol) in DMF (5 mL) was stirred at rt for 2 h. H$_2$O was added and the aqueous phase was extracted with EtOAc. The organic phase was washed with H$_2$O, brine, dried over MgSO$_4$ and concentrated to dryness. The crude mixture was purified by flash chromatography over silica gel (Grace® 12 g, 15-40 μm, mobile phase gradient: DCM/MeOH from 100:0 to 97:3). The pure fractions were collected and evaporated to dryness. The residue (85 mg) was taken up in DIPE and the solid was filtered off and dried under vacuum to give compound 27 (50 mg, 26%).

Compound 28

2-[(3*S)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-yl]-2-methylpropanamide

28

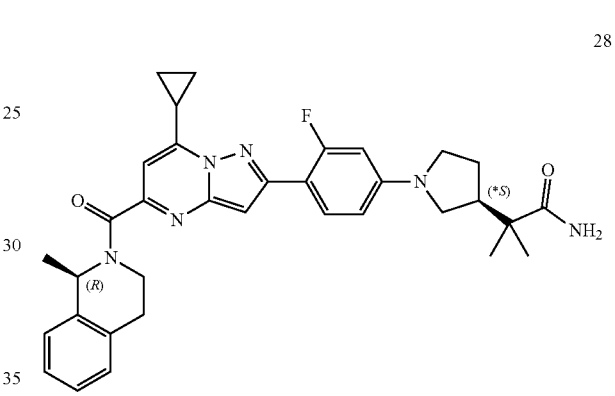

Compound 28 was synthesized from intermediate I34 according to the procedure reported for the synthesis of compound 27. The crude mixture was purified by flash chromatography over silica gel (15-40 μm, 12 g Grace®, mobile phase gradient: DCM/MeOH from 100:0 to 97:3). The pure fractions were collected and evaporated to dryness. The product was lyophilized with MeCN/H$_2$O (80:20) to give compound 28 (56 mg, 36%).

Compound 29

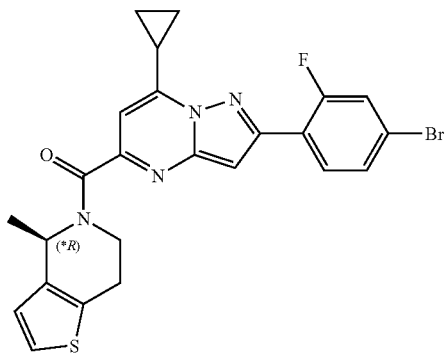
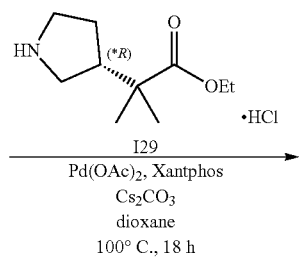

I29
Pd(OAc)$_2$, Xantphos
Cs$_2$CO$_3$
dioxane
100° C., 18 h

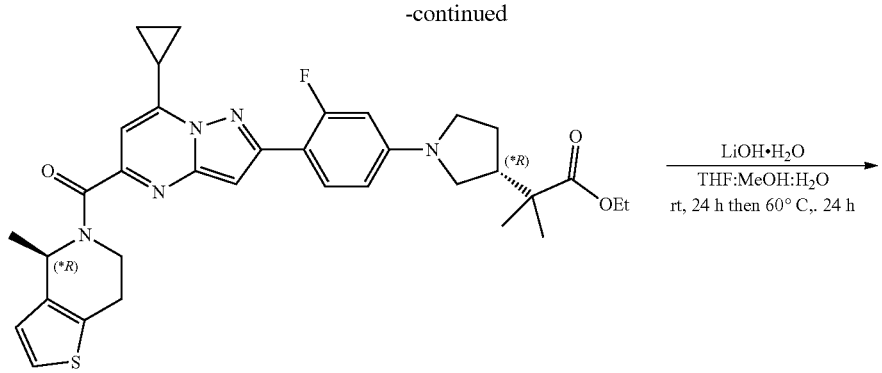

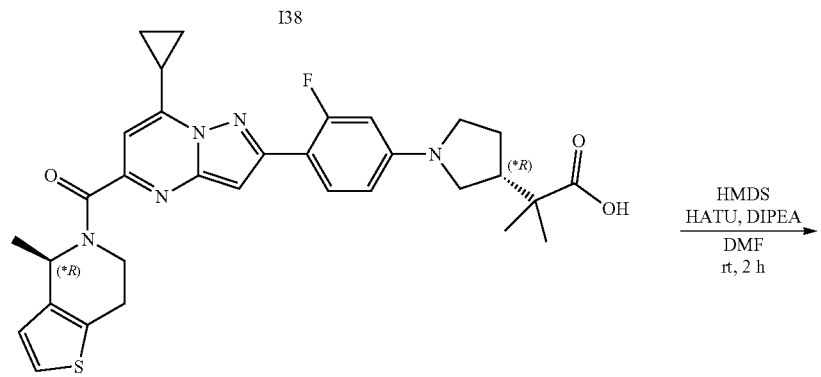

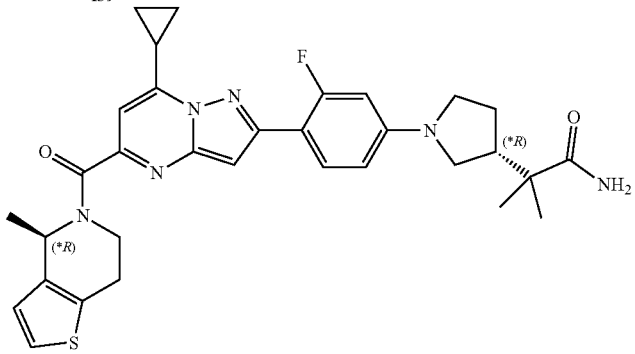

Intermediate I38

Ethyl 2-[(3*R)-1-(4-{7-cyclopropyl-5-[(4*R)-4-methyl-4,5,6,7-tetrahydro-thieno[3,2-c]pyridine-5-carbonyl]pyrazolo[1,5-a]pyrimidin-2-yl}-3-fluorophenyl)pyrrolidin-3-yl]-2-methylpropanoate

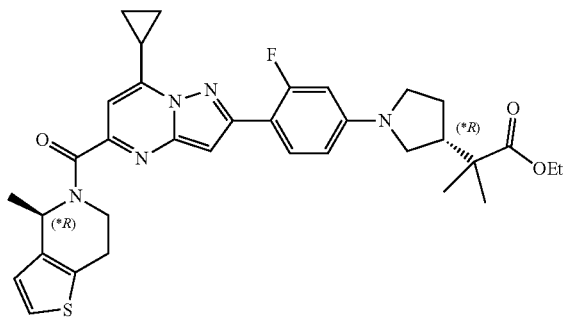

A mixture of 2-(4-bromo-2-fluorophenyl)-7-cyclopropyl-5-[(4*R)-4-methyl-4,5,6,7-tetrahydro-thieno[3,2-c]pyridine-5-carbonyl]pyrazolo[1,5-a]pyrimidine [2035419-01-1] (300 mg, 0.59 mmol), intermediate I29 (195 mg, 0.88 mmol), cesium carbonate (573 mg, 1.76 mmol) and XantPhos (33.9 mg, 58.6 µmol) was purged with nitrogen. 1,4-Dioxane (7 mL) was added and the mixture was degassed with nitrogen. Palladium acetate (13.2 mg, 58.6 µmol) was added. The reaction mixture was purged with nitrogen and stirred at 100° C. for 18 h. The reaction mixture was diluted with EtOAc and H₂O. The layers were separated and the aqueous phase was extracted with EtOAc (twice). The combined organic extracts were washed with brine, dried over MgSO₄, filtered and the solvent was removed under reduced pressure. The crude mixture was purified by preparative LC (irregular SiOH, 15-40 µm, 24 g Grace®, liquid injection (DCM), mobile phase gradient: heptane/EtOAc from 100:0 to 75:25) to give intermediate I38 (120 mg, 33%).

Intermediate I39

2-[(3\*R)-1-(4-{7-Cyclopropyl-5-[(4\*R)-4-methyl-4,5,6,7-tetrahydro-thieno[3,2-c]pyridine-5-carbonyl]pyrazolo[1,5-a]pyrimidin-2-yl}-3-fluorophenyl)pyrrolidin-3-yl]-2-methyl-propanoic acid

Compound 29

2-[(3\*R)-1-(4-{7-Cyclopropyl-5-[(4\*R)-4-methyl-4,5,6,7-tetrahydro-thieno[3,2-c]pyridine-5-carbonyl]pyrazolo[1,5-a]pyrimidin-2-yl}-3-fluorophenyl)pyrrolidin-3-yl]-2-methyl-propanamide

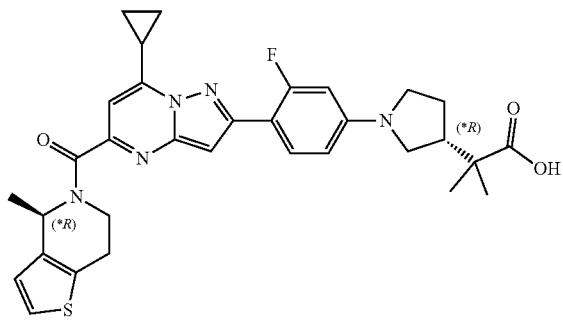

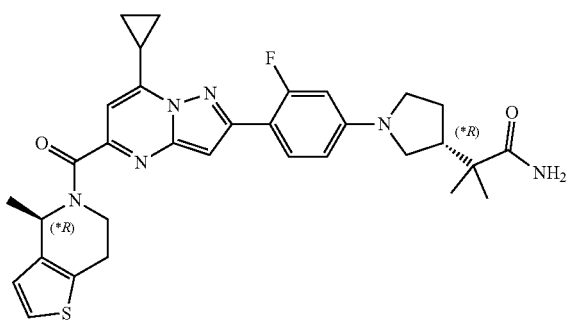

Lithium hydroxide monohydrate (24.5 mg, 0.59 mmol) was added to a solution of intermediate I38 (0.12 g, 195 µmol) in THF (5 mL), MeOH (1 mL) and H₂O (0.6 mL). The reaction mixture was stirred at rt for 24 h and at 60° C. for another 24 h. Few drops of H₂O were added followed by a 3N aqueous solution of HCl. The layers were separated and the aqueous phase was extracted with DCM (twice). The combined organic extracts were washed with H₂O, dried over MgSO₄, filtered and evaporated under reduced pressure. The crude mixture was purified by preparative LC (irregular SiOH, 15-40 µm, 4 g Grace®, liquid injection (DCM), mobile phase gradient: DCM/MeOH from 100:0 to 97:3) to afford intermediate I39 (75 mg, 65%).

A solution of intermediate I39 (75.0 mg, 0.13 mmol), HMDS (32.5 µL, 0.15 mmol), HATU (72.8 mg, 0.19 mmol) and DIPEA (44.0 µL, 0.26 mmol) in DMF (2 mL) was stirred at rt for 2 h. The reaction mixture was diluted with H₂O and EtOAc. The layers were separated and the aqueous phase was extracted with EtOAc. The organic phase was washed with H₂O, brine, dried over MgSO₄ and concentrated to dryness. The crude compound was purified by flash chromatography over silica gel (15-40 µm, 4 g Grace®, mobile phase gradient: DCM/MeOH from 100:0 to 97:3). The pure fractions were collected and evaporated to dryness. The product was lyophilized (MeCN/H₂O, 80:20) to give compound 29 (41 mg, 55%).

Compound 30 and Compound 31

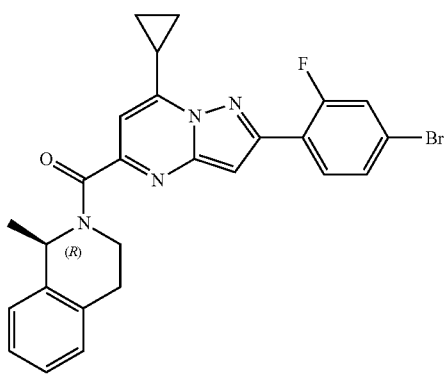

[2035421-61-3]

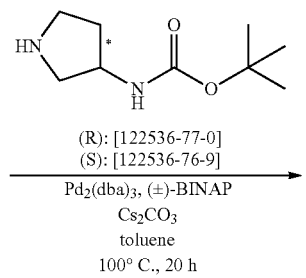

(R): [122536-77-0]
(S): [122536-76-9]

Pd₂(dba)₃, (±)-BINAP
Cs₂CO₃
toluene
100° C., 20 h

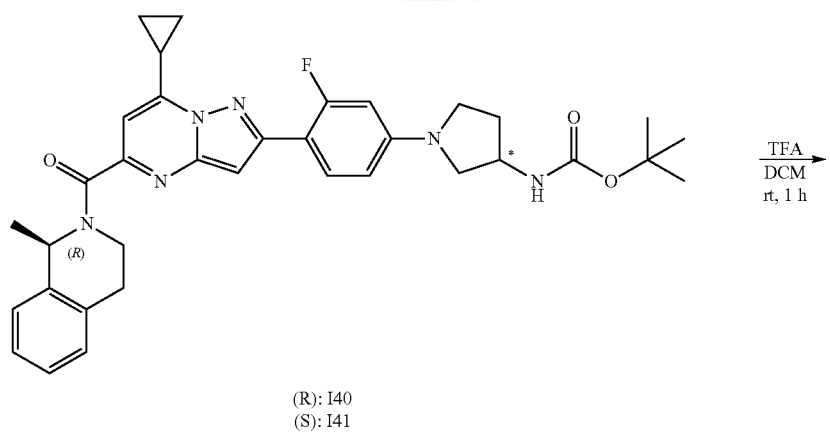
(R): I40
(S): I41
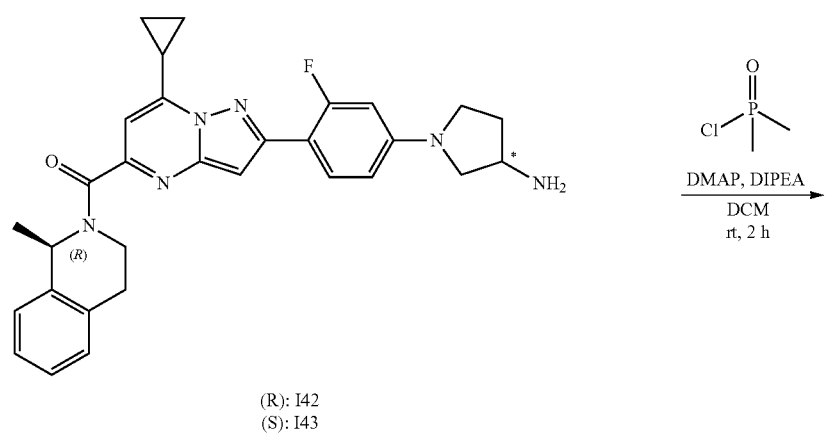
(R): I42
(S): I43
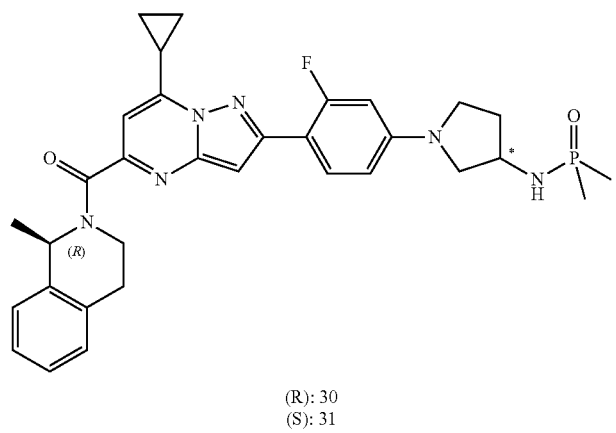
(R): 30
(S): 31

Intermediate I40

Tert-butyl N-[(3R)-1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-yl]carbamate

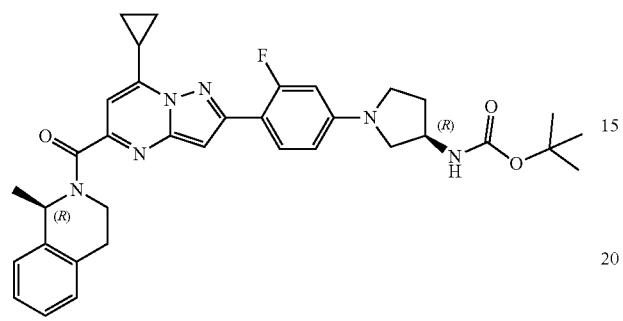

A Schenlk tube was charged with (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (500 mg, 0.95 mmol), (R)-3-(boc-amino)pyrrolidine [122536-77-0] (355 mg, 1.91 mmol), cesium carbonate (1.09 g, 3.34 mmol) and toluene (20 mL). The mixture was purged with nitrogen. (±)-BINAP (59.3 mg, 95.3 μmol) and tris(dibenzylideneacetone)dipalladium (87.2 mg, 95.3 μmol) were added. The reaction mixture was purged with nitrogen and stirred at 100° C. for 20 h. The reaction mixture was diluted with brine and EtOAc. The layers were separated and the aqueous phase was extracted with EtOAc (twice). The combined organic extracts were dried over MgSO₄, filtered and evaporated under reduced pressure. The crude mixture was purified by preparative LC (irregular SiOH, 15-40 μm, 40 g GraceResolv™, liquid injection (DCM), mobile phase gradient: heptane/EtOAc from 90:10 to 60:40) to afford intermediate I40 (542 mg, 93%) as a yellow foam.

Intermediate I41

Tert-butyl N-[(3S)-1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-yl]carbamate

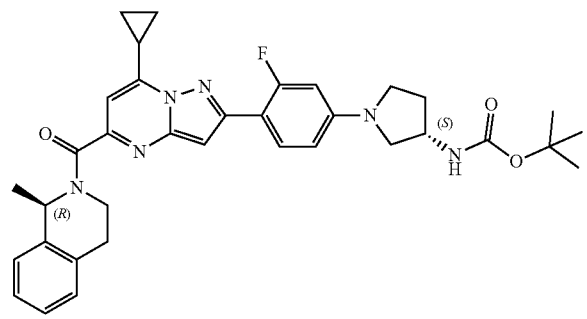

Intermediate I41 was synthesized from (1R)-2-[2-(4-bromo-2-fluorophenyl)-7-cyclo-propylpyrazolo[1,5-a]pyrimidine-5-carbonyl]-1-methyl-1,2,3,4-tetrahydroisoquinoline [2035421-61-3] and (S)-3-(boc-amino)pyrrolidine [122536-76-9] according to the procedure reported for the synthesis of intermediate I40. Intermediate I41 (570 mg, 98%) was obtained as a yellow foam.

Intermediate I42

(3R)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-amine

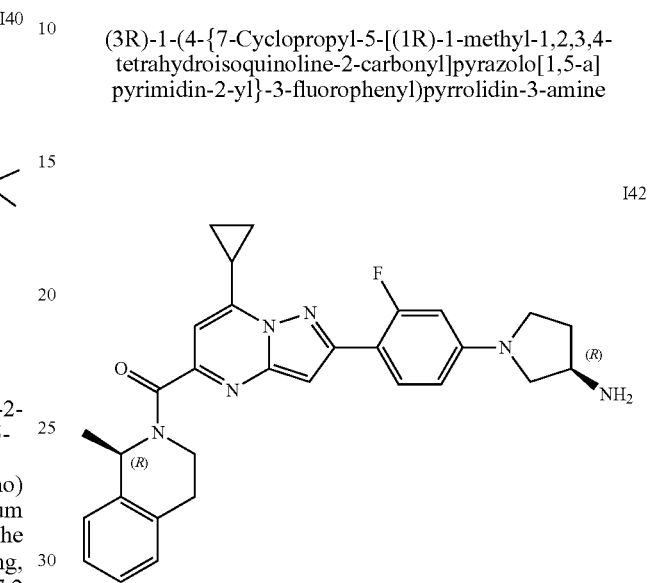

TFA (1.60 mL, 20.9 mmol) was added to a solution of intermediate I40 (401 mg, 65.7 μmol) in DCM (8 mL). The reaction mixture was stirred at rt for 1 h. DCM and a saturated aqueous solution of NaHCO₃ were added. The layers were separated and the organic phase was dried over MgSO₄, filtered and the solvent was removed under reduced pressure to afford intermediate I42 (358 mg) as a yellow gum. The product was engaged in the next step without further purification.

Intermediate I43

(3S)-1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)pyrrolidin-3-amine

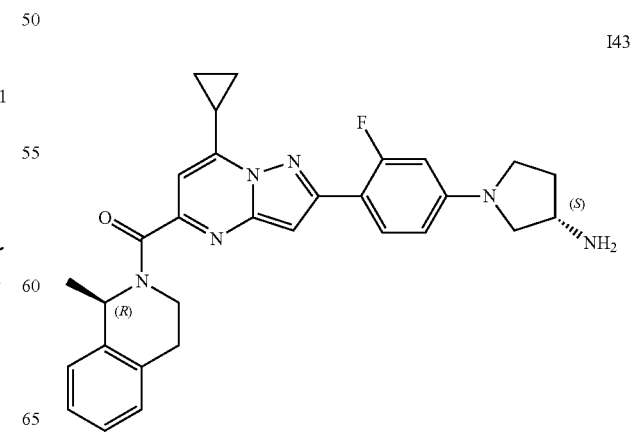

Intermediate I43 was synthesized from intermediate I41 according to the procedure reported for the synthesis of intermediate I42. Intermediate I43 (450 mg) was obtained as a yellow gum and engaged in the next step without further purification.

Compound 30

(1R)-2-(7-Cyclopropyl-2-{4-[(3R)-3-[(dimethylphosphoryl)amino]pyrrolidin-1-yl]-2-fluorophenyl}pyrazolo[1,5-a]pyrimidine-5-carbonyl)-1-methyl-1,2,3,4-tetrahydro-isoquinoline

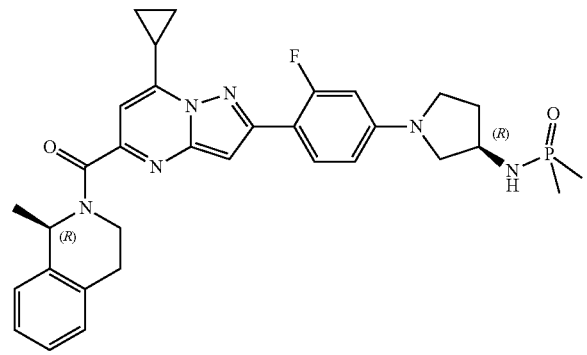

Dimethylphosphinic chloride (360 μL, 0.72 mmol) was added to a mixture of intermediate I42 (354 mg, 638 μmol, 92% purity), DIPEA (242 μL, 1.40 mmol) and DMAP (7.79 mg, 63.8 μmol) in DCM (5.6 mL). The reaction mixture was stirred at rt for 2 h. The reaction mixture was diluted with DCM and washed with a 10% aqueous solution of NaHCO₃. The organic phase was dried over MgSO₄, filtered and evaporated under reduced pressure. The crude mixture was purified by preparative LC (irregular SiOH, 15-40 μm, 24 g GraceResolv™, liquid injection (DCM), mobile phase: gradient DCM/MeOH from 100:0 to 96:4). The residue was taken up in MeOH, evaporated and triturated with Et₂O. The solid was filtered off and dried under high vacuum at 50° C. for 2 h to give compound 30 (199 mg, 53%) as a yellowish solid.

Compound 31

(1R)-2-(7-Cyclopropyl-2-{4-[(3S)-3-[(dimethylphosphoryl)amino]pyrrolidin-1-yl]-2-fluorophenyl}pyrazolo[1,5-a]pyrimidine-5-carbonyl)-1-methyl-1,2,3,4-tetrahydro-isoquinoline

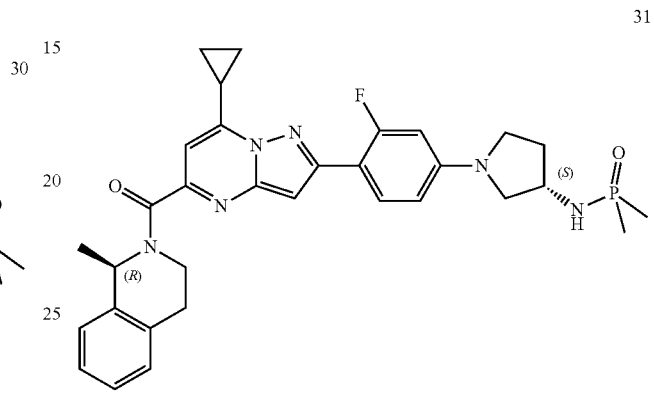

Compound 31 was synthesized from intermediate I43 according to the procedure reported for the synthesis of compound 30. The product was dried under high vacuum at 50° C. for 20 h to give compound 31 (233 mg, 58%) as a yellowish solid.

Compound 76

N-[(3S)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidin-3-yl]-2,2,2-trifluoroacetamide

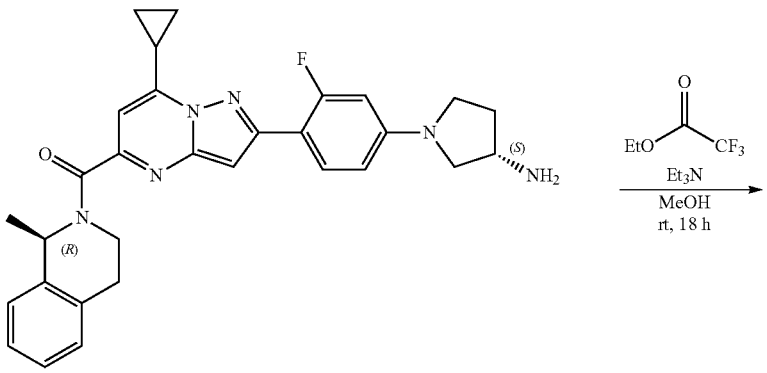

-continued

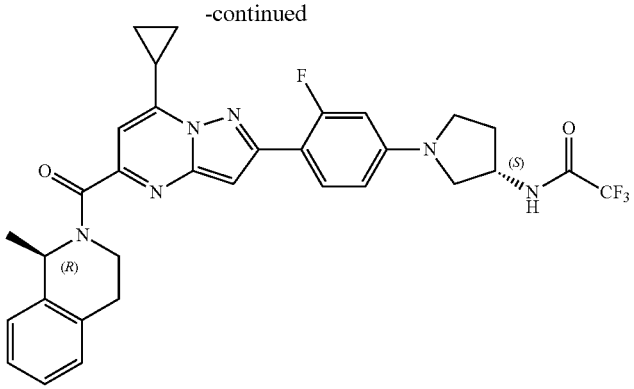

76

In a sealed tube Et₃N (32 µL, 0.23 mmol) and ethyl trifluoroacetate (30 µL, 0.25 mmol) were added to a solution of intermediate I43 (100 mg, 196 µmol) in MeOH (0.8 mL). The reaction mixture was stirred at rt for 18 h. The reaction mixture was diluted with H₂O and EtOAc. The layers were separated and the aqueous phase was extracted with EtOAc (twice). The combined organic extracts were dried over MgSO₄, filtered and concentrated under reduced pressure. The crude mixture was purified by preparative LC (irregular SiOH, 15-40 µm, 24 g GraceResolv™, liquid injection (DCM), mobile phase gradient: heptane/EtOAc from 90:10 to 60:40). The residue was crystallized from MeOH. The solid was filtered off and dried under high vacuum at 50° C. for 20 h to give compound 76 (53 mg, 45%) as a yellow solid.

Compounds 32, Compound 33, Compound 34 and Compound 35

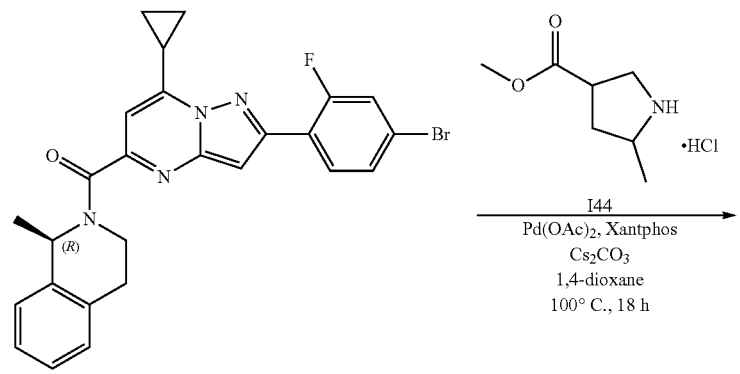

[2035421-61-3]

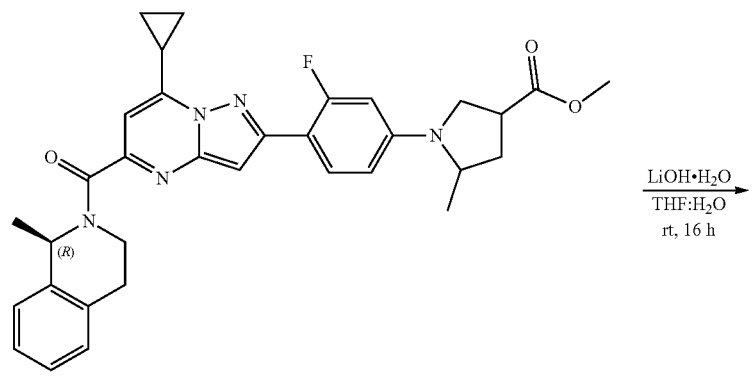

I45

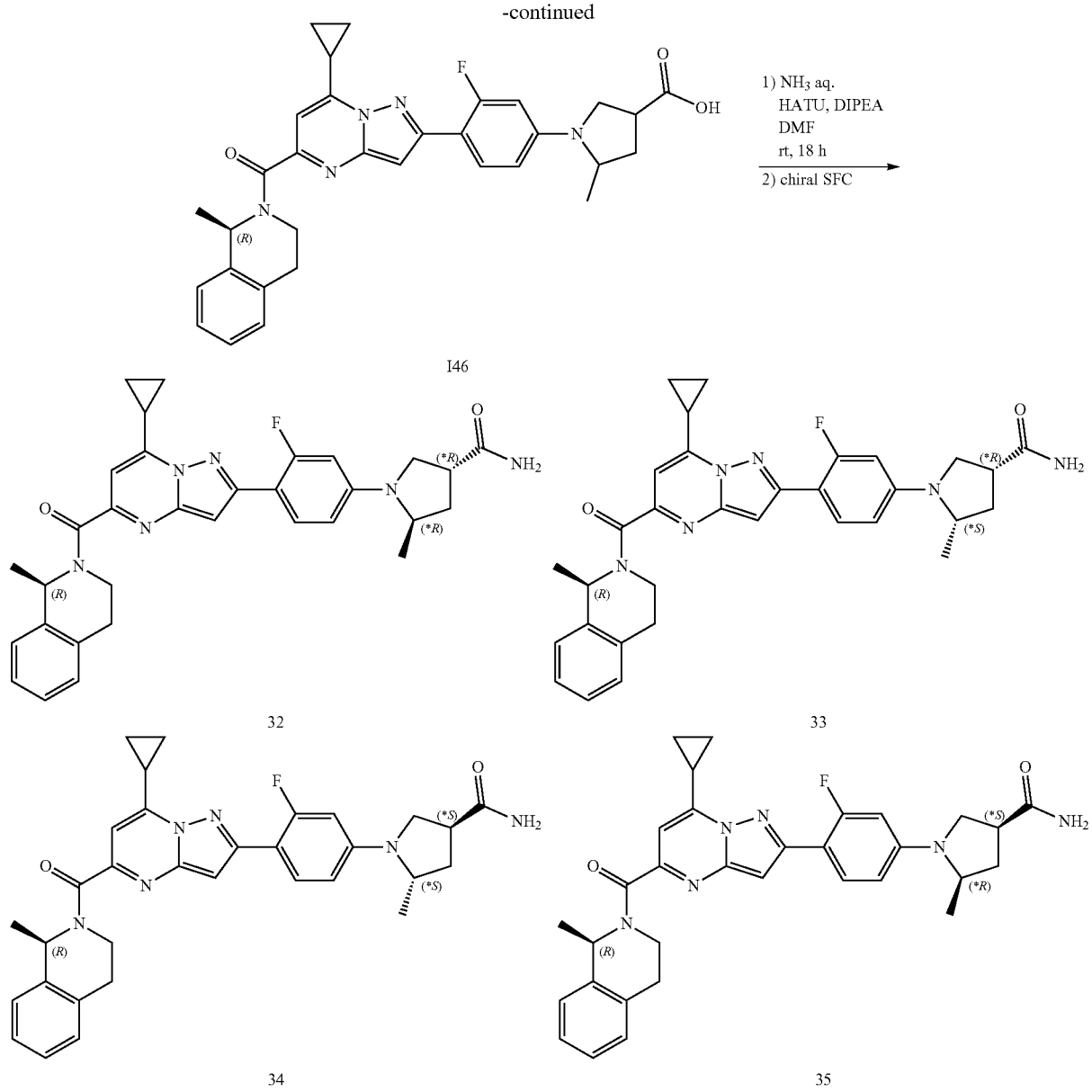
Synthesis of Intermediate I44
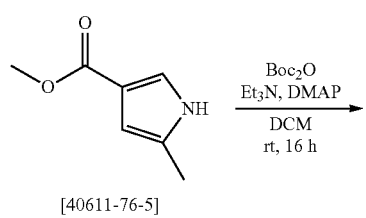
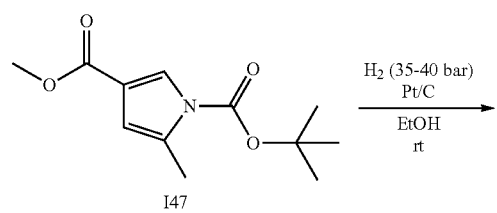
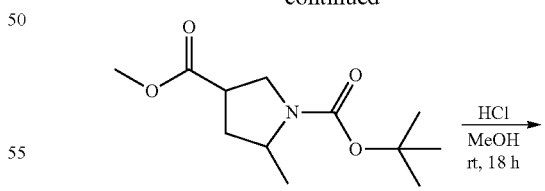

Intermediate I47

1-Tert-butyl 3-methyl 5-methyl-1H-pyrrole-1,3-dicarboxylate

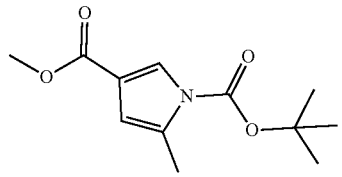

I47

A sealed tube was charged with DMAP (8.78 mg, 71.8 µmol), 5-methyl-1H-pyrrole-3-carboxylic acid methyl ester [40611-76-5] (100 mg, 0.72 mmol), Boc20 (154 µL, 0.72 mmol), triethylamine (0.30 mL, 2.16 mmol) and anhydrous DCM (2 mL). The reaction mixture was stirred at rt for 18 h. H₂O, a saturated aqueous solution of NaHCO₃ and EtOAc were added. The layers were separated and the aqueous phase was extracted with EtOAc (twice). The combined organic extracts were dried over MgSO₄, filtered and evaporated under reduced pressure to afford intermediate I47 (170 mg, 99%).

Intermediate I48

1-Tert-butyl 3-methyl 5-methylpyrrolidine-1,3-dicarboxylate

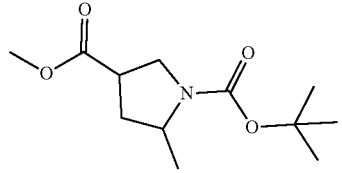

I48

In an autoclave, a mixture of intermediate I47 (1.25 g, 5.22 mmol) and platinum on carbon (1 wt %, 4.1 g, 209 µmol) in EtOH (38 mL) was stirred at rt under 35 bar of H₂ for 16 h. Platinum on carbon (1 wt %, 1.02 g, 52 µmol) was added and the reaction mixture was stirred at rt under 40 bar of H₂. Platinum on carbon (1 wt %, 1.02 g, 52 µmol) was added and the reaction mixture was stirred at rt under 40 bar of H₂. The reaction mixture was filtered over Celite® and the filtrate was concentrated under reduced pressure. The crude mixture was purified by preparative LC (irregular SiOH, 15-40 µm, 40 g GraceResolv™, liquid injection (DCM), mobile phase gradient: heptane/EtOAc from 80:20 to 0:100) to afford intermediate I48 (850 mg, 67%) as a colorless oil.

Intermediate I44

Methyl 5-methylpyrrolidine-3-carboxylate hydrochloride

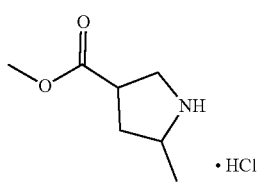

I44

Hydrochloric acid (3.0 M in CPME, 12.5 mL, 37.5 mmol) was added dropwise to a solution of intermediate I48 (850 mg, 3.49 mmol) in MeOH (5.0 mL). The reaction mixture was stirred at rt for 18 h and the solvent was removed under reduced pressure. The residue was co-evaporated with toluene to give intermediate I44 (627 mg, quant.) as a colorless oil.

Synthesis of compounds 32, 33, 34 and 35

Intermediate I45

Methyl 1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)-5-methylpyrrolidine-3-carboxylate

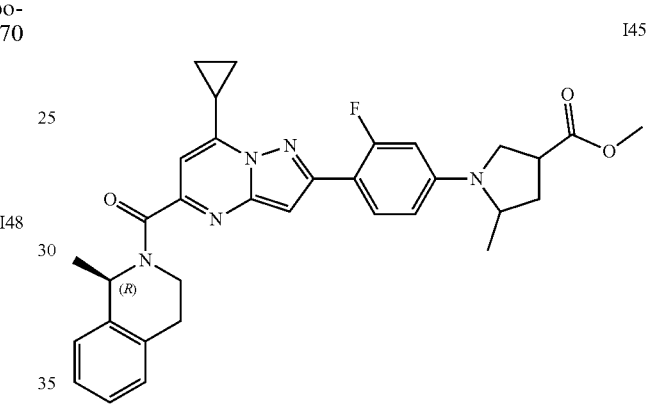

I45

A sealed tube was charged with (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (703 mg, 1.39 mmol), intermediate I44 (250 mg, 1.39 mmol) and cesium carbonate (1.36 g, 4.18 mmol) and purged with nitrogen. 1,4-Dioxane (11 mL) was added and the mixture was degassed with nitrogen. Palladium acetate (31.2 mg, 0.14 mmol) and XantPhos (80.5 mg, 0.14 mmol) were added. The reaction mixture was stirred at 100° C. for 18 h. The reaction mixture was poured out into water and the aqueous phase was extracted with EtOAc. The combined organic extracts were washed with brine, dried over MgSO₄ and concentrated to dryness. The crude mixture was purified by preparative LC (irregular SiOH, 15-40 µm, 40 g GraceResolv™, liquid injection (DCM), mobile phase gradient: heptane/EtOAc from 90:10 to 50:50) to afford intermediate I45 (260 mg, 33%) as a yellowish solid.

Intermediate I46

1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)-5-methylpyrrolidine-3-carboxylic acid

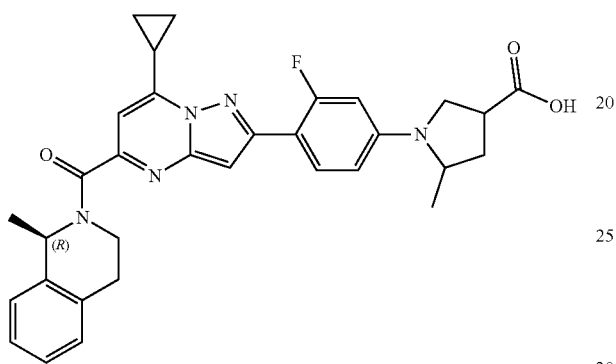

I46

Lithium hydroxide monohydrate (151 mg, 3.59 mmol) was added to a solution of intermediate I45 (680 mg, 1.20 mmol) in THF (27 mL) and H₂O (6.8 mL). The reaction mixture was stirred at rt for 16 h. A 10% aqueous solution of KHSO₄ was added until pH 6. The aqueous phase was extracted with EtOAc. The combined organic extracts were washed with H₂O, dried over MgSO₄, filtered and evaporated under reduced pressure. The crude mixture was purified by preparative LC (irregular SiOH, 15-40 μm, 40 g GraceResolv™, liquid injection (DCM), mobile phase gradient: heptane/EtOAc/AcOH from 80:19.5:0.5 to 40:58.5:1.5) to afford intermediate I46 (660 mg, quant.).

Compounds 32, 33, 34 and 35

(3*R,5*R)-1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)-5-methylpyrrolidine-3-carboxamide (3*R,5*S)-1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)-5-methylpyrrolidine-3-carboxamide (3*S,5*R)-1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)-5-methylpyrrolidine-3-carboxamide (3*S,5*S)-1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)-5-methylpyrrolidine-3-carboxamide

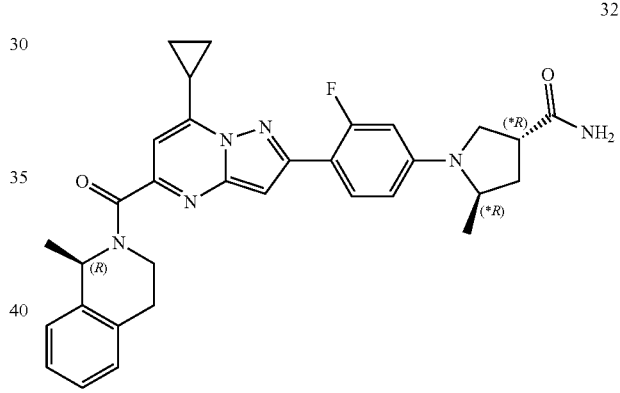

32

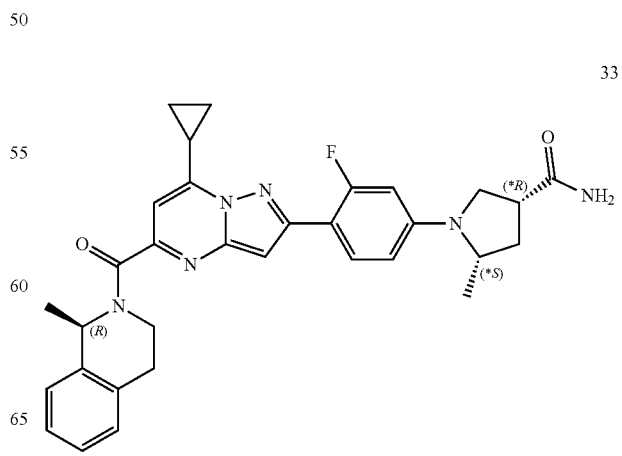

33

34

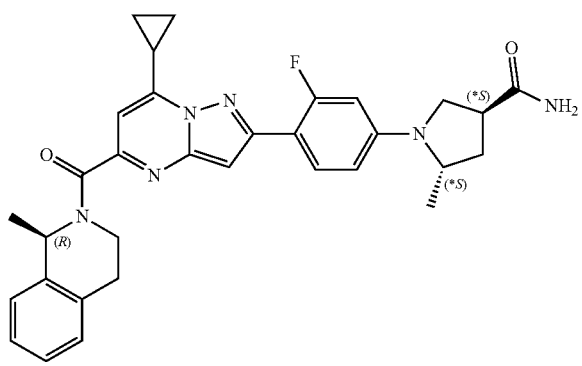

35

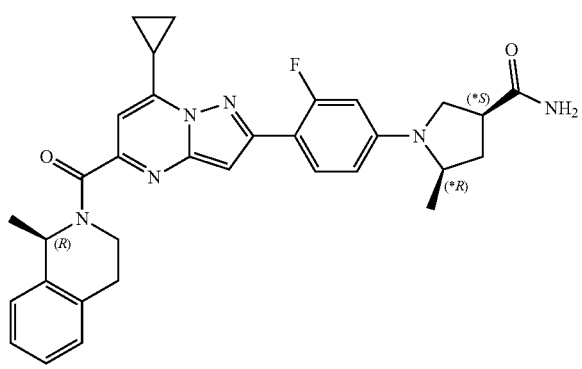

A mixture of intermediate I46 (660 mg, 1.19 mmol), HATU (680 mg, 1.79 mmol) and DIPEA (616 μL, 3.58 mmol) in DMF (20 mL) was stirred at rt for 1 h. Ammonia (28% in $H_2O$, 403 μL, 5.96 mmol) was added and the reaction mixture was stirred at rt for 18 h. The reaction mixture was diluted with $H_2O$ and EtOAc. The layers were separated and the organic phase was washed with a 1% aqueous solution of $NaHCO_3$ (twice), dried over $MgSO_4$, filtered and evaporated under reduced pressure. The crude mixture was purified by preparative LC (irregular SiOH, 15-40 μm, 80 g GraceResolv™, liquid injection (DCM), mobile phase gradient: DCM/i-PrOH from 100:0 to 80:20) to afford a mixture of diasteroisomers (550 mg, 83%) as a yellow oil.

The sample was combined with another sample (123 mg) and the diastereoisomers were separated via chiral SFC (Stationary phase: CHIRACEL OJ-H 5 μm 250*30 mm, Mobile phase: 58% $CO_2$, 42% MeOH (0.3% i-$PrNH_2$)). Four fractions (A, B, C and D) were isolated. After evaporation of the solvent, the residue of fraction A was taken up in EtOH, the solid was filtered off and dried under vacuum at 50° C. for 16 h to give compound 32 (94 mg, 11%). The residue of fraction B was crystallized from EtOAc, filtered off and dried under vacuum at 50° C. for 16 h to give compound 35 (168 mg, 20%). The residue of fraction C was crystallized from EtOAc. The solid was filtered off and dried under vacuum at 50° C. for 16 h to give compound 34 (94 mg, 11%). The residue of fraction D was taken-up in EtOH, the solid was filtered off and dried under vacuum at 50° C. for 16 h to give compound 33 (164 mg, 20%).

Compounds 80, 81, 82 and 83

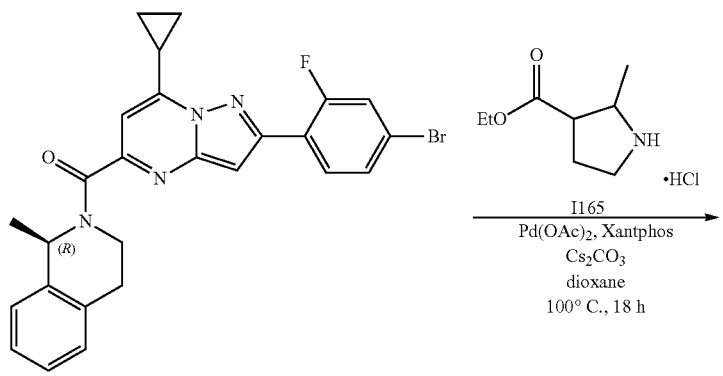

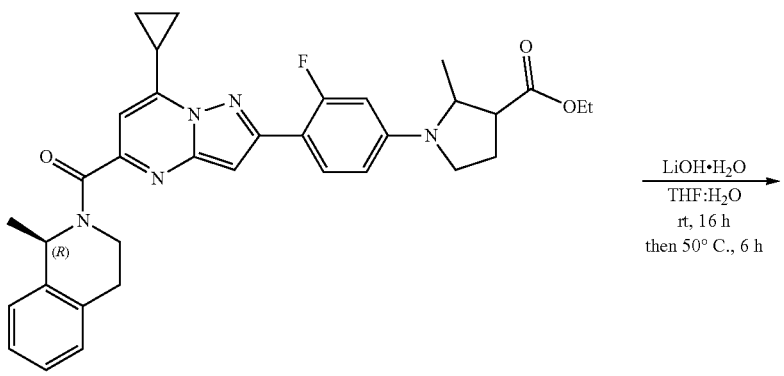

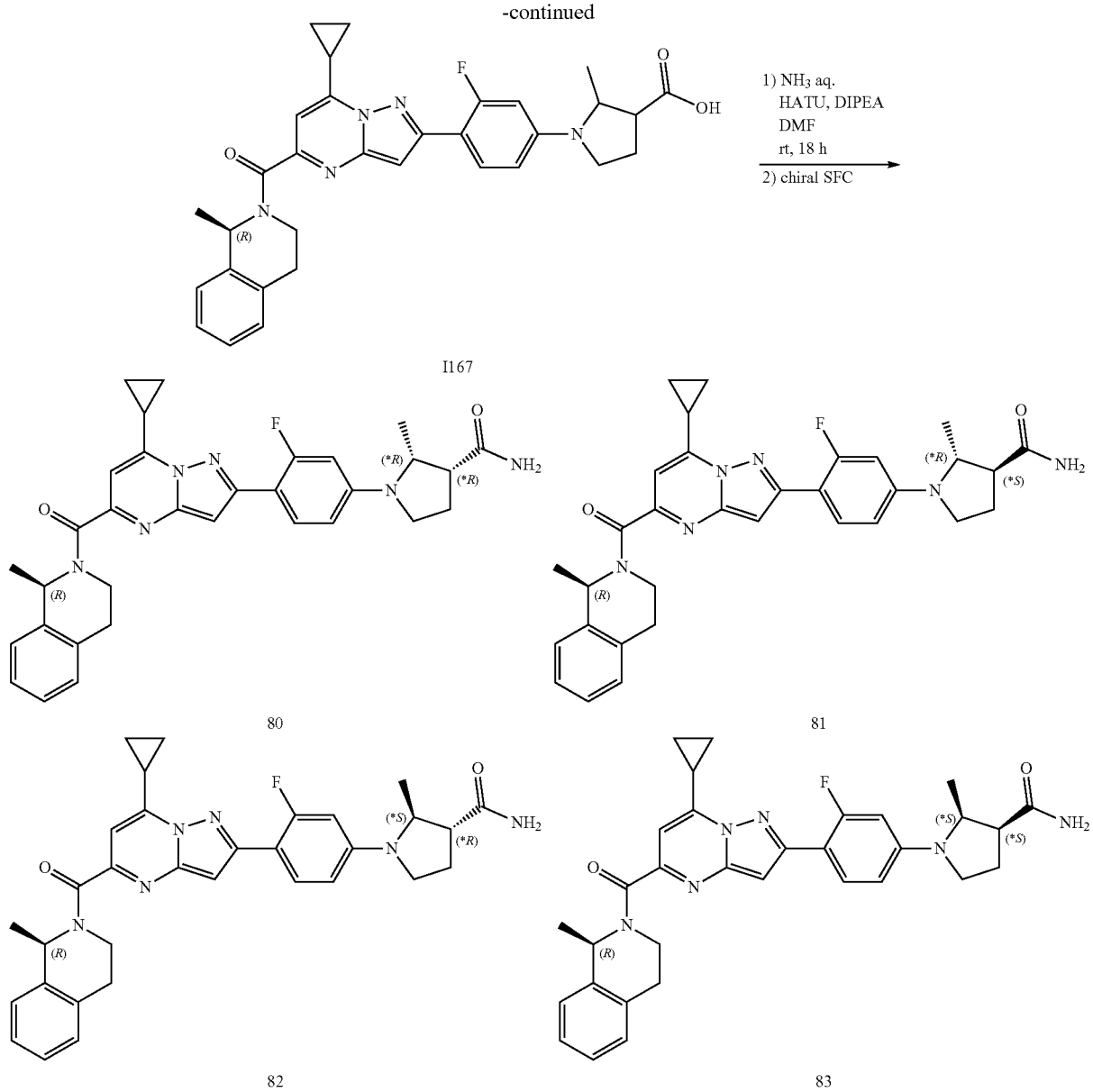

Synthesis of Intermediate I165

Ethyl 2-methylpyrrolidine-3-carboxylate hydrochloride

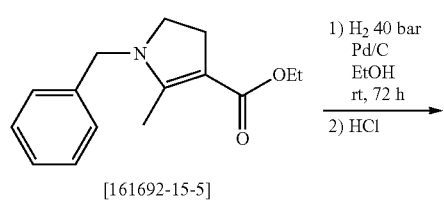

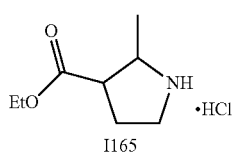

A mixture of ethyl 1-benzyl-2-methyl-4,5-dihydro-1H-pyrrole-3-carboxylate [161692-15-5] (3.60 g, 14.7 mmol) and Pd/C (10%, 1.56 g, 1.47 mmol) in EtOH (73 mL) was stirred at rt under hydrogen atmosphere (40 bars) for 72 h. The reaction mixture was filtered over a pad of Celite® and hydrogen chloride (3.0 M in CPME, 5.9 mL, 18 mmol) was added to the filtrate. The solvent was evaporated under vacuum to afford intermediate I165 (2.6 g, 91%). The product was engaged in the next step as such.

Synthesis of Compounds 80, 81, 82 and 83

Intermediate I166

Ethyl 1-(4-{7-cyclopropyl-5-[(1R)-1-methyl-1,2,3,4-tetrahydroisoquinoline-2-carbonyl]-pyrazolo[1,5-a]pyrimidin-2-yl}-3-fluorophenyl)-2-methylpyrrolidine-3-carboxylate

I166

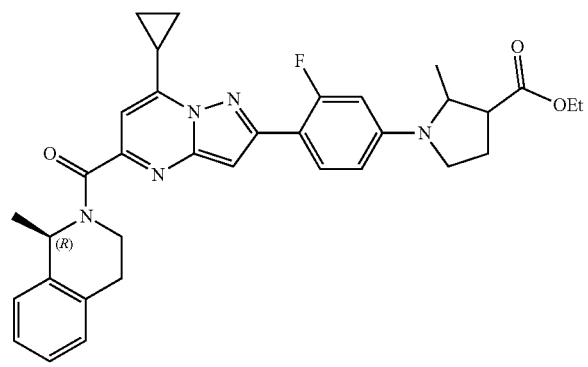

In a sealed tube were added (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (2.81 g, 5.56 mmol), intermediate I165 (1.40 g, 7.23 mmol) and cesium carbonate (5.44 g, 16.7 mmol). The mixture was purged with nitrogen. 1,4-Dioxane (45 mL) was added and the mixture was degassed with nitrogen. Palladium acetate (125 mg, 556 μmol) and XantPhos (322 mg, 556 μmol) were added. The reaction mixture was stirred at 100° C. for 18 h. The reaction mixture was poured out into water and the aqueous phase was extracted with EtOAc. The combined organic extracts were washed with brine, dried over MgSO₄, filtered and evaporated to dryness. The crude mixture was purified by preparative LC (irregular SiOH, 15-40 μm, 120 g GraceResolv™, liquid injection (DCM), mobile phase gradient: heptane/EtOAc from 90:10 to 60:40) to afford intermediate I166 (1.93 g, 60%) as a yellowish solid.

Intermediate I167

1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)-2-methylpyrrolidine-3-carboxylic acid

I167

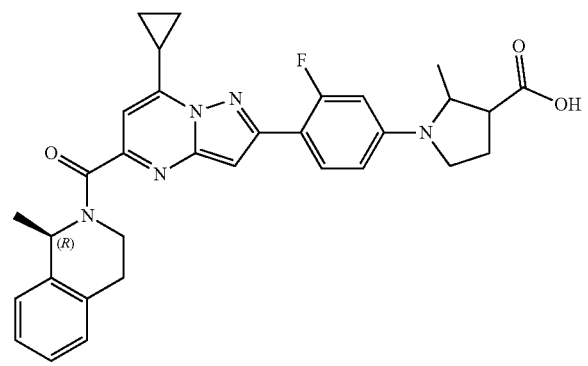

Lithium hydroxide monohydrate (995 mg, 23.7 mmol) was added to a solution of intermediate I166 (1.93 g, 3.32 mmol) in THF (34 mL) and H₂O (11 mL). The reaction mixture was stirred at rt for 16 h and at 50° C. for 6 h. A 10% aqueous solution of KHSO₄ was added until pH 6 and the aqueous phase was extracted with EtOAc. The combined organic extracts were washed with H₂O, dried over MgSO₄, filtered and concentrated in vacuo. The crude mixture was purified by preparative LC (irregular SiOH, 15-40 μm, 80 g GraceResolv™, liquid injection (DCM), mobile phase gradient: heptane/EtOAc/AcOH from 80:19.5:0.5 to 30:68:2 to afford intermediate I167 (1.59 g, 87%).

Compounds 80, 81, 82 and 83

(2*R,3*R)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-2-methylpyrrolidine-3-carboxamide (2*R,3*S)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-2-methylpyrrolidine-3-carboxamide (2*S,3*R)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-2-methylpyrrolidine-3-carboxamide (2*S,3*S)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-2-methylpyrrolidine-3-carboxamide

80

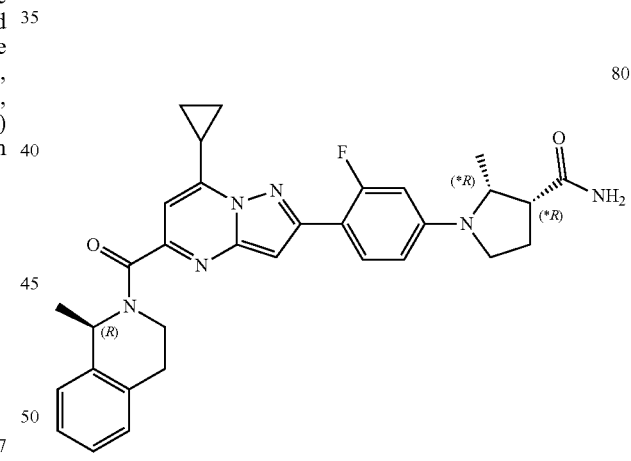

81

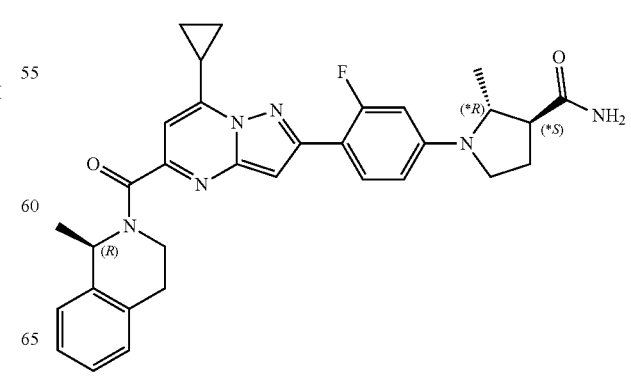

113

82

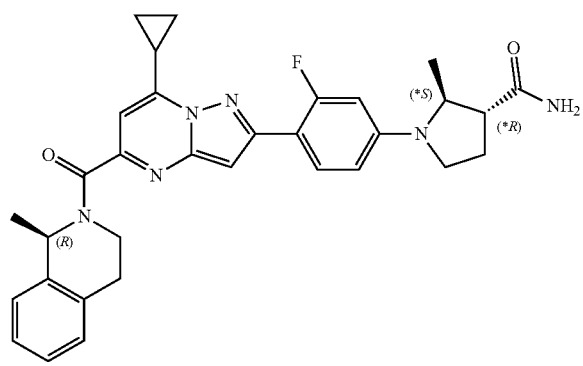

83

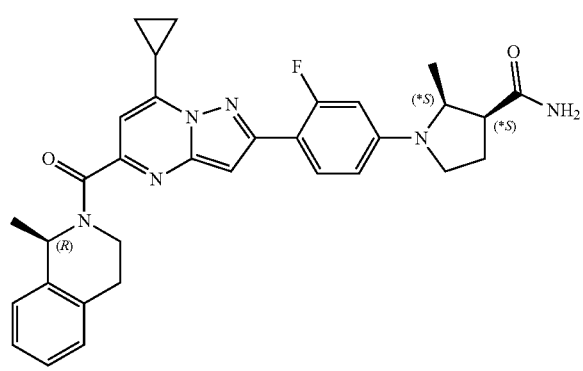

A mixture of intermediate I167 (1.59 g, 2.87 mmol), HATU (1.64 g, 4.31 mmol) and DIPEA (1.49 mL, 8.62 mmol) in DMF (48 mL) was stirred at rt for 1 h. Ammonia (28% in H₂O, 1.0 mL, 14.4 mmol) was added and the reaction mixture was stirred at rt for 18 h. The reaction mixture was diluted with H₂O and EtOAc. The layers were separated and the organic phase was washed with 1% aqueous solution of NaHCO₃ (twice), dried over MgSO₄, filtered and evaporated in vacuo. The crude mixture was purified by preparative LC (irregular SiOH, 15-40 µm, 80 g GraceResolv™, liquid injection (DCM), mobile phase gradient: DCM/i-PrOH from 100:0 to 80:20) to deliver a mixture of diastereoisomers (1.3 g, 82%). The diastereoisomers (700 mg) were separated by chiral SFC (Stationary phase: CHIRALPAK AS-H 5 µm 250*20 mm, Mobile phase: 60% CO₂, 40% MeOH (0.3% i-PrNH₂)). The separated diastereoisomers were taken up in Et₂O. The solid was filtered off and dried under vacuum at 50° C. for 16 h to give compound 81 (60 mg, 4%), compound 80 (180 mg, 11%) and compound 82 (65 mg, 4%). The last residue was taken up in EtOH. The solid was filtered off and dried under vacuum at 50° C. for 16 h to give compound 83 (215 mg, 14%).

General Scheme

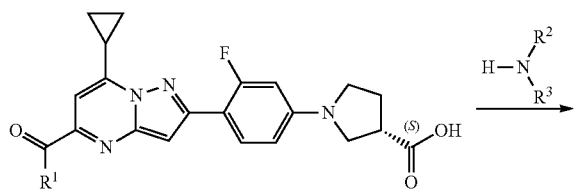

114

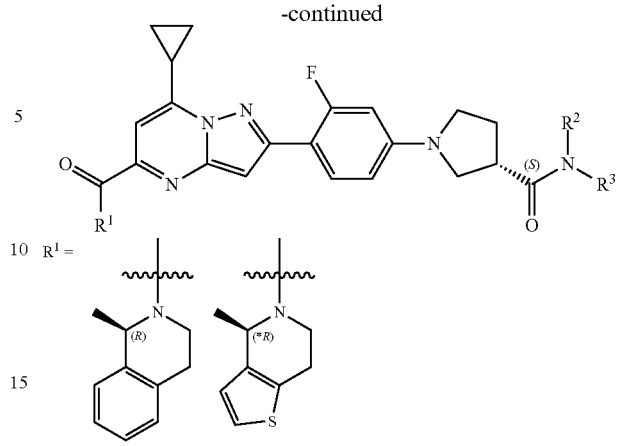

Compound 36

(3S)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidine-3-carboxamide

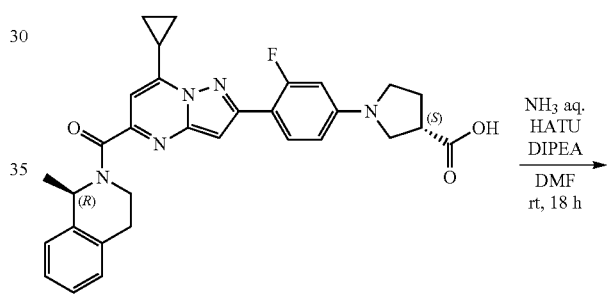

[2035416-78-3]

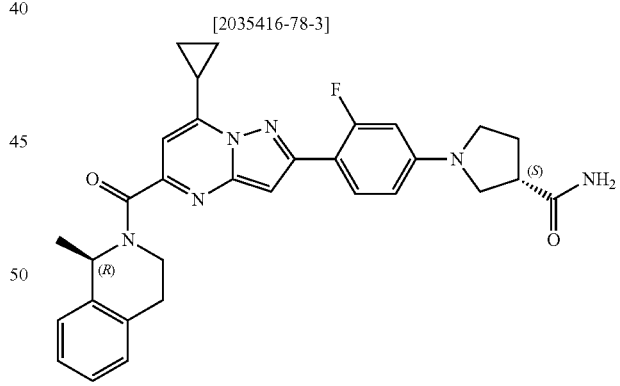

36

A mixture of (3S)-1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidine-3-carboxylic acid [2035416-78-3] (10.5 g, 18.4 mmol), HATU (10.5 g, 27.6 mmol) and DIPEA (10 mL, 58.0 mmol) in DMF (180 ml) was stirred at rt for 1 h. Ammonia (28% in H₂O, 15 mL, 222 mmol) was added and the reaction mixture was stirred at rt for 18 h. H₂O, brine and EtOAc were added. The layers were separated and the aqueous phase was extracted with EtOAc (twice). The combined organic extracts were washed

Compound 37

(3S)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)-N-methylpyrrolidine-3-carboxamide

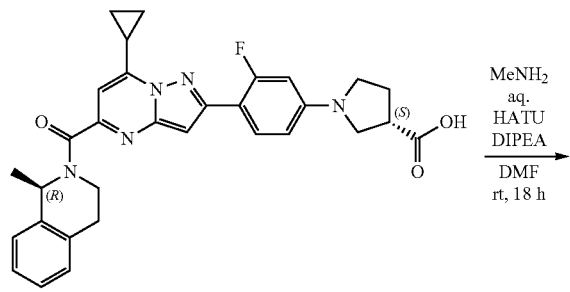

[2035416-78-3]

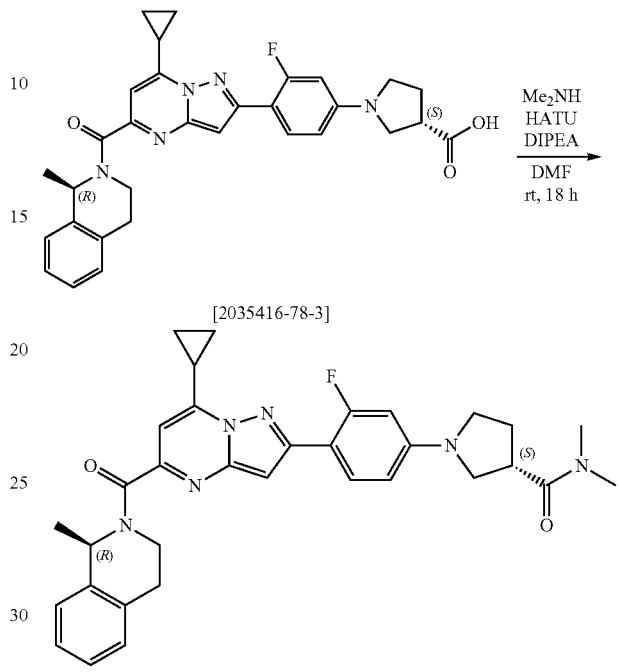

37

A mixture of (3S)-1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidine-3-carboxylic acid [2035416-78-3] (180 mg, 333 μmol), HATU (190 mg, 500 μmol) and DIPEA (172 μL, 1.00 mmol) in DMF (9 mL) was stirred at rt for 1 h. Methylamine (40% in H$_2$O, 144 μL, 1.67 mmol) was added and the reaction mixture was stirred at rt for 18 h. The reaction mixture was diluted with H$_2$O and EtOAc. The layers were separated and the organic phase was washed with a 1% aqueous solution of NaHCO$_3$ (twice), dried over MgSO$_4$, filtered and evaporated under reduced pressure. The crude mixture was purified by preparative LC (irregular SiOH, 15-40 μm, 40 g GraceResolv™, liquid injection (DCM), mobile phase gradient: DCM/i-PrOH from 100:0 to 80:20) to give compound 37 (135 mg, 73%) as a yellow oil.

Compound 38

(3S)-1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)-N,N-dimethylpyrrolidine-3-carboxamide

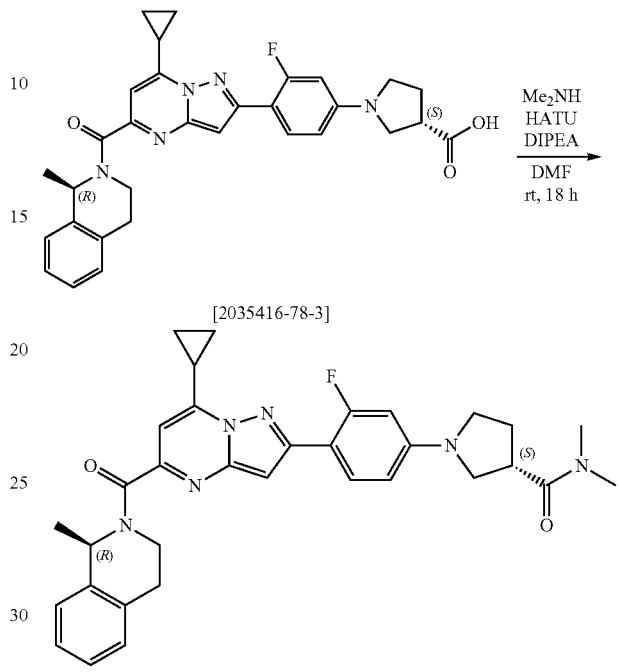

38

Compound 38 was synthesized from (3S)-1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidine-3-carboxylic acid [2035416-78-3] and dimethylamine (2.0 M in THF) [124-40-3] according to the procedure reported for the synthesis of compound 37. The crude mixture was purified by preparative LC (irregular SiOH, 15-40 μm, 24 g GraceResolv™, liquid injection (DCM), mobile phase gradient: heptane/EtOAc from 40:60 to 0:100) to give compound 38 (102 mg, 54%) as a yellow oil.

Compound 39

(3S)—N-Cyano-1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidine-3-carboxamide

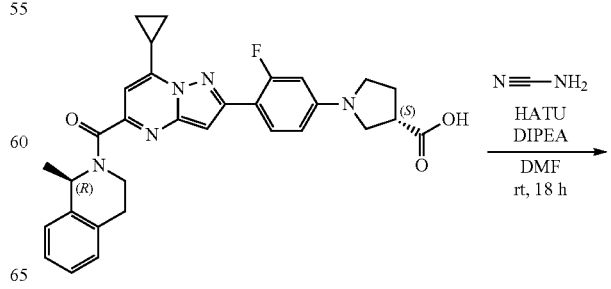

[2035416-78-3]

117

-continued

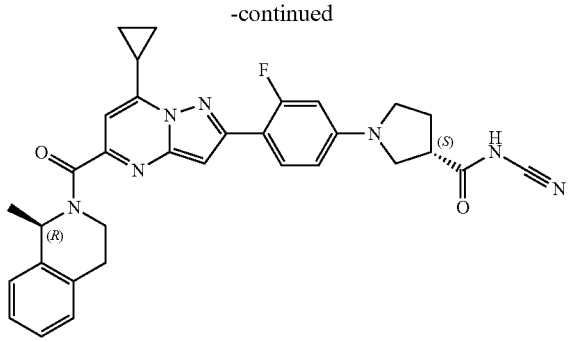

39

Compound 39 was synthesized from (3S)-1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)-pyrrolidine-3-carboxylic acid [2035416-78-3] and cyanamide [420-04-2] according to the procedure reported for the synthesis of compound 37. The crude mixture was purified by preparative LC (irregular SiOH, 15-40 μm, 24 g GraceResolv™, liquid injection (DCM), mobile phase gradient: DCM/i-PrOH from 100:0 to 50:50) to give a yellow oil (90 mg). A second purification was performed by preparative LC (spherical C18, 25 μm, 40 g YMC-ODS-25, dry loading (Celite®), mobile phase gradient: (0.2% aq.NH$_4$HCO$_3$)/MeCN from 85:15 to 45:55) to give after freeze-drying compound 39 (70.0 mg, 27%) as a yellow solid.

Compound 40

(3S)-1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)-N-methanesulfonylpyrrolidine-3-carboxamide

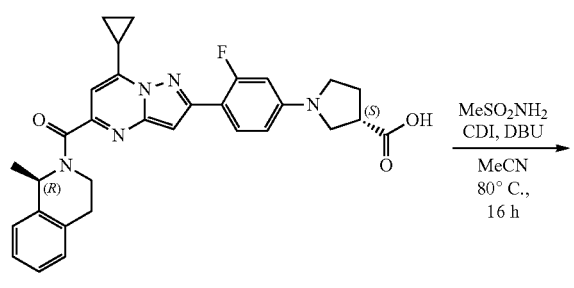

118

A mixture of (3S)-1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)pyrrolidine-3-carboxylic acid [2035416-78-3] (200 mg, 371 μmol) and CDI (180 mg, 1.11 mmol) in MeCN (5 mL) was stirred at rt for 2 h. DBU (221 μL, 1.48 mmol) and methanesulfonamide [3144-09-0] (141 mg, 1.48 mmol) were added and the reaction mixture was stirred at 80° C. for 16 h. Brine, 1N aqueous solution of HCl and EtOAc were added. The layers were separated and the aqueous phase was extracted with EtOAc (twice). The combined organic extracts were washed with a solution of water and brine (1:1), dried over MgSO$_4$, filtered and evaporated under reduced pressure. The crude mixture was purified by preparative LC (spherical C18, 25 μm, 40 g YMC-ODS-25, dry loading (Celite®), mobile phase gradient: (0.2% aq.NH$_4$HCO$_3$)/MeCN from 85:15 to 45:55). The fractions containing the product were combined and 1N aqueous solution of HCl and EtOAc were added. The layers were separated and the aqueous phase was extracted. The organic phase was washed with brine, dried over MgSO$_4$, filtered and evaporated under reduced pressure. The mixture was purified by preparative LC (spherical C18 25 μm, 40 g YMC-ODS-25, dry loading (Celite®), mobile phase gradient (0.2% aq.NH$_4$HCO$_3$)/MeCN from 75:25 to 50:50). The residue (182 mg) was dissolved in MeCN (5 mL) and CDI (180 mg, 1.11 mmol) was added. The mixture was stirred at rt for 2 h and DBU (221 μL, 1.48 mmol) and methanesulfonamide (141 mg, 1.48 mmol) were added. The reaction mixture was stirred at 80° C. for 16 h. Brine, an aqueous solution of 1N HCl and EtOAc were added. The layers were separated and the aqueous phase was extracted with EtOAc (twice). The combined organic extracts were washed with a solution of water and brine (1:1), dried over MgSO$_4$, filtered and evaporated under reduced pressure. The crude mixture was purified by preparative LC (spherical C18 25 μm, 40 g YMC-ODS-25, dry loading (Celite®), mobile phase gradient: (0.2% aq.NH$_4$HCO$_3$)/MeCN from 85:15 to 45:55) to give after freeze-drying compound 40 (131 mg, 57%) as a yellow solid.

Compound 41

(3S)-1-(4-{7-Cyclopropyl-5-[(4*R)-4-methyl-4,5,6,7-tetrahydro-thieno[3,2-c]pyridine-5-carbonyl]pyrazolo[1,5-a]pyrimidin-2-yl}-3-fluorophenyl)-N-methanesulfonylpyrrolidine-3-carboxamide

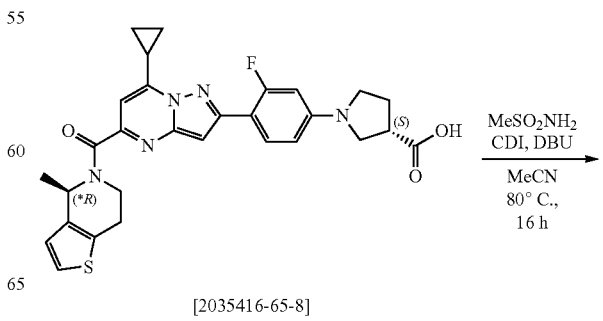

-continued

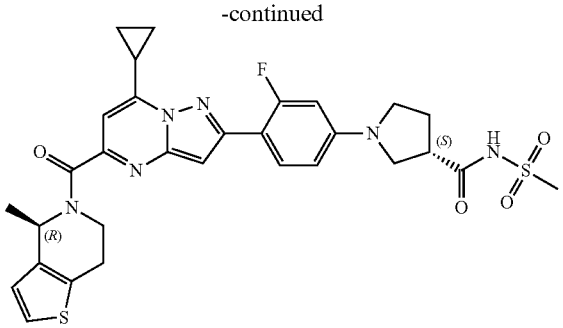

41

A mixture of (3S)-1-(4-{7-cyclopropyl-5-[(4*R)-4-methyl-4,5,6,7-tetrahydro-thieno[3,2-c]pyridine-5-carbonyl]pyrazolo[1,5-a]pyrimidin-2-yl}-3-fluorophenyl)pyrrolidine-3-carboxylic acid [2035416-65-8] (153 mg, 0.28 mmol) and CDI (54.6 mg, 0.34 mmol) in MeCN (3 mL) was stirred at rt for 2 h. DBU (62.8 µL, 0.42 mmol) and methanesulfonamide [3144-09-0] (40.0 mg, 0.42 mmol) were added. The resulting mixture was stirred at 80° C. for 16 h. Brine, 1N aqueous solution of HCl and DCM were added. The layers were separated and the aqueous phase was extracted with DCM (twice). The combined organic extracts were washed with a solution of water and brine (1:1), dried over MgSO₄, filtered and evaporated under reduced pressure. The crude mixture was purified by preparative LC (irregular SiOH 15-40 µm, 12 g GraceResolv™, liquid injection (DCM), mobile phase gradient: DCM/MeOH from 100:0 to 99:1). The residue was crystallized from MeOH, filtered off and dried under high vacuum at 50° C. for 18 h to give compound 41 (93 mg, 53%) as a yellow solid.

General Scheme

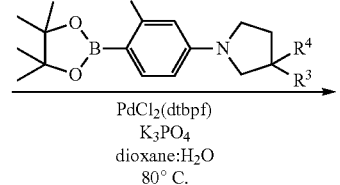

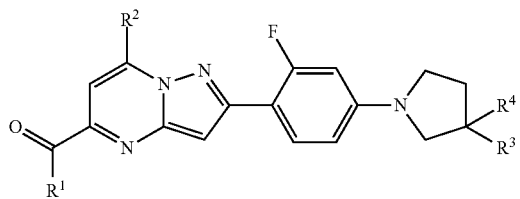

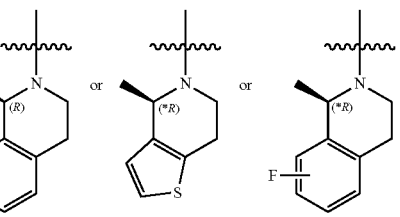

R² = cyclopropyl or 2-pyridine

Compound 84

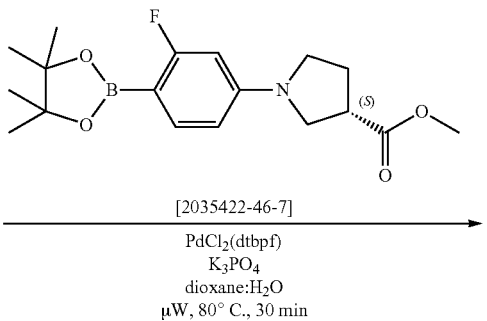

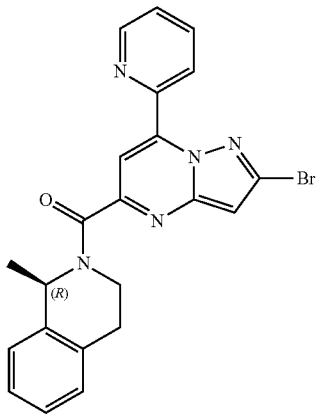

I168

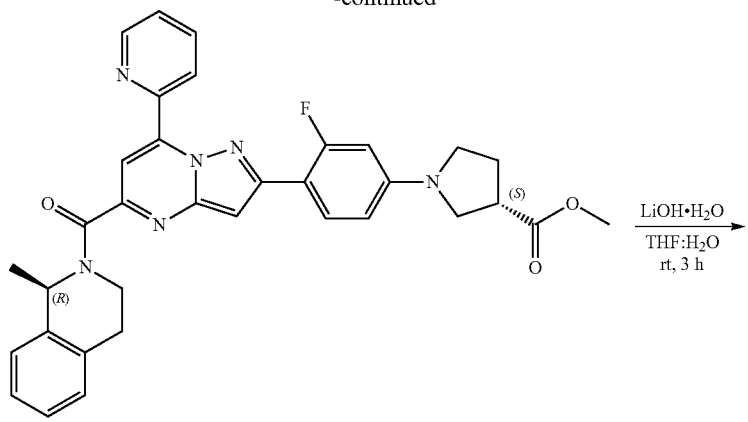
I169
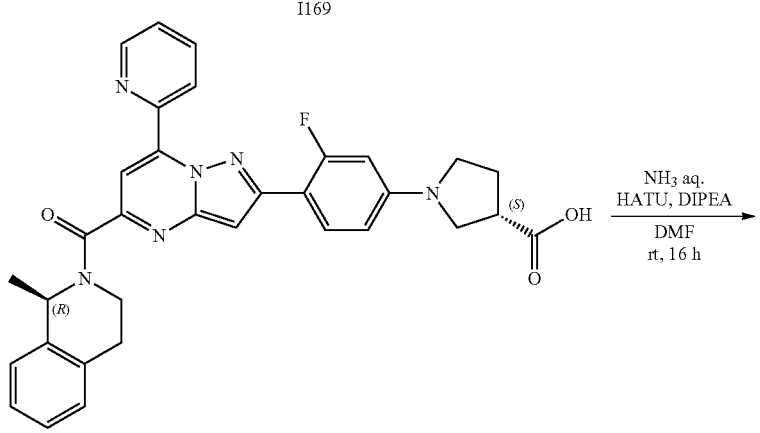
I170
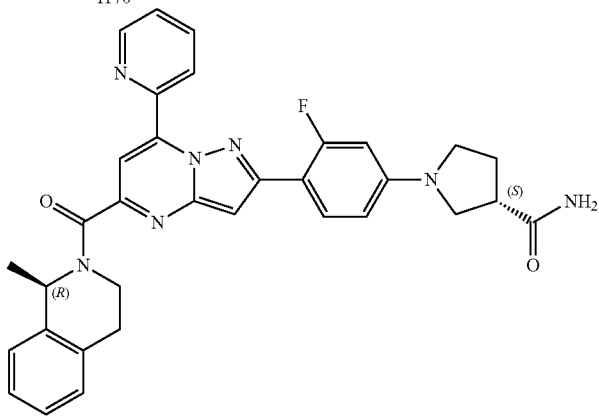
84
Synthesis of intermediate I168
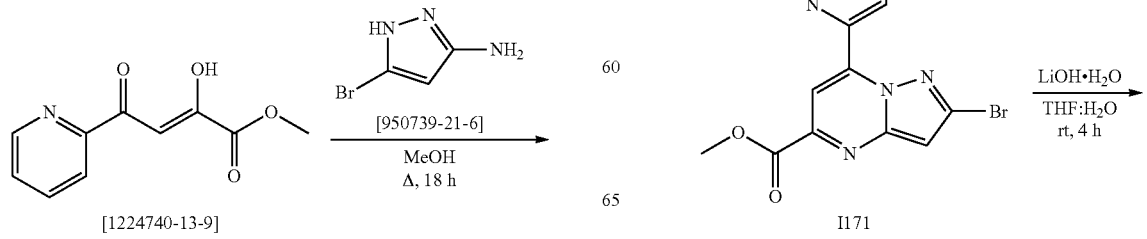

-continued

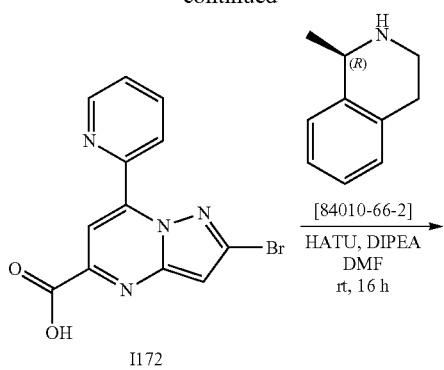

I172

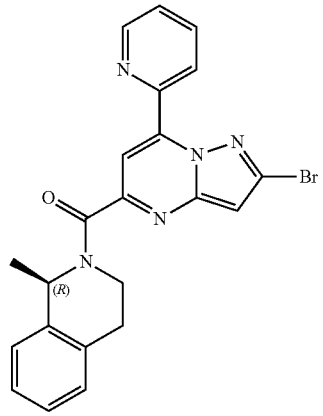

I168

Intermediate I171

Methyl 2-bromo-7-(pyridin-2-yl)pyrazolo[1,5-a]pyrimidine-5-carboxylate

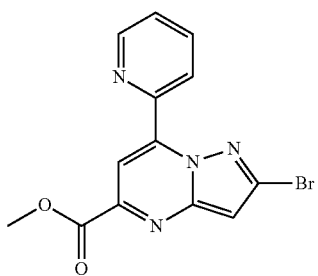

A mixture of methyl 2-hydroxy-4-oxo-4-(pyridin-2-yl)but-2-enoate [1224740-13-9] (730 mg, 3.52 mmol) and 3-bromo-1H-pyrazol-5-amine [950739-21-6] (628 mg, 3.88 mmol) in MeOH (17 mL) was stirred under reflux for 18 h. The reaction mixture was cooled to rt and the precipitate was filtered off, rinsed with MeOH and dried. The residue (546 mg) was purified via achiral SFC (Stationary phase: Lux Cellulose-2 5 µm 250*30 mm, mobile phase: 60% $CO_2$, 40% MeOH) to afford intermediate I171 (147 mg, 13%) as a yellow solid.

Intermediate I172

Methyl 2-bromo-7-(pyridin-2-yl)pyrazolo[1,5-a]pyrimidine-5-carboxylic acid

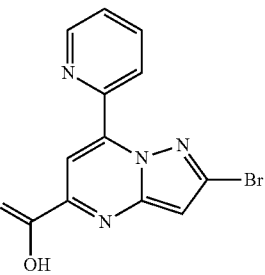

Lithium hydroxide monohydrate (21.1 mg, 883 µmol) was added to a solution of intermediate I171 (147 mg, 0.44 mmol) in THF (5 mL) and $H_2O$ (2.5 mL). The reaction mixture was stirred at rt for 4 h. A 10% aqueous solution of $KHSO_4$ was added until pH 3 and the mixture was diluted with EtOAc. The layers were separated and the organic phase was washed with brine and $H_2O$ (twice), dried over $MgSO_4$, filtered and concentrated to dryness to afford intermediate I172 (134 mg, 95%) as a yellow solid.

Intermediate I168

(1R)-2-[2-Bromo-7-(pyridin-2-yl)pyrazolo[1,5-a]pyrimidine-5-carbonyl]-1-methyl-1,2,3,4-tetrahydroisoquinoline

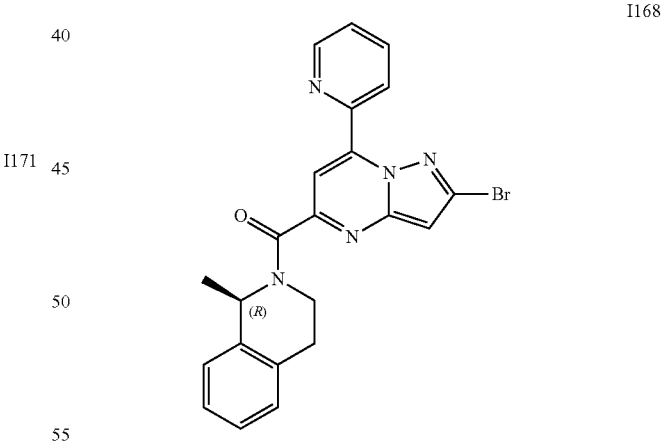

HATU (207 mg, 546 µmol) was added to a mixture of intermediate I172 (134 mg, 420 µmol), (1R)-1-methyl-1,2,3,4-tetrahydroisoquinoline [84010-66-2] (68.0 mg, 462 µmol) and DIPEA (220 µL, 1.26 mmol) in DMF (3.8 mL). The reaction mixture was stirred at rt for 16 h. The reaction mixture was diluted with $H_2O$. The layers were separated and the aqueous phase was extracted with EtOAc. The combined organic extracts were washed with brine (3 times), dried over $MgSO_4$, filtered and evaporated to dryness. The crude mixture was purified by flash chromatography (irregular SiOH, 15-40 µm, 12 g GraceResolv™, dry loading (SiOH), mobile phase gradient: heptane/EtOAc from 90:10 to 60:40) to afford intermediate I168 (113 mg, 60%) as a yellow solid.

Synthesis of Compound 84

Intermediate I169

Methyl (3S)-1-(3-fluoro-4-{5-[(1R)-1-methyl-1,2,3,4-tetrahydroisoquinoline-2-carbonyl]-7-(pyridin-2-yl)pyrazolo[1,5-a]pyrimidin-2-yl}phenyl)pyrrolidine-3-carboxylate

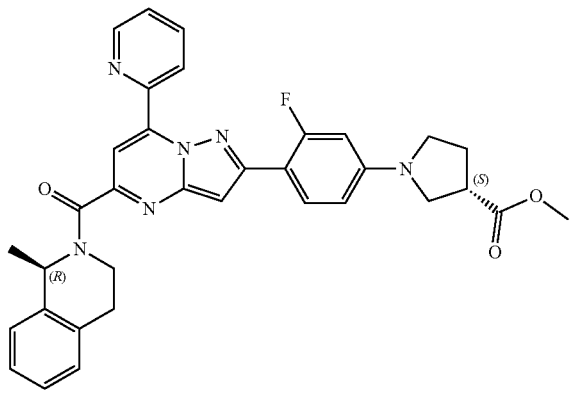

I169

A sealed tube was charged with intermediate I168 (98.0 mg, 219 µmol), methyl (3S)-1-[3-fluoro-4-(tetramethyl-1,3,2-dioxaborolan-2-yl)phenyl]pyrrolidine-3-carboxylate [2035422-46-7] (84.0 mg, 0.24 mmol), potassium phosphate tribasic (141 mg, 0.67 mmol), 1,4-dioxane (3.2 mL) and H₂O (0.6 mL) and purged with nitrogen. [1,1'-Bis(di-tert-butylphosphino)ferrocene]palladium dichloride (14.5 mg, 22.3 µmol) was added and the mixture was purged again with nitrogen. The reaction mixture was heated at 80° C. using a single mode microwave (Biotage® Initiator EXP 60) with a power output ranging from 0 to 400 W for 30 min. The reaction mixture was combined with another fraction (15 mg, 33.5 µmol) and diluted with H₂O and EtOAc. The layers were separated and the organic phase was washed with brine (twice), dried over MgSO₄, filtered and concentrated in vacuo. The crude mixture was purified by flash chromatography (irregular SiOH, 15-40 µm, 12 g GraceResolv™, dry loading (SiOH), mobile phase gradient: heptane/EtOAc from 70:30 to 0:100) to afford intermediate I169 (113 mg, 75%) as an orange foam.

Intermediate I170

(3S)-1-(3-Fluoro-4-{5-[(1R)-1-methyl-1,2,3,4-tetrahydroisoquinoline-2-carbonyl]-7-(pyridin-2-yl)pyrazolo[1,5-a]pyrimidin-2-yl}phenyl)pyrrolidine-3-carboxylic acid

I170

Lithium hydroxide monohydrate (13.7 mg, 574 µmol) was added to a solution of intermediate I169 (113 mg, 191 µmol) in THF (1.2 mL) and H₂O (0.6 mL). The reaction mixture was stirred at rt for 3 h. A 10% aqueous solution of KHSO₄ was added until pH 3 and the mixture was diluted with EtOAc. The layers were separated and the organic phase was washed with brine and H₂O (twice), dried over MgSO₄, filtered and concentrated to dryness to afford intermediate I170 (117 mg, quant., 95% purity) as an orange solid.

Compound 84

(3S)-1-(3-Fluoro-4-{5-[(1R)-1-methyl-1,2,3,4-tetrahydroisoquinoline-2-carbonyl]-7-(pyridin-2-yl)pyrazolo[1,5-a]pyrimidin-2-yl}phenyl)pyrrolidine-3-carboxamide

84

A mixture of intermediate I170 (117 mg, 193 µmol, 95% purity), HATU (110 mg, 289 µmol) and DIPEA (100 µL, 578

μmol) in DMF (1.9 mL) was stirred at rt for 10 min. Ammonia (30% in H₂O, 365 μL, 5.78 mmol) was added and the reaction mixture was stirred at rt for 16 h. The reaction mixture was diluted with EtOAc and H₂O. The layers were separated and the organic phase was washed with H₂O and brine (twice), dried over MgSO₄, filtered and concentrated in vacuo. The crude mixture was purified by flash chromatography (irregular SiOH, 15-40 μm, 12 g GraceResolv™, liquid injection (DCM), mobile phase gradient: heptane/EtOAc from 50:50 to 0:100). The residue (88 mg) was purified by reverse phase (spherical C18, 25 μm, 40 g YMC-ODS-25, dry loading (Celite®), mobile phase gradient: (0.2% aq.NH₄HCO₃)/MeCN from 65:35 to 0:100). The fractions containing the product were combined, concentrated to dryness and co-evaporated with MeOH and MeCN (twice). The solid was dried under high vacuum at 60° C. for 16 h to give compound 84 (58 mg, 52%) as an orange solid.

Compound 42 and Compound 43

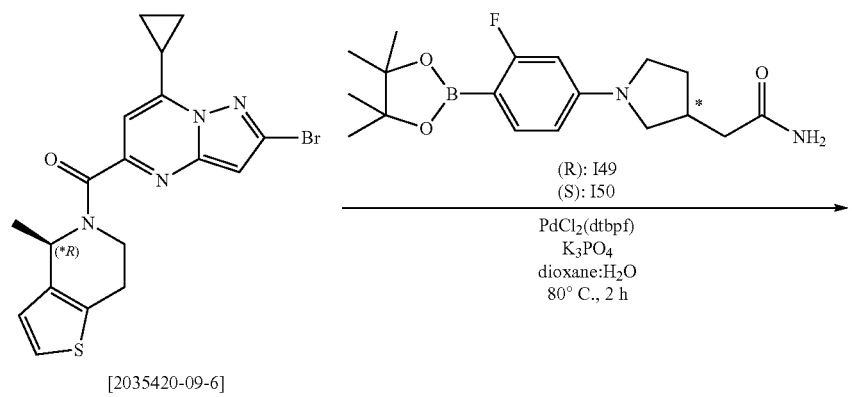

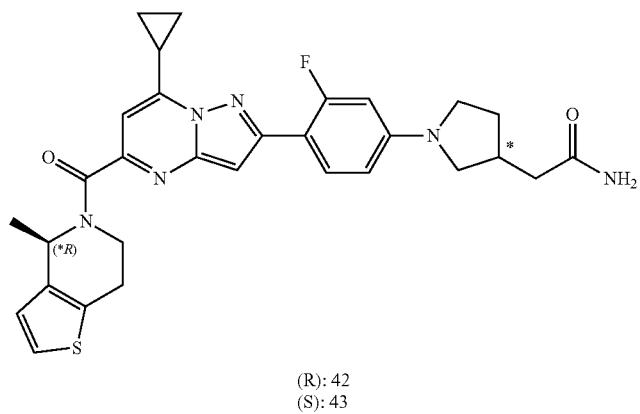

(R): 42
(S): 43

Synthesis of the Intermediates I49 and I50

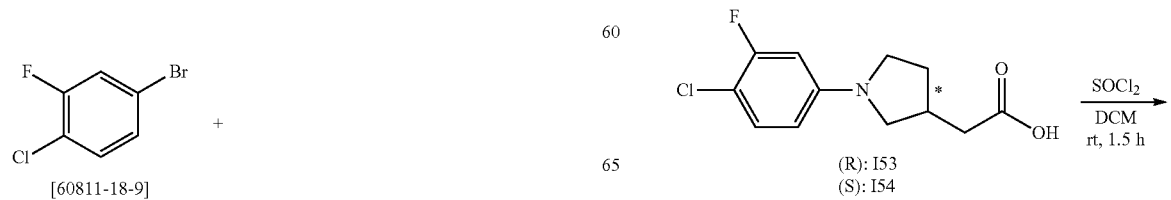

-continued

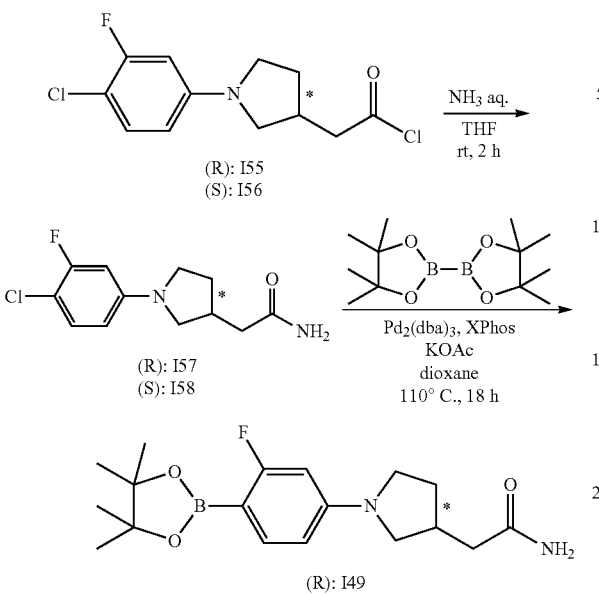

(R): I55
(S): I56

(R): I57
(S): I58

(R): I49
(S): I50

Intermediate I51

Methyl 2-[(3R)-1-(4-chloro-3-fluorophenyl)pyrrolidin-3-yl]acetate

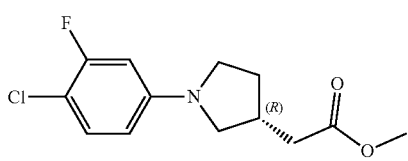

I51

A Schlenk tube was charged with 4-bromo-1-chloro-2-fluorobenzene [60811-18-9] (1.02 mL, 8.35 mmol), potassium phosphate tribasic (4.73 g, 22.3 mmol), methyl (3R)-3-pyrrolidinylacetate hydrochloride [1024038-31-0] (1.00 g, 5.57 mmol) and 1,4-dioxane (45 mL) and purged with nitrogen for 5 min. Tri-tert-butylphosphonium tetrafluoroborate (0.16 g, 0.56 mmol) and palladium acetate (62.5 mg, 0.28 mmol) were added and the reaction mixture was purged with nitrogen for 2 min. The reaction mixture was stirred at 100° C. for 18 h. The reaction mixture was diluted with EtOAc and H$_2$O. The layers were separated and the aqueous phase was extracted with EtOAc (twice). The combined organic extracts were dried over MgSO$_4$, filtered and the solvent was removed under reduced pressure. The crude mixture was purified by preparative LC (irregular SiOH, 15-40 μm, 40 g GraceResolv™, liquid injection (DCM/heptane), mobile phase gradient: heptane/EtOAc from 80:20 to 60:40) to afford intermediate I51 (880 mg, 58%) as a colorless oil.

Intermediate I52

Methyl 2-[(3S)-1-(4-chloro-3-fluorophenyl)pyrrolidin-3-yl]acetate

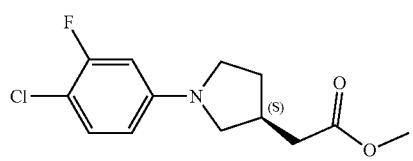

I52

Intermediate I52 was synthesized from 4-bromo-1-chloro-2-fluorobenzene [60811-18-9] and methyl (3S)-3-pyrrolidinylacetate hydrochloride [1024038-33-2] according to the procedure reported for the synthesis of intermediate I51. The crude mixture was purified by preparative LC (irregular SiOH, 15-40 μm, 40 g GraceResolv™, dry loading (SiOH), mobile phase: heptane/EtOAc 80:20) to afford intermediate I52 (830 mg, 55%) as a colorless oil.

Intermediate I53

2-[(3R)-1-(4-Chloro-3-fluorophenyl)pyrrolidin-3-yl]acetic acid

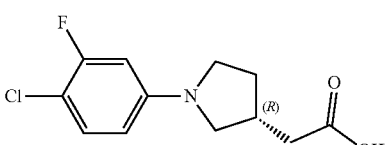

I53

Intermediate I51 (880 mg, 3.24 mmol) was solubilized in THF (10 mL) and a solution of lithium hydroxide monohydrate (680 mg, 16.2 mmol) in H$_2$O (5 mL) was added. The reaction mixture was stirred at rt for 3 days. A 10% aqueous solution of KHSO$_4$ and EtOAc were added. The layers were separated and the aqueous phase was extracted with EtOAc (twice). The combined organic extracts were dried over MgSO$_4$, filtered and evaporated under reduced pressure to afford intermediate I53 (840 mg, quant.) as a white solid.

Intermediate I54

2-[(3S)-1-(4-Chloro-3-fluorophenyl)pyrrolidin-3-yl]acetic acid

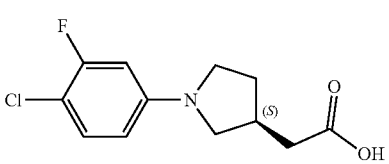

I54

Intermediate I54 was synthesized from intermediate I52 according to the procedure reported for the synthesis of intermediate I53. Intermediate I54 (800 mg, quant.) was obtained as a white solid.

Intermediate I55

2-[(3R)-1-(4-Chloro-3-fluorophenyl)pyrrolidin-3-yl]acetyl chloride

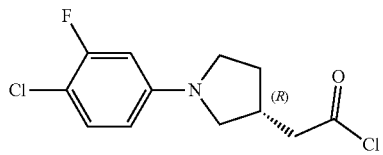

Thionyl chloride (307 µL, 4.24 mmol) was added to a solution of intermediate I53 (840 mg, 3.26 mmol) in DCM (30 mL). The reaction mixture was stirred at rt for 90 min. The mixture was evaporated under reduced pressure to afford intermediate I55 (900 mg, quant.). The product was used in the next step without any purification.

Intermediate I56

2-[(3S)-1-(4-Chloro-3-fluorophenyl)pyrrolidin-3-yl]acetyl chloride

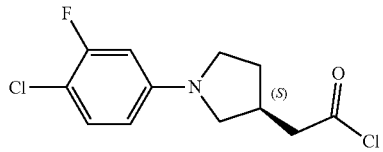

Intermediate I56 (856 mg, quant.) was synthesized from intermediate I54 according to the procedure reported for the synthesis of intermediate I55.

Intermediate I57

2-[(3R)-1-(4-Chloro-3-fluorophenyl)pyrrolidin-3-yl]acetamide

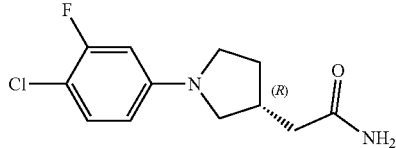

Ammonia (28% in H$_2$O, 30 mL, 444 mmol) was added to a solution of intermediate I55 (900 mg, 3.26 mmol) in THF (30 mL). The reaction mixture was stirred at rt for 2 h. The reaction mixture was diluted with brine and EtOAc. The layers were separated and the aqueous phase was extracted with EtOAc (twice). The combined organic extracts were dried over MgSO$_4$, filtered and evaporated under reduced pressure. The crude mixture was purified by preparative LC (irregular SiOH, 15-40 µm, 24 g GraceResolv™, liquid injection (DCM), mobile phase gradient: DCM/MeOH/aq.NH$_3$ from 100:0:0 to 90:10:1) to afford intermediate I57 (588 mg, 63%, 90% purity) as a white solid.

Intermediate I58

2-[(3S)-1-(4-Chloro-3-fluorophenyl)pyrrolidin-3-yl]acetamide

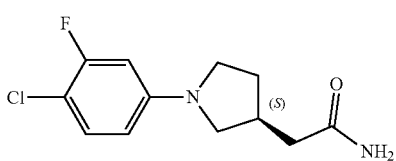

Intermediate I58 was synthesized from intermediate I56 according to the procedure reported for the synthesis of intermediate I57. Intermediate I58 (741 mg, 85%, 91% purity) was obtained as a white solid.

Intermediate I49

2-[(3R)-1-[3-Fluoro-4-(tetramethyl-1,3,2-dioxaborolan-2-yl)phenyl]pyrrolidin-3-yl]acetamide

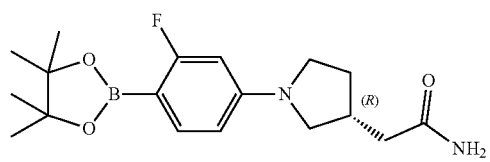

A sealed tube was charged with intermediate I57 (541 mg, 2.11 mmol), bis(pinacolato)diboron (0.64 g, 2.53 mmol), acetic acid potassium salt (0.41 g, 4.22 mmol) and 1,4-dioxane (14 mL) and purged with nitrogen for 10 min. XPhos (301 mg, 0.63 mmol) and tris(dibenzylideneacetone)dipalladium (193 mg, 0.21 mmol) were added and the reaction mixture was purged with nitrogen. The reaction mixture was stirred at 110° C. for 18 h. The reaction mixture was filtered over Celite®. EtOAc and brine were added to the filtrate. The layers were separated and the aqueous phase was extracted with EtOAc (twice). The combined organic extracts were dried over MgSO$_4$, filtered and evaporated under reduced pressure. The crude mixture was purified by preparative LC (irregular SiOH, 15-40 µm, 24 g GraceResolv™, dry loading (SiOH), mobile phase gradient: DCM/MeOH/aq.NH$_3$ from 100:0:0 to 90:10:1) to afford intermediate I49 (587 mg, 67%, 84% purity) as a grey solid.

Intermediate I50

2-[(3S)-1-[3-Fluoro-4-(tetramethyl-1,3,2-dioxaborolan-2-yl)phenyl]pyrrolidin-3-yl]acetamide

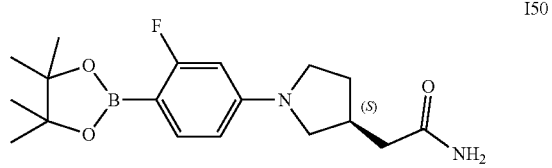

Intermediate I50 was synthesized from intermediate I58 according to the procedure reported for the synthesis of intermediate I49. Intermediate I50 (935 mg, 77%, 83% purity) was obtained as a grey solid.

Synthesis of Compounds 42 and 43

Compound 42

2-[(3R)-1-(4-{7-Cyclopropyl-5-[(4*R)-4-methyl-4,5,6,7-tetrahydro-thieno[3,2-c]pyridine-5-carbonyl]pyrazolo[1,5-a]pyrimidin-2-yl}-3-fluorophenyl)pyrrolidin-3-yl]acetamide

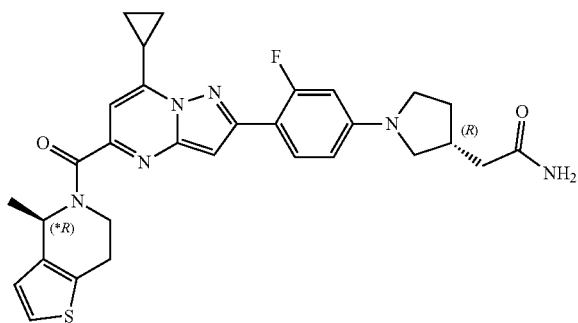

A sealed tube was charge with 2-bromo-7-cyclopropyl-5-[(4*R)-4-methyl-4,5,6,7-tetrahydro-thieno[3,2-c]pyridine-5-carbonyl]pyrazolo[1,5-a]pyrimidine [2035420-09-6] (200 mg, 0.479 mmol), intermediate I49 (278 mg, 0.67 mmol, 84% purity), potassium phosphate tribasic (305 mg, 1.44 mmol), 1,4-dioxane (6 mL) and H₂O (2 mL) and purged with nitrogen. [1,1'-Bis(di-tert-butylphosphino)ferrocene] dichloropalladium (31.2 mg, 47.9 μmol) was added and the reaction mixture was purged with nitrogen. The reaction mixture was stirred at 80° C. for 2 h. The reaction mixture was filtered over Celite®. EtOAc and brine were added to the filtrate. The layers were separated and the aqueous phase was extracted with EtOAc (twice). The combined organic extracts were dried over MgSO₄, filtered and evaporated under reduced pressure. The crude mixture was purified by preparative LC (irregular SiOH, 15-40 μm, 24 g GraceResolv™, liquid injection (DCM), mobile phase gradient: DCM/MeOH/aq.NH₃ from 100:0:0 to 96:4:0.4). The residue was co-evaporated with MeOH and triturated with MeOH. The solid was filtered off and dried under high vacuum at 50° C. for 24 h to give compound 42 (115 mg, 43%) as a yellow solid.

Compound 43

2-[(3S)-1-(4-{7-Cyclopropyl-5-[(4*R)-4-methyl-4,5,6,7-tetrahydro-thieno[3,2-c]pyridine-5-carbonyl]pyrazolo[1,5-a]pyrimidin-2-yl}-3-fluorophenyl)pyrrolidin-3-yl]acetamide

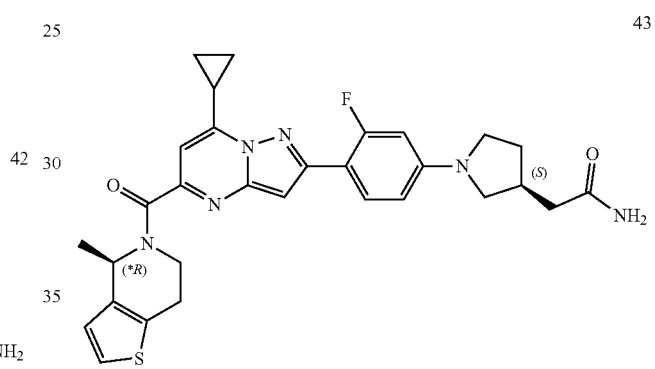

Compound 43 was synthesized from 2-bromo-7-cyclopropyl-5-[(4*R)-4-methyl-4,5,6,7-tetrahydro-thieno[3,2-c]pyridine-5-carbonyl]pyrazolo[1,5-a]pyrimidine [2035420-09-6] and intermediate I50 according to the procedure reported for the synthesis of compound 42. Compound 43 (161 mg, 60%) was obtained as a yellow solid.

Compound 44 and Compound 45

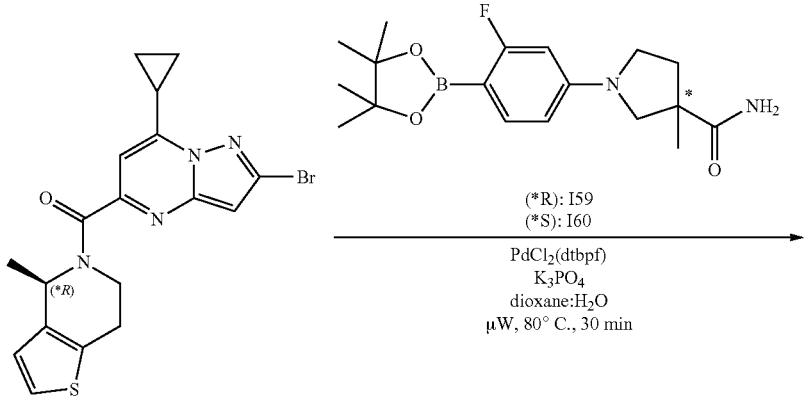

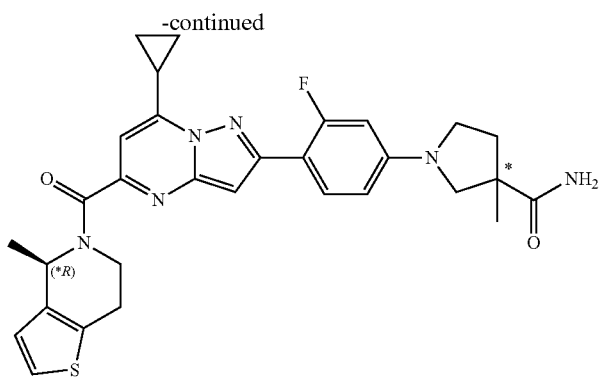
(*R, *R): 44
(*R, *S): 45
Synthesis of Intermediates I59 and I60
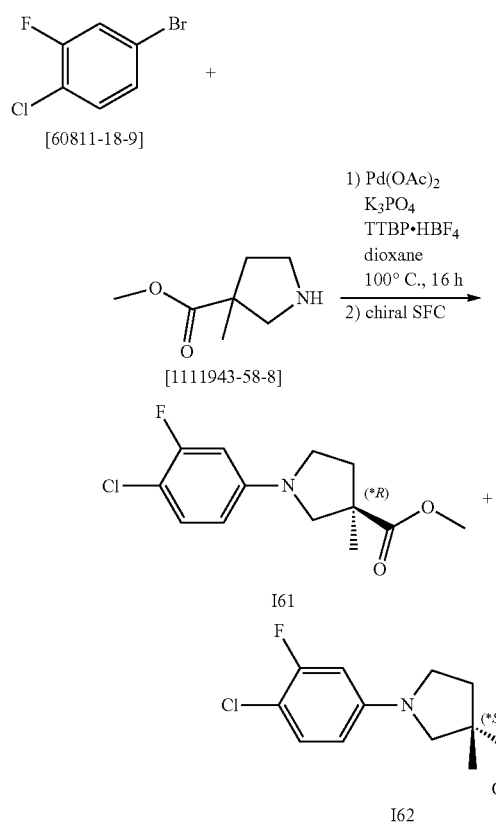
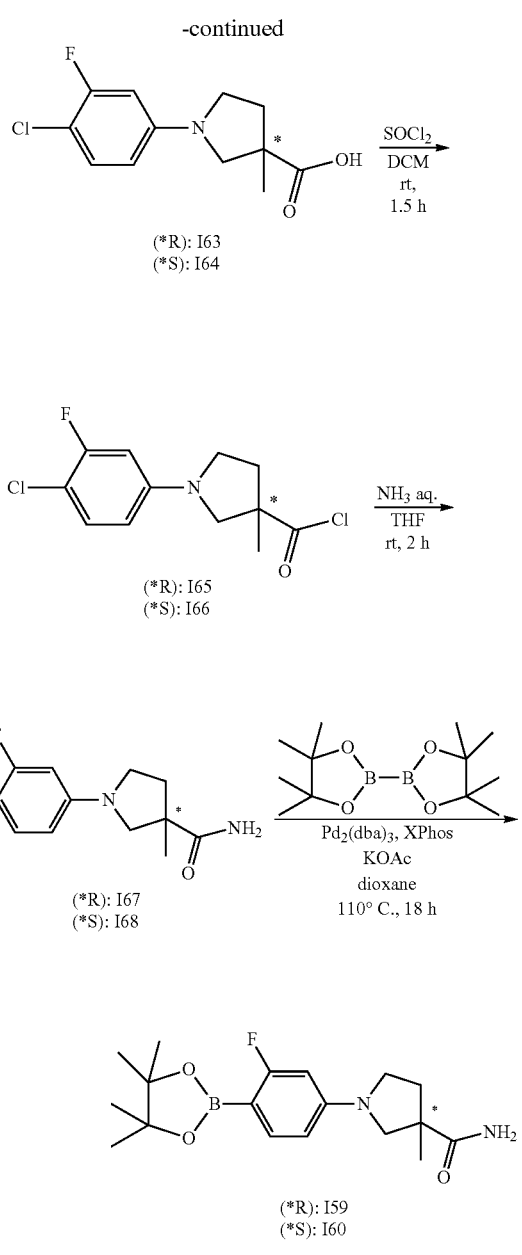

Intermediates I61 and I62

(*R)-Methyl 1-(4-chloro-3-fluorophenyl)-3-methylpyrrolidine-3-carboxylate (*S)-methyl 1-(4-chloro-3-fluorophenyl)-3-methylpyrrolidine-3-carboxylate

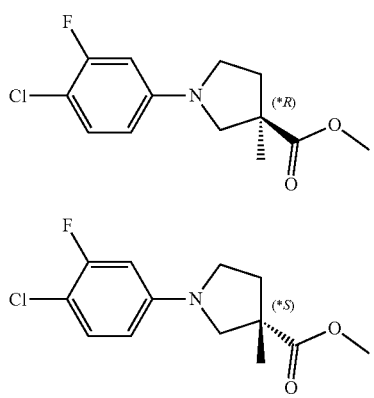

A sealed tube was charged with 4-bromo-1-chloro-2-fluorobenzene [60811-18-9] (4.0 mL, 32.8 mmol), potassium phosphate tribasic (15.3 g, 72.3 mmol), methyl 3-methylpyrrolidine-3-carboxylate [1111943-58-8] (3.45 g, 24.1 mmol), tri-tert-butylphosphonium tetrafluoroborate (638 mg, 2.20 mmol) and 1,4 dioxane (163 mL) and purged with nitrogen (3 times). Palladium acetate (247 mg, 1.10 mmol) was added and the reaction mixture was stirred at 100° C. for 16 h. The reaction mixture was diluted with EtOAc and H₂O. The layers were separated and the aqueous phase was extracted with EtOAc (twice). The combined organic extracts were washed with brine, dried over MgSO₄, filtered and evaporated under reduced pressure. The crude mixture was purified by preparative LC (irregular SiOH, 15-40 µm, 120 g GraceResolv™, liquid injection (heptane), mobile phase gradient: heptane/EtOAc from 100:0 to 70:30). The enantiomers (3.81 g) were separated via chiral SFC (Stationary phase: Whelk O1 (S,S) 5 µm 250*21.1 mm, Mobile phase: 90% CO₂, 10% MeOH) to afford I61 (1.7 g, 26%) as a colorless oil and I62 (1.67 g, 26%) as a colorless oil.

Intermediate I63

(3*R)-1-(4-Chloro-3-fluorophenyl)-3-methylpyrrolidine-3-carboxylic acid

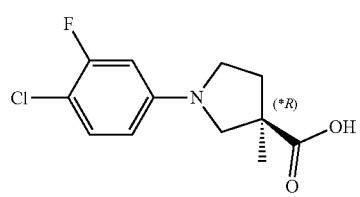

In a sealed tube lithium hydroxide monohydrate (344 mg, 8.19 mmol) was added to a solution of intermediate I61 (445 mg, 1.64 mmol) in THF (13 mL) and H₂O (6.5 mL). The reaction mixture was stirred at rt for 20 h. A 10% aqueous solution of KHSO₄ and EtOAc were added. The layers were separated and the aqueous phase was extracted with EtOAc (twice). The combined organic extracts were dried over MgSO₄, filtered and evaporated under reduced pressure. The residue (465 mg) was taken up in Et₂O and evaporated under reduced pressure to afford intermediate I63 (415 mg, 98%).

Intermediate I64

(3*S)-1-(4-Chloro-3-fluorophenyl)-3-methylpyrrolidine-3-carboxylic acid

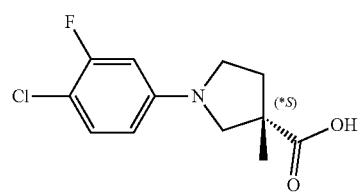

Intermediate I64 was synthesized from intermediate I62 according to the procedure reported for the synthesis of intermediate I63. Intermediate I64 (395 mg, 99%) was obtained as a yellow solid.

Intermediate I65

(3*R)-1-(4-Chloro-3-fluorophenyl)-3-methylpyrrolidine-3-carbonyl chloride

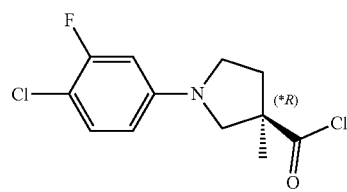

Thionyl chloride (145 µL, 2.00 mmol) was added to a solution of intermediate I63 (395 mg, 1.53 mmol) in DCM (14 mL). The reaction mixture was stirred at rt for 1.5 h. The mixture was evaporated under reduced pressure to afford intermediate I65 (423 mg, quant.). The product was used in the next step without any purification.

Intermediate I66

(3*S)-1-(4-Chloro-3-fluorophenyl)-3-methylpyrrolidine-3-carbonyl chloride

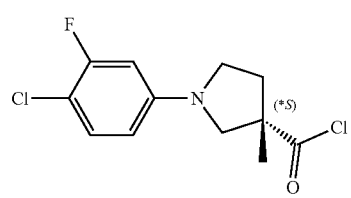

Intermediate I66 was synthesized from intermediate I64 according to the procedure reported for the synthesis of intermediate I65. Intermediate I66 (401 mg, quant.) was used in the next step without any purification.

Intermediate I67

(3*R)-1-(4-Chloro-3-fluorophenyl)-3-methylpyrrolidine-3-carboxamide

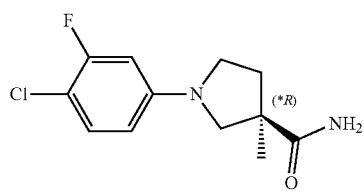

Ammonia (28% in $H_2O$, 14 mL, 207 mmol) was added to a solution of intermediate I65 (423 mg, 1.53 mmol) in THF (14 mL). The reaction mixture was stirred at rt for 2 h. The reaction mixture was diluted with brine and EtOAc. The layers were separated and the aqueous phase was extracted with EtOAc (twice). The combined organic extracts were dried over $MgSO_4$, filtered and evaporated under reduced pressure. The crude product was purified by preparative LC (irregular SiOH, 15-40 μm, 12 g GraceResolv™, liquid injection (DCM), mobile phase gradient: DCM/MeOH/aq.$NH_3$ from 100:0:0 to 90:10:1) to afford intermediate I67 (286 mg, 73%) as a yellowish solid.

Intermediate I68

(3*S)-1-(4-Chloro-3-fluorophenyl)-3-methylpyrrolidine-3-carboxamide

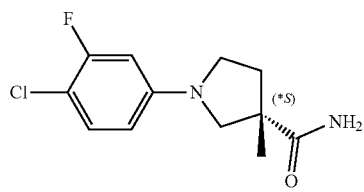

Intermediate I68 was synthesized from intermediate I66 according to the procedure reported for the synthesis of intermediate I67. Intermediate I68 (259 mg, 69%) was obtained as a yellowish solid.

Intermediate I59

(3*R)-1-[3-Fluoro-4-(tetramethyl-1,3,2-dioxaborolan-2-yl)phenyl]-3-methylpyrrolidine-3-carboxamide

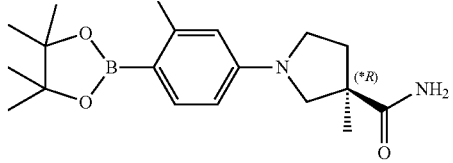

A sealed tube was charged with intermediate I67 (286 mg, 1.11 mmol), bis(pinacolato)diboron (567 mg, 2.23 mmol), acetic acid potassium salt (219 mg, 2.23 mmol) and 1,4-dioxane (10 mL) and was purged with nitrogen. Tris(dibenzylideneacetone)dipalladium (102 mg, 0.11 mmol) and XPhos (159 mg, 0.33 mmol) were added and the mixture was purged with nitrogen. The reaction mixture was stirred at 110° C. for 18 h. The reaction mixture was diluted with EtOAc and $H_2O$. The layers were separated and the aqueous phase was extracted with EtOAc (twice). The combined organic extracts were washed with brine, dried over $MgSO_4$, filtered and evaporated under reduced pressure. The crude mixture was purified by preparative LC (irregular SiOH, 15-40 μm, 24 g Grace®, dry loading (Celite®), mobile phase gradient: DCM/MeOH from 100:0 to 95:5) to afford intermediate I59 (393 mg, 73%, 72% purity) as a yellowish oil that crystallized on standing.

Intermediate I60

(3*S)-1-[3-Fluoro-4-(tetramethyl-1,3,2-dioxaborolan-2-yl)phenyl]-3-methylpyrrolidine-3-carboxamide

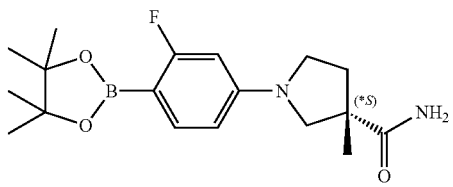

Intermediate I60 was synthesized from intermediate I68 according to the procedure reported for the synthesis of intermediate I59. The crude mixture was purified by preparative LC (irregular SiOH, 15-40 μm, 24 g Grace®, liquid injection (DCM), mobile phase gradient: DCM/MeOH from 100:0 to 95:5) to afford intermediate I60 (449 mg, 89%, 70% purity) as a yellowish oil that crystallized on standing.

141

Synthesis of Compounds 44 and 45

Compound 44

(3*R)-1-(4-{7-Cyclopropyl-5-[(4*R)-4-methyl-4,5,6,7-tetrahydro-thieno[3,2-c]pyridine-5-carbonyl]pyrazolo[1,5-a]pyrimidin-2-yl}-3-fluorophenyl)-3-methylpyrrolidine-3-carboxamide

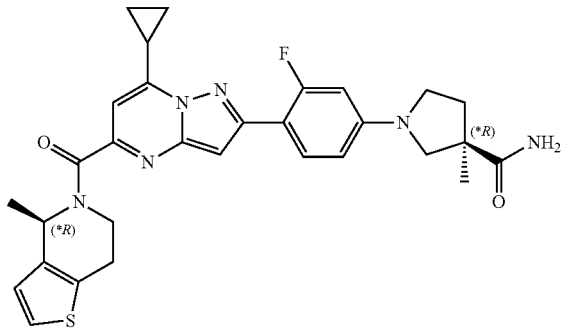

44

A sealed tube was charged with 2-bromo-7-cyclopropyl-5-[(4*R)-4-methyl-4,5,6,7-tetrahydro-thieno[3,2-c]pyridine-5-carbonyl]pyrazolo[1,5-a]pyrimidine [2035420-09-6] (248 mg, 0.59 mmol), intermediate I59 (345 mg, 0.71 mmol, 72% purity), potassium phosphate tribasic (431 mg, 2.03 mmol), 1,4-dioxane (11 mL) and H₂O (4 mL) and purged with nitrogen. [1,1'-Bis(di-tert-butylphosphino)ferrocene]dichloropalladium (42.7 mg, 65.4 μmol) was added and the mixture was purged with nitrogen. The reaction mixture was heated at 80° C. using a single mode microwave (Biotage® Initiator EXP 60) with a power output ranging from 0 to 400 W for 30 min. The reaction mixture was diluted with EtOAc and H₂O. The layers were separated and the organic phase was washed with brine, dried over MgSO₄, filtered and concentrated under reduced pressure. The crude mixture was purified by preparative LC (irregular SiOH, 15-40 μm, 24 g GraceResolv™, mobile phase gradient: heptane/(EtOAc/MeOH 9:1) from 70:30 to 50:50). The residue was triturated with pentane and the solid was filtered off and dried under high vacuum at 50° C. for 30 h to give compound 44 (193 mg, 58%) as a yellow solid.

Compound 45

(3*S)-1-(4-{7-Cyclopropyl-5-[(4*R)-4-methyl-4,5,6,7-tetrahydro-thieno[3,2-c]pyridine-5-carbonyl]pyrazolo[1,5-a]pyrimidin-2-yl}-3-fluorophenyl)-3-methylpyrrolidine-3-carboxamide

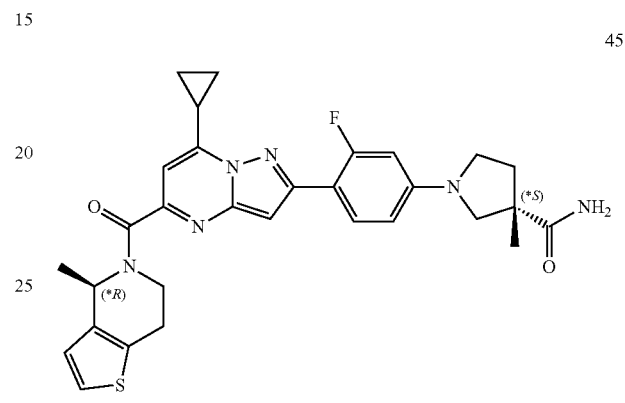

45

Compound 45 was synthesized from 2-bromo-7-cyclopropyl-5-[(4*R)-4-methyl-4,5,6,7-tetrahydro-thieno[3,2-c]pyridine-5-carbonyl]pyrazolo[1,5-a]pyrimidine [2035420-09-6] and intermediate I60 according to the procedure reported for the synthesis of compound 44. Compound 45 (275 mg, 71%) was obtained as a yellow solid.

Compound 46

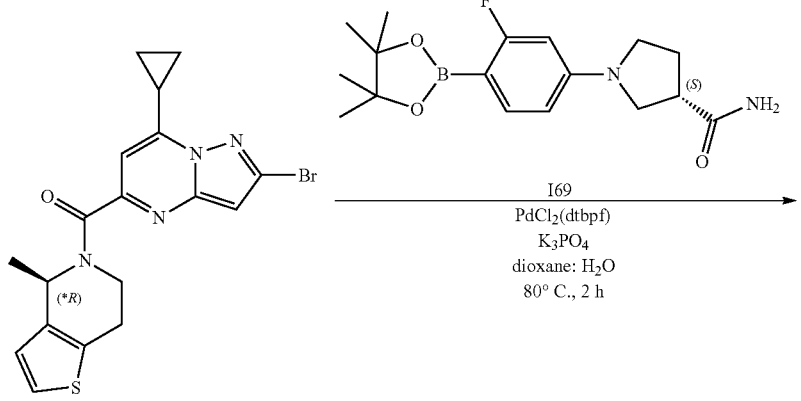

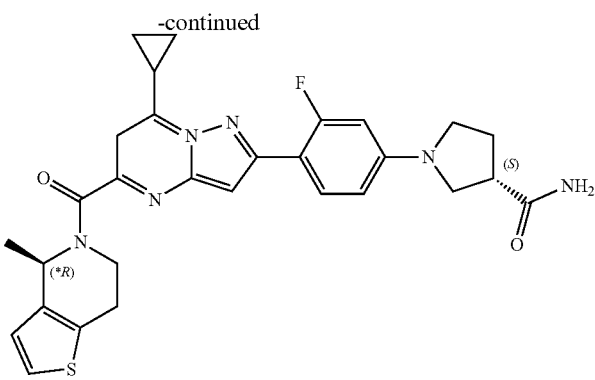

46

Synthesis of Intermediate I69

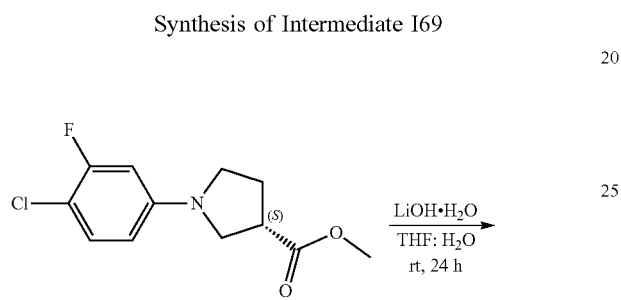

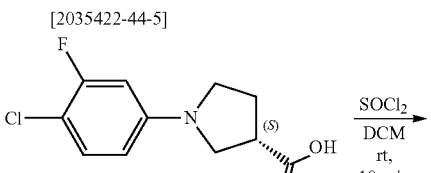

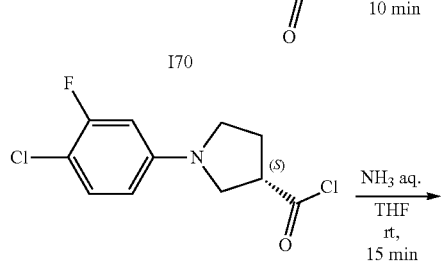

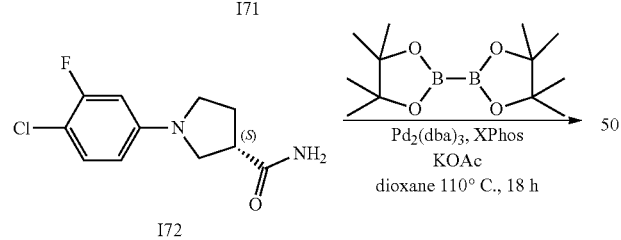

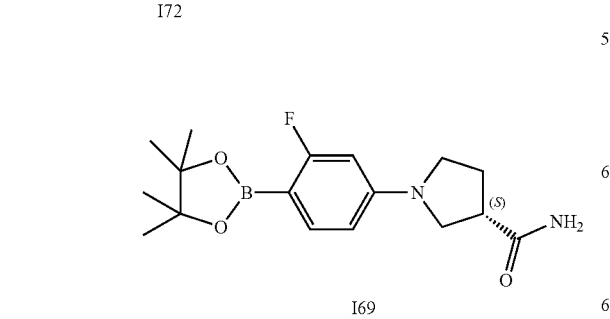

Intermediate I70

(3S)-1-(4-Chloro-3-fluorophenyl)pyrrolidine-3-carboxylic acid

I70

Lithium hydroxide monohydrate (3.34 g, 79.6 mmol) was added to a solution of methyl (3S)-1-(4-chloro-3-fluorophenyl)pyrrolidine-3-carboxylate [2035422-44-5] (4.10 g, 15.9 mmol) in THF (100 mL) and H₂O (50 mL). The reaction mixture was stirred at rt for 24 h. A 10% aqueous solution of KHSO₄ and EtOAc were added. The layers were separated and the aqueous phase was extracted with EtOAc (twice). The combined organic extracts were dried over MgSO₄, filtered and concentrated under reduced pressure to afford intermediate I70 (3.8 g, 98%) as an orange solid.

Intermediate I71

(3S)-1-(4-Chloro-3-fluorophenyl)pyrrolidine-3-carbonyl chloride

I71

Thionyl chloride (77.4 µL, 1.0.7 mmol) was added to a solution of intermediate I70 (200 mg, 0.82 mmol) in DCM (8 mL). The reaction mixture was stirred at rt for 10 min and evaporated under reduced pressure to afford intermediate I71 (215 mg, quant.).

Intermediate I72

(3S)-1-(4-Chloro-3-fluorophenyl)pyrrolidine-3-carboxamide

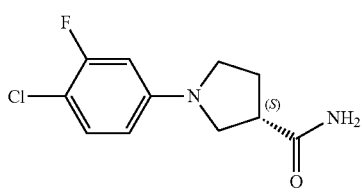

I72

Ammonia (28% in H$_2$O, 120 mL, 1.77 mol) was added to a solution of intermediate I71 (3.23 g, 12.3 mmol) in THF (120 mL). The reaction mixture was stirred at rt for 15 min. The reaction mixture was diluted with brine and EtOAc. The layers were separated and the aqueous phase was extracted with EtOAc (twice). The combined organic extracts were dried over MgSO$_4$, filtered and evaporated under reduced pressure. The crude mixture was purified by preparative LC (irregular SiOH, 15-40 µm, 80 g GraceResolv™, liquid injection (DCM), mobile phase gradient: DCM/MeOH from 100:0 to 96:4) to afford intermediate I72 (2.38 g, 80%) as a white solid.

Intermediate I69

(3S)-1-[3-Fluoro-4-(tetramethyl-1,3,2-dioxaborolan-2-yl)phenyl]pyrrolidine-3-carboxamide

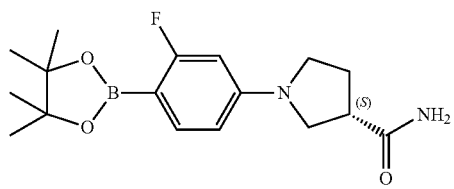

I69

A sealed tube was charged with intermediate I72 (3.22 g, 13.3 mmol), bis(pinacolato)-diboron (6.75 g, 26.6 mmol) and potassium acetate (2.61 g, 26.6 mmol) in 1,4-dioxane (115 mL) and purged with nitrogen. Tris(dibenzylideneacetone)dipalladium (1.22 g, 1.33 mmol) and XPhos (1.90 g, 3.98 mmol) were added and the mixture was purged with nitrogen. The reaction mixture was stirred at 110° C. for 18 h. The reaction mixture was filtered over Celite®. EtOAc, brine and H$_2$O were added to the filtrate. The layers were separated and the aqueous phase was extracted with EtOAc (twice). The combined organic extracts were washed with brine, dried over MgSO$_4$, filtered and concentrated under reduced pressure. The crude mixture was purified by preparative LC (irregular SiOH, 15-40 µm, 80 g Grace®, liquid injection (DCM), mobile phase gradient: DCM/MeOH from 100:0 to 96:4) to give intermediate I69 (5.24 g, 78%, 66% purity) as a colorless oil.

Synthesis of Compound 46

(3S)-1-(4-{7-Cyclopropyl-5-[(4*R)-4-methyl-4,5,6,7-tetrahydro-thieno[3,2-c]pyridine-5-carbonyl]pyrazolo[1,5-a]pyrimidin-2-yl}-3-fluorophenyl)pyrrolidine-3-carboxamide

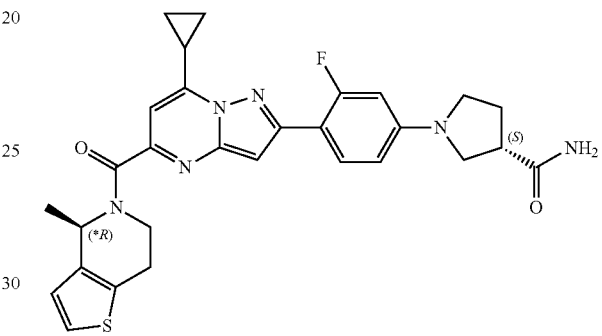

46

A sealed tube was charged with 2-bromo-7-cyclopropyl-5-[(4*R)-4-methyl-4,5,6,7-tetrahydro-thieno[3,2-c]pyridine-5-carbonyl]pyrazolo[1,5-a]pyrimidine [2035420-09-6] (200 mg, 0.48 mmol), intermediate I69 (291 mg, 0.58 mmol, 66% purity), potassium phosphate (0.31 g, 1.44 mmol), 1,4-dioxane (5 mL) and H$_2$O (1.5 mL) and purged with nitrogen. [1,1'-Bis(di-tert-butylphosphino)ferrocene]dichloropalladium (23.4 mg, 35.9 µmol) was added and the mixture was purged with nitrogen. The reaction mixture was stirred at 80° C. for 2 h. The reaction mixture was filtered over Celite®. EtOAc and brine were added to the filtrate. The layers were separated and the aqueous phase was extracted with EtOAc (twice). The combined organic extracts were dried over MgSO$_4$, filtered and concentrated under reduced pressure. The crude mixture was purified by preparative LC (irregular SiOH, 15-40 µm, 80 g Grace®, liquid injection (DCM), mobile phase gradient: DCM/MeOH from 100:0 to 96:4). The residue was co-evaporated with MeOH and triturated in MeOH. The solid was filtered off, rinsed with MeOH and dried under high vacuum at 50° C. for 24 h to give compound 46 (210 mg, 80%) as a yellow solid.

Compound 47
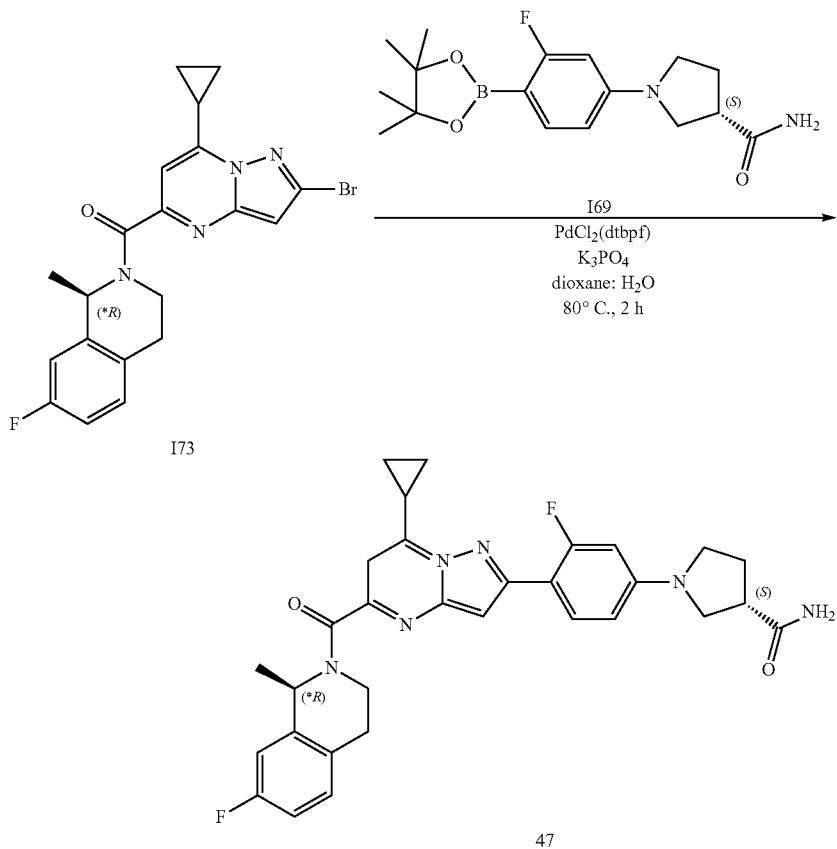
Synthesis of intermediate I73
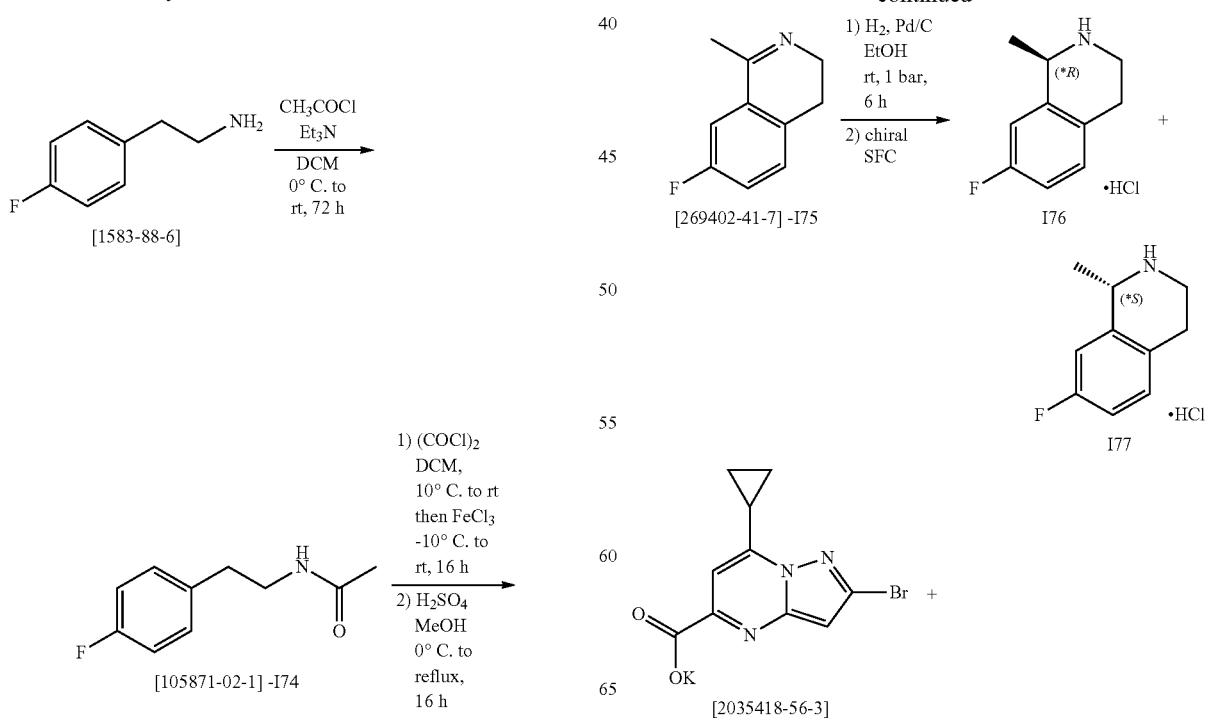

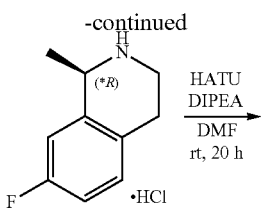

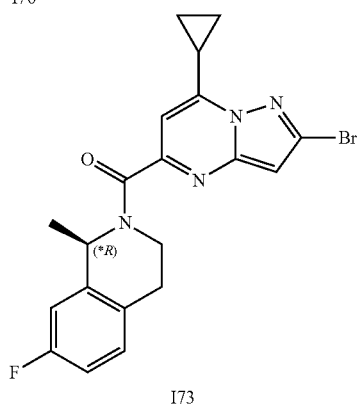

Intermediate I74

N-[2-(4-Fluorophenyl)ethyl]acetamide

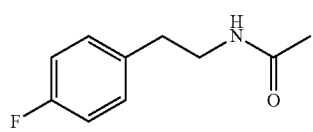

Acetyl chloride (0.27 mmol, 20.0 mL) was added dropwise to a mixture of 2-(4-fluoro-phenyl)ethylamine [1583-88-6] (34.6 g, 249 mmol) and Et₃N (52.0 mL, 373 mmol) in DCM (200 mL) at 0° C. The resulting mixture was stirred at rt for 72 h. The reaction mixture was diluted with DCM. The mixture was washed with a 10% aqueous solution of NaHCO₃, brine, dried over MgSO₄, filtered and the solvent was removed in vacuo to afford intermediate I74 (48.2 g, quant.).

Intermediate I75

7-Fluoro-1-methyl-3,4-dihydroisoquinoline

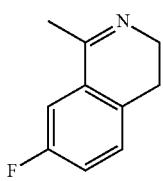

Oxalyl chloride (2.0 M in DCM, 67.5 mL, 135 mmol) and oxalyl chloride neat (11.5 mL, 136 mmol) were added dropwise to a solution of intermediate I74 (48.2 g, 266 mmol) in DCM (2.7 L) at 10° C. The resulting mixture was stirred at rt for 30 min and cooled down to −10° C. Iron chloride (III) [7705-08-0] (52.0 g, 0.32 mol) was added portionwise. The reaction mixture was stirred at rt for 16 h. The reaction mixture was quenched by the addition of a 3N aqueous solution of HCl and diluted with DCM. The layers were separated and the aqueous phase was extracted with DCM (twice). The combined organic extracts were dried over MgSO₄, filtered and the solvent was removed in vacuo. The residue (59.2 g) was dissolved in MeOH (2.4 L) and sulfuric acid (2.26 mol, 120 mL) was added dropwise carefully at 0° C. The resulting mixture was stirred under reflux for 16 h. The solvent was removed in vacuo. The residue was dissolved in DCM and a 3N aqueous solution of HCl was added. The layers were separated and the organic phase was washed with a 3N aqueous solution of HCl (once). The combined aqueous extracts were basified with ammonia (28% in H₂O) and extracted with DCM (twice). The combined organic extracts were dried over MgSO₄, filtered and the solvent was removed in vacuo to afford intermediate I75 (34.3 g, 63%, 80% purity).

Intermediates I76 and I77

(1*R)-7-Fluoro-1-methyl-1,2,3,4-tetrahydroisoquinoline hydrochloride (1*S)-7-Fluoro-1-methyl-1,2,3,4-tetrahydroisoquinoline hydrochloride

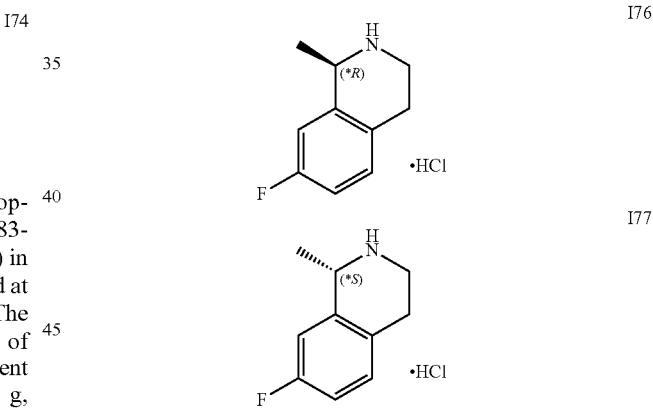

The reaction was performed on 2 batches of 84 mmol of I75.

To a solution of intermediate I75 (17.2 g, 84.0 mmol, 80% purity) in EtOH (500 mL) was added Pd/C (10 wt. %, 1.80 g, 1.70 mmol). The reaction mixture was stirred at rt under H₂ atmosphere (1 bar) for 6 h. The two batches were combined. The reaction mixture was filtered over Celite® and HCl (3.0 M in CPME, 67.2 mL, 0.20 mol) was added to the filtrate at 0° C. The resulting mixture was stirred at rt for 5 min and evaporated to dryness. The residue was triturated in Et₂O and the solid was filtered off to give a mixture of enantiomers (33 g) as a white solid. The enantiomers were separated via chiral SFC (Stationary phase: Chiralpak AD-H 5 μm 250*30 mm, Mobile phase: 78% CO₂, 22% i-PrOH (1.0% i-PrNH₂)) to give I76 (11.5 g) and I77 (15.5 g). Intermediate I76 was taken up in HCl (3.0 M in CPME, 25 mL) and EtOH (10 mL). The resulting suspension was stirred for 5 min and Et₂O was added (200 mL). The solid was filtered off and dried to give intermediate I76 (10.5 g, 31%). Intermediate I77 was taken up in DCM and 1M aqueous solution of NaOH. The layers were separated and the aqueous phase was extracted with DCM (once). The combined organic extracts were washed with brine, dried over MgSO₄, filtered and the solvent was removed in vacuo. The residue (11.1 g) was dissolved in EtOH (100 mL) and HCl (3.0 M in CPME, 25 mL) was added at 0° C. The mixture was evaporated to dryness. The solid was triturated with Et₂O, filtered off and dried to give intermediate I77 (11.6 g, 34%).

Intermediate I73

(1*R)-2-{2-Bromo-7-cyclopropylpyrazolo[1,5-a]pyrimidine-5-carbonyl}-7-fluoro-1-methyl-1,2,3,4-tetrahydroisoquinoline

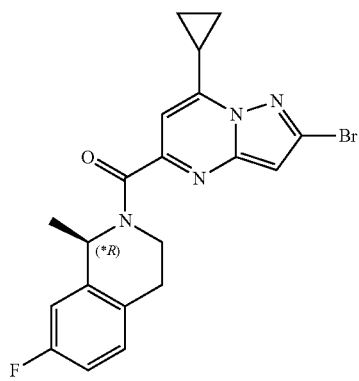

I73

To a mixture of potassium 2-bromo-7-cyclopropylpyrazolo[1,5-a]pyrimidine-5-carboxylate [2035418-56-3], intermediate I76 (2.46 g, 12.3 mmol) and DIPEA (4.90 mL, 28.4 mmol) in DMF (54 mL) was added HATU (5.34 g, 14.1 mmol). The reaction mixture was stirred at rt for 20 h. A saturated aqueous solution of NaHCO₃, brine and EtOAc were added. The layers were separated and the aqueous phase was extracted with EtOAc (twice). The combined organic extracts were washed with brine (4 times), dried over MgSO₄, filtered and evaporated under reduced pressure. The crude mixture was purified by preparative LC (irregular SiOH, 15-40 μm, 220 g GraceResolv™, liquid injection (DCM), mobile phase gradient: heptane/EtOAc from 100:0 to 60:40). A first fraction of pure intermediate I73 (1.20 g, 30%) was obtained, while the second fraction containing impurities was purified again by preparative LC (irregular SiOH, 40 μm 120 g, mobile phase: 100% DCM). A second crop of intermediate I73 (1.3 g, 32%) was isolated. Intermediate I73 (2.50 g, 62%) was obtained as a white foam.

Synthesis of Compound 47

(3S)-1-(4-{7-Cyclopropyl-5-[(1*R)-7-fluoro-1-methyl-1,2,3,4-tetrahydroisoquinoline-2-carbonyl]pyrazolo[1,5-a]pyrimidin-2-yl}-3-fluorophenyl)pyrrolidine-3-carboxamide

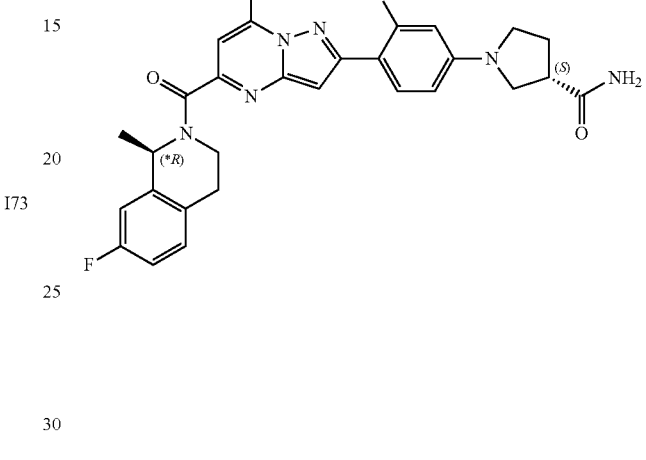

47

A sealed tube was charged with (1*R)-2-{2-bromo-7-cyclopropylpyrazolo[1,5-a]pyrimidine-5-carbonyl}-7-fluoro-1-methyl-1,2,3,4-tetrahydroisoquinoline I73 (200 mg, 0.47 mmol), intermediate I69 (283 mg, 0.56 mmol), potassium phosphate tribasic (297 mg, 1.40 mmol), 1,4-dioxane (5 mL) and H₂O (1.5 mL) and purged with nitrogen. [1,1'-Bis(di-tert-butylphosphino)ferrocene] dichloropalladium (22.8 mg, 34.9 μmol) was added and the mixture was purged again with nitrogen. The reaction mixture was stirred at 80° C. for 2 h. The reaction mixture was filtered over Celite®. EtOAc and brine were added to the filtrate. The layers were separated and the aqueous phase was extracted with EtOAc (twice). The combined organic extracts were dried over MgSO₄, filtered and concentrated under reduced pressure. The crude mixture was purified by preparative LC (irregular SiOH, 15-40 μm, 80 g GraceResolv™, liquid injection (DCM), mobile phase gradient: DCM/MeOH from 100:0 to 96:4). The pure fractions were combined while fractions containing impurities were subjected to a second purification by preparative LC (irregular SiOH, 15-40 μm, 80 g GraceResolv™, liquid injection (DCM), mobile phase gradient: DCM/MeOH from 100:0 to 98:2). The residue was co-evaporated with MeOH and triturated in MeOH. The solid was filtered off, rinsed with MeOH and dried under high vacuum at 50° C. for 24 h to give compound 47 (185 mg, 71%) as a yellow solid.

Compound 48
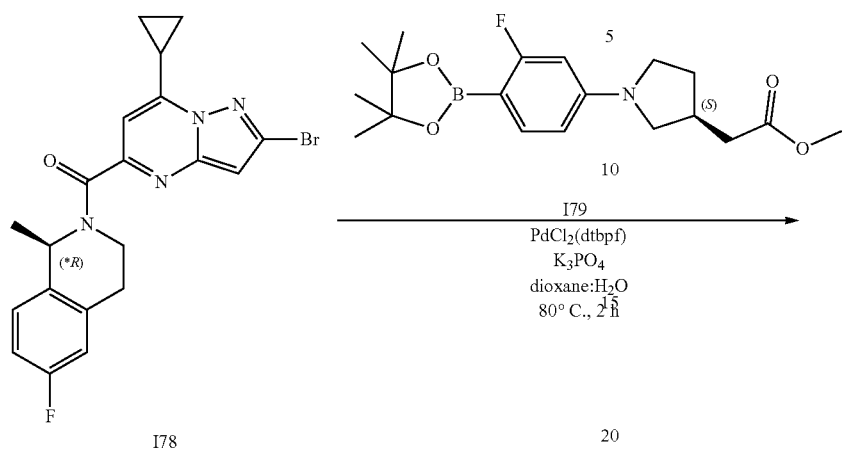
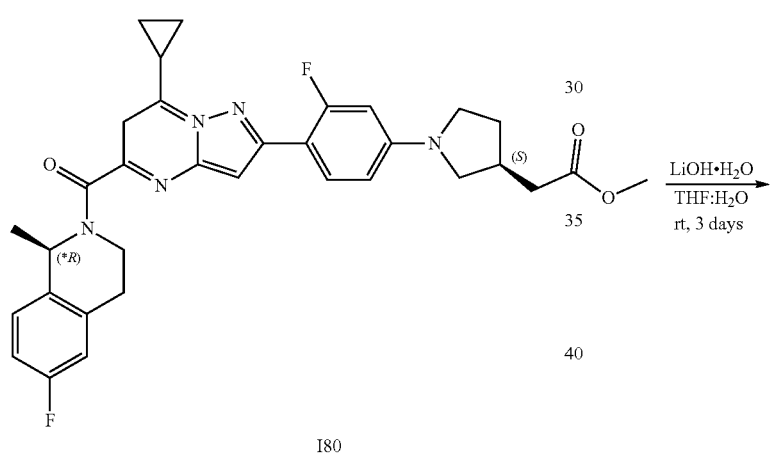
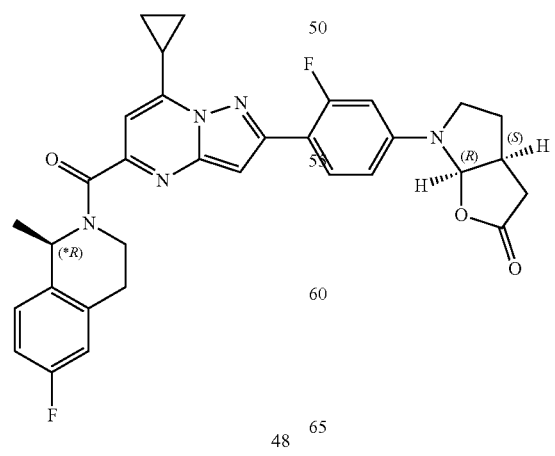
48

Synthesis of intermediate I78

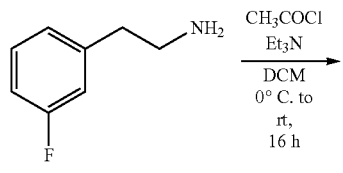

[404-70-6]

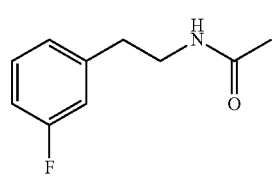

[125058-99-3] -I81

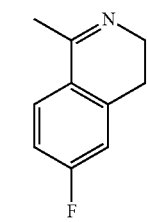 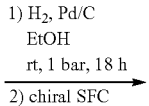

[1176414-50-8] -I82

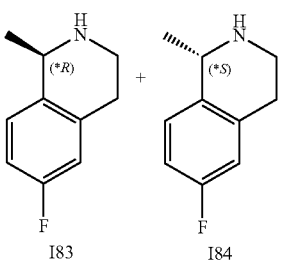

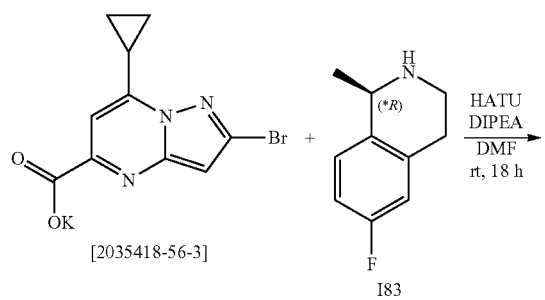

[2035418-56-3]

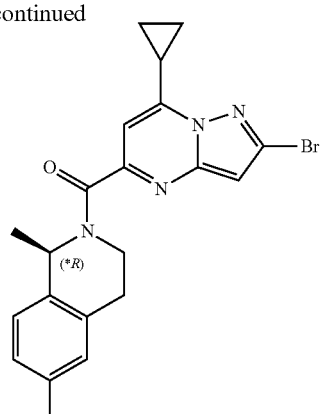

I78

Intermediate I81

N-[2-(3-Fluorophenyl)ethyl]acetamide

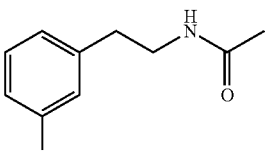

Acetyl chloride (16.0 mL, 225 mmol) was added dropwise at 0° C. to a mixture of 3-fluorophenethylamine [404-70-6] (25.0 g, 180 mmol) and Et$_3$N (38.5 mL, 270 mmol) in DCM (500 mL). The reaction mixture was stirred at rt for 16 h. The reaction was quenched by the addition of an aqueous solution of NaHCO$_3$. The layers were separated and the aqueous phase was extracted with DCM. The combined organic extracts were washed with brine, dried over MgSO$_4$, filtered and the solvent was removed in vacuo to afford intermediate I81 (35.3 g, quant.) as a yellow oil.

Intermediate I82

6-Fluoro-1-methyl-3,4-dihydroisoquinoline

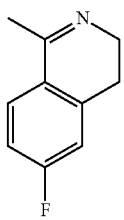

In a 5 L jacketed reactor equipped with a thermoregulator and mechanical stirring, oxalyl chloride (2.0 M in DCM, 108 mL, 216 mmol) was added dropwise to a solution intermediate I81 (35.3 g, 180 mmol) in DCM (1.7 L) at 10° C. The resulting mixture was stirred at rt for 30 min and cooled down to −10° C. Iron chloride [7705-08-0] (35.0 g, 216 mmol) was added portionwise. The reaction mixture was stirred at rt for 18 h. The reaction mixture was quenched by the addition of a 3N aqueous solution of HCl and diluted with DCM. The layers were separated and the aqueous phase was extracted with DCM (twice). The combined organic extracts were dried over MgSO₄, filtered and the solvent was removed in vacuo. The residue (43.6 g) was dissolved in MeOH (1.6 L) in a 5 L jacketed reactor equiped with thermoregulator and mechanical stirring. Sulfuric acid (1.54 mol, 82.0 mL) was added dropwise carefully at 0° C. The resulting mixture was stirred under reflux for 16 h. The solvent was removed in vacuo. The residue was dissolved in DCM and a 3N aqueous solution of HCl was added. The layers were separated and the organic phase was washed with a 3N aqueous solution of HCl (twice). The combined aqueous extracts were basified with ammonia (28% in H₂O) and extracted with DCM (twice). The combined organic extracts were dried over MgSO₄, filtered and the solvent was removed in vacuo to afford intermediate I82 (28.9 g, 90% purity).

Intermediates I83 and I84

(1*R)-6-Fluoro-1-methyl-1,2,3,4-tetrahydroisoquinoline (I83) and (1*S)-6-fluoro-1-methyl-1,2,3,4-tetrahydroisoquinoline (I84)

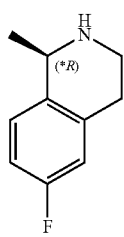

I83

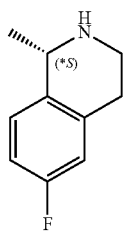

I84

EtOH (400 mL) and Pd/C (10%, 3.39 g, 3.19 mmol) were charged in a Parr flask. A solution of intermediate I82 (28.9 g, 159 mmol, 90% purity) in EtOH (500 mL) was added. The reaction was pressurized with H₂ at 1 bar and stirred at rt for 18 h. The reaction mixture was filtered through a pad of Celite® and rinsed with MeOH. The filtrate was treated with HCl (3.0 M in CPME, 63.8 mL, 191 mmol) at 0° C. The resulting mixture was stirred at rt for 5 min and evaporated to dryness. The residue was triturated in Et₂O and the solid was filtered off. The solid was purified by preparative LC (irregular SiOH, 15-40 μm, 330 g Grace®, dry loading (Celite®), mobile phase gradient: DCM/MeOH/aq.NH₃ from 98:2:0.2 to 96:4:0.4) to afford a mixture of enantiomers (20.3 g). The enantiomers were separated via chiral SFC (Stationary phase: Chiralpak AD-H 5 μm 250*30 mm, Mobile phase: 80% CO₂, 20% i-PrOH (0.3% i-PrNH₂)) to give I83 (9.73 g) and I84 (9.68 g). The enantiomers were treated separately. Intermediates I83 and I84 were dissolved in EtOAc and an aqueous solution of NaHCO₃ was added. The layers were separated and the aqueous phase was extracted with EtOAc. The combined organic extracts were dired over MgSO₄, filtered and the solvent was removed in vacuo to give intermediates I83 (8.74 g, 32%) and I84 (8.34 g, 30%) as colorless oils.

Intermediate I78

(1*R)-2-{2-Bromo-7-cyclopropylpyrazolo[1,5-a]pyrimidine-5-carbonyl}-6-fluoro-1-methyl-1,2,3,4-tetrahydroisoquinoline

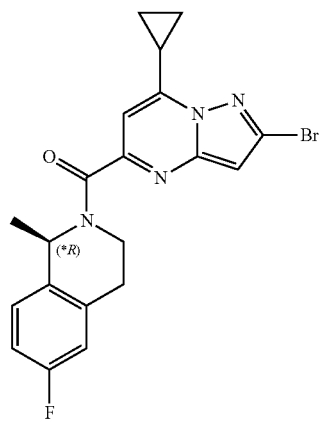

I78

HATU (6.91 g, 18.2 mmol) was added to a mixture of potassium 2-bromo-7-cyclopropyl-pyrazolo[1,5-a]pyrimidine-5-carboxylate [2035418-56-3] (3.23 g, 10.1 mmol), intermediate I83 (2.00 g, 12.1 mmol) and DIPEA (4.35 mL, 25.2 mmol) in DMF (50 mL). The reaction mixture was stirred at rt for 18 h. A saturated aqueous solution of NaHCO₃, brine, H₂O and EtOAc were added. The layers were separated and the aqueous phase was extracted with EtOAc. The combined organic extracts were washed with a solution of brine and water (9:1) (3 times), dried over MgSO₄, filtered, rinsed with EtOAc and evaporated under reduced pressure. The crude mixture was purified by preparative LC (irregular SiOH, 15-40 μm, 80 g GraceResolv™, liquid injection (DCM), mobile phase gradient: heptane/EtOAc from 90:10 to 70:30) to give intermediate I78 (4.5 g, quant.) as a white gum.

Synthesis of Intermediate I79

Methyl 2-[(3S)-1-[3-fluoro-4-(tetramethyl-1,3,2-dioxaborolan-2-yl)phenyl]pyrrolidin-3-yl]acetate

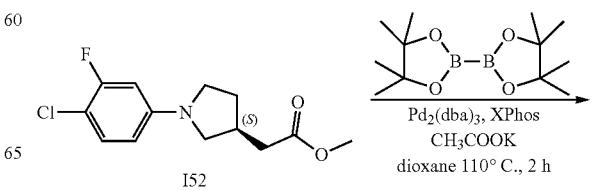

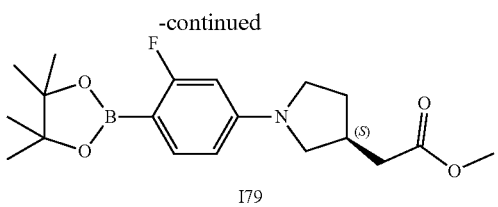

I79

A sealed tube was charged with intermediate I52 (1.40 g, 5.15 mmol), bis(pinacolato)-diboron (1.57 g, 6.18 mmol), acetic acid potassium salt (1.01 g, 10.3 mmol) and 1,4-dioxane (35 mL) and purged with nitrogen. XPhos (737 mg, 1.55 mmol) and tris(dibenzylideneacetone)dipalladium (472 mg, 0.52 mmol) were added and the mixture was purged with nitrogen. The reaction mixture was stirred at 100° C. for 18 h and then at 110° C. for 2 h. The reaction mixture was filtered over a pad of Celite®. EtOAc and brine were added to the filtrate. The layers were separated and the aqueous phase was extracted with EtOAc (twice). The combined organic extracts were dried over MgSO$_4$, filtered and concentrated under reduced pressure. The crude mixture was purified by preparative LC (irregular SiOH, 15-40 µm, 80 g GraceResolv™, liquid injection (DCM), mobile phase gradient: heptane/EtOAc from 95:5 to 80:20) to give intermediate I79 (1.1 g, 59%) as a grey solid.

Synthesis of Compound 48

Intermediate I80

Methyl 2-[(3S)-1-(4-{7-cyclopropyl-5-[(1*R)-6-fluoro-1-methyl-1,2,3,4-tetrahydro-isoquinoline-2-carbonyl]pyrazolo[1,5-a]pyrimidin-2-yl}-3-fluorophenyl)pyrrolidin-3-yl]acetate

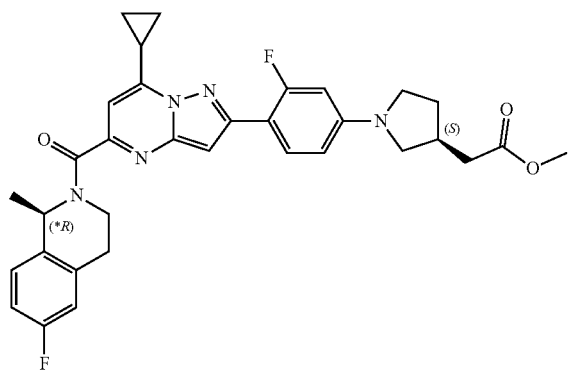

I80

A sealed tube was charged with intermediate I78 (253 mg, 0.59 mmol), intermediate I79 (300 mg, 0.83 mmol), potassium phosphate tribasic (376 mg, 1.77 mmol), 1,4-dioxane (7 mL) and H$_2$O (2.5 mL) and purged with nitrogen. [1,1'-bis(di-tert-butylphosphino)-ferrocene] palladium dichloride (38.4 mg, 59.0 µmol) was added. The reaction mixture was purged with nitrogen and stirred at 80° C. for 2 h. The reaction mixture was filtered over Celite®. EtOAc and brine were added to the filtrate. The layers were separated and the aqueous phase was extracted with EtOAc (twice). The combined organic extracts were dried over MgSO$_4$, filtered and concentrated under reduced pressure. The crude mixture was purified by preparative LC (irregular SiOH, 15-40 µm, 24 g GraceResolv™, liquid injection (DCM), mobile phase gradient: heptane/EtOAc from 90:10 to 60:40) to afford intermediate I80 (271 mg, 75%, 95% purity) as a yellow solid.

Compound 48

(3 aS,6aR)-6-(4-{7-Cyclopropyl-5-[(1*R)-6-fluoro-1-methyl-1,2,3,4-tetrahydro-isoquinoline-2-carbonyl]pyrazolo[1,5-a]pyrimidin-2-yl}-3-fluorophenyl)-hexahydro-2H-furo[2,3-b]pyrrol-2-one

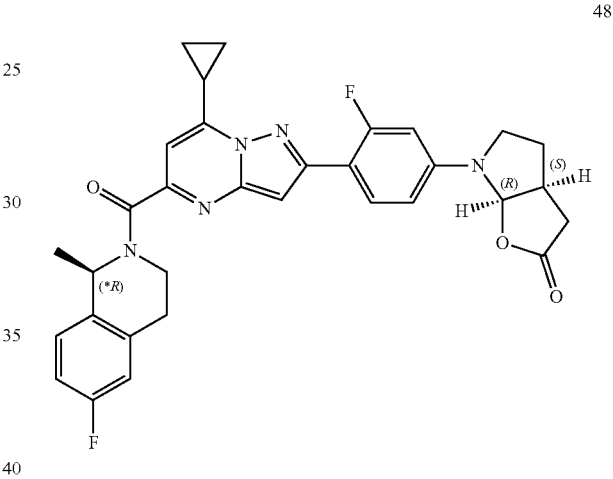

48

Intermediate I80 (271 mg, 0.44 mmol, 95% purity) was solubilized in THF (5 mL) and a solution of lithium hydroxide monohydrate (92.2 mg, 2.19 mmol) in H$_2$O (2.5 mL) was added. The reaction mixture was stirred at rt for 3 days. Brine, a 10% aqueous solution of KHSO$_4$ and EtOAc were added. The layers were separated and the aqueous phase was extracted with EtOAc (twice). The combined organic extracts were dried over MgSO$_4$, filtered and evaporated under reduced pressure. The crude mixture was purified by preparative LC (regular SiOH, 30 µm, 25 g Interchim®, liquid injection (DCM), mobile phase gradient: heptane/EtOAc/AcOH from 90:10:0.25 to 60:40:1). The residue was co-evaporated with MeOH and triturated in MeOH. The solid was filtered off, rinsed with MeOH and dried under high vacuum at 50° C. for 2 days to afford a white solid (250 mg). The batch was split in two samples A and B that were purified independently by preparative LC (Stationary phase: irregular SiOH 40 g, Mobile phase: 98% DCM, 2% MeOH). Compound 48 was dried under high vacuum to give a yellow solid (50 mg, 20%).

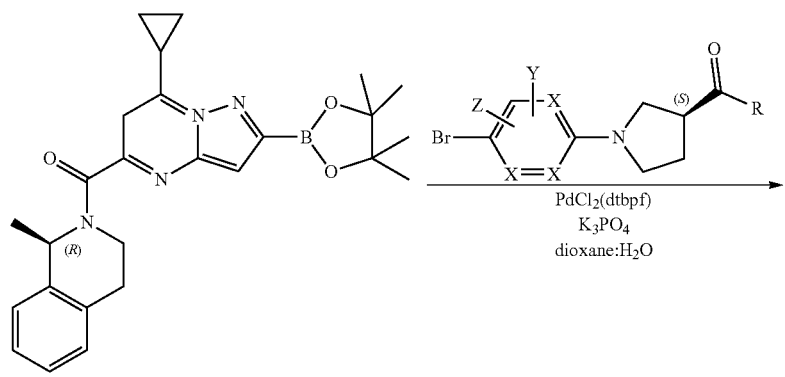
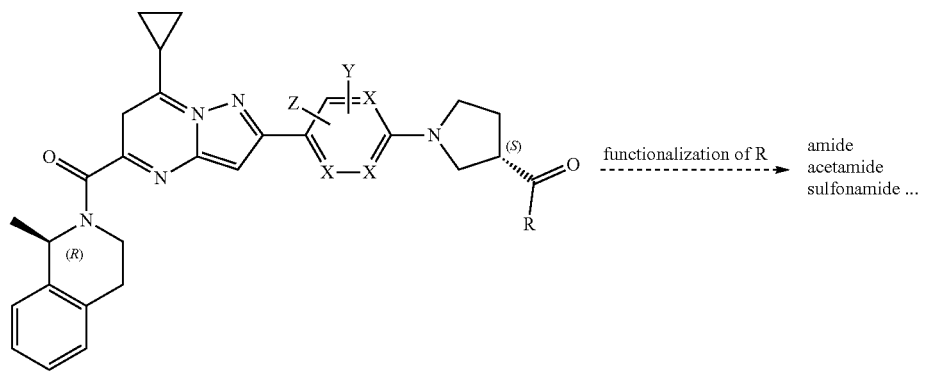
Compound 49
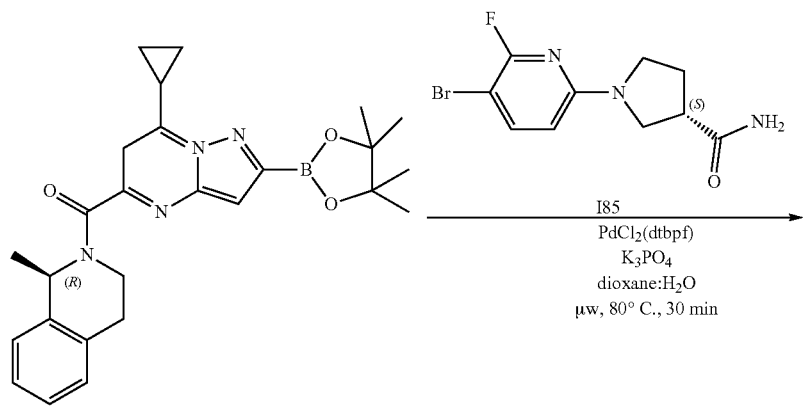
[2035421-36-2]

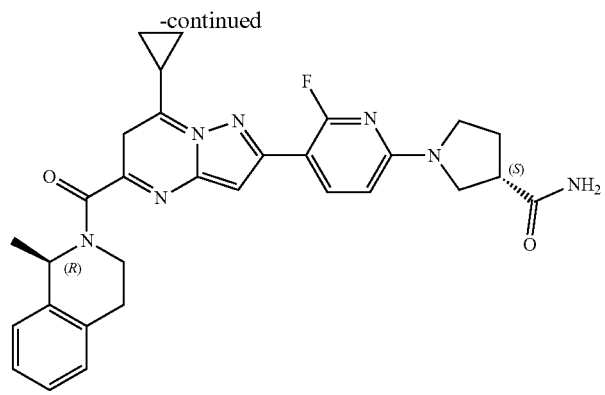

49

Synthesis of Intermediate I85

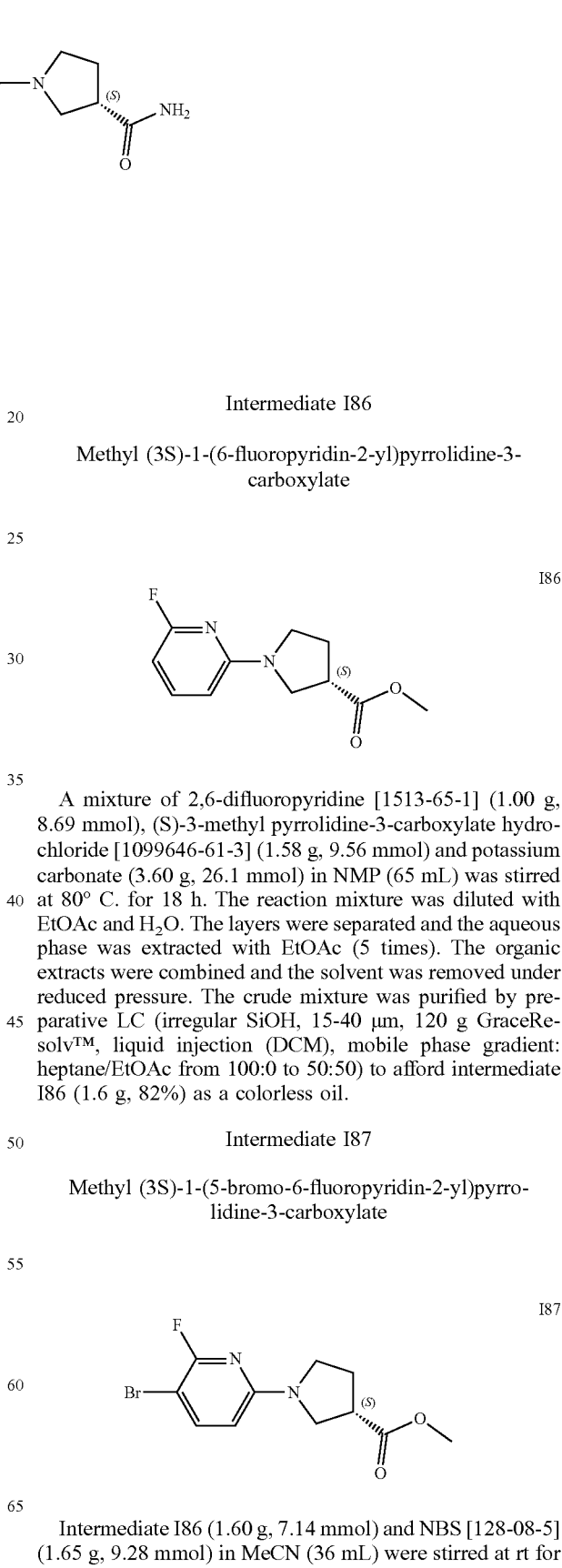

Intermediate I86

Methyl (3S)-1-(6-fluoropyridin-2-yl)pyrrolidine-3-carboxylate

A mixture of 2,6-difluoropyridine [1513-65-1] (1.00 g, 8.69 mmol), (S)-3-methyl pyrrolidine-3-carboxylate hydrochloride [1099646-61-3] (1.58 g, 9.56 mmol) and potassium carbonate (3.60 g, 26.1 mmol) in NMP (65 mL) was stirred at 80° C. for 18 h. The reaction mixture was diluted with EtOAc and H$_2$O. The layers were separated and the aqueous phase was extracted with EtOAc (5 times). The organic extracts were combined and the solvent was removed under reduced pressure. The crude mixture was purified by preparative LC (irregular SiOH, 15-40 μm, 120 g GraceResolv™, liquid injection (DCM), mobile phase gradient: heptane/EtOAc from 100:0 to 50:50) to afford intermediate I86 (1.6 g, 82%) as a colorless oil.

Intermediate I87

Methyl (3S)-1-(5-bromo-6-fluoropyridin-2-yl)pyrrolidine-3-carboxylate

Intermediate I86 (1.60 g, 7.14 mmol) and NBS [128-08-5] (1.65 g, 9.28 mmol) in MeCN (36 mL) were stirred at rt for 18 h. The mixture was evaporated under reduced pressure. The crude mixture was purified by preparative LC (irregular SiOH, 15-40 μm, 80 g GraceResolv™, liquid injection (DCM), mobile phase gradient: heptane/EtOAc from 100:0 to 50:50) to afford intermediate I87 (1.58 g, 61%, 84% purity) as a colorless oil.

Intermediate I88

(3S)-1-(5-Bromo-6-fluoropyridin-2-yl)pyrrolidine-3-carboxylic acid

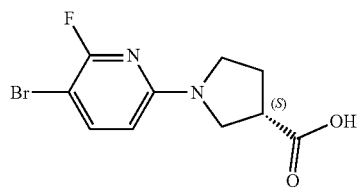

I88

Lithium hydroxide monohydrate (41.9 mg, 1.00 mmol) was added to a solution of intermediate I87 (120 mg, 0.33 mmol, 84% purity) in THF (2.9 mL) and H$_2$O (0.9 mL). The reaction mixture was stirred at rt for 16 h. A 10% aqueous solution of KHSO$_4$ was added until pH 6 and the aqueous phase was extracted with EtOAc. The combined organic extracts were washed with H$_2$O, dried over MgSO$_4$, filtered and concentrated under reduced pressure. The crude mixture was purified by preparative LC (irregular SiOH, 15-40 μm, 24 g GraceResolv™, liquid injection (DCM), mobile phase gradient: heptane/EtOAc/AcOH from 60:39:1 to 20:80:2) to afford intermediate I88 (96 mg, quant.).

Intermediate I85

(3S)-1-(5-Bromo-6-fluoropyridin-2-yl)pyrrolidine-3-carboxamide

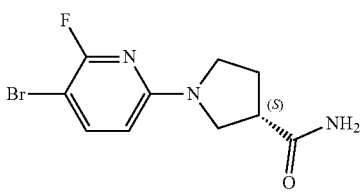

I85

A mixture of intermediate I88 (96.3 mg, 0.33 mmol), HATU (165 mg, 0.43 mmol) and DIPEA (172 μL, 1.0 mmol) in DCM (1.9 mL) was stirred at rt for 1 h. Ammonia (28% in H$_2$O, 0.11 mL, 1.67 mmol) was added and the reaction mixture was stirred at rt for 18 h. The reaction mixture was diluted with H$_2$O and EtOAc. The layers were separated and the aqueous phase was extracted with EtOAc (twice), dried over MgSO$_4$ and evaporated under reduced pressure. The crude mixture was purified by preparative LC (regular SiOH, 30 μm, 12 g GraceResolv™, dry loading (Celite®), mobile phase gradient: DCM/MeOH/aq.NH$_3$ from 99:1:0.1 to 90:10:1). The residue was suspended in DCM and filtered off to afford intermediate I85 (62 mg, 65%) as a yellow solid.

Synthesis of compound 49

(3S)-1-(5-{7-Cyclopropyl-5-[(1R)-1-methyl-1,2,3,4-tetrahydroisoquinoline-2-carbonyl]-pyrazolo[1,5-a]pyrimidin-2-yl}-6-fluoropyridin-2-yl)pyrrolidine-3-carboxamide

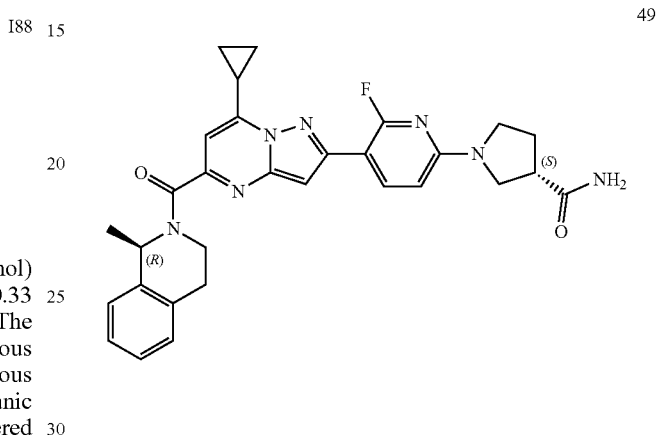

49

A sealed tube was charged with intermediate I85 (62.0 mg, 0.22 mmol), (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (190 mg, 0.22 mmol, 52% purity), potassium phosphate tribasic (137 mg, 0.65 mmol), 1,4-dioxane (2.2 mL) and H$_2$O (0.5 mL) and purged with nitrogen. [1,1'-Bis(di-tert-butylphosphino)ferrocene] palladium dichloride (14.0 mg, 21.5 μmol) was added and the mixture was purged with nitrogen. The reaction mixture was heated at 80° C. using a single mode microwave (Biotage® Initiator EXP 60) with a power output ranging from 0 to 400 W for 30 min. The reaction mixture was diluted with EtOAc. The layers were separated and the organic phase was washed with brine, dried over MgSO$_4$, filtered and evaporated under reduced pressure. The crude mixture was purified by preparative LC (regular SiOH, 30 μm, 24 g Interchim®, liquid injection (DCM), mobile phase gradient: DCM/i-PrOH from 100:0 to 80:20). A second purification was performed by preparative LC (regular SiOH, 30 μm, 24 g Interchim®, liquid injection (DCM), mobile phase gradient: DCM/i-PrOH from 100:0 to 80:20). The mixture (79 mg) was purified by preparative LC (spherical C18 25 μm, 40 g YMC-ODS-25, dry loading (Celite®), mobile phase gradient: (0.2% aq.NH$_4$HCO$_3$)/MeCN from 65:35 to 25:75). The residue was taken up in MeCN and DIPE, concentrated under reduced pressure and dried under high vacuum at 50° C. for 16 h to give compound 49 (70 mg, 60%) as a white solid.

Compound 50

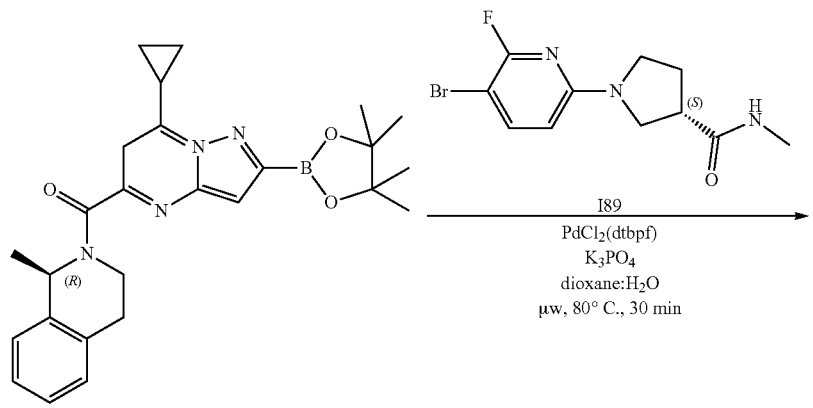

[2035421-36-2]

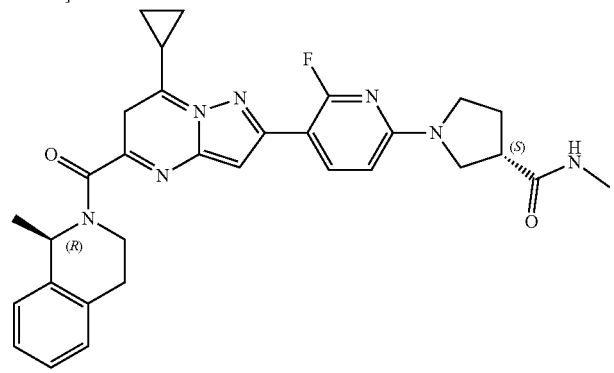

50

Synthesis of Intermediate I89

(3S)-1-(5-Bromo-6-fluoropyridin-2-yl)-N-methylpyrrolidine-3-carboxamide

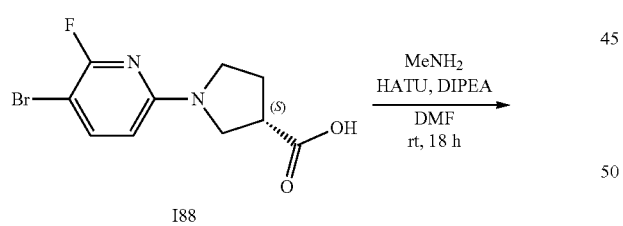

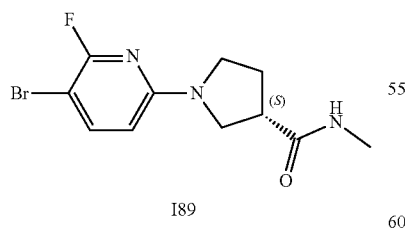

I89

A mixture of intermediate I88 (220 mg, 761 μmol), HATU (434 mg, 1.14 mmol) and DIPEA (393 μL, 2.28 mmol) in DMF (21 mL) was stirred at rt for 1 h. Methylamine (2.0 M in THF, 1.9 mL, 3.81 mmol) was added and the reaction mixture was stirred at rt for 18 h. The reaction mixture was diluted with H₂O and EtOAc. The layers were separated and the organic phase was washed with a 1% aqueous solution of NaHCO₃ (twice), dried over MgSO₄, filtered and evaporated under reduced pressure. The crude mixture was purified by preparative LC (irregular SiOH, 15-40 μm, 12 g GraceResolv™, liquid injection (DCM), mobile phase gradient: DCM/i-PrOH from 100:0 to 80:20) to afford intermediate I89 (220 mg, 96%) as a yellow oil.

Synthesis of Compound 50

(3S)-1-(5-{7-Cyclopropyl-5-[(1R)-1-methyl-1,2,3,4-tetrahydroisoquinoline-2-carbonyl]-pyrazolo[1,5-a]pyrimidin-2-yl}-6-fluoropyridin-2-yl)-N-methylpyrrolidine-3-carboxamide

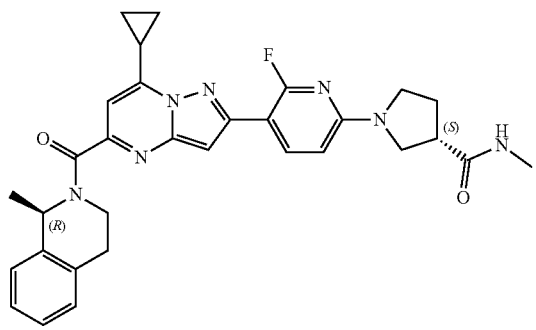

50

A sealed tube was charged with intermediate I89 (220 mg, 0.73 mmol), (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (538 mg, 0.73 mmol, 62% purity), potassium phosphate tribasic (0.46 g, 2.18 mmol), 1,4-dioxane (5.0 mL) and H₂O (1.3 mL) and purged with nitrogen. [1,1'-Bis(di-tert-butylphosphino)ferrocene] palladium dichloride (47.5 mg, 72.8 μmol) was added and the mixture was purged with nitrogen. The reaction mixture was heated at 80° C. using a single mode microwave (Biotage® Initiator EXP 60) with a power output ranging from 0 to 400 W for 30 min. The reaction mixture was diluted with EtOAc and the organic phase was washed with brine, dried over MgSO₄, filtered and evaporated under reduced pressure. The crude mixture was purified by preparative LC (irregular SiOH, 30 μm, 24 g GraceResolv™, liquid injection (DCM), mobile phase gradient: DCM/i-PrOH from 99:1 to 80:20). A second purification was carried out by reverse phase (spherical C18 25 μm, 40 g YMC-ODS-25, liquid injection (MeCN/H₂O), mobile phase gradient: (0.2% aq.NH₄HCO₃)/MeCN from 65:35 to 25:75). The residue was taken up in MeCN. The solid was filtered off and dried under high vacuum at 50° C. for 16 h to give compound 50 (190 mg, 47%).

Compound 51

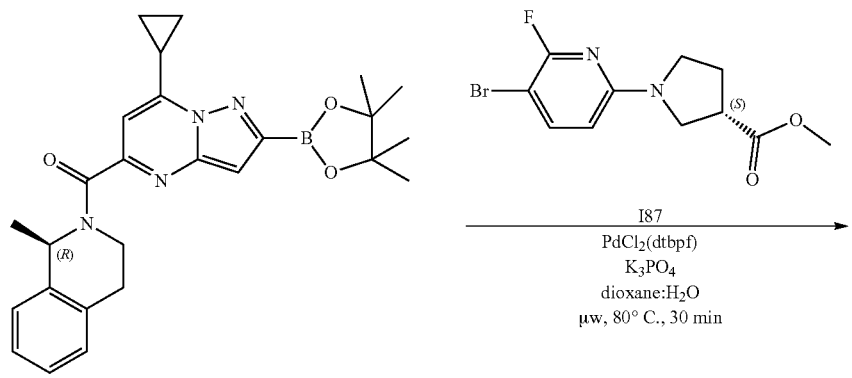

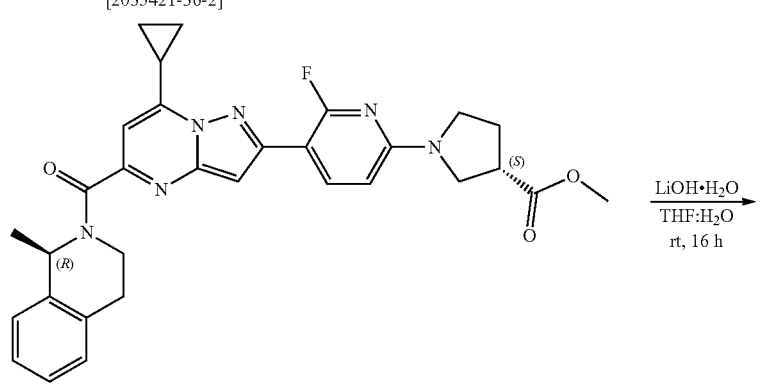

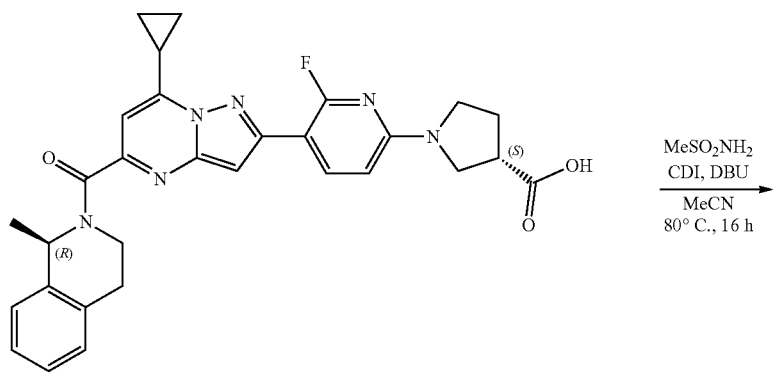

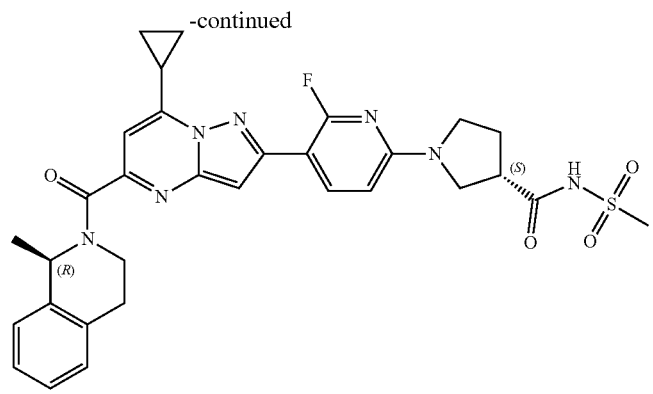

51

Intermediate I90

Methyl (3S)-1-(5-{7-cyclopropyl-5-[(1R)-1-methyl-1,2,3,4-tetrahydroisoquinoline-2-carbonyl]pyrazolo[1,5-a]pyrimidin-2-yl}-6-fluoropyridin-2-yl)pyrrolidine-3-carboxylate

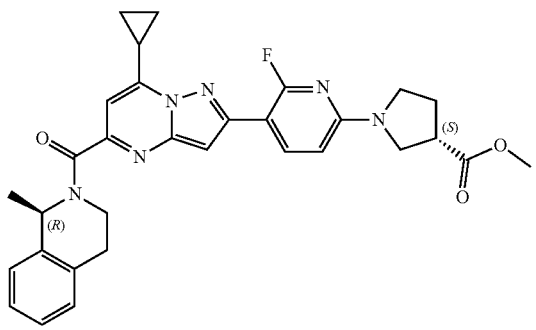

I90

A sealed tube was charged with intermediate I87 (180 mg, 0.50 mmol, 84% purity), (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (289 mg, 0.50 mmol, 69% purity), potassium phosphate tribasic (323 mg, 1.52 mmol), 1,4-dioxane (5.5 mL) and H₂O (1.4 mL) and purged with nitrogen. [1,1'-Bis(di-tert-butylphosphino)ferrocene] palladium dichloride (33.2 mg, 50.9 µmol) was added and the mixture was purged with nitrogen. The reaction mixture was heated at 80° C. using a single mode microwave (Biotage® Initiator EXP 60) with a power output ranging from 0 to 400 W for 30 min. The reaction mixture was diluted with EtOAc and the organic phase was washed with brine, dried over MgSO₄, filtered and evaporated under reduced pressure. The crude mixture was purified by preparative LC (regular SiOH, 30 µm, 24 g GraceResolv™, liquid injection (DCM), mobile phase gradient: heptane/EtOAc from 80:20 to 60:40) to afford intermediate I90 (200 mg, 72%) as a yellow foam.

Intermediate I91

(3S)-1-(5-{7-Cyclopropyl-5-[(1R)-1-methyl-1,2,3,4-tetrahydroisoquinoline-2-carbonyl]-pyrazolo[1,5-a]pyrimidin-2-yl}-6-fluoropyridin-2-yl)pyrrolidine-3-carboxylic acid

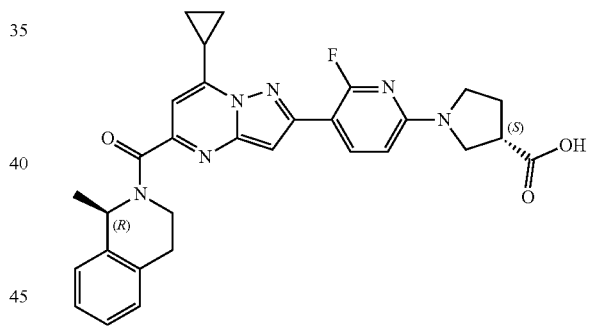

I91

Lithium hydroxide monohydrate (45.4 mg, 1.08 mmol) was added to a solution of intermediate I90 (200 mg, 361 µmol) in THF (3.1 mL) and H₂O (980 µL). The reaction mixture was stirred at rt for 16 h. A 10% aqueous solution of KHSO₄ was added until pH 6 and the aqueous phase was extracted with EtOAc. The organic phase was washed with H₂O, dried over MgSO₄, filtered and concentrated under reduced pressure. The crude mixture was purified by preparative LC (irregular SiOH, 15-40 µm, 24 g GraceResolv™, liquid injection (DCM), mobile phase gradient: heptane/EtOAc/AcOH from 30:46.5:1.5 to 0:97.5:2.5 to afford intermediate I91 (160 mg, 82%).

Compound 51

(3S)-1-(5-{7-Cyclopropyl-5-[(1R)-1-methyl-1,2,3,4-tetrahydroisoquinoline-2-carbonyl]-pyrazolo[1,5-a]pyrimidin-2-yl}-6-fluoropyridin-2-yl)-N-methanesulfonylpyrrolidine-3-carboxamide

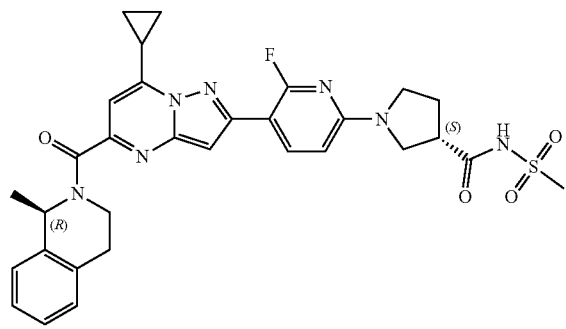

51

A mixture of intermediate I91 (160 mg, 260 µmol) and CDI (57.2 mg, 0.35 mmol) in MeCN (3 mL) was stirred at rt for 2 h. DBU (65.8 µL, 0.44 mmol) and methanesulfonamide [3144-09-0] (41.9 mg, 0.44 mmol) were added. The reaction mixture was stirred at 80° C. for 16 h. Brine, a 1N aqueous solution of HCl and EtOAc were added. The layers were separated and the aqueous phase was extracted with EtOAc (twice). The combined organic extracts were washed with a solution of water and brine (1:1), dried over MgSO₄, filtered and evaporated under reduced pressure. The crude mixture was purified by preparative LC (irregular SiOH, 15-40 µm, 40 g GraceResolv™, liquid injection (DCM), mobile phase gradient: DCM/MeOH from 100:0 to 92:8) to give compound 51 (60 mg, 33%) as a yellow foam.

Compound 86

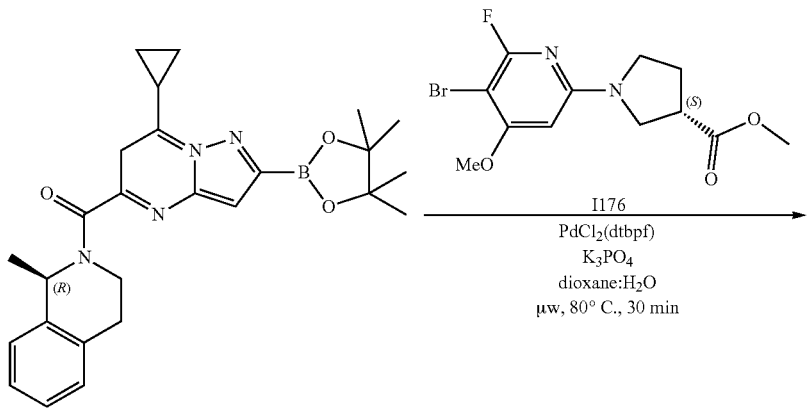

[2035421-36-2]

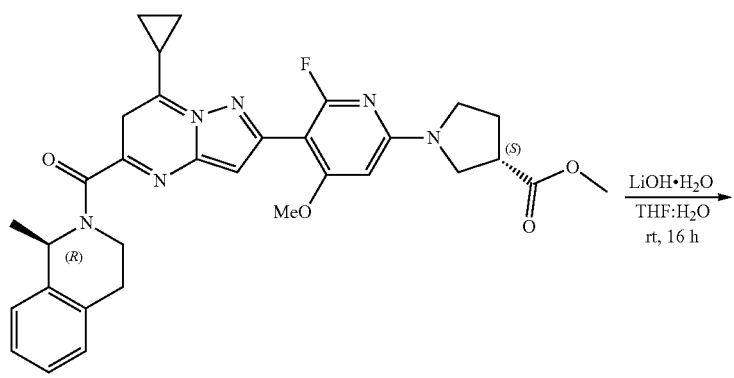

I177

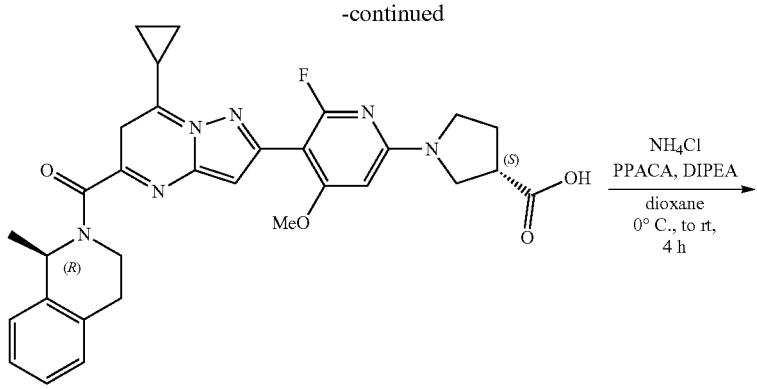

I178

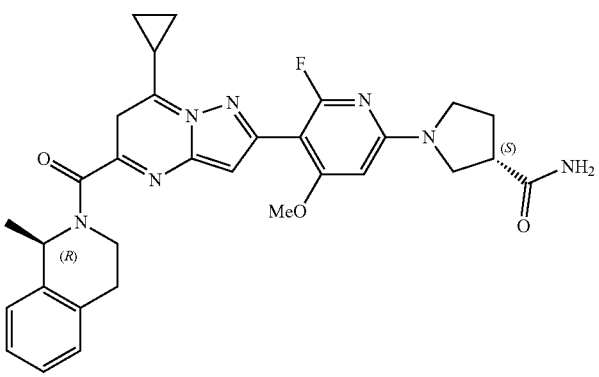

86

Synthesis of Intermediate I176

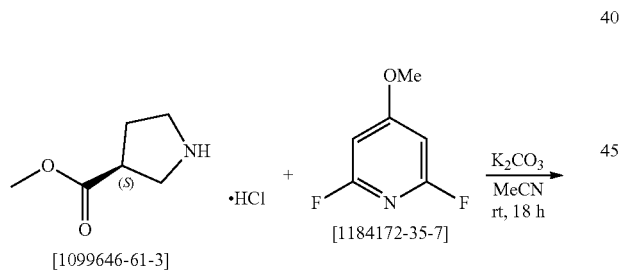

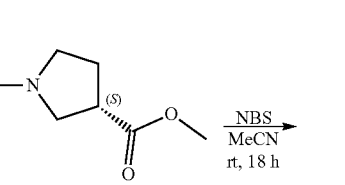

I179

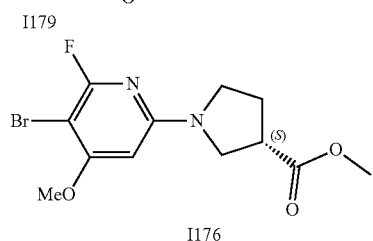

I176

Intermediate I179

Methyl (3S)-1-(6-fluoro-4-methoxypyridin-2-yl)pyrrolidine-3-carboxylate

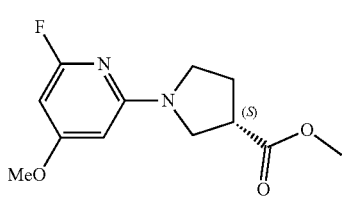

I179

A mixture of 2,6-difluoro-4-methoxypyridine [1184172-35-7] (100 mg, 689 μmol), (S)-methyl pyrrolidine-3-carboxylate hydrochloride [1099646-61-3] (114 mg, 689 μmol) and potassium carbonate (286 mg, 2.07 mmol) in MeCN (6.9 mL) was stirred at rt for 18 h. The reaction mixture was filtered over a pad of Celite® and the filtrate was concentrated in vacuo. The crude mixture was purified by preparative LC (irregular SiOH, 15-40 μm, 12 g GraceResolv™, liquid injection (DCM), mobile phase gradient: heptane/EtOAc from 90:10 to 60:40) to afford intermediate I179 (68 mg, 38%) as a yellow oil.

Intermediate I176

Methyl (3S)-1-(5-bromo-6-fluoro-4-methoxypyridin-2-yl)pyrrolidine-3-carboxylate

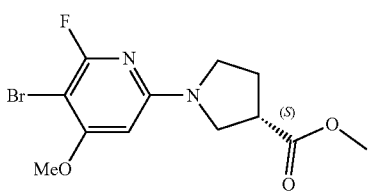

I176

A mixture of intermediate I179 (425 mg, 1.67 mmol) and NBS (298 mg, 1.67 mmol) in MeCN (8.4 mL) was stirred at rt for 18 h. The solvent was evaporated in vacuo. The crude mixture was purified by preparative LC (irregular SiOH, 15-40 µm, 12 g Grace®, liquid injection (DCM), mobile phase gradient: heptane/EtOAc from 99:1 to 40:60) to give intermediate I176 (556 mg, 87%).

Synthesis of Compound 86

Intermediate I177

Methyl (3S)-1-(5-{7-cyclopropyl-5-[(1R)-1-methyl-1,2,3,4-tetrahydroisoquinoline-2-carbonyl]pyrazolo[1,5-a]pyrimidin-2-yl}-6-fluoro-4-methoxypyridin-2-yl)pyrrolidine-3-carboxylate

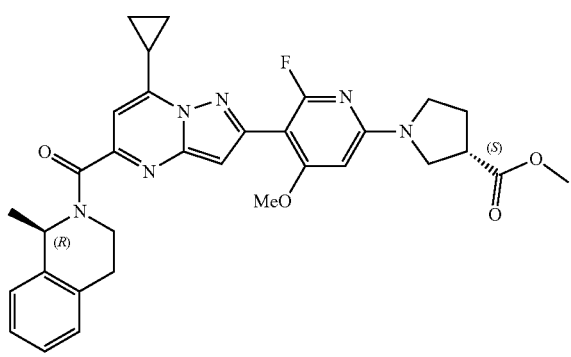

I177

A sealed tube was charged with intermediate I176 (120 mg, 0.36 mmol), (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (236 mg, 0.36 mmol, 70% purity), potassium phosphate tribasic (229 mg, 1.08 mmol), 1,4-dioxane (3.1 mL) and H$_2$O (0.8 mL) and purged with nitrogen. [1,1'-Bis(di-tert-butylphosphino)ferrocene] palladium dichloride (23.5 mg, 36.0 µmol) was added and the mixture was purged again with nitrogen. The reaction mixture was heated at 80° C. using a single mode microwave (Biotage® Initiator EXP 60) with a power output ranging from 0 to 400 W for 30 min. The reaction mixture was diluted with EtOAc. The layers were separated and the organic phase was washed with brine, dried over MgSO$_4$, filtered and evaporated in vacuo. The crude mixture was purified by preparative LC (irregular SiOH, 15-40 µm, 24 g Grace®, liquid injection (DCM), mobile phase gradient: heptane/EtOAc from 80:20 to 20:80) to afford intermediate I177 (195 mg, 93%).

Intermediate I178

(3S)-1-(5-{7-Cyclopropyl-5-[(1R)-1-methyl-1,2,3,4-tetrahydroisoquinoline-2-carbonyl]-pyrazolo[1,5-a]pyrimidin-2-yl}-6-fluoro-4-methoxypyridin-2-yl)pyrrolidine-3-carboxylic acid

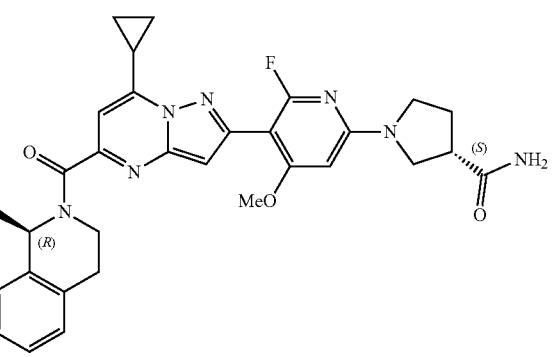

I178

Lithium hydroxide monohydrate (41.9 mg, 1.00 mmol) was added to a solution of intermediate I177 (195 mg, 334 µmol) in THF (2.9 mL) and H$_2$O (0.9 mL). The reaction mixture was stirred at rt for 16 h. A 10% aqueous solution of KHSO$_4$ was added until pH 6 and the aqueous phase was extracted with EtOAc. The combined organic extracts were washed with H$_2$O, dried over MgSO$_4$, filtered and concentrated in vacuo to afford intermediate I178 (185 mg, 97%).

Compound 86

(3S)-1-(5-{7-Cyclopropyl-5-[(1R)-1-methyl-1,2,3,4-tetrahydroisoquinoline-2-carbonyl]-pyrazolo[1,5-a]pyrimidin-2-yl}-6-fluoro-4-methoxypyridin-2-yl)pyrrolidine-3-carboxamide

86

A mixture of intermediate I178 (185 mg, 324 µmol), ammonium chloride (69.4 mg, 1.30 mmol) and DIPEA (467 µL, 2.71 mmol) in 1,4-dioxane (2.5 mL) was stirred at 0° C. PPACA (50% wt in EtOAc, 463 µL, 778 µmol) was added slowly. The reaction mixture was stirred at 0° C. for 10 min and at rt for 4 h. The reaction mixture was diluted with H₂O and EtOAc. The layers were separated and the aqueous phase was extracted with EtOAc. The combined organic extracts were washed with a 10% aqueous solution of KHSO₄ and brine, dried over MgSO₄, filtered and evaporated in vacuo. The crude mixture was purified by preparative LC (spherical C18 25 μm, 40 g YMC-ODS-25, dry loading (Celite®), mobile phase gradient: (0.2% aq.NH₄HCO₃)/MeCN from 75:25 to 35:65). The residue was solubilized in Et₂O and evaporated in vacuo. The product was dried under vacuum at 50° C. for 72 h and at 65° C. for 8 h to give compound 86 (100 mg, 54%).

Compound 87

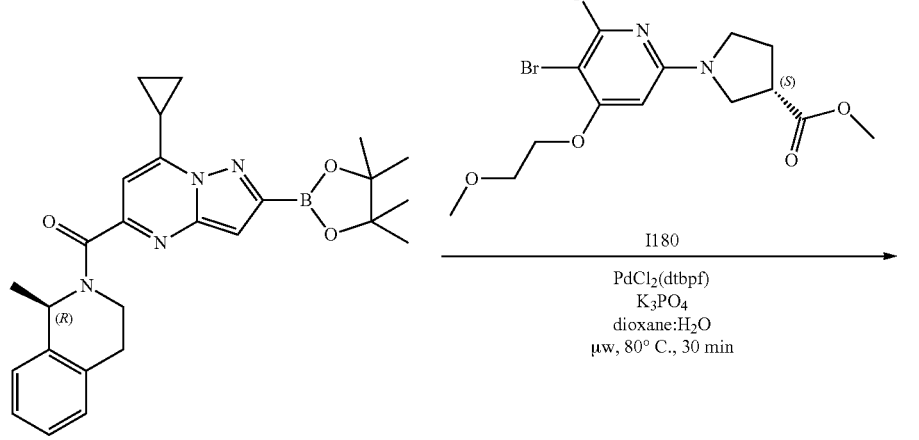

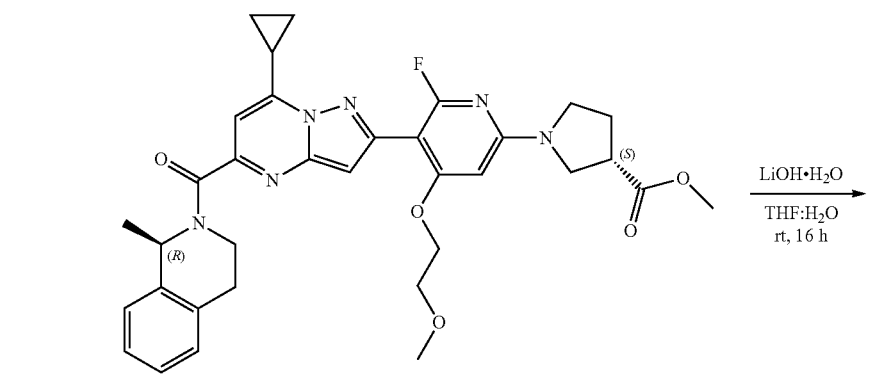

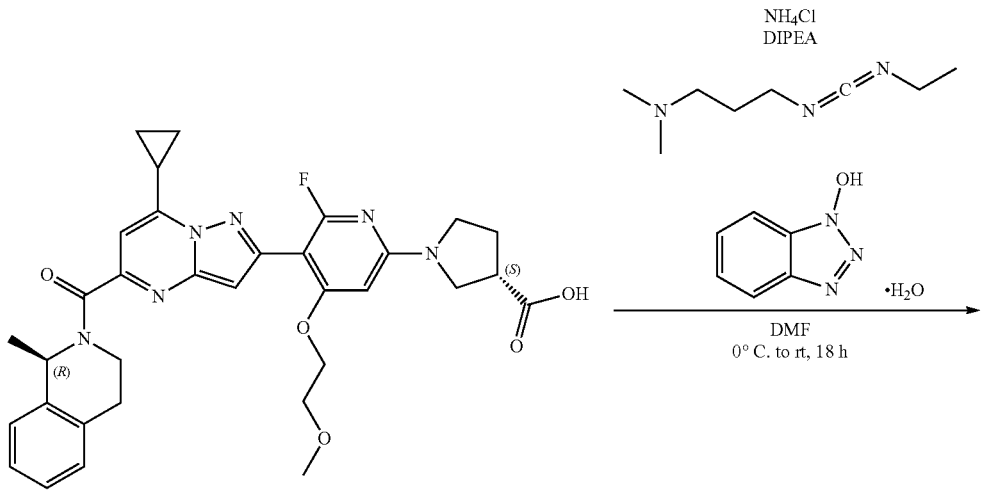

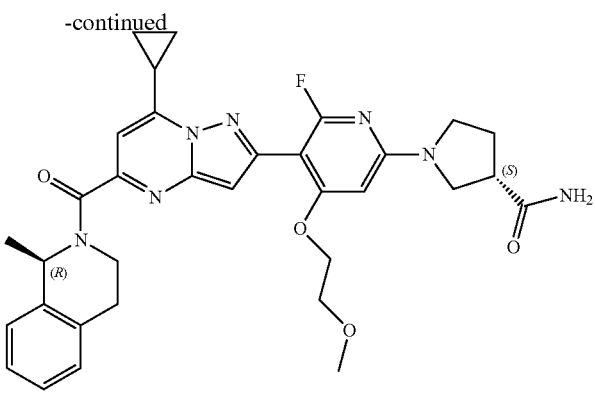

87

Synthesis of Intermediate I180

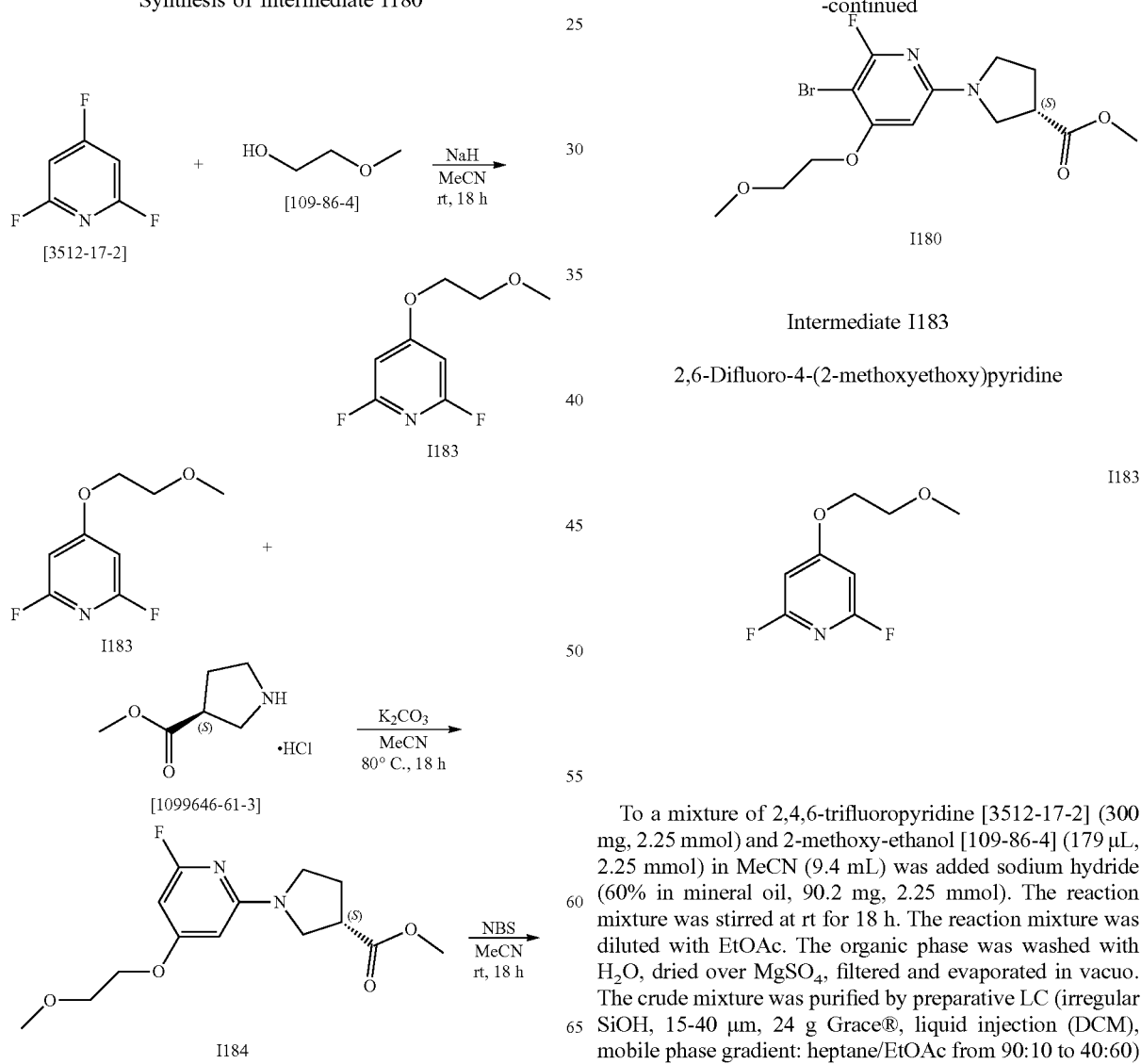

Intermediate I183

2,6-Difluoro-4-(2-methoxyethoxy)pyridine

To a mixture of 2,4,6-trifluoropyridine [3512-17-2] (300 mg, 2.25 mmol) and 2-methoxy-ethanol [109-86-4] (179 µL, 2.25 mmol) in MeCN (9.4 mL) was added sodium hydride (60% in mineral oil, 90.2 mg, 2.25 mmol). The reaction mixture was stirred at rt for 18 h. The reaction mixture was diluted with EtOAc. The organic phase was washed with $H_2O$, dried over $MgSO_4$, filtered and evaporated in vacuo. The crude mixture was purified by preparative LC (irregular SiOH, 15-40 µm, 24 g Grace®, liquid injection (DCM), mobile phase gradient: heptane/EtOAc from 90:10 to 40:60) to afford intermediate I183 (230 mg, 54%).

183

Intermediate I184

Methyl (3S)-1-[6-fluoro-4-(2-methoxyethoxy)pyridin-2-yl]pyrrolidine-3-carboxylate

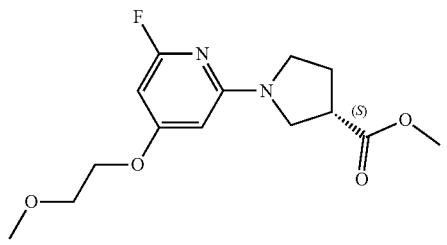

I184

A mixture of intermediate I183 (230 mg, 1.22 mmol), (S)-methyl pyrrolidine-3-carboxylate hydrochloride [1099646-61-3] (201 mg, 1.22 mmol) and potassium carbonate (504 mg, 3.65 mmol) in MeCN (12 mL) was stirred at 80° C. for 18 h. The reaction mixture was filtered over a pad of Celite® and the filtrate was concentrated in vacuo. The crude mixture was purified by preparative LC (irregular SiOH, 15-40 µm, 24 g GraceResolv™, liquid injection (DCM), mobile phase gradient: heptane/EtOAc from 90:10 to 60:40) to afford intermediate I184 (150 mg, 41%) as a yellow oil.

Intermediate I180

Methyl (3S)-1-[5-bromo-6-fluoro-4-(2-methoxyethoxy)pyridin-2-yl]pyrrolidine-3-carboxylate

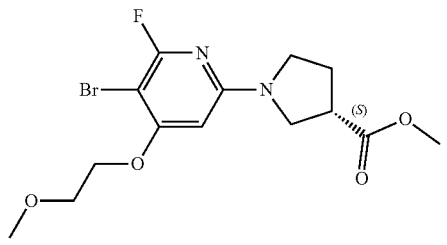

I180

A mixture of intermediate I184 (150 mg, 503 µmol) and NBS (89.5 mg, 503 mmol) in MeCN (2.5 mL) was stirred at rt for 18 h. The solvent was evaporated in vacuo. The crude mixture was purified by preparative LC (irregular SiOH, 15-40 µm, 24 g GraceResolv™, liquid injection (DCM), mobile phase gradient: heptane/EtOAc from 90:10 to 40:60) to afford intermediate I180 (218 mg, 93%) as a yellow oil.

184

Synthesis of Compound 87

Intermediate I181

Methyl (3S)-1-(5-{7-cyclopropyl-5-[(1R)-1-methyl-1,2,3,4-tetrahydroisoquinoline-2-carbonyl]pyrazolo[1,5-a]pyrimidin-2-yl}-6-fluoro-4-(2-methoxyethoxy)pyridin-2-yl)pyrrolidine-3-carboxylate

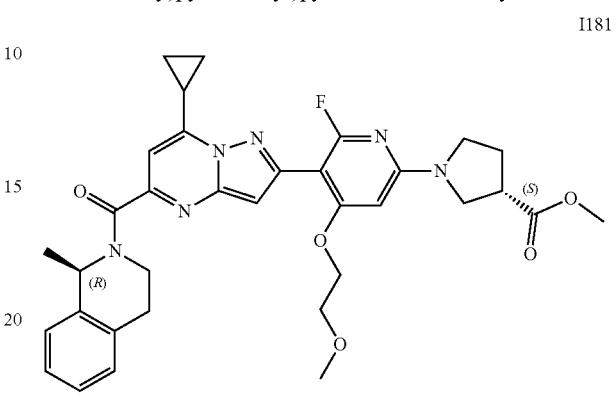

I181

A sealed tube was charged with intermediate I180 (124 mg, 329 µmol), (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (215 mg, 329 µmol, 70% purity), potassium phosphate tribasic (209 mg, 986 µmol), 1,4-dioxane (2.8 mL) and H₂O (0.7 mL) and purged with nitrogen. [1,1'-Bis(di-tert-butylphosphino)ferrocene]palladium dichloride (21.4 mg, 32.9 µmol) was added and the mixture was purged again with nitrogen. The reaction mixture was heated at 80° C. using a single mode microwave (Biotage® Initiator EXP 60) with a power output ranging from 0 to 400 W for 30 min. The reaction mixture was diluted with EtOAc. The organic phase was washed with brine, dried over MgSO₄, filtered and evaporated in vacuo. The crude mixture was purified by preparative LC (irregular SiOH, 15-40 µm, 24 g Grace®, liquid injection (DCM), mobile phase gradient: heptane/EtOAc from 80:20 to 20:80) to afford intermediate I181 (185 mg, 90%).

Intermediate I182

(3S)-1-(5-{7-Cyclopropyl-5-[(1R)-1-methyl-1,2,3,4-tetrahydroisoquinoline-2-carbonyl]pyrazolo[1,5-a]pyrimidin-2-yl}-6-fluoro-4-(2-methoxyethoxy)pyridin-2-yl)pyrrolidine-3-carboxylic acid

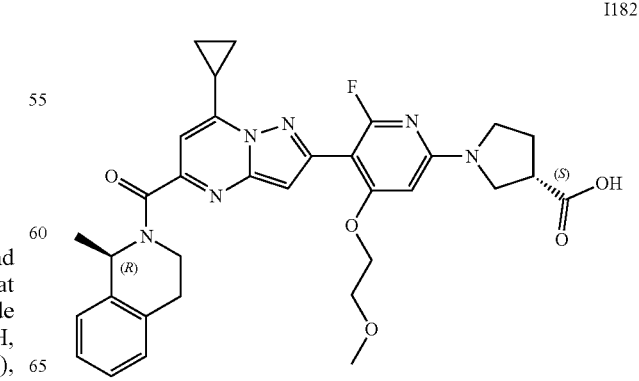

I182

Lithium hydroxide monohydrate (37.0 mg, 883 μmol) was added to a solution of intermediate I181 (185 mg, 294 μmol) in THF (2.6 mL) and H₂O (0.8 mL). The reaction mixture was stirred at rt for 16 h. A 10% aqueous solution of KHSO₄ was added until pH 6 and the aqueous phase was extracted with EtOAc. The combined organic extracts were washed with H₂O, dried over MgSO₄, filtered and concentrated to afford intermediate I182 (170 mg, 94%).

Compound 87

(3S)-1-(5-{7-Cyclopropyl-5-[(1R)-1-methyl-1,2,3,4-tetrahydroisoquinoline-2-carbonyl]-pyrazolo[1,5-a]pyrimidin-2-yl}-6-fluoro-4-(2-methoxyethoxy)pyridin-2-yl)pyrrolidine-3-carboxamide

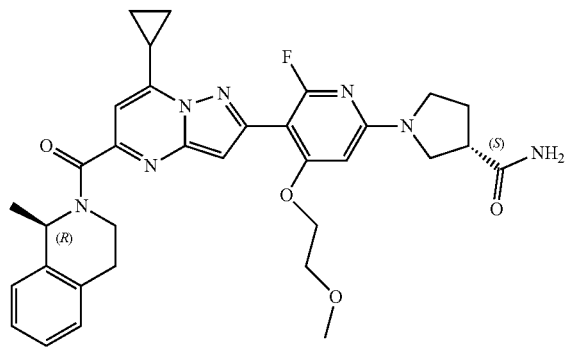

A mixture of intermediate I182 (170 mg, 277 μmol), ammonium chloride (17.8 mg, 332 μmol), 1-(3-dimethylaminopropyl)-3-ethylcarbodiimide (51.5 mg, 332 μmol) and 1-hydroxybenzotriazole hydrate (63.5 mg, 415 μmol) in DMF (14 mL) was stirred at 0° C. DIPEA (238 μL, 1.38 mmol) was added slowly and the reaction mixture was stirred at rt for 18 h. The reaction mixture was evaporated in vacuo. The residue was dissolved in brine and EtOAc. The layers were separated and the aqueous phase was extracted with EtOAc. The combined organic extracts were dried over MgSO₄, filtered and evaporated in vacuo. The crude mixture was purified by reverse phase (Stationary phase: YMC-actus Triart C18 10 μm 30*150 mm, Mobile phase gradient: (0.2% aq.NH₄HCO₃)/MeCN from 70:30 to 30:70). The residue was suspended in MeCN (~2 mL) and stirred under reflux until complete solubilization. The heating source was stopped and the flask was left in the oil bath with a gentle stirring while crystallization occurred (4 h). The solid was filtered off, washed with MeCN and dried under vacuum at 50° C. for 18 h to give compound 87 (115 mg, 68%) as a white solid.

Compound 52

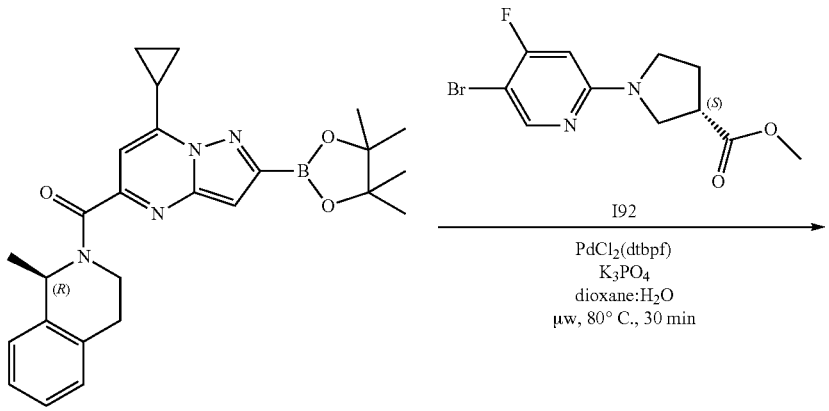

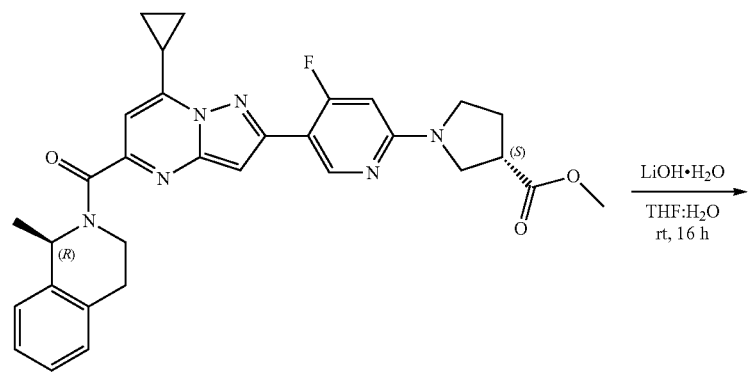

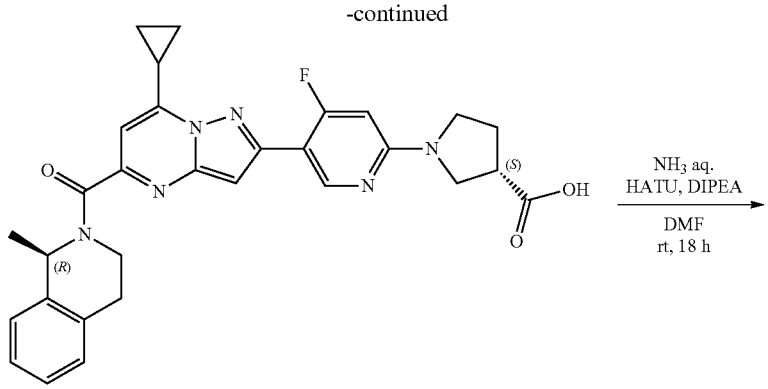
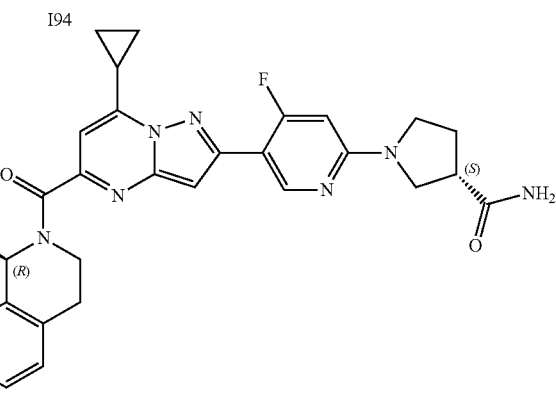
I94
52
Synthesis of Intermediate I92
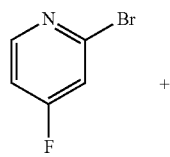
[357927-50-5]
+
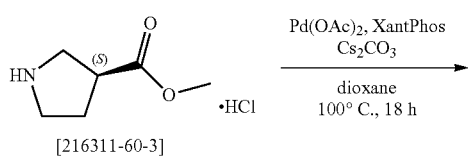
[216311-60-3]
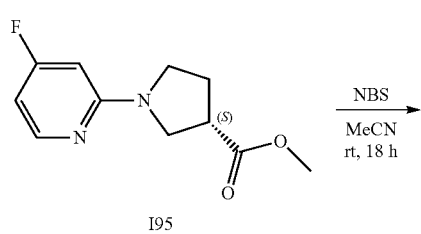
I95
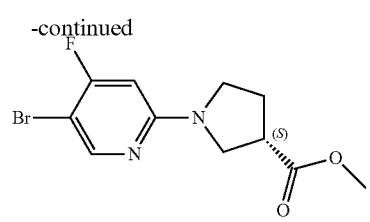
I92
Intermediate I95
Methyl (3S)-1-(4-fluoropyridin-2-yl)pyrrolidine-3-carboxylate
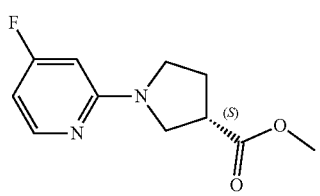
I95
A sealed tube was charged with 2-bromo-4-fluoropyridine [357927-50-5] (200 mg, 1.14 mmol), (S)-methyl pyrrolidine-3-carboxylate hydrochloride [216311-60-3] (188 mg, 1.14 mmol) and cesium carbonate (1.11 g, 3.41 mmol) and purged with nitrogen. 1,4-Dioxane (9.2 mL) was added and the mixture was degassed with nitrogen. Palladium acetate (25.5 mg, 0.11 mmol) and XantPhos (65.8 mg, 0.11 mmol) were added. The reaction mixture was stirred at 100° C. for 18 h. The reaction mixture was poured out into water and the aqueous phase was extracted with EtOAc and filtered over Celite®. The filtrate was washed with brine, dried over MgSO$_4$, filtered and evaporated to dryness. The crude mixture was purified by preparative LC (irregular SiOH, 15-40 μm, 12 g GraceResolv™, liquid injection (DCM), mobile phase gradient: heptane/EtOAc from 90:10 to 40:60) to afford intermediate I95 (32 mg, 13%) as a colorless oil.

Intermediate I92

Methyl (3S)-1-(5-bromo-4-fluoropyridin-2-yl)pyrrolidine-3-carboxylate

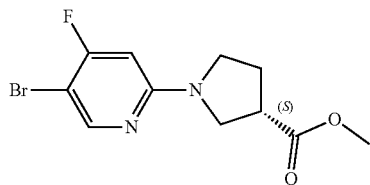

A mixture of intermediate I95 (60.0 mg, 268 μmol) and NBS (47.6 mg, 268 μmol) in MeCN (2.7 mL) was stirred at rt for 18 h. The mixture was evaporated under reduced pressure. The crude product was purified by preparative LC (irregular SiOH, 15-40 μm, 12 g GraceResolv™, liquid injection (DCM), mobile phase gradient: heptane/EtOAc from 100:0 to 50:50) to afford intermediate I92 (68 mg, 84%) as a colorless oil.

Synthesis of Compound 52

Intermediate I93

Methyl (3S)-1-(5-{7-cyclopropyl-5-[(1R)-1-methyl-1,2,3,4-tetrahydroisoquinoline-2-carbonyl]pyrazolo[1,5-a]pyrimidin-2-yl}-4-fluoropyridin-2-yl)pyrrolidine-3-carboxylate

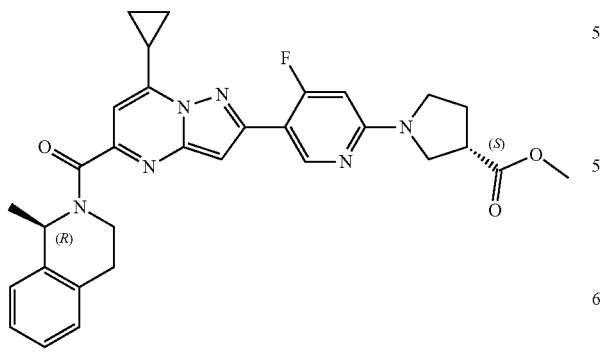

A sealed tube was charged with intermediate I92 (234 mg, 0.77 mmol), (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (472 mg, 0.77 mmol, 75% purity), potassium phosphate tribasic (492 mg, 2.32 mmol), 1,4-dioxane (7.8 mL) and H$_2$O (2.0 mL) and purged with nitrogen. [1,1'-Bis(di-tert-butylphosphino)ferrocene] palladium acetate (50.3 mg, 77.2 μmol) was added and the mixture was purged with nitrogen. The reaction mixture was heated at 80° C. using a single mode microwave (Biotage® Initiator EXP 60) with a power output ranging from 0 to 400 W for 30 min. The reaction mixture was diluted with EtOAc and the organic phase was washed with brine, dried over MgSO$_4$, filtered and evaporated under reduced pressure. The crude mixture was purified by preparative LC (regular SiOH, 30 μm, 80 g Interchim®, liquid injection (DCM), mobile phase gradient: heptane/EtOAc from 40:60 to 0:100) to afford intermediate I93 (400 mg, 93%) as a yellow oil.

Intermediate I94

(3S)-1-(5-{7-Cyclopropyl-5-[(1R)-1-methyl-1,2,3,4-tetrahydroisoquinoline-2-carbonyl]pyrazolo[1,5-a]pyrimidin-2-yl}-4-fluoropyridin-2-yl)pyrrolidine-3-carboxylic acid

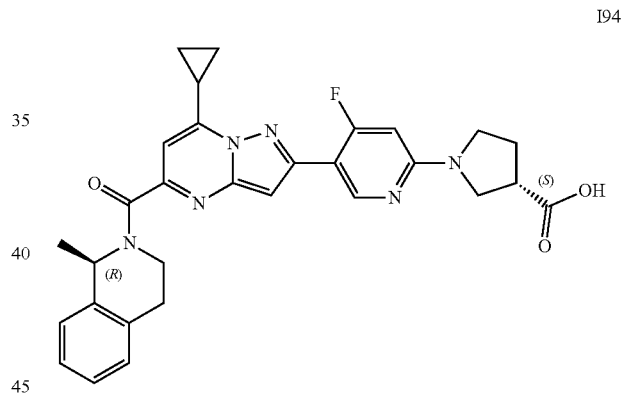

Lithium hydroxide monohydrate (90.8 mg, 2.16 mmol) was added to a solution of intermediate I93 (400 mg, 0.72 mmol) in THF (6.3 mL) and H$_2$O (2.0 mL). The reaction mixture was stirred at rt for 16 h. A 10% aqueous solution of KHSO$_4$ was added until pH 6 and the aqueous phase was extracted with EtOAc. The organic layer was washed with H$_2$O, dried over MgSO$_4$, filtered and concentrated under reduced pressure. The crude mixture was purified by preparative LC (irregular SiOH, 15-40 μm, 24 g GraceResolv™, liquid injection (DCM), mobile phase gradient: heptane/EtOAc/AcOH from 80:19.5:0.5 to 0:97.5:2.5) to afford intermediate I94 (380 mg, 97%).

Compound 52

(3S)-1-(5-{7-Cyclopropyl-5-[(1R)-1-methyl-1,2,3,4-tetrahydroisoquinoline-2-carbonyl]-pyrazolo[1,5-a]pyrimidin-2-yl}-4-fluoropyridin-2-yl)pyrrolidine-3-carboxamide

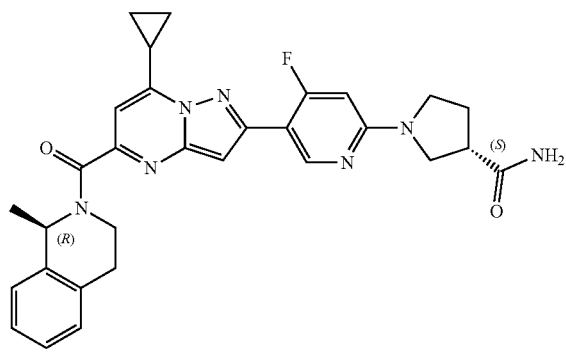

A mixture of intermediate I94 (180 mg, 333 μmol), HATU (190 mg, 499 μmol) and DIPEA (172 μL, 1.0 mmol) in DMF (9 mL) was stirred at rt for 1 h. Ammonia (28% in H₂O, 113 μL, 1.67 mmol) was added and the reaction mixture was stirred at rt for 18 h. The reaction mixture was diluted with H₂O and EtOAc. The layers were separated and the aqueous phase was extracted with EtOAc (twice). The combined organic extracts were dried over MgSO₄, filtered and evaporated under reduced pressure. The crude mixture was purified by preparative LC (regular SiOH, 30 μm, 24 g GraceResolv™, liquid injection (DCM), mobile phase gradient: DCM/i-PrOH from 100:0 to 70:30). The residue (120 mg) was dissolved in DCM and washed with a 1% aqueous solution of NaHCO₃ (3 times), brine, dried over MgSO₄, filtered and concentrated in vacuo to give compound 52 (90 mg, 50%).

Compound 53

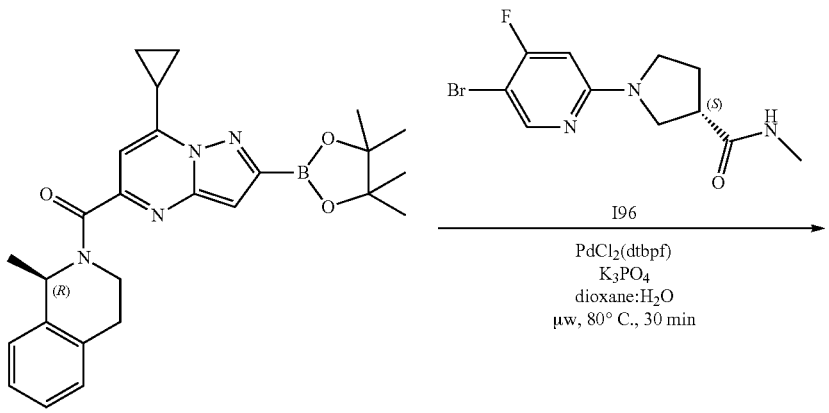

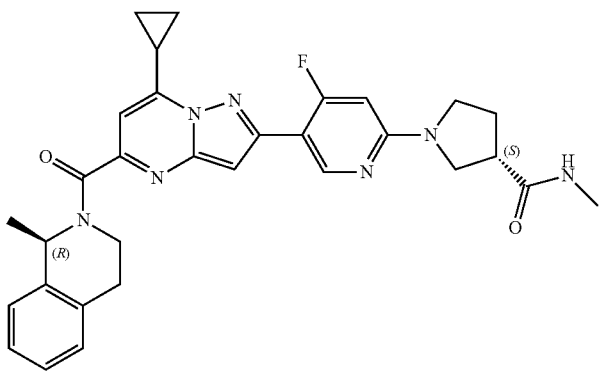

Synthesis of Intermediate I96

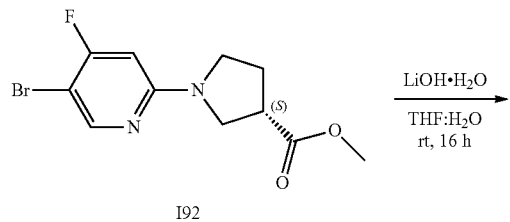

I92

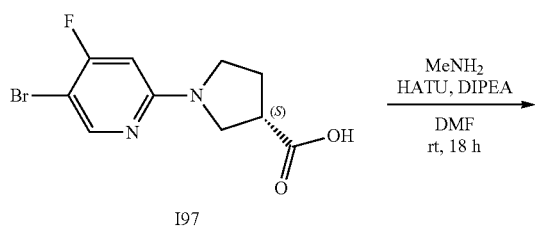

I97

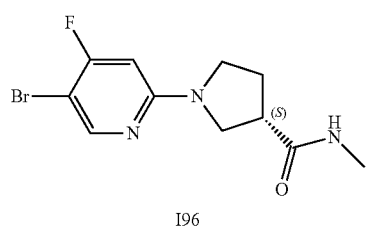

I96

Intermediate I97

(3S)-1-(5-Bromo-4-fluoropyridin-2-yl)pyrrolidine-3-carboxylic acid

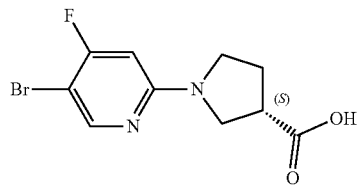

Lithium hydroxide monohydrate (66.4 mg, 1.58 mmol) was added to a solution of intermediate I92 (160 mg, 0.53 mmol) in THF (12 mL) and H$_2$O (3.0 mL). The reaction mixture was stirred at rt for 16 h. A 10% aqueous solution of KHSO$_4$ was added until pH 6 and the aqueous phase was extracted with EtOAc. The combined organic extracts were washed with H$_2$O, dried over MgSO$_4$, filtered and concentrated under reduced pressure to afford intermediate I97 (150 mg, 98%) as a yellow foam.

Intermediate I96

(3S)-1-(5-Bromo-4-fluoropyridin-2-yl)-N-methylpyrrolidine-3-carboxamide

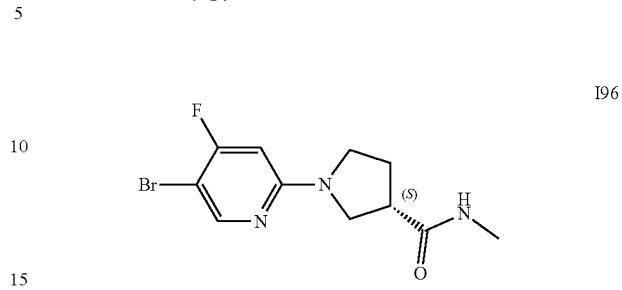

A mixture of intermediate I97 (150 mg, 519 µmol), HATU (296 mg, 0.78 mmol) and DIPEA (268 µL, 1.56 mmol) in DMF (8 mL) was stirred at rt for 1 h. Methylamine (2.0 M in THF, 1.30 mL, 2.59 mmol) was added and the reaction mixture was stirred at rt for 18 h. The reaction mixture was diluted with H$_2$O and EtOAc. The layers were separated. The organic phase was washed with a 1% aqueous solution of NaHCO$_3$ (twice), dried over MgSO$_4$ and concentrated under reduced pressure. The crude mixture was purified by preparative LC (irregular SiOH, 15-40 µm, 24 g GraceResolv™, liquid injection (DCM), mobile phase gradient: DCM/i-PrOH from 100:0 to 80:20) to afford intermediate I96 (140 mg, 89%) as a yellow oil.

Synthesis of Compound 53

(3S)-1-(5-{7-Cyclopropyl-5-[(1R)-1-methyl-1,2,3,4-tetrahydroisoquinoline-2-carbonyl]-pyrazolo[1,5-a]pyrimidin-2-yl}-4-fluoropyridin-2-yl)-N-methylpyrrolidine-3-carboxamide

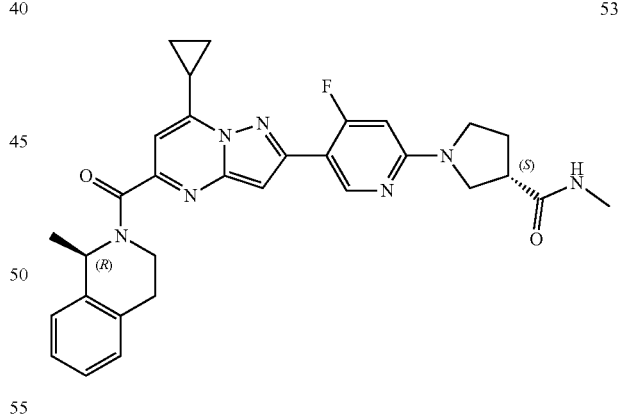

53

A sealed tube was charged with intermediate I96 (140 mg, 0.46 mmol), (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (212 mg, 0.46 mmol, 63% purity), potassium phosphate tribasic (0.29 g, 1.39 mmol), 1,4-dioxane (3.2 mL) and H$_2$O (0.8 mL) and purged with nitrogen. [1,1'-Bis(di-tert-butylphosphino)ferrocene] palladium dichloride (30.2 mg, 46.3 µmol) was added and the mixture was purged with nitrogen. The reaction mixture was heated at 80° C. using a single mode microwave (Biotage® Initiator EXP 60) with a power output ranging from 0 to 400 W for 30 min. The reaction mixture

Compound 54

(3S)-1-(5-{7-Cyclopropyl-5-[(1R)-1-methyl-1,2,3,4-tetrahydroisoquinoline-2-carbonyl]-pyrazolo[1,5-a]pyrimidin-2-yl}-4-fluoropyridin-2-yl)-N-methanesulfonylpyrrolidine-3-carboxamide

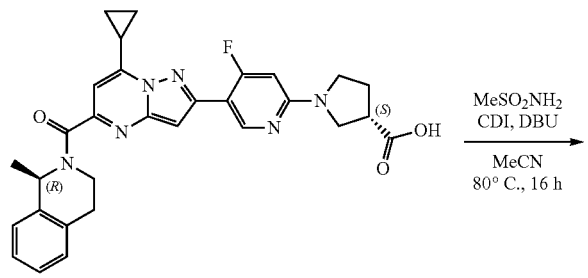

I94

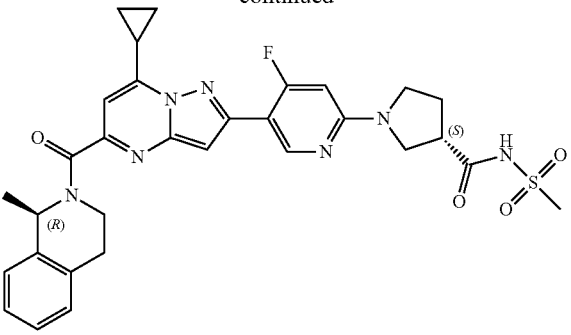

54

A mixture of intermediate I94 (185 mg, 342 μmol) and CDI (83.2 mg, 0.51 mmol) in MeCN (3.5 mL) was stirred at rt for 2 h. DBU (102 μL, 0.68 mmol) and methanesulfonamide [3144-09-0] (65.1 mg, 0.68 mmol) were added. The reaction mixture was stirred at 80° C. for 16 h. A 1N aqueous solution of HCl and EtOAc were added. The layers were separated and the aqueous phase was extracted with EtOAc (twice). The combined organic extracts were washed with a solution of water and brine (1:1), dried over MgSO₄, filtered and evaporated under reduced pressure. The crude mixture was purified by preparative LC (irregular SiOH, 15-40 μm, 24 g GraceResolv™, liquid injection (DCM), mobile phase gradient: DCM/MeOH from 100:0 to 92:8). A second purification was carried out: preparative LC (spherical C18 25 μm, 40 g YMC-ODS-25, dry loading (Celite®), mobile phase gradient: (0.2% aq.NH₄HCO₃)/MeCN from 85:15 to 45:55). The product was freeze-dried to give compound 54 (140 mg, 66%) as a white solid.

Compound 88

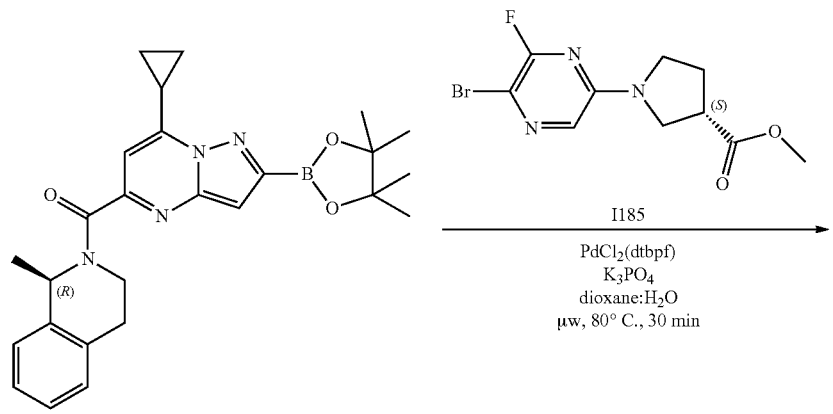

197
198
-continued
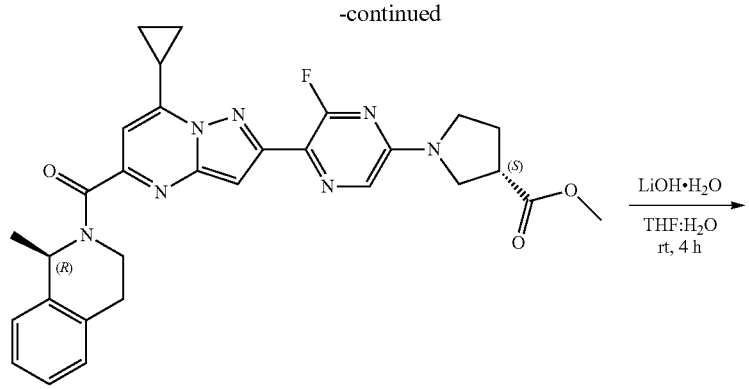
I186
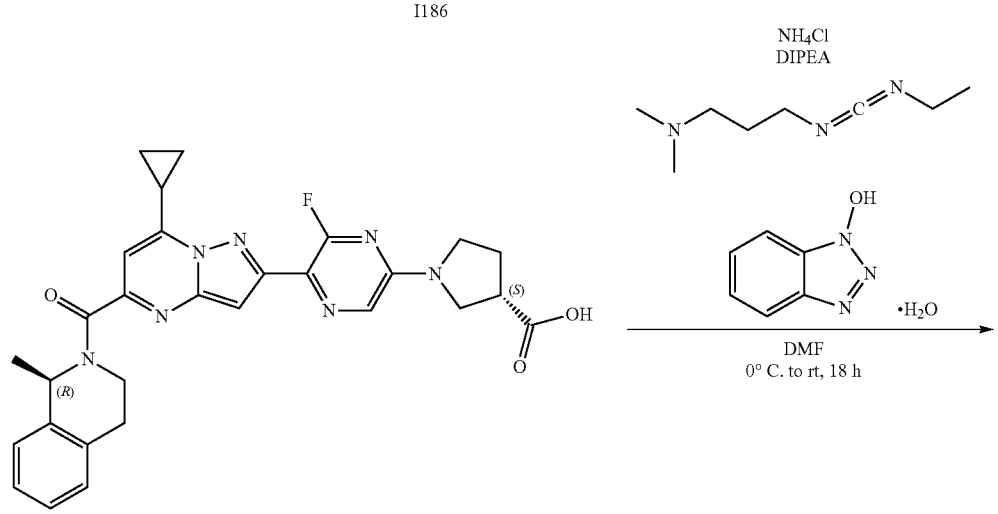
I187
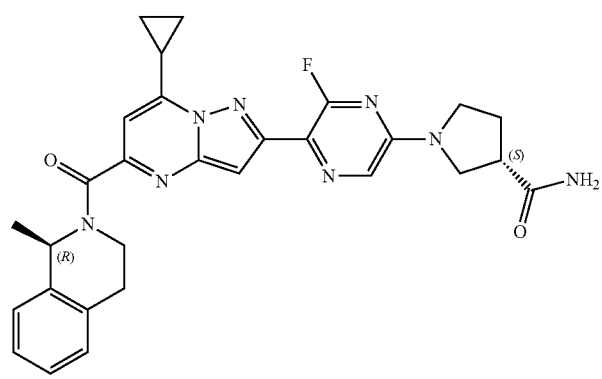
88
Synthesis of Intermediate I185
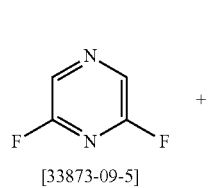
[33873-09-5]
-continued
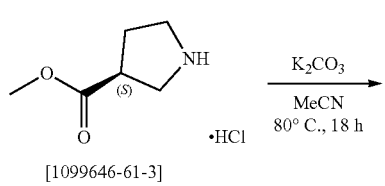
[1099646-61-3]

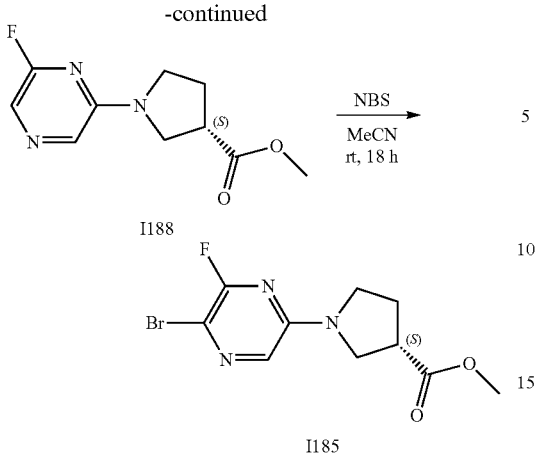

Intermediate I188

Methyl (3S)-1-(6-fluoropyrazin-2-yl)pyrrolidine-3-carboxylate

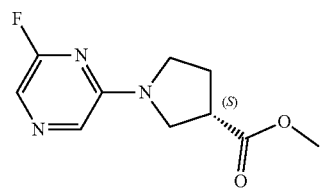

A mixture of 2,6-difluoropyrazine [33873-09-5] (726 mg, 6.26 mmol), (S)-methyl pyrrolidine-3-carboxylate hydrochloride [1099646-61-3] (1.14 g, 6.88 mmol) and potassium carbonate (2.59 g, 18.8 mmol) in MeCN (48 mL) was stirred at 80° C. for 18 h. The reaction mixture was diluted with $H_2O$ and EtOAc. The layers were separated and the aqueous phase was extracted with EtOAc (twice). The combined organic extracts were dried over $MgSO_4$, filtered and concentrated in vacuo to afford intermediate I188 (1.1 g, 77%).

Intermediate I185

Methyl (3S)-1-(5-bromo-6-fluoropyrazin-2-yl)pyrrolidine-3-carboxylate

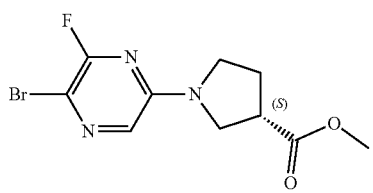

A mixture of intermediate I188 (1.00 g, 4.59 mmol) and NBS (817 mg, 4.59 mmol) in MeCN (51 mL) was stirred at rt for 18 h. The reaction mixture was diluted with $H_2O$ and EtOAc. The layers were separated and the aqueous phase was extracted with EtOAc (twice). The combined organic extracts were washed with an aqueous solution of $NaHCO_3$ (twice), dried over $MgSO_4$, filtered and concentrated in vacuo to afford intermediate I185 (1.42 g).

Synthesis of Compound 88

Intermediate I186

Methyl (3S)-1-(5-{7-cyclopropyl-5-[(1R)-1-methyl-1,2,3,4-tetrahydroisoquinoline-2-carbonyl]pyrazolo[1,5-a]pyrimidin-2-yl}-6-fluoropyrazin-2-yl)pyrrolidine-3-carboxylate

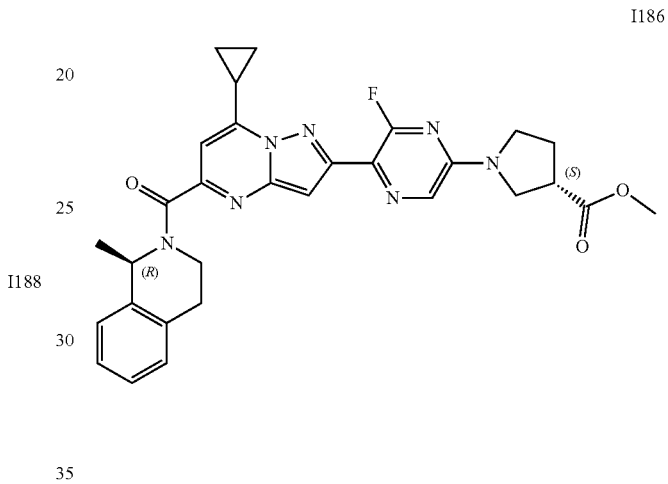

A sealed tube was charged with intermediate I185 (207 mg, 682 μmol), (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (527 mg, 1.02 mmol, 89% purity), potassium phosphate tribasic (434 mg, 2.05 mmol), 1,4-dioxane (13 mL) and $H_2O$ (2 mL) and purged with nitrogen. [1,1'-Bis(di-tert-butylphosphino)ferrocene] palladium dichloride (44.4 mg, 68.2 μmol) was added and the mixture was purged again with nitrogen. The reaction mixture was heated at 80° C. using a single mode microwave (Biotage® Initiator EXP 60) with a power output ranging from 0 to 400 W for 30 min. The reaction mixture was diluted with EtOAc and brine. The layers were separated and the aqueous phase was extracted with EtOAc. The combined organic extracts were washed with $H_2O$ (twice), dried over $MgSO_4$, filtered and concentrated in vacuo. The crude mixture was purified by preparative LC (irregular SiOH, 15-40 μm, 40 g GraceResolv™, liquid injection (DCM), mobile phase gradient: DCM/EtOAc from 100:0 to 70:30). A second purification was performed by preparative LC (irregular SiOH, 15-40 μm, 24 g GraceResolv™, liquid injection (DCM), mobile phase gradient: heptane/(EtOAc/MeOH (9:1)) from 90:10 to 60:40) to afford intermediate I186 (100 mg, 26%) as a pale yellow solid.

201

Intermediate I187

(3S)-1-(5-{7-Cyclopropyl-5-[(1R)-1-methyl-1,2,3,4-tetrahydroisoquinoline-2-carbonyl]-pyrazolo[1,5-a]pyrimidin-2-yl}-6-fluoropyrazin-2-yl)pyrrolidine-3-carboxylic acid

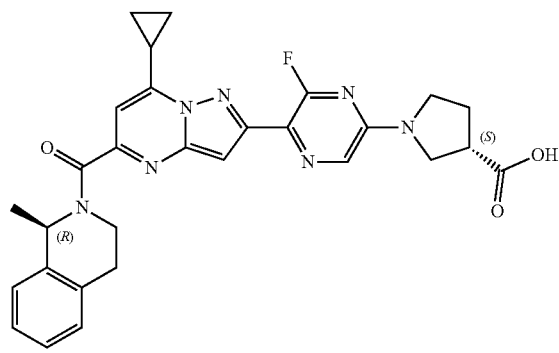

I187

Lithium hydroxide monohydrate (41.6 mg, 0.99 mmol) was added to a solution of intermediate I186 (100 mg, 0.18 mmol) in THF (5.2 mL) and H₂O (1.3 mL). The reaction mixture was stirred at rt for 4 h. A 10% aqueous solution of KHSO₄ was added until pH 6 and the aqueous phase was extracted with EtOAc. The combined organic extracts were washed with H₂O, dried over MgSO₄, filtered and evaporated in vacuo to afford intermediate I187 (90 mg, 81%, 88% purity) as a yellow oil.

202

Compound 88

(3S)-1-(5-{7-Cyclopropyl-5-[(1R)-1-methyl-1,2,3,4-tetrahydroisoquinoline-2-carbonyl]-pyrazolo[1,5-a]pyrimidin-2-yl}-6-fluoropyrazin-2-yl)pyrrolidine-3-carboxamide

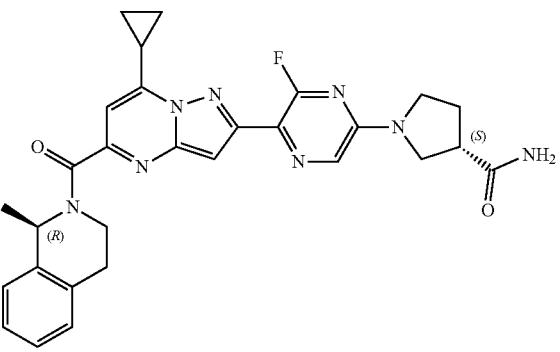

88

A mixture of intermediate I187 (80.0 mg, 0.13 mmol, 88% purity), ammonium chloride (8.34 mg, 156 μmol), 1-(3-dimethylaminopropyl)-3-ethylcarbodiimide (27.6 μL, 156 μmol) and 1-hydroxybenzotriazole hydrate (29.9 mg, 195 μmol) in DMF (6.4 mL) was stirred at 0° C. DIPEA (112 μL, 0.65 mmol) was added slowly. The reaction mixture was stirred at rt for 18 h. The reaction mixture was evaporated in vacuo. The residue was dissolved in brine and EtOAc. The layers were separated and the aqueous phase was extracted with EtOAc. The combined organic extracts were dried over MgSO₄, filtered and evaporated in vacuo. The residue was triturated with MeCN. The solid was filtered off and dried. The residue (45 mg) was purified by reverse phase (Stationary phase: YMC-actus Triart C18 10 nm 30*150 mm, Mobile phase gradient: (0.2% aq.NH₄HCO₃)/MeCN from 65:35 to 25:75). The residue (24 mg) was solubilized in MeCN (2 mL), extended with water (10 mL) and freeze-dried to give compound 88 (19 mg, 27%) as a yellow fluffy solid.

Compound 89

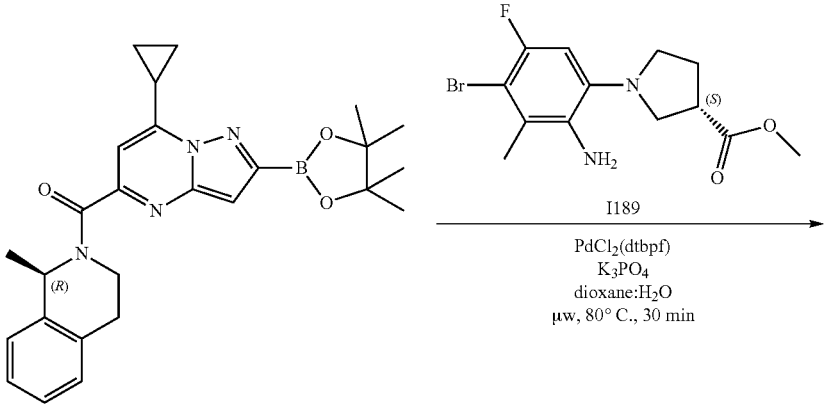

-continued
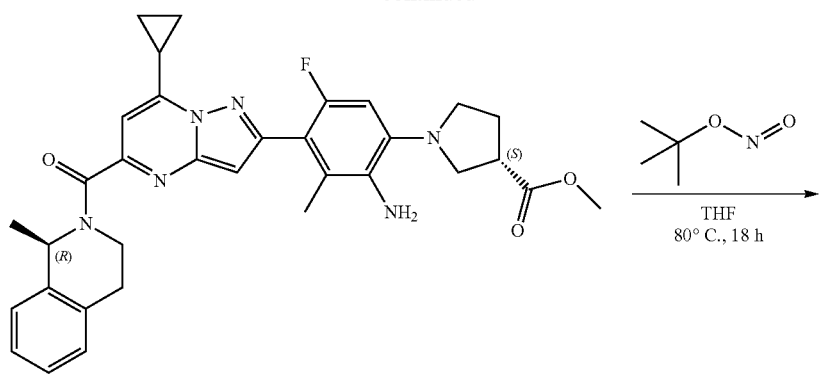
I190
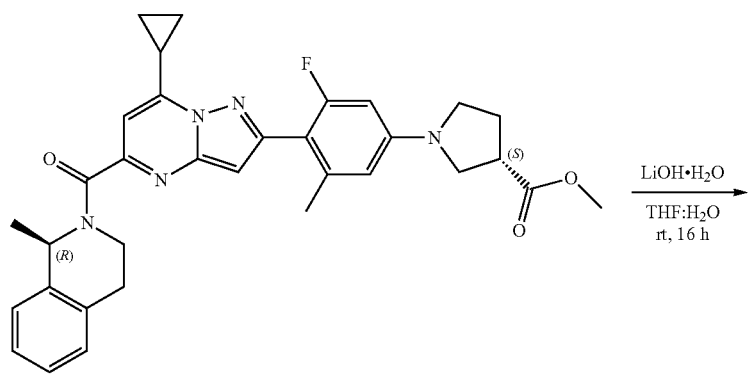
I191
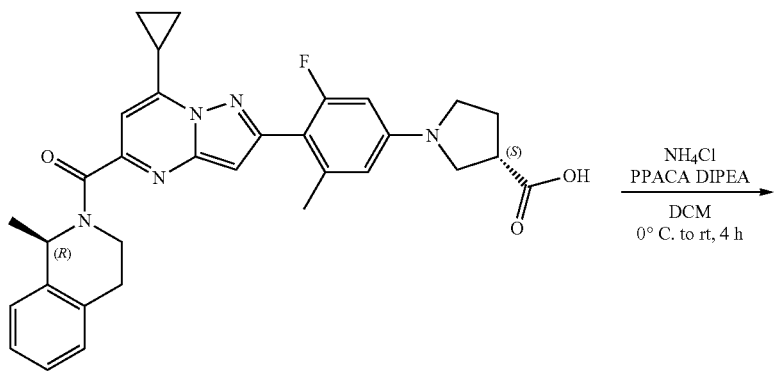
I192
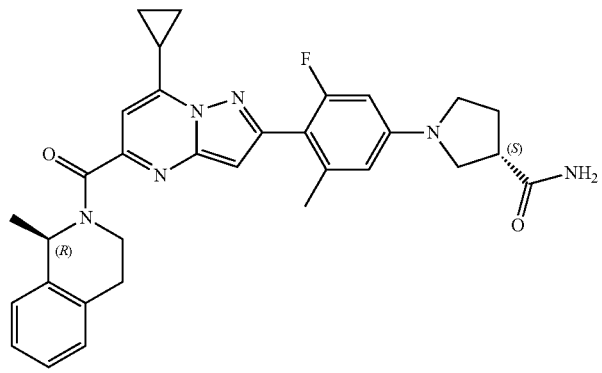
89

Synthesis of Intermediate I189

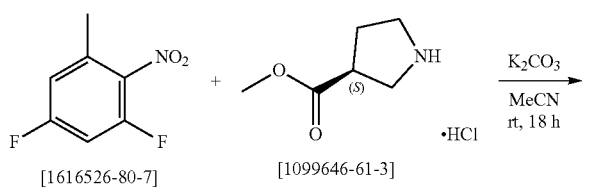

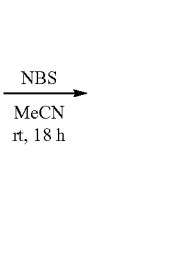

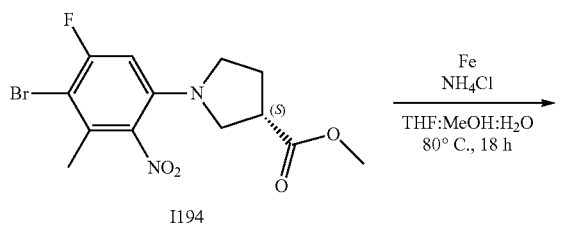

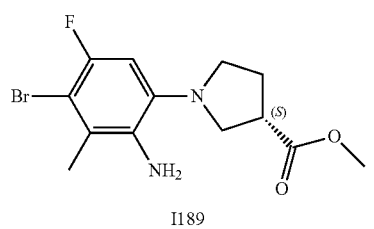

Intermediate I193

Methyl (3S)-1-(5-fluoro-3-methyl-2-nitrophenyl)pyrrolidine-3-carboxylate

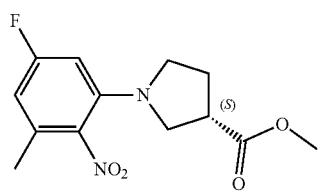

A mixture of 1,5-difluoro-3-methyl-2-nitrobenzene [1616526-80-7] (125 mg, 722 µmol), (S)-methyl pyrrolidine-3-carboxylate hydrochloride [1099646-61-3] (132 mg, 795 µmol) and potassium carbonate (299 mg, 2.17 mmol) in MeCN (7.2 mL) was stirred at rt for 18 h. The reaction mixture was filtered over a pad of Celite® and the filtrate was evaporated in vacuo. The crude mixture was purified by preparative LC (irregular SiOH, 15-40 µm, 24 g GraceResolv™, liquid injection (DCM), mobile phase gradient: heptane/EtOAc from 99:1 to 60:40) to afford intermediate I193 (118 mg, 58%) as a yellow oil.

Intermediate I194

Methyl (3S)-1-(4-bromo-5-fluoro-3-methyl-2-nitrophenyl)pyrrolidine-3-carboxylate

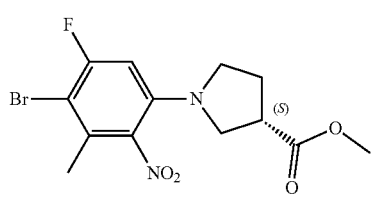

A mixture of intermediate I193 (725 mg, 2.57 mmol) and NBS (457 mg, 2.57 mmol) in MeCN (12.8 mL) was stirred at rt for 18 h. The solvent was evaporated in vacuo to afford intermediate I194 (1.10 g, 95%, 80% purity).

Intermediate I189

Methyl (3S)-1-(2-amino-4-bromo-5-fluoro-3-methylphenyl)pyrrolidine-3-carboxylate

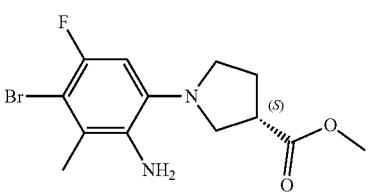

In a sealed tube a mixture of intermediate I194 (1.10 g, 2.44 mmol, 80% purity), iron (680 mg, 12.2 mmol) and ammonium chloride (1.31 g, 24.4 mmol) in THF (7.7 mL), MeOH (7.7 mL) and $H_2O$ (3.9 mL) was stirred at 80° C. for 18 h. The reaction mixture was diluted with EtOAc and $H_2O$. The layers were separated and the organic phase was washed with brine, dried over $MgSO_4$, filtered and evaporated in vacuo. The crude mixture was purified by preparative LC (irregular SiOH, 15-40 µm, 12 g Grace®, liquid injection (DCM), mobile phase gradient: heptane/EtOAc from 99:1 to 60:40) to afford intermediate I189 (666 mg, 83%) as a colorless oil.

Synthesis of Compound 89

Intermediate I190

Methyl (3S)-1-(2-amino-4-{7-cyclopropyl-5-[(1R)-1-methyl-1,2,3,4-tetrahydro-isoquinoline-2-carbonyl]pyrazolo[1,5-a]pyrimidin-2-yl}-5-fluoro-3-methylphenyl)-pyrrolidine-3-carboxylate

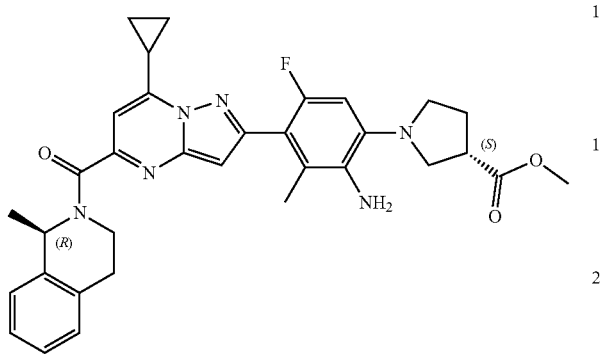

I190

A sealed tube was charged with intermediate I189 (615 mg, 1.86 mmol), (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (1.22 g, 1.86 mmol, 70% purity), potassium phosphate tribasic (1.18 g, 5.57 mmol), 1,4-dioxane (15.8 mL) and H₂O (4.0 mL) and purged with nitrogen. [1,1'-Bis(di-tert-butylphosphino)ferrocene] palladium dichloride (121 mg, 186 µmol) was added and the mixture was purged again with nitrogen. The reaction mixture was heated at 80° C. using a single mode microwave (Biotage® Initiator EXP 60) with a power output ranging from 0 to 400 W for 30 min. The reaction mixture was diluted with EtOAc. The organic phase was washed with brine, dried over MgSO₄, filtered and evaporated in vacuo. The crude mixture was combined with other samples (105 mg, 317 µmol and 50 mg, 151 µmol) and purified by preparative LC (irregular SiOH, 15-40 µm, 40 g Grace®, liquid injection (DCM), mobile phase gradient: heptane/EtOAc from 80:20 to 20:80) to afford intermediate I190 (1.4 g, 78%, 75% purity).

Intermediate I191

Methyl (3S)-1-(4-{7-cyclopropyl-5-[(1R)-1-methyl-1,2,3,4-tetrahydroisoquinoline-2-carbonyl]pyrazolo[1,5-a]pyrimidin-2-yl}-3-fluoro-5-methylphenyl)pyrrolidine-3-carboxylate

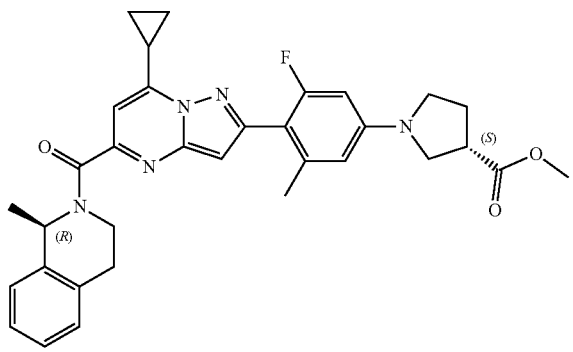

I191

In a sealed tube a mixture of intermediate I190 (700 mg, 901 µmol, 75% purity) and tert-butyl nitrite (118 µL, 991 µmol) in THF (14.7 mL) was stirred at 80° C. for 18 h. The solvent was evaporated in vacuo. The crude mixture was purified by preparative LC (irregular SiOH, 15-40 µm, 24 g Grace®, liquid injection (DCM), mobile phase gradient: heptane/EtOAc from 80:20 to 0:100) to afford intermediate I191 (186 mg, 36%).

Intermediate I192

(3S)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluoro-5-methylphenyl)pyrrolidine-3-carboxylic acid

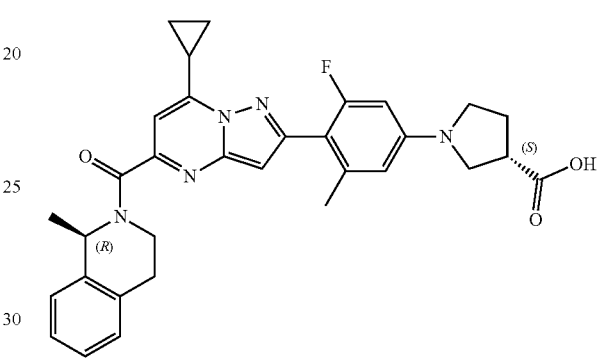

I192

Lithium hydroxide monohydrate (62.1 mg, 1.48 mmol) was added to a solution of intermediate I191 (280 mg, 493 µmol) in THF (4.3 mL) and H₂O (1.3 mL). The reaction mixture was stirred at rt for 16 h. A 10% aqueous solution of KHSO₄ was added until pH 6 and the aqueous phase was extracted with EtOAc. The combined organic extracts were washed with H₂O, dried over MgSO₄, filtered and concentrated in vacuo to afford intermediate I192 (250 mg, 92%) as a yellow foam.

Compound 89

(3S)-1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluoro-5-methylphenyl)pyrrolidine-3-carboxamide

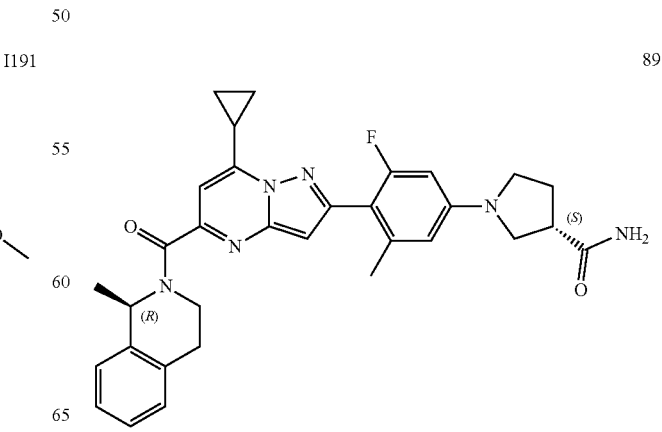

89

A mixture of intermediate I192 (220 mg, 397 μmol), ammonium chloride (85.0 mg, 1.59 mmol) and DIPEA (572 μL, 3.32 mmol) in DCM (2.2 mL) was stirred at 0° C. PPACA (50 wt. % in EtOAc, 572 μL, 0.96 mmol) was added slowly. The reaction mixture was stirred at 0° C. for 10 min and at rt for 4 h. The reaction mixture was cooled to 0° C. and ammonium chloride (85.0 mg, 1.59 mmol), DIPEA (572 μL, 3.32 mmol) and PPACA (50 wt. % in EtOAc, 572 μL, 0.96 mmol) were added slowly. The reaction mixture was stirred at 0° C. for 10 min and at rt for 4 h. The reaction mixture was diluted with H₂O and EtOAc. The layers were separated and the aqueous phase was extracted with EtOAc. The combined organic extracts were washed with a 10% aqueous solution of KHSO₄ and brine, dried over MgSO₄, filtered and evaporated in vacuo. The crude mixture was purified by preparative LC (irregular SiOH, 15-40 μm, 24 g Grace®, liquid injection (DCM), mobile phase gradient: DCM/i-PrOH from 99:1 to 85:15). A second purification was carried out by preparative LC (spherical C18 25 μm, 40 g YMC-ODS-25, dry loading (Celite®), mobile phase gradient: (0.2% aq.NH₄HCO₃)/MeCN from 65:35 to 25:75). The residue was solubilized in EtOAc, concentrated to dryness and dried under vacuum at 50° C. for 72 h and at 65° C. for 8 h to give compound 89 (100 mg, 46%).

Compound 55

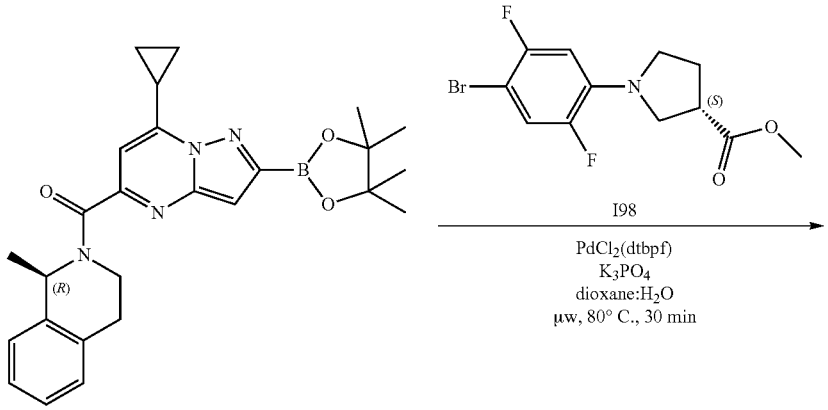

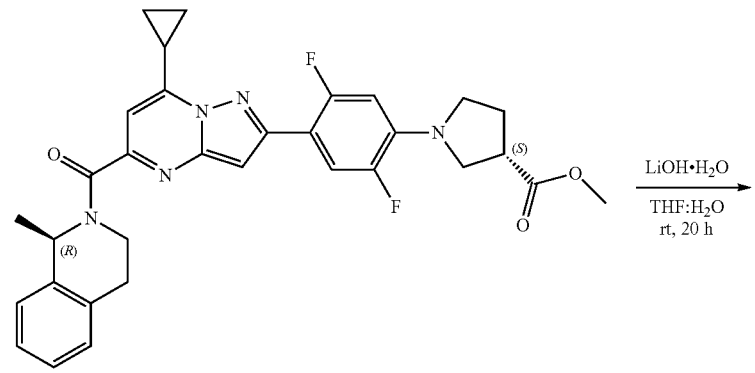

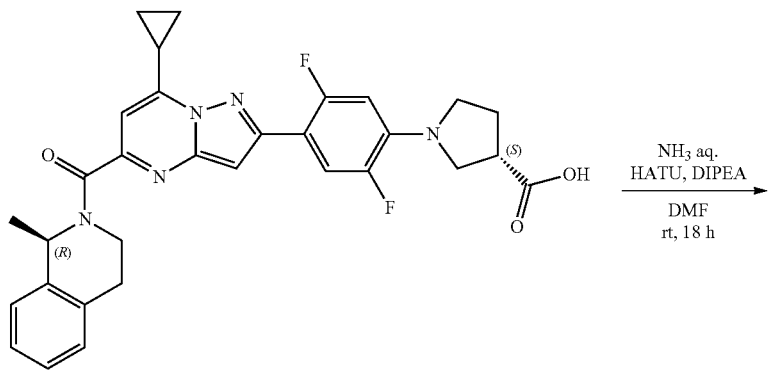

-continued

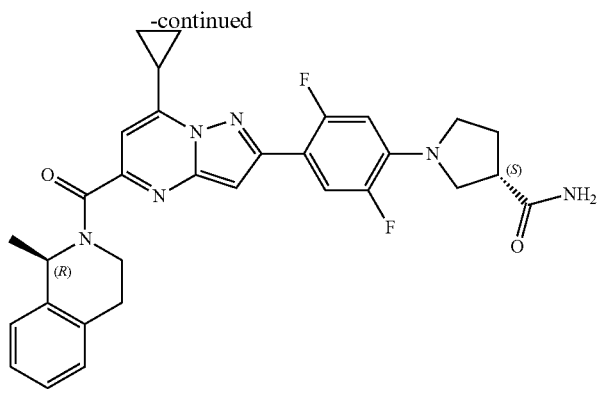

Synthesis of Intermediate I98

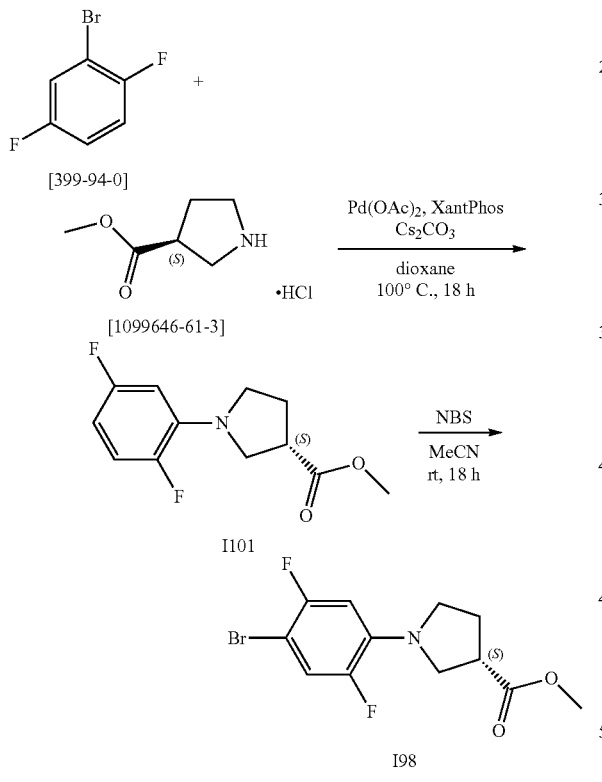

Intermediate I101

Methyl (3S)-1-(2,5-difluorophenyl)pyrrolidine-3-carboxylate

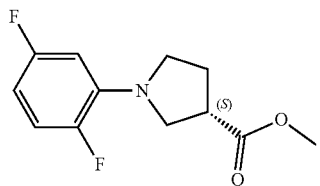

A mixture of (S)-methyl pyrrolidine-3-carboxylate hydrochloride [1099646-61-3] (1.00 g, 6.04 mmol), 1-bromo-2,5-difluorobenzene [399-94-0] (1.02 mL, 9.06 mmol) and cesium carbonate (5.90 g, 18.1 mmol) in 1,4-dioxane (50 mL) was purged with nitrogen for 15 min. XantPhos (349 mg, 0.60 mmol) and palladium acetate (136 mg, 0.60 mmol) were added and the resulting mixture was purged with nitrogen. The reaction mixture was stirred at 100° C. for 18 h. The reaction mixture was filtered through a pad of Celite®. EtOAc and brine were added to the filtrate. The layers were separated and the aqueous phase was extracted with EtOAc (twice). The combined organic extracts were dried over MgSO$_4$, filtered and evaporated under reduced pressure. The crude mixture was purified by preparative LC (regular SiOH, 30 μm, 80 g Grace®, liquid injection (DCM), mobile phase gradient: heptane/EtOAc from 100:0 to 80:20) to afford intermediate I101 (780 mg, 54%) as a colorless oil.

Intermediate I98

Methyl (3S)-1-(4-bromo-2,5-difluorophenyl)pyrrolidine-3-carboxylate

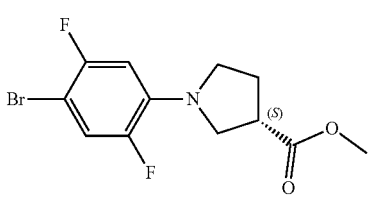

To a solution of intermediate I101 (780 mg, 3.23 mmol) in MeCN (28 mL) was slowly added NBS (633 mg, 3.56 mmol). The reaction mixture was stirred at rt for 18 h. The reaction mixture was diluted with EtOAc and H$_2$O. The layers were separated and the aqueous phase was extracted with EtOAc. The combined organic extracts were washed with brine, dried over MgSO$_4$, filtered and evaporated under reduced pressure. The crude mixture was purified by preparative LC (regular SiOH, 30 μm, 80 g Grace®, liquid injection (DCM), mobile phase gradient: heptane/EtOAc from 100:0 to 90:10) to afford intermediate I98 (817 mg, 79%) as a white powder.

Synthesis of Compound 55

Intermediate I99

Methyl (3S)-1-(4-{7-cyclopropyl-5-[(1R)-1-methyl-1,2,3,4-tetrahydroisoquinoline-2-carbonyl]pyrazolo[1,5-a]pyrimidin-2-yl}-2,5-difluorophenyl)pyrrolidine-3-carboxylate

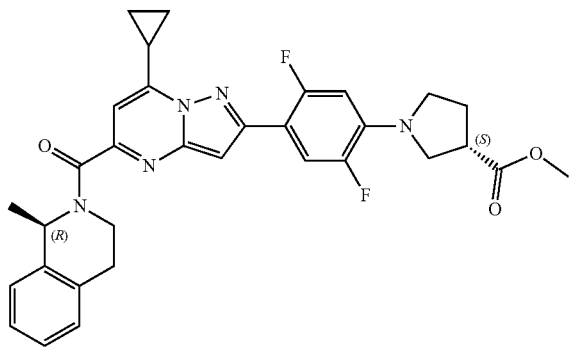

I99

A sealed tube was charged intermediate I98 (200 mg, 625 µmol), (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (551 mg, 625 µmol, 52% purity), potassium phosphate tribasic (451 mg, 2.12 mmol), 1,4-dioxane (10 mL) and H₂O (3 mL) and purged with nitrogen. [1,1'-Bis-(di-tert-butylphosphino)ferrocene] palladium dichloride (44.8 mg 68.8 µmol) was added and the mixture was purged with nitrogen. The reaction mixture was heated at 80° C. using a single mode microwave (Biotage® Initiator EXP 60) with a power output ranging from 0 to 400 W for 30 min. The reaction mixture was diluted with EtOAc and the organic phase was washed with brine, dried over MgSO₄, filtered and concentrated under reduced pressure. The crude mixture was purified by preparative LC (irregular SiOH, 15-40 µm, 80 g Grace®, dry loading (SiOH), mobile phase gradient: heptane/EtOAc from 100:0 to 60:40). The residue (397 mg) was purified by preparative LC (spherical C18 25 µm, 40 g YMC-ODS-25, dry loading (C18), mobile phase gradient: (0.2% aq.NH₄HCO₃)/MeCN from 60:40 to 0:100) to afford intermediate I99 (320 mg, 88%) as a yellow solid.

Intermediate I100

(3S)-1-(4-{7-Cyclopropyl-5-[(1R)-1-methyl-1,2,3,4-tetrahydroisoquinoline-2-carbonyl]-pyrazolo[1,5-a]pyrimidin-2-yl}-2,5-difluorophenyl)pyrrolidine-3-carboxylic acid

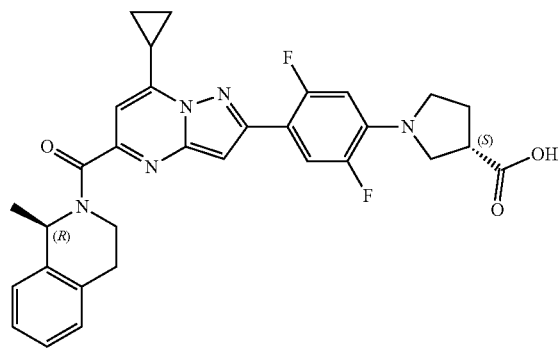

I100

Lithium hydroxide monohydrate (117 mg, 2.80 mmol) was added to a solution of intermediate I99 (320 mg, 0.56 mmol) in THF (9 mL) and H₂O (1.8 mL). The reaction mixture was stirred at rt for 20 h. A 10% aqueous solution of KHSO₄ and EtOAc were added. The layers were separated and the aqueous phase was extracted with EtOAc. The combined organic extracts were washed with brine, dried over MgSO₄, filtered and concentrated under reduced pressure. The crude mixture was purified by preparative LC (spherical C18 25 µm, 40 g YMC-ODS-25, dry loading (C18), mobile phase gradient: (0.2% aq.NH₄HCO₃)/MeCN from 75:25 to 35:65), to give intermediate I100 (280 mg, 90%) as a yellow solid.

Compound 55

(3S)-1-(4-{7-Cyclopropyl-5-[(1R)-1-methyl-1,2,3,4-tetrahydroisoquinoline-2-carbonyl]-pyrazolo[1,5-a]pyrimidin-2-yl}-2,5-difluorophenyl)pyrrolidine-3-carboxamide

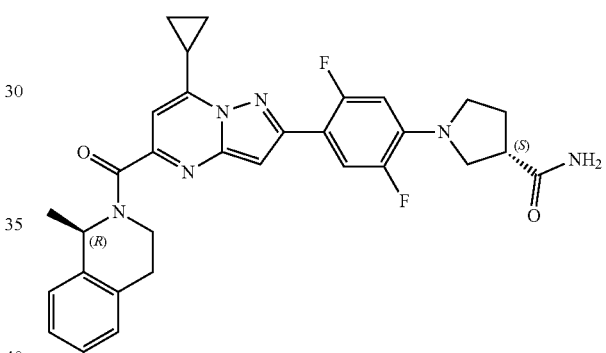

55

A mixture of intermediate I100 (142 mg, 255 µmol), HATU (145 mg, 382 µmol) and DIPEA (132 µL, 0.76 mmol) in DMF (7 mL) was stirred at rt for 1 h. Ammonia (28% in H₂O, 86.1 µL, 1.27 mmol) was added and the reaction mixture was stirred at rt for 18 h. The reaction mixture was diluted with H₂O and EtOAc. The layers were separated and the aqueous phase was extracted with EtOAc (twice). The combined organic extracts were dried over MgSO₄, filtered and evaporated under reduced pressure. The crude mixture was purified by preparative LC (spherical C18 25 µm, 40 g YMC-ODS-25, dry loading (C18), mobile phase gradient (0.2% aq.NH₄HCO₃)/MeCN from 60:40 to 0:100). A second purification was carried out: preparative LC (spherical C18 25 µm, 40 g YMC-ODS-25, dry loading (C18), mobile phase gradient: (0.2% aq.NH₄HCO₃)/MeCN from 60:40 to 0:100). The residue (80 mg) was purified by reverse phase (Stationary phase: YMC-actus Triart C18 10 µm 30*150 mm, Mobile phase gradient: (0.2% aq. NH₄HCO₃)/MeCN from 50:50 to 0:100) to give compound 55 (60 mg, 47%) as a white solid.

Compound 85
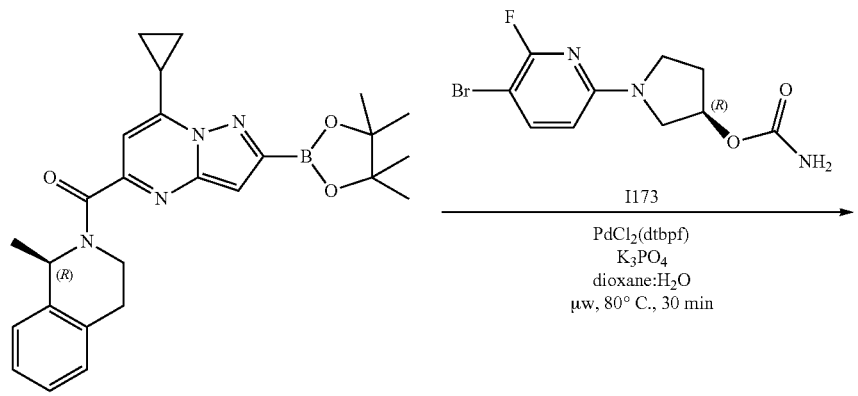
[2035421-36-2]
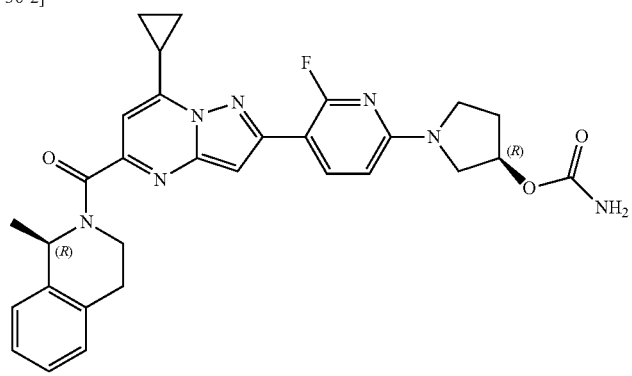
85
Synthesis of Intermediate I173
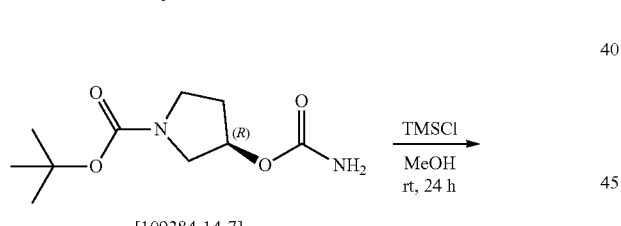
[109384-14-7]
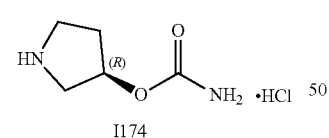
I174
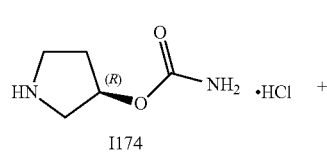
I174
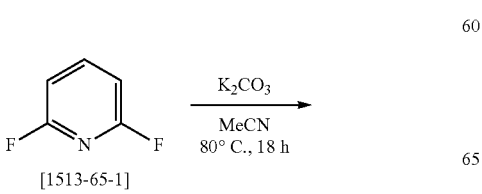
[1513-65-1]
-continued
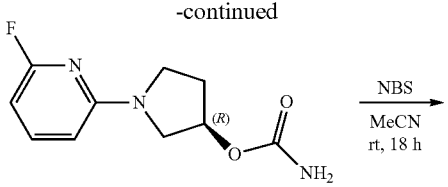
I175
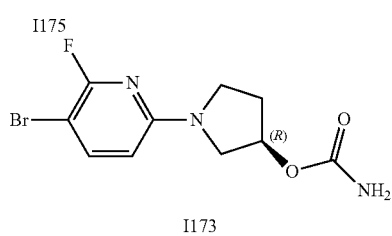
I173
Intermediate I174
(3R)-Pyrrolidin-3-yl carbamate hydrochloride
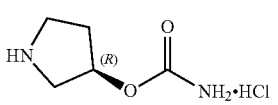
I174

A solution of tert-butyl (3R)-3-(carbamoyloxy)pyrrolidine-1-carboxylate [109384-14-7] (4.28 g, 18.6 mmol) and chlorotrimethylsilane (9.5 mL, 74.8 mmol) in MeOH (90 mL) was stirred at rt for 24 h. The mixture was evaporated in vacuo to afford intermediate I174 (3.02 g, 98%).

Intermediate I175

(3R)-1-(6-Fluoropyridin-2-yl)pyrrolidin-3-yl carbamate

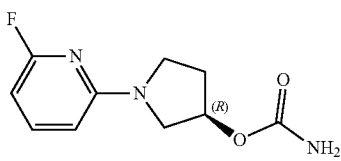

A mixture of 2,6-difluoropyridine [1513-65-1] (628 mg, 5.46 mmol), intermediate I174 (1.00 g, 6.00 mmol) and potassium carbonate (2.26 g, 16.4 mmol) in MeCN (42 mL) was stirred at 80° C. for 18 h. The reaction mixture was diluted with H₂O and EtOAc. The layers were separated and the aqueous phase was extracted with EtOAc (twice). The combined organic extracts were dried over MgSO₄, filtered and concentrated in vacuo. The crude mixture was purified by preparative LC (irregular SiOH, 15-40 μm, 24 g GraceResolv™, dry loading (Celite®), mobile phase gradient: heptane/EtOAc from 90:10 to 50:50) to afford intermediate I175 (187.9 mg, 15%) as a white solid.

Intermediate I173

(3R)-1-(5-Bromo-6-fluoropyridin-2-yl)pyrrolidin-3-yl carbamate

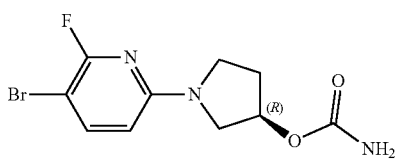

A mixture of intermediate I175 (188 mg, 834 μmol) and NBS (149 mg, 834 μmol) in MeCN (9.2 mL) was stirred at rt for 18 h. The reaction mixture was diluted with H₂O and EtOAc. The layers were separated and the aqueous phase was extracted with EtOAc (twice). The combined organic extracts were washed with NaHCO₃ (twice), dried over MgSO₄, filtered and concentrated in vacuo. The crude mixture was purified by preparative LC (irregular SiOH, 15-40 μm, 24 g GraceResolv™, dry loading (Celite®), mobile phase gradient: heptane/EtOAc from 80:20 to 50:50) to afford intermediate I173 (180 mg, 71%) as a white solid.

Synthesis of Compound 85

(3R)-1-(5-{7-Cyclopropyl-5-[(1R)-1-methyl-1,2,3,4-tetrahydroisoquinoline-2-carbonyl]-pyrazolo[1,5-a]pyrimidin-2-yl}-6-fluoropyridin-2-yl)pyrrolidin-3-yl carbamate

A sealed tube was charged with intermediate I173 (120 mg, 395 μmol), (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (305 mg, 592 μmol, 89% purity), potassium phosphate tribasic (251 mg, 1.18 mmol), 1,4-dioxane (7.3 mL) and H₂O (1.1 mL) and purged with nitrogen. [1,1'-Bis(di-tert-butylphosphino)ferrocene] palladium dichloride (25.7 mg, 39.5 μmol) was added and the mixture was purged again with nitrogen. The reaction mixture was heated at 80° C. using a single mode microwave (Biotage® Initiator EXP 60) with a power output ranging from 0 to 400 W for 30 min. The reaction mixture was diluted with EtOAc and brine. The layers were separated and the aqueous phase was extracted with EtOAc. The combined organic extracts were washed with H₂O (twice), dried over MgSO₄, filtered and concentrated in vacuo. The crude mixture was purified by preparative LC (irregular SiOH, 15-40 μm, 24 g GraceResolv™, liquid injection (DCM), mobile phase gradient: DCM/EtOAc from 100:0 to 80:20). The residue (100 mg) was triturated with MeCN. The solid was filtered off and dried under high vacuum at 50° C. for 2 h to give compound 85 (28 mg, 13%) as a pale yellow solid.

General Scheme

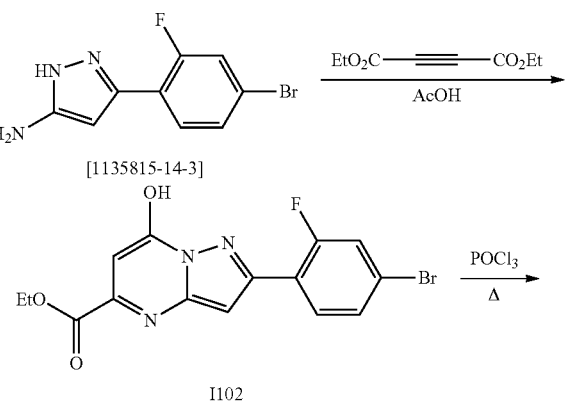

219
-continued

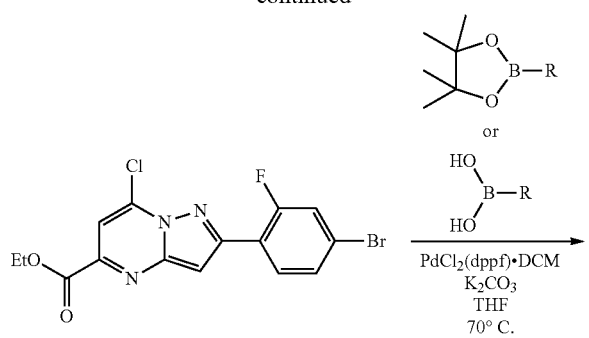

220
-continued

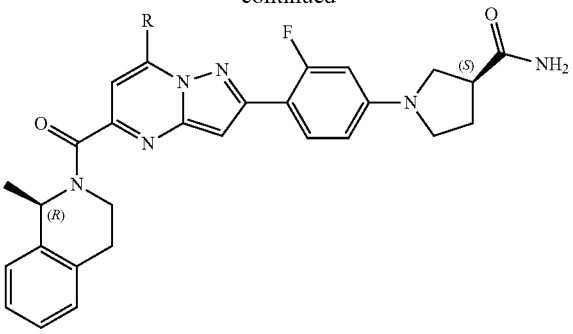

56-64 and 90
R = Ph, 4-OMe—Ph, 4-Me—Ph, 4-Cl—Ph, 4-F—Ph, 4-CF$_3$—Ph, 4-CN—Ph, 4-pyridine, pyrimidine, 3-fluoro-5-pyridine Synthesis of Intermediates I102 and I103

Intermediate I102

Ethyl 2-(4-bromo-fluorophenyl)-7-hydroxypyrazolo[1,5-a]pyrimidine-5-carboxylate

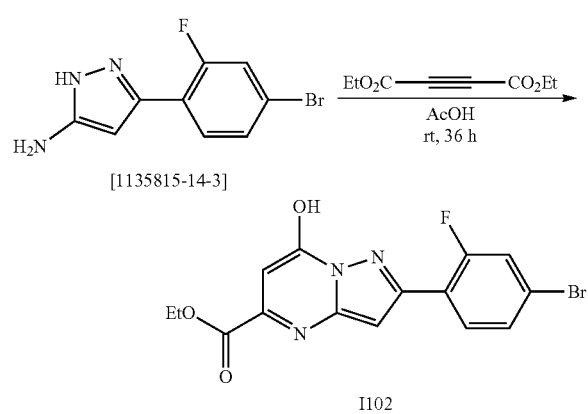

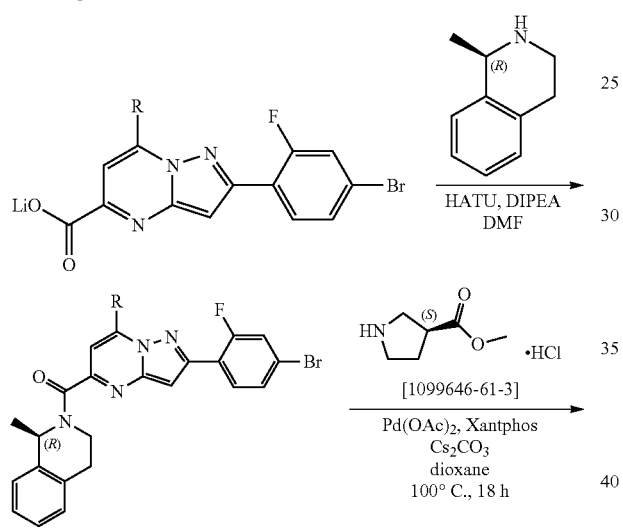

A mixture of 3-(4-bromo-2-fluorophenyl)-1H-pyrazol-5-amine (15.0 g, 58.6 mmol) and diethyl acetylenedicarboxylate (9.40 mL, 58.6 mmol) in acetic acid (110 mL) was stirred at rt for 36 h. The reaction mixture was diluted with EtOAc and heptane (30:60) (150 mL) and the mixture was stirred for 30 min. The precipitate was filtered off and dried under vacuum to afford intermediate I102 (18.6 g, 84%).

Intermediate I103

Ethyl 2-(4-bromo-2-fluorophenyl)-7-chloropyrazolo[1,5-a]pyrimidine-5-carboxylate

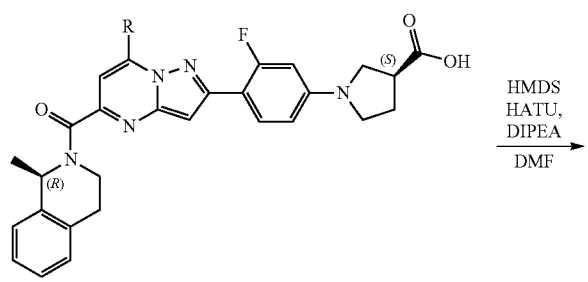

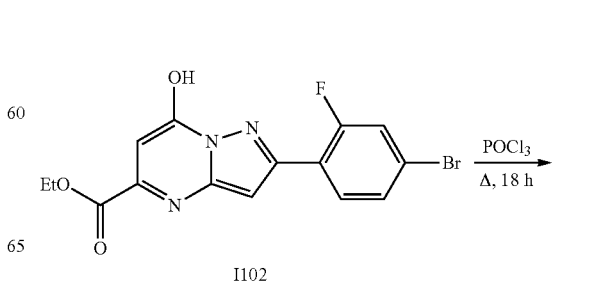

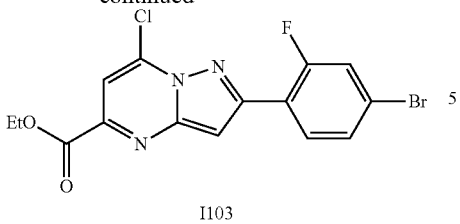

A mixture of intermediate I102 (15.0 g, 39.5 mmol) in phosphorous (V) oxychloride (147 mL) was stirred under reflux for 18 h. The solvent was evaporated to dryness. H$_2$O was added slowly to the residue and the mixture was stirred at 0° C. for 30 min. The precipitate was filtered off and dried under vacuum to afford intermediate I103 (15.3 g, 97%).

Synthesis of Compounds 56 to 64 and 90

Compound 56

Intermediate I104

Ethyl 2-(4-bromo-2-fluorophenyl)-7-phenylpyrazolo[1,5-a]pyrimidine-5-carboxylate

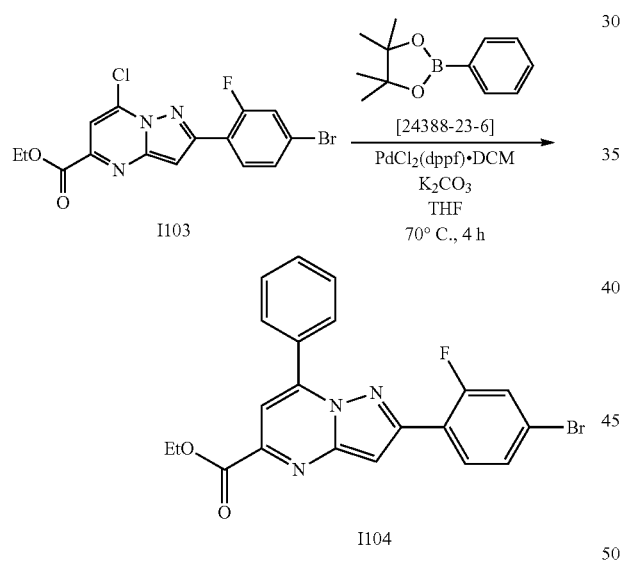

A mixture of intermediate I103 (1.50 g, 3.76 mmol) and 2-phenyl-4,4,5,5-tetramethyl-1,2,3-dioxaborolane [24388-23-6] (691 mg, 3.39 mmol) in THF (30 mL) was degassed with nitrogen for 10 min. [1,1'-Bis(diphenylphosphino)ferrocene]dichloropalladium, complex with dichloromethane (308 mg, 376 µmol) and potassium carbonate (2.0 M in H$_2$O, 5.64 mL, 11.3 mmol) were added and the reaction mixture was stirred at 70° C. for 4 h. The reaction mixture was poured out into water and EtOAc. The layers were separated and the organic phase was washed with brine, dried over MgSO$_4$, filtered and evaporated to dryness. The crude mixture was purified by flash chromatography over silica gel (15-40 µm, cartridge 80 g, mobile phase gradient: heptane/EtOAc from 100:0 to 70:30) to afford intermediate I104 (1.15 g, 69%). The product was used in the next step without further purification.

Intermediate I105

Lithio 2-(4-bromo-2-fluorophenyl)-7-phenylpyrazolo[1,5-a]pyrimidine-5-carboxylate

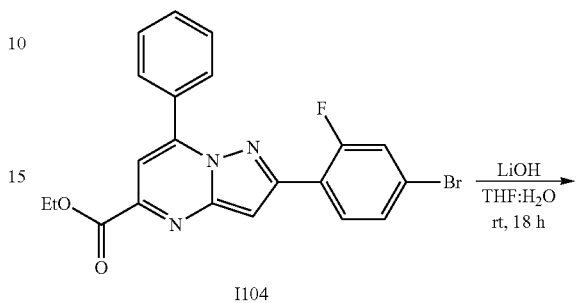

A mixture of intermediate I104 (1.15 g, 2.61 mmol) and lithium hydroxide (125 mg, 5.22 mmol) in THF (13 mL) and H$_2$O (3 mL) was stirred at rt for 18 h. The solvent was evaporated under reduced pressure. Few drops of H$_2$O were added to the residue. The precipitate was filtered off and dried under vacuum to afford intermediate I105 (1.2 g). The product was used in the next step without further purification.

Intermediate I106

(1R)-2-[2-(4-Bromo-2-fluorophenyl)-7-phenylpyrazolo[1,5-a]pyrimidine-5-carbonyl]-1-methyl-1,2,3,4-tetrahydroisoquinoline

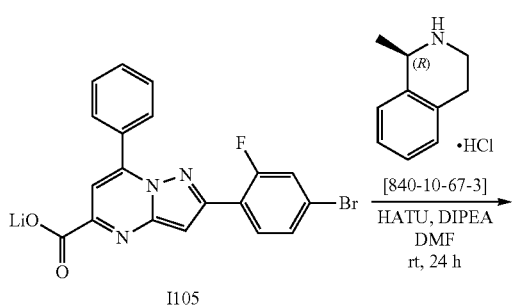

223
-continued

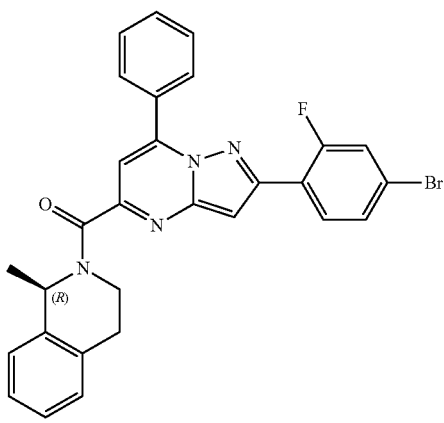

I106

224
-continued

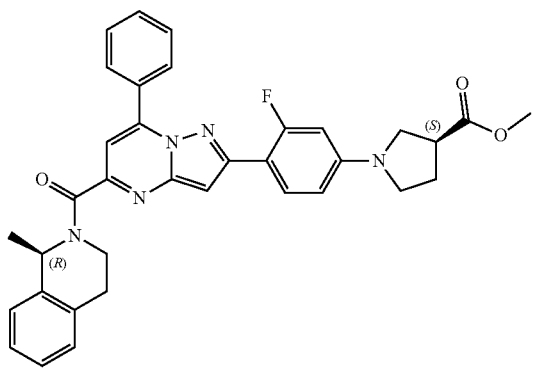

I107

DIPEA (1.38 mL, 7.89 mmol) and HATU (1.30 g, 3.42 mmol) were added to a mixture of (1R)-1-methyl-1,2,3,4-tetrahydroisoquinoline hydrochloride [84010-67-3] (0.58 g, 3.16 mmol) and intermediate I105 (1.10 g, 2.63 mmol) in DMF (30 mL). The reaction mixture was stirred at rt for 24 h. The reaction mixture was poured out into water and the aqueous phase was extracted with EtOAc. The combined organic extracts were washed with brine, dried over MgSO$_4$, filtered and evaporated to dryness. The crude mixture was purified by flash chromatography over silica gel (15-40 μm, 80 g GraceResolv™, mobile phase gradient: heptane/EtOAc from 100:0 to 75:25) to afford intermediate I106 (1.3 g, 66%, 72% purity).

A mixture of intermediate I106 (1.3 g, 1.73 mmol, 72% purity), (S)-methyl pyrrolidine-3-carboxylate hydrochloride [1099646-61-3] (419 mg, 2.08 mmol), cesium carbonate (1.69 g, 5.19 mmol) and XantPhos (100 mg, 0.17 mmol) was purged with nitrogen. 1,4-Dioxane (20 mL) was added and the mixture was purged again with nitrogen. Palladium acetate (38.8 mg, 0.17 mmol) was added. The reaction mixture was purged with nitrogen and stirred at 100° C. for 18 h. The reaction mixture was diluted with EtOAc and H$_2$O. The layers were separated and the aqueous phase was extracted with EtOAc (twice). The combined organic extracts were washed with brine, dried over MgSO$_4$, filtered and the solvent was removed under reduced pressure. The crude mixture was purified by preparative LC (irregular SiOH, 15-40 μm, 40 g Grace®, liquid injection (DCM), mobile phase gradient: heptane/EtOAc from 100:0 to 70:30) to afford intermediate I107 (550 mg, 54%).

Intermediate I107

Methyl (3S)-1-(3-fluoro-4-{5-[(1R)-1-methyl-1,2,3,4-tetrahydroisoquinoline-2-carbonyl]-7-phenylpyrazolo[1,5-a]pyrimidin-2-yl}phenyl)pyrrolidine-3-carboxylate Intermediate I108

(3S)-1-(3-Fluoro-4-{5-[(1R)-1-methyl-1,2,3,4-tetrahydroisoquinoline-2-carbonyl]-7-phenylpyrazolo[1,5-a]pyrimidin-2-yl}phenyl)pyrrolidine-3-carboxylic acid

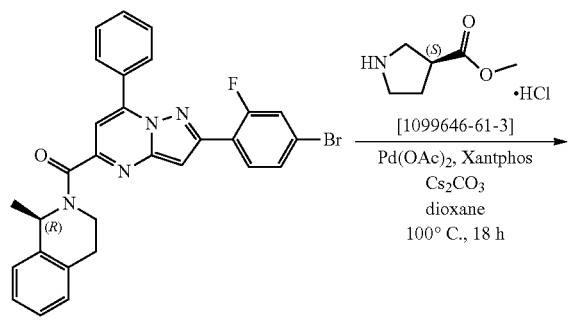

I106

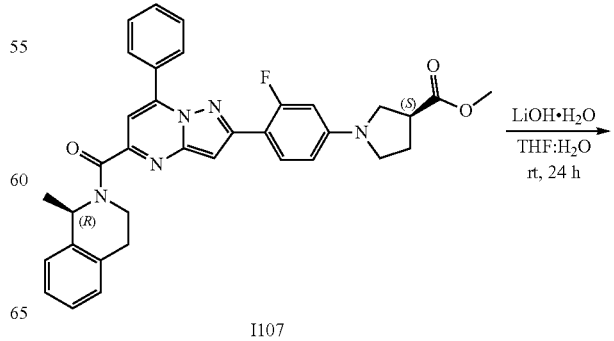

I107

-continued

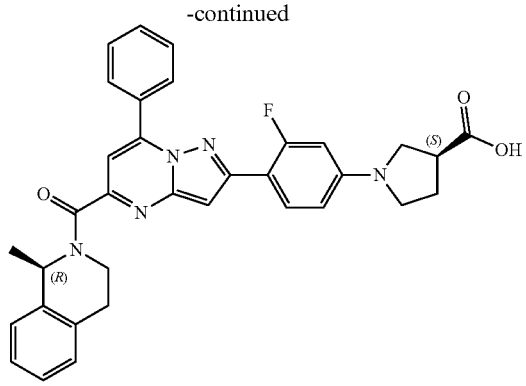

I108

Lithium hydroxide monohydrate (195 mg, 4.66 mmol) was added to a solution of intermediate I107 (550 mg, 0.93 mmol) in THF (7.6 mL) and H$_2$O (2.5 mL). The reaction mixture was stirred at rt for 24 h. Few drops of H$_2$O were added followed by a 3N aqueous solution of HCl. The layers were separated and the aqueous phase was extracted with DCM (twice). The combined organic extracts were dried over MgSO$_4$, filtered and evaporated under reduced pressure to afford intermediate I108 (470 mg, 88%). The product was used as such in the next step.

Compound 56

(3S)-1-(3-Fluoro-4-{5-[(1R)-1-methyl-1,2,3,4-tetrahydroisoquinoline-2-carbonyl]-7-phenylpyrazolo[1,5-a]pyrimidin-2-yl}phenyl)pyrrolidine-3-carboxamide

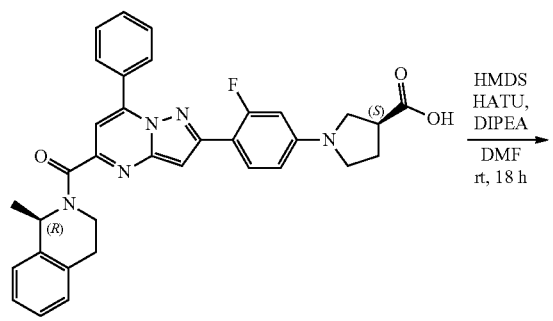

A mixture of intermediate I108 (230 mg, 0.40 mmol), HMDS (102 µL, 0.48 mmol), HATU (228 mg, 0.60 mmol) and DIPEA (138 µL, 0.80 mmol) in DMF (5 mL) was stirred at rt for 18 h. The reaction mixture was diluted with H$_2$O and the aqueous phase was extracted with EtOAc. The combined organic extracts were washed with H$_2$O, brine, dried over MgSO$_4$, filtered and evaporated to dryness. The crude mixture was purified by flash chromatography over silica gel (15-40 µm, 12 g Grace®, mobile phase gradient: DCM/MeOH from 100:0 to 96:4). The pure fractions were collected and concentrated to dryness. The residue (155 mg) was taken up in Et$_2$O, filtered and dried under vacuum to give compound 56 (101 mg, 44%).

Compound 57

Intermediate I109

Ethyl 2-(4-bromo-2-fluorophenyl)-7-(4-methoxyphenyl)pyrazolo[1,5-a]pyrimidine-5-carboxylate

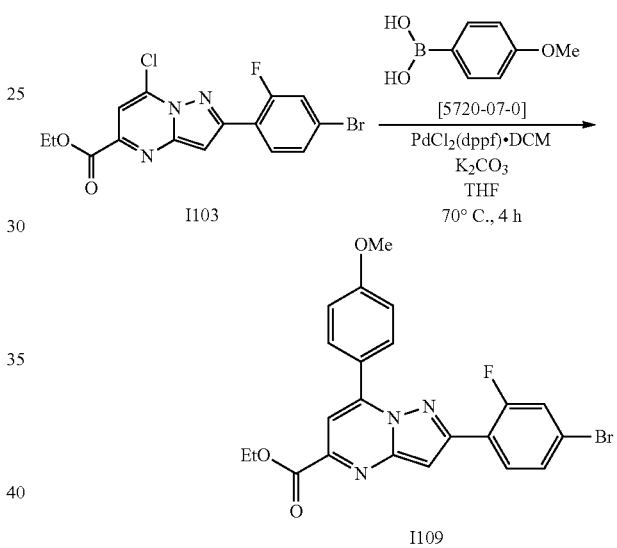

Intermediate I109 (880 mg, 54%, 87% purity) was synthesized from intermediate I103 and 4-methoxyphenylboronic acid [5720-07-0] according to the procedure reported for the synthesis of intermediate I104.

Intermediate I110

Lithio 2-(4-bromo-2-fluorophenyl)-7-(4-methoxyphenyl)pyrazolo[1,5-a]pyrimidine-5-carboxylate

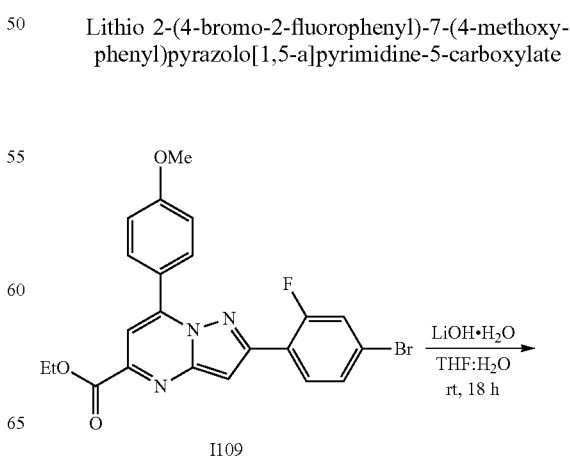

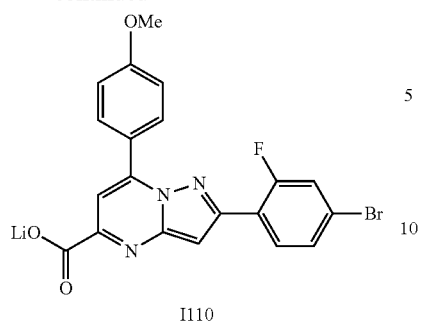

Intermediate I110 (150 mg, 90%) was synthesized from intermediate I109 and lithium hydroxide monohydrate according to the procedure reported for the synthesis of intermediate I105.

Intermediate I111

(1R)-2-[2-(4-Bromo-2-fluorophenyl)-7-(4-methoxyphenyl)pyrazolo[1,5-a]pyrimidine-5-carbonyl]-1-methyl-1,2,3,4-tetrahydroisoquinoline

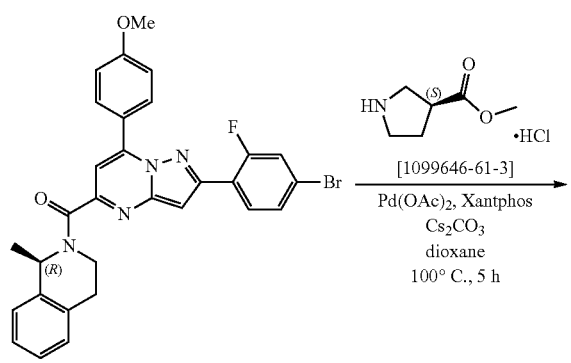

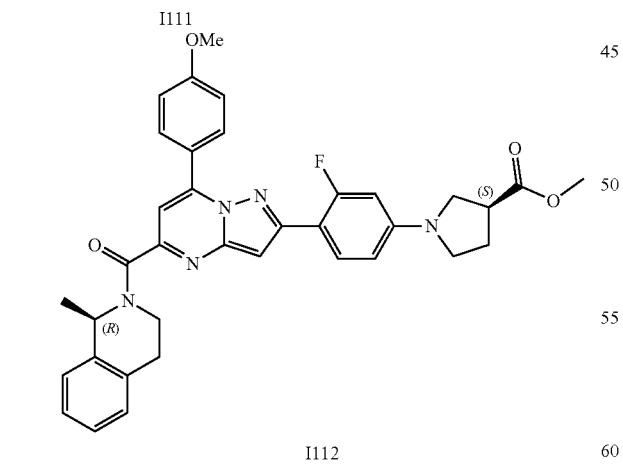

Intermediate I111 (740 mg, 48%) was synthesized from intermediate I110 and (1R)-1-methyl-1,2,3,4-tetrahydroisoquinolone hydrochloride [84010-67-3] according to the procedure reported for the synthesis of intermediate I106 with a reaction time of 48 h.

Intermediate I112

Methyl (3S)-1-{3-fluoro-4-[7-(4-methoxyphenyl)-5-[(1R)-1-methyl-1,2,3,4-tetrahydroisoquinoline-2-carbonyl]pyrazolo[1,5-a]pyrimidin-2-yl]phenyl}pyrrolidine-3-carboxylate

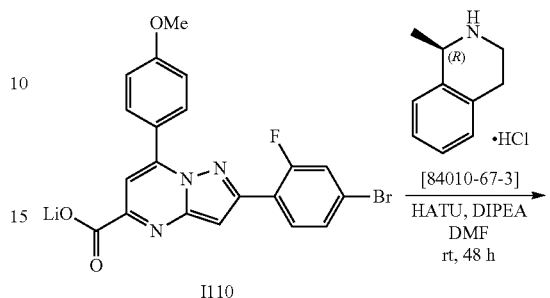

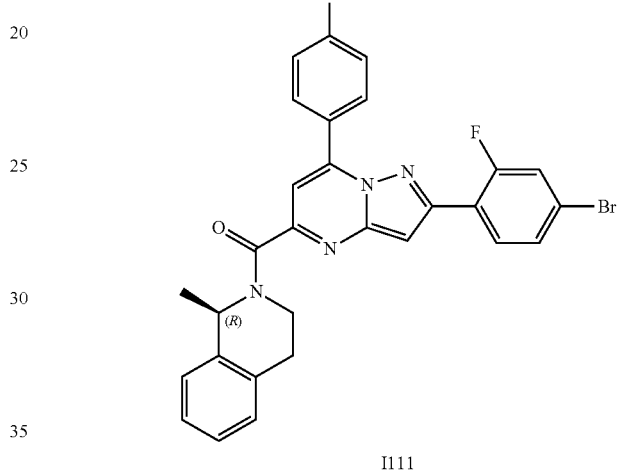

Intermediate I112 (290 mg, 67%) was synthesized from intermediate I111 and (S)-methyl pyrrolidine-3-carboxylate hydrochloride [1099646-61-3] according to the procedure reported for the synthesis of intermediate I107 with a shorter reaction time of 5 h.

Intermediate I113

(3S)-1-{3-Fluoro-4-[7-(4-methoxyphenyl)-5-[(1R)-1-methyl-1,2,3,4-tetrahydroisoquino-line-2-carbonyl]pyrazolo[1,5-a]pyrimidin-2-yl]phenyl}pyrrolidine-3-carboxylic acid

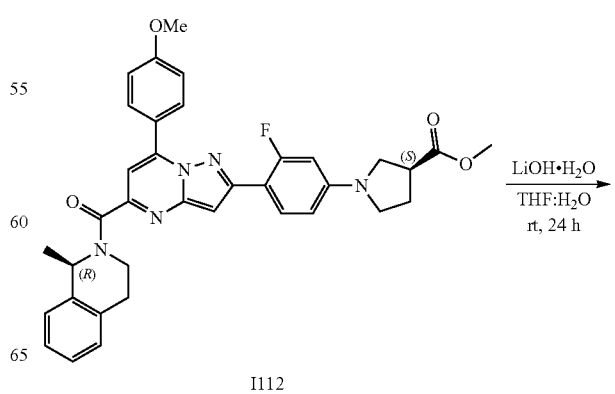

-continued

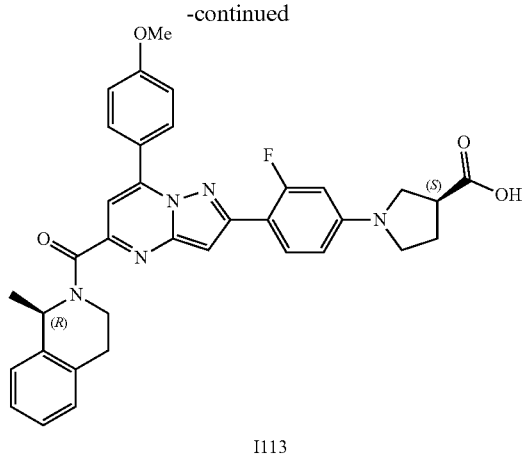

I113

Intermediate I113 was synthesized from intermediate I112 according to the procedure reported for the synthesis of intermediate I108. The crude mixture was purified by flash chromatography over silica gel (15-40 μm, cartridge 24 g, mobile phase gradient: DCM/MeOH from 100:0 to 97:3) to afford intermediate I113 (245 mg, 93%).

Compound 57

(3S)-1-{3-Fluoro-4-[7-(4-methoxyphenyl)-5-[(1R)-1-methyl-1,2,3,4-tetrahydro-isoquinoline-2-carbonyl]pyrazolo[1,5-a]pyrimidin-2-yl]phenyl}pyrrolidine-3-carboxamide

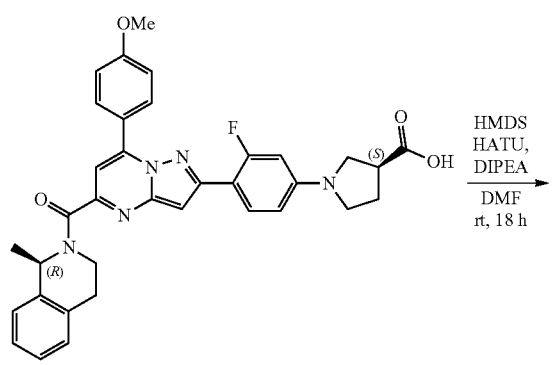

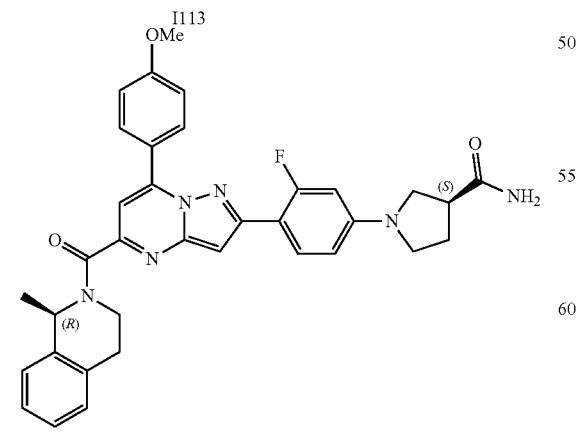

57

Compound 57 (117 mg, 56%) was synthesized from intermediate I113 according to the procedure reported for the synthesis of compound 56.

Compound 58

Intermediate I114

Ethyl 2-(4-bromo-2-fluorophenyl)-7-(4-methylphenyl)pyrazolo[1,5-a]pyrimidine-5-carboxylate

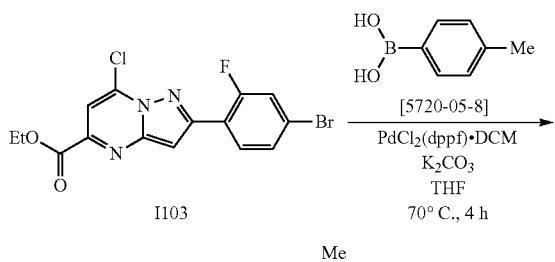

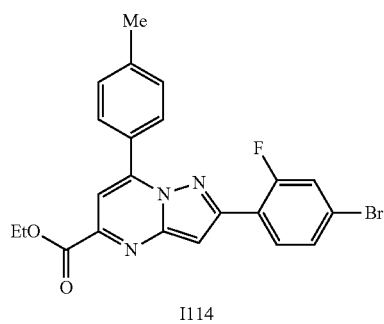

I114

Intermediate I114 (1.35 g, 70%, 88% purity) was synthesized from intermediate I103 and 4-tolylboronic acid [5720-05-8] according to the procedure reported for the synthesis of intermediate I104.

Intermediate I115

Lithio 2-(4-bromo-2-fluorophenyl)-7-(4-methylphenyl)pyrazolo[1,5-a]pyrimidine-5-carboxylate

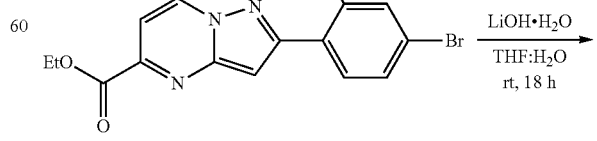

I114

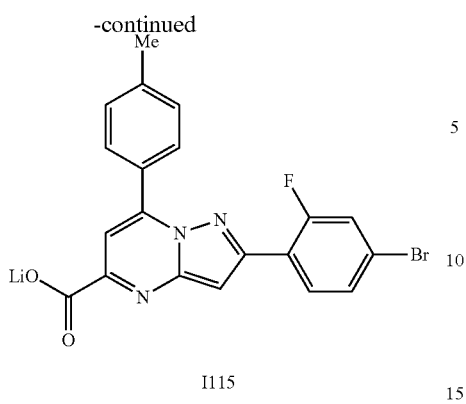

Intermediate I115 (1.5 g) was synthesized from intermediate I114 and lithium hydroxide monohydrate according to the procedure reported for the synthesis of intermediate I105.

Intermediate I116

(1R)-2-[2-(4-Bromo-2-fluorophenyl)-7-(4-methylphenyl)pyrazolo[1,5-a]pyrimidine-5-carbonyl]-1-methyl-1,2,3,4-tetrahydroisoquinoline Intermediate I117

Methyl (3S)-1-(3-fluoro-4-{5-[(1R)-1-methyl-1,2,3,4-tetrahydroisoquinoline-2-carbonyl]-7-(4-methylphenyl)pyrazolo[1,5-a]pyrimidin-2-yl}phenyl)pyrrolidine-3-carboxylate

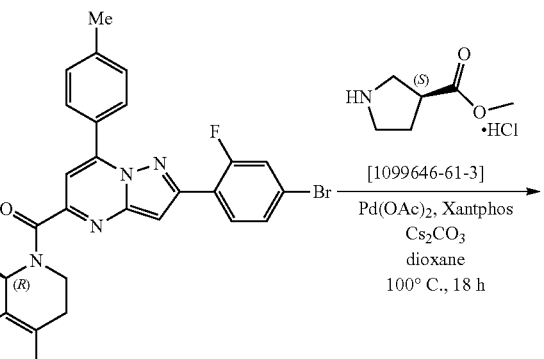

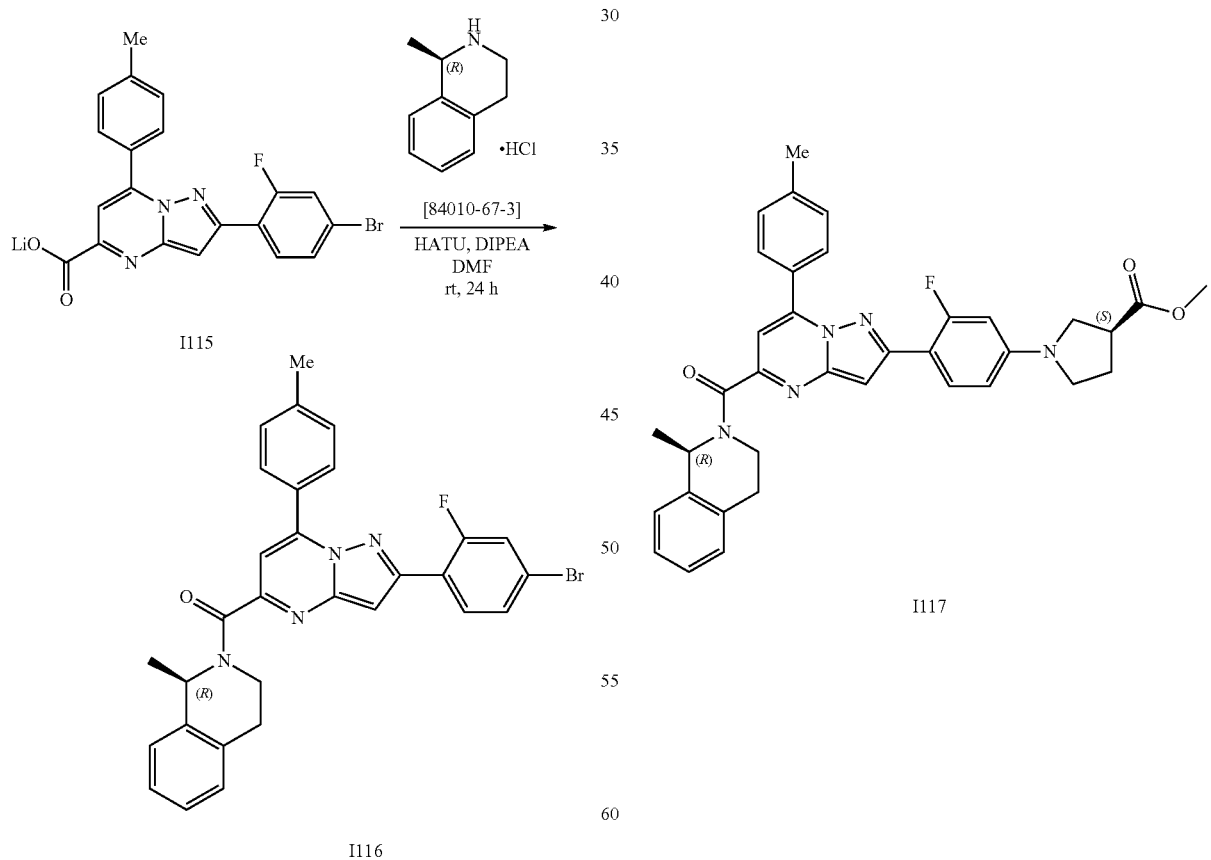

Intermediate I116 (1.25 g, 65%) was synthesized from intermediate I115 and (1R)-1-methyl-1,2,3,4-tetrahydroisoquinoline hydrochloride [84010-67-3] according to the procedure reported for the synthesis of intermediate I106.

Intermediate I117 (300 mg, 61%) was synthesized from intermediate I116 and (S)-methyl pyrrolidine-3-carboxylate hydrochloride [1099646-61-3] according to the procedure reported for the synthesis of intermediate I107.

233

Intermediate I118

(3S)-1-(3-Fluoro-4-{5-[(1R)-1-methyl-1,2,3,4-tetra-hydroisoquinoline-2-carbonyl]-7-(4-methylphenyl)pyrazolo[1,5-a]pyrimidin-2-yl}phenyl)pyrrolidine-3-carboxylic acid

234

Compound 58

(3S)-1-(3-Fluoro-4-{5-[(1R)-1-methyl-1,2,3,4-tetra-hydroisoquinoline-2-carbonyl]-7-(4-methylphenyl)pyrazolo[1,5-a]pyrimidin-2-yl}phenyl)pyrrolidine-3-carboxamide

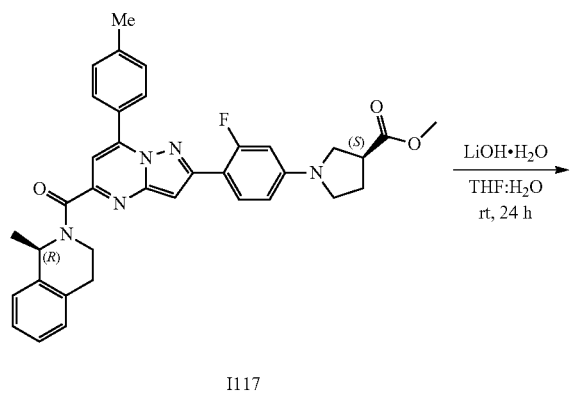

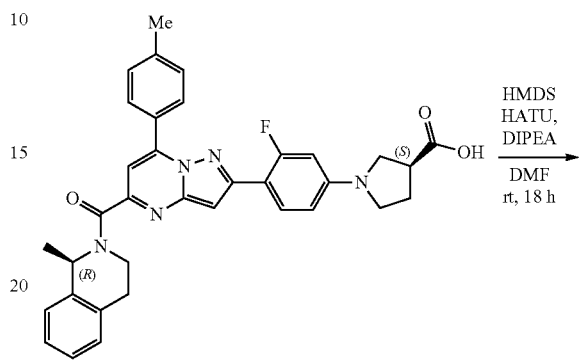

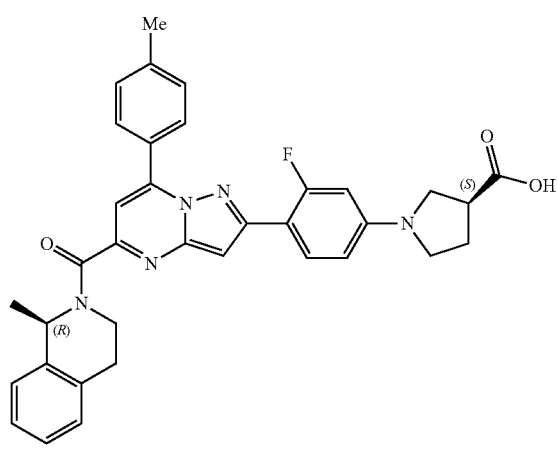

Intermediate I118 was synthesized from intermediate I117 according to the procedure reported for the synthesis of intermediate I107. The crude mixture was purified by flash chromatography on silica gel (15-40 μm, cartridge 12 g, mobile phase gradient: DCM/MeOH from 100:0 to 96:4). The pure fractions were collected and evaporated to dryness to afford intermediate I118 (255 mg, 87%).

Compound 58 (102 mg, 51%) was synthesized from intermediate I118 according to the procedure reported for the synthesis of compound 56.

Compound 59

Intermediate I119

Ethyl 2-(4-bromo-2-fluorophenyl)-7-(4-chlorophenyl)pyrazolo[1,5-a]pyrimidine-5-carboxylate

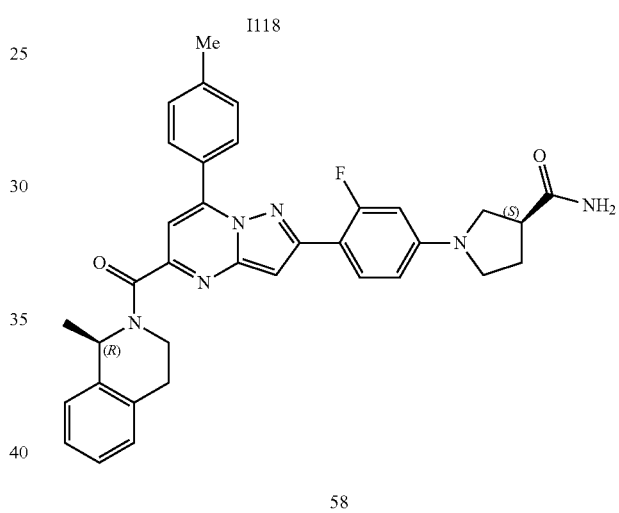

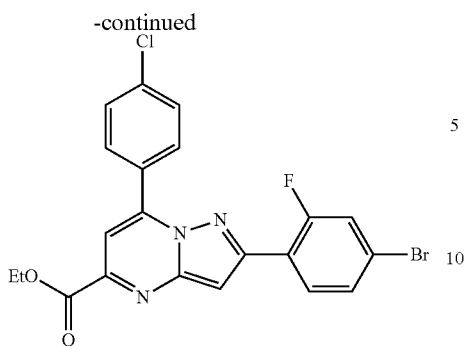

I119

A mixture of intermediate I103 (2.00 g, 5.02 mmol) and 4-chlorophenylboronic acid [1679-18-1] (706 mg, 4.52 mmol) in THF (40 mL) was degassed with nitrogen for 10 min. [1,1'-Bis(diphenylphosphino)ferrocene]dichloropalladium, complex with dichloromethane (410 mg, 0.50 mmol) and potassium carbonate (2.0 M in H₂O, 7.53 mL, 15.1 mmol) were added and the reaction mixture was stirred at 70° C. for 18 h. The reaction mixture was poured out into water and the precipitated was filtered off. The solid was dried under vacuum at 60° C. to afford intermediate I119 (2.2 g, 92%). The product was sued in the next step without further purification.

Intermediate I120

Lithio 2-(4-bromo-2-fluorophenyl)-7-(4-chlorophenyl)pyrazolo[1,5-a]pyrimidine-5-carboxylate

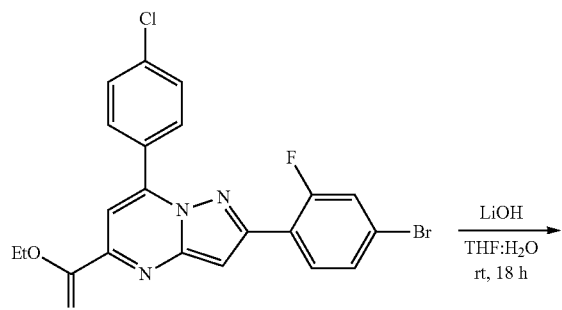

Intermediate I120 (2.0 g, 95%) was synthesized from intermediate I119 and lithium hydroxide according to the procedure reported for the synthesis of intermediate I105.

Intermediate I121

(1R)-2-[2-(4-Bromo-2-fluorophenyl)-7-(4-chlorophenyl)pyrazolo[1,5-a]pyrimidine-5-carbonyl]-1-methyl-1,2,3,4-tetrahydroisoquinoline

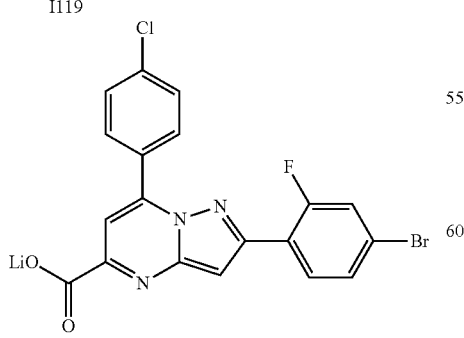

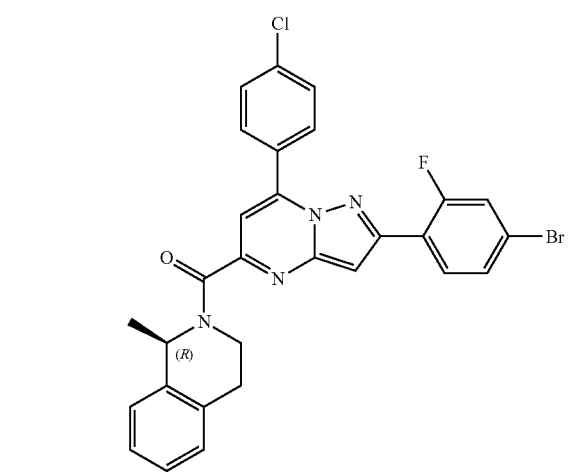

I121

Intermediate I121 (1.4 g, 55%) was synthesized from intermediate I120 and (1R)-1-methyl-1,2,3,4-tetrahydroisoquinoline hydrochloride [84010-67-3] according to the procedure reported for the synthesis of intermediate I106.

Intermediate I122

Methyl (3S)-1-{4-[7-(4-chlorophenyl)-5-[(1R)-1-methyl-1,2,3,4-tetrahydroisoquinoline-2-carbonyl]pyrazolo[1,5-a]pyrimidin-2-yl]-3-fluorophenyl}pyrrolidine-3-carboxylate

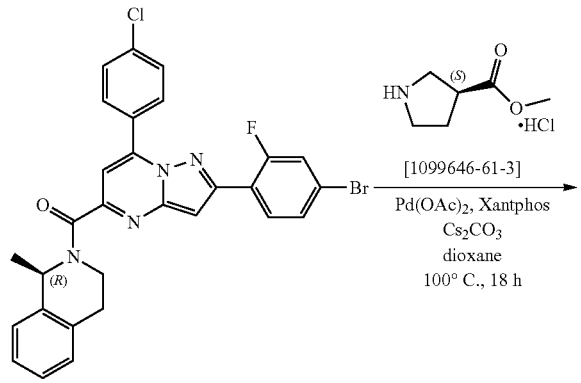

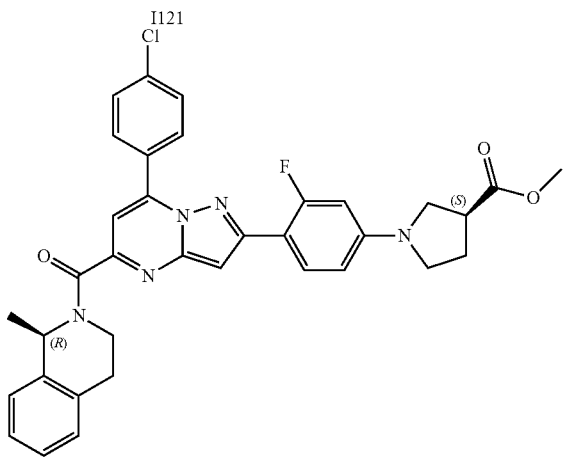

Intermediate I122 (290 mg, 48%) was synthesized from intermediate I121 and (S)-methyl pyrrolidine-3-carboxylate hydrochloride [1099646-61-3] according to the procedure reported for the synthesis of intermediate I107.

Intermediate I123

(3S)-1-{4-[7-(4-Chlorophenyl)-5-[(1R)-1-methyl-1,2,3,4-tetrahydroisoquinoline-2-carbonyl]pyrazolo[1,5-a]pyrimidin-2-yl]-3-fluorophenyl}pyrrolidine-3-carboxylic acid

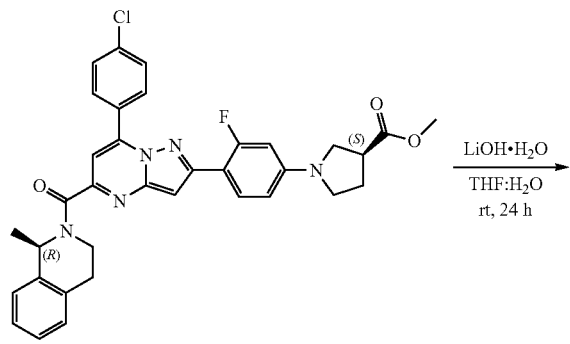

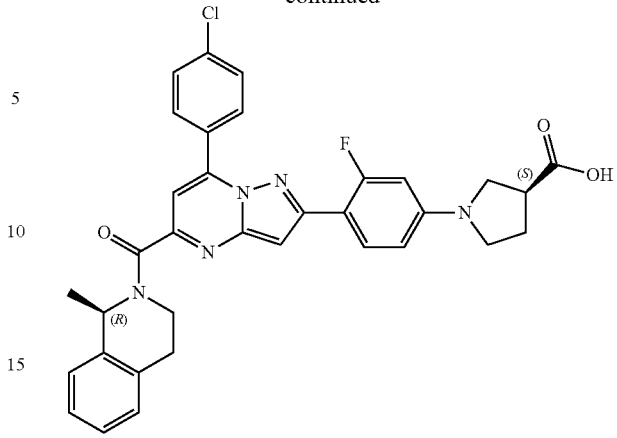

Intermediate I123 (245 mg, 86%) was synthesized from intermediate I122 according to the procedure reported for the synthesis of intermediate I107.

Compound 59

(3S)-1-{4-[7-(4-Chlorophenyl)-5-[(1R)-1-methyl-1,2,3,4-tetrahydroisoquinoline-2-carbonyl]pyrazolo[1,5-a]pyrimidin-2-yl]-3-fluorophenyl}pyrrolidine-3-carboxamide

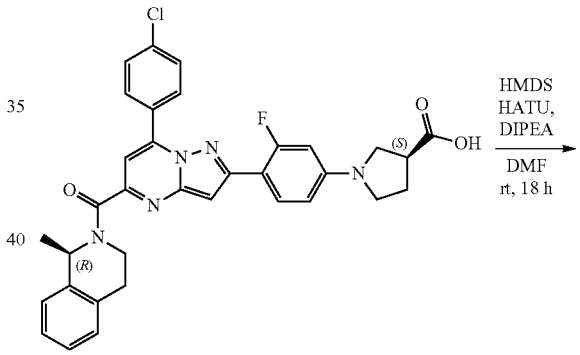

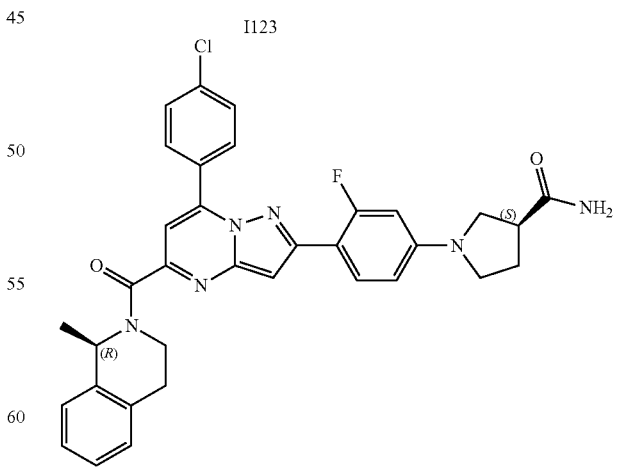

Compound 59 was synthesized from intermediate I123 according to the procedure reported for the synthesis of compound 56. The residue (125 mg) was taken up in DIPE. The solid was filtered off and dried under vacuum to give compound 59 (85 mg, 45%).

Compound 60

Intermediate I124

Ethyl 2-(4-bromo-2-fluorophenyl)-7-(4-fluorophenyl)pyrazolo[1,5-a]pyrimidine-5-carboxylate

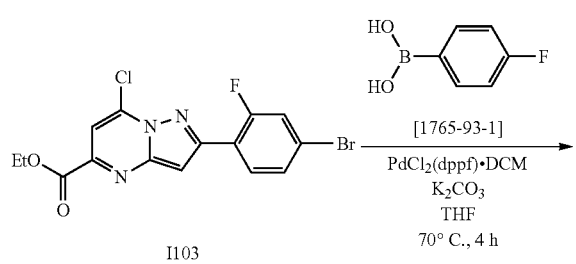

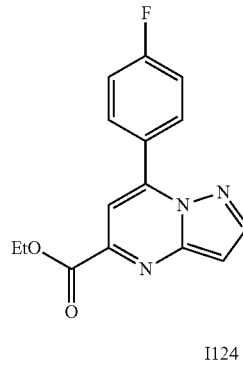

Intermediate I124 (940 mg, 48%) was synthesized from intermediate I103 and 4-fluorobenzeneboronic acid [1765-93-1] according to the procedure reported for the synthesis of intermediate I119 with a shorter reaction time of 4 h.

Intermediate I125

Lithio 2-(4-bromo-2-fluorophenyl)-7-(4-fluorophenyl)pyrazolo[1,5-a]pyrimidine-5-carboxylate

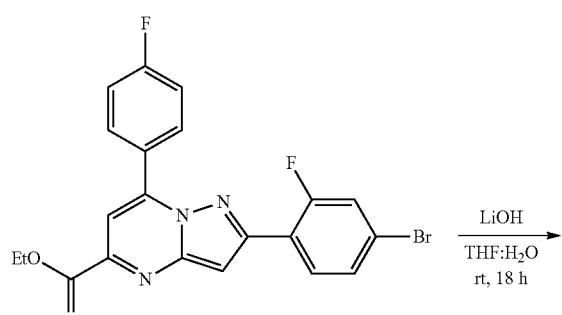

Intermediate I125 (940 mg) was synthesized from intermediate I124 and lithium hydroxide according to the procedure reported for the synthesis of intermediate I105.

Intermediate I126

(1R)-2-[2-(4-Bromo-2-fluorophenyl)-7-(4-fluorophenyl)pyrazolo[1,5-a]pyrimidine-5-carbonyl]-1-methyl-1,2,3,4-tetrahydroisoquinoline

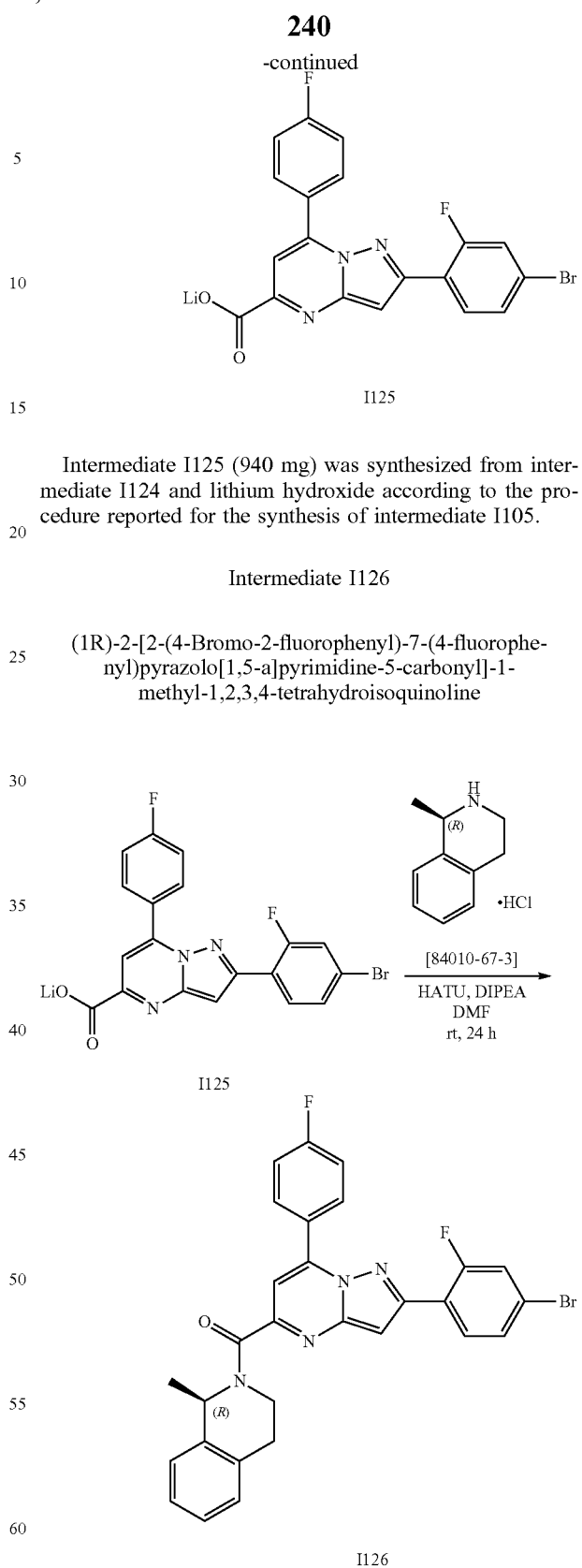

Intermediate I126 (970 mg, 79%) was synthesized from intermediate I125 and (1R)-1-methyl-1,2,3,4-tetrahydroisoquinoline hydrochloride [84010-67-3] according to the procedure reported for the synthesis of intermediate I106.

Intermediate I127

Methyl (3S)-1-{3-fluoro-4-[7-(4-fluorophenyl)-5-[(1R)-1-methyl-1,2,3,4-tetrahydroisoquinoline-2-carbonyl]pyrazolo[1,5-a]pyrimidin-2-yl]phenyl}pyrrolidine-3-carboxylate

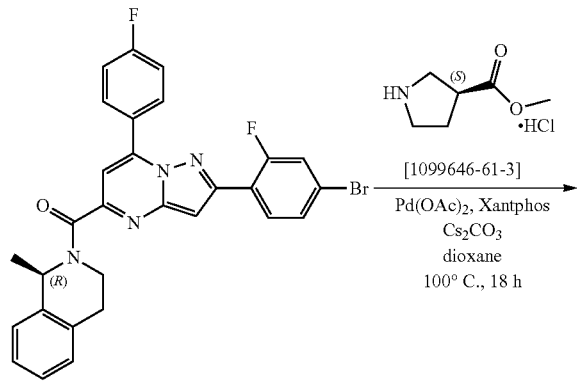

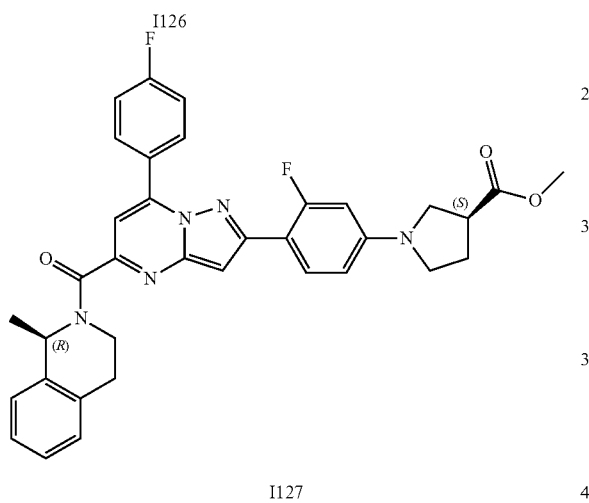

Intermediate I127 (340 mg, 65%) was synthesized from intermediate I126 and (S)-methyl pyrrolidine-3-carboxylate hydrochloride [1099646-61-3] according to the procedure reported for the synthesis of intermediate I107.

Intermediate I128

(3S)-1-{3-Fluoro-4-[7-(4-fluorophenyl)-5-[(1R)-1-methyl-1,2,3,4-tetrahydroisoquinoline-2-carbonyl]pyrazolo[1,5-a]pyrimidin-2-yl]phenyl}pyrrolidine-3-carboxylic acid

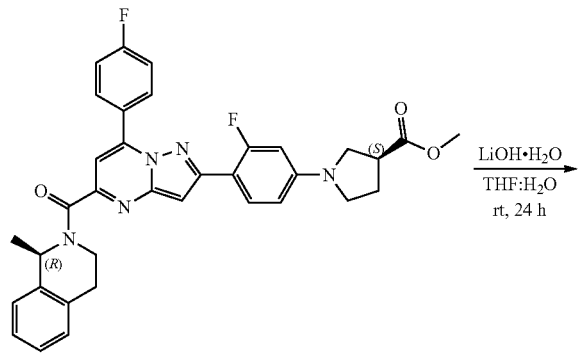

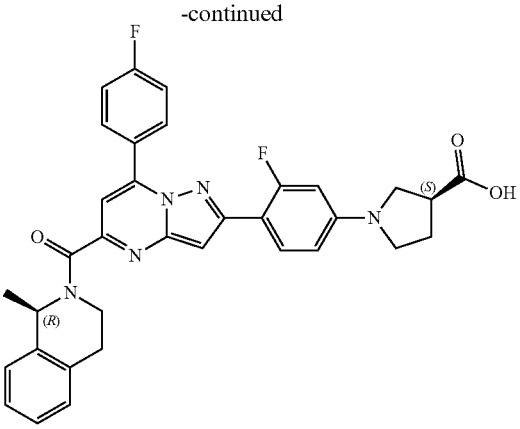

Intermediate I128 (300 mg, 90%) was synthesized from intermediate I127 according to the procedure reported for the synthesis of intermediate I107.

Compound 60

(3S)-1-{3-Fluoro-4-[7-(4-fluorophenyl)-5-[(1R)-1-methyl-1,2,3,4-tetrahydroisoquinoline-2-carbonyl]pyrazolo[1,5-a]pyrimidin-2-yl]phenyl}pyrrolidine-3-carboxamide

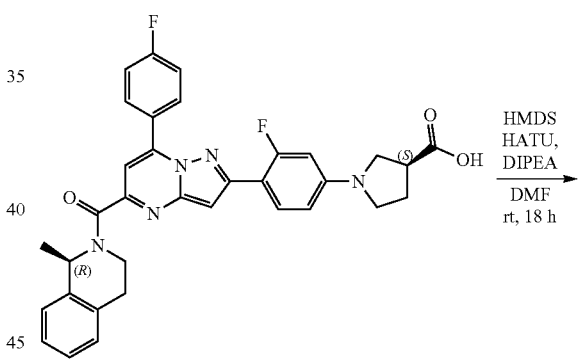

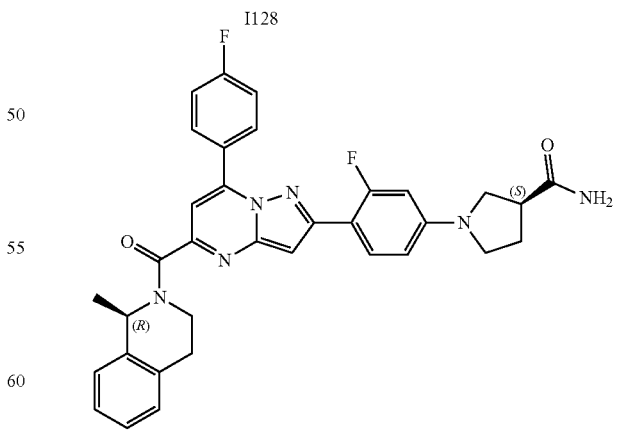

Compound 60 was synthesized from intermediate I128 according to the procedure reported for the synthesis of compound 56. The residue (190 mg) was taken up in DIPE.

The solid was filtered off and dried under vacuum to give compound 60 (125 mg, 42%).

Compound 61

Intermediate I129

Ethyl 2-(4-bromo-2-fluorophenyl)-7-[4-(trifluoromethyl)phenyl]pyrazolo[1,5-a]-pyrimidine-5-carboxylate

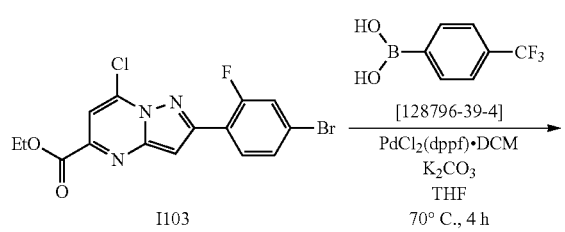

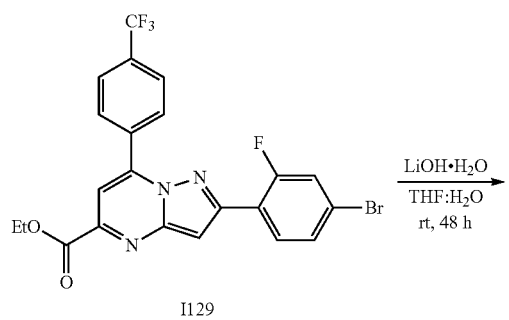

Intermediate I129 (1.1 g, 51%) was synthesized from intermediate I103 and 4-(trifluoromethyl)phenylboronic acid [128796-39-4] according to the procedure reported for the synthesis of intermediate I104.

Intermediate I130

Lithio 2-(4-bromo-2-fluorophenyl)-7-[4-(trifluoromethyl)phenyl]pyrazolo[1,5-a]pyrimidine-5-carboxylate

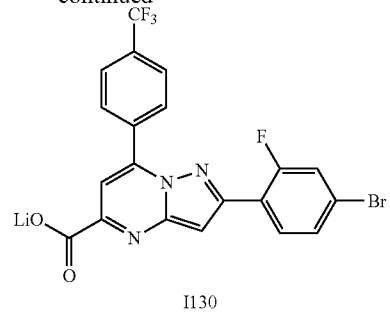

Intermediate I130 (1.1 g) was synthesized from intermediate I129 and lithium hydroxide monohydrate according to the procedure reported for the synthesis of intermediate I105 with a reaction time of 48 h.

Intermediate I131

(1R)-2-[2-(4-Bromo-2-fluorophenyl)-7-[4-(trifluoromethyl)phenyl]pyrazolo[1,5-a]pyrimidine-5-carbonyl]-1-methyl-1,2,3,4-tetrahydroisoquinoline

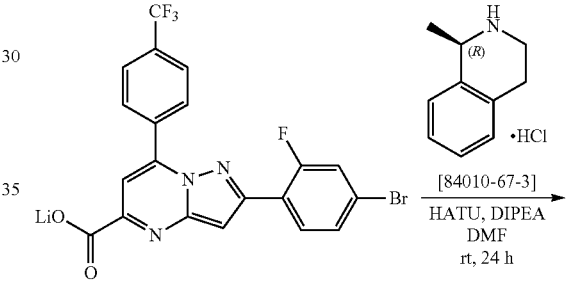

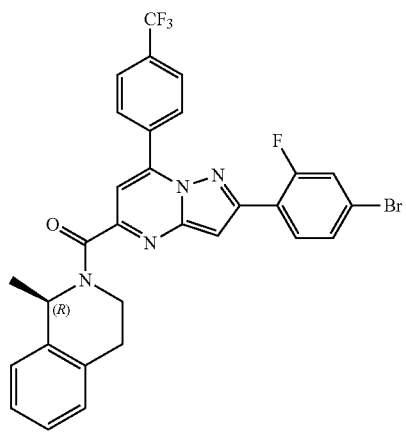

Intermediate I131 (1.17 g, 74%, 87% purity) was synthesized from intermediate I130 and (1R)-1-methyl-1,2,3,4-tetrahydroisoquinoline hydrochloride [84010-67-3] according to the procedure reported for the synthesis of intermediate I106.

Intermediate I132

Methyl (3S)-1-(3-fluoro-4-{5-[(1R)-1-methyl-1,2,3,4-tetrahydroisoquinoline-2-carbonyl]-7-[4-(trifluoromethyl)phenyl]pyrazolo[1,5-a]pyrimidin-2-yl}phenyl)pyrrolidine-3-carboxylate

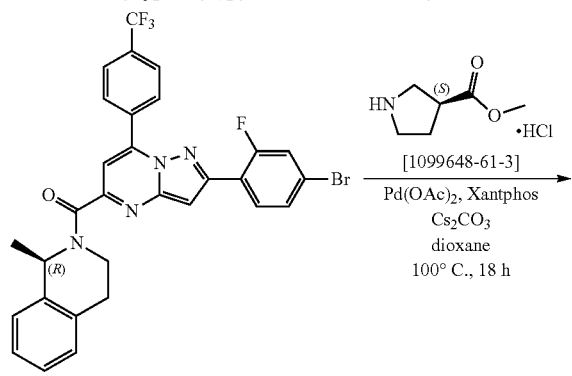

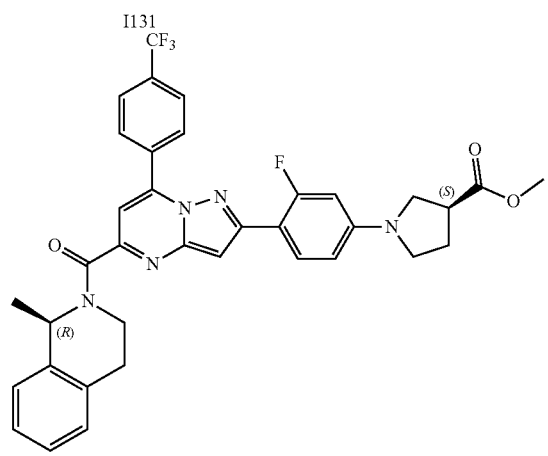

I132

Intermediate I132 (240 mg, 57%) was synthesized from intermediate I131 and (S)-methyl pyrrolidine-3-carboxylate hydrochloride [1099646-61-3] according to the procedure reported for the synthesis of intermediate I107.

Intermediate I133

(3S)-1-(3-Fluoro-4-{5-[(1R)-1-methyl-1,2,3,4-tetrahydroisoquinoline-2-carbonyl]-7-[4-(trifluoromethyl)phenyl]pyrazolo[1,5-a]pyrimidin-2-yl}phenyl)pyrrolidine-3-carboxylic acid

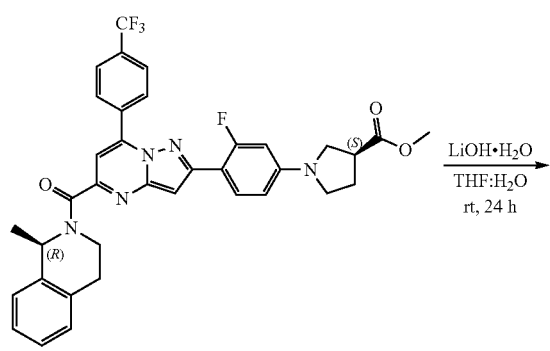

I132

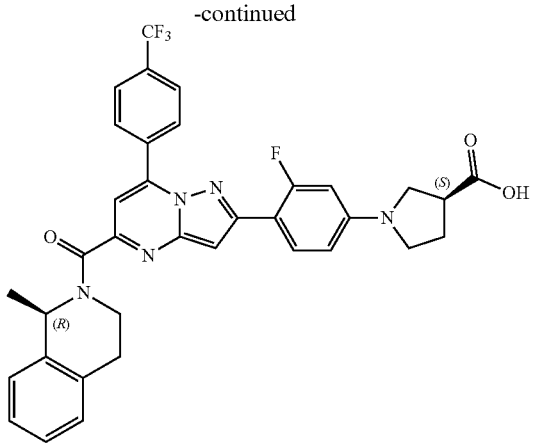

I133

Intermediate I133 (210 mg, 66%) was synthesized from intermediate I132 according to the procedure reported for the synthesis of intermediate I107.

Compound 61

(3S)-1-(3-Fluoro-4-{5-[(1R)-1-methyl-1,2,3,4-tetrahydroisoquinoline-2-carbonyl]-7-[4-(trifluoromethyl)phenyl]pyrazolo[1,5-a]pyrimidin-2-yl}phenyl)pyrrolidine-3-carboxamide

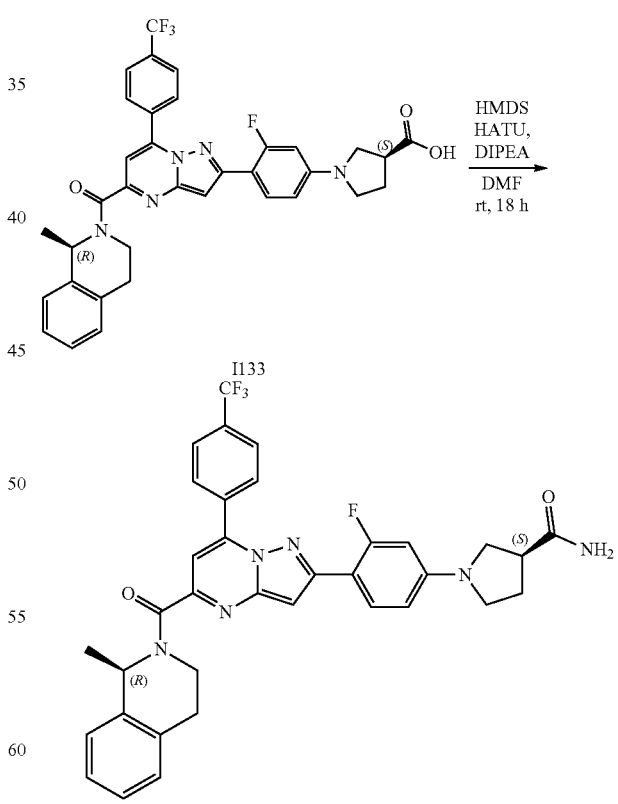

61

Compound 61 (82 mg, 44%) was synthesized from intermediate I133 according to the procedure reported for the synthesis of compound 56.

Compound 62

Intermediate I134

Ethyl 2-(4-bromo-2-fluorophenyl)-7-(4-cyanophenyl)pyrazolo[1,5-a]pyrimidine-5-carboxylate

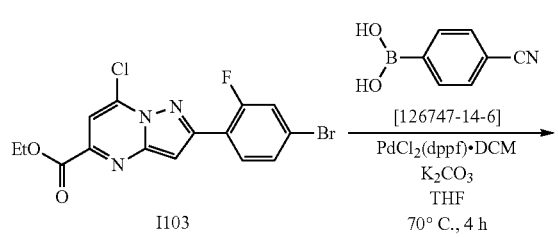

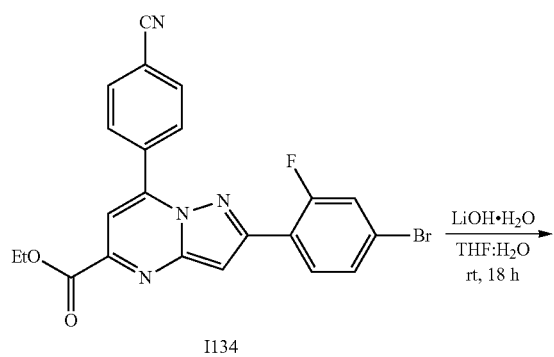

Intermediate I134 (730 mg, 42%) was synthesized from intermediate I103 and 4-cyanophenylboronic acid [126747-14-6] according to the procedure reported for the synthesis of intermediate I104.

Intermediate I135

Lithio 2-(4-bromo-2-fluorophenyl)-7-(4-cyanophenyl)pyrazolo[1,5-a]pyrimidine-5-carboxylate

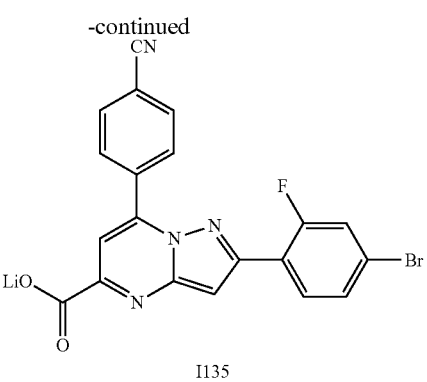

Intermediate I135 (0.8 g) was synthesized from intermediate I134 and lithium hydroxide monohydrate according to the procedure reported for the synthesis of intermediate I105.

Intermediate I136

4-[2-(4-Bromo-2-fluorophenyl)-5-[(1R)-1-methyl-1,2,3,4-tetrahydroisoquinoline-2-carbonyl]pyrazolo[1,5-a]pyrimidin-7-yl]benzonitrile

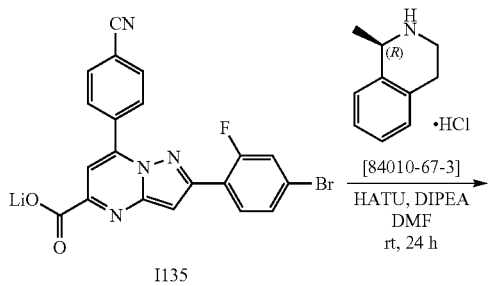

Intermediate I136 (620 mg, 61%) was synthesized from intermediate I135 and (1R)-1-methyl-1,2,3,4-tetrahydroisoquinoline hydrochloride [84010-67-3] according to the procedure reported for the synthesis of intermediate I106.

Intermediate I137

Methyl (3S)-1-{4-[7-(4-cyanophenyl)-5-[(1R)-1-methyl-1,2,3,4-tetrahydroisoquinoline-2-carbonyl]pyrazolo[1,5-a]pyrimidin-2-yl]-3-fluorophenyl}pyrrolidine-3-carboxylate

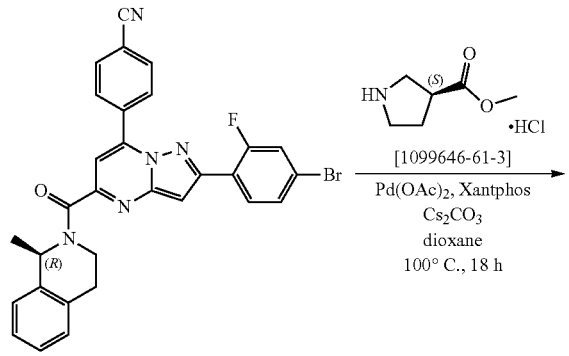

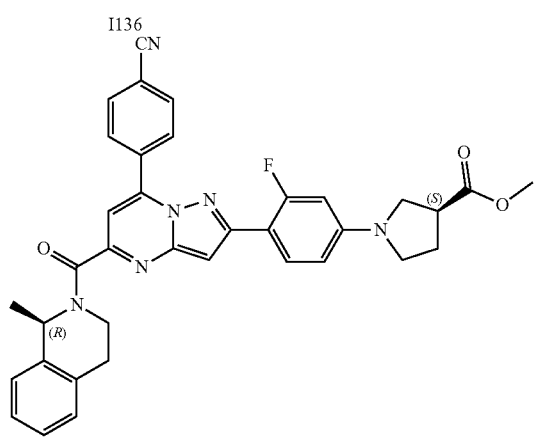

Intermediate I137 (380 mg, 56%) was synthesized from intermediate I136 and (S)-methyl pyrrolidine-3-carboxylate hydrochloride [1099646-61-3] according to the procedure reported for the synthesis of intermediate I107.

Intermediate I138

(3S)-1-{4-[7-(4-Cyanophenyl)-5-[(1R)-1-methyl-1,2,3,4-tetrahydroisoquinoline-2-carbonyl]pyrazolo[1,5-a]pyrimidin-2-yl]-3-fluorophenyl}pyrrolidine-3-carboxylic acid

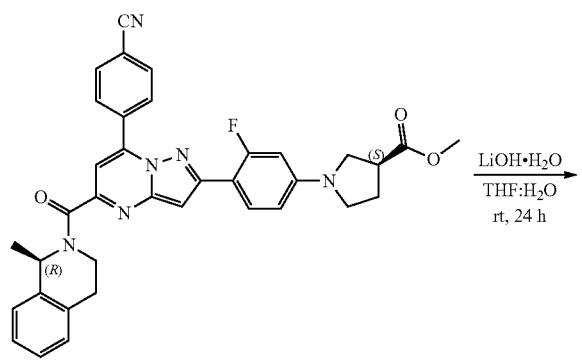

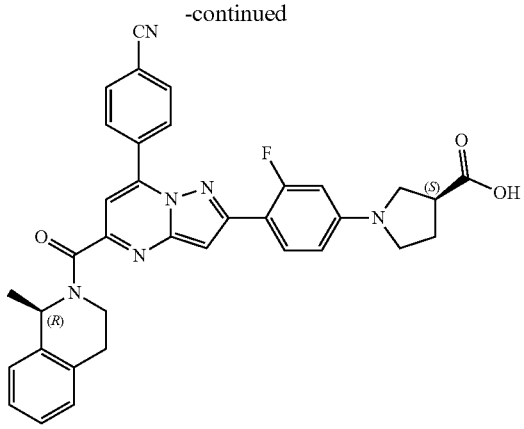

Intermediate I138 was synthesized from intermediate I137 according to the procedure reported for the synthesis of intermediate I107. The crude mixture was purified by flash chromatography on silica gel (15-40 μm, Grace® 12 g, mobile phase gradient: DCM/MeOH from 100:0 to 96:4). The pure fractions were collected and evaporated to dryness to afford intermediate I138 (265 mg, 71%).

Compound 62

(3S)-1-{4-[7-(4-Cyanophenyl)-5-[(1R)-1-methyl-1,2,3,4-tetrahydroisoquinoline-2-carbonyl]pyrazolo[1,5-a]pyrimidin-2-yl]-3-fluorophenyl}pyrrolidine-3-carboxamide

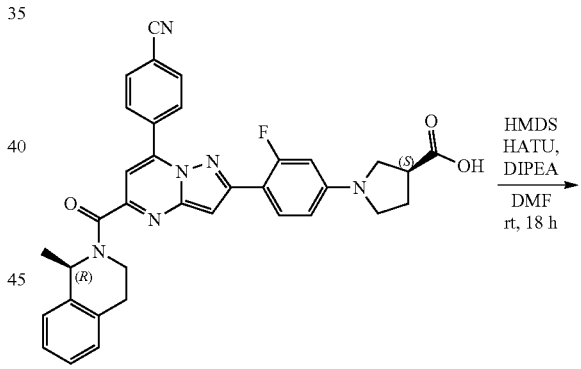

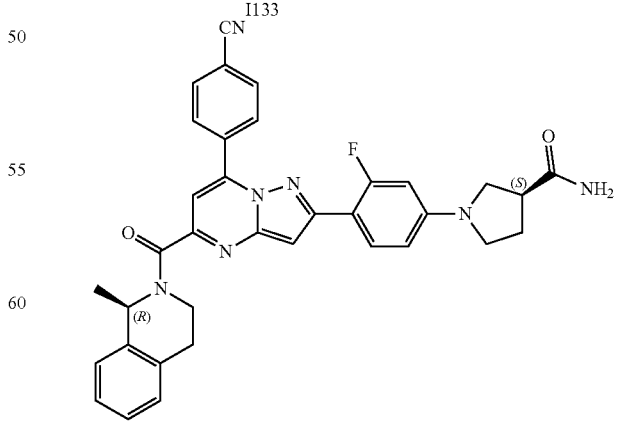

Compound 62 was synthesized from intermediate I133 according to the procedure reported for the synthesis of compound 56. The residue (125 mg) was taken up in DIPE and DCM (3 drops). The solid was filtered off and dried under vacuum to give compound 62 (45 mg, 20%).

Compound 63

Intermediate I139

Ethyl 2-(4-bromo-2-fluorophenyl)-7-(pyridin-4-yl)pyrazolo[1,5-a]pyrimidine-5-carboxylate

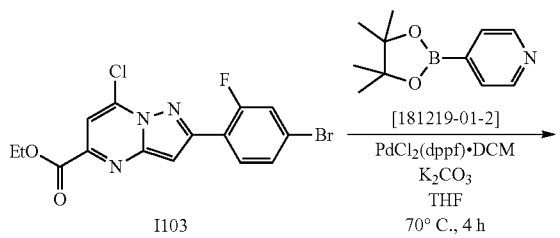

Intermediate I139 was synthesized from intermediate I103 and 4-pyridineboronic acid pinacol ester [181219-01-2] according to the procedure reported for the synthesis of intermediate I104. The crude mixture was purified by flash chromatography over silica gel (15-40 μm, 40 g GraceResolv™, mobile phase gradient: heptane/EtOAc from 90:10 to 50:50) to afford intermediate I139 (350 mg, 21%).

Intermediate I140

Lithio 2-(4-bromo-2-fluorophenyl)-7-(pyridin-4-yl)pyrazolo[1,5-a]pyrimidine-5-carboxylate

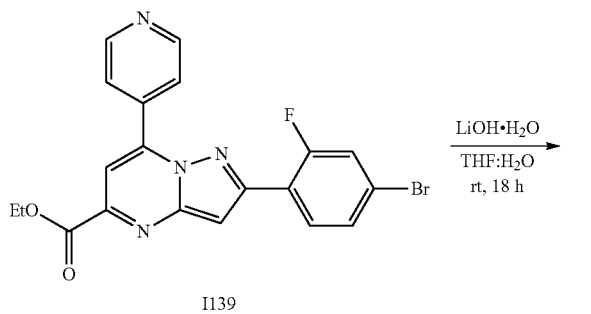

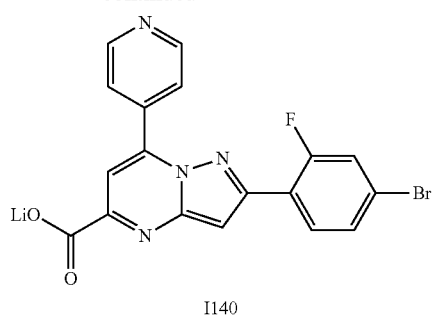

Intermediate I140 (410 mg) was synthesized from intermediate I139 and lithium hydroxide monohydrate according to the procedure reported for the synthesis of intermediate I105.

Intermediate I141

(1R)-2-[2-(4-Bromo-2-fluorophenyl)-7-(pyridin-4-yl)pyrazolo[1,5-a]pyrimidine-5-carbonyl]-1-methyl-1,2,3,4-tetrahydroisoquinoline

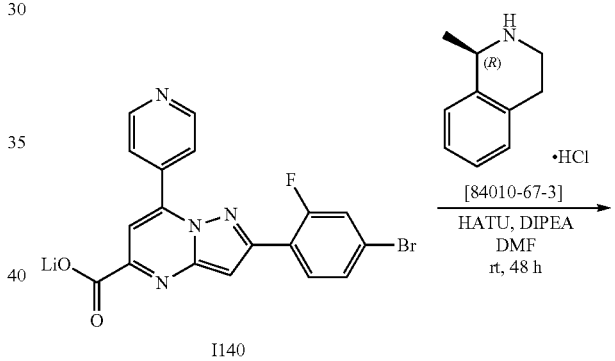

Intermediate I141 (345 mg, 67%) was synthesized from intermediate I140 and (1R)-1-methyl-1,2,3,4-tetrahydroisoquinoline hydrochloride [84010-67-3] according to the procedure reported for the synthesis of intermediate I106 with a reaction time of 48 h.

Intermediate I142

Methyl (3S)-1-(3-fluoro-4-{5-[(1R)-1-methyl-1,2,3,4-tetrahydroisoquinoline-2-carbonyl]-7-(pyridin-4-yl)pyrazolo[1,5-a]pyrimidin-2-yl}phenyl)pyrrolidine-3-carboxylate

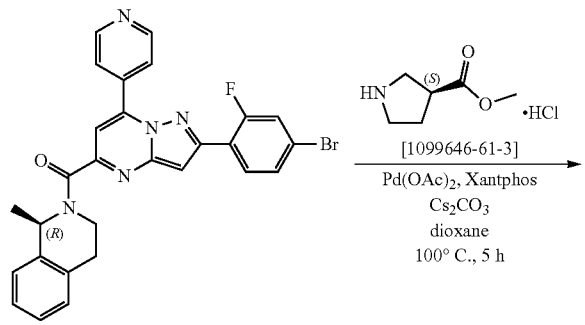

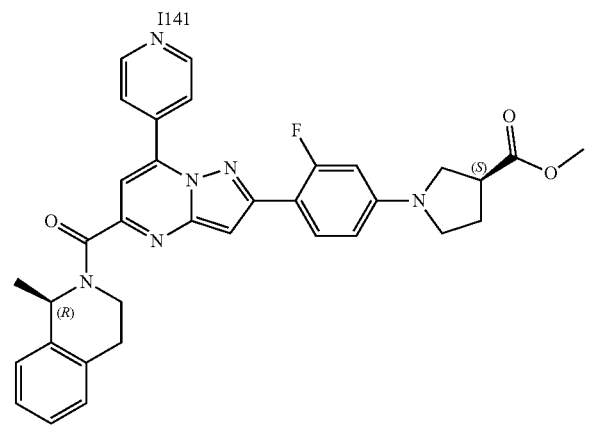

I142

Intermediate I142 was synthesized from intermediate I141 and (S)-methyl pyrrolidine-3-carboxylate hydrochloride [1099646-61-3] according to the procedure reported for the synthesis of intermediate I107 with a reaction time of 5 h. The crude mixture was purified by preparative LC (irregular SiOH, 15-40 µm, 40 g Grace®, liquid injection (DCM), mobile phase gradient: DCM/MeOH from 100:0 to 95:5) to afford intermediate I142 (220 mg, 59%).

Intermediate I143

(3S)-1-(3-Fluoro-4-{5-[(1R)-1-methyl-1,2,3,4-tetrahydroisoquinoline-2-carbonyl]-7-(pyridin-4-yl)pyrazolo[1,5-a]pyrimidin-2-yl}phenyl)pyrrolidine-3-carboxylic acid

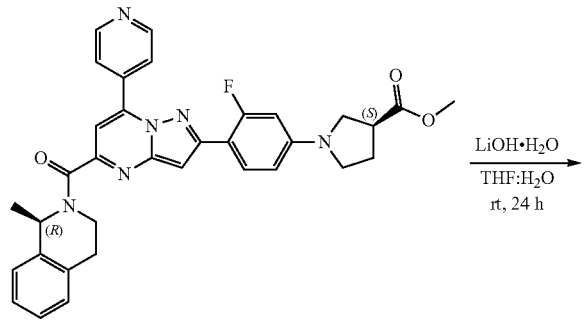

I142

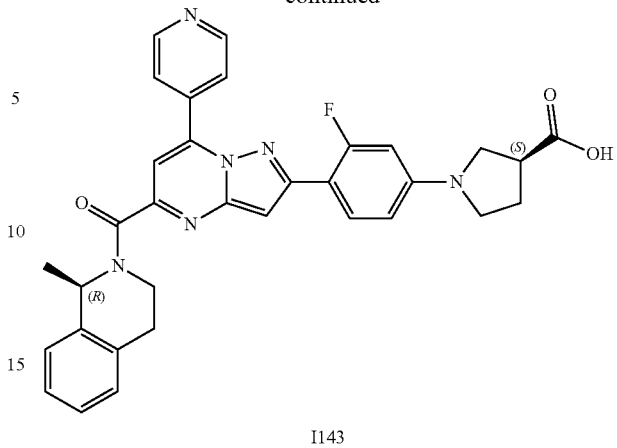

I143

Intermediate I143 was synthesized from intermediate I142 according to the procedure reported for the synthesis of intermediate I107. The crude mixture was purified by flash chromatography on silica gel (15-40 µm, 12 g Grace®, mobile phase gradient: DCM/MeOH from 100:0 to 96:4). The pure fractions were collected and evaporated to dryness. The residue (125 mg) was taken up in DIPE. The solid was filtered off and dried under vacuum to afford intermediate I143 (39 mg, 18%).

Compound 63

(3S)-1-(3-Fluoro-4-{5-[(1R)-1-methyl-1,2,3,4-tetrahydroisoquinoline-2-carbonyl]-7-(pyridin-4-yl)pyrazolo[1,5-a]pyrimidin-2-yl}phenyl)pyrrolidine-3-carboxamide

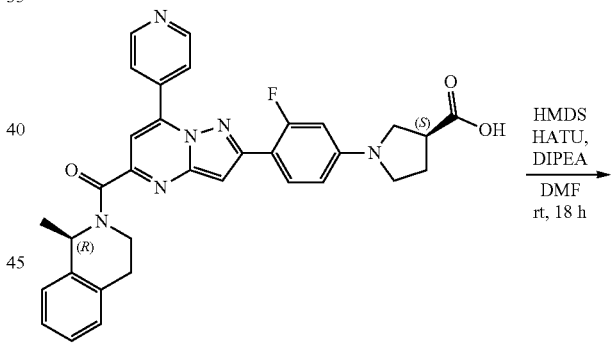

I143

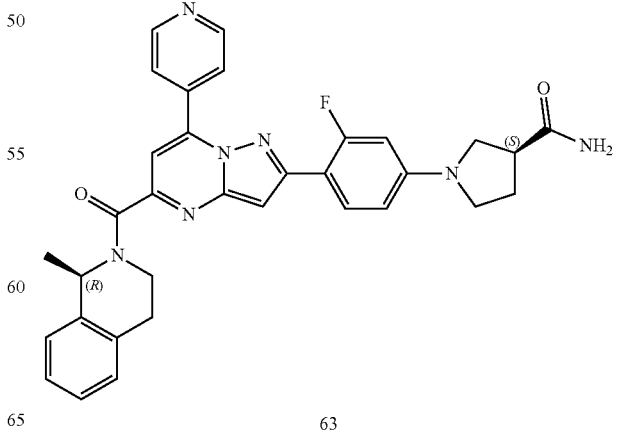

63

Compound 63 was synthesized from intermediate I143 according to the procedure reported for the synthesis of compound 56. The residue (53 mg) was taken up in DIPE. The solid was filtered off and dried under vacuum to give compound 63 (23 mg, 27%).

Compound 64

Intermediate I144

Ethyl 2-(4-bromo-2-fluorophenyl)-7-(pyrimidin-5-yl)pyrazolo[1,5-a]pyrimidine-5-carboxylate

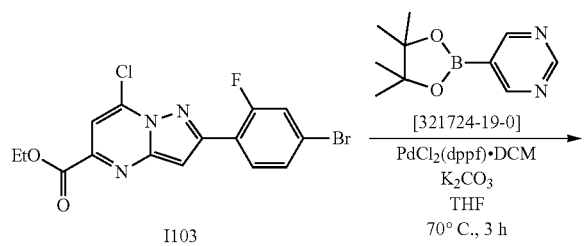

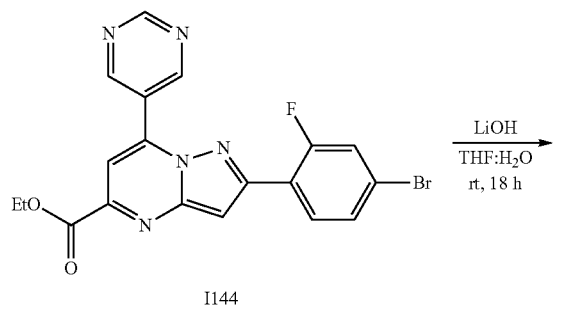

Intermediate I144 (3.4 g) was synthesized from intermediate I103 and 5-pyrimidineboronic acid pinacol ester [321724-19-0] according to the procedure reported for the synthesis of intermediate I119 with a shorter reaction time of 3 h.

Intermediate I145

Lithio 2-(4-bromo-2-fluorophenyl)-7-(pyrimidin-5-yl)pyrazolo[1,5-a]pyrimidine-5-carboxylate

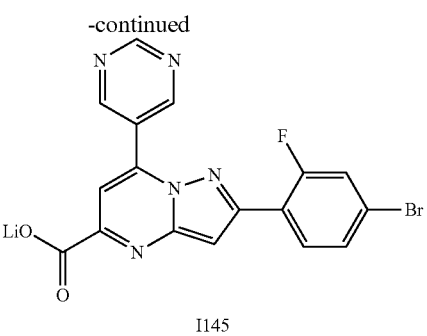

Intermediate I145 (3.0 g, 99%) was synthesized from intermediate I144 and lithium hydroxide according to the procedure reported for the synthesis of intermediate I105.

Intermediate I146

(1R)-2-[2-(4-Bromo-2-fluorophenyl)-7-(pyrimidin-5-yl)pyrazolo[1,5-a]pyrimidine-5-carbonyl]-1-methyl-1,2,3,4-tetrahydroisoquinoline

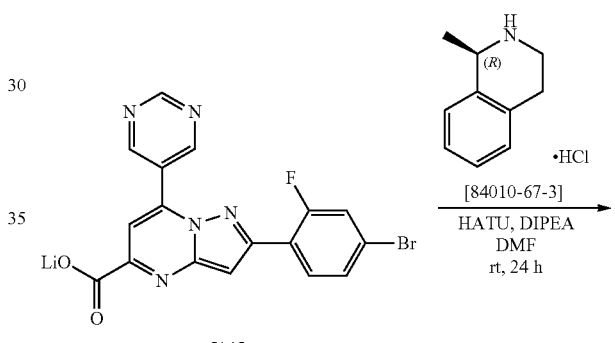

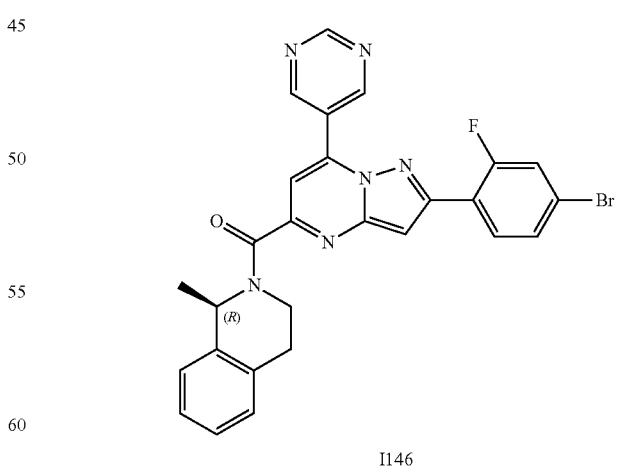

Intermediate I146 (1.32 g, 34%) was synthesized from intermediate I145 and (1R)-1-methyl-1,2,3,4-tetrahydroisoquinoline hydrochloride [84010-67-3] according to the procedure reported for the synthesis of intermediate I106.

Intermediate I147

Methyl (3S)-1-(3-fluoro-4-{5-[(1R)-1-methyl-1,2,3,4-tetrahydroisoquinoline-2-carbonyl]-7-(pyrimidin-5-yl)pyrazolo[1,5-a]pyrimidin-2-yl}phenyl)pyrrolidine-3-carboxylate

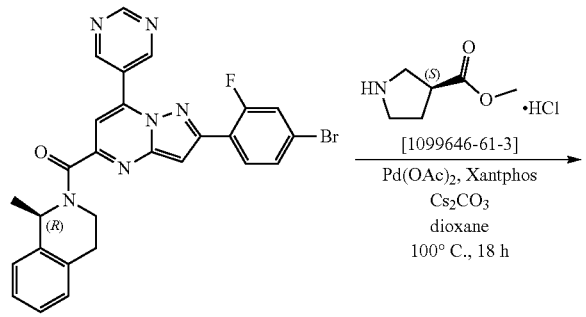

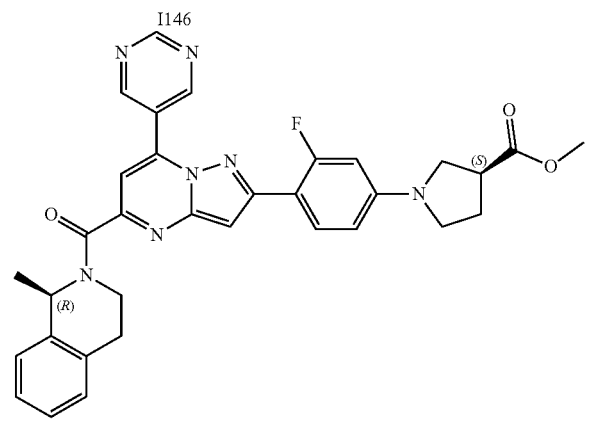

I147

Intermediate I147 was synthesized from intermediate I146 and (S)-methyl pyrrolidine-3-carboxylate hydrochloride [1099646-61-3] according to the procedure reported for the synthesis of intermediate I107. The crude mixture was purified by preparative LC (irregular SiOH, 15-40 μm, 40 g Grace®, liquid injection (DCM), mobile phase gradient: DCM/MeOH from 100:0 to 96:4) to afford intermediate I147 (180 mg, 25%).

Intermediate I148

(3S)-1-(3-Fluoro-4-{5-[(1R)-1-methyl-1,2,3,4-tetrahydroisoquinoline-2-carbonyl]-7-(pyrimidin-5-yl)pyrazolo[1,5-a]pyrimidin-2-yl}phenyl)pyrrolidine-3-carboxylic acid

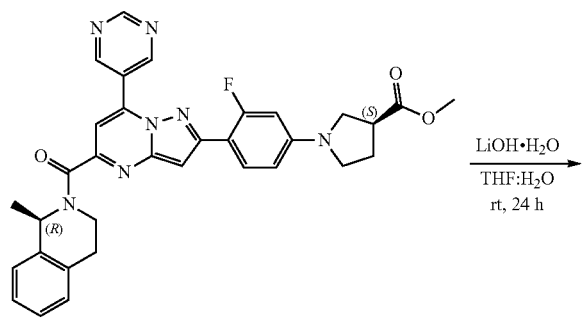

I147

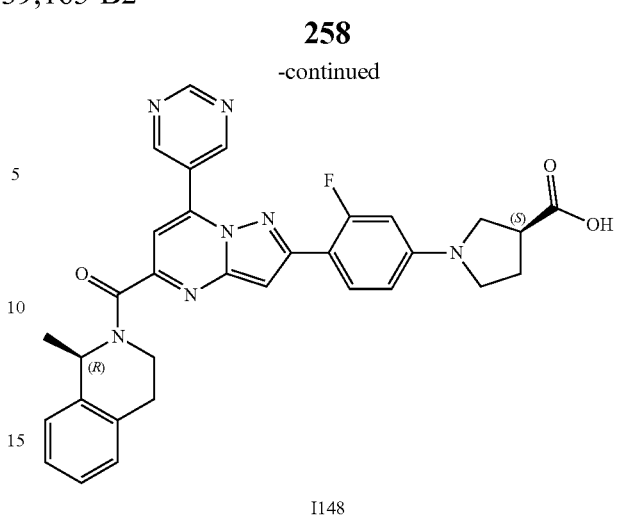

I148

Intermediate I148 was synthesized from intermediate I147 according to the procedure reported for the synthesis of intermediate I107. The crude mixture was purified by flash chromatography on silica gel (15-40 μm, 24 g Grace®, mobile phase gradient: DCM/MeOH from 100:0 to 96:4). The pure fractions were collected and evaporated to dryness to afford intermediate I148 (130 mg, 74%).

Compound 64

(3S)-1-(3-Fluoro-4-{5-[(1R)-1-methyl-1,2,3,4-tetrahydroisoquinoline-2-carbonyl]-7-(pyrimidin-5-yl)pyrazolo[1,5-a]pyrimidin-2-yl}phenyl)pyrrolidine-3-carboxamide

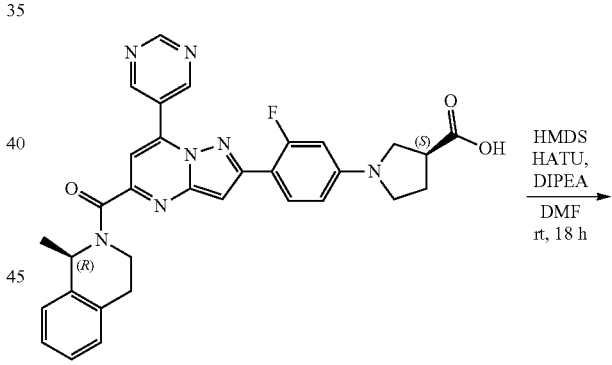

I148

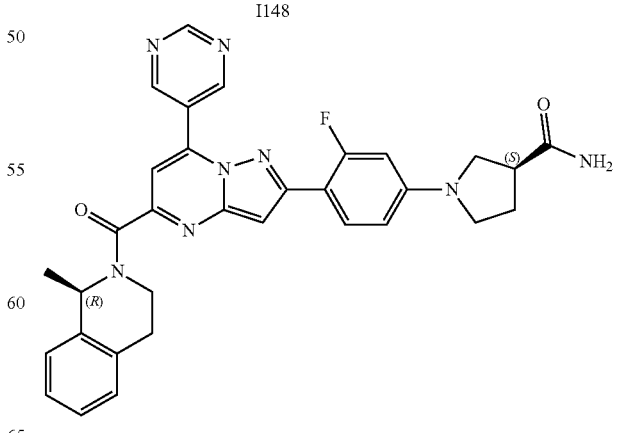

64

Compound 64 was synthesized from intermediate I148 according to the procedure reported for the synthesis of compound 56. The residue (75 mg) was taken up in DIPE. The solid was filtered off and dried under vacuum to give compound 64 (40 mg, 42%).

Compound 90

Intermediate I195

Ethyl 2-(4-bromo-2-fluorophenyl)-7-(5-fluoropyridin-3-yl)pyrazolo[1,5-a]pyrimidine-5-carboxylate

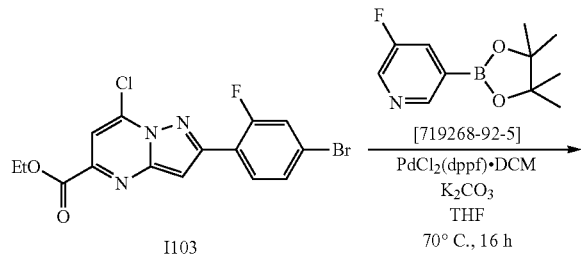

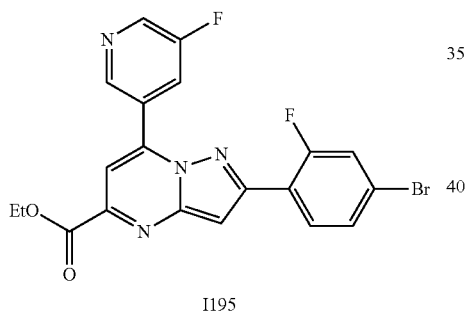

Intermediate I195 was synthesized from intermediate I103 and 3-fluoro-5-(4,4,5,5-tetramethyl-1,3,2-dioxaborolan-2-yl)pyridine [719268-92-5] according to the procedure reported for the synthesis of intermediate I104 with a reaction time of 16 h. The reaction mixture was filtered over a pad of Celite® and washed with $H_2O$ and EtOAc. The filtrate was decanted and the organic layer was washed with $H_2O$ (twice), dried over $MgSO_4$, filtered and evaporated to dryness. The crude mixture was purified by flash chromatography (irregular SiOH, 15-40 µm, 25 g GraceResolv™, liquid injection (DCM), mobile phase gradient: heptane/EtOAc from 90:10 to 0:100) to afford intermediate I195 (246 mg, 43%) as a yellow solid.

Intermediate I196

2-(4-Bromo-2-fluorophenyl)-7-(5-fluoropyridin-3-yl)pyrazolo[1,5-a]pyrimidine-5-carboxylic acid

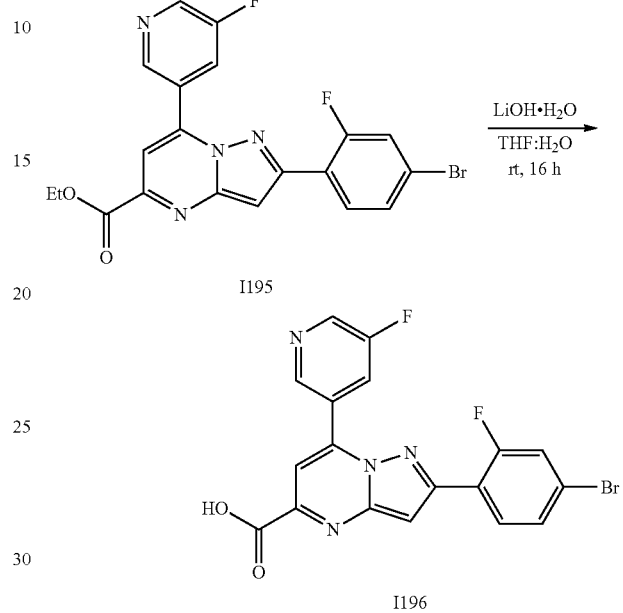

Lithium hydroxide monohydrate (86.5 mg, 2.06 mmol) was added to a solution of intermediate I195 (246 mg, 412 µmol) in THF (10 mL) and $H_2O$ (4 mL). The reaction mixture was stirred at rt for 16 h. A 10% aqueous solution of $KHSO_4$ was added until pH 3 and the mixture was diluted with EtOAc. The suspension was filtered off to afford intermediate I196 (122 mg, 60%, 87% purity).

Intermediate I197

(1R)-2-[2-(4-Bromo-2-fluorophenyl)-7-(5-fluoropyridin-3-yl)pyrazolo[1,5-a]pyrimidine-5-carbonyl]-1-methyl-1,2,3,4-tetrahydroisoquinoline

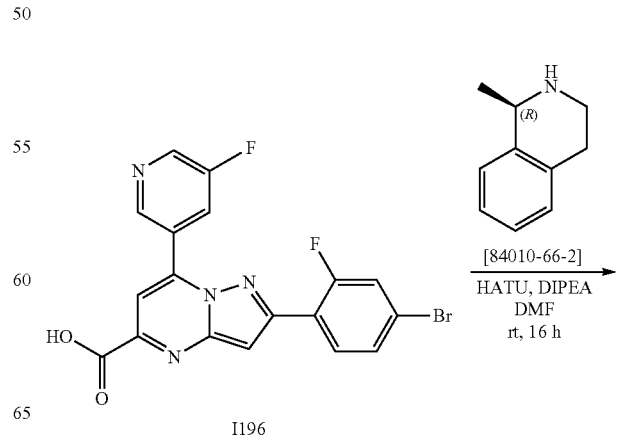
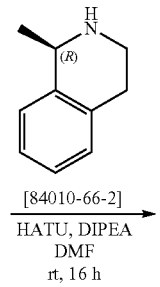

-continued

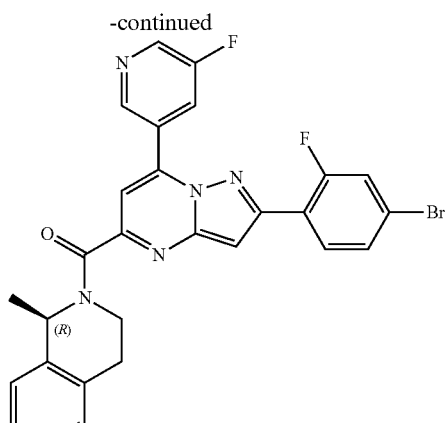

I197

Intermediate I197 (100 mg, 72%) was synthesized from intermediate I196 and (1R)-1-methyl-1,2,3,4-tetrahydroisoquinoline [84010-66-2] according to the procedure reported for the synthesis of intermediate I106 with a reaction time of 16 h.

Intermediate I198

Methyl (3S)-1-{3-fluoro-4-[7-(5-fluoropyridin-3-yl)-5-[(1R)-1-methyl-1,2,3,4-tetrahydroisoquinoline-2-carbonyl]pyrazolo[1,5-a]pyrimidin-2-yl]phenyl}pyrrolidine-3-carboxylate

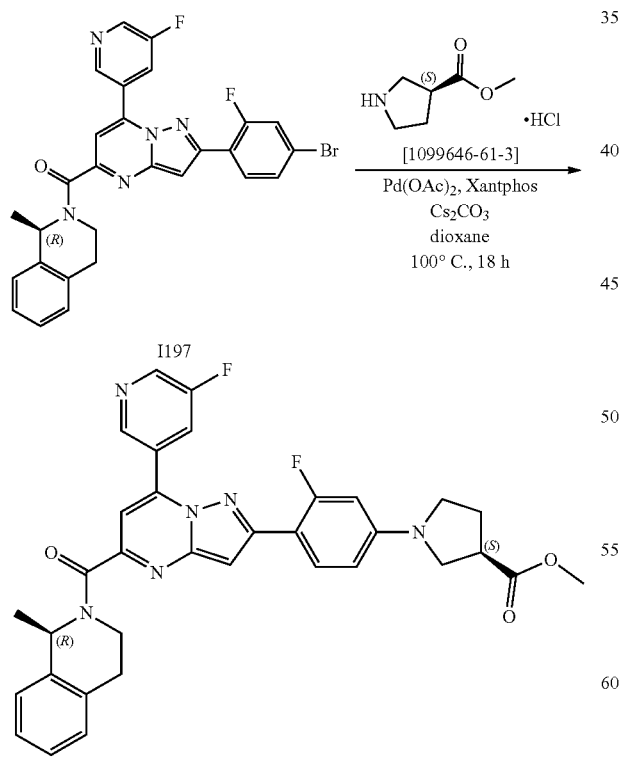

I198

Intermediate I198 was synthesized from intermediate I197 and (S)-methyl pyrrolidine-3-carboxylate hydrochloride [1099646-61-3] according to the procedure reported for the synthesis of intermediate I107. The reaction mixture was filtered over a pad of Celite® and washed with EtOAc and $H_2O$. The filtrate was decanted and the organic phase was washed with $H_2O$ (twice), dried over $MgSO_4$, filtered and evaporated to dryness. The crude mixture was purified by flash chromatography (irregular SiOH, 15-40 μm, 12 g GraceResolv™, liquid injection (DCM), mobile phase gradient: heptane/EtOAc from 90:10 to 60:40) to afford intermediate I198 (81 mg, 75%) as a yellow solid.

Intermediate I199

(3S)-1-{3-Fluoro-4-[7-(5-fluoropyridin-3-yl)-5-[(1R)-1-methyl-1,2,3,4-tetrahydroisoquinoline-2-carbonyl]pyrazolo[1,5-a]pyrimidin-2-yl]phenyl}pyrrolidine-3-carboxylic acid

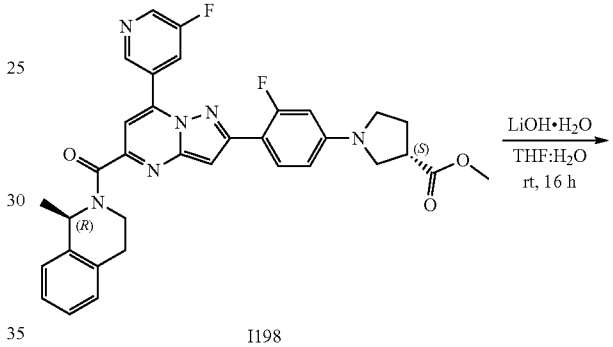

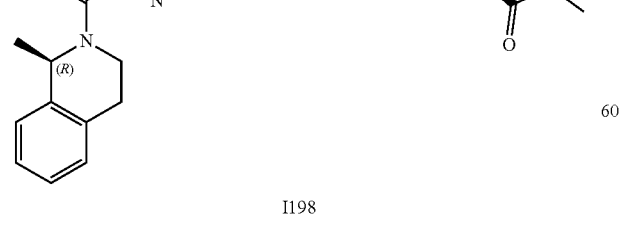

I199

Lithium hydroxide monohydrate (17.2 mg, 0.41 mmol) was added to a solution of intermediate I198 (81.0 mg, 133 μmol) in THF (1.2 mL) and $H_2O$ (0.4 mL). The reaction mixture was stirred at rt for 16 h. A 10% aqueous solution of $KHSO_4$ was added until pH 3 and the aqueous phase was extracted with EtOAc (twice). The combined organic extracts were washed with brine, dried over $MgSO_4$, filtered and concentrated to dryness to afford intermediate I199 (68 mg, 86%) as an orange solid.

Compound 90

(3S)-1-{3-Fluoro-4-[7-(5-fluoropyridin-3-yl)-5-[(1R)-1-methyl-1,2,3,4-tetrahydro-isoquinoline-2-carbonyl]pyrazolo[1,5-a]pyrimidin-2-yl]phenyl}pyrrolidine-3-carboxamide

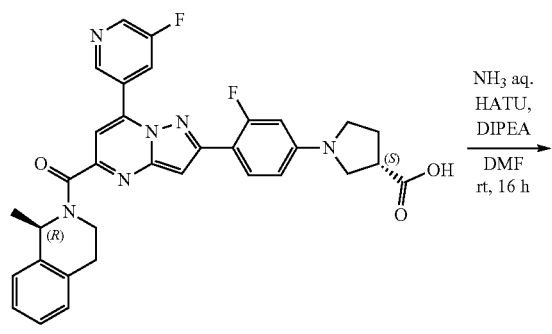

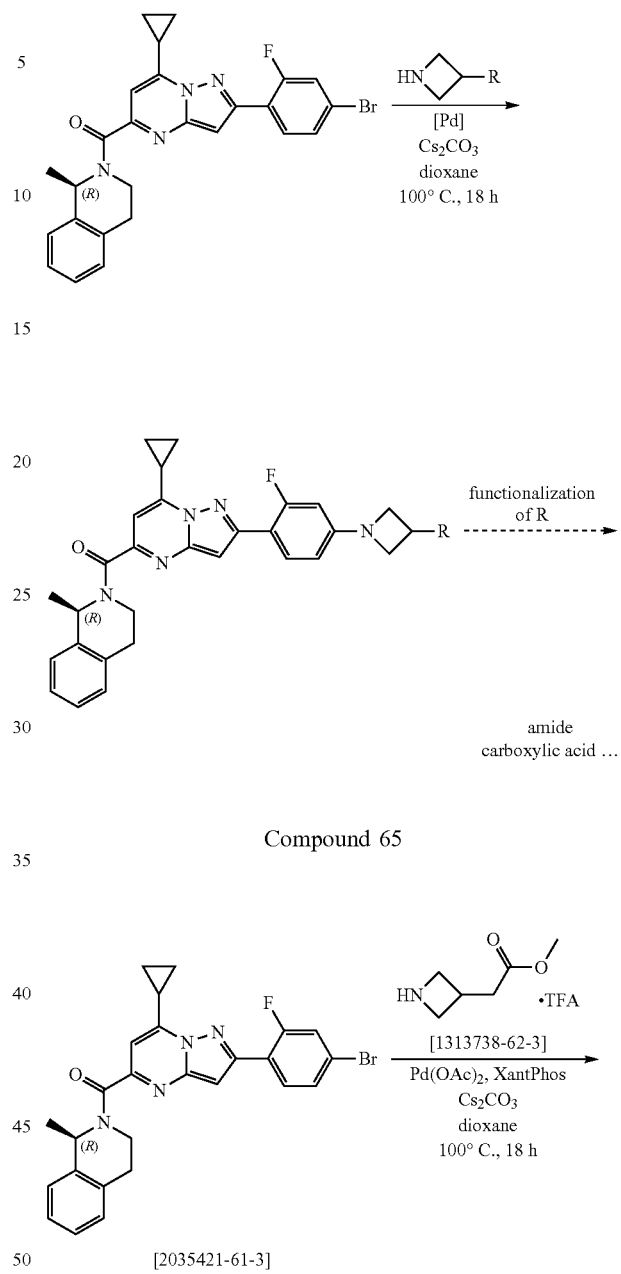

General scheme

Compound 65

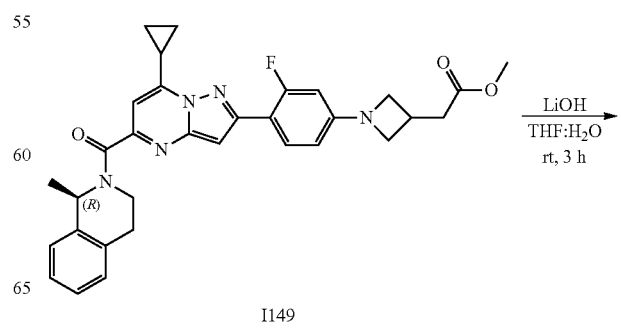

In a screw cap vial a mixture of intermediate I199 (68.0 mg, 114 μmol), HATU (65.0 mg, 171 μmol) and DIPEA (59 μL, 343 μmol) in DMF (1.1 mL) was stirred at rt for 30 min. Ammonia (30% in $H_2O$, 216 μL, 3.43 mmol) was added and the reaction mixture was stirred at rt for 16 h. The reaction mixture was diluted with EtOAc and $H_2O$. Additional amount of HATU (21 mg, 55 μmol), DIPEA (20 μL, 114 μmol) and ammonia (30% in $H_2O$, 100 μL, 1.58 mmol) were added. The reaction mixture was stirred at rt for 20 h. The layers were separated and the organic phase was washed with $H_2O$ and brine (3 times), dried over $MgSO_4$, filtered and concentrated in vacuo. The crude mixture was purified by flash chromatography (irregular SiOH, 15-40 μm, 12 g GraceResolv™, liquid injection (DCM), mobile phase gradient: heptane/EtOAc from 50:50 to 0:100). The residue (25 mg) was dried under high vacuum at 60° C. for 16 h to give compound 90 (18 mg, 27%) as an orange solid.

-continued

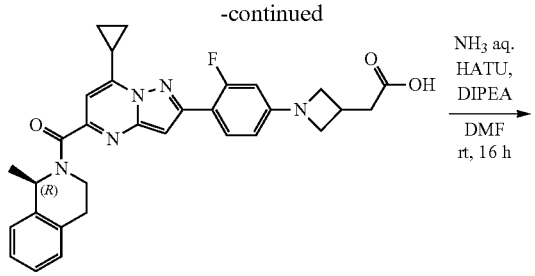
I149

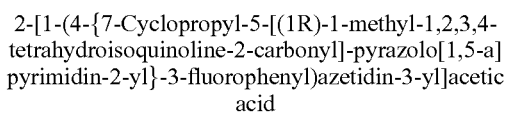

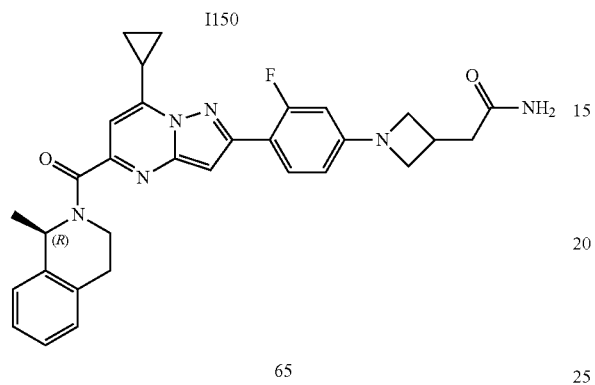
I150

Intermediate I149

Methyl 2-[1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)azetidin-3-yl]acetate A mixture of (1R)-2-[2-(4-bromo-2-fluorophenyl)-7-cyclopropylpyrazolo[1,5-a]pyrimidine-5-carbonyl]-1-methyl-1,2,3,4-tetrahydroisoquinoline [2035421-61-3] (250 mg, 495 μmol), methyl-3-azetidineacetate trifluoroacetate salt [1313738-62-3] (144 mg, 594 μmol) and cesium carbonate (645 mg, 1.98 mmol) in 1,4-dioxane (5.9 mL) was degassed with nitrogen. Palladium acetate (11.1 mg, 49.5 μmol) and XantPhos (28.6 mg, 49.5 μmol) were added and the mixture was purged again with nitrogen. The reaction mixture was stirred at 100° C. for 18 h. The reaction mixture was combined with another fraction (50 mg, 98.9 μmol) and diluted with EtOAc and H₂O. The mixture was filtered over a pad of Celite® and the filtrate was decanted. The organic phase was washed with brine, dried over MgSO₄, filtered and concentrated to dryness. The crude mixture was purified by flash chromatography (irregular SiOH, 15-40 μm, 12 g GraceResolv™, liquid injection (DCM), mobile phase gradient: heptane/EtOAc from 90:10 to 20:80) to afford intermediate I149 (178 mg, 54%) as a yellow foam.

Intermediate I150

2-[1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)azetidin-3-yl]acetic acid

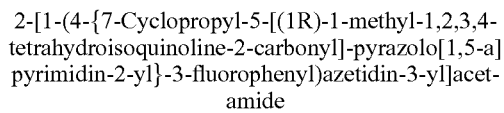

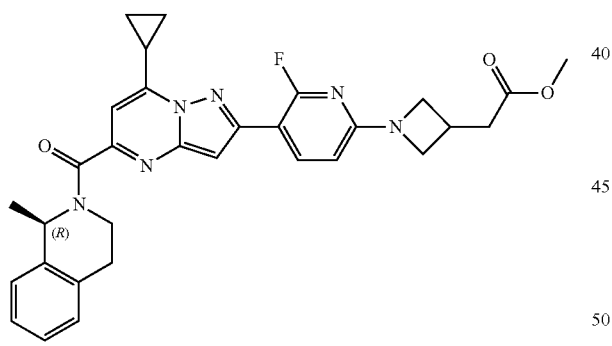

Lithium hydroxide (23.1 mg, 965 μmol) was added to a solution of intermediate I149 (178 mg, 322 μmol) in THF (3.6 mL) and H₂O (1.5 mL). The reaction mixture was stirred at rt for 3 h. A 10% aqueous solution of KHSO₄ was added until pH 3 and the mixture was diluted with EtOAc. The layers were separated and the organic phase was washed with brine and H₂O (twice), dried over MgSO₄, filtered and concentrated to dryness to afford intermediate I150 (183 mg, 95%, 90% purity) as a yellow solid.

Compound 65

2-[1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)azetidin-3-yl]acetamide

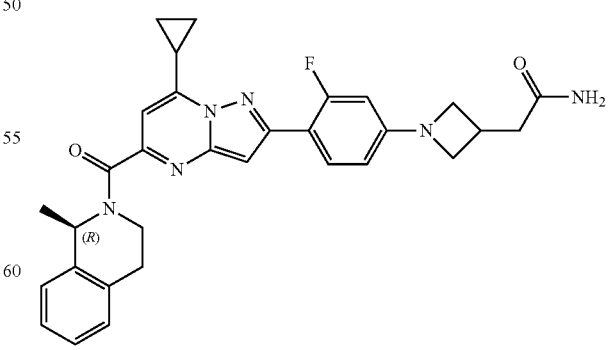

HATU (174 mg, 458 μmol) was added to a mixture of intermediate I150 (183 mg, 305 μmol, 90% purity) and DIPEA (158 μL, 916 μmol) in DMF (3 mL). The mixture was stirred at rt for 10 min and ammonia (30% in $H_2O$, 578 µL, 9.16 mmol) was added. The reaction mixture was stirred at rt for 16 h. A saturated aqueous solution of $NaHCO_3$, brine and EtOAc were added. The layers were separated and the aqueous phase was extracted with EtOAc (twice). The combined organic extracts were washed with brine (twice), dried over $MgSO_4$, filtered and concentrated to dryness. The crude mixture was purified by flash chromatography (irregular SiOH, 15-40 µm, 12 g GraceResolv™, liquid injection (DCM), mobile phase gradient: heptane/EtOAc from 70:30 to 0:100). EtOAc was added and a precipitate was formed. The suspension was concentrated under reduced pressure to dryness and the product was dried under high vacuum to give compound 65 (104 mg, 63%) as a yellow solid.

Compound 66

2-[1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)azetidin-3-yl]-N-methylacetamide

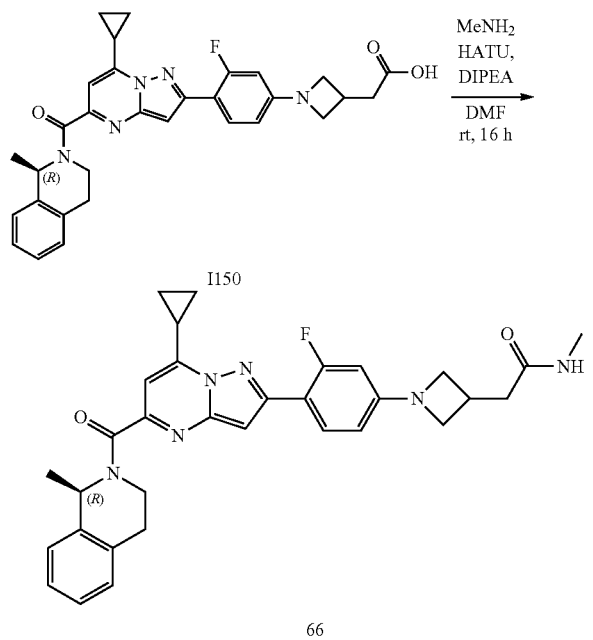

HATU (154 mg, 406 µmol) was added to a mixture of intermediate I150 (146 mg, 271 µmol) and DIPEA (140 µL, 812 µmol) in DMF (2.6 mL). The reaction mixture was stirred at rt for 10 min and methylamine (2.0 M in THF, 162 µL, 324 µmol) was added. The reaction mixture was stirred at rt for 2 h. Methylamine (2.0 M in THF, 298 µL, 595 µmol) was added again and the reaction mixture was stirred at rt for 16 h. $H_2O$, brine and EtOAc were added. The layers were separated and the organic phase was washed with brine (3 times), dried over $MgSO_4$, filtered and concentrated under reduced pressure. The crude mixture was purified by flash chromatography (irregular SiOH, 15-40 µm, 12 g GraceResolv™, liquid injection (DCM), mobile phase gradient: heptane/EtOAc from 70:30 to 0:100). EtOAc was added and the mixture was concentrated under reduced pressure to dryness. The product was dried under high vacuum at 60° C. for 16 h to give compound 66 (72 mg, 48%) as a yellow solid.

Compound 67

1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)azetidin-3-ol

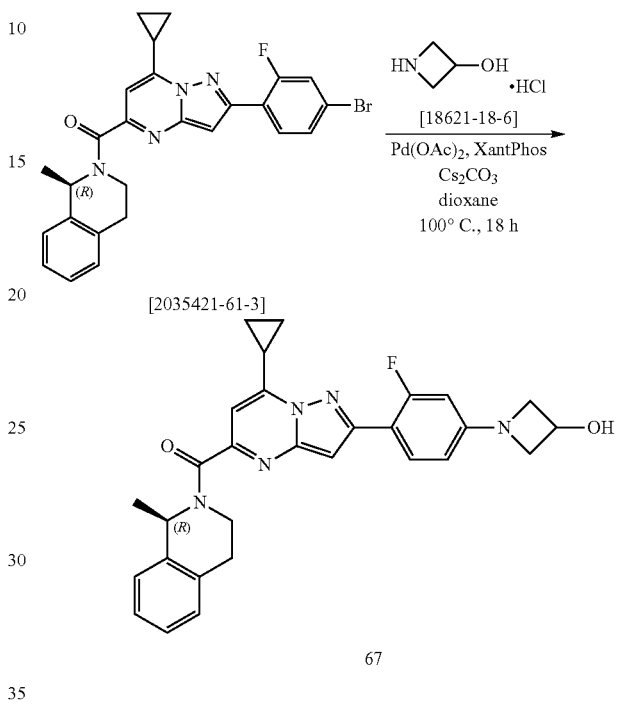

In a screw cap vial were added (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (250 mg, 495 µmol) 3-hydroxyazetidine hydrochloride [18621-18-6] (65.0 mg, 594 µmol), cesium carbonate (644 mg, 1.98 mmol) and 1,4-dioxane (5.9 mL). The mixture was purged with nitrogen. XantPhos (28.6 mg, 49.5 µmol) and palladium acetate (11.1 mg, 49.5 µmol) were added and the reaction mixture was purged again with nitrogen and stirred at 100° C. for 18 h. The reaction mixture was filtered over a pad of Celite® and washed with EtOAc and $H_2O$. The filtrate was decanted and the organic phase was washed with $H_2O$ (twice), dried over $MgSO_4$, filtered and evaporated to dryness. The crude mixture was purified by flash chromatography (irregular SiOH, 15-40 µm, 12 g GraceResolv™, dry loading (SiOH), mobile phase gradient: heptane/EtOAc from 90:10 to 60:40). A second purification by flash chromatography was performed (irregular SiOH, 15-40 µm, 12 g GraceResolv™, dry loading (SiOH), mobile phase gradient: heptane/EtOAc from 90:10 to 60:40). The solid (103 mg) was purified by reverse phase (spherical C18, 25 µm, 40 g YMC-ODS-25, dry loading (Celite®), mobile phase gradient: (0.2% aq.$NH_4HCO_3$)/MeOH from 50:50 to 0:100). The fractions containing the product were collected, concentrated to dryness and co-evaporated with MeOH (twice). The product was dried under high vacuum at 60° C. for 20 h to give compound 67 (80 mg, 33%) as a yellow solid.

269

Compound 91

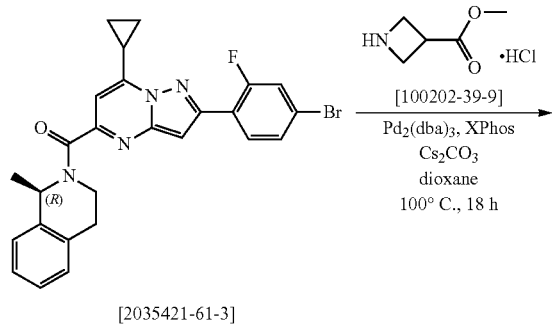

[2035421-61-3]

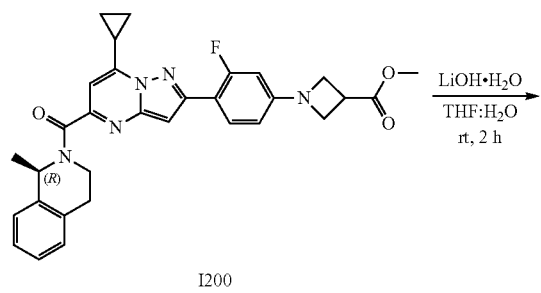

I200

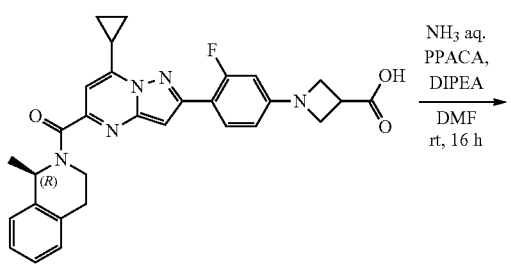

I201

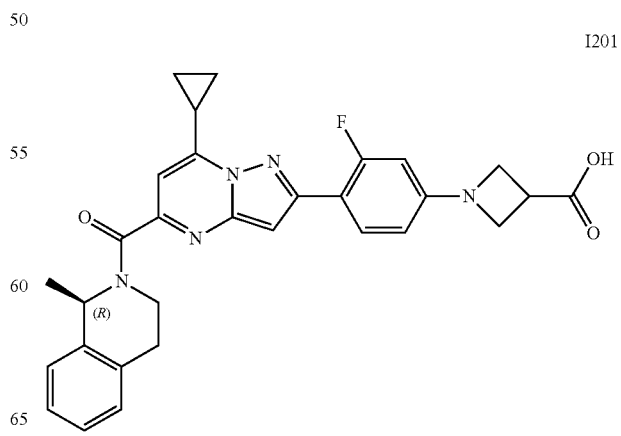

91

270

Intermediate I200

Methyl 1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)azetidine-3-carboxylate

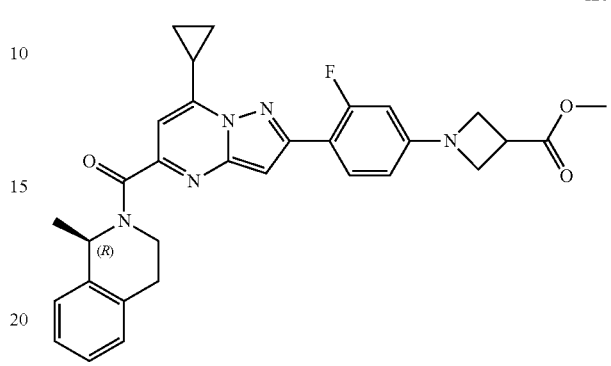

A mixture of (1R)-2-[2-(4-bromo-2-fluorophenyl)-7-cyclopropylpyrazolo[1,5-a]pyrimidine-5-carbonyl]-1-methyl-1,2,3,4-tetrahydroisoquinoline [2035421-61-3] (250 mg, 495 µmol), methyl azetidine-3-carboxylate hydrochloride [100202-39-9] (112 mg, 742 µmol) and cesium carbonate (645 mg, 1.98 mmol) in 1,4-dioxane (9 mL) was degassed with nitrogen. Tris(dibenzylideneacetone)dipalladium (18.1 mg, 19.8 µmol) and XPhos (21.2 mg, 44.5 µmol) were added and the mixture was purged with nitrogen. The reaction mixture was stirred at 100° C. for 18 h. The reaction mixture was filtered over a pad of Celite® and washed with H₂O and EtOAc. The filtrate was decanted and the organic phase was washed with brine (twice), dried over MgSO₄, filtered and concentrated in vacuo. The crude mixture was purified by flash chromatography (irregular SiOH, 15-40 µm, 12 g GraceResolv™, dry loading (SiOH), mobile phase gradient: heptane/EtOAc from 80:20 to 20:80) to afford intermediate I200 (249 mg, 93%) as a yellow foam.

Intermediate I201

1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)azetidine-3-carboxylic acid Lithium hydroxide monohydrate (38.7 mg, 923 μmol) was added to a solution of intermediate I200 (249 mg, 461 μmol) in THF (3.5 mL) and H₂O (1.5 mL). The reaction mixture was stirred at rt for 2 h. A 10% aqueous solution of KHSO₄ was added until pH 3 and the mixture was diluted with EtOAc. The layers were separated and the organic phase was washed with brine and water (twice), dried over MgSO₄, filtered and concentrated to dryness to afford intermediate I201 (245 mg, 89%) as a yellow solid.

Compound 91

1-(4-{7-Cyclopropyl-5-[(1R)-1-methyl-1,2,3,4-tetrahydroisoquinoline-2-carbonyl]pyrazolo[1,5-a]pyrimidin-2-yl}-3-fluorophenyl)azetidine-3-carboxamide

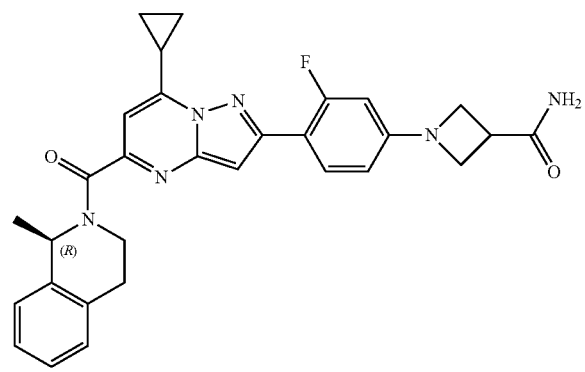

91

At 0° C. PPACA (50 wt. % in EtOAc, 617 μL, 1.04 mmol) was added dropwise to a mixture of intermediate I201 (218 mg, 415 μmol), DIPEA (357 μL, 2.07 mmol) and ammonia (28% in H₂O, 841 μL, 12.4 mmol) in DMF (4 mL). The reaction mixture was stirred at rt for 16 h. The layers were separated and the organic phase was washed with 1M aqueous solution of NaOH and brine (3 times), dried over MgSO₄, filtered and concentrated in vacuo. The crude mixture was purified by preparative LC (irregular SiOH, 15-40 μm, 12 g GraceResolv™, liquid injection (DCM), mobile phase gradient: heptane/EtOAc from 50:50 to 0:100). The residue (63 mg) was dried under high vacuum at 60° C. for 16 h to give compound 91 (58 mg, 27%) as a yellow solid.

General scheme

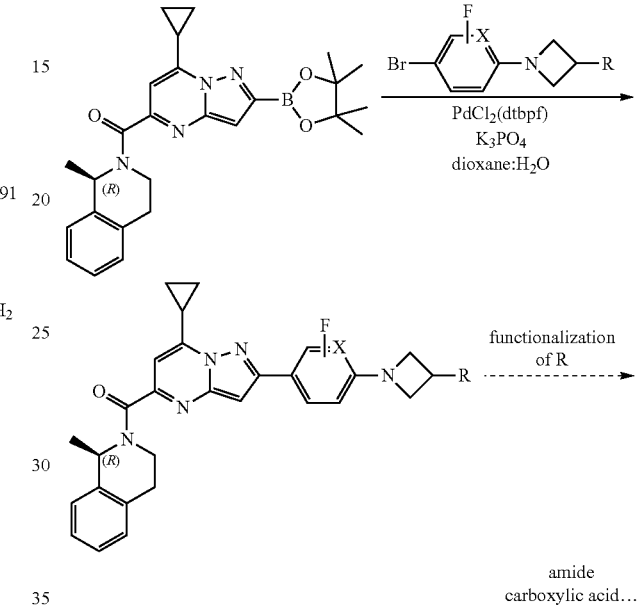

Compound 92

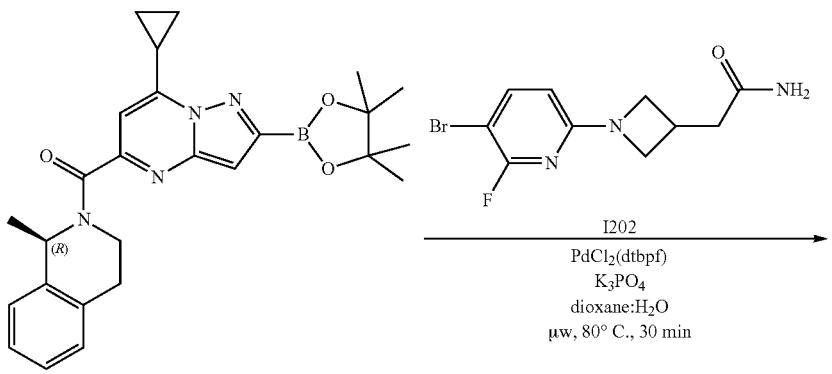

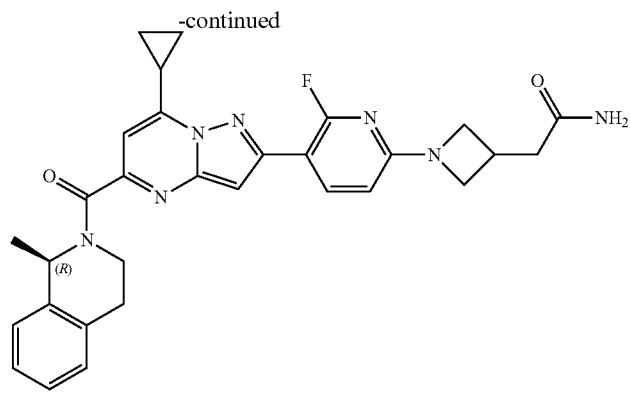

92

Synthesis of Intermediate I202

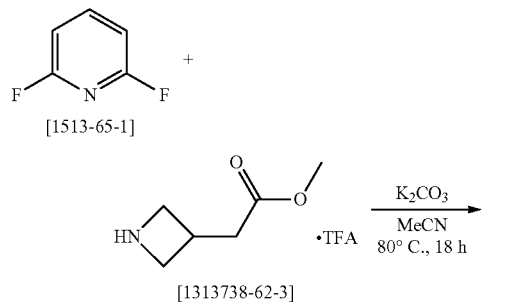

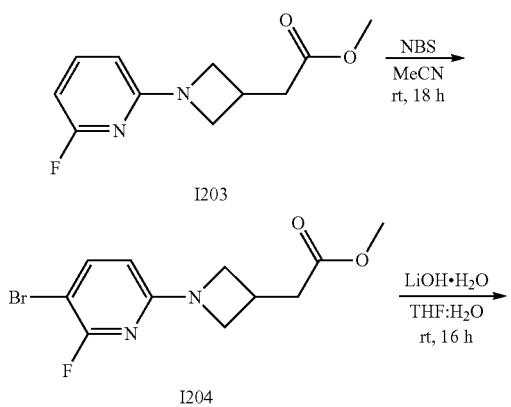

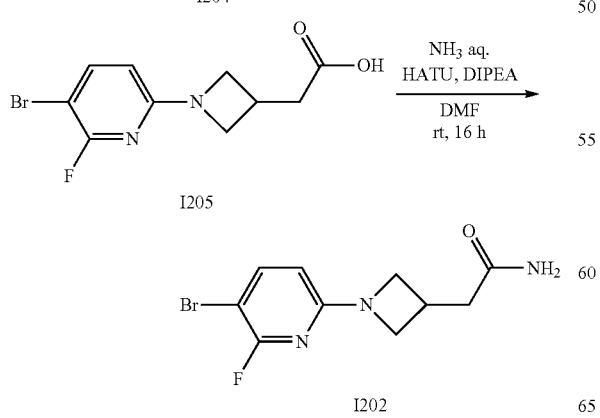

Intermediate I203

Methyl 2-[1-(6-fluoropyridin-2-yl)azetidin-3-yl]acetate

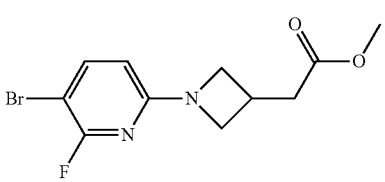

Methyl 3-azetidine acetate trifluoroacetate salt [1313738-62-3] (275 mg, 1.13 mmol) and potassium carbonate (426 mg, 3.08 mmol) were added to a solution of 2,6-difluoropyridine [1513-65-1] (93.2 µL, 1.03 mmol) in MeCN (7 mL). The reaction mixture was stirred at 80° C. for 18 h. The reaction mixture was filtered over a pad of Celite® and the filtrate was concentrated to dryness. The crude mixture was purified by preparative LC (irregular SiOH, 15-40 µm, 12 g GraceResolv™, liquid injection (DCM), mobile phase gradient: heptane/EtOAc from 100:0 to 50:50) to afford intermediate I203 (195 mg, 85%) as a colorless oil.

Intermediate I204

Methyl 2-[1-(5-bromo-6-fluoropyridin-2-yl)azetidin-3-yl]acetate

A mixture of intermediate I203 (195 mg, 0.87 mmol) and NBS (186 mg, 1.05 mmol) in MeCN (9 mL) was stirred at rt for 18 h. The reaction mixture was concentrated to dryness. The crude mixture was purified by flash chromatography (irregular SiOH, 15-40 µm, 12 g GraceResolv™, dry loading (SiOH), mobile phase gradient: heptane/EtOAc from 90:10 to 60:40) to afford intermediate I204 (147 mg, 56%) as a white solid.

Intermediate I205

2-[1-(5-Bromo-6-fluoropyridin-2-yl)azetidin-3-yl] acetic acid

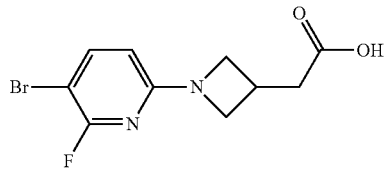

Lithium hydroxide monohydrate (61 mg, 1.45 mmol) was added to a solution of intermediate I204 (147 mg, 485 µmol) in THF (4 mL) and H₂O (1.3 mL). The reaction mixture was stirred at rt for 16 h. A 10% aqueous solution of KHSO₄ was added until pH 6 and the aqueous phase was extracted with EtOAc. The combined organic extracts were washed with H₂O, dried over MgSO₄, filtered and concentrated in vacuo to afford intermediate I205 (135 mg, 96%) as a white solid.

Intermediate I202

2-[1-(5-Bromo-6-fluoropyridin-2-yl)azetidin-3-yl] acetamide

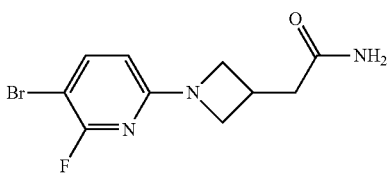

A mixture of intermediate I205 (135 mg, 467 µmol), HATU (266 mg, 700 µmol) and DIPEA (241 µL, 1.40 mmol) in DMF (2.3 mL) was stirred at rt for 30 min. Ammonia (30% in H₂O, 884 µL, 14.0 mmol) was added and the reaction mixture was stirred at rt for 16 h. The reaction mixture was diluted with EtOAc and H₂O. The layers were separated and the organic phase was washed with water and brine (3 times), dried over MgSO₄, filtered and concentrated. The crude mixture was purified by flash chromatography (irregular SiOH, 15-40 µm, 12 g GraceResolv™, dry loading (SiOH), mobile phase gradient: heptane/EtOAc from 50:50 to 0:100) to afford intermediate I202 (94 mg, 70%) as a white solid.

Synthesis of Compound 92

2-[1-(5-{7-Cyclopropyl-5-[(1R)-1-methyl-1,2,3,4-tetrahydroisoquinoline-2-carbonyl]-pyrazolo[1,5-a]pyrimidin-2-yl}-6-fluoropyridin-2-yl)azetidin-3-yl] acetamide

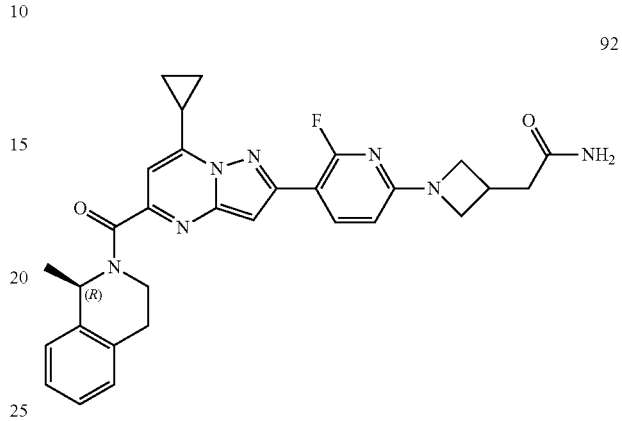

A sealed tube was charged with (1R)-2-[7-cyclopropyl-2-(tetramethyl-1,3,2-dioxaborolan-2-yl)pyrazolo[1,5-a]pyrimidine-5-carbonyl]-1-methyl-1,2,3,4-tetrahydroisoquinoline [2035421-36-2] (150 mg, 203 µmol, 62% purity), intermediate I202 (64 mg, 223 µmol), potassium phosphate tribasic (129 mg, 609 µmol), 1,4-dioxane (2.5 mL) and H₂O (0.6 mL) and purged with nitrogen. [1,1'-Bis(di-tert-butylphosphino)ferrocene]dichloropalladium (13.2 mg, 20.3 µmol) was added and the mixture was purged again with nitrogen. The reaction mixture was heated at 80° C. using a single mode microwave (Biotage® Initiator EXP 60) with a power output ranging from 0 to 400 W for 30 min. The reaction mixture was diluted with EtOAc and H₂O. The layers were separated and the organic phase was washed with brine (twice), dried over MgSO₄, filtered and concentrated to dryness. The crude mixture was purified by flash chromatography (irregular SiOH, 15-40 µm, 25 g GraceResolv™, liquid injection (DCM), mobile phase gradient: heptane/EtOAc from 50:50 to 0:100). The residue was taken up in EtOAc, sonicated and concentrated to dryness. The solid was dried under high vacuum at 60° C. for 16 h to give compound 92 (47 mg, 43%) as a yellow solid.

General scheme

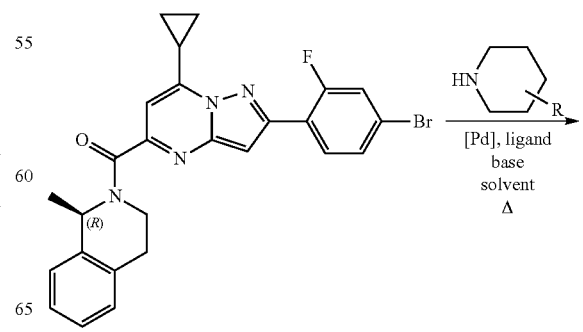

277

-continued

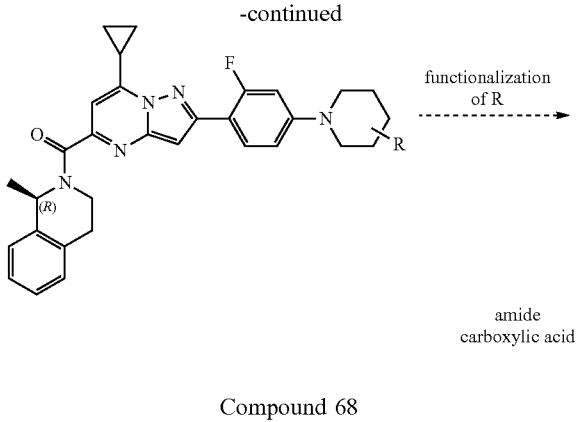

Compound 68

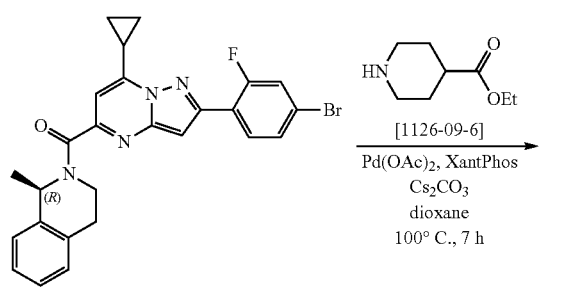

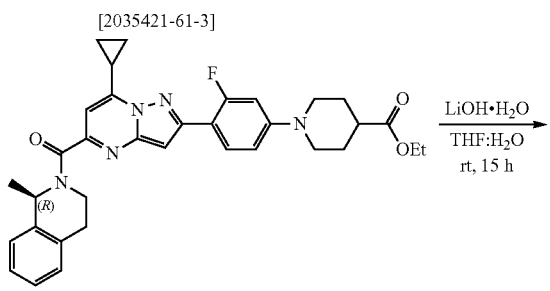

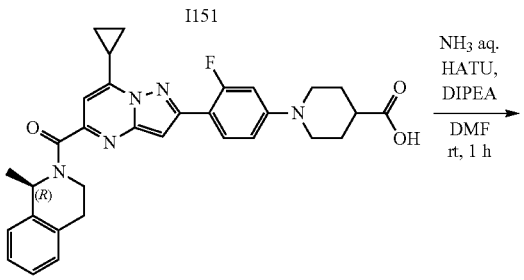

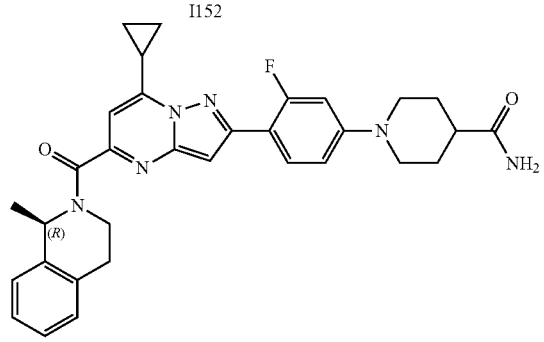

68

278

Intermediate I151

Ethyl 1-(4-{7-cyclopropyl-5-[(1R)-1-methyl-1,2,3,4-tetrahydroisoquinoline-2-carbonyl]-pyrazolo[1,5-a]pyrimidin-2-yl}-3-fluorophenyl)piperidine-4-carboxylate

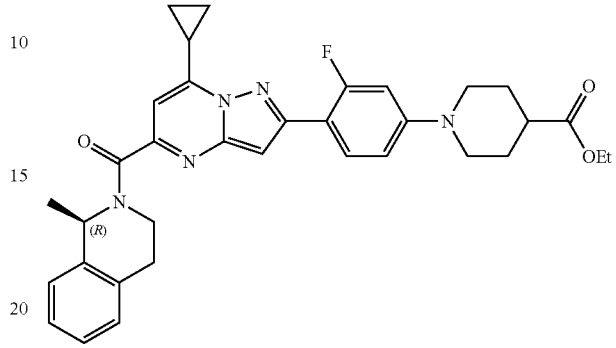

A mixture of (1R)-2-[2-(4-bromo-2-fluorophenyl)-7-cyclopropylpyrazolo[1,5-a]-pyrimidine-5-carbonyl]-1-methyl-1,2,3,4-tetrahydroisoquinoline [2035421-61-3] (200 mg, 0.40 mmol), ethyl piperidine-4-carboxylate [1126-09-6] (87.1 mg, 0.55 mmol), cesium carbonate (516 mg, 1.58 mmol) and XantPhos (27.5 mg, 47.5 μmol) was purged with nitrogen. 1,4-Dioxane (5 mL) was added and the mixture was purged again with nitrogen. Palladium acetate (10.6 mg, 47.5 μmol) was added. The reaction mixture was purged with nitrogen and stirred at 100° C. for 7 h. The reaction mixture was diluted with EtOAc and H₂O. The layers were separated and the aqueous phase was extracted with EtOAc (twice). The combined organic extracts were washed with brine, dried over MgSO₄, filtered and the solvent was removed under reduced pressure. The crude mixture was purified by flash chromatography over silica gel (Interchim® 40 g, 30 μM, liquid injection (DCM), mobile phase gradient: heptane/EtOAc from 90:10 to 60:40) to afford intermediate I151 (180 mg, 78%) as a yellow solid.

Intermediate I152

1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)piperidine-4-carboxylic acid

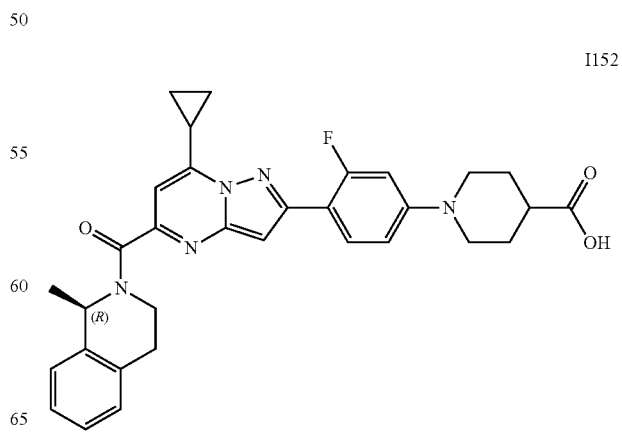

A mixture of intermediate I151 (171 mg, 0.29 mmol) and lithium hydroxide monohydrate (86.4 mg, 2.06 mmol) in THF (5 mL) and H₂O (1.5 mL) was stirred at rt for 15 h. An aqueous solution of citric acid (7 equiv. in 10 ml) was added and the aqueous phase was extracted with EtOAc. The combined organic extracts were washed with brine, dried over MgSO₄, filtered and evaporated to dryness to afford intermediate I152 (160 mg, 98%) as a beige solid.

Compound 68

1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)piperidine-4-carboxamide

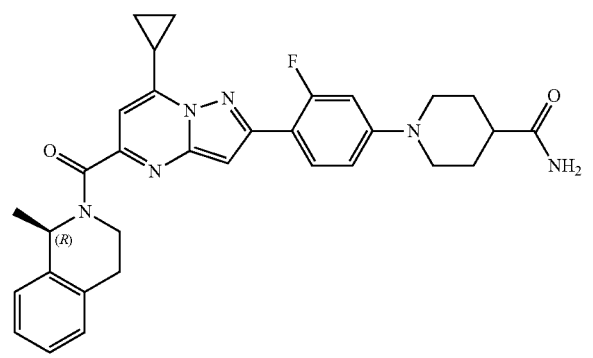

To a solution of intermediate I152 (0.16 g, 0.29 mmol) in DMF (4 mL) were added DIPEA (0.15 mL, 0.87 mmol) and HATU (0.17 g, 0.43 mmol). The mixture was stirred at rt for 15 min. Ammonia (30% in H₂O, 33 μL, 1.73 mmol) was added and the reaction mixture was stirred at rt for 1 h. The reaction mixture was diluted with H₂O and EtOAc. The layers were separated and the organic phase was washed with H₂O (3 times) and brine, dried over MgSO₄, filtered and evaporated to dryness. The crude mixture was purified by flash chromatography over silica gel (Interchim® 12 g, 30 μM, liquid injection (DCM), mobile phase gradient: DCM/MeOH, from 100:0 to 97:3) to give compound 68 (75 mg, 47%) as a yellow solid.

Compound 69

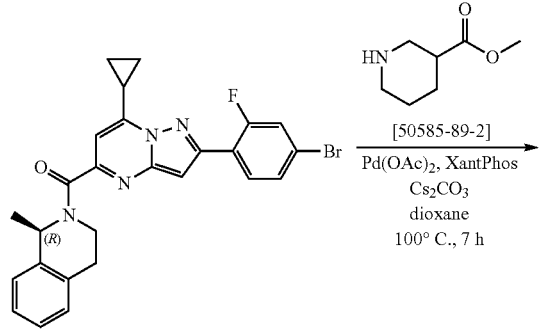

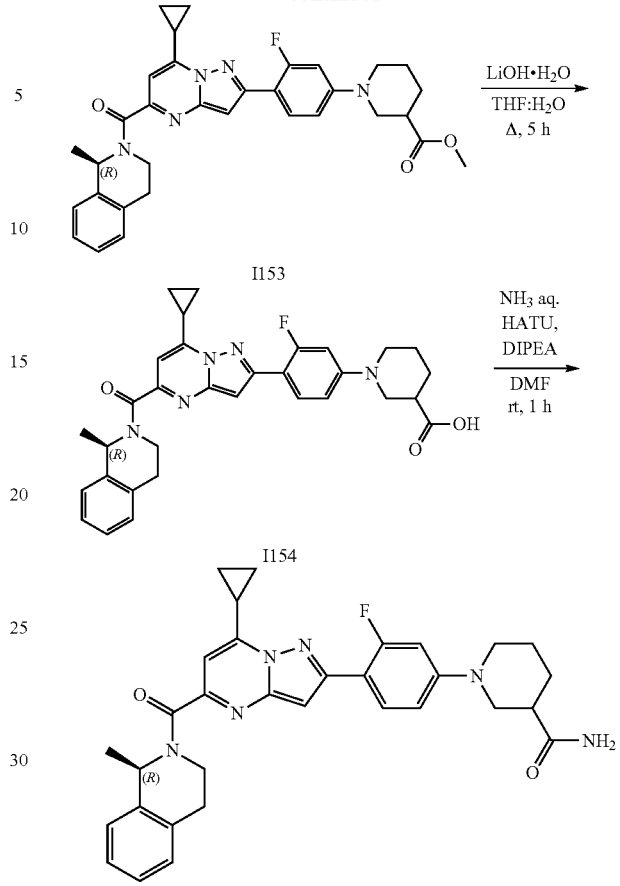

Intermediate I153

Methyl 1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)piperidine-3-carboxylate

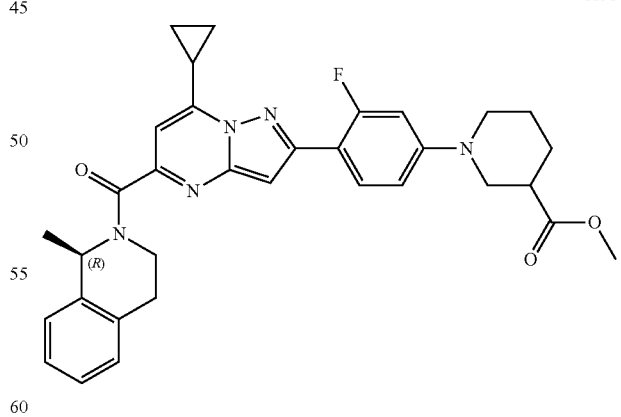

Intermediate I153 was synthesized from (1R)-2-[2-(4-bromo-2-fluorophenyl)-7-cyclopropylpyrazolo[1,5-a]pyrimidine-5-carbonyl]-1-methyl-1,2,3,4-tetrahydro-iso quino line [2035421-61-3] and methyl piperidine-3-carboxylate [50585-89-2] according to the procedure reported for the synthesis of intermediate I151. Intermediate I153 (0.18 g, 65%) was obtained as a yellow solid.

Intermediate I154
1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)piperidine-3-carboxylic acid

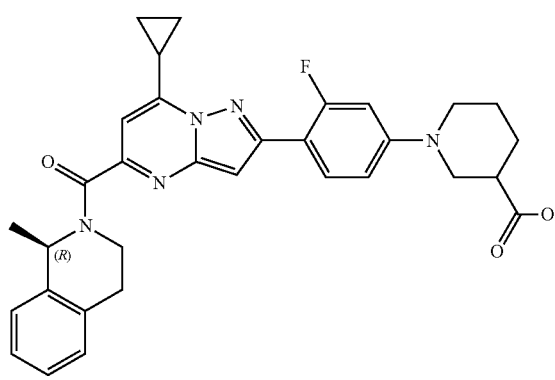

I154

Intermediate I154 was synthesized from intermediate I153 according to the procedure reported for the synthesis of intermediate I152. The reaction mixture was stirred under reflux for 5 h. Intermediate I154 (0.17 g, 98%) was obtained as a yellow solid.

Compound 69
1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)piperidine-3-carboxamide

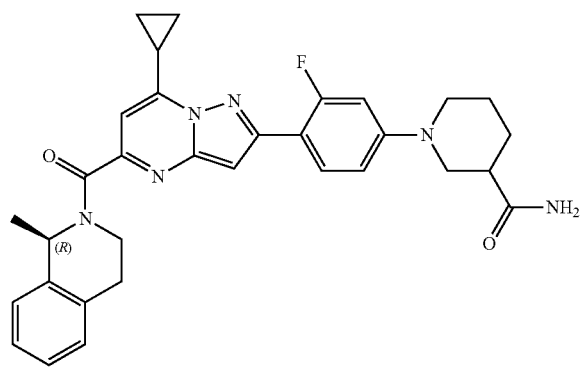

69

Compound 69 was synthesized from intermediate I154 according to the procedure reported for the synthesis of compound 68. Compound 69 (80 mg, 49%) was obtained as a yellow solid.

Compound 70

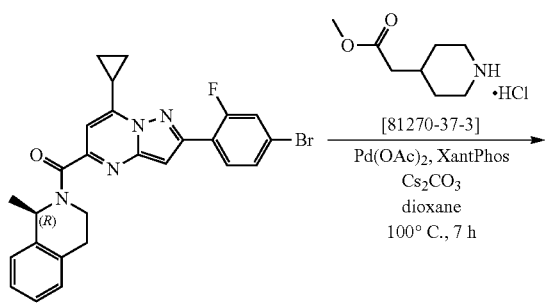

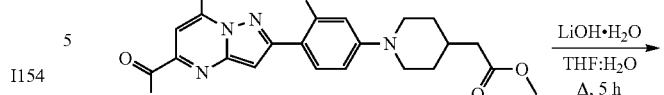

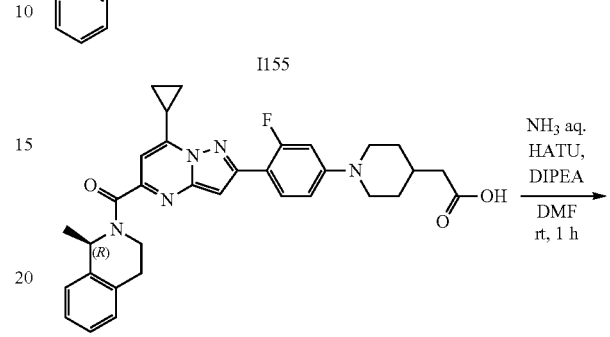

I155

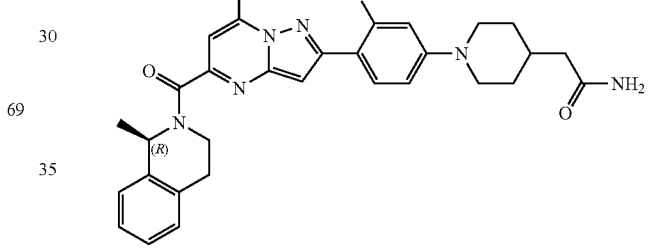

I156

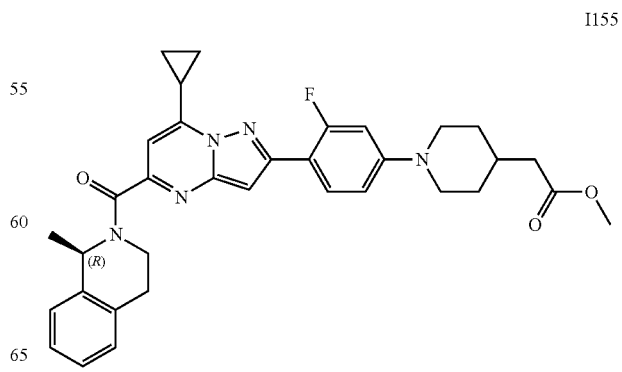

70

Intermediate I155
Methyl 2-[1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)piperidin-4-yl]acetate

I155

Intermediate I155 was synthesized from (1R)-2-[2-(4-bromo-2-fluorophenyl)-7-cyclopropylpyrazolo[1,5-a]pyrimidine-5-carbonyl]-1-methyl-1,2,3,4-tetrahydro-isoquinoline [2035421-61-3] and methyl 2-(piperidine-4-yl)acetate hydrochloride [81270-37-3] according to the procedure reported for the synthesis of intermediate I151. Intermediate I155 (023 g, 65%) was obtained as a yellow solid.

Intermediate I156

2-[1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)piperidin-4-yl] acetic acid

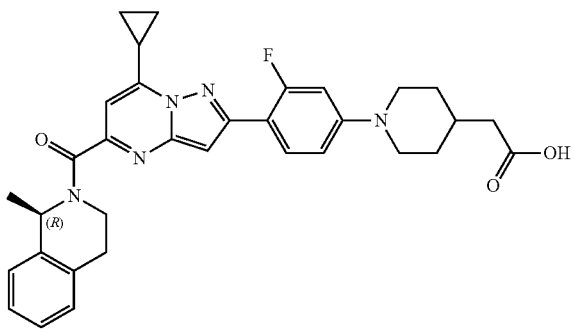

I156

Intermediate I156 was synthesized from intermediate I155 according to the procedure reported for the synthesis of intermediate I152. The reaction mixture was stirred under reflux for 5 h. Intermediate I156 (0.21 g, quant.) was obtained as a yellow solid.

Compound 70

2-[1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)piperidin-4-yl] acetamide

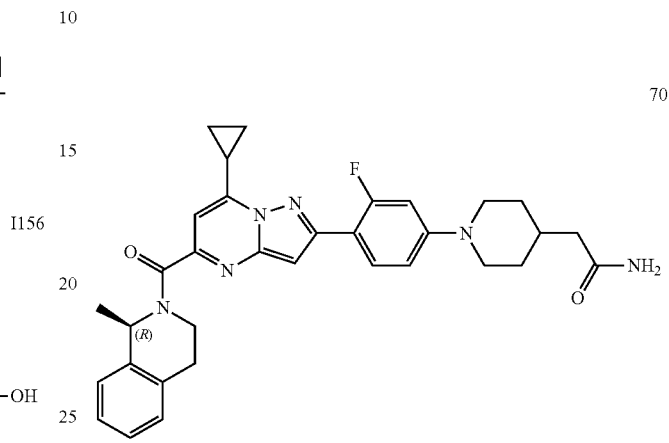

70

Compound 70 was synthesized from intermediate I156 according to the procedure reported for the synthesis of compound 68. Compound 70 (85 mg, 40%) was obtained as a beige solid.

Compound 71

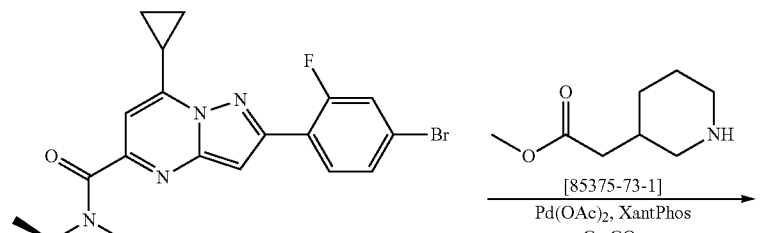

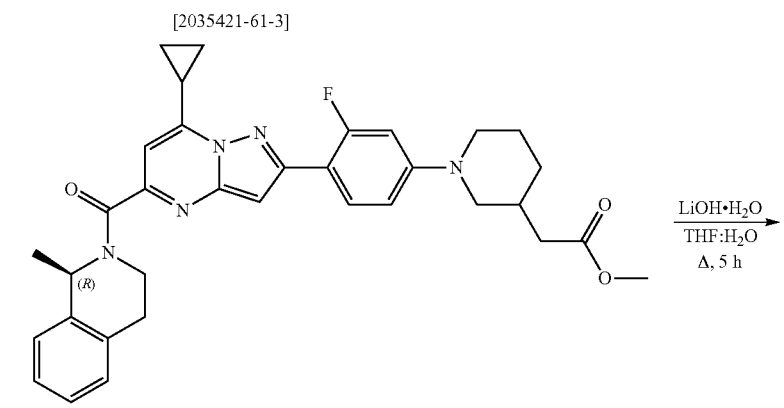

I157

-continued

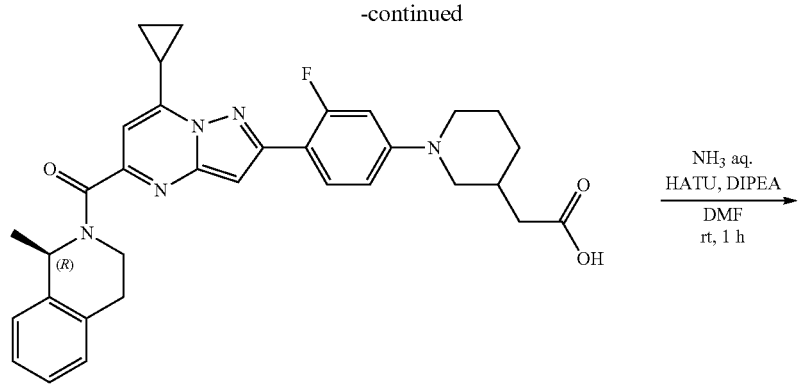

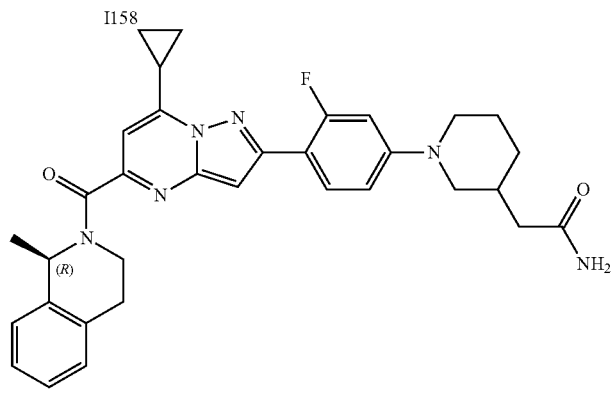

Intermediate I157

Methyl 2-[1-(4-{7-cyclopropyl-5-[(1R)-1-methyl-1,2,3,4-tetrahydroisoquinoline-2-carbonyl]pyrazolo[1,5-a]pyrimidin-2-yl}-3-fluorophenyl)piperidin-3-yl]acetate

Intermediate I158

2-[1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)piperidin-3-yl]acetic acid

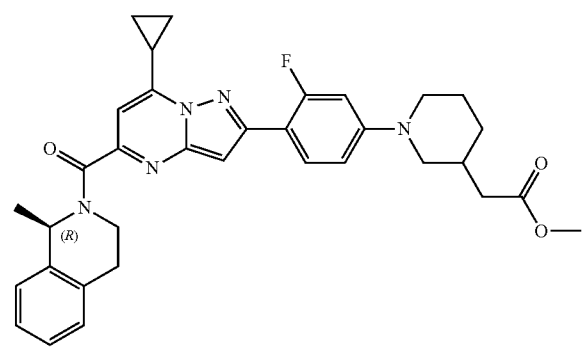

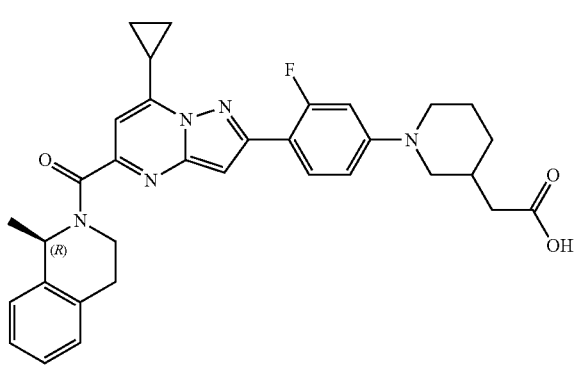

Intermediate I157 was synthesized from (1R)-2-[2-(4-bromo-2-fluorophenyl)-7-cyclopropylpyrazolo[1,5-a]pyrimidine-5-carbonyl]-1-methyl-1,2,3,4-tetrahydroisoquinoline [2035421-61-3] and methyl 3-piperidinyl acetate [85375-73-1] according to the procedure reported for the synthesis of intermediate I151. Intermediate I157 (0.23 g, 67%) was obtained as a yellow solid.

Intermediate I158 was synthesized from intermediate I157 according to the procedure reported for the synthesis of intermediate I152. The reaction mixture was stirred under reflux for 5 h. Intermediate I158 (214 mg, quant.) was obtained as a yellow solid.

Compound 71

2-[1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)piperidin-3-yl]acetamide

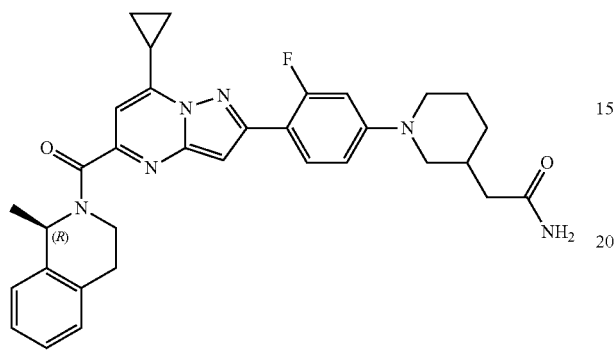

Compound 71 was synthesized from intermediate I158 according to the procedure reported for the synthesis of compound 68. Compound 71 (90 mg, 42%) was obtained as a yellow solid.

Compound 72

1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)-N-methylpiperidine-4-carboxamide

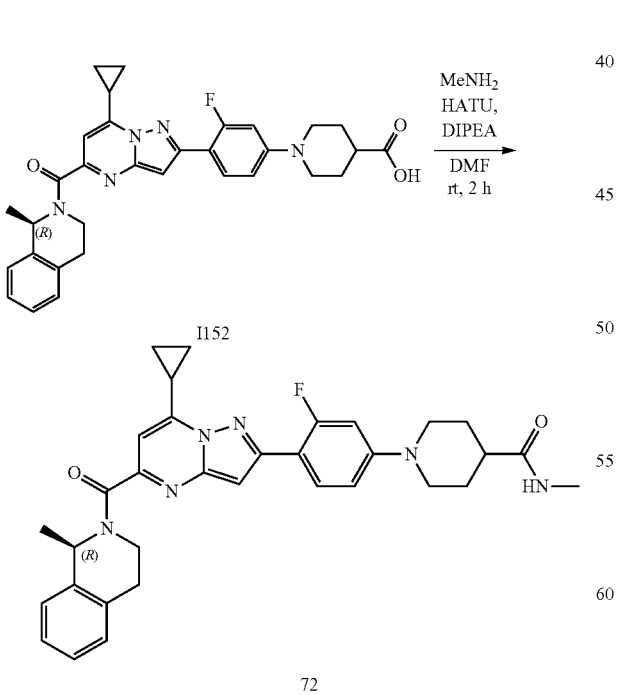

To a solution of intermediate I152 (207 mg, 0.37 mmol) in DMF (2.5 mL) was added DIPEA (0.19 mL, 1.12 mmol) and HATU (0.21 g, 0.56 mmol). The mixture was stirred at rt for 15 min and methylamine (2.0 M in THF, 0.11 mL, 2.22 mmol) was added dropwise. The reaction mixture was stirred at rt for 2 h. The reaction mixture was diluted with H₂O and EtOAc. The layers were separated and the organic phase was washed with H₂O (3 times), brine, dried over MgSO₄, filtered and evaporated to dryness to give compound 72 (110 mg, 52%) as a beige solid.

Compound 73

1-(4-{7-Cyclopropyl-5-[(1R)-1-methyl-1,2,3,4-tetrahydroisoquinoline-2-carbonyl]-pyrazolo[1,5-a]pyrimidin-2-yl}-3-fluorophenyl)-N-methylpiperidine-3-carboxamide

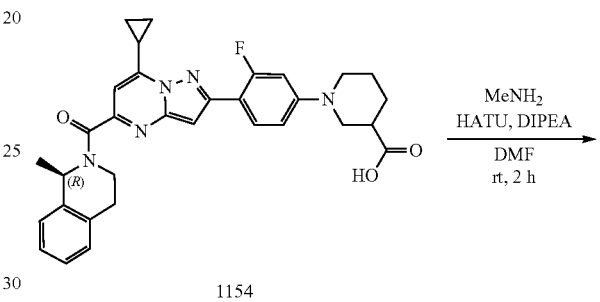

Compound 73 was synthesized from intermediate I154 according to the procedure reported for the synthesis of compound 72. The product was purified by flash chromatography over silica gel (30 μm, 12 g Interchim®, liquid injection (DCM), mobile phase gradient: DCM/MeOH from 100:0 to 98:2) to give compound 73 (160 mg, 64%) as a yellow solid.

Compound 74

1-(4-{7-Cyclopropyl-5-[(1R)-1-methyl-1,2,3,4-tetra-hydroisoquinoline-2-carbonyl]-pyrazolo[1,5-a]pyrimidin-2-yl}-3-fluorophenyl)piperidin-4-ol

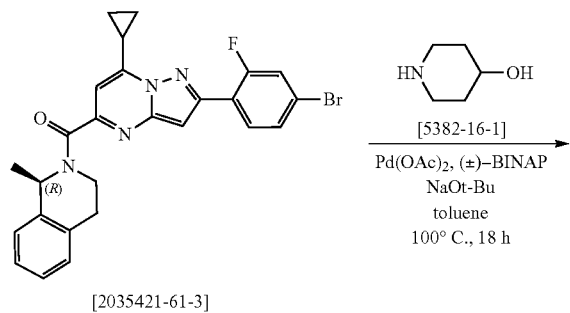

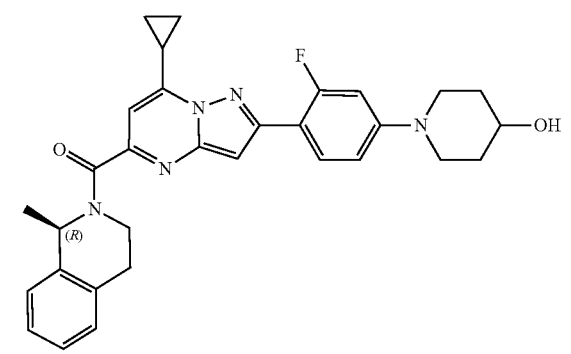

74

In a screw cap vial were added (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (200 mg, 396 µmol), 4-hydroxypiperidine [5382-16-1] (40.0 mg, 396 µmol), sodium tert-butoxide (76.1 mg, 0.79 mmol) and toluene (3.3 mL). The mixture was purged with nitrogen. Palladium acetate (4.44 mg, 19.8 µmol) and (±)-BINAP (12.3 mg, 19.8 µmol) were added and the reaction mixture was purged again with nitrogen. The reaction mixture was stirred at 100° C. for 18 h. The reaction mixture was diluted with EtOAc and H₂O and filtered over a pad of Celite®. The filtrate was decanted and the organic phase was washed with H₂O (twice), dried over MgSO₄, filtered and concentrated to dryness. The crude mixture was purified by flash chromatography (irregular SiOH, 15-40 µm, 12 g GraceResolv™, dry loading (SiOH), mobile phase gradient: heptane/EtOAc from 50:50 to 0:100). The solid was dried under high vacuum at 60° C. for 16 h to give compound 74 (99 mg, 46%) as a yellow solid.

Compound 75

1-(4-{7-Cyclopropyl-5-[(1R)-1-methyl-1,2,3,4-tetra-hydroisoquinoline-2-carbonyl]-pyrazolo[1,5-a]pyrimidin-2-yl}-3-fluorophenyl)piperidin-3-ol

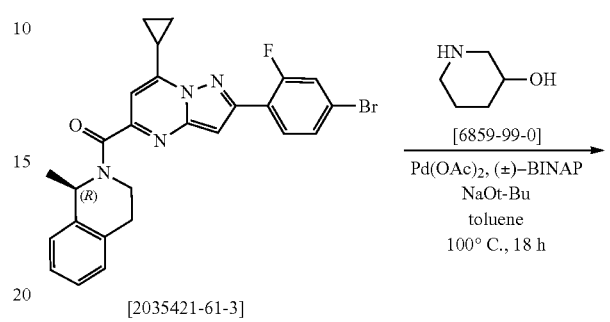

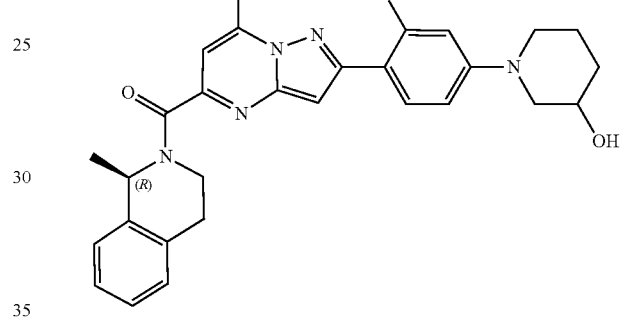

75

Compound 75 was synthesized from (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] and 3-hydroxypiperidine [6859-99-0] according to the procedure reported for the synthesis of compound 74. Compound 75 (140 mg, 54%) was obtained as a yellow solid.

Synthesis of Compound 93

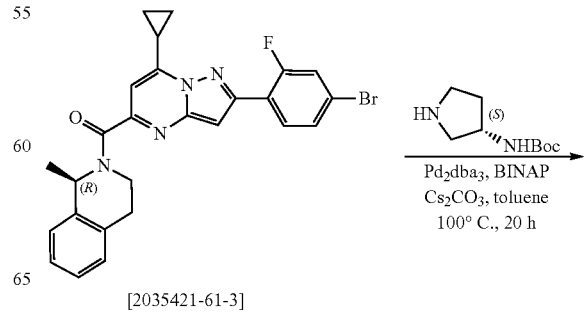

-continued

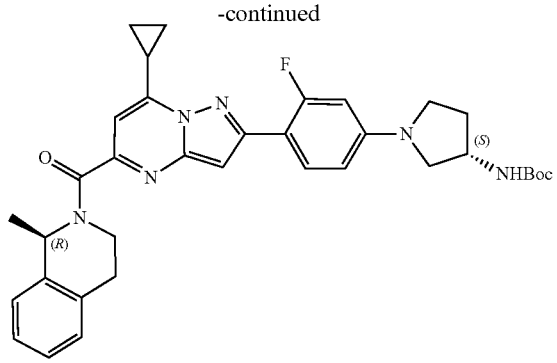

J1

↓ TFA, DCM
rt, 1 h

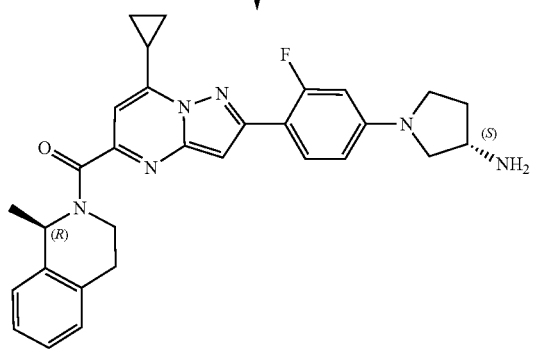

93

Intermediate J1 tert-butyl ((S)-1-(4-(7-cyclopropyl-5-((R)-1-methyl-1,2,3,4-tetrahydroisoquinoline-2-carbonyl)pyrazolo[1,5-a]pyrimidin-2-yl)-3-fluorophenyl)pyrrolidin-3-yl)carbamate

J1

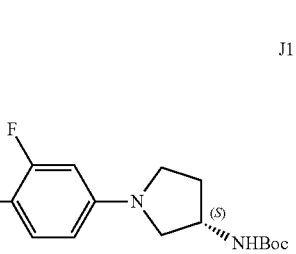

In a Schlenk tube, a mixture of (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (300 mg; 0.572 mmol), (S)-3-(BOC-amino)pyrrolidine (214 mg; 1.15 mmol) and $Cs_2CO_3$ (657 mg; 2.015 mmol) in toluene (12 mL) was degassed with $N_2$. BINAP (36 mg; 0.058 mmol) and $Pd_2dba_3$ (53 mg; 0.058 mmol) were added and the reaction mixture was purged with $N_2$. The mixture was heated at 100° C. for 20 h. Brine and EtOAc were added to the reaction mixture, the aqueous layer was extracted with EtOAc (twice). The combined organic layers were dried over $MgSO_4$ and evaporated in vacuo. The residue was purified by preparative LC (irregular SiOH 15-40 μm, 40 g GraceResolv®, mobile phase gradient: from DCM/EtOAc: 100/0 to 70/30) to give Intermediate J1 as a yellow solid (0.315 g, 90%).

Compound 93

(2-(4-((S)-3-aminopyrrolidin-1-yl)-2-fluorophenyl)-7-cyclopropylpyrazolo[1,5-a]pyrimidin-5-yl)((R)-1-methyl-3,4-dihydroisoquinolin-2(1H)-yl)methanone

93

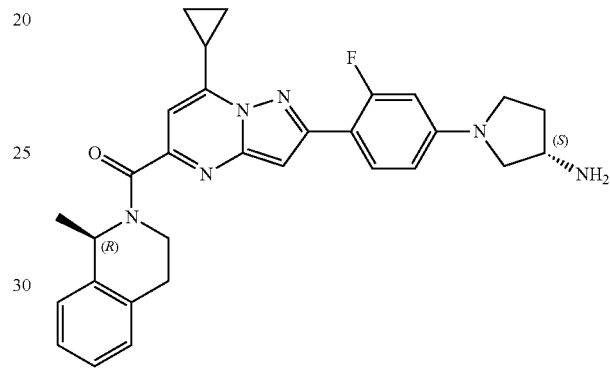

TFA (1.2 mL; 15 mmol) was added to a solution of intermediate J1 (315 mg; 0.516 mmol) in DCM (6.2 mL). The reaction mixture was stirred at rt for 1 h. DCM and an aqueous solution of $NaHCO_3$ (sat) were added. The layers were separated, and the organic layer was dried over $MgSO_4$, filtered and the solvent was removed in vacuo to give 226 mg of a yellow foam which was triturated in MTBE then filtered over frit and dried under high vacuum at 50° C. overnight to give compound 93 as a yellow solid (120 mg, 46%).

Compound 94

(7-cyclopropyl-2-(2-fluoro-4-((S)-3-((2,2,2-trifluoro-ethyl)amino)pyrrolidin-1-yl)phenyl)pyrazolo[1,5-a]pyrimidin-5-yl)((R)-1-methyl-3,4-dihydroisoquinolin-2(1H)-yl)methanone

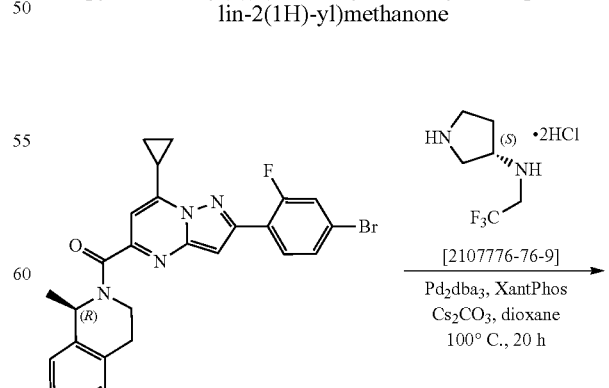

[2035421-61-3]

293

-continued

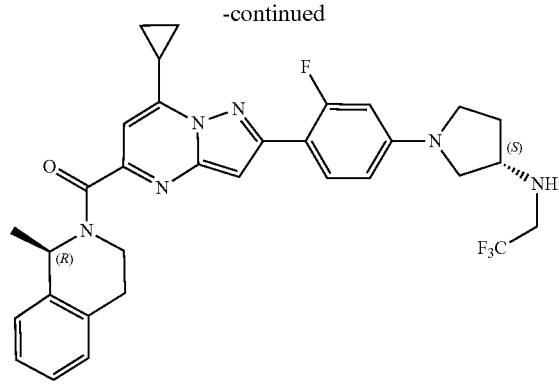

94

In a Schenlk tube, a mixture of (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (127 mg; 0.243 mmol), (3S)—N-(2,2,2-trifluoroethyl)pyrrolidin-3-amine hydrochloride [2107776-76-9] (100 mg; 0.365 mmol)) and $Cs_2CO_3$ (396 mg; 1.22 mmol) in dioxane (5 mL) was degassed with $N_2$. $Pd(OAc)_2$ (5 mg; 24 μmol) and XantPhos (14 mg; 0.024 mmol) were added and the reaction mixture was purged with $N_2$. The mixture was heated at 100° C. for 20 h. Brine and EtOAc were added to the reaction mixture, the aqueous layer was extracted with EtOAc (twice). The combined organic layers were dried over $MgSO_4$ and evaporated in vacuo. The residue was purified by preparative LC (irregular SiOH, 15-40 μm, 12 g GraceResolv®, mobile phase gradient: from heptane/EtOAc 90/10 to 60/40) the pure fraction was collected and evaporated to dryness. The residue was purified by Reverse phase (Stationary phase: YMC-actus Triart® C18 10 μm 30*150 mm, Mobile phase: Gradient from 35% aq. $NH_4HCO_3$ 0.2%, 65% MeCN to 0% aq. $NH_4HCO_3$ 0.2%, 100% MeCN) to give a yellow oil which was taken up in MTBE (~2 mL). Heptane was added until solid appeared and the mixture was evaporated in vacuo then dried under high vacuum to give compound 94 as a yellow solid (56 mg, 39%).

Compound 95

(7-cyclopropyl-2-(4-((3R,4S)-3,4-dihydroxypyrrolidin-1-yl)-2-fluorophenyl)pyrazolo[1,5-a]pyrimidin-5-yl)((R)-1-methyl-3,4-dihydroisoquinolin-2(1H)-yl) methanone

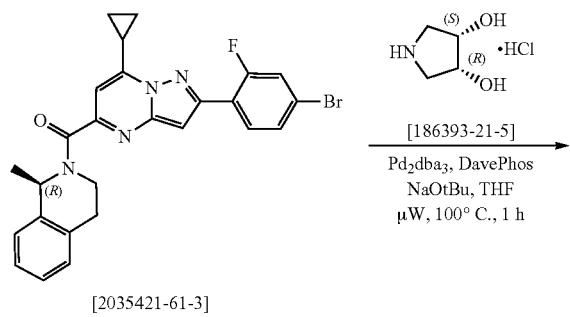

294

-continued

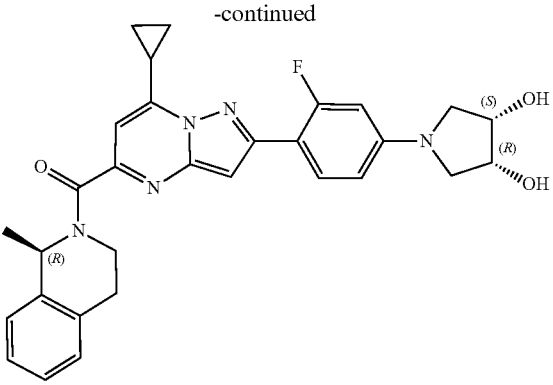

95

In a sealed tube, a mixture of (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (250 mg, 0.475 mmol), $NaO^tBu$ (160 mg, 1.66 mmol) and cis-Pyrrolidine-3,4-diol hydrochloride [186393-21-5] (99 mg, 0.712 mmol) in THF (5.6 mL) was degassed with $N_2$ for 10 min. DavePhos (19 mg, 0.048 mmol) and $Pd_2dba_3$ (43 mg, 0.048 mmol) were added and the reaction mixture was purged with $N_2$. The mixture was heated at 100° C. using a single mode microwave (Biotage Initiator® EXP 60) with a power output ranging from 0 to 400 W for 1 h. Water and EtOAc were added. The aqueous layer was extracted with EtOAc (twice), the combined organic layers were dried over $MgSO_4$, filtered and concentrated in vacuo. The residue was purified by preparative LC (irregular SiOH 15-40 μm, 24 g GraceResolv®, mobile phase gradient: from DCM/Isopropanol 99/1 to 88/12) The fractions containing product were collected and evaporated to dryness. The residue was purified by preparative LC (spherical C18 25 μm, 40 g YMC-ODS-25, dry loading (Celite®), mobile phase gradient 0.2% aq. $NH_4HCO_3$/ MeCN from 65:35 to 25:75). The fractions containing product were evaporated, then taken-up in EtOAc and evaporated again three times to give 90 mg of a solid which was taken-up with MTBE and stirred at 50° C. for 24 h. The suspension was cooled down to rt, filtered over glass frit and washed with MTBE (2×2 mL). The solid was dried under vacuum to give compound 95 as a yellow solid (60 mg, 24%).

Compound 96

(7-cyclopropyl-2-(2-fluoro-4-((trans)-3-hydroxy-4-methoxypyrrolidin-1-yl)phenyl)pyrazolo[1,5-a]pyrimidin-5-yl)((R)-1-methyl-3,4-dihydroisoquinolin-2(1H)-yl)methanone

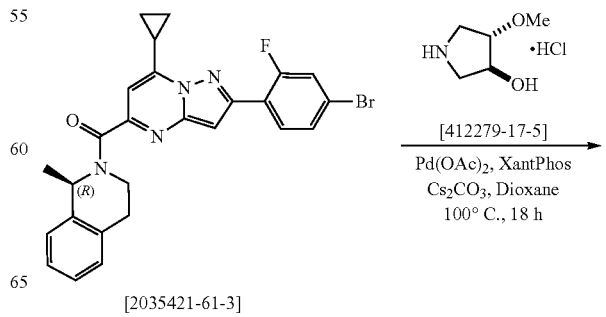

295
-continued

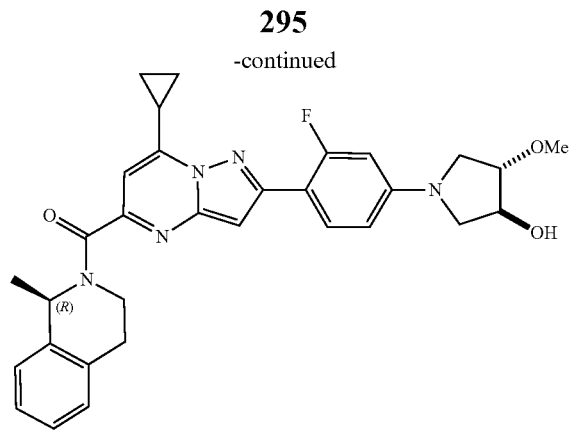

96

A mixture of (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (200 mg, 0.38 mmol), trans-4-methoxy-3-pyrrolidinol hydrochloride (70 mg, 0.46 mmol) and $Cs_2CO_3$ (371 mg, 1.14 mmol) was charged in a sealed tube and purged with $N_2$. Dioxane (7.9 mL, 93 mmol) was added and the mixture was degassed with $N_2$, then Pd(OAc)$_2$ (8.5 mg, 0.038 mmol) and XantPhos (22 mg, 0.038 mmol) were added. The reaction mixture was stirred and heated at 100° C. for 18 h. Water and EtOAc were added to the reaction mixture. The layers were separated. The aqueous layer was extracted twice with EtOAc. The combined organic layers were washed with brine, dried over $MgSO_4$ and evaporated in vacuo. The residue was purified by preparative LC (irregular SiOH 15-40 μm, 24 g GraceResolv®, mobile phase gradient: from heptane 75%, EtOAc 25% to Heptane 0%, EtOAc 100%) to give 250 mg of a white gum. The product was purified by preparative LC (spherical C18 25 μm, 40 g YMC-ODS-25, mobile phase gradient 0.2% aq. $NH_4HCO_3$/MeCN from 60:40 to 10:90). The fractions containing product were evaporated under vacuum and the residue was taken-up in $Et_2O$ and evaporated under vacuum three times and the sample was dried under vacuum to give compound 96 as a yellow solid (110 mg, 53%).

Synthesis of Compound 97

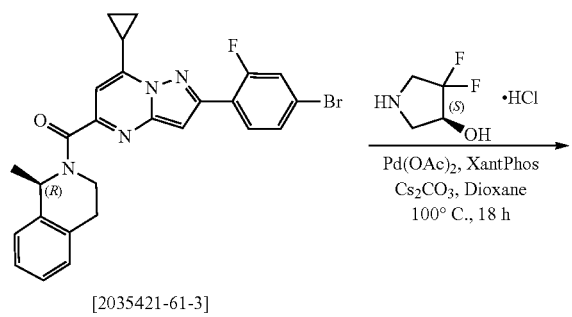

[2035421-61-3]

296
-continued

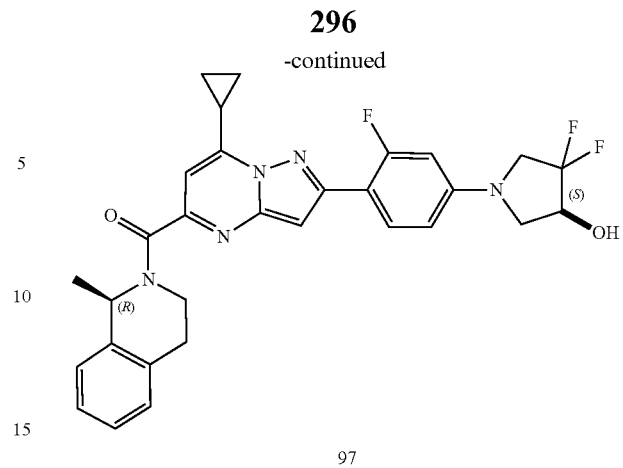

97

4,4-difluoro-3S-hydroxypyrrolidine hydrochloride 4,4-difluoro-3S-hydroxypyrrolidine hydrochloride was synthetized with the same procedure as the 3R enantiomer described in *J. Org. Chem.* 2016, 81, 4359-4363.

Compound 97

(7-cyclopropyl-2-(4-((S)-3,3-difluoro-4-hydroxypyrrolidin-1-yl)-2-fluorophenyl)pyrazolo[1,5-a]pyrimidin-5-yl)((R)-1-methyl-3,4-dihydroisoquinolin-2(1H)-yl)methanone

97

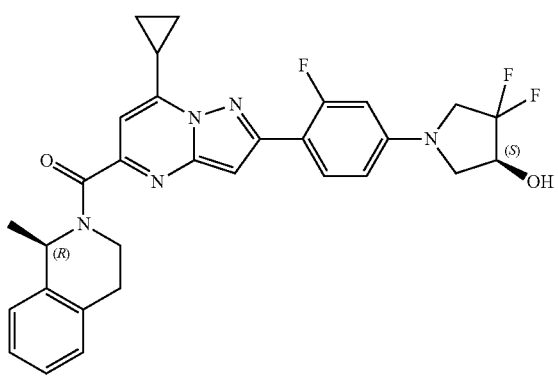

A mixture of (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (149 mg, 0.295 mmol) 4,4-difluoro-3S-hydroxypyrrolidine hydrochloride (47 mg, 0.295 mmol) and $Cs_2CO_3$ (480 mg, 1.47 mmol) was charged in a sealed tube and purged with $N_2$. Dioxane (6.0 mL) was added and the mixture was degassed with $N_2$, then Pd(OAc)$_2$ (6.6 mg, 0.030 mmol) and XantPhos (17 mg, 0.030 mmol) were added. The reaction mixture was stirred and heated at 100° C. for 18 h. The reaction mixture was poured out into water and extracted with EtOAc. The organic layer was washed with brine, dried (MgSO$_4$) and evaporated till dryness. The residue was purified by preparative LC (irregular SiOH, 15-40 μm, GraceResolv® 24 g, mobile phase gradient: from heptane/EtOAc 80/20 to 0/100). The fractions containing product were evaporated under vacuum. The residue was taken up with $Et_2O$ and evaporated to dryness (3 times) to give a yellow solid which was taken-up with $Et_2O$ and the suspension was filtered and dried under high vacuum to give compound 97 as yellow solid (65 mg, 40%).

Synthesis of Compound 98
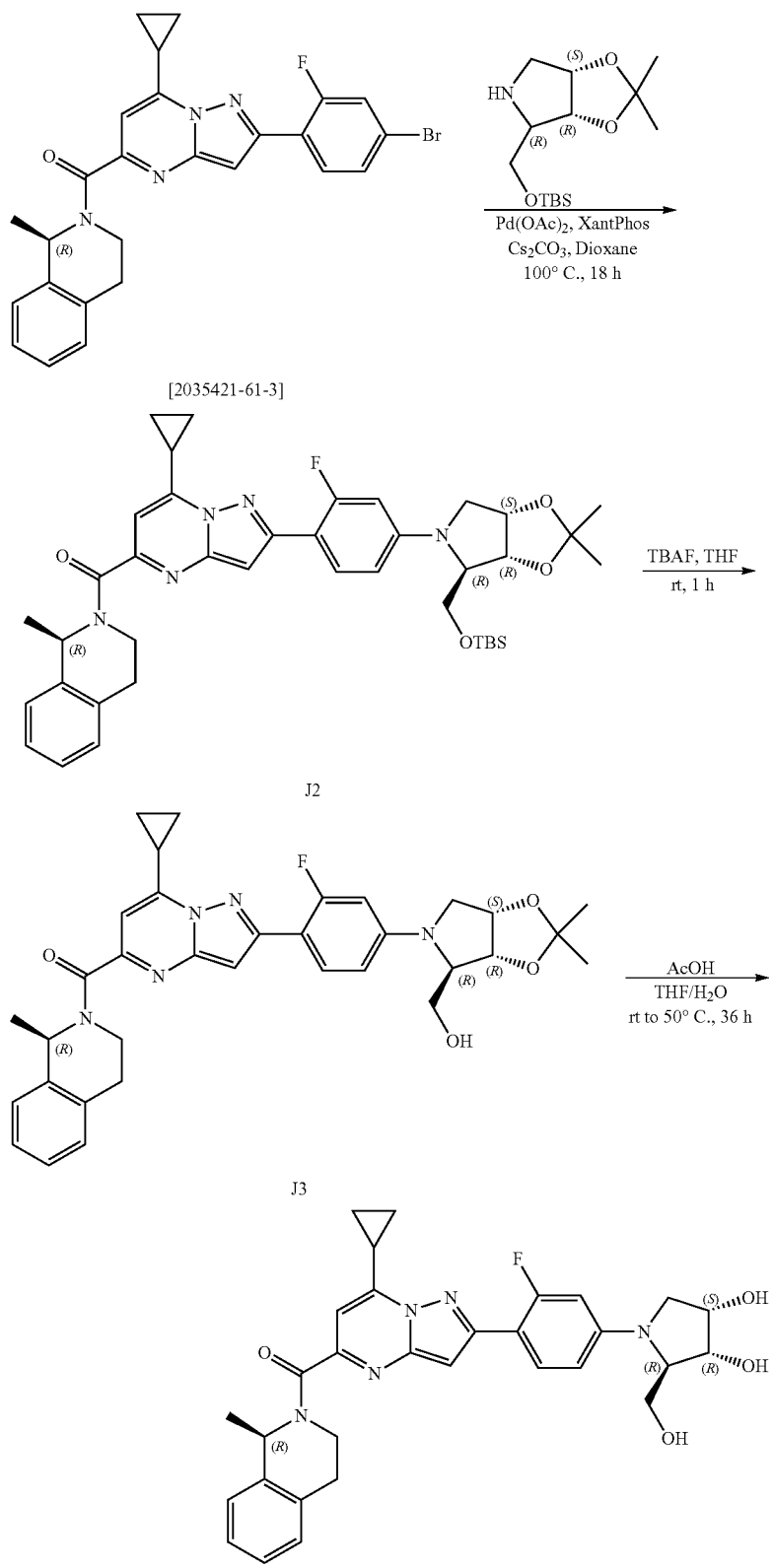

Intermediate J2

(2-(4-((3aR,4R,6aS)-4-(((tert-butyldimethylsilyl)oxy)methyl)-2,2-dimethyltetrahydro-5H-[1,3]dioxolo[4,5-c]pyrrol-5-yl)-2-fluorophenyl)-7-cyclopropylpyrazolo[1,5-a]pyrimidin-5-yl)((R)-1-methyl-3,4-dihydroisoquinolin-2(1H)-yl)methanone

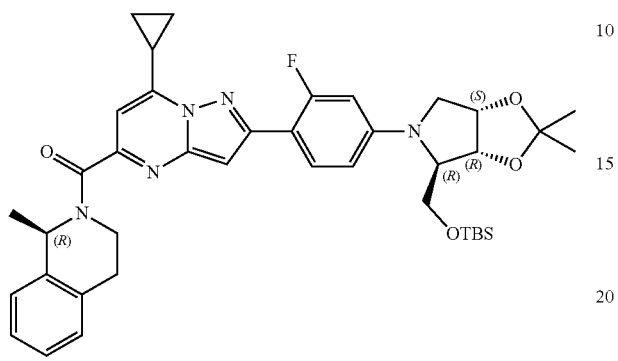

J2

A mixture of (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (200 mg, 0.396 mmol), [153172-31-7] (0.171 g, 0.594 mmol) and Cs$_2$CO$_3$ (387 mg, 1.19 mmol) was charged in a sealed tube and purged with N$_2$. Dioxane (8.2 mL) was added and the mixture was degassed with N$_2$, then Pd(OAc)$_2$ (8.8 mg, 0.040 mmol) and XantPhos (23 mg, 0.040 mmol) were added. The reaction mixture was purged with N$_2$ then was stirred and heated at 100° C. for 18 h. The reaction mixture was poured out into water and extracted with EtOAc. The organic layer was washed with brine, dried (MgSO$_4$), filtered and evaporated till dryness. The residue was purified by preparative LC (irregular SiOH, 15-40 μm, GraceResolv® 24 g, mobile phase gradient: from heptane/EtOAc 99/1 to 30/70). The fractions containing product were evaporated under vacuum to give intermediate J2 (230 mg, 70% purity, 57%)

Intermediate J3

(7-cyclopropyl-2-(2-fluoro-4-((3 aR,4R,6aS)-4-(hydroxymethyl)-2,2-dimethyltetrahydro-5H-[1,3]dioxolo[4,5-c]pyrrol-5-yl)phenyl)pyrazolo[1,5-a]pyrimidin-5-yl)((R)-1-methyl-3,4-dihydroisoquinolin-2(1H)-yl)methanone

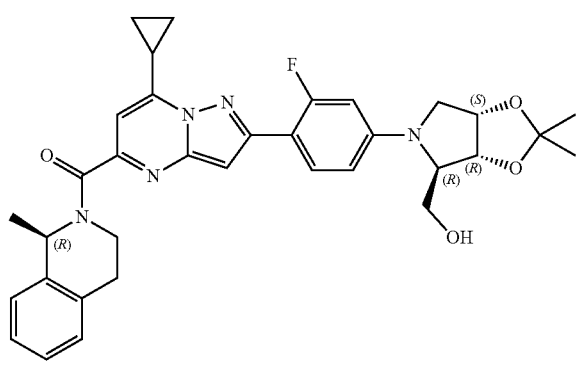

J3

TBAF 1M in THF (238 μL, 0.238 mmol) was added dropwise to a stirred solution of intermediate J2 (230 mg, 0.226 mmol, 70% purity) in THF (4.2 mL) at rt. The mixture was stirred at rt for 1 h. Then, the mixture was diluted with sat$_{aq}$NaCl and water and extracted with EtOAc. The organic layer was separated, washed with sat$_{aq}$NaCl, dried over MgSO$_4$, filtered and concentrated in vacuo. The residue was purified by preparative LC (irregular SiOH 15-40 μm, 12 g GraceResolv®, dry loading (Celite®), mobile phase gradient: from Heptane/EtOAc 80/20 to 20/80) to give intermediate J3 as a white solid. (135 mg, quant).

Compound 98

(7-cyclopropyl-2-(4-42R,3R,4S)-3,4-dihydroxy-2-(hydroxymethyl)pyrrolidin-1-yl)-2-fluorophenyl)pyrazolo[1,5-a]pyrimidin-5-yl)((R)-1-methyl-3,4-dihydroisoquinolin-2(1H)-yl)methanone

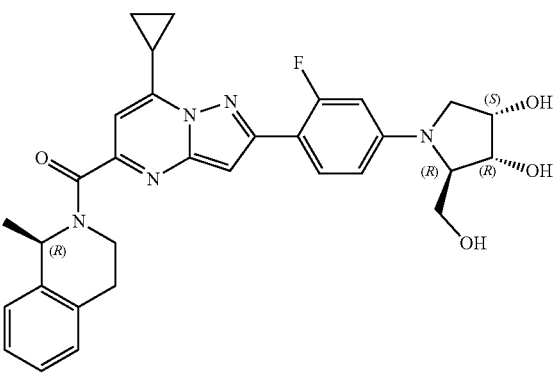

98

A mixture of intermediate J3 (135 mg, 0.226 mmol), AcOH (2.1 mL, 36 mmol), in THF (0.8 mL) and H$_2$O (0.8 mL) was stirred at rt for 18 h, then at 50° C. for 18 h. Water and EtOAc were added. The aqueous layer was extracted with EtOAc (twice), the combined organic layers were dried over MgSO$_4$, filtered, concentrated in vacuo and coevaporated (3 times) with EtOAc. The residue was purified by preparative LC (irregular SiOH 15-40 μm, 24 g GraceResolv®, mobile phase gradient: from DCM/PrOH 99/1 to 84/16). The fraction containing product was evaporated and the residue was taken-up in MeCN and evaporated under vacuum three times. Then it was taken-up in MeCN, the suspension was filtered and dried under high vacuum to give compound 98 as yellow solid (54 mg, 43%).

Compound 99

(7-cyclopropyl-2-(2-fluoro-4-((trans)-3-hydroxy-4-methylpyrrolidin-1-yl)phenyl)pyrazolo[1,5-a]pyrimidin-5-yl)((R)-1-methyl-3,4-dihydroisoquinolin-2(1H)-yl)methanone

Compound 100

(7-cyclopropyl-2-(4-((3R,4R)-3,4-dihydroxypyrrolidin-1-yl)-2-fluorophenyl)pyrazolo[1,5-a]pyrimidin-5-yl)((R)-1-methyl-3,4-dihydroisoquinolin-2(1H)-yl)methanone

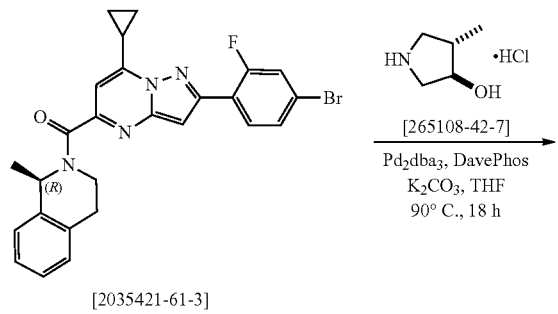

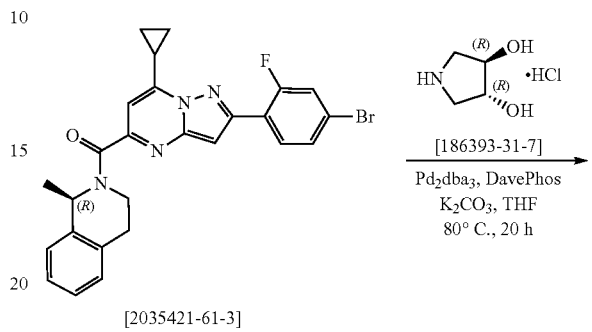

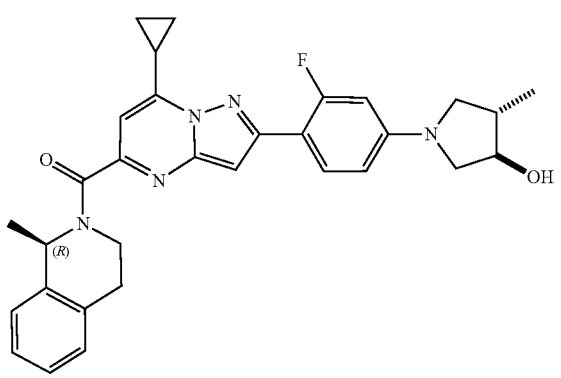

99

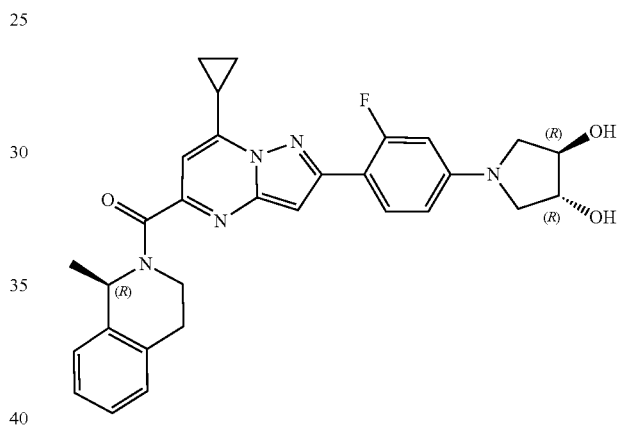

100

A mixture of (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (300 mg; 0.594 mmol), Trans-4-Methylpyrrolidin-3-ol hydrochloride (82 mg; 0.594 mmol) and $K_2CO_3$ (287 mg; 2.08 mmol) was charged in a sealed tube and purged with $N_2$. THF (4 mL) was added and the mixture was degassed with $N_2$, then DavePhos (23 mg; 59.4 µmol) and $Pd_2(dba)_3$ (54 mg; 59.4 µmol) were added. The reaction mixture was purged with $N_2$ then was stirred and heated at 90° C. for 18 h. Water and EtOAc were added. The aqueous layer was extracted with EtOAc (twice), the combined organic layers were dried over $MgSO_4$, filtered, concentrated in vacuo and purified by preparative LC (irregular SiOH 15-40 µm, 24 g GraceResolv®, mobile phase gradient: from DCM/MeOH 100:0 to 90:10) The fraction containing product was collected and evaporated to dryness. The residue was purified by preparative LC (spherical C18 25 µm, 40 g YMC-ODS-25, mobile phase gradient 0.2% aq. $NH_4HCO_3$/MeCN from 50:50 to 0:100) The fractions containing product were extracted with EtOAc. The organic layer was dried ($MgSO_4$), evaporated to give 163 mg of a yellow foam which was precipitated with EtOAc and heptane, filtered and dried to give compound 99 as yellow solid (105 mg, 34%).

In a sealed tube, a mixture of (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (300 mg; 0.59 mmol), 3R,4R-Pyrrolidinediol (85.7 mg; 0.83 mmol) and $K_2CO_3$ (287 mg; 2.08 mmol) in THF (7 mL) was degassed with $N_2$ for 10 min. DavePhos (23.4 mg; 59.4 µmol) and $Pd_2(dba)_3$ (54.4 mg; 59.4 µmol) were added and the reaction mixture was purged with $N_2$. The mixture was heated at 80° C. for 20 h. Water and EtOAc were added to the mixture and an extraction was performed. The combined organic layers were washed with brine, dried over $MgSO_4$, filtered, evaporated and purified by preparative LC (irregular SiOH, 15-40 µm, 50 g Merck, mobile phase gradient: from DCM/$^i$PrOH 100/0 to 90/10) to give 145 mg of a yellow oil. This fraction was taken up in MeOH (3 times) and evaporated then the residue was coevaporated in $^i$PrOAc (3 times) to give compound 100 as a yellow solid (135 mg, 43%).

Compound 101

(S)-1-(4-(7-cyclopropyl-5-((R)-1-methyl-1,2,3,4-tetrahydroisoquinoline-2-carbonyl)pyrazolo[1,5-a]pyrimidin-2-yl)-3-fluorophenyl)pyrrolidine-3-carbothioamide

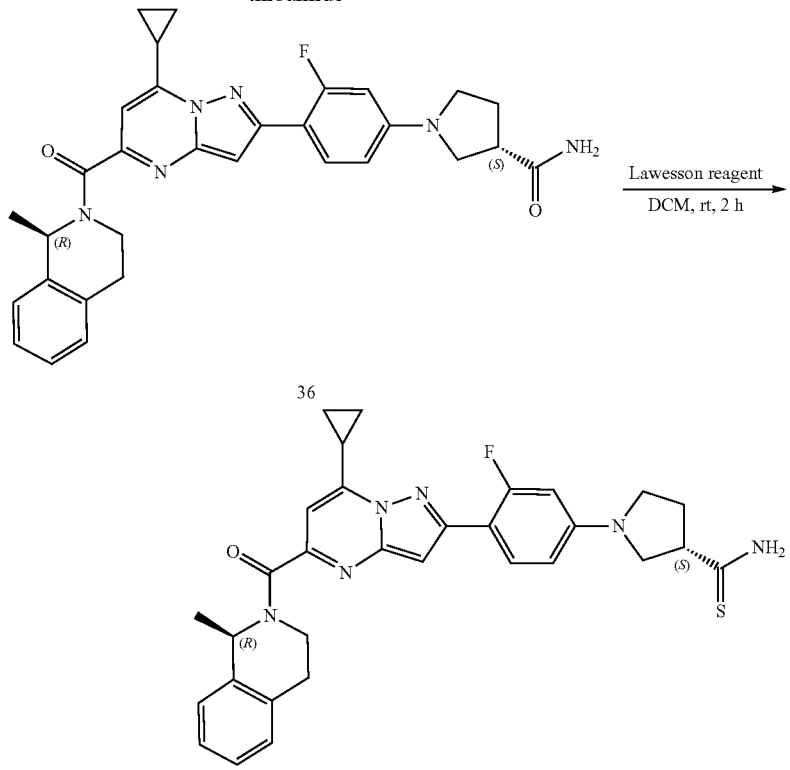

A mixture of compound 36 (118 mg; 0.22 mmol), Lawesson reagent (53 mg; 0.13 mmol) and DCM (1 mL) was stirred at rt for 2 h. The mixture was directly purified by flash chromatography (irregular SiOH 15-40 µm, 40 g GraceResolv®, mobile phase gradient, Heptane/EtOAc from 90/10 to 30/70). The fractions containing product were evaporated and coevaporated with EtOH. The solid was dried under vacuum to give compound 101 as a yellow solid (73 mg, 60%).

Compound 102

(7-cyclopropyl-2-(4-((3S,4S)-3,4-dihydroxypyrrolidin-1-yl)-2-fluorophenyl)pyrazolo[1,5-a]pyrimidin-5-yl)((R)-1-methyl-3,4-dihydroisoquinolin-2(1H)-yl)methanone

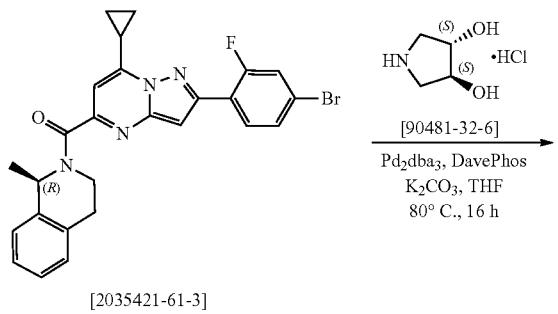

-continued

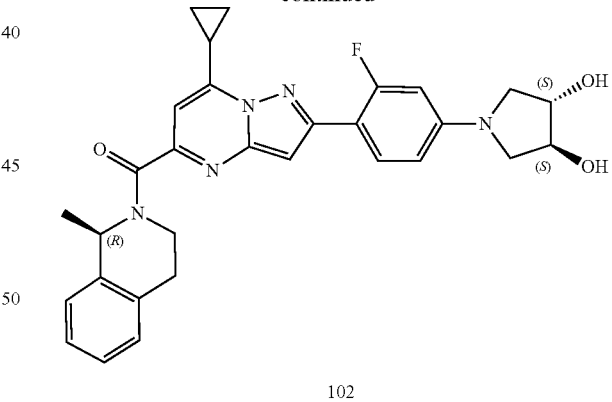

Under $N_2$, a mixture of (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (6.8 g, 13.5 mmol) 3S, 4S-Pyrrolidinediol (1.9 g, 18.8 mmol) and $K_2CO_3$ (6.5 g, 47.1 mmol) in THF (125 mL) was degassed with $N_2$ for 10 min. DavePhos (530 mg, 1.35 mmol) and $Pd_2dba_3$ (1.2 g, 1.35 mmol) were added and the reaction mixture was purged with $N_2$. The mixture was heated at reflux (80° C.) for 16 h. Water and EtOAc were added. The aqueous layer was extracted with EtOAc (twice), the combined organic layers were dried over $MgSO_4$, filtered, concentrated in vacuo and purified by preparative LC (irregular SiOH 15-40 µm, 330 g GraceResolv®, mobile phase gradient: from DCM/MeOH 100/0 to 90/10) The fractions containing product were collected and evaporated to dryness. The residue and SiliaMetS® Thiol (1.2 g; 1.61 mmol) in THF (100 mL) was stirred at rt for 3 h, then filtered over Celite® and the filtrate was evaporated to dryness to give 4.8 g of a yellow foam. The solid was suspended in EtOAc (~210 mL in total) and heated at reflux until complete solubilization. Then the heating source was stopped (the flask was kept in the oil bath during the crystallization with a gentle stirring allowing slow cooling) for 42 h. The suspension was cooled down to rt, filtered over glass frit, washed with cold EtOAc. The solid was dried under vacuum to give 2.75 g of a first batch of compound 102 as a yellow solid. The filtrate was evaporated, the residue was suspended in EtOAc (~60 mL in total) and heated at reflux until complete solubilization (oil bath 90° C.). Then the heating source was stopped (the flask was kept in the oil bath during the crystallization with a gentle stirring allowing slow cooling) for 42 h. The suspension was cooled down to rt, filtered over glass frit, washed with cooled EtOAc. The solid was dried under vacuum at 50° C. for 2 h to give 0.944 g of a second batch of compound 102 as a yellow solid. Both batches and 22 mL of EtOAc were stirred at rt for 24 h. The suspension was filtered over glass frit, washed with cold EtOAc. The solid was dried under vacuum to give compound 102 as a yellow solid (3.27 g, 46%).

Synthesis of Compound 103 and 104

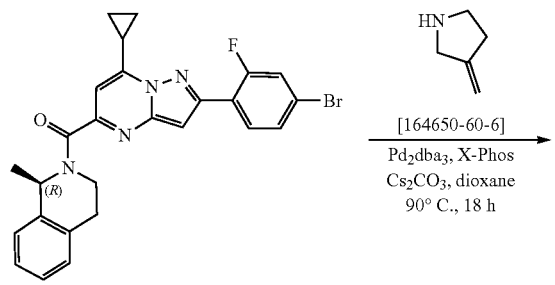

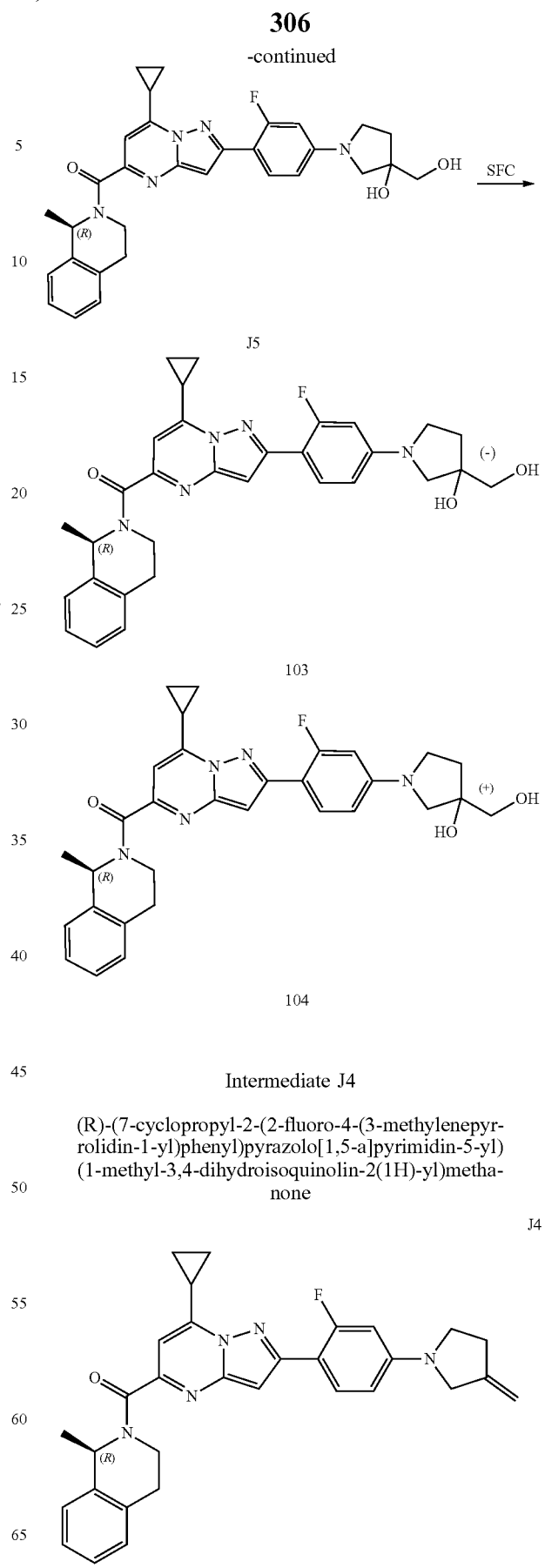

Intermediate J4

(R)-(7-cyclopropyl-2-(2-fluoro-4-(3-methylenepyrrolidin-1-yl)phenyl)pyrazolo[1,5-a]pyrimidin-5-yl)(1-methyl-3,4-dihydroisoquinolin-2(1H)-yl)methanone A mixture of (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (325 mg; 0.644 mmol), Cs$_2$CO$_3$ (1.05 g; 3.22 mmol) and 3-methylidenepyrrolidine.TFA (294 mg; 0.644 mmol) was charged in a sealed tube and purged with N$_2$. Dioxane (6 ml) was added and the mixture was degassed with N$_2$, then Pd$_2$dba$_3$ (29.5 mg; 0.0322 mmol) and X-Phos (46 mg; 0.096 mmol) were added. The reaction mixture was purged with N$_2$ then was stirred and heated at 90° C. for 18 h. Water and EtOAc were added, the layers were separated. The aqueous layer was extracted with EtOAc (twice), the combined organic layers were dried over MgSO$_4$, filtered, concentrated in vacuo and purified by preparative LC (irregular SiOH 15-40 μm, 40 g GraceResolv®, mobile phase gradient: Heptane/EtOAc: from 90/10 to 60/40) to give intermediate J4 as a yellow solid (259 mg, 70%).

Intermediate J5

(7-cyclopropyl-2-(2-fluoro-4-(3-hydroxy-3-(hydroxymethyl)pyrrolidin-1-yl)phenyl)pyrazolo[1,5-a]pyrimidin-5-yl)((R)-1-methyl-3,4-dihydroisoquinolin-2(1H)-yl)methanone

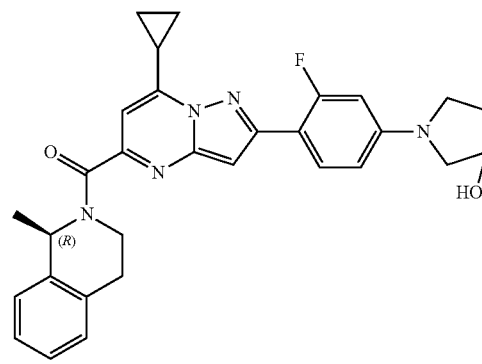

J5

NMO (141 mg; 1.20 mmol) and OsO4 2.5% in $^t$BuOH (0.263 ml; 0.0201 mmol) were added to a solution of J4 (234 mg; 0.401 mmol) in a mixture of acetone (2 ml) and H$_2$O (0.2 ml). The reaction mixture was stirred at rt for 3.5 h. The reaction mixture was quenched with a 10% aqueous solution of Na$_2$S$_2$O$_3$ and the resulting mixture was stirred at rt for 30 min. DCM was added and the layers were separated. The aqueous layer was extracted with DCM/MeOH (90/10) mixture (3 times). The organic layers were combined, washed with water, dried over MgSO$_4$, filtered and concentrated. The residue was purified by preparative LC (irregular SiOH, 15-40 μm, 12 g GraceResov®, mobile phase gradient: DCM/MeOH: from 99/1 to 95/5). The fraction containing product was combined and evaporated to dryness. The residue was purified by preparative LC (spherical C18, 25 μm, 40 g YMC-ODS-25, mobile phase gradient 0.2% aq. NH$_4$HCO$_3$/MeCN from 65:35 to 25:75) to give 128 mg of a yellow solid. This solid was purified again by preparative LC (spherical C18, 25 μm, 40 g YMC-ODS-25, mobile phase gradient 0.2% aq. NH$_4$HCO$_3$/MeCN from 65:35 to 25:75) the fractions containing product were extented with water and freeze-dried to give a yellow solid. The solid and SiliaMetS® Thiol (30 mg; 0.0401 mmol) in THF (3 mL) was stirred at rt for 18 h, then filtered over PTFE and the filtrate was evaporated to dryness to give Intermediate J5 as yellow solid (80 mg, 37%).

Compound 103 & 104

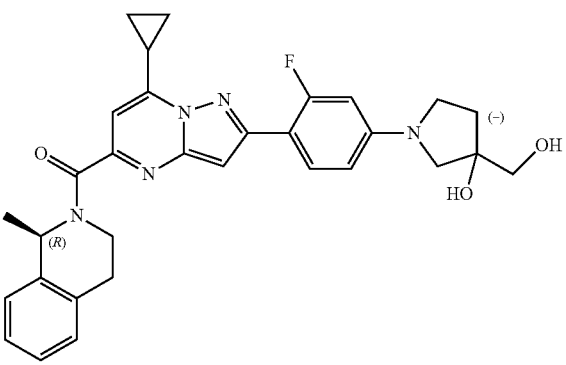

103

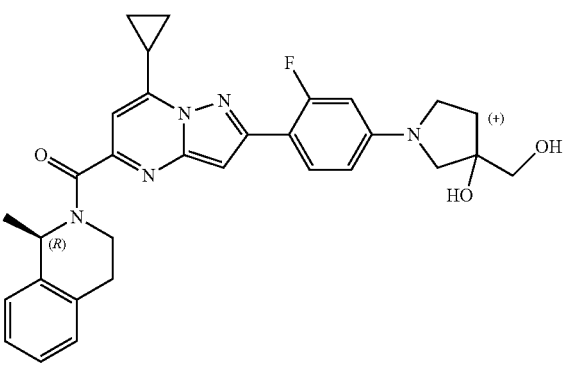

104

J5 was separated via chiral SFC (Stationary phase: CHIRALPAK AS-H 5 μm 250*20 mm, Mobile phase: 75% CO$_2$, 25% EtOH (0.3% $^i$PrNH$_2$)) the fractions contained product were evaporated to dryness then diluted with MeCN, extented with water and freeze-dried to give 28 mg of compound 103 having a (−) specific optical rotation as a yellow solid and 28 mg of compound 104 having a (+) specific optical rotation as a yellow solid.

Synthesis of Compound 105

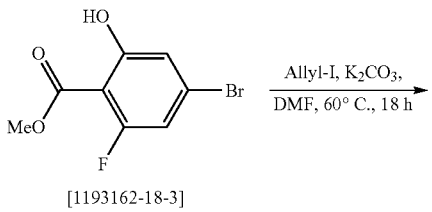

[1193162-18-3]

309
-continued
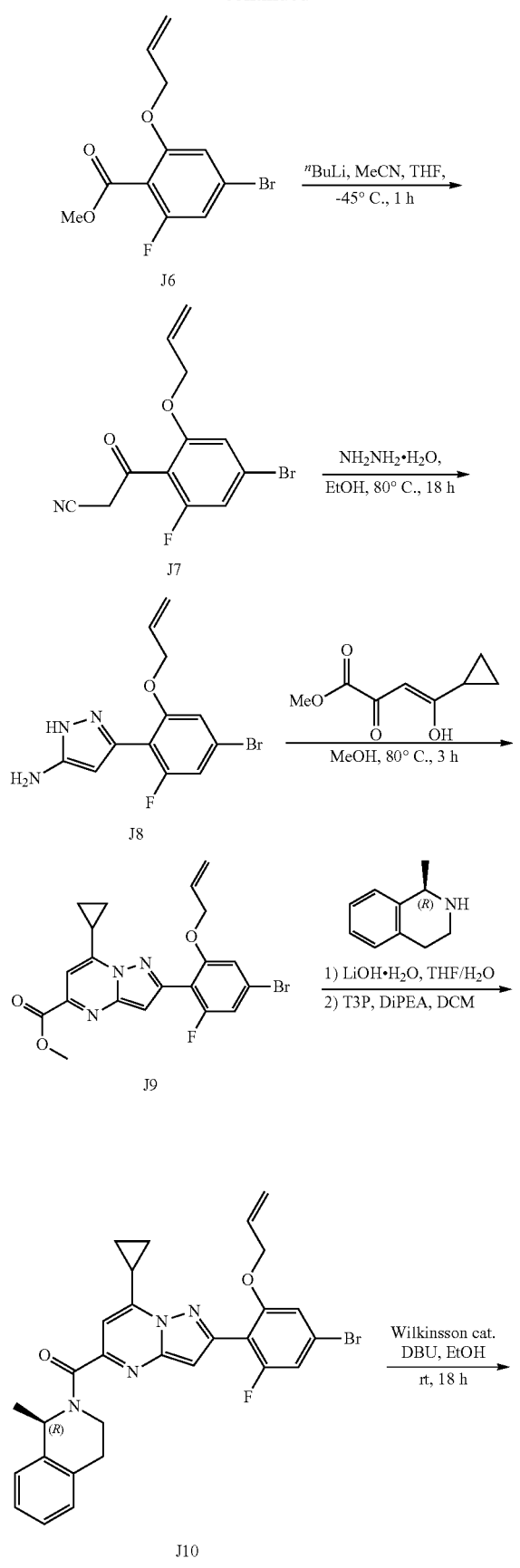
310
-continued
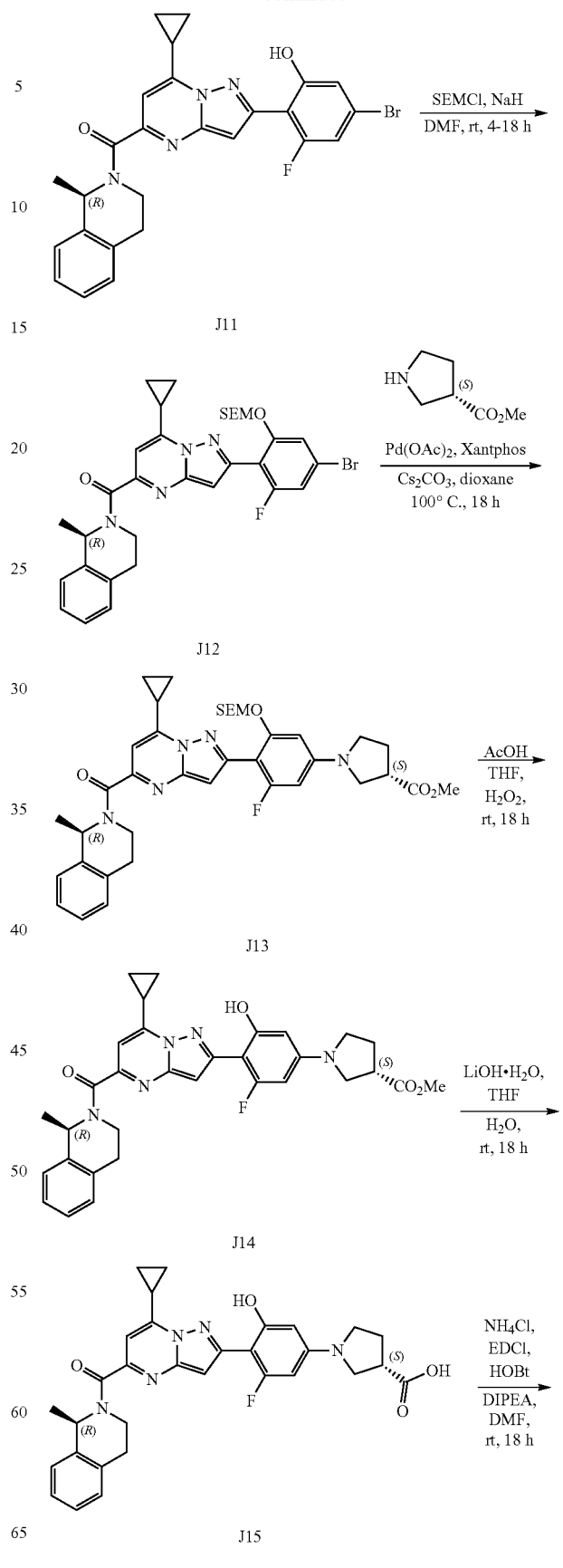

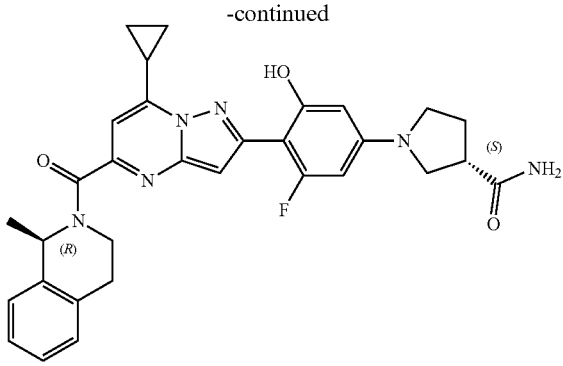

105

Intermediate J6 methyl 2-(allyloxy)-4-bromo-6-fluorobenzoate

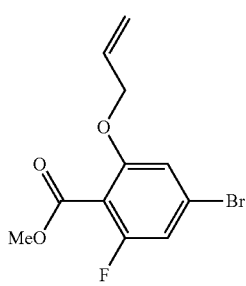

A mixture of Methyl 4-bromo-2-fluoro-6-hydroxybenzoate [1193162-18-3] (5 g; 20.1 mmol), allyl iodide (5.5 mL; 60.2 mmol) and $K_2CO_3$ (8.76 g; 63.3 mmol) in DMF (80 mL) was stirred at 60° C. for 18 h. EtOAc and water were added, and an extraction was performed. The organic layer was washed with brine, dried (MgSO$_4$), filtered, evaporated and purified by preparative LC (irregular SiOH, 15-40 μm, 220 g GraceResolv®, mobile phase gradient: from heptane/EtOAc 100/0 to 85/15) to give intermediate J6 as a white solid (5.55 g, 96%).

Intermediate J7

3-(2-(allyloxy)-4-bromo-6-fluorophenyl)-3-oxopropanenitrile

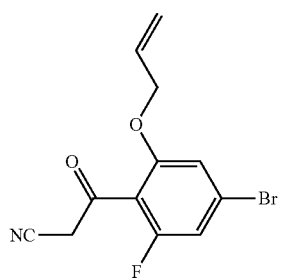

Under $N_2$, "BuLi 1.6M in hexanes (57 mL; 91.9 mmol) was added to THF (100 mL) at −78° C. then a solution of MeCN (4.78 mL; 91.6 mmol) was added dropwise. The resulting slurry was stirred for 1 h at −78° C. then a solution of intermediate J6 (13.4 g; 46.4 mmol) in THF (150 mL) was added. After 30 min at −78° C. the reaction mixture was warmed to −45° C. and allowed to stir for 1 h. The reaction was quenched with HCl 1N and then extracted with EtOAc. The organic layer was separated, washed with water then brine, dried (MgSO$_4$), filtered and evaporated to give intermediate J7 as orange oil (14.4 g, Quant.).

Intermediate J8

3-(2-(allyloxy)-4-bromo-6-fluorophenyl)-1H-pyrazol-5-amine

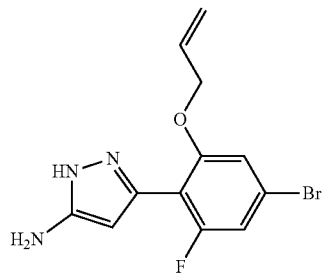

A mixture of intermediate J7 (14.4 g; 48.3 mmol) and Hydrazine hydrate (80% purity) (2.95 mL; 48.3 mmol) in EtOH (192 mL) was stirred at 80° C. for 18 h. The mixture was evaporated to give intermediate J8 as yellow solid (14.4 g, 96%).

Intermediate J9 methyl 2-(2-(allyloxy)-4-bromo-6-fluorophenyl)-7-cyclopropyl-pyrazolo[1,5-a]pyrimidine-5-carboxylate

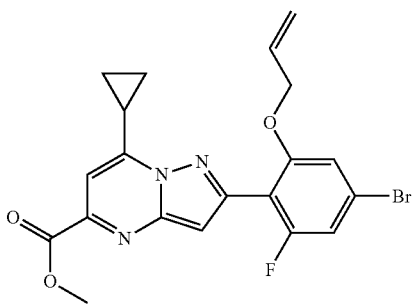

A mixture of J8 (14.4 g; 46.1 mmol) and Methyl 4-cyclopropyl-2,4-dioxobutanoate [167408-67-5] (8.26 g; 46.1 mmol) in EtOH (200 mL) was stirred at 80° C. for 3 h. The mixture was cooled to rt and a precipitate was formed. The precipitate was filtered and dried on the frit to give intermediate J9 as yellow solid (7.96 g, 38%).

Intermediate J10

(R)-(2-(2-(allyloxy)-4-bromo-6-fluorophenyl)-7-cyclopropylpyrazolo[1,5-a]pyrimidin-5-yl)(1-methyl-3,4-dihydroisoquinolin-2(1H)-yl)methanone

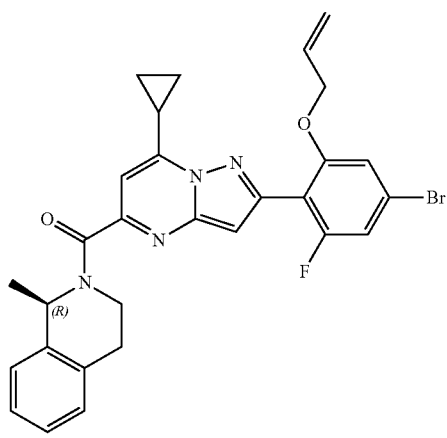

A mixture of J9 (7.96 g; 17.8 mmol), LiOH.H₂O (4.12 g; 98.1 mmol), THF (80 mL) and H₂O (23 mL) was stirred at rt for 2 days. EtOAc and 10% aq. KHSO₄ were added to the mixture and an extraction was performed. The organic layer was washed with brine, dried (MgSO₄) and evaporated to give 6.57 g of acid intermediate as yellow solid. The acid (6.57 g; 15.2 mmol), 1R-methyl-1,2,3,4-tetrahydroisoquinoline (2.59 g; 17.6 mmol) and DiPEA (13 mL; 76 mmol) in DCM (77 mL) were stirred at 0° C. T3P (22.6 mL; 37.9 mmol) was added slowly (5 min.) at 0° C. The mixture was stirred at 0° C. for 10 min then at rt for 3 h. Water and EtOAc were added. An extraction was performed. The organic layer was washed with brine, dried (MgSO₄) and evaporated to give intermediate J10 as a brown foam (9.0 g, Quant.).

Intermediate J11

(R)-(2-(4-bromo-2-fluoro-6-hydroxyphenyl)-7-cyclopropylpyrazolo[1,5-a]pyrimidin-5-yl)(1-methyl-3,4-dihydroisoquinolin-2(1H)-yl)methanone

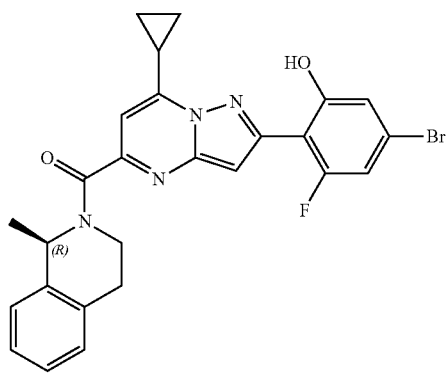

A mixture of J10 (5 g; 8.91 mmol), Wilkinson catalyst (824 mg; 0.89 mmol), DBU (1.33 mL; 8.91 mmol) and EtOH (60 mL) was stirred at rt for 18 h. The mixture was evaporated and purified by preparative LC (irregular SiOH 15-40 μm, GraceResolv® 220 g, dry loading (Celite®) mobile phase Heptane/EtOAc from 100:0 to 70:30) to give 2 g of intermediate J11 as brown solid, and 2 impure fractions (3 g and 2.4 g). The first impure fraction (3 g) was purified by Reverse phase LC (Stationary phase: spherical C18 25 μm, 300 g YMC-ODS-25, dry loading (C18), Mobile phase: Gradient: 0.2% aq. NH₄HCO₃/MeCN, from 50:50 to 0:100). The fractions containing the product were combined, MeCN was evaporated in vacuo, water and EtOAc were added and an extraction was performed. The organic layer was washed with water, dried over MgSO₄, filtered and evaporated to give 700 mg of intermediate ill as a brown oil. The second impure fraction (2.4 g) was purified by Reverse phase LC (Stationary phase: spherical C18 25 μm, 300 g YMC-ODS-25, dry loading (C18), Mobile phase: Gradient: 0.2% aq. NH₄HCO₃/MeCN, from 50:50 to 0:100). The fractions containing the product were combined, MeCN was evaporated in vacuo, water and EtOAc were added and an extraction was performed. The organic layer was washed with water, dried over MgSO₄, filtered and evaporated to give 1 g of intermediate ill as a brown foam (Global yield 80%, 3.7 g).

Intermediate J12

(R)-(2-(4-bromo-2-fluoro-6-((2-(trimethylsilyl)ethoxy)methoxy)phenyl)-7-cyclopropylpyrazolo[1,5-a]pyrimidin-5-yl)(1-methyl-3,4-dihydroisoquinolin-2(1H)-yl)methanone

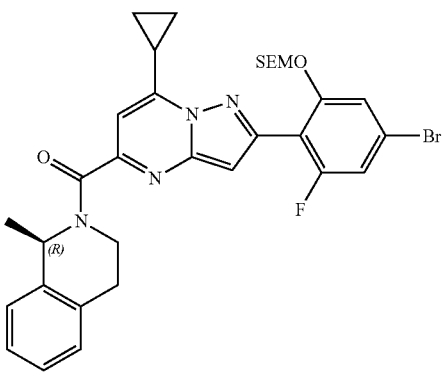

A mixture of J11 (2.7 g; 5.18 mmol) and NaH 60% in mineral oil (311 mg; 7.77 mmol) in DMF (20 mL) was stirred at 0° C. for 15 min. SEMCl (1.83 mL; 10.4 mmol) was added slowly at 0° C. under N₂. The mixture was stirred at rt for 4 h. An extraction was performed with EtOAc and water. The organic layer was washed with brine, dried (MgSO₄), evaporated and purified by preparative LC (irregular SiOH, 15-40 μm, 120 g GraceResolv®, mobile phase gradient: from heptane/EtOAc 100/0 to 70/30) to give intermediate J12 as a colorless oil (2.3 g, 68%).

Intermediate J13 methyl (S)-1-(4-(7-cyclopropyl-5-((R)-1-methyl-1,2,3,4-tetrahydroisoquinoline-2-carbonyl)pyrazolo[1,5-a]pyrimidin-2-yl)-3-fluoro-5-((2-(trimethylsilyl)ethoxy)-methoxy)phenyl)pyrrolidine-3-carboxylate

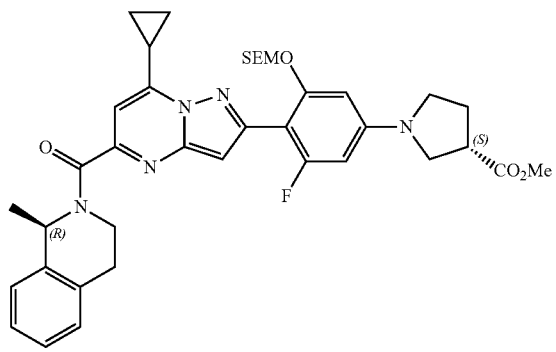

J13

A sealed tube was charged with J12 (800 mg; 1.23 mmol), (S)-methyl Pyrrolidine-3-carboxylate hydrochloride (238 mg; 1.44 mmol), Cs$_2$CO$_3$ (1.17 g; 3.59 mmol) and dioxane (13 mL) and purged with N$_2$. XantPhos (69 mg; 0.12 mmol) was added and the mixture was purged again with N$_2$, then Pd(OAc)$_2$ (27 mg; 0.12 mmol) was added. The reaction mixture was purged with N$_2$ and heated at 100° C. for 17 h. The mixture was filtered through a pad of Celite®, water and EtOAc were added and an extraction was performed. The combined organic layers were washed with brine, dried over MgSO$_4$, filtered, evaporated and purified by preparative LC (irregular SiOH 15-40 μm, 24 g GraceResolv®, mobile phase gradient: from heptane/EtOAc 100/0 to 50/50) to give intermediate J13 as a yellow foam (578 mg, 67%).

Intermediate J14 methyl (S)-1-(4-(7-cyclopropyl-5-((R)-1-methyl-1,2,3,4-tetrahydroisoquinoline-2-carbonyl)pyrazolo[1,5-a]pyrimidin-2-yl)-3-fluoro-5-hydroxyphenyl)pyrrolidine-3-carboxylate

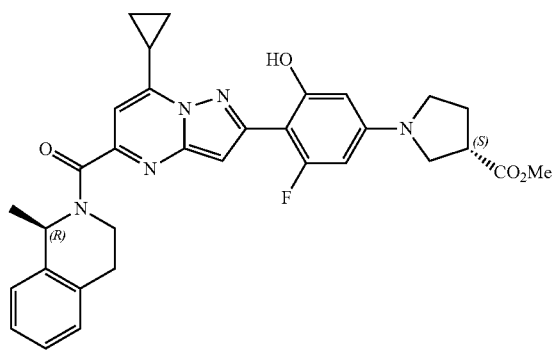

J14

A mixture of J13 (2.5 g; 3.57 mmol), AcOH (30 mL), THF (10 mL) and H$_2$O (10 mL) was stirred at rt for 18 h. AqNaHCO$_3$ and EtOAc were added and an extraction was performed. The organic layer was washed with brine, dried (MgSO$_4$), filtered, evaporated and purified by preparative LC (irregular SiOH 15-40 μm, 220 g GraceResolv®, mobile phase gradient: from heptane/EtOAc 100/0 to 50/50) to give intermediate J14 as a yellow solid (1.56 g, 77%).

Intermediate J15

(S)-1-(4-(7-cyclopropyl-5-((R)-1-methyl-1,2,3,4-tetrahydroisoquinoline-2-carbonyl)pyrazolo[1,5-a]pyrimidin-2-yl)-3-fluoro-5-hydroxyphenyl)pyrrolidine-3-carboxylic acid

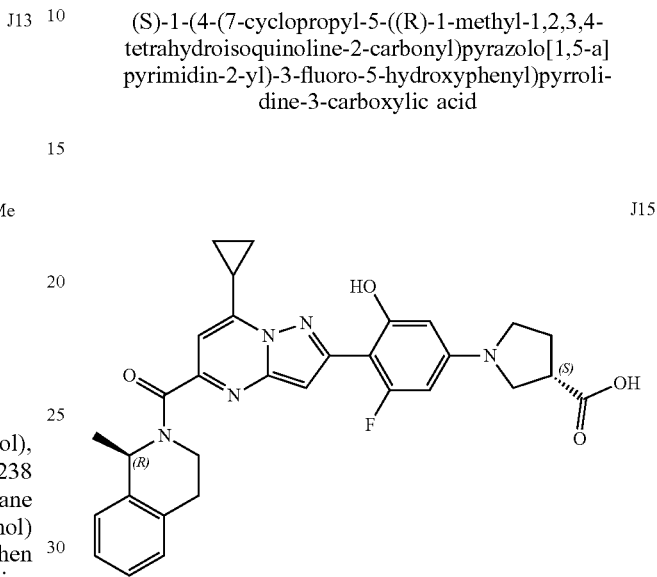

J15

A mixture of J14 (600 mg; 1.05 mmol), LiOH.H$_2$O (243 mg; 5.80 mmol), THF (5 mL) and H$_2$O (1 mL) was stirred at rt for 18 h. EtOAc and 10% aq. KHSO$_4$ were added to the mixture and an extraction was performed. The organic layer was washed with brine, dried (MgSO$_4$) and evaporated to give intermediate J15 as yellow solid (550 mg, 94%).

Compound 105

(S)-1-(4-(7-cyclopropyl-5-((R)-1-methyl-1,2,3,4-tetrahydroisoquinoline-2-carbonyl)pyrazolo[1,5-a]pyrimidin-2-yl)-3-fluoro-5-hydroxyphenyl)pyrrolidine-3-carboxamide

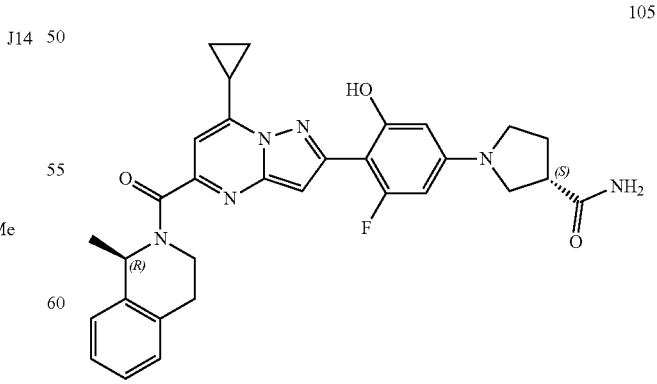

105

A mixture of J15 (250 mg; 0.45 mmol), ammonium chloride (48 mg; 0.90 mmol), EDCl (140 mg; 0.90 mmol) and HOBt.H$_2$O (138 mg; 0.90 mmol) in DMF (8 mL) was stirred at 0° C. DiPEA (0.39 mL; 2.25 mmol) was added slowly at 0° C. The mixture was stirred at rt for 18 h. EtOAc and brine were added to the mixture and an extraction was performed. The combined organic layers were washed with brine, dried over MgSO₄, filtered, evaporated and purified by Reverse phase LC (Stationary phase: spherical C18 25 μm, 40 g YMC-ODS-25, dry loading (C18), Mobile phase: Gradient: 0.2% aq. NH₄HCO₃/MeCN, from 65:35 to 25:75).

MeCN was evaporated, EtOAc was added and an extraction was performed. The combined organic layers were washed with brine, dried over MgSO₄, filtered, evaporated and coevaporated 3 times with EtOAc, to give compound 105 as a yellow solid (140 mg, 56%).

Synthesis of Compound 106

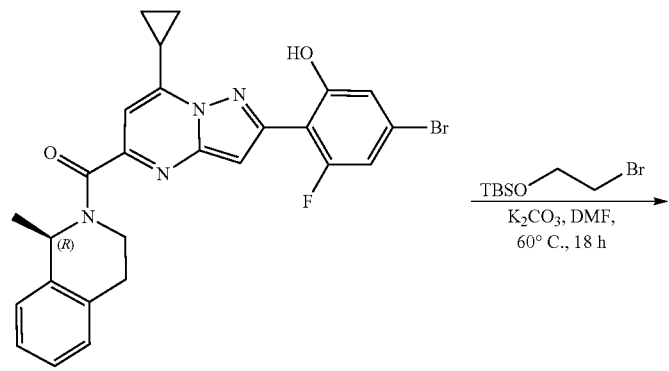

J11

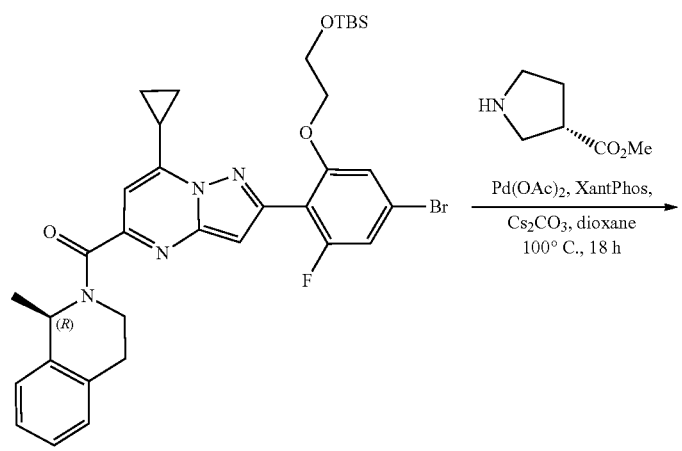

J16

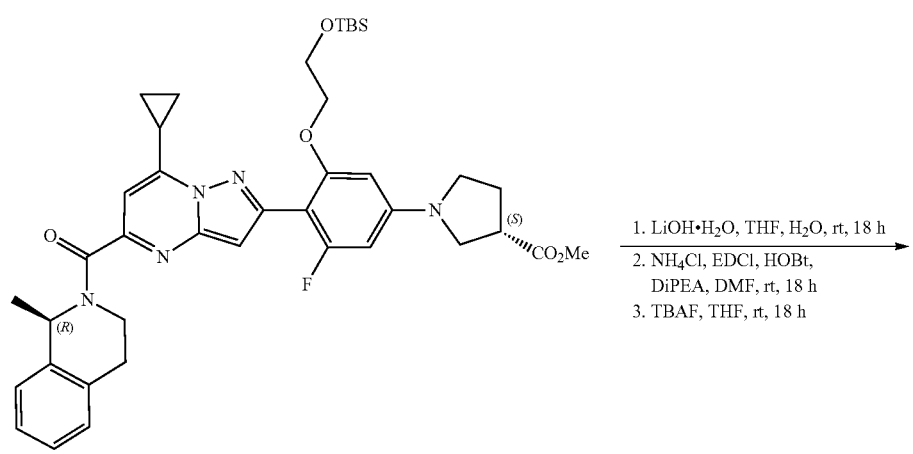

J17

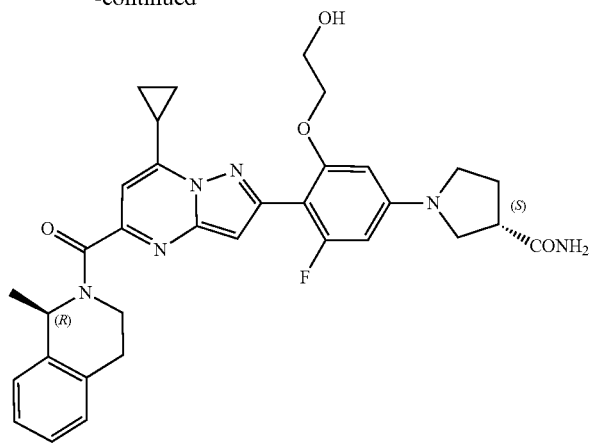

106

Intermediate J16

(R)-(2-(4-bromo-2-(2-((tert-butyldimethylsilyl)oxy)ethoxy)-6-fluorophenyl)-7-cyclopropylpyrazolo[1,5-a]pyrimidin-5-yl)(1-methyl-3,4-dihydroisoquinolin-2(1H)-yl)methanone

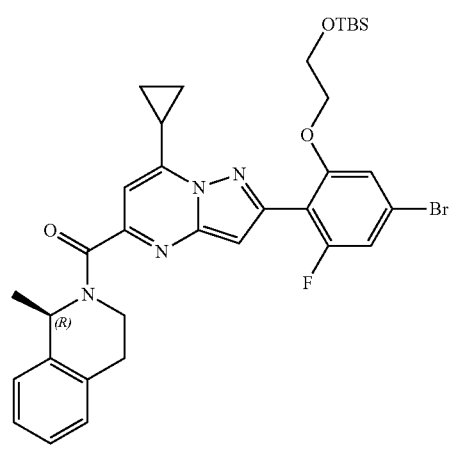

A mixture of J11 (226 mg; 0.43 mmol), (2-bromotethoxy)-tert-butyldimethylsilane (93 μL; 0.43 mmol) and K₂CO₃ (189 mg; 1.37 mmol) in DMF (5 mL) was stirred at 60° C. for 18 h. EtOAc and water were added and an extraction was performed. The organic layer was washed with brine, dried (MgSO₄), evaporated and purified by preparative LC (irregular SiOH, 15-40 μm, 120 g GraceResolv®, mobile phase gradient: from heptane/EtOAc 100/0 to 70/30) to give intermediate J16 as a colorless oil (243 mg, 82%).

Intermediate J17 methyl (S)-1-(3-(2-((tert-butyldimethylsilyl)oxy)ethoxy)-4-(7-cyclopropyl-5-((R)-1-methyl-1,2,3,4-tetrahydroisoquinoline-2-carbonyl)pyrazolo[1,5-a]pyrimidin-2-yl)-5-fluorophenyl)pyrrolidine-3-carboxylate

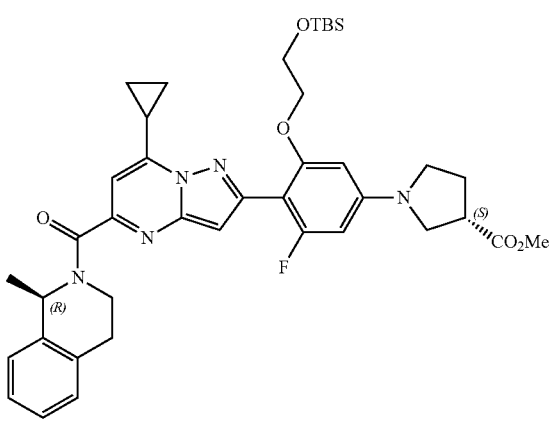

A sealed tube was charged with J16 (243 mg; 0.36 mmol), (S)-methyl Pyrrolidine-3-carboxylate hydrochloride (59 mg; 0.36 mmol), Cs₂CO₃ (349 mg; 1.1 mmol) in dioxane (4 mL) and purged with N₂. XantPhos (21 mg; 0.036 mmol) and Pd(OAc)₂ (8 mg; 0.036 mmol) were added and the mixture was purged again with N₂. The mixture was stirred at 100° C. for 18 h. EtOAc and water were added to the mixture. An extraction was performed. the organic layer was washed with brine, dried (MgSO₄) evaporated and purified by preparative LC (irregular SiOH, 15-40 μm, 40 g GraceResolv®, mobile phase gradient: from heptane/EtOAc 100/0 to 40/60) to give intermediate J17 as yellow foam (188 mg, 72%).

Compound 106

(S)-1-(4-(7-cyclopropyl-5-((R)-1-methyl-1,2,3,4-tetrahydroisoquinoline-2-carbonyl)pyrazolo[1,5-a]pyrimidin-2-yl)-3-fluoro-5-(2-hydroxyethoxy)phenyl)pyrrolidine-3-carboxamide

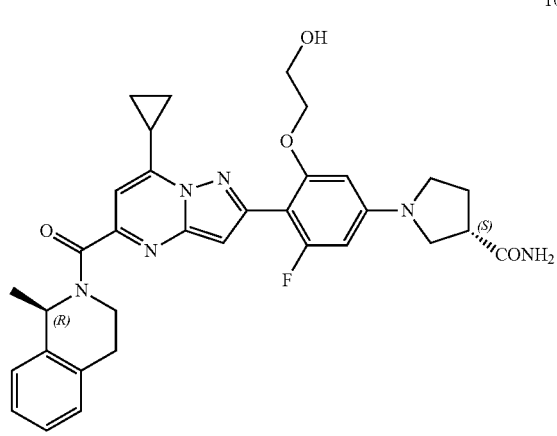

106

LiOH.H₂O (58 mg; 1.4 mmol) was added to a solution of J16 (188 mg; 0.26 mmol) in THF (7 mL) and H₂O (3 mL) and the reaction mixture was stirred at rt for 18 h. An aqueous solution of KHSO₄ 10% was added until pH=6 and the aqueous layer was extracted with EtOAc. The organic layer was washed with water, dried over MgSO₄, filtered and evaporated to give 190 mg of a yellow solid. To this solid, NH₄Cl (28 mg; 0.52 mmol), EDCl.HCl (80 mg; 0.418 mmol) and HOBt.H₂O (79 mg; 0.52 mmol) in DMF (4 mL) were added. Then DIPEA (222 µL; 1.3 mmol) was added slowly at 0° C. and the mixture was stirred at rt for 18 h. Brine and EtOAc were added and an extraction was performed. The organic layer was washed with brine (3×), dried (MgSO₄), filtered and evaporated to give 182 mg of a yellow solid. TBAF 1M in THF (0.255 mL; 0.255 mmol) and THF (2 mL) were added and the mixture was stirred at rt for 18 h. Brine and EtOAc were added and an extraction was performed. The organic layer was dried (MgSO₄), evaporated and purified by preparative LC (spherical C18 25 µm, 40 g YMC-ODS-25, mobile phase gradient 0.2% aq. NH₄HCO₃/MeCN from 95:05 to 30:70) the fraction containing product was concentrated, EtOAc was added and an extraction was performed. The organic layer was dried (MgSO₄), filtered and evaporated to give compound 106 as yellow solid (82 mg, 54%).

Compound 107

(7-cyclopropyl-2-(2-fluoro-4-(cis-3-fluoro-4-hydroxypyrrolidin-1-yl)phenyl)pyrazolo[1,5-a]pyrimidin-5-yl)((R)-1-methyl-3,4-dihydroisoquinolin-2(1H)-yl)methanone

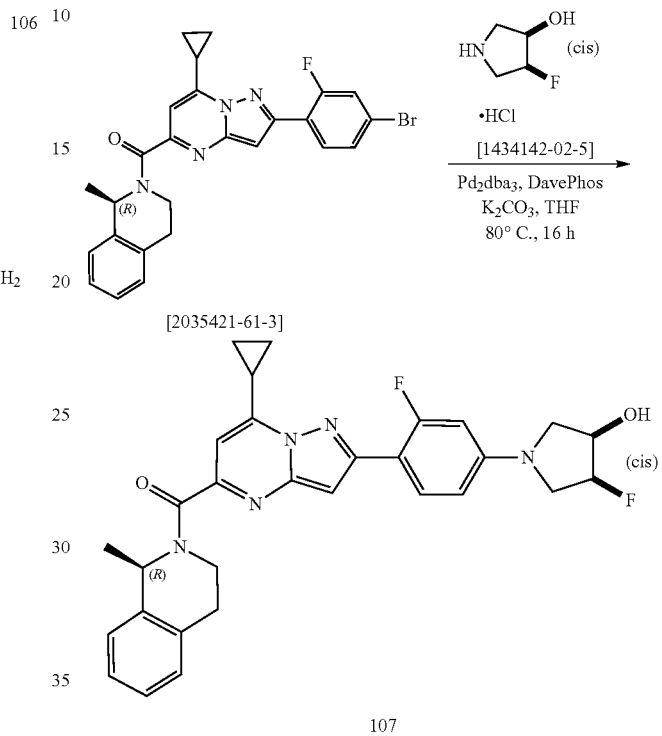

107

In a sealed tube, a mixture of (1R)-2-[2-(4-bromo-2-fluorophenyl)-7-cyclopropyl-pyrazolo[1,5-a]pyrimidine-5-carbonyl]-1-methyl-1,2,3,4-tetrahydroisoquinoline [2035421-61-3] (200 mg; 0.396 mmol), cis-4-fluoropyrrolidin-3-ol hydrochloride [1434142-02-5] (79 mg; 0.56 mmol) and K₂CO₃ (219 mg; 1.58 mmol) in THF (4.7 mL) was degassed with N₂ for 10 min. DavePhos (16 mg; 0.040 mmol) and Pd₂dba₃ (36 mg; 0.040 mmol) were added and the reaction mixture was purged with N₂. The mixture was heated at 80° C. for 20 h. Water and EtOAc were added and an extraction was performed. The organic layer was dried over MgSO₄, filtered and concentrated under reduced pressure. The residue was purified by preparative LC (irregular SiOH 15-40 µm, 12 g GraceResolv®, mobile phase gradient: from DCM/MeOH 100/00 to 97/3). The fraction containing product was combined and evaporated to dryness. The residue was purified by Reverse phase (Stationary phase: YMC-actus Triart® C18 10 µm 30*150 mm, Mobile phase: Gradient from 40% aq. NH₄HCO₃ 0.2%, 60% MeCN to 10% aq. NH₄HCO₃ 0.2%, 90% MeCN) to give 102 mg of a yellow gum which was taken up in a mixture of EtOAc and Heptane, evaporated in vacuo to give 100 mg of yellow foam. The solid was purified again by Reverse phase (Stationary phase: YMC-actus Triart® C18 10 µm 30*150 mm, Mobile phase: Gradient from 40% aq. NH₄HCO₃ 0.2%, 60% MeCN to 10% aq. NH₄HCO₃ 0.2%, 90% MeCN). The fractions containing product were collected and evaporated. The residue was taken up in MeCN (2 mL) extended with water (10 mL) and freeze-dried to give compound 107 as a fluffy yellow solid (39 mg, 19%).

C. COMPOUND IDENTIFICATION

¹H-NMR

¹H NMR spectra were recorded on a Bruker Avance DRX 400 spectrometer using internal deuterium lock and equipped with reverse double-resonance (¹H, ¹³C, SEI) probe head with z gradients and operating at 400 MHz for proton and 100 MHz for carbon and a Bruker Avance 500 MHz spectrometer equipped with a Bruker 5 mm BBFO probe head with z gradients and operating at 500 MHz for proton and 125 MHz for carbon.

NMR spectra were recorded at ambient temperature unless otherwise stated.

Data are reported as follow: chemical shift in parts per million (ppm) relative to TMS (δ=0 ppm) which was used as internal standard, integration, multiplicity (s=singulet, d=doublet, t=triplet, q=quartet, quin=quintuplet, sex=sextuplet, m=multiplet, b=broad, or a combination of these), coupling constant(s) J in Hertz (Hz).

Compound 1

Major Rotamer (65%)

¹H NMR (500 MHz, DMSO-$d_6$) δ ppm 8.03 (t, J=8.7 Hz, 1H), 7.32 (d, J=7.3 Hz, 1H), 7.10-7.25 (m, 3H), 6.94-6.98 (m, 1H), 6.82 (br s, 1H), 6.53-6.61 (m, 2H), 5.59 (q, J=6.6 Hz, 1H), 3.81 (dd, J=13.9, 4.1 Hz, 1H), 3.55-3.70 (m, 3H), 3.34-3.53 (m, 3H), 2.83-3.07 (m, 2H), 2.72 (br d, J=16.4 Hz, 1H), 2.34-2.46 (m, 1H), 2.22-2.34 (m, 1H), 1.52 (d, J=6.9 Hz, 3H), 1.30-1.37 (m, 2H), 1.21-1.30 (m, 2H).

Minor Rotamer (35%)

¹H NMR (500 MHz, DMSO-$d_6$) δ ppm 8.03 (t, J=8.7 Hz, 1H), 7.10-7.25 (m, 3H), 7.07 (br d, J=7.6 Hz, 1H), 6.94-6.98 (m, 1H), 6.78 (s, 1H), 6.53-6.61 (m, 2H), 4.96 (q, J=6.8 Hz, 1H), 4.51-4.59 (m, 1H), 3.55-3.70 (m, 3H), 3.34-3.53 (m, 2H), 3.22-3.30 (m, 1H), 2.83-3.07 (m, 3H), 2.34-2.46 (m, 1H), 2.22-2.34 (m, 1H), 1.55 (d, J=6.6 Hz, 3H), 1.30-1.37 (m, 2H), 1.21-1.30 (m, 2H).

Compound 2

Major Rotamer (65%)

¹H NMR (400 MHz, DMSO-$d_6$) δ ppm 16.31 (br s, 1H), 8.02 (t, J=8.8 Hz, 1H), 7.32 (br d, J=7.1 Hz, 1H), 7.06-7.26 (m, 3H), 6.92-6.97 (m, 1H), 6.81 (s, 1H), 6.58 (br d, J=9.1 Hz, 1H), 6.51 (dd, J=14.7, 1.5 Hz, 1H), 5.58 (q, J=6.7 Hz, 1H), 3.97 (quin, J=7.2 Hz, 1H), 3.77-3.87 (m, 2H), 3.60 (dd, J=9.9, 6.8 Hz, 1H), 3.42-3.54 (m, 3H), 2.85-3.06 (m, 2H), 2.71 (br d, J=16.2 Hz, 1H), 2.44-2.57 (m, 1H partially obscured by DMSO peak), 2.25-2.35 (m, 1H), 1.52 (d, J=6.6 Hz, 3H), 1.30-1.38 (m, 2H), 1.22-1.29 (m, 2H).

Minor Rotamer (35%)

¹H NMR (400 MHz, DMSO-$d_6$) δ ppm 16.31 (br s, 1H), 8.02 (t, J=8.8 Hz, 1H), 7.06-7.26 (m, 4H), 6.92-6.97 (m, 1H), 6.77 (s, 1H), 6.58 (br d, J=9.1 Hz, 1H), 6.51 (dd, J=14.7, 1.5 Hz, 1H), 4.96 (q, J=6.6 Hz, 1H), 4.55 (br d, J=12.1 Hz, 1H), 3.97 (quin, J=7.2 Hz, 1H), 3.77-3.87 (m, 1H), 3.60 (dd, J=9.9, 6.8 Hz, 1H), 3.42-3.54 (m, 3H), 2.85-3.06 (m, 3H), 2.44-2.57 (m, 1H partially obscured by DMSO peak), 2.25-2.35 (m, 1H), 1.55 (d, J=7.1 Hz, 3H), 1.30-1.38 (m, 2H), 1.22-1.29 (m, 2H).

Compound 3

Major Rotamer (65%)

¹H NMR (400 MHz, DMSO-$d_6$) δ ppm 16.34 (br s, 1H), 8.03 (t, J=8.6 Hz, 1H), 7.32 (d, J=7.1 Hz, 1H), 7.05-7.26 (m, 3H), 6.91-6.97 (m, 1H), 6.81 (s, 1H), 6.58 (br d, J=8.6 Hz, 1H), 6.51 (dd, J=14.7, 2.0 Hz, 1H), 5.58 (q, J=6.9 Hz, 1H), 3.98 (quin, J=7.2 Hz, 1H), 3.77-3.88 (m, 2H), 3.60 (dd, J=9.6, 6.6 Hz, 1H), 3.41-3.55 (m, 3H), 2.85-3.07 (m, 2H), 2.71 (br d, J=15.7 Hz, 1H), 2.39-2.50 (m, 1H obscured by solvent peak), 2.23-2.36 (m, 1H), 1.52 (d, J=6.6 Hz, 3H), 1.30-1.38 (m, 2H), 1.20-1.29 (m, 2H).

Minor Rotamer (35%)

¹H NMR (400 MHz, DMSO-$d_6$) δ ppm 16.34 (br s, 1H), 8.03 (t, J=8.6 Hz, 1H), 7.05-7.26 (m, 4H), 6.91-6.97 (m, 1H), 6.77 (s, 1H), 6.58 (br d, J=8.6 Hz, 1H), 6.51 (dd, J=14.7, 2.0 Hz, 1H), 4.96 (q, J=6.9 Hz, 1H), 4.50-4.59 (m, 1H), 3.98 (quin, J=7.2 Hz, 1H), 3.77-3.88 (m, 1H), 3.60 (dd, J=9.6, 6.6 Hz, 1H), 3.41-3.55 (m, 2H), 3.21-3.28 (m, 1H), 2.85-3.07 (m, 3H), 2.39-2.50 (m, 1H obscured by solvent peak), 2.23-2.36 (m, 1H), 1.55 (d, J=7.1 Hz, 3H), 1.30-1.38 (m, 2H), 1.20-1.29 (m, 2H).

Compound 4

Major Rotamer (65%)

¹H NMR (500 MHz, DMSO-$d_6$) δ ppm 12.43 (br s, 1H), 8.03 (t, J=8.8 Hz, 1H), 7.32 (d, J=7.6 Hz, 1H), 7.06-7.25 (m, 3H), 6.92-6.98 (m, 1H), 6.81 (s, 1H), 6.56 (br d, J=8.8 Hz, 1H), 6.48 (br dd, J=14.5, 1.6 Hz, 1H), 5.59 (q, J=6.6 Hz, 1H), 3.81 (br dd, J=13.7, 3.6 Hz, 1H), 3.64-3.71 (m, 1H), 3.60 (quin, J=7.1 Hz, 1H), 3.38-3.56 (m, 4H), 2.83-3.06 (m, 2H), 2.62-2.74 (m, 1H), 2.34-2.44 (m, 1H), 2.19-2.27 (m, 1H), 1.52 (d, J=6.6 Hz, 3H), 1.30-1.37 (m, 2H), 1.21-1.30 (m, 2H).

Minor Rotamer (35%)

¹H NMR (500 MHz, DMSO-$d_6$) δ ppm 12.43 (br s, 1H), 8.03 (t, J=8.8 Hz, 1H), 7.06-7.25 (m, 3H), 6.92-6.98 (m, 1H), 6.78 (s, 1H), 6.75 (d, J=8.5 Hz, 1H), 6.56 (br d, J=8.8 Hz, 1H), 6.48 (br dd, J=14.5, 1.6 Hz, 1H), 4.96 (q, J=6.6 Hz, 1H), 4.52-4.58 (m, 1H), 3.64-3.71 (m, 1H), 3.60 (quin, J=7.1 Hz, 1H), 3.38-3.56 (m, 3H), 3.23-3.29 (m, 1H), 2.83-3.06 (m, 3H), 2.34-2.44 (m, 1H), 2.19-2.27 (m, 1H), 1.56 (d, J=6.6 Hz, 3H), 1.30-1.37 (m, 2H), 1.21-1.30 (m, 2H).

Compound 5

Major Rotamer (65%)

¹H NMR (400 MHz, DMSO-$d_6$) δ ppm 8.00 (t, J=8.8 Hz, 1H), 7.31 (d, J=7.1 Hz, 1H), 7.05-7.26 (m, 3H), 6.90-6.96 (m, 1H), 6.81 (s, 1H), 6.53 (dd, J=8.6, 1.5 Hz, 1H), 6.45 (dd, J=13.9, 1.5 Hz, 1H), 5.58 (q, J=6.7 Hz, 1H), 4.61 (d, J=6.1 Hz, 2H), 4.54 (d, J=6.1 Hz, 2H), 3.81 (br dd, J=14.2, 4.04 Hz, 1H), 3.59 (s, 2H), 3.41-3.50 (m, 1H), 3.29-3.37 (m, 2H partially obscured by $H_2O$ peak), 2.85-3.06 (m, 2H), 2.71 (br d, J=16.7 Hz, 1H), 2.29 (t, J=6.8 Hz, 2H), 1.51 (d, J=7.1 Hz, 3H), 1.29-1.38 (m, 2H), 1.21-1.29 (m, 2H).

Minor Rotamer (35%)

¹H NMR (400 MHz, DMSO-$d_6$) δ ppm 8.00 (t, J=8.8 Hz, 1H), 7.05-7.26 (m, 4H), 6.90-6.96 (m, 1H), 6.77 (s, 1H), 6.53 (dd, J=8.6, 1.5 Hz, 1H), 6.45 (dd, J=13.9, 1.5 Hz, 1H), 4.93 (q, J=6.1 Hz, 1H), 4.61 (d, J=6.1 Hz, 2H), 4.54 (d, J=6.1 Hz, 2H), 4.50-4.58 (m, 1H), 3.59 (s, 2H), 3.29-3.37 (m, 2H partially obscured by $H_2O$ peak), 3.21-3.29 (m, 1H), 2.85-3.06 (m, 3H), 2.29 (t, J=6.8 Hz, 2H), 1.54 (d, J=7.1 Hz, 3H), 1.29-1.38 (m, 2H), 1.21-1.29 (m, 2H).

Compound 6

Major Rotamer (65%)

$^1$H NMR (400 MHz, DMSO-$d_6$) δ ppm 8.02 (t, J=8.8 Hz, 1H) 7.32 (d, J=7.1 Hz, 1H), 7.06-7.25 (m, 3H), 6.92-6.96 (m, 1H), 6.81 (s, 1H), 6.52 (dd, J=8.6, 2.0 Hz, 1H), 6.46 (dd, J=14.7, 1.5 Hz, 1H), 5.58 (q, J=6.4 Hz, 1H), 4.26 (q, J=13.1 Hz, 4H), 3.77-3.84 (m, 1H), 3.60 (s, 2H), 3.38-3.50 (m, 3H), 2.84-3.05 (m, 2H), 2.71 (br d, J=16.2 Hz, 1H), 2.28-2.33 (m, 2H), 1.52 (d, J=6.6 Hz, 3H), 1.30-1.37 (m, 2H), 1.29-1.21 (m, 2H).

Minor Rotamer (35%)

$^1$H NMR (400 MHz, DMSO-$d_6$) δ ppm 8.02 (t, J=8.8 Hz, 1H), 7.06-7.25 (m, 4H) 6.92-6.96 (m, 1H), 6.77 (s, 1H), 6.52 (dd, J=8.6, 2.0 Hz, 1H), 6.45 (dd, J=14.7, 1.5 Hz, 1H), 4.95 (q, J=7.1 Hz, 1H), 4.52-4.58 (m, 1H), 4.26 (q, J=13.1 Hz, 4H), 3.60 (s, 2H), 3.38-3.50 (m, 2H), 3.22-3.30 (m, 1H), 2.84-3.05 (m, 3H), 2.28-2.33 (m, 2H), 1.54 (d, J=7.1 Hz, 3H), 1.30-1.37 (m, 2H), 1.29-1.21 (m, 2H).

Compound 7

Major Rotamer (65%)

$^1$H NMR (400 MHz, DMSO-$d_6$) δ ppm 8.19 (br d, J=6.6 Hz, 1H), 8.01 (t, J=8.8 Hz, 1H), 7.32 (br d, J=7.6 Hz, 1H), 7.05-7.25 (m, 3H), 6.91-6.96 (m, 1H), 6.80 (s, 1H), 6.52 (br d, J=9.1 Hz, 1H), 6.46 (br d, J=14.7 Hz, 1H), 5.58 (q, J=7.1 Hz, 1H), 4.34-4.42 (m, 1H), 3.77-3.85 (m, 1H), 3.55 (br dd, J=10.1, 6.1 Hz, 1H), 3.34-3.50 (m, 3H), 3.14 (br dd, J=10.1, 3.5 Hz, 1H), 2.85-3.06 (m, 2H), 2.71 (br d, J=16.7 Hz, 1H), 2.13-2.24 (m, 1H), 1.86-1.96 (m, 1H), 1.82 (s, 3H), 1.52 (d, J=6.6 Hz, 3H), 1.30-1.38 (m, 2H), 1.19-1.30 (m, 2H).

Minor Rotamer (35%)

$^1$H NMR (400 MHz, DMSO-$d_6$) δ ppm 8.19 (br d, J=6.6 Hz, 1H), 8.01 (t, J=8.8 Hz, 1H), 7.05-7.25 (m, 4H), 6.91-6.96 (m, 1H), 6.77 (s, 1H), 6.52 (br d, J=9.1 Hz, 1H), 6.46 (br d, J=14.7 Hz, 1H), 4.96 (q, J=6.6 Hz, 1H), 4.51-4.59 (m, 1H), 4.34-4.42 (m, 1H), 3.55 (br dd, J=10.1, 6.1 Hz, 1H), 3.34-3.50 (m, 2H), 3.21-3.30 (m, 1H), 3.14 (br dd, J=10.1, 3.5 Hz, 1H), 2.85-3.06 (m, 3H), 2.13-2.24 (m, 1H), 1.86-1.96 (m, 1H), 1.83 (s, 3H), 1.55 (d, J=6.6 Hz, 3H), 1.30-1.38 (m, 2H), 1.19-1.30 (m, 2H).

Compound 8

Major Rotamer (65%)

$^1$H NMR (500 MHz, DMSO-$d_6$) δ ppm 8.19 (d, J=6.9 Hz, 1H), 8.01 (t, J=8.8 Hz, 1H), 7.32 (d, J=7.6 Hz, 1H), 7.21-7.25 (m, 1H), 7.10-7.21 (m, 2H), 6.94 (d, J=3.5 Hz, 1H), 6.81 (s, 1H), 6.53 (br d, J=8.8 Hz, 1H), 6.46 (dd, J=14.5, 1.9 Hz, 1H), 5.59 (q, J=6.8 Hz, 1H), 4.35-4.42 (m, 1H), 3.81 (br dd, J=13.7, 3.6 Hz, 1H), 3.56 (dd, J=9.9, 6.5 Hz, 1H), 3.33-3.50 (m, 3H), 3.14 (dd, J=10.1, 4.1 Hz, 1H), 2.85-3.05 (m, 2H), 2.72 (br d, J=16.1 Hz, 1H), 2.15-2.23 (m, 1H), 1.88-1.95 (m, 1H), 1.82 (s, 3H), 1.52 (d, J=6.9 Hz, 3H), 1.30-1.37 (m, 2H), 1.22-1.30 (m, 2H).

Minor Rotamer (35%)

$^1$H NMR (500 MHz, DMSO-$d_6$) δ ppm 8.19 (d, J=6.9 Hz, 1H), 8.01 (t, J=8.8 Hz, 1H), 7.10-7.21 (m, 3H), 7.06-7.09 (m, 1H), 6.93 (d, J=3.5 Hz, 1H), 6.77 (s, 1H), 6.53 (br d, J=8.8 Hz, 1H), 6.46 (dd, J=14.5, 1.9 Hz, 1H), 4.96 (q, J=6.5 Hz, 1H), 4.52-4.58 (m, 1H), 4.35-4.42 (m, 1H), 3.56 (dd, J=9.9, 6.5 Hz, 1H), 3.33-3.50 (m, 2H), 3.23-3.30 (m, 1H), 3.14 (dd, J=10.1, 4.1 Hz, 1H), 2.85-3.05 (m, 3H), 2.15-2.23 (m, 1H), 1.88-1.95 (m, 1H), 1.82 (s, 3H), 1.55 (d, J=6.6 Hz, 3H), 1.30-1.37 (m, 2H), 1.22-1.30 (m, 2H).

Compound 9

Major Rotamer (65%)

$^1$H NMR (400 MHz, DMSO-$d_6$) δ ppm 8.00 (t, J=9.1 Hz, 1H), 7.55 (br d, J=6.1 Hz, 1H), 7.32 (br d, J=7.6 Hz, 1H), 7.05-7.25 (m, 3H), 6.90-6.96 (m, 1H), 6.80 (s, 1H), 6.51 (br d, J=8.6 Hz, 1H), 6.44 (br d, J=14.7 Hz, 1H), 5.58 (q, J=6.9 Hz, 1H), 4.16-4.25 (m, 1H), 3.81 (br dd, J=12.9, 2.8 Hz, 1H), 3.51-3.60 (m, 1H), 3.55 (s, 3H), 3.34-3.51 (m, 3H), 3.16 (br dd, J=9.6, 4.6 Hz, 1H), 2.85-3.06 (m, 2H), 2.71 (br d, J=16.2 Hz, 1H), 2.14-2.25 (m, 1H), 1.87-2.02 (m, 1H), 1.50 (d, J=7.1 Hz, 3H), 1.30-1.38 (m, 2H), 1.20-1.29 (m, 2H).

Minor Rotamer (35%)

$^1$H NMR (400 MHz, DMSO-$d_6$) δ ppm 8.00 (t, J=9.1 Hz, 1H), 7.55 (br d, J=6.1 Hz, 1H), 7.05-7.25 (m, 4H), 6.90-6.96 (m, 1H), 6.77 (s, 1H), 6.51 (br d, J=8.6 Hz, 1H), 6.44 (br d, J=14.7 Hz, 1H), 4.96 (q, J=6.6 Hz, 1H), 4.55 (br d, J=12.6 Hz, 1H), 4.16-4.25 (m, 1H), 3.55 (s, 3H), 3.34-3.51 (m, 3H), 3.21-3.29 (m, 1H), 3.16 (br dd, J=9.6, 4.6 Hz, 1H), 2.85-3.06 (m, 3H), 2.14-2.25 (m, 1H), 1.87-2.02 (m, 1H), 1.55 (d, J=7.1 Hz, 3H), 1.30-1.38 (m, 2H) 1.20-1.29 (m, 2H).

Compound 10

Major Rotamer (65%)

$^1$H NMR (400 MHz, DMSO-$d_6$) δ ppm 8.00 (t, J=8.8 Hz, 1H), 7.55 (br d, J=6.1 Hz, 1H), 7.32 (br d, J=7.6 Hz, 1H), 7.05-7.26 (m, 3H), 6.91-6.95 (m, 1H), 6.80 (s, 1H), 6.51 (br d, J=9.1 Hz, 1H), 6.45 (dd, J=14.7, 1.5 Hz, 1H), 5.58 (q, J=6.6 Hz, 1H), 4.16-4.25 (m, 1H), 3.81 (br dd, J=12.9, 3.8 Hz, 1H), 3.52-3.59 (m, 4H), 3.39-3.51 (m, 3H), 3.13-3.20 (m, 1H), 2.82-3.06 (m, 2H), 2.71 (br d, J=17.2 Hz, 1H), 2.13-2.24 (m, 1H), 1.88-1.99 (m, 1H), 1.52 (d, J=7.1 Hz, 3H), 1.29-1.37 (m, 2H), 1.20-1.29 (m, 2H).

Minor Rotamer (35%)

$^1$H NMR (400 MHz, DMSO-$d_6$) δ ppm 8.00 (t, J=8.8 Hz, 1H), 7.55 (br d, J=6.1 Hz, 1H), 7.05-7.26 (m, 4H), 6.91-6.95 (m, 1H), 6.77 (s, 1H), 6.51 (br d, J=9.1 Hz, 1H), 6.45 (dd, J=14.7, 1.5 Hz, 1H), 4.96 (q, J=6.6 Hz, 1H), 4.51-4.58 (m, 1H), 4.16-4.25 (m, 1H), 3.52-3.59 (m, 3H), 3.39-3.51 (m, 2H), 3.21-3.29 (m, 1H), 3.13-3.20 (m, 1H), 2.82-3.06 (m, 3H), 2.67-2.76 (m, 1H), 2.13-2.24 (m, 1H), 1.88-1.99 (m, 1H), 1.53 (d, J=7.1 Hz, 3H), 1.29-1.37 (m, 2H), 1.20-1.29 (m, 2H).

Compound 11

Major Rotamer (65%)

$^1$H NMR (400 MHz, DMSO-$d_6$) δ ppm 8.00 (t, J=8.6 Hz, 1H), 7.48 (br d, J=7.1 Hz, 1H), 7.29-7.35 (m, 1H), 7.05-7.25 (m, 3H), 6.94 (br s, 1H), 6.80 (br s, 1H), 6.53 (br d, J=9.1 Hz, 1H), 6.47 (br d, J=14.2 Hz, 1H), 5.54-5.62 (m, 1H), 4.03-4.13 (m, 1H), 3.76-3.85 (m, 1H), 3.59-3.67 (m, 1H), 3.39-3.52 (m, 2H), 3.32-3.37 (m, 1H partially obscured by H$_2$O), 3.17-3.24 (m, 1H), 3.00 (s, 3H), 2.82-2.98 (m, 2H), 2.65-2.76 (m, 1H), 2.23-2.32 (m, 1H), 1.93-2.04 (m, 1H), 1.47-1.54 (m, 3H), 1.30-1.40 (m, 2H), 1.20-1.30 (m, 2H).

Minor Rotamer (35%)

$^1$H NMR (400 MHz, DMSO-$d_6$) δ ppm 8.00 (t, J=8.6 Hz, 1H), 7.48 (br d, J=7.1 Hz, 1H), 7.05-7.25 (m, 4H), 6.94 (br s, 1H), 6.77 (br s, 1H), 6.53 (br d, J=9.1 Hz, 1H), 6.47 (br d, J=14.2 Hz, 1H), 4.91-5.00 (m, 1H), 4.51-4.58 (m, 1H), 4.03-4.13 (m, 1H), 3.59-3.67 (m, 1H), 3.39-3.52 (m, 2H), 3.24-3.28 (m, 1H), 3.17-3.24 (m, 1H), 3.00 (s, 3H), 2.82-

2.98 (m, 3H), 2.23-2.32 (m, 1H), 1.93-2.04 (m, 1H), 1.58-1.53 (m, 3H), 1.30-1.40 (m, 2H), 1.20-1.30 (m, 2H).

Compound 12

Major Rotamer (65%)

$^1$H NMR (500 MHz, DMSO-d$_6$) δ ppm 8.01 (t, J=8.7 Hz, 1H), 7.49 (d, J=6.6 Hz, 1H), 7.32 (d, J=7.3 Hz, 1H), 7.06-7.25 (m, 3H), 6.91-6.96 (m, 1H), 6.81 (s, 1H), 6.53 (br d, J=8.8 Hz, 1H), 6.47 (br d, J=14.8 Hz, 1H), 5.59 (q, J=6.6 Hz, 1H), 4.05-4.13 (m, 1H), 3.81 (br dd, J=12.5, 3.3 Hz, 1H), 3.63 (br dd, J=9.8, 6.6 Hz, 1H), 3.41-3.50 (m, 2H), 3.33-3.36 (m, 1H), 3.21 (dd, J=9.9, 5.5 Hz, 1H), 3.01 (s, 3H), 2.83-2.98 (m, 2H), 2.72 (br d, J=16.4 Hz, 1H), 2.23-2.33 (m, 1H), 1.93-2.03 (m, 1H), 1.52 (d, J=6.9 Hz, 3H), 1.30-1.38 (m, 2H), 1.21-1.30 (m, 2H).

Minor Rotamer (35%)

$^1$H NMR (500 MHz, DMSO-d$_6$) δ ppm 8.01 (t, J=8.7 Hz, 1H), 7.49 (d, J=6.6 Hz, 1H), 7.06-7.25 (m, 4H), 6.91-6.96 (m, 1H), 6.77 (s, 1H), 6.53 (br d, J=8.8 Hz, 1H), 6.47 (br d, J=14.8 Hz, 1H), 4.96 (q, J=6.7 Hz, 1H), 4.52-4.59 (m, 1H), 4.05-4.13 (m, 1H), 3.63 (br dd, J=9.8, 6.6 Hz, 1H), 3.41-3.50 (m, 2H), 3.24-3.30 (m, 1H), 3.21 (dd, J=9.9, 5.5 Hz, 1H), 3.02-3.06 (m, 1H), 3.01 (s, 3H), 2.83-2.98 (m, 2H), 2.23-2.33 (m, 1H), 1.93-2.03 (m, 1H), 1.55 (d, J=6.6 Hz, 3H), 1.30-1.38 (m, 2H), 1.21-1.30 (m, 2H).

Compound 13

Major Rotamer (65%)

$^1$H NMR (500 MHz, DMSO-d$_6$) δ ppm 7.99 (t, J=8.8 Hz, 1H), 7.32 (d, J=7.6 Hz, 1H), 7.06-7.25 (m, 3H), 6.91-6.95 (m, 1H), 6.80 (s, 1H), 6.51 (dd, J=8.7, 1.7 Hz, 1H), 6.43 (dd, J=14.8, 1.6 Hz, 1H), 5.59 (q, J=6.4 Hz, 1H), 5.01 (d, J=3.8 Hz, 1H), 4.43 (br s, 1H), 3.82 (br dd, J=13.7, 4.3 Hz, 1H), 3.33-3.50 (m, 4H), 3.16 (br d, J=10.4 Hz, 1H), 2.82-3.05 (m, 2H), 2.72 (br d, J=16.1 Hz, 1H), 2.02-2.11 (m, 1H), 1.89-1.96 (m, 1H), 1.52 (d, J=6.6 Hz, 3H), 1.30-1.37 (m, 2H), 1.22-1.29 (m, 2H).

Minor Rotamer (35%)

$^1$H NMR (500 MHz, DMSO-d$_6$) δ ppm 7.99 (t, J=8.8 Hz, 1H), 7.06-7.25 (m, 4H), 6.91-6.95 (m, 1H), 6.76 (s, 1H), 6.51 (dd, J=8.7, 1.7 Hz, 1H), 6.43 (dd, J=14.8, 1.6 Hz, 1H), 5.01 (d, J=3.8 Hz, 1H), 4.97 (q, J=6.6 Hz, 1H), 4.52-4.58 (m, 1H), 4.43 (br s, 1H), 3.60 (dt, J=12.1, 6.1 Hz, 1H), 3.33-3.50 (m, 2H), 3.23-3.28 (m, 1H), 3.16 (br d, J=10.4 Hz, 1H), 2.82-3.05 (m, 3H), 2.02-2.11 (m, 1H), 1.89-1.96 (m, 1H), 1.55 (d, J=6.6 Hz, 3H), 1.30-1.37 (m, 2H), 1.22-1.29 (m, 2H).

Compound 14

Major Rotamer (65%)

$^1$H NMR (400 MHz, DMSO-d$_6$) δ ppm 7.99 (t, J=8.8 Hz, 1H), 7.32 (br d, J=7.1 Hz, 1H), 7.05-7.25 (m, 3H), 6.90-6.94 (m, 1H), 6.80 (s, 1H), 6.51 (dd, J=8.8, 1.8 Hz, 1H), 6.43 (dd, J=14.4, 1.3 Hz, 1H), 5.58 (q, J=6.6 Hz, 1H), 5.02 (d, J=3.5 Hz, 1H), 4.42 (br s, 1H), 3.77-3.85 (m, 1H), 3.34-3.51 (m, 4H), 3.16 (br d, J=10.1 Hz, 1H), 2.85-3.07 (m, 2H), 2.71 (br d, J=16.2 Hz, 1H), 2.00-2.12 (m, 1H), 1.88-1.97 (m, 1H), 1.52 (d, J=7.1 Hz, 3H), 1.21-1.37 (m, 4H).

Minor Rotamer (35%)

$^1$H NMR (400 MHz, DMSO-d$_6$) δ ppm 7.99 (t, J=8.8 Hz, 1H), 7.05-7.25 (m, 4H), 6.90-6.94 (m, 1H), 6.76 (s, 1H), 6.51 (dd, J=8.8, 1.8 Hz, 1H), 6.43 (dd, J=14.4, 1.3 Hz, 1H), 5.02 (d, J=3.5 Hz, 1H), 4.96 (q, J=6.6 Hz, 1H), 4.51-4.59 (m, 1H), 4.42 (br s, 1H), 3.34-3.51 (m, 3H), 3.22-3.29 (m, 1H), 3.16 (br d, J=10.1 Hz, 1H), 2.85-3.07 (m, 3H), 2.00-2.12 (m, 1H), 1.88-1.97 (m, 1H), 1.55 (br d, J=7.1 Hz, 3H), 1.21-1.37 (m, 4H).

Compound 15

Major Rotamer (65%)

$^1$H NMR (400 MHz, DMSO-d$_6$) δ ppm 8.01 (br t, J=8.8 Hz, 1H), 7.32 (br d, J=8.1 Hz, 1H), 7.05-7.25 (m, 3H), 6.91-6.96 (m, 1H), 6.81 (s, 1H), 6.54 (br d, J=8.6 Hz, 1H), 6.49 (br d, J=15.2 Hz, 1H), 5.54-5.62 (m, 1H), 5.27 (br s, 1H), 3.81 (br d, J=14.2 Hz, 1H), 3.60 (br dd, J=10.9, 4.3 Hz, 1H), 3.30-3.51 (m, 5H, partially obscured by H$_2$O peak), 2.85-3.07 (m, 2H), 2.64-2.75 (m, 1H), 2.55-2.62 (m, 3H), 2.19-2.29 (m, 1H), 2.04-2.14 (m, 1H), 1.52 (br d, J=7.1 Hz, 3H), 1.30-1.38 (m, 2H), 1.21-1.29 (m, 2H).

Minor Rotamer (35%)

$^1$H NMR (400 MHz, DMSO-d$_6$) δ ppm 8.01 (br t, J=8.8 Hz, 1H), 7.05-7.25 (m, 4H), 6.91-6.96 (m, 1H), 6.77 (s, 1H), 6.54 (br d, J=8.6 Hz, 1H), 6.49 (br d, J=15.2 Hz, 1H), 5.27 (br s, 1H), 4.92-5.00 (m, 1H), 4.51-4.59 (m, 1H), 3.60 (br dd, J=10.9, 4.3 Hz, 1H), 3.30-3.51 (m, 3H partially obscured by H$_2$O peak), 3.21-3.28 (m, 1H), 2.85-3.07 (m, 3H), 2.64-2.75 (m, 1H), 2.55-2.62 (m, 3H), 2.19-2.29 (m, 1H), 2.04-2.14 (m, 1H), 1.54 (br d, J=7.6 Hz, 3H), 1.30-1.38 (m, 2H), 1.21-1.29 (m, 2H).

Compound 16

Major Rotamer (65%)

$^1$H NMR (400 MHz, DMSO-d$_6$) δ ppm 8.01 (t, J=8.8 Hz, 1H), 7.32 (br d, J=7.6 Hz, 1H), 7.05-7.25 (m, 4H), 6.91-6.95 (m, 1H), 6.81 (s, 1H), 6.55 (br d, J=9.6 Hz, 1H), 6.48 (br d, J=14.7 Hz, 1H), 5.58 (q, J=6.7 Hz, 1H), 5.27 (br s, 1H), 3.81 (br dd, J=14.2, 3.5 Hz, 1H), 3.61 (br dd, J=11.1, 4.6 Hz, 1H), 3.34-3.51 (m, 4H), 2.85-3.07 (m, 2H), 2.71 (br d, J=16.7 Hz, 1H), 2.54-2.59 (m, 3H), 2.19-2.30 (m, 1H), 2.08-2.13 (m, 1H), 1.52 (d, J=6.6 Hz, 3H), 1.29-1.38 (m, 2H), 1.20-1.29 (m, 2H).

Minor Rotamer (35%)

$^1$H NMR (400 MHz, DMSO-d$_6$) δ ppm 8.01 (t, J=8.8 Hz, 1H), 7.05-7.25 (m, 5H), 6.91-6.95 (m, 1H), 6.77 (s, 1H), 6.55 (br d, J=9.6 Hz, 1H), 6.48 (br d, J=14.7 Hz, 1H), 5.27 (br s, 1H), 4.91-5.00 (m, 1H), 4.51-4.59 (m, 1H), 3.61 (br dd, J=11.1, 4.6 Hz, 1H), 3.34-3.51 (m, 2H), 3.21-3.29 (m, 1H), 2.85-3.07 (m, 3H), 2.64-2.76 (m, 1H), 2.54-2.59 (m, 3H), 2.19-2.30 (m, 1H), 2.08-2.13 (m, 1H), 1.54 (d, J=7.1 Hz, 3H), 1.29-1.38 (m, 2H), 1.20-1.29 (m, 2H).

Compound 17

Major Rotamer (65%)

$^1$H NMR (400 MHz, DMSO-d$_6$) δ ppm 8.02 (t, J=8.3 Hz, 1H), 7.32 (d, J=6.1 Hz, 1H), 7.05-7.25 (m, 3H), 6.93-6.97 (m, 1H), 6.81 (s, 1H), 6.54-6.64 (m, 2H), 5.58 (q, J=7.1 Hz, 1H), 4.10-4.18 (m, 1H), 3.78-3.85 (m, 1H), 3.70 (d, J=7.1 Hz, 2H), 3.36-3.56 (m, 3H), 3.09 (s, 3H), 2.82-3.06 (m, 2H), 2.68-2.76 (m, 1H), 2.39-2.46 (m, 2H), 1.52 (br d, J=6.6 Hz, 3H), 1.20-1.38 (m, 4H).

Minor Rotamer (35%)

$^1$H NMR (400 MHz, DMSO-d$_6$) δ ppm 8.02 (t, J=8.3 Hz, 1H), 7.05-7.25 (m, 4H), 6.93-6.97 (m, 1H), 6.78 (s, 1H), 6.54-6.64 (m, 2H), 4.96 (q, J=6.9 Hz, 1H), 4.51-4.59 (m, 1H), 4.10-4.18 (m, 1H), 3.70 (d, J=7.1 Hz, 2H), 3.36-3.56 (m, 2H), 3.21-3.28 (m, 1H), 3.09 (s, 3H), 2.82-3.06 (m, 3H), 2.39-2.46 (m, 2H), 1.55 (br d, J=7.1 Hz, 3H), 1.20-1.38 (m, 4H).

Compound 18

Major Rotamer (65%)
¹H NMR (400 MHz, DMSO-d$_6$) δ ppm 8.02 (t, J=8.6 Hz, 1H), 7.32 (br d, J=7.1 Hz, 1H), 7.05-7.25 (m, 3H), 6.93-6.98 (m, 1H), 6.82 (s, 1H), 6.54-6.64 (m, 2H), 5.58 (q, J=7.1 Hz, 1H), 4.14 (quin, J=6.7 Hz, 1H), 3.81 (br dd, J=13.6, 4.6 Hz, 1H), 3.70 (d, J=7.1 Hz, 2H), 3.32-3.65 (m, 3H), 3.09 (s, 3H), 2.85-3.06 (m, 2H), 2.71 (br d, J=16.2 Hz, 1H), 2.38-2.46 (m, 2H), 1.52 (d, J=7.1 Hz, 3H), 1.30-1.39 (m, 2H), 1.21-1.30 (m, 2H).
Minor Rotamer (35%)
¹H NMR (400 MHz, DMSO-d$_6$) δ ppm 8.02 (t, J=8.6 Hz, 1H), 7.05-7.25 (m, 4H), 6.93-6.98 (m, 1H), 6.78 (s, 1H), 6.54-6.64 (m, 2H), 4.96 (q, J=6.1 Hz, 1H), 4.51-4.59 (m, 1H), 4.14 (quin, J=6.7 Hz, 1H), 3.70 (d, J=7.1 Hz, 2H), 3.32-3.65 (m, 2H), 3.22-3.31 (m, 1H), 3.09 (s, 3H), 2.85-3.06 (m, 3H), 2.38-2.46 (m, 2H), 1.55 (d, J=6.6 Hz, 3H), 1.30-1.39 (m, 2H), 1.21-1.30 (m, 2H).

Compound 19

Major Rotamer (65%)
¹H NMR (400 MHz, DMSO-d$_6$) δ ppm 8.03 (t, J=8.8 Hz, 1H), 7.32 (d, J=7.1 Hz, 1H), 7.04-7.26 (m, 5H), 6.93-6.97 (m, 1H), 6.81 (s, 1H), 6.57 (dd, J=9.1, 2.0 Hz, 1H), 6.51 (dd, J=14.2, 2.0 Hz, 1H), 5.58 (q, J=7.1 Hz, 1H), 3.89-3.97 (m, 1H), 3.77-3.85 (m, 1H), 3.61-3.73 (m, 2H), 3.37-3.54 (m, 3H), 2.85-3.06 (m, 2H), 2.71 (br d, J=16.7 Hz, 1H), 2.35-2.43 (m, 2H), 1.52 (d, J=6.6 Hz, 3H), 1.30-1.38 (m, 2H), 1.22-1.29 (m, 2H).
Minor Rotamer (35%)
¹H NMR (400 MHz, DMSO-d$_6$) δ ppm 8.03 (t, J=8.8 Hz, 1H), 7.04-7.26 (m, 6H), 6.93-6.97 (m, 1H), 6.78 (s, 1H), 6.57 (dd, J=9.1, 2.0 Hz, 1H), 6.51 (dd, J=14.2, 2.0 Hz, 1H), 4.97 (q, J=7.1 Hz, 1H), 4.51-4.58 (m, 1H), 3.89-3.97 (m, 1H), 3.61-3.73 (m, 2H), 3.37-3.54 (m, 2H), 3.22-3.29 (m, 1H), 2.85-3.06 (m, 3H), 2.35-2.43 (m, 2H), 1.55 (d, J=6.6 Hz, 3H), 1.30-1.38 (m, 2H), 1.22-1.29 (m, 2H).

Compound 20

Major Rotamer (65%)
¹H NMR (400 MHz, DMSO-d$_6$) δ ppm 11.78 (br s, 1H), 7.96 (t, J=8.8 Hz, 1H), 7.25 (d, J=7.6 Hz, 1H), 6.99-7.20 (m, 3H), 6.86-6.91 (m, 1H), 6.75 (s, 1H), 6.45-6.55 (m, 2H), 5.52 (q, J=6.9 Hz, 1H), 4.30-4.38 (m, 1H), 3.72-3.78 (m, 1H), 3.58-3.71 (m, 2H), 3.33-3.46 (m, 3H), 2.78-3.01 (m, 2H), 2.65 (br d, J=16.2 Hz, 1H), 2.29-2.39 (m, 2H partially obscured by H$_2$O peak), 1.97 (s, 3H), 1.45 (d, J=6.6 Hz, 3H), 1.23-1.32 (m, 2H), 1.16-1.23 (m, 2H).
Minor Rotamer (35%)
¹H NMR (400 MHz, DMSO-d$_6$) δ ppm 11.78 (br s, 1H), 7.96 (t, J=8.8 Hz, 1H), 6.99-7.20 (m, 4H), 6.86-6.91 (m, 1H), 6.71 (s, 1H), 6.45-6.55 (m, 2H), 4.89 (q, J=7.1 Hz, 1H), 4.45-4.52 (m, 1H), 4.30-4.38 (m, 1H), 3.58-3.71 (m, 2H), 3.33-3.46 (m, 2H), 3.15-3.22 (m, 1H), 2.78-3.01 (m, 3H), 2.29-2.39 (m, 2H partially obscured by H$_2$O peak), 1.97 (s, 3H), 1.48 (d, J=7.1 Hz, 3H), 1.23-1.32 (m, 2H), 1.16-1.23 (m, 2H).

Compound 21

Major Rotamer (65%)
¹H NMR (400 MHz, DMSO-d$_6$) δ ppm 8.02 (t, J=8.8 Hz, 1H), 7.32 (br d, J=7.6 Hz, 1H), 7.06-7.26 (m, 4H), 6.93-6.97 (m, 1H), 6.81 (s, 1H), 6.58 (br d, J=8.65 Hz, 1H), 6.53 (br d, J=14.7 Hz, 1H), 5.58 (q, J=7.1 Hz, 1H), 4.08-4.16 (m, 1H), 3.81 (br dd, J=13.9, 3.8 Hz, 1H), 3.34-3.73 (m, 5H), 2.85-3.07 (m, 2H), 2.71 (br d, J=16.7 Hz, 1H), 2.64 (d, J=5.1 Hz, 3H), 2.32-2.41 (m, 2H), 1.52 (d, J=6.6 Hz, 3H), 1.21-1.38 (m, 4H).
Minor Rotamer (35%)
¹H NMR (400 MHz, DMSO-d$_6$) δ ppm 8.02 (t, J=8.8 Hz, 1H), 7.06-7.26 (m, 5H), 6.93-6.97 (m, 1H), 6.78 (s, 1H), 6.58 (br d, J=8.6 Hz, 1H) 6.53 (br d, J=14.7 Hz, 1H), 4.96 (q, J=6.1 Hz, 1H), 4.51-4.59 (m, 1H), 4.08-4.16 (m, 1H), 3.34-3.73 (m, 4H), 3.21-3.31 (m, 1H), 2.85-3.07 (m, 3H), 2.64 (d, J=5.1 Hz, 3H), 2.32-2.41 (m, 2H), 1.55 (br d, J=7.1 Hz, 3H), 1.21-1.38 (m, 4H).

Compound 22

Major Rotamer (65%)
¹H NMR (400 MHz, DMSO-d$_6$) δ ppm 8.02 (br t, J=8.6 Hz, 1H), 7.32 (br d, J=7.1 Hz, 1H), 7.05-7.26 (m, 3H), 6.92-6.98 (m, 1H), 6.81 (s, 1H), 6.52-6.64 (m, 2H), 5.58 (q, J=6.2 Hz, 1H), 4.23 (quin, J=7.3 Hz, 1H), 3.77-3.86 (m, 1H), 3.71 (br t, J=9.4 Hz, 1H), 3.32-3.60 (m, 5H), 2.90-3.07 (m, 1H), 2.87 (s, 6H), 2.68-2.76 (m, 1H), 2.24-2.45 (m, 2H partially obscured by DMSO peak), 1.52 (br d, J=6.6 Hz, 3H), 1.21-1.38 (m, 4H).
Minor Rotamer (35%)
¹H NMR (400 MHz, DMSO-d$_6$) δ ppm 8.02 (br t, J=8.6 Hz, 1H), 7.05-7.26 (m, 4H), 6.92-6.98 (m, 1H), 6.78 (s, 1H), 6.52-6.64 (m, 2H), 4.96 (q, J=6.6 Hz, 1H), 4.55 (br d, J=10.1 Hz, 1H), 4.23 (quin, J=7.3 Hz, 1H), 3.71 (br t, J=9.4 Hz, 1H), 3.32-3.60 (m, 4H), 3.20-3.29 (m, 1H), 2.90-3.07 (m, 2H), 2.87 (s, 6H), 2.24-2.45 (m, 2H partially obscured by DMSO peak), 1.55 (br d, J=6.6 Hz, 3H), 1.21-1.38 (m, 4H).

Compound 23

Major Rotamer (70%)
¹H NMR (500 MHz, DMSO-d$_6$) δ ppm 7.99 (br t, J=8.5 Hz, 1H), 7.37 (br s, 1H), 7.32 (br d, J=7.3 Hz, 1H), 7.06-7.25 (m, 3H), 6.75-6.95 (m, 3H), 6.48 (d, J=8.5 Hz, 1H), 6.39 (d, J=14.5 Hz, 1H), 5.59 (q, J=6.0 Hz, 1H), 3.81 (br dd, J=12.8, 3.0 Hz, 1H), 3.22-3.50 (m, 3H), 3.12 (br d, J=9.8 Hz, 1H), 2.83-3.06 (m, 2H), 2.67-2.75 (m, 2H), 2.18-2.27 (m, 2H), 1.95-2.03 (m, 1H), 1.77-1.85 (m, 1H), 1.52 (br d, J=6.6 Hz, 3H), 1.21-1.37 (m, 4H), 1.14 (s, 3H).
Minor Rotamer (30%)
¹H NMR (500 MHz, DMSO-d$_6$) δ ppm 7.99 (br t, J=8.5 Hz, 1H), 7.37 (br s, 1H), 7.06-7.25 (m, 4H), 6.75-6.95 (m, 3H), 6.48 (br d, J=8.5 Hz, 1H), 6.39 (br d, J=14.5 Hz, 1H), 4.96 (q, J=6.6 Hz, 1H), 4.55 (br d, J=10.7 Hz, 1H), 3.22-3.50 (m, 3H), 3.12 (br d, J=9.8 Hz, 1H), 2.83-3.06 (m, 2H), 2.67-2.75 (m, 2H), 2.18-2.27 (m, 2H), 1.95-2.03 (m, 1H), 1.77-1.85 (m, 1H), 1.55 (br d, J=6.6 Hz, 3H), 1.21-1.37 (m, 4H), 1.14 (s, 3H).

Compound 24

Major Rotamer (70%)
¹H NMR (500 MHz, DMSO-d$_6$) δ ppm 7.99 (br t, J=8.7 Hz, 1H), 7.29-7.40 (m, 2H), 7.06-7.25 (m, 3H), 6.90-6.95 (m, 1H), 6.74-6.87 (m, 2H), 6.48 (d, J=8.5 Hz, 1H), 6.39 (d, J=14.5 Hz, 1H), 5.59 (q, J=6.6 Hz, 1H), 3.81 (br dd, J=13.1, 3.9 Hz, 1H), 3.21-3.52 (m, 4H), 3.12 (br d, J=9.5 Hz, 1H), 2.82-3.06 (m, 2H), 2.67-2.76 (m, 2H), 2.17-2.29 (m, 2H), 1.95-2.05 (m, 1H), 1.77-1.85 (m, 1H), 1.52 (br d, J=6.6 Hz, 3H), 1.20-1.40 (m, 4H), 1.14 (s, 3H).

Minor Rotamer (30%)

¹H NMR (500 MHz, DMSO-d$_6$) δ ppm 7.99 (br t, J=8.7 Hz, 1H), 7.29-7.40 (m, 1H), 7.06-7.25 (m, 4H), 6.90-6.95 (m, 1H), 6.74-6.87 (m, 2H), 6.48 (br d, J=8.5 Hz, 1H), 6.39 (br d, J=14.5 Hz, 1H), 4.96 (q, J=6.6 Hz, 1H), 4.55 (br d, J=14.2 Hz, 1H), 3.21-3.52 (m, 4H), 3.12 (br d, J=9.5 Hz, 1H), 2.82-3.06 (m, 3H), 2.17-2.29 (m, 2H), 1.95-2.05 (m, 1H), 1.77-1.85 (m, 1H), 1.55 (br d, J=6.6 Hz, 3H), 1.20-1.40 (m, 4H), 1.14 (s, 3H).

Compound 25

Major Rotamer (65%)

¹H NMR (500 MHz, DMSO-d$_6$) δ ppm 7.96-8.03 (m, 1H), 7.34-7.40 (m, 2H), 7.02 (d, J=5.0 Hz, 1H), 6.91-6.95 (m, 1H), 6.76-6.86 (m, 2H), 6.48 (d, J=8.5 Hz, 1H), 6.39 (d, J=14.8 Hz, 1H), 5.53 (q, J=6.2 Hz, 1H), 3.92 (br dd, J=13.6, 4.7 Hz, 1H), 3.34-3.45 (m, 4H), 3.12 (br d, J=9.8 Hz, 1H), 2.80-3.01 (m, 2H), 2.75 (br d, J=16.4 Hz, 1H), 2.18-2.27 (m, 2H), 1.96-2.03 (m, 1H), 1.77-1.85 (m, 1H), 1.46 (br d, J=6.6 Hz, 3H), 1.31-1.38 (m, 2H), 1.22-1.29 (m, 2H), 1.14 (s, 3H).

Minor Rotamer (35%)

¹H NMR (500 MHz, DMSO-d$_6$) δ ppm 7.96-8.03 (m, 1H), 7.34-7.40 (m, 1H), 7.29 (d, J=5.4 Hz, 1H), 6.91-6.95 (m, 1H), 6.76-6.86 (m, 3H), 6.48 (d, J=8.5 Hz, 1H), 6.39 (d, J=14.8 Hz, 1H), 4.90 (q, J=6.9 Hz, 1H), 4.70 (br dd, J=12.3, 4.1 Hz, 1H), 3.34-3.45 (m, 3H), 3.16-3.25 (m, 1H), 3.12 (br d, J=9.8 Hz, 1H), 2.80-3.01 (m, 3H), 2.18-2.27 (m, 2H), 1.96-2.03 (m, 1H), 1.77-1.85 (m, 1H), 1.50 (br d, J=6.6 Hz, 3H), 1.31-1.38 (m, 2H), 1.22-1.29 (m, 2H), 1.14 (s, 3H).

Compound 26

Major Rotamer (70%)

¹H NMR (500 MHz, DMSO-d$_6$) δ ppm 7.95-8.03 (m, 1H), 7.34-7.41 (m, 2H), 7.02 (d, J=5.0 Hz, 1H), 6.91-6.95 (m, 1H), 6.76-6.86 (m, 2H), 6.48 (d, J=8.8 Hz, 1H), 6.39 (d, J=14.2 Hz, 1H), 5.53 (q, J=6.3 Hz, 1H), 3.93 (dd, J=13.2, 4.4 Hz, 1H), 3.29-3.46 (m, 3H), 3.16-3.26 (m, 1H), 3.12 (br d, J=9.8 Hz, 1H), 2.81-3.00 (m, 2H), 2.75 (br d, J=15.1 Hz, 1H), 2.18-2.27 (m, 2H), 1.95-2.03 (m, 1H), 1.76-1.85 (m, 1H), 1.46 (d, J=6.6 Hz, 3H), 1.21-1.39 (m, 4H), 1.14 (s, 3H).

Minor Rotamer (30%)

¹H NMR (500 MHz, DMSO-d$_6$) δ ppm 7.95-8.03 (m, 1H), 7.34-7.41 (m, 1H), 7.29 (d, J=5.0 Hz, 1H), 6.91-6.95 (m, 1H), 6.76-6.86 (m, 3H), 6.48 (d, J=8.8 Hz, 1H), 6.39 (d, J=14.2 Hz, 1H), 4.90 (q, J=6.6 Hz, 1H), 4.70 (dd, J=12.6, 4.7 Hz, 1H), 3.29-3.46 (m, 4H), 3.12 (br d, J=9.8 Hz, 1H), 2.81-3.00 (m, 3H), 2.18-2.27 (m, 2H), 1.95-2.03 (m, 1H), 1.76-1.85 (m, 1H), 1.50 (d, J=6.6 Hz, 3H), 1.21-1.39 (m, 4H), 1.14 (s, 3H).

Compound 27

Major Rotamer (65%)

¹H NMR (500 MHz, DMSO-d$_6$) δ ppm 7.99 (br t, J=8.8 Hz, 1H), 7.32 (br d, J=7.3 Hz, 1H), 7.06-7.25 (m, 4H), 6.89-6.95 (m, 2H), 6.80 (s, 1H), 6.50 (br d, J=8.5 Hz, 1H), 6.42 (br d, J=15.1 Hz, 1H), 5.59 (q, J=6.6 Hz, 1H), 3.81 (br dd, J=13.6, 3.5 Hz, 1H), 3.39-3.50 (m, 2H), 3.21-3.31 (m, 2H), 3.13 (br t, J=9.6 Hz, 1H), 2.83-3.07 (m, 2H), 2.70 (br d, J=21.1 Hz, 1H), 2.54-2.62 (m, 1H), 1.92-2.00 (m, 1H), 1.75-1.86 (m, 1H), 1.52 (d, J=6.6 Hz, 3H), 1.30-1.38 (m, 2H), 1.22-1.29 (m, 2H), 1.13 (s, 6H).

Minor Rotamer (35%)

¹H NMR (500 MHz, DMSO-d$_6$) δ ppm 7.99 (br t, J=8.8 Hz, 1H), 7.06-7.25 (m, 5H), 6.89-6.95 (m, 2H), 6.76 (s, 1H), 6.50 (br d, J=8.5 Hz, 1H), 6.42 (br d, J=15.1 Hz, 1H), 4.96 (q, J=6.5 Hz, 1H), 4.55 (br dd, J=12.9, 3.2 Hz, 1H), 3.39-3.50 (m, 2H), 3.21-3.31 (m, 2H), 3.13 (br t, J=9.6 Hz, 1H), 2.83-3.07 (m, 3H), 2.54-2.62 (m, 1H), 1.92-2.00 (m, 1H), 1.75-1.86 (m, 1H), 1.55 (d, J=6.9 Hz, 3H), 1.30-1.38 (m, 2H), 1.22-1.29 (m, 2H), 1.13 (s, 6H).

Compound 28

Major Rotamer (65%)

¹H NMR (500 MHz, DMSO-d$_6$) δ ppm 7.99 (t, J=8.8 Hz, 1H), 7.32 (d, J=7.6 Hz, 1H), 7.05-7.25 (m, 4H), 6.89-6.95 (m, 2H), 6.80 (s, 1H), 6.50 (d, J=8.8 Hz, 1H), 6.42 (dd, J=14.8, 1.6 Hz, 1H), 5.58 (q, J=6.5 Hz, 1H), 3.81 (br dd, J=13.6, 4.1 Hz, 1H), 3.40-3.51 (m, 2H), 3.22-3.31 (m, 2H), 3.13 (t, J=9.6 Hz, 1H), 2.86-3.05 (m, 2H), 2.70 (br d, J=20.8 Hz, 1H), 2.55-2.63 (m, 1H), 1.92-2.00 (m, 1H), 1.75-1.85 (m, 1H), 1.52 (d, J=6.6 Hz, 3H), 1.31-1.38 (m, 2H), 1.21-1.29 (m, 2H), 1.13 (s, 6H).

Minor Rotamer (35%)

¹H NMR (500 MHz, DMSO-d$_6$) δ ppm 7.99 (t, J=8.8 Hz, 1H), 7.05-7.25 (m, 5H), 6.89-6.95 (m, 2H), 6.76 (s, 1H), 6.50 (d, J=8.8 Hz, 1H), 6.42 (dd, J=14.8, 1.6 Hz, 1H), 4.96 (q, J=6.5 Hz, 1H), 4.55 (br dd, J=12.9, 2.8 Hz, 1H), 3.40-3.51 (m, 2H), 3.22-3.31 (m, 2H), 3.13 (t, J=9.6 Hz, 1H), 2.86-3.05 (m, 3H), 2.55-2.63 (m, 1H), 1.92-2.00 (m, 1H), 1.75-1.85 (m, 1H), 1.55 (d, J=6.9 Hz, 3H), 1.31-1.38 (m, 2H), 1.21-1.29 (m, 2H), 1.13 (s, 6H).

Compound 29

Major Rotamer (70%)

¹H NMR (500 MHz, DMSO-d$_6$) δ ppm 7.99 (t, J=8.8 Hz, 1H), 7.38 (d, J=5.0 Hz, 1H), 7.13 (br s, 1H), 7.02 (d, J=5.0 Hz, 1H), 6.89-6.95 (m, 2H), 6.79-6.81 (m, 1H), 6.50 (br d, J=8.8 Hz, 1H), 6.42 (br d, J=14.8 Hz, 1H), 5.53 (q, J=6.8 Hz, 1H), 3.92 (br dd, J=13.7, 4.6 Hz, 1H), 3.38-3.45 (m, 2H), 3.09-3.29 (m, 3H), 2.90-3.01 (m, 2H), 2.70 (br d, J=17.0 Hz, 1H), 2.55-2.62 (m, 1H), 1.92-2.00 (m, 1H), 1.75-1.85 (m, 1H), 1.46 (d, J=6.6 Hz, 3H), 1.31-1.37 (m, 2H), 1.21-1.29 (m, 2H), 1.13 (s, 6H).

Minor Rotamer (30%)

¹H NMR (500 MHz, DMSO-d$_6$) δ ppm 7.98 (t, J=8.8 Hz, 1H), 7.29 (d, J=5.0 Hz, 1H), 7.13 (br s, 1H), 6.89-6.95 (m, 2H), 6.79-6.81 (m, 1H), 6.77 (s, 1H), 6.50 (br d, J=8.8 Hz, 1H), 6.42 (br d, J=14.8 Hz, 1H), 4.90 (q, J=6.7 Hz, 1H), 4.70 (br dd, J=12.8, 4.6 Hz, 1H), 3.38-3.45 (m, 2H), 3.09-3.29 (m, 3H), 2.90-3.01 (m, 3H), 2.55-2.62 (m, 1H), 1.92-2.00 (m, 1H), 1.75-1.85 (m, 1H), 1.50 (d, J=6.6 Hz, 3H), 1.31-1.37 (m, 2H), 1.21-1.29 (m, 2H), 1.13 (s, 6H).

Compound 30

Major Rotamer (65%)

¹H NMR (400 MHz, DMSO-d$_6$) δ ppm 8.00 (br t, J=8.8 Hz, 1H), 7.31 (br d, J=7.1 Hz, 1H), 7.05-7.26 (m, 3H), 6.93 (br s, 1H), 6.80 (s, 1H), 6.51 (br d, J=8.6 Hz, 1H), 6.44 (br d, J=15.2 Hz, 1H), 5.55-5.62 (m, 1H), 4.66 (br t, J=9.1 Hz, 1H), 3.86-3.95 (m, 1H), 3.77-3.85 (m, 1H), 3.52-3.59 (m, 1H), 3.41-3.51 (m, 2H), 2.85-3.12 (m, 3H), 2.68-2.76 (m, 1H), 2.15-2.25 (m, 1H), 1.83-1.95 (m, 1H), 1.49-1.57 (m, 3H), 1.38 (s, 3H), 1.34 (s, 3H), 1.21-1.34 (m, 4H).

Minor Rotamer (35%)

¹H NMR (400 MHz, DMSO-d$_6$) δ ppm 8.00 (br t, J=8.8 Hz, 1H), 7.05-7.26 (m, 4H), 6.93 (br s, 1H), 6.76 (s, 1H), 6.51 (br d, J=8.6 Hz, 1H), 6.44 (br d, J=15.2 Hz, 1H), 4.92-4.99 (m, 1H), 4.66 (br t, J=9.1 Hz, 1H), 4.51-4.58 (m, 1H), 3.86-3.95 (m, 1H), 3.52-3.59 (m, 1H), 3.41-3.51 (m, 1H), 3.22-3.29 (m, 1H), 2.85-3.12 (m, 4H), 2.15-2.25 (m, 1H), 1.83-1.95 (m, 1H), 1.49-1.57 (m, 3H), 1.38 (s, 3H), 1.34 (s, 3H), 1.21-1.34 (m, 4H).

Compound 31

Major Rotamer (65%)
$^1$H NMR (500 MHz, DMSO-d$_6$) δ ppm 8.00 (t, J=8.7 Hz, 1H), 7.32 (d, J=7.3 Hz, 1H), 7.06-7.25 (m, 3H), 6.91-6.96 (m, 1H), 6.80 (s, 1H), 6.51 (br d, J=8.5 Hz, 1H), 6.44 (dd, J=14.8, 1.3 Hz, 1H), 5.59 (q, J=6.6 Hz, 1H), 4.66 (t, J=9.0 Hz, 1H), 3.86-3.95 (m, 1H), 3.78-3.84 (m, 1H), 3.56 (dd, J=9.8, 6.6 Hz, 1H), 3.42-3.50 (m, 2H), 3.08 (dd, J=9.8, 6.0 Hz, 1H), 2.83-3.05 (m, 2H), 2.72 (br d, J=16.4 Hz, 1H), 2.16-2.24 (m, 1H), 1.84-1.94 (m, 1H), 1.52 (d, J=6.6 Hz, 3H), 1.38 (s, 3H), 1.35 (s, 3H), 1.30-1.34 (m, 2H), 1.22-1.28 (m, 2H).
Minor Rotamer (35%)
$^1$H NMR (500 MHz, DMSO-d$_6$) δ ppm 8.00 (t, J=8.7 Hz, 1H), 7.06-7.25 (m, 4H), 6.91-6.96 (m, 1H), 6.77 (s, 1H), 6.51 (br d, J=8.5 Hz, 1H), 6.44 (dd, J=14.8, 1.3 Hz, 1H), 4.96 (q, J=6.7 Hz, 1H), 4.66 (t, J=9.0 Hz, 1H), 4.52-4.58 (m, 1H), 3.86-3.95 (m, 1H), 3.56 (dd, J=9.8, 6.6 Hz, 1H), 3.42-3.50 (m, 1H), 3.23-3.30 (m, 1H), 3.08 (dd, J=9.8, 6.0 Hz, 1H), 2.83-3.05 (m, 3H), 2.16-2.24 (m, 1H), 1.84-1.94 (m, 1H), 1.55 (d, J=6.6 Hz, 3H), 1.38 (s, 3H), 1.35 (s, 3H), 1.30-1.34 (m, 2H), 1.22-1.28 (m, 2H).

Compound 32

Major Rotamer (65%)
$^1$H NMR (500 MHz, DMSO-d$_6$) δ ppm 7.99 (br t, J=8.7 Hz, 1H), 7.51 (br s, 1H), 7.32 (br d, J=7.6 Hz, 1H), 7.06-7.26 (m, 3H), 7.02 (br s, 1H), 6.90-6.95 (m, 1H), 6.80 (s, 1H), 6.53 (br d, J=8.5 Hz, 1H), 6.45 (br d, J=14.5 Hz, 1H), 5.59 (q, J=6.6 Hz, 1H), 4.02-4.11 (m, 1H), 3.82 (br dd, J=13.2, 4.1 Hz, 1H), 3.55 (t, J=8.5 Hz, 1H), 3.40-3.52 (m, 1H), 3.22-3.36 (m, 2H partially obscured by H$_2$O peak), 2.84-3.06 (m, 2H), 2.72 (br d, J=16.1 Hz, 1H), 2.11-2.21 (m, 1H), 1.91 (br dd, J=11.8, 6.5 Hz, 1H), 1.52 (br d, J=6.6 Hz, 3H), 1.30-1.37 (m, 2H), 1.21-1.29 (m, 2H), 1.16 (d, J=6.0 Hz, 3H).
Minor Rotamer (35%)
$^1$H NMR (500 MHz, DMSO-d$_6$) δ ppm 7.99 (br t, J=8.7 Hz, 1H), 7.51 (br s, 1H), 7.06-7.26 (m, 4H), 7.02 (br s, 1H), 6.90-6.95 (m, 1H), 6.77 (s, 1H), 6.53 (br d, J=8.5 Hz, 1H), 6.45 (br d, J=14.5 Hz, 1H), 4.97 (q, J=6.5 Hz, 1H), 4.55 (br d, J=12.6 Hz, 1H), 4.02-4.11 (m, 1H), 3.55 (t, J=8.5 Hz, 1H), 3.40-3.52 (m, 1H), 3.22-3.36 (m, 2H partially obscured by H$_2$O peak), 2.84-3.06 (m, 3H), 2.11-2.21 (m, 1H), 1.91 (br dd, J=11.8, 6.5 Hz, 1H), 1.55 (br d, J=6.6 Hz, 3H), 1.30-1.37 (m, 2H), 1.21-1.29 (m, 2H), 1.16 (d, J=6.0 Hz, 3H).

Compound 33

Major Rotamer (65%)
$^1$H NMR (500 MHz, DMSO-d$_6$) δ ppm 7.99 (t, J=8.8 Hz, 1H), 7.49 (br s, 1H), 7.32 (d, J=7.3 Hz, 1H), 7.05-7.26 (m, 3H), 7.01 (br s, 1H), 6.91-6.96 (m, 1H), 6.81 (s, 1H), 6.56 (br d, J=8.8 Hz, 1H), 6.48 (br d, J=14.8 Hz, 1H), 5.59 (q, J=6.6 Hz, 1H), 3.93-4.02 (m, 1H), 3.82 (br dd, J=13.7, 4.3 Hz, 1H), 3.55-3.62 (m, 1H), 3.42-3.53 (m, 2H), 2.86-3.06 (m, 3H), 2.72 (br d, J=16.1 Hz, 1H), 2.39-2.47 (m, 1H), 1.87-1.95 (m, 1H), 1.52 (d, J=6.6 Hz, 3H), 1.30-1.37 (m, 2H), 1.23-1.30 (m, 2H), 1.18 (d, J=6.0 Hz, 3H).
Minor Rotamer (35%)
$^1$H NMR (500 MHz, DMSO-d$_6$) δ ppm 7.99 (t, J=8.8 Hz, 1H), 7.49 (br s, 1H), 7.05-7.26 (m, 4H), 7.01 (br s, 1H), 6.91-6.96 (m, 1H), 6.77 (s, 1H), 6.56 (br d, J=8.8 Hz, 1H), 6.48 (br d, J=14.8 Hz, 1H), 4.97 (q, J=6.6 Hz, 1H), 4.51-4.58 (m, 1H), 3.93-4.02 (m, 1H), 3.55-3.62 (m, 1H), 3.42-3.53 (m, 1H), 3.22-3.30 (m, 1H), 2.86-3.06 (m, 4H), 2.39-2.47 (m, 1H), 1.87-1.95 (m, 1H), 1.55 (d, J=6.6 Hz, 3H), 1.30-1.37 (m, 2H), 1.23-1.30 (m, 2H), 1.18 (d, J=6.3 Hz, 3H).

Compound 34

Major Rotamer (65%)
$^1$H NMR (500 MHz, DMSO-d$_6$) δ ppm 7.99 (br t, J=8.7 Hz, 1H), 7.51 (br s, 1H), 7.32 (br d, J=7.3 Hz, 1H), 7.06-7.25 (m, 3H), 7.02 (br s, 1H), 6.90-6.96 (m, 1H), 6.80 (s, 1H), 6.53 (br d, J=8.5 Hz, 1H), 6.45 (br d, J=14.8 Hz, 1H), 5.59 (q, J=6.4 Hz, 1H), 4.04-4.11 (m, 1H), 3.82 (br dd, J=13.6, 3.8 Hz, 1H), 3.55 (br t, J=8.5 Hz, 1H), 3.42-3.50 (m, 1H), 3.22-3.36 (m, 2H partially obscured by H$_2$O peak), 2.85-3.06 (m, 2H), 2.72 (br d, J=16.4 Hz, 1H), 2.12-2.21 (m, 1H), 1.91 (br dd, J=11.5, 6.8 Hz, 1H), 1.52 (d, J=6.9 Hz, 3H), 1.30-1.37 (m, 2H), 1.22-1.30 (m, 2H), 1.16 (d, J=6.0 Hz, 3H).
Minor Rotamer
$^1$H NMR (500 MHz, DMSO-d$_6$) δ ppm 7.99 (br t, J=8.7 Hz, 1H), 7.51 (br s, 1H), 7.06-7.25 (m, 4H), 7.02 (br s, 1H), 6.90-6.96 (m, 1H), 6.76 (s, 1H), 6.53 (br d, J=8.5 Hz, 1H), 6.45 (br d, J=14.8 Hz, 1H), 4.97 (q, J=6.2 Hz, 1H), 4.55 (br dd, J=12.9, 3.2 Hz, 1H), 4.04-4.11 (m, 1H), 3.55 (br t, J=8.5 Hz, 1H), 3.42-3.50 (m, 1H), 3.22-3.36 (m, 2H partially obscured by H$_2$O peak), 2.85-3.06 (m, 3H), 2.12-2.21 (m, 1H), 1.91 (br dd, J=11.5, 6.8 Hz, 1H), 1.55 (d, J=6.9 Hz, 3H), 1.30-1.37 (m, 2H), 1.22-1.30 (m, 2H), 1.16 (d, J=6.0 Hz, 3H).

Compound 35

Major Rotamer (65%)
$^1$H NMR (500 MHz, DMSO-d$_6$) δ ppm 7.99 (br t, J=8.8 Hz, 1H), 7.49 (br s, 1H), 7.32 (br d, J=7.6 Hz, 1H), 7.06-7.26 (m, 3H), 7.01 (br s, 1H), 6.91-6.96 (m, 1H), 6.81 (s, 1H), 6.57 (br d, J=8.8 Hz, 1H), 6.48 (br d, J=15.1 Hz, 1H), 5.59 (q, J=6.6 Hz, 1H), 3.94-4.02 (m, 1H), 3.82 (br dd, J=13.7, 3.6 Hz, 1H), 3.55-3.61 (m, 1H), 3.42-3.53 (m, 2H), 2.83-3.06 (m, 3H), 2.72 (br d, J=16.1 Hz, 1H), 2.39-2.48 (m, 1H), 1.87-1.95 (m, 1H), 1.52 (br d, J=6.9 Hz, 3H), 1.30-1.38 (m, 2H), 1.22-1.30 (m, 2H), 1.18 (d, J=6.0 Hz, 3H).
Minor Rotamer (35%)
$^1$H NMR (500 MHz, DMSO-d$_6$) δ ppm 7.99 (br t, J=8.8 Hz, 1H), 7.49 (br s, 1H), 7.06-7.26 (m, 4H), 7.01 (br s, 1H), 6.91-6.96 (m, 1H), 6.77 (s, 1H), 6.57 (br d, J=8.8 Hz, 1H), 6.48 (br d, J=15.1 Hz, 1H), 4.97 (q, J=6.4 Hz, 1H), 4.55 (br d, J=10.4 Hz, 1H), 3.94-4.02 (m, 1H), 3.55-3.61 (m, 1H), 3.42-3.53 (m, 1H), 3.23-3.30 (m, 1H), 2.83-3.06 (m, 4H), 2.39-2.48 (m, 1H), 1.87-1.95 (m, 1H), 1.55 (br d, J=6.9 Hz, 3H), 1.30-1.38 (m, 2H), 1.22-1.30 (m, 2H), 1.18 (d, J=6.0 Hz, 3H).

Compound 36

Major Rotamer (65%)
$^1$H NMR (500 MHz, DMSO-d$_6$) δ ppm 8.00 (t, J=8.8 Hz, 1H), 7.51 (br s, 1H), 7.32 (d, J=7.6 Hz, 1H), 7.06-7.25 (m, 3H), 7.01 (br s, 1H), 6.91-6.95 (m, 1H), 6.81 (s, 1H), 6.52 (br d, J=8.8 Hz, 1H), 6.45 (br d, J=14.5 Hz, 1H), 5.59 (q, J=6.8 Hz, 1H), 3.81 (br dd, J=13.6, 3.8 Hz, 1H), 3.46-3.54 (m, 1H), 3.34-3.46 (m, 3H), 3.29-3.32 (m, 1H partially obscured by H₂O peak), 3.10 (quin, J=7.6 Hz 1H), 2.85-3.05 (m, 2H), 2.72 (br d, J=16.1 Hz, 1H), 2.16-2.24 (m, 1H), 2.06-2.15 (m, 1H), 1.52 (d, J=6.6 Hz, 3H), 1.30-1.38 (m, 2H), 1.22-1.30 (m, 2H).
Minor Rotamer (35%)
¹H NMR (500 MHz, DMSO-d₆) δ ppm 8.00 (t, J=8.8 Hz, 1H), 7.51 (br s, 1H), 7.06-7.25 (m, 4H), 7.01 (br s, 1H), 6.91-6.95 (m, 1H), 6.77 (s, 1H), 6.52 (br d, J=8.8 Hz, 1H), 6.45 (br d, J=14.5 Hz, 1H), 4.96 (q, J=6.6 Hz, 1H), 4.55 (br dd, J=12.6, 3.2 Hz, 1H), 3.46-3.54 (m, 1H), 3.34-3.46 (m, 2H), 3.29-3.32 (m, 1H partially obscured by H₂O peak), 3.22-3.26 (m, 1H), 3.10 (quin, J=7.6 Hz, 1H), 2.85-3.05 (m, 3H), 2.16-2.24 (m, 1H), 2.06-2.15 (m, 1H), 1.55 (d, J=6.9 Hz, 3H), 1.30-1.38 (m, 2H), 1.22-1.30 (m, 2H).

Compound 37

Major Rotamer (65%)
¹H NMR (500 MHz, DMSO-d₆) δ ppm 7.97-8.03 (m, 2H), 7.32 (d, J=7.3 Hz, 1H), 7.06-7.25 (m, 3H), 6.94 (d, J=3.5 Hz, 1H), 6.80 (s, 1H), 6.52 (dd, J=8.8, 1.9 Hz, 1H), 6.45 (dd, J=14.8, 1.9 Hz, 1H), 5.59 (q, J=6.6 Hz, 1H), 3.81 (br dd, J=13.7, 3.6 Hz, 1H), 3.32-3.54 (m, 5H), 3.04-3.12 (m, 1H), 2.83-3.04 (m, 2H), 2.72 (br d, J=16.1 Hz, 1H), 2.62 (d, J=4.4 Hz, 3H), 2.14-2.22 (m, 1H), 2.06-2.14 (m, 1H), 1.52 (d, J=6.6 Hz, 3H), 1.30-1.37 (m, 2H), 1.22-1.30 (m, 2H).
Minor Rotamer (35%)
¹H NMR (500 MHz, DMSO-d₆) δ ppm 7.97-8.03 (m, 2H), 7.06-7.25 (m, 4H), 6.93 (d, J=3.5 Hz, 1H), 6.77 (s, 1H), 6.52 (dd, J=8.8, 1.9 Hz, 1H), 6.45 (dd, J=14.8, 1.9 Hz, 1H), 4.96 (q, J=6.6 Hz, 1H), 4.52-4.58 (m, 1H), 3.32-3.54 (m, 4H), 3.23-3.30 (m, 1H), 3.04-3.12 (m, 1H), 2.83-3.04 (m, 3H), 2.62 (d, J=4.4 Hz, 3H), 2.14-2.22 (m, 1H), 2.06-2.14 (m, 1H), 1.55 (d, J=6.6 Hz, 3H), 1.30-1.37 (m, 2H), 1.22-1.30 (m, 2H).

Compound 38

Major Rotamer (65%)
¹H NMR (500 MHz, DMSO-d₆) δ ppm 8.00 (t, J=8.8 Hz, 1H), 7.32 (d, J=7.3 Hz, 1H), 7.06-7.25 (m, 3H), 6.94 (d, J=3.8 Hz, 1H), 6.80 (s, 1H), 6.53 (dd, J=8.8, 1.9 Hz, 1H), 6.46 (dd, J=14.7, 2.1 Hz, 1H), 5.59 (q, J=6.6 Hz, 1H), 3.81 (br dd, J=13.9, 3.5 Hz, 1H), 3.53-3.60 (m, 3H), 3.33-3.51 (m, 4H), 3.09 (s, 3H), 2.89-3.05 (m, 2H), 2.86 (s, 3H), 2.72 (br d, J=16.1 Hz, 1H), 2.18-2.26 (m, 1H), 2.06-2.14 (m, 1H), 1.52 (d, J=6.9 Hz, 3H), 1.30-1.37 (m, 2H), 1.22-1.30 (m, 2H).
Minor Rotamer (35%)
¹H NMR (500 MHz, DMSO-d₆) δ ppm 8.00 (br d, J=8.8 Hz, 1H), 7.06-7.25 (m, 4H), 6.93 (d, J=3.5 Hz, 1H), 6.77 (s, 1H), 6.53 (dd, J=8.8, 1.9 Hz, 1H), 6.46 (dd, J=14.7, 2.1 Hz, 1H), 4.96 (q, J=6.7 Hz, 1H), 4.52-4.58 (m, 1H), 3.53-3.60 (m, 2H), 3.33-3.51 (m, 3H), 3.21-3.30 (m, 1H), 3.09 (s, 3H), 2.89-3.05 (m, 3H), 2.86 (s, 3H), 2.18-2.26 (m, 1H), 2.06-2.14 (m, 1H), 1.55 (d, J=6.9 Hz, 3H), 1.30-1.37 (m, 2H), 1.22-1.30 (m, 2H).

Compound 39

Major Rotamer (65%)
¹H NMR (400 MHz, DMSO-d₆) δ ppm 8.00 (t, J=8.8 Hz, 1H), 7.32 (d, J=7.6 Hz, 1H), 7.05-7.26 (m, 4H), 6.91-6.96 (m, 1H), 6.80 (s, 1H), 6.52 (br d, J=9.1 Hz, 1H), 6.45 (br d, J=14.7 Hz, 1H), 5.58 (q, J=7.1 Hz, 1H), 3.77-3.85 (m, 1H), 3.35-3.55 (m, 5H), 3.09-3.19 (m, 1H), 2.84-3.07 (m, 2H), 2.71 (br d, J=16.2 Hz, 1H), 2.10-2.26 (m, 2H), 1.52 (d, J=6.6 Hz, 3H), 1.30-1.39 (m, 2H), 1.20-1.30 (m, 2H).
Minor Rotamer (35%)
¹H NMR (400 MHz, DMSO-d₆) δ ppm 8.00 (t, J=8.8 Hz, 1H), 7.05-7.26 (m, 4H), 6.91-6.96 (m, 2H), 6.76 (s, 1H), 6.52 (br d, J=9.1 Hz, 1H), 6.45 (br d, J=14.7 Hz, 1H), 4.96 (q, J=6.4 Hz, 1H), 4.51-4.58 (m, 1H), 3.35-3.55 (m, 5H), 3.09-3.19 (m, 1H), 2.84-3.07 (m, 3H), 2.10-2.26 (m, 2H), 1.54 (d, J=7.1 Hz, 3H), 1.30-1.39 (m, 2H), 1.20-1.30 (m, 2H).

Compound 40

Major Rotamer (65%)
¹H NMR (400 MHz, DMSO-d₆) δ ppm 11.94 (br s, 1H), 8.01 (t, J=8.8 Hz, 1H), 7.32 (d, J=7.6 Hz, 1H), 7.05-7.25 (m, 3H), 6.91-6.97 (m, 1H), 6.80 (s, 1H), 6.54 (br d, J=9.1 Hz, 1H), 6.47 (dd, J=14.9, 1.8 Hz, 1H), 5.58 (q, J=6.6 Hz, 1H), 3.81 (br dd, J=13.1, 4.0 Hz, 1H), 3.35-3.57 (m, 5H), 3.21-3.29 (m, 1H), 3.19 (s, 3H), 2.85-3.06 (m, 2H), 2.71 (br d, J=16.2 Hz, 1H), 2.21-2.30 (m, 1H), 2.11-2.21 (m, 1H), 1.52 (d, J=7.1 Hz, 3H), 1.30-1.38 (m, 2H), 1.22-1.29 (m, 2H).
Minor Rotamer (35%)
¹H NMR (400 MHz, DMSO-d₆) δ ppm 11.94 (br s, 1H), 8.01 (t, J=8.8 Hz, 1H), 7.05-7.25 (m, 4H), 6.91-6.97 (m, 1H), 6.77 (s, 1H), 6.54 (br d, J=9.1 Hz, 1H), 6.47 (dd, J=14.9, 1.8 Hz, 1H), 4.96 (q, J=6.2 Hz, 1H), 4.51-4.58 (m, 1H), 3.35-3.57 (m, 5H), 3.21-3.29 (m, 1H), 3.19 (s, 3H), 2.85-3.06 (m, 3H), 2.21-2.30 (m, 1H), 2.11-2.21 (m, 1H), 1.55 (d, J=6.6 Hz, 3H), 1.30-1.38 (m, 2H), 1.22-1.29 (m, 2H).

Compound 41

Major Rotamer (65%)
¹H NMR (400 MHz, DMSO-d₆) δ ppm 11.97 (s, 1H), 8.01 (t, J=8.8 Hz, 1H), 7.38 (d, J=5.6 Hz, 1H), 7.02 (d, J=5.1 Hz, 1H), 6.92-6.96 (m, 1H), 6.77-6.82 (m, 1H), 6.54 (br d, J=8.6 Hz, 1H), 6.48 (br d, J=14.7 Hz, 1H), 5.53 (q, J=7.1 Hz, 1H), 3.92 (br dd, J=13.6, 4.6 Hz, 1H), 3.52-3.59 (m, 1H), 3.33-3.48 (m, 4H), 3.27 (s, 3H), 3.15-3.26 (m, 1H), 2.81-3.00 (m, 2H), 2.74 (br d, J=14.7 Hz, 1H), 2.23-2.31 (m, 1H), 2.12-2.21 (m, 1H), 1.46 (d, J=6.6 Hz, 3H), 1.30-1.37 (m, 2H), 1.22-1.29 (m, 2H).
Minor Rotamer (35%)
¹H NMR (400 MHz, DMSO-d₆) δ ppm 11.97 (s, 1H), 7.98 (t, J=8.6 Hz, 1H), 7.29 (d, J=5.1 Hz, 1H), 6.92-6.96 (m, 1H), 6.77-6.82 (m, 2H), 6.54 (br d, J=8.6 Hz, 1H), 6.48 (br d, J=14.7 Hz, 1H), 4.90 (q, J=6.1 Hz, m, 1H), 4.67-4.74 (m, 1H), 3.52-3.59 (m, 1H), 3.33-3.48 (m, 4H), 3.27 (s, 3H), 3.15-3.26 (m, 1H), 2.81-3.00 (m, 3H), 2.23-2.31 (m, 1H), 2.12-2.21 (m, 1H), 1.50 (d, J=6.6 Hz, 3H), 1.30-1.37 (m, 2H), 1.22-1.29 (m, 2H).

Compound 42

Major Rotamer (65%)
¹H NMR (500 MHz, DMSO-d₆) δ ppm 7.99 (t, J=8.8 Hz, 1H), 7.34-7.40 (m, 2H), 7.02 (d, J=5.0 Hz, 1H), 6.92-6.95 (m, 1H), 6.77-6.86 (m, 2H), 6.50 (br d, J=8.8 Hz, 1H), 6.41 (br d, J=14.8 Hz, 1H), 5.53 (q, J=6.5 Hz, 1H), 3.92 (br dd, J=13.9, 4.7 Hz, 1H), 3.49 (dd, J=9.0, 7.7 Hz, 1H), 3.36-3.45 (m, 2H), 3.27-3.31 (m, 2H), 2.82-3.01 (m, 3H), 2.75 (br dd, J=15.9, 2.1 Hz, 1H), 2.58-2.68 (m, 1H), 2.24 (d, J=7.6 Hz, 2H), 2.10-2.18 (m, 1H), 1.64-1.74 (m, 1H), 1.46 (d, J=6.6 Hz, 3H), 1.30-1.38 (m, 2H), 1.21-1.29 (m, 2H).

Minor Rotamer (35%)

¹H NMR (500 MHz, DMSO-d$_6$) δ ppm 7.99 (t, J=8.8 Hz, 1H), 7.34-7.40 (m, 1H), 7.29 (d, J=5.0 Hz, 1H), 6.92-6.95 (m, 1H), 6.77-6.86 (m, 3H), 6.50 (br d, J=8.8 Hz, 1H), 6.41 (br d, J=14.8 Hz, 1H), 4.90 (q, J=6.3 Hz, 1H), 4.70 (br dd, J=12.6, 4.4 Hz, 1H), 3.49 (dd, J=9.0, 7.7 Hz, 1H), 3.36-3.45 (m, 1H), 3.27-3.31 (m, 1H), 3.21 (td, J=12.3 Hz, 1H), 2.82-3.01 (m, 4H), 2.58-2.68 (m, 1H), 2.24 (d, J=7.6 Hz, 2H), 2.10-2.18 (m, 1H), 1.64-1.74 (m, 1H), 1.50 (d, J=6.6 Hz, 3H), 1.30-1.38 (m, 2H), 1.21-1.29 (m, 2H).

Compound 43

Major Rotamer (65%)

¹H NMR (500 MHz, DMSO-d$_6$) δ ppm 7.99 (br t, J=8.8 Hz, 1H), 7.34-7.40 (m, 2H), 7.02 (d, J=5.4 Hz, 1H), 6.91-6.95 (m, 1H), 6.77-6.86 (m, 2H), 6.50 (br d, J=8.8 Hz, 1H), 6.41 (br d, J=14.8 Hz, 1H), 5.53 (q, J=6.4 Hz, 1H), 3.92 (br dd, J=13.7, 4.6 Hz, 1H), 3.49 (br t, J=8.4 Hz, 1H), 3.35-3.44 (m, 2H), 3.27-3.32 (m, 1H), 2.83-3.01 (m, 3H), 2.75 (br dd, J=16.1, 2.2 Hz, 1H), 2.58-2.68 (m, 1H), 2.24 (d, J=7.6 Hz, 2H), 2.10-2.18 (m, 1H), 1.64-1.74 (m, 1H), 1.46 (d, J=6.6 Hz, 3H), 1.30-1.37 (m, 2H), 1.22-1.30 (m, 2H).

Minor Rotamer (35%)

¹H NMR (500 MHz, DMSO-d$_6$) δ ppm 7.99 (br t, J=8.8 Hz, 1H), 7.34-7.40 (m, 1H), 7.29 (d, J=5.0 Hz, 1H), 6.91-6.95 (m, 1H), 6.77-6.86 (m, 3H), 6.50 (br d, J=8.8 Hz, 1H), 6.41 (br d, J=14.8 Hz, 1H), 4.90 (q, J=6.5 Hz, 1H), 4.70 (br dd, J=12.9, 4.4 Hz, 1H), 3.49 (br t, J=8.4 Hz, 1H), 3.35-3.44 (m, 1H), 3.27-3.32 (m, 1H), 3.21 (br td, J=12.2, 4.3 Hz, 1H), 2.83-3.01 (m, 4H), 2.58-2.68 (m, 1H), 2.24 (d, J=7.6 Hz, 2H), 2.10-2.18 (m, 1H), 1.64-1.74 (m, 1H), 1.50 (d, J=6.6 Hz, 3H), 1.30-1.37 (m, 2H), 1.22-1.30 (m, 2H).

Compound 44

Major Rotamer (65%)

¹H NMR (500 MHz, DMSO-d$_6$) δ ppm 8.00 (t, J=8.8 Hz, 1H), 7.35-7.40 (m, 2H), 7.00-7.05 (m, 2H), 6.92-6.95 (m, 1H), 6.77-6.82 (m, 1H), 6.49 (br d, J=8.8 Hz, 1H), 6.41 (dd, J=14.7, 1.7 Hz, 1H), 5.53 (q, J=6.6 Hz, 1H), 3.92 (dd, J=13.7, 4.9 Hz, 1H), 3.72 (d, J=9.8 Hz, 1H), 3.33-3.45 (m, 3H), 3.12 (d, J=9.8 Hz, 1H), 2.80-3.00 (m, 2H), 2.75 (dd, J=16.2, 2.7 Hz, 1H), 2.33-2.40 (m, 1H), 1.85-1.92 (m, 1H), 1.46 (d, J=6.9 Hz, 3H), 1.31 (s, 3H), 1.21-1.29 (m, 4H).

Minor Rotamer (35%)

¹H NMR (500 MHz, DMSO-d$_6$) δ ppm 7.99 (br t, J=8.8 Hz, 1H), 7.35-7.40 (m, 1H), 7.29 (d, J=5.0 Hz, 1H), 7.00-7.05 (m, 1H), 6.92-6.95 (m, 1H), 6.77-6.82 (m, 2H), 6.49 (br d, J=8.8 Hz, 1H), 6.41 (dd, J=14.7, 1.7 Hz, 1H), 4.90 (q, J=6.5 Hz, 1H), 4.70 (br dd, J=12.8, 4.3 Hz, 1H), 3.72 (d, J=9.8 Hz, 1H), 3.33-3.45 (m, 2H), 3.21 (td, J=12.3, 4.4 Hz, 1H), 3.12 (d, J=9.8 Hz, 1H), 2.80-3.00 (m, 3H), 2.33-2.40 (m, 1H), 1.85-1.92 (m, 1H), 1.50 (d, J=6.6 Hz, 3H), 1.31 (s, 3H), 1.21-1.29 (m, 4H).

Compound 45

Major Rotamer (65%)

¹H NMR (400 MHz, DMSO-d$_6$) δ ppm 8.00 (t, J=8.8 Hz, 1H), 7.34-7.40 (m, 2H), 7.00-7.04 (m, 2H), 6.91-6.95 (m, 1H), 6.76-6.81 (m, 1H), 6.49 (br d, J=9.1 Hz, 1H), 6.40 (dd, J=14.7, 2.0 Hz, 1H), 5.53 (q, J=6.7 Hz, 1H), 3.92 (dd, J=13.9, 5.3 Hz, 1H), 3.72 (d, J=10.1 Hz, 1H), 3.33-3.45 (m, 3H), 3.12 (d, J=10.1 Hz, 1H), 2.81-3.01 (m, 2H), 2.75 (dd, J=16.4, 2.7 Hz, 1H), 2.34-2.41 (m, 1H), 1.84-1.93 (m, 1H), 1.46 (d, J=7.1 Hz, 3H), 1.31 (s, 3H), 1.22-1.29 (m, 4H).

Minor Rotamer (35%)

¹H NMR (400 MHz, DMSO-d$_6$) δ ppm 7.99 (br t, J=8.8 Hz, 1H), 7.34-7.40 (m, 1H), 7.29 (d, J=5.1 Hz, 1H), 7.00-7.04 (m, 1H), 6.91-6.95 (m, 1H), 6.76-6.81 (m, 2H), 6.49 (br d, J=9.1 Hz, 1H), 6.40 (dd, J=14.7, 2.0 Hz, 1H), 4.90 (q, J=6.1 Hz, 1H), 4.70 (dd, J=12.6, 4.0 Hz, 1H), 3.72 (d, J=10.1 Hz, 1H), 3.33-3.45 (m, 2H), 3.16-3.25 (m, 1H), 3.12 (d, J=10.1 Hz, 1H), 2.81-3.01 (m, 3H), 2.34-2.41 (m, 1H), 1.84-1.93 (m, 1H), 1.49 (d, J=6.6 Hz, 3H), 1.31 (s, 3H), 1.22-1.29 (m, 4H).

Compound 46

Major Rotamer (65%)

¹H NMR (500 MHz, DMSO-d$_6$) δ ppm 8.00 (t, J=8.8 Hz, 1H), 7.49 (br s, 1H), 7.38 (d, J=5.0 Hz, 1H), 7.01 (d, J=5.4 Hz, 1H), 6.98 (br s, 1H), 6.92-6.95 (m, 1H), 6.77-6.81 (m, 1H), 6.52 (br d, J=8.8 Hz, 1H), 6.44 (dd, J=14.8, 1.6 Hz, 1H), 5.53 (q, J=6.8 Hz, 1H), 3.93 (dd, J=13.7, 4.9 Hz, 1H), 3.48-3.53 (m, 1H), 3.36-3.45 (m, 3H), 3.31-3.35 (m, 1H), 3.09 (quin, J=7.6 Hz, 1H), 2.80-3.00 (m, 2H), 2.75 (dd, J=15.9, 2.7 Hz, 1H), 2.16-2.24 (m, 1H), 2.06-2.15 (m, 1H), 1.46 (d, J=6.6 Hz, 3H), 1.30-1.37 (m, 2H), 1.23-1.30 (m, 2H).

Minor Rotamer (35%)

¹H NMR (500 MHz, DMSO-d$_6$) δ ppm 7.99 (br t, J=8.8 Hz, 1H), 7.49 (br s, 1H), 7.29 (d, J=5.0 Hz, 1H), 6.98 (br s, 1H), 6.92-6.95 (m, 1H), 6.77-6.81 (m, 2H), 6.52 (br d, J=8.8 Hz, 1H), 6.44 (dd, J=14.8, 1.6 Hz, 1H), 4.91 (q, J=6.3 Hz, 1H), 4.71 (br dd, J=12.5, 4.6 Hz, 1H), 3.48-3.53 (m, 1H), 3.36-3.45 (m, 2H), 3.31-3.35 (m, 1H), 3.17-3.24 (m, 1H), 3.09 (quin, J=7.6 Hz, 1H), 2.80-3.00 (m, 3H), 2.16-2.24 (m, 1H), 2.06-2.15 (m, 1H), 1.50 (d, J=6.6 Hz, 3H), 1.30-1.37 (m, 2H), 1.23-1.30 (m, 2H).

Compound 47

Major Rotamer (65%)

¹H NMR (500 MHz, DMSO-d$_6$) δ ppm 8.00 (t, J=8.8 Hz, 1H), 7.49 (br s, 1H), 7.18-7.26 (m, 2H), 6.91-7.07 (m, 3H), 6.80 (s, 1H), 6.52 (dd, J=8.8, 1.9 Hz, 1H), 6.44 (dd, J=14.8, 1.6 Hz, 1H), 5.60 (q, J=6.8 Hz, 1H), 3.83 (br dd, J=13.6, 4.1 Hz, 1H), 3.47-3.54 (m, 1H), 3.32-3.47 (m, 4H), 3.09 (quin, J=7.6 Hz, 1H), 2.83-3.01 (m, 2H), 2.71 (br d, J=16.1 Hz, 1H), 2.16-2.25 (m, 1H), 2.06-2.15 (m, 1H), 1.52 (d, J=6.9 Hz, 3H), 1.30-1.37 (m, 2H), 1.22-1.30 (m, 2H).

Minor Rotamer (35%)

¹H NMR (500 MHz, DMSO-d$_6$) δ ppm 8.00 (t, J=8.8 Hz, 1H), 7.49 (br s, 1H), 7.18-7.26 (m, 1H), 6.91-7.07 (m, 4H), 6.76 (s, 1H), 6.52 (dd, J=8.8, 1.9 Hz, 1H), 6.44 (dd, J=14.8, 1.6 Hz, 1H), 4.98 (q, J=6.4 Hz, 1H), 4.55 (dt, J=12.8, 3.7 Hz, 1H), 3.47-3.54 (m, 1H), 3.32-3.47 (m, 3H), 3.20-3.28 (m, 1H), 3.09 (quin, J=7.6 Hz, 1H), 2.83-3.01 (m, 3H), 2.16-2.25 (m, 1H), 2.06-2.15 (m, 1H), 1.55 (d, J=6.6 Hz, 3H), 1.30-1.37 (m, 2H), 1.22-1.30 (m, 2H).

Compound 48

Major Rotamer (65%)

¹H NMR (500 MHz, DMSO-d$_6$) δ ppm 8.09 (t, J=8.8 Hz, 1H), 7.38 (dd, J=8.1, 5.7 Hz, 1H), 6.99-7.09 (m, 3H), 6.84 (s, 1H), 6.81-6.85 (m, 1H), 6.77 (dd, J=14.2, 2.2 Hz, 1H), 6.16 (d, J=6.0 Hz, 1H), 5.59 (q, J=6.4 Hz, 1H), 3.82 (br dd, J=13.7, 4.3 Hz, 1H), 3.59 (td, J=8.6, 3.9 Hz, 1H), 3.49-3.55 (m, 1H), 3.41-3.48 (m, 1H), 3.16-3.23 (m, 1H), 2.94-3.05 (m, 2H), 2.87-2.94 (m, 2H), 2.74 (br d, J=16.7 Hz, 1H), 2.28-2.35 (m, 1H), 1.78-1.86 (m, 1H), 1.51 (d, J=6.9 Hz, 3H), 1.31-1.39 (m, 2H), 1.22-1.30 (m, 2H).
Minor Rotamer (35%)
$^1$H NMR (500 MHz, DMSO-d$_6$) δ ppm 8.09 (t, J=8.8 Hz, 1H), 7.14 (dd, J=8.5, 6.0 Hz, 1H), 6.99-7.09 (m, 2H), 6.96 (td, J=8.7, 2.5 Hz, 1H), 6.81-6.85 (m, 1H), 6.80 (s, 1H), 6.77 (dd, J=14.2, 2.2 Hz, 1H), 6.16 (d, J=6.0 Hz, 1H), 4.97 (q, J=6.7 Hz, 1H), 4.54 (dt, J=12.6, 3.8 Hz, 1H), 3.59 (td, J=8.6, 3.9 Hz, 1H), 3.49-3.55 (m, 1H), 3.24-3.28 (m, 1H), 3.16-3.23 (m, 1H), 2.94-3.05 (m, 3H), 2.87-2.94 (m, 2H), 2.28-2.35 (m, 1H), 1.78-1.86 (m, 1H), 1.53 (d, J=6.6 Hz, 3H), 1.31-1.39 (m, 2H), 1.22-1.30 (m, 2H).

Compound 49

Major Rotamer (65%)
$^1$H NMR (400 MHz, DMSO-d$_6$) δ ppm 8.36 (t, J=9.4 Hz, 1H), 7.51 (br s, 1H), 7.32 (d, J=7.1 Hz, 1H), 7.05-7.25 (m, 3H), 7.00 (br s, 1H), 6.91-6.95 (m, 1H), 6.82 (s, 1H), 6.53 (dd, J=8.6, 1.5 Hz, 1H), 5.58 (q, J=6.9 Hz, 1H), 3.81 (br dd, J=13.4, 3.8 Hz, 1H), 3.39-3.69 (m, 5H), 2.83-3.13 (m, 3H), 2.71 (br d, J=16.2 Hz, 1H), 2.15-2.25 (m, 1H), 2.04-2.15 (m, 1H), 1.52 (d, J=7.1 Hz, 3H), 1.30-1.38 (m, 2H), 1.20-1.30 (m, 2H).
Minor Rotamer (35%)
$^1$H NMR (400 MHz, DMSO-d$_6$) δ ppm 8.36 (t, J=9.4 Hz, 1H), 7.51 (br s, 1H), 7.05-7.25 (m, 4H), 7.00 (br s, 1H), 6.91-6.95 (m, 1H), 6.79 (s, 1H), 6.53 (dd, J=8.6, 1.5 Hz, 1H), 4.96 (q, J=6.6 Hz, 1H), 4.50-4.59 (m, 1H), 3.39-3.69 (m, 4H), 3.21-3.29 (m, 1H), 2.83-3.13 (m, 4H), 2.15-2.25 (m, 1H), 2.04-2.15 (m, 1H), 1.55 (br d, J=6.6 Hz, 3H), 1.30-1.38 (m, 2H), 1.20-1.30 (m, 2H).

Compound 50

Major Rotamer (65%)
$^1$H NMR (500 MHz, DMSO-d$_6$) δ ppm 8.36 (t, J=9.3 Hz, 1H), 8.00 (q, J=4.4 Hz, 1H), 7.32 (d, J=7.6 Hz, 1H), 7.06-7.26 (m, 3H), 6.91-6.97 (m, 1H), 6.83 (s, 1H), 6.53 (br d, J=8.2 Hz, 1H), 5.58 (q, J=6.5 Hz, 1H), 3.81 (br dd, J=13.9, 3.8 Hz, 1H), 3.63-3.70 (m, 1H), 3.55-3.62 (m, 1H), 3.40-3.53 (m, 3H), 2.82-3.11 (m, 3H), 2.72 (br d, J=16.1 Hz, 1H), 2.62 (d, J=4.4 Hz, 3H), 2.14-2.23 (m, 1H), 2.04-2.14 (m, 1H), 1.52 (d, J=6.9 Hz, 3H), 1.30-1.38 (m, 2H), 1.21-1.30 (m, 2H).
Minor Rotamer (35%)
$^1$H NMR (500 MHz, DMSO-d$_6$) δ ppm 8.36 (t, J=9.3 Hz, 1H), 8.00 (q, J=4.4 Hz, 1H), 7.06-7.26 (m, 4H), 6.91-6.97 (m, 1H), 6.79 (s, 1H), 6.53 (br d, J=8.2 Hz, 1H), 4.96 (q, J=6.7 Hz, 1H), 4.52-4.59 (m, 1H), 3.63-3.70 (m, 1H), 3.55-3.62 (m, 1H), 3.40-3.53 (m, 2H), 3.23-3.30 (m, 1H), 2.82-3.11 (m, 4H), 2.62 (d, J=4.4 Hz, 3H), 2.14-2.23 (m, 1H), 2.04-2.14 (m, 1H), 1.55 (d, J=6.6 Hz, 3H), 1.30-1.38 (m, 2H), 1.21-1.30 (m, 2H).

Compound 51

Major Rotamer (65%)
$^1$H NMR (500 MHz, DMSO-d$_6$) δ ppm 11.99 (br s, 1H), 8.38 (t, J=9.3 Hz, 1H), 7.32 (d, J=7.3 Hz, 1H), 7.05-7.26 (m, 3H), 6.92-6.98 (m, 1H), 6.83 (s, 1H), 6.56 (br dd, J=7.3, 1.0 Hz, 1H), 5.58 (q, J=6.5 Hz, 1H), 3.81 (dd, J=14.0, 3.9 Hz, 1H), 3.66-3.73 (m, 1H), 3.58-3.64 (m, 1H), 3.42-3.57 (m, 3H), 3.25 (s, 3H), 3.21-3.29 (m, 1H), 2.83-3.06 (m, 3H), 2.72 (br d, J=16.4 Hz, 1H), 2.23-2.32 (m, 1H), 2.13-2.22 (m, 1H), 1.52 (d, J=6.9 Hz, 3H), 1.24-1.37 (m, 4H).
Minor Rotamer (35%)
$^1$H NMR (500 MHz, DMSO-d$_6$) δ ppm 11.99 (br s, 1H), 8.38 (t, J=9.3 Hz, 1H), 7.05-7.26 (m, 4H), 6.92-6.98 (m, 1H), 6.79 (s, 1H), 6.56 (br dd, J=7.3, 1.0 Hz, 1H), 4.96 (q, J=6.6 Hz, 1H), 4.52-4.58 (m, 1H), 3.66-3.73 (m, 1H), 3.58-3.64 (m, 1H), 3.42-3.57 (m, 2H), 3.25 (s, 3H), 3.21-3.29 (m, 2H), 2.83-3.06 (m, 3H), 2.23-2.32 (m, 1H), 2.13-2.22 (m, 1H), 1.55 (d, J=6.6 Hz, 3H), 1.24-1.37 (m, 4H).

Compound 52

Major Rotamer (65%)
$^1$H NMR (400 MHz, DMSO-d$_6$) δ ppm 8.84 (d, J=11.1 Hz, 1H), 7.52 (br s, 1H), 7.32 (br d, J=7.6 Hz, 1H), 6.95-7.27 (m, 5H), 6.84 (s, 1H), 6.45 (br d, J=14.2 Hz, 1H), 5.59 (q, J=6.6 Hz, 1H), 3.80 (br dd, J=13.4, 4.0 Hz, 1H), 3.40-3.73 (m, 5H), 2.85-3.13 (m, 3H), 2.71 (br d, J=16.2 Hz, 1H), 2.03-2.25 (m, 2H), 1.48-1.54 (m, 3H), 1.22-1.40 (m, 4H).
Minor Rotamer (35%)
$^1$H NMR (400 MHz, DMSO-d$_6$) δ ppm 8.84 (d, J=11.1 Hz, 1H), 7.52 (br s, 1H), 6.95-7.27 (m, 6H), 6.81 (s, 1H), 6.45 (br d, J=14.2 Hz, 1H), 4.95 (q, J=6.6 Hz, 1H), 4.50-4.61 (m, 1H), 3.40-3.73 (m, 4H), 3.21-3.30 (m, 1H), 2.85-3.13 (m, 4H), 2.03-2.25 (m, 2H), 1.52-1.59 (m, 3H), 1.22-1.40 (m, 4H).

Compound 53

Major Rotamer (65%)
$^1$H NMR (400 MHz, DMSO-d$_6$) δ ppm 8.84 (d, J=11.1 Hz, 1H), 8.00 (q, J=4.6 Hz, 1H), 7.32 (br d, J=7.1 Hz, 1H), 7.05-7.25 (m, 3H), 6.95-7.00 (m, 1H), 6.84 (s, 1H), 6.45 (d, J=14.2 Hz, 1H), 5.58 (q, J=6.6 Hz, 1H), 3.80 (br dd, J=13.6, 4.0 Hz, 1H), 3.56-3.73 (m, 2H), 3.39-3.53 (m, 3H), 2.85-3.11 (m, 3H), 2.68-2.76 (m, 1H), 2.62 (d, J=4.6 Hz, 3H), 2.03-2.23 (m, 2H), 1.48-1.58 (m, 3H), 1.22-1.38 (m, 4H).
Minor Rotamer (35%)
$^1$H NMR (400 MHz, DMSO-d$_6$) δ ppm 8.84 (d, J=11.1 Hz, 1H), 8.00 (q, J=4.6 Hz, 1H), 7.05-7.25 (m, 4H), 6.95-7.00 (m, 1H), 6.81 (s, 1H), 6.45 (d, J=14.2 Hz, 1H), 4.91-4.99 (m, 1H), 4.51-4.59 (m, 1H), 3.56-3.73 (m, 2H), 3.39-3.53 (m, 2H), 3.21-3.29 (m, 1H), 2.85-3.11 (m, 4H), 2.62 (d, J=4.6 Hz, 3H), 2.03-2.23 (m, 2H), 1.48-1.58 (m, 3H), 1.22-1.38 (m, 4H).

Compound 54

Major Rotamer (65%)
$^1$H NMR (500 MHz, DMSO-d$_6$) δ ppm 11.97 (br s, 1H), 8.85 (d, J=11.4 Hz, 1H), 7.32 (d, J=7.3 Hz, 1H), 7.06-7.25 (m, 3H), 6.99 (br d, J=2.8 Hz, 1H), 6.85 (s, 1H), 6.48 (br d, J=13.9 Hz, 1H), 5.59 (q, J=6.7 Hz, 1H), 3.77-3.84 (m, 1H), 3.67-3.74 (m, 1H), 3.59-3.65 (m, 1H), 3.51-3.58 (m, 1H), 3.42-3.51 (m, 2H), 3.18-3.28 (m, 1H), 3.22 (s, 3H), 2.86-3.05 (m, 2H), 2.71 (br d, J=16.3 Hz, 1H), 2.21-2.30 (m, 1H), 2.12-2.21 (m, 1H), 1.52 (d, J=6.6 Hz, 3H), 1.31-1.37 (m, 2H), 1.24-1.31 (m, 2H).
Minor Rotamer (35%)
$^1$H NMR (500 MHz, DMSO-d$_6$) δ ppm 11.97 (br s, 1H), 8.84 (d, J=11.4 Hz, 1H), 7.06-7.25 (m, 4H), 6.98 (br d, J=2.8 Hz, 1H), 6.81 (s, 1H), 6.48 (br d, J=13.9 Hz, 1H), 4.95 (q, J=6.6 Hz, 1H), 4.52-4.58 (m, 1H), 3.67-3.74 (m, 1H), 3.59-3.65 (m, 1H), 3.51-3.58 (m, 1H), 3.42-3.51 (m, 1H), 3.18-3.28 (m, 2H), 3.22 (s, 3H), 2.86-3.05 (m, 3H), 2.21-2.30 (m, 1H), 2.12-2.21 (m, 1H), 1.54 (d, J=6.6 Hz, 3H), 1.31-1.37 (m, 2H), 1.24-1.31 (m, 2H).

Compound 55

Major Rotamer (65%)

$^1$H NMR (500 MHz, DMSO-d$_6$) δ ppm 7.81 (dd, J=14.5, 6.9 Hz, 1H), 7.50 (br s, 1H), 7.32 (d, J=7.3 Hz, 1H), 7.21-7.25 (m, 1H), 7.15-7.21 (m, 2H), 6.97-7.03 (m, 2H), 6.84 (s, 1H), 6.64 (dd, J=13.6, 7.6 Hz, 1H), 5.58 (q, J=6.6 Hz, 1H), 3.80 (br dd, J=13.7, 3.9 Hz, 1H), 3.59-3.66 (m, 1H), 3.53-3.59 (m, 1H), 3.42-3.52 (m, 3H), 2.83-3.07 (m, 3H), 2.71 (br d, J=16.1 Hz, 1H), 2.11-2.19 (m, 1H), 2.00-2.09 (m, 1H), 1.52 (d, J=6.9 Hz, 3H), 1.31-1.38 (m, 2H), 1.22-1.30 (m, 2H).

Minor Rotamer (35%)

$^1$H NMR (500 MHz, DMSO-d$_6$) δ ppm 7.81 (dd, J=14.5, 6.9 Hz, 1H), 7.50 (br s, 1H), 7.15-7.21 (m, 2H), 7.10-7.15 (m, 1H), 7.08 (d, J=7.6 Hz, 1H), 6.97-7.03 (m, 2H), 6.81 (s, 1H), 6.64 (dd, J=13.6, 7.6 Hz, 1H), 4.95 (q, J=6.7 Hz, 1H), 4.54 (br dd, J=12.6, 3.8 Hz, 1H), 3.59-3.66 (m, 1H), 3.53-3.59 (m, 1H), 3.42-3.52 (m, 2H), 3.22-3.30 (m, 1H), 2.83-3.07 (m, 4H), 2.11-2.19 (m, 1H), 2.00-2.09 (m, 1H), 1.54 (d, J=6.6 Hz, 3H), 1.31-1.38 (m, 2H), 1.22-1.30 (m, 2H).

Compound 56

Major Rotamer (65%)

$^1$H NMR (500 MHz, DMSO-d$_6$) δ ppm 8.28-8.31 (m, 2H), 7.91 (t, J=8.7 Hz, 1H), 7.61-7.68 (m, 3H), 7.51 (br s, 1H), 7.32-7.40 (m, 2H), 7.09-7.27 (m, 3H), 7.03-7.08 (m, 1H), 7.00 (br s, 1H), 6.51 (br d, J=8.8 Hz, 1H), 6.45 (br d, J=14.8 Hz, 1H), 5.63 (q, J=6.8 Hz, 1H), 3.99 (br dd, J=14.0, 4.3 Hz, 1H), 3.46-3.58 (m, 2H), 3.27-3.44 (m, 3H partially obscured by H$_2$O peak), 3.03-3.12 (m, 2H), 2.76 (br d, J=16.7 Hz, 1H), 2.16-2.23 (m, 1H), 2.05-2.14 (m, 1H), 1.55 (d, J=6.9 Hz, 3H).

Minor Rotamer (35%)

$^1$H NMR (500 MHz, DMSO-d$_6$) δ ppm 8.24-8.28 (m, 2H), 7.91 (t, J=8.7 Hz, 1H), 7.61-7.68 (m, 3H), 7.51 (br s, 1H), 7.32-7.40 (m, 1H), 7.09-7.27 (m, 4H), 7.03-7.08 (m, 1H), 7.00 (br s, 1H), 6.51 (br d, J=8.8 Hz, 1H), 6.45 (br d, J=14.8 Hz, 1H), 5.14 (q, J=6.9 Hz, 1H), 4.59 (br dd, J=12.6, 3.8 Hz, 1H), 3.46-3.58 (m, 1H), 3.27-3.44 (m, 3H partially obscured by H$_2$O peak), 3.03-3.12 (m, 2H), 2.85-3.00 (m, 2H), 2.16-2.23 (m, 1H), 2.05-2.14 (m, 1H), 1.61 (d, J=6.6 Hz, 3H).

Compound 57

Major Rotamer (65%)

$^1$H NMR (500 MHz, DMSO-d$_6$) δ ppm 8.39 (d, J=8.8 Hz, 2H), 7.94 (t, J=8.7 Hz, 1H), 7.51 (br s, 1H), 7.37 (s, 1H), 7.32-7.36 (m, 1H), 7.09-7.42 (m, 8H), 6.98-7.05 (m, 1H), 6.51 (br d, J=8.8 Hz, 1H), 6.45 (br d, J=14.5 Hz, 1H), 5.63 (q, J=6.3 Hz, 1H), 3.97 (br dd, J=13.9, 3.8 Hz, 1H), 3.90 (s, 3H), 3.47-3.56 (m, 2H), 3.36-3.44 (m, 2H), 3.26-3.32 (m, 1H partially obscured by H$_2$O peak), 3.02-3.12 (m, 2H), 2.75 (br d, J=17.0 Hz, 1H), 2.16-2.24 (m, 1H), 2.06-2.15 (m, 1H), 1.55 (d, J=6.6 Hz, 3H).

Minor Rotamer (35%)

$^1$H NMR (500 MHz, DMSO-d$_6$) δ ppm 8.35 (d, J=8.8 Hz, 2H), 7.94 (t, J=8.7 Hz, 1H), 7.51 (br s, 1H), 7.32-7.36 (m, 1H), 7.09-7.27 (m, 6H), 6.98-7.05 (m, 2H), 6.51 (br d, J=8.8 Hz, 1H), 6.45 (br d, J=14.5 Hz, 1H), 5.12 (q, J=6.0 Hz, 1H), 4.59 (br dd, J=13.2, 3.8 Hz, 1H), 3.89 (s, 3H), 3.47-3.56 (m, 1H), 3.36-3.44 (m, 2H), 3.26-3.32 (m, 1H partially obscured by H$_2$O peak), 3.02-3.12 (m, 2H), 2.85-2.99 (m, 2H), 2.16-2.24 (m, 1H), 2.06-2.15 (m, 1H), 1.60 (d, J=6.6 Hz, 3H).

Compound 58

Major Rotamer (65%)

$^1$H NMR (500 MHz, DMSO-d$_6$) δ ppm 8.23 (br d, J=7.9 Hz, 2H), 7.91 (br t, J=8.7 Hz, 1H), 7.42-7.48 (m, 3H), 7.31-7.40 (m, 2H), 7.08-7.27 (m, 3H), 6.97-7.08 (m, 2H), 6.51 (br d, J=8.5 Hz, 1H), 6.45 (br d, J=14.8 Hz, 1H), 5.63 (q, J=6.5 Hz, 1H), 3.98 (br dd, J=13.1, 3.6 Hz, 1H), 3.45-3.57 (m, 2H), 3.35-3.44 (m, 2H), 3.02-3.18 (m, 2H), 2.75 (br d, J=16.1 Hz, 1H), 2.41-2.47 (m, 4H), 2.15-2.25 (m, 1H), 2.05-2.15 (m, 1H), 1.55 (br d, J=6.6 Hz, 3H).

Minor Rotamer (35%)

$^1$H NMR (500 MHz, DMSO-d$_6$) δ ppm 8.20 (br d, J=7.9 Hz, 2H), 7.91 (br t, J=8.7 Hz, 1H), 7.42-7.48 (m, 3H), 7.31-7.40 (m, 1H), 7.08-7.27 (m, 4H), 6.97-7.08 (m, 2H), 6.51 (br d, J=8.5 Hz, 1H), 6.45 (br d, J=14.8 Hz, 1H), 5.13 (q, J=6.4 Hz, 1H), 4.59 (br dd, J=13.2, 4.4 Hz, 1H), 3.45-3.57 (m, 2H), 3.35-3.44 (m, 2H), 3.02-3.18 (m, 1H), 2.85-3.00 (m, 2H), 2.41-2.47 (m, 4H), 2.15-2.25 (m, 1H), 2.05-2.15 (m, 1H), 1.60 (br d, J=6.6 Hz, 3H).

Compound 59

Major Rotamer (65%)

$^1$H NMR (500 MHz, DMSO-d$_6$) δ ppm 8.34 (d, J=8.5 Hz, 2H), 7.92 (t, J=8.7 Hz, 1H), 7.69-7.74 (m, 2H), 7.51 (br s, 1H), 7.43 (s, 1H), 7.34 (d, J=7.6 Hz, 1H), 7.08-7.26 (m, 3H), 7.04-7.08 (m, 1H), 7.00 (br s, 1H), 6.50 (br d, J=8.8 Hz, 1H), 6.45 (br d, J=14.8 Hz, 1H), 5.63 (q, J=6.5 Hz, 1H), 3.95-4.01 (m, 1H), 3.46-3.59 (m, 2H), 3.27-3.44 (m, 3H partially obscured by H$_2$O peak), 3.02-3.12 (m, 2H), 2.75 (br d, J=17.0 Hz, 1H), 2.16-2.24 (m, 1H), 2.05-2.14 (m, 1H), 1.55 (d, J=6.6 Hz, 3H).

Minor Rotamer (35%)

$^1$H NMR (500 MHz, DMSO-d$_6$) δ ppm 8.31 (d, J=8.5 Hz, 2H), 7.92 (t, J=8.7 Hz, 1H), 7.69-7.74 (m, 2H), 7.51 (br s, 1H), 7.38 (s, 1H), 7.08-7.26 (m, 4H), 7.04-7.08 (m, 1H), 7.00 (br s, 1H), 6.50 (br d, J=8.8 Hz, 1H), 6.45 (br d, J=14.8 Hz, 1H), 5.13 (q, J=6.6 Hz, 1H), 4.56-4.62 (m, 1H), 3.46-3.59 (m, 1H), 3.27-3.44 (m, 3H partially obscured by H$_2$O peak), 3.02-3.12 (m, 2H), 2.85-2.99 (m, 2H), 2.16-2.24 (m, 1H), 2.05-2.14 (m, 1H), 1.60 (d, J=6.6 Hz, 3H).

Compound 60

Major Rotamer (65%)

$^1$H NMR (500 MHz, DMSO-d$_6$) δ ppm 8.34-8.44 (m, 2H), 7.92 (t, J=8.8 Hz, 1H), 7.45-7.54 (m, 3H), 7.41 (s, 1H), 7.34 (d, J=7.6 Hz, 1H), 7.08-7.27 (m, 3H), 7.03-7.07 (m, 1H), 6.94-7.02 (m, 1H), 6.50 (br d, J=8.8 Hz, 1H), 6.45 (dd, J=14.5, 1.6 Hz, 1H), 5.63 (q, J=6.7 Hz, 1H), 3.98 (br dd, J=13.4, 3.9 Hz, 1H), 3.47-3.57 (m, 2H), 3.27-3.45 (m, 3H partially obscured by H$_2$O peak), 3.03-3.12 (m, 2H), 2.75 (br d, J=16.1 Hz, 1H), 2.16-2.24 (m, 1H), 2.05-2.15 (m, 1H), 1.55 (d, J=6.6 Hz, 3H).

Minor Rotamer (35%)

$^1$H NMR (500 MHz, DMSO-d$_6$) δ ppm 8.34-8.44 (m, 2H), 7.92 (t, J=8.8 Hz, 1H), 7.45-7.54 (m, 3H), 7.36 (s, 1H), 7.08-7.27 (m, 4H), 7.03-7.07 (m, 1H), 6.94-7.02 (m, 1H), 6.50 (br d, J=8.8 Hz, 1H), 6.45 (dd, J=14.5, 1.6 Hz, 1H), 5.13 (q, J=6.7 Hz, 1H), 4.59 (br dd, J=12.8, 4.9 Hz, 1H), 3.47-3.57 (m, 1H), 3.27-3.45 (m, 3H partially obscured by H$_2$O peak), 3.03-3.12 (m, 2H), 2.85-3.00 (m, 2H), 2.16-2.24 (m, 1H), 2.05-2.15 (m, 1H), 1.61 (d, J=6.6 Hz, 3H).

Compound 61

Major Rotamer (65%)

$^1$H NMR (500 MHz, DMSO-$d_6$) δ ppm 8.49 (d, J=8.2 Hz, 2H), 7.98-8.05 (m, 2H), 7.91 (t, J=8.8 Hz, 1H), 7.42-7.51 (m, 2H), 7.34 (d, J=7.3 Hz, 1H), 7.07-7.27 (m, 4H), 6.98 (br s, 1H), 6.49 (br d, J=8.8 Hz, 1H), 6.45 (dd, J=14.7, 1.7 Hz, 1H), 5.64 (q, J=6.5 Hz, 1H), 4.00 (br dd, J=13.9, 3.8 Hz, 1H), 3.46-3.58 (m, 2H), 3.27-3.44 (m, 3H), 3.03-3.12 (m, 2H), 2.76 (br d, J=16.7 Hz, 1H), 2.16-2.24 (m, 1H), 2.06-2.14 (m, 1H), 1.56 (d, J=6.6 Hz, 3H).

Minor Rotamer (35%)

$^1$H NMR (500 MHz, DMSO-$d_6$) δ ppm 8.46 (d, J=8.2 Hz, 2H), 7.98-8.05 (m, 2H), 7.91 (t, J=8.8 Hz, 1H), 7.42-7.51 (m, 2H), 7.07-7.27 (m, 5H), 6.98 (br s, 1H), 6.49 (br d, J=8.8 Hz, 1H), 6.45 (dd, J=14.7, 1.7 Hz, 1H), 5.15 (q, J=6.8 Hz, 1H), 4.59 (br dd, J=13.1, 4.6 Hz, 1H), 3.46-3.58 (m, 1H), 3.27-3.44 (m, 3H), 3.03-3.12 (m, 2H), 2.85-3.00 (m, 2H), 2.16-2.24 (m, 1H), 2.06-2.14 (m, 1H), 1.61 (d, J=6.6 Hz, 3H).

Compound 62

Major Rotamer $^1$H NMR (500 MHz, DMSO-$d_6$) δ ppm 8.47 (d, J=8.2 Hz, 2H), 8.09-8.14 (m, 2H), 7.90 (t, J=8.8 Hz, 1H), 7.43-7.53 (m, 2H), 7.34 (br d, J=7.6 Hz, 1H), 7.07-7.27 (m, 4H), 7.00 (br s, 1H), 6.49 (br d, J=8.8 Hz, 1H), 6.45 (br d, J=15.1 Hz, 1H), 5.63 (q, J=6.8 Hz, 1H), 3.99 (br dd, J=13.1, 3.9 Hz, 1H), 3.46-3.57 (m, 2H), 3.28-3.44 (m, 3H partially obscured by H$_2$O peak), 3.02-3.12 (m, 2H), 2.75 (br d, J=16.4 Hz, 1H), 2.16-2.23 (m, 1H), 2.05-2.14 (m, 1H), 1.55 (d, J=6.9 Hz, 3H).

Minor Rotamer $^1$H NMR (500 MHz, DMSO-$d_6$) δ ppm 8.44 (br d, J=8.5 Hz, 2H), 8.09-8.14 (m, 2H), 7.90 (t, J=8.8 Hz, 1H), 7.43-7.53 (m, 2H), 7.07-7.27 (m, 5H), 7.00 (br s, 1H), 6.49 (br d, J=8.8 Hz, 1H), 6.45 (br d, J=15.1 Hz, 1H), 5.11-5.17 (m, 1H), 4.56-4.62 (m, 1H), 3.46-3.57 (m, 1H), 3.28-3.44 (m, 3H partially obscured by H$_2$O peak), 3.02-3.12 (m, 2H), 2.85-2.99 (m, 2H), 2.16-2.23 (m, 1H), 2.05-2.14 (m, 1H), 1.61 (br d, J=6.6 Hz, 3H).

Compound 63

Major Rotamer (65%)

$^1$H NMR (500 MHz, DMSO-$d_6$) δ ppm 8.84-8.91 (m, 2H), 8.28 (br d, J=5.4 Hz, 2H), 7.93 (br t, J=8.7 Hz, 1H), 7.49-7.58 (m, 2H), 7.34 (br d, J=7.6 Hz, 1H), 7.06-7.27 (m, 4H), 7.00 (br s, 1H), 6.51 (br d, J=8.8 Hz, 1H), 6.46 (br d, J=14.5 Hz, 1H), 5.64 (q, J=6.1 Hz, 1H), 3.95-4.02 (m, 1H), 3.47-3.58 (m, 2H), 3.36-3.44 (m, 2H), 3.03-3.12 (m, 3H), 2.75 (br d, J=16.1 Hz, 1H), 2.16-2.24 (m, 1H), 2.06-2.15 (m, 1H), 1.56 (br d, J=6.6 Hz, 3H).

Minor Rotamer (35%)

$^1$H NMR (500 MHz, DMSO-$d_6$) δ ppm 8.84-8.91 (m, 2H), 8.25 (br d, J=5.7 Hz, 2H), 7.93 (br t, J=8.7 Hz, 1H), 7.49-7.58 (m, 2H), 7.06-7.27 (m, 5H), 7.00 (br s, 1H), 6.51 (br d, J=8.8 Hz, 1H), 6.46 (br d, J=14.5 Hz, 1H), 5.10-5.17 (m, 1H), 4.56-4.63 (m, 1H), 3.47-3.58 (m, 2H), 3.36-3.44 (m, 2H), 3.03-3.12 (m, 2H), 2.85-3.00 (m, 2H), 2.16-2.24 (m, 1H), 2.06-2.15 (m, 1H), 1.61 (br d, J=6.6 Hz, 3H).

Compound 64

Major Rotamer (65%)

$^1$H NMR (400 MHz, DMSO-$d_6$) δ ppm 9.68 (s, 2H), 9.34-9.46 (m, 1H), 7.90 (br t, J=8.6 Hz, 1H), 7.67 (s, 1H), 7.50 (br s, 1H), 6.95-7.37 (m, 6H), 6.52 (br d, J=8.6 Hz, 1H), 6.45 (br d, J=14.7 Hz, 1H), 5.59-5.68 (m, 1H), 3.96 (br d, J=9.6 Hz, 1H), 3.45-3.66 (m, 2H), 3.33-3.44 (m, 3H), 3.01-3.20 (m, 2H), 2.75 (br d, J=17.7 Hz, 1H), 2.04-2.26 (m, 2H), 1.56 (br d, J=6.1 Hz, 3H).

Minor Rotamer (35%)

$^1$H NMR (400 MHz, DMSO-$d_6$) δ ppm 9.65 (s, 2H), 9.34-9.46 (m, 1H), 7.90 (br t, J=8.6 Hz, 1H), 7.63 (s, 1H), 7.50 (br s, 1H), 6.95-7.37 (m, 6H), 6.52 (br d, J=8.6 Hz, 1H), 6.45 (br d, J=14.7 Hz, 1H), 5.08-5.16 (m, 1H), 4.60 (br d, J=11.1 Hz, 1H), 3.45-3.66 (m, 1H), 3.33-3.44 (m, 3H), 3.01-3.20 (m, 2H), 2.84-3.01 (m, 2H), 2.04-2.26 (m, 2H), 1.61 (br d, J=6.1 Hz, 3H).

Compound 65

Major Rotamer (65%)

$^1$H NMR (400 MHz, DMSO-$d_6$) δ ppm 7.98 (t, J=8.5 Hz, 1H), 7.29-7.41 (m, 2H), 7.05-7.25 (m, 3H), 6.91-6.96 (m, 1H), 6.85 (br s, 1H), 6.81 (s, 1H), 6.31-6.41 (m, 2H), 5.58 (q, J=6.8 Hz, 1H), 4.04 (t, J=7.8 Hz, 2H), 3.81 (br dd, J=13.1, 3.5 Hz, 1H), 3.59 (dd, J=7.3, 5.9 Hz, 2H), 3.42-3.51 (m, 1H), 2.85-3.06 (m, 3H), 2.71 (br d, J=16.1 Hz, 1H), 2.44-2.48 (m, 2H partially obscured by DMSO peak), 1.52 (d, J=6.7 Hz, 3H), 1.30-1.37 (m, 2H), 1.21-1.29 (m, 2H).

Minor Rotamer (35%)

$^1$H NMR (400 MHz, DMSO-$d_6$) δ ppm 7.98 (t, J=8.5 Hz, 1H), 7.29-7.41 (m, 2H), 7.05-7.25 (m, 4H), 6.91-6.96 (m, 1H), 6.85 (br s, 1H), 6.78 (s, 1H), 6.31-6.41 (m, 2H), 4.96 (q, J=6.7 Hz, 1H), 4.51-4.59 (m, 1H), 4.04 (t, J=7.8 Hz, 2H), 3.59 (dd, J=7.3, 5.9 Hz, 2H), 3.22-3.30 (m, 1H), 2.85-3.06 (m, 4H), 2.44-2.48 (m, 2H partially obscured by DMSO peak), 1.55 (d, J=6.6 Hz, 3H), 1.30-1.37 (m, 2H), 1.21-1.29 (m, 2H).

Compound 66

Major Rotamer (65%)

$^1$H NMR (500 MHz, DMSO-$d_6$) δ ppm 7.98 (t, J=8.5 Hz, 1H), 7.81-7.85 (m, 1H), 7.32 (d, J=7.6 Hz, 1H), 7.06-7.25 (m, 3H), 6.94 (d, J=3.5 Hz, 1H), 6.81 (s, 1H), 6.37 (dd, J=8.7, 2.0 Hz, 1H), 6.34 (br d, J=13.6 Hz, 1H), 5.58 (q, J=6.5 Hz, 1H), 4.03 (t, J=7.7 Hz, 2H), 3.81 (br dd, J=13.6, 3.8 Hz, 1H), 3.59 (dd, J=7.4, 5.8 Hz, 2H), 3.42-3.50 (m, 1H), 2.81-3.05 (m, 3H), 2.71 (br d, J=16.7 Hz, 1H), 2.58 (d, J=4.4 Hz, 3H), 2.47-2.49 (m, 2H), 1.52 (d, J=6.9 Hz, 3H), 1.30-1.37 (m, 2H), 1.22-1.30 (m, 2H).

Minor Rotamer (35%)

$^1$H NMR (500 MHz, DMSO-$d_6$) δ ppm 7.98 (br t, J=8.7 Hz, 1H), 7.81-7.85 (m, 1H), 7.06-7.25 (m, 4H), 6.93 (d, J=3.5 Hz, 1H), 6.78 (s, 1H), 6.37 (dd, J=8.7, 2.0 Hz, 1H), 6.34 (br d, J=13.6 Hz, 1H), 4.96 (q, J=6.7 Hz, 1H), 4.52-4.58 (m, 1H), 4.03 (t, J=7.7 Hz, 2H), 3.59 (dd, J=7.4, 5.8 Hz, 2H), 3.23-3.30 (m, 1H), 2.81-3.05 (m, 4H), 2.58 (d, J=4.4 Hz, 3H), 2.47-2.49 (m, 2H), 1.55 (d, J=6.6 Hz, 3H), 1.30-1.37 (m, 2H), 1.22-1.30 (m, 2H).

Compound 67

Major Rotamer (65%)

$^1$H NMR (500 MHz, DMSO-$d_6$) δ ppm 7.98 (br t, J=8.4 Hz, 1H), 7.32 (br d, J=7.3 Hz, 1H), 7.06-7.26 (m, 3H), 6.92-6.96 (m, 1H), 6.81 (s, 1H), 6.33-6.43 (m, 2H), 5.70 (d, J=6.3 Hz, 1H), 5.58 (q, J=7.0 Hz, 1H), 4.58-4.65 (m, 1H), 4.16 (t, J=7.3 Hz, 2H), 3.81 (br dd, J=13.2, 4.1 Hz, 1H), 3.63

(dd, J=7.9, 4.7 Hz, 2H), 3.43-3.50 (m, 1H), 2.83-3.06 (m, 2H), 2.72 (br d, J=16.4 Hz, 1H), 1.52 (d, J=6.6 Hz, 3H), 1.30-1.36 (m, 2H), 1.21-1.29 (m, 2H).
Minor Rotamer (35%)
¹H NMR (500 MHz, DMSO-d₆) δ ppm 7.98 (br t, J=8.4 Hz, 1H), 7.06-7.26 (m, 4H), 6.92-6.96 (m, 1H), 6.78 (s, 1H), 6.33-6.43 (m, 2H), 5.70 (d, J=6.3 Hz, 1H), 4.96 (q, J=6.4 Hz, 1H), 4.58-4.65 (m, 1H), 4.51-4.57 (m, 1H), 4.16 (t, J=7.3 Hz, 2H), 3.63 (dd, J=7.9, 4.7 Hz, 2H), 3.22-3.29 (m, 1H), 2.83-3.06 (m, 3H), 1.55 (d, J=6.6 Hz, 3H), 1.30-1.36 (m, 2H), 1.21-1.29 (m, 2H).

Compound 68

Major Rotamer (65%)
¹H NMR (500 MHz, DMSO-d₆) δ ppm 8.00 (t, J=9.0 Hz, 1H), 7.28-7.36 (m, 2H), 7.06-7.25 (m, 3H), 6.95-6.99 (m, 1H), 6.92 (br d, J=8.8 Hz, 1H), 6.88 (br d, J=15.1 Hz, 1H), 6.83 (s, 1H), 6.80 (br s, 1H), 5.59 (q, J=6.8 Hz, 1H), 3.89 (br d, J=12.9 Hz, 2H), 3.82 (br dd, J=13.9, 3.8 Hz, 1H), 3.43-3.50 (m, 1H), 2.97-3.05 (m, 1H), 2.91-2.97 (m, 1H), 2.79-2.91 (m, 2H), 2.72 (br d, J=16.4 Hz, 1H), 2.29-2.38 (m, 1H), 1.76-1.83 (m, 2H), 1.62 (br qd, J=12.2, 3.6 Hz, 2H), 1.52 (d, J=6.9 Hz, 3H), 1.31-1.38 (m, 2H), 1.24-1.30 (m, 2H).
Minor Rotamer (35%)
¹H NMR (500 MHz, DMSO-d₆) δ ppm 8.00 (t, J=9.0 Hz, 1H), 7.28-7.36 (m, 1H), 7.06-7.25 (m, 4H), 6.95-6.99 (m, 1H), 6.92 (br d, J=8.8 Hz, 1H), 6.88 (br d, J=15.1 Hz, 1H), 6.80 (br s, 1H), 6.79 (s, 1H), 4.97 (q, J=6.6 Hz, 1H), 4.55 (br dd, J=12.9, 3.2 Hz, 1H), 3.89 (br d, J=12.9 Hz, 2H), 3.23-3.30 (m, 1H), 2.91-2.97 (m, 2H), 2.79-2.91 (m, 3H), 2.29-2.38 (m, 1H), 1.76-1.83 (m, 2H), 1.62 (br qd, J=12.2, 3.6 Hz, 2H), 1.55 (d, J=6.6 Hz, 3H), 1.31-1.38 (m, 2H), 1.24-1.30 (m, 2H).

Compound 69

Major Rotamer (65%)
¹H NMR (400 MHz, DMSO-d₆) δ ppm 8.00 (t, J=8.9 Hz, 1H), 7.41 (br s, 1H), 7.32 (d, J=7.2 Hz, 1H), 7.05-7.25 (m, 3H), 6.86-7.00 (m, 4H), 6.83 (s, 1H), 5.59 (q, J=6.6 Hz, 1H), 3.89 (br d, J=13.0 Hz, 1H), 3.78-3.86 (m, 2H), 3.41-3.52 (m, 1H), 2.86-3.07 (m, 3H), 2.78-2.85 (m, 1H), 2.72 (br d, J=16.3 Hz, 1H), 2.36-2.46 (m, 1H), 1.85-1.93 (m, 1H), 1.68-1.76 (m, 1H), 1.50-1.65 (m, 2H), 1.52 (d, J=6.8 Hz, 3H), 1.30-1.39 (m, 2H), 1.22-1.30 (m, 2H).
Minor Rotamer (35%)
¹H NMR (400 MHz, DMSO-d₆) δ ppm 8.00 (t, J=8.9 Hz, 1H), 7.41 (br s, 1H), 7.05-7.25 (m, 4H), 6.86-7.00 (m, 4H), 6.80 (s, 1H), 4.97 (q, J=6.6 Hz, 1H), 4.55 (br dd, J=11.6, 3.9 Hz, 1H), 3.89 (br d, J=13.0 Hz, 1H), 3.78-3.86 (m, 1H), 3.22-3.31 (m, 1H), 2.86-3.07 (m, 4H), 2.78-2.85 (m, 1H), 2.36-2.46 (m, 1H), 1.85-1.93 (m, 1H), 1.68-1.76 (m, 1H), 1.50-1.65 (m, 2H), 1.55 (br d, J=6.7 Hz, 3H), 1.30-1.39 (m, 2H), 1.22-1.30 (m, 2H).

Compound 70

Major Rotamer (65%)
¹H NMR (500 MHz, DMSO-d₆) δ ppm 7.99 (t, J=9.0 Hz, 1H), 7.32 (d, J=7.6 Hz, 1H), 7.27 (br s, 1H), 7.05-7.25 (m, 3H), 6.95-6.98 (m, 1H), 6.90 (br d, J=8.8 Hz, 1H), 6.85 (dd, J=15.4, 1.9 Hz, 1H), 6.82 (s, 1H), 6.76 (br s, 1H), 5.59 (q, J=6.6 Hz, 1H), 3.79-3.89 (m, 3H), 3.43-3.50 (m, 1H), 2.98-3.05 (m, 1H), 2.86-2.98 (m, 1H), 2.81 (t, J=11.7 Hz, 2H), 2.72 (br d, J=16.4 Hz, 1H), 2.01 (s, 2H), 1.85-1.95 (m, 1H), 1.74 (br d, J=11.7 Hz, 2H), 1.52 (d, J=6.6 Hz, 3H), 1.31-1.37 (m, 2H), 1.22-1.30 (m, 4H).
Minor Rotamer (35%)
¹H NMR (500 MHz, DMSO-d₆) δ ppm 7.99 (t, J=9.0 Hz, 1H), 7.27 (br s, 1H), 7.05-7.25 (m, 4H), 6.95-6.98 (m, 1H), 6.90 (br d, J=8.8 Hz, 1H), 6.85 (dd, J=15.4, 1.9 Hz, 1H), 6.79 (s, 1H), 6.76 (br s, 1H), 4.97 (q, J=6.5 Hz, 1H), 4.55 (br dd, J=13.1, 3.3 Hz, 1H), 3.79-3.89 (m, 2H), 3.23-3.30 (m, 1H), 2.86-2.98 (m, 3H), 2.81 (t, J=11.7 Hz, 2H), 2.03 (s, 2H), 1.85-1.95 (m, 1H), 1.74 (br d, J=11.7 Hz, 2H), 1.55 (d, J=6.6 Hz, 3H), 1.31-1.37 (m, 2H), 1.22-1.30 (m, 4H).

Compound 71

Major Rotamer (65%)
¹H NMR (400 MHz, DMSO-d₆) δ ppm 7.99 (br t, J=8.9 Hz, 1H), 7.34 (br s, 1H), 7.32 (br d, J=7.9 Hz, 1H), 7.06-7.26 (m, 3H), 6.94-6.98 (m, 1H), 6.88 (br d, J=8.9 Hz, 1H), 6.83 (s, 1H), 6.80-6.86 (m, 2H), 5.59 (q, J=6.6 Hz, 1H), 3.72-3.86 (m, 3H), 3.42-3.51 (m, 1H), 2.82-3.07 (m, 3H), 2.72 (br d, J=16.3 Hz, 1H), 2.63 (dd, J=12.1, 10.5 Hz, 1H), 1.92-2.14 (m, 3H), 1.74-1.83 (m, 1H), 1.65-1.73 (m, 1H), 1.52 (br d, J=6.8 Hz, 3H), 1.30-1.38 (m, 2H), 1.24-1.30 (m, 2H), 1.12-1.23 (m, 2H).
Minor Rotamer (35%)
¹H NMR (400 MHz, DMSO-d₆) δ ppm 7.99 (br t, J=8.9 Hz, 1H), 7.34 (br s, 1H), 7.06-7.26 (m, 4H), 6.94-6.98 (m, 1H), 6.88 (br d, J=8.9 Hz, 1H), 6.80-6.86 (m, 2H), 6.79 (s, 1H), 4.97 (q, J=6.5 Hz, 1H), 4.55 (br dd, J=12.0, 3.3 Hz, 1H), 3.72-3.86 (m, 2H), 3.22-3.31 (m, 1H), 2.82-3.07 (m, 4H), 2.63 (dd, J=12.1, 10.5 Hz, 1H), 1.92-2.14 (m, 3H), 1.74-1.83 (m, 1H), 1.65-1.73 (m, 1H), 1.55 (br d, J=6.7 Hz, 3H), 1.30-1.38 (m, 2H), 1.24-1.30 (m, 2H), 1.12-1.23 (m, 2H).

Compound 72

Major Rotamer (65%)
¹H NMR (500 MHz, DMSO-d₆) δ ppm 8.00 (br t, J=8.5 Hz, 1H), 7.76 (br d, J=3.8 Hz, 1H), 7.32 (br d, J=7.3 Hz, 1H), 7.06-7.27 (m, 3H), 6.85-7.00 (m, 3H), 6.83 (s, 1H), 5.59 (q, J=6.3 Hz, 1H), 3.89 (d, J=12.3 Hz, 2H), 3.82 (br d, J=9.8 Hz, 1H), 3.46 (br t, J=11.2 Hz, 1H), 2.79-3.06 (m, 4H), 2.72 (br d, J=15.8 Hz, 1H), 2.58 (d, J=4.1 Hz, 3H), 2.29-2.38 (m, 1H), 1.72-1.80 (m, 1H), 1.59-1.69 (m, 2H), 1.52 (br d, J=6.3 Hz, 3H), 1.30-1.38 (m, 2H), 1.23-1.30 (m, 2H).
Minor Rotamer (35%)
¹H NMR (500 MHz, DMSO-d₆) δ ppm 8.00 (br t, J=8.5 Hz, 1H), 7.76 (br d, J=3.8 Hz, 1H), 7.06-7.27 (m, 4H), 6.85-7.00 (m, 3H), 6.79 (s, 1H), 4.97 (q, J=6.3 Hz, 1H), 4.55 (br d, J=9.8 Hz, 1H), 3.89 (d, J=12.3 Hz, 2H), 3.22-3.30 (m, 1H), 2.79-3.06 (m, 5H), 2.58 (d, J=4.1 Hz, 3H), 2.29-2.38 (m, 1H), 1.72-1.80 (m, 2H), 1.59-1.69 (m, 2H), 1.55 (br d, J=6.6 Hz, 3H), 1.30-1.38 (m, 2H), 1.23-1.30 (m, 2H).

Compound 73

Major Rotamer (65%)
¹H NMR (500 MHz, DMSO-d₆) δ ppm 8.00 (br t, J=8.8 Hz, 1H), 7.86 (br d, J=4.4 Hz, 1H), 7.32 (br d, J=7.6 Hz, 1H), 7.06-7.26 (m, 3H), 6.85-7.00 (m, 3H), 6.83 (s, 1H), 5.59 (q, J=6.3 Hz, 1H), 3.78-3.92 (m, 3H), 3.43-3.52 (m, 1H), 2.79-3.06 (m, 3H), 2.67-2.75 (m, 2H), 2.60 (br d, J=4.1 Hz, 3H), 2.35-2.45 (m, 1H), 1.85 (br d, J=10.7 Hz, 1H), 1.68-1.76 (m, 1H), 1.56-1.67 (m, 2H), 1.52 (br d, J=6.6 Hz, 3H), 1.31-1.38 (m, 2H), 1.23-1.30 (m, 2H).

Minor Rotamer (35%)
¹H NMR (500 MHz, DMSO-d₆) δ ppm 8.00 (br t, J=8.8 Hz, 1H), 7.86 (br d, J=4.4 Hz, 1H), 7.06-7.26 (m, 3H), 6.85-7.00 (m, 4H), 6.79 (s, 1H), 4.97 (q, J=6.0 Hz, 1H), 4.55 (br d, J=11.0 Hz, 1H), 3.78-3.92 (m, 2H), 3.22-3.30 (m, 1H), 2.79-3.06 (m, 4H), 2.67-2.75 (m, 1H), 2.60 (br d, J=4.1 Hz, 3H), 2.35-2.45 (m, 1H), 1.85 (br d, J=10.7 Hz, 1H), 1.68-1.76 (m, 1H), 1.56-1.67 (m, 2H), 1.55 (br d, J=6.6 Hz, 3H), 1.31-1.38 (m, 2H), 1.23-1.30 (m, 2H).

Compound 74

Major Rotamer (65%)
¹H NMR (500 MHz, DMSO-d₆) δ ppm 7.99 (br t, J=9.0 Hz, 1H), 7.32 (br d, J=7.3 Hz, 1H), 7.06-7.26 (m, 3H), 6.94-6.98 (m, 1H), 6.91 (br d, J=9.1 Hz, 1H), 6.86 (br d, J=15.4 Hz, 1H), 6.83 (s, 1H), 5.59 (q, J=6.8 Hz, 1H), 4.72 (d, J=4.1 Hz, 1H), 3.81 (br dd, J=12.9, 4.1 Hz, 1H), 3.65-3.73 (m, 3H), 3.43-3.50 (m, 1H), 2.83-3.06 (m, 4H), 2.72 (br d, J=16.1 Hz, 1H), 1.79-1.86 (m, 2H), 1.52 (d, J=6.6 Hz, 3H), 1.41-1.50 (m, 2H), 1.31-1.38 (m, 2H), 1.22-1.30 (m, 2H).
Minor Rotamer (35%)
¹H NMR (500 MHz, DMSO-d₆) δ ppm 7.99 (br t, J=9.0 Hz, 1H), 7.06-7.26 (m, 4H), 6.94-6.98 (m, 1H), 6.91 (br d, J=9.1 Hz, 1H), 6.86 (br d, J=15.4 Hz, 1H), 6.79 (s, 1H), 4.96 (q, J=6.6 Hz, 1H), 4.72 (d, J=4.1 Hz, 1H), 4.55 (br dd, J=12.3, 3.2 Hz, 1H), 3.65-3.73 (m, 3H), 3.23-3.30 (m, 1H), 2.83-3.06 (m, 5H), 1.79-1.86 (m, 2H), 1.55 (d, J=6.9 Hz, 3H), 1.41-1.50 (m, 2H), 1.31-1.38 (m, 2H), 1.22-1.30 (m, 2H).

Compound 75

Major Rotamer (65%)
¹H NMR (500 MHz, DMSO-d₆) δ ppm 7.99 (br t, J=9.0 Hz, 1H), 7.32 (d, J=7.3 Hz, 1H), 7.06-7.25 (m, 3H), 6.94-6.98 (m, 1H), 6.88 (br d, J=8.8 Hz, 1H), 6.82 (s, 1H), 6.82 (br dd, J=15.3, 1.4 Hz, 1H), 5.59 (q, J=6.6 Hz, 1H), 4.87 (d, J=4.4 Hz, 1H), 3.81 (br dd, J=13.7, 3.9 Hz, 1H), 3.71 (br d, J=12.6 Hz, 1H), 3.55-3.66 (m, 2H), 3.42-3.51 (m, 1H), 2.83-3.05 (m, 3H), 2.69-2.76 (m, 2H), 1.87-1.94 (m, 1H), 1.73-1.80 (m, 1H), 1.52 (d, J=6.6 Hz, 3H), 1.28-1.41 (m, 4H), 1.22-1.30 (m, 2H).
Minor Rotamer (35%)
¹H NMR (500 MHz, DMSO-d₆) δ ppm 7.99 (br t, J=9.0 Hz, 1H), 7.06-7.25 (m, 4H), 6.94-6.98 (m, 1H), 6.88 (br d, J=8.8 Hz, 1H), 6.82 (br dd, J=15.3, 1.4 Hz, 1H), 6.79 (s, 1H), 4.96 (q, J=6.6 Hz, 1H), 4.87 (d, J=4.4 Hz, 1H), 4.55 (br dd, J=12.1, 4.3 Hz, 1H), 3.71 (br d, J=12.6 Hz, 1H), 3.55-3.66 (m, 2H), 3.23-3.30 (m, 1H), 2.83-3.05 (m, 4H), 2.69-2.76 (m, 1H), 1.87-1.94 (m, 1H), 1.73-1.80 (m, 1H), 1.55 (d, J=6.6 Hz, 3H), 1.28-1.41 (m, 4H), 1.22-1.30 (m, 2H).

Compound 76

Major Rotamer (65%)
¹H NMR (400 MHz, DMSO-d₆) δ ppm 9.76 (br s, 1H), 8.02 (t, J=8.9 Hz, 1H), 7.32 (d, J=7.2 Hz, 1H), 7.09-7.26 (m, 3H), 6.92-6.97 (m, 1H), 6.81 (s, 1H), 6.55 (br d, J=8.7 Hz, 1H), 6.49 (br d, J=14.7 Hz, 1H), 5.59 (q, J=6.6 Hz, 1H), 4.49-4.59 (m, 1H), 3.81 (br dd, J=13.6, 4.5 Hz, 1H), 3.64 (dd, J=10.2, 6.8 Hz, 1H), 3.44-3.52 (m, 2H), 3.35-3.44 (m, 1H), 3.28-3.31 (m, 1H), 2.85-3.06 (m, 2H), 2.72 (br d, J=16.1 Hz, 1H), 2.23-2.32 (m, 1H), 2.02-2.12 (m, 1H), 1.52 (d, J=6.7 Hz, 3H), 1.30-1.38 (m, 2H), 1.21-1.30 (m, 2H).

Minor Rotamer (35%)
¹H NMR (400 MHz, DMSO-d₆) δ ppm 9.76 (br s, 1H), 8.02 (t, J=8.9 Hz, 1H), 7.09-7.26 (m, 3H), 7.05-7.09 (m, 1H), 6.92-6.97 (m, 1H), 6.78 (s, 1H), 6.55 (br d, J=8.7 Hz, 1H), 6.49 (br d, J=14.7 Hz, 1H), 4.96 (q, J=6.9 Hz, 1H), 4.49-4.59 (m, 2H), 3.64 (dd, J=10.2, 6.8 Hz, 1H), 3.44-3.52 (m, 1H), 3.35-3.44 (m, 2H), 3.21-3.28 (m, 1H), 2.85-3.06 (m, 3H), 2.23-2.32 (m, 1H), 2.02-2.12 (m, 1H), 1.55 (d, J=6.7 Hz, 3H), 1.30-1.38 (m, 2H), 1.21-1.30 (m, 2H).

Compound 77

Major Rotamer (65%)
¹H NMR (500 MHz, DMSO-d₆) δ ppm 8.01 (t, J=8.8 Hz, 1H), 7.32 (d, J=7.6 Hz, 1H), 7.20-7.25 (m, 1H), 7.15-7.20 (m, 2H), 6.94 (d, J=3.8 Hz, 1H), 6.81 (s, 1H), 6.66 (br s, 1H), 6.55 (br d, J=8.8 Hz, 1H), 6.52 (br s, 1H), 6.49 (br dd, J=14.5, 1.6 Hz, 1H), 5.59 (q, J=6.6 Hz, 1H), 5.23 (br s, 1H), 3.81 (br dd, J=13.9, 3.5 Hz, 1H), 3.60 (dd, J=11.5, 4.6 Hz, 1H), 3.41-3.51 (m, 2H), 3.33-3.41 (m, 2H), 2.83-3.06 (m, 2H), 2.72 (br d, J=16.4 Hz, 1H), 2.19-2.29 (m, 1H), 2.06-2.13 (m, 1H), 1.52 (d, J=6.6 Hz, 3H), 1.30-1.37 (m, 2H), 1.21-1.30 (m, 2H).
Minor Rotamer (35%)
¹H NMR (500 MHz, DMSO-d₆) δ ppm 8.01 (t, J=8.8 Hz, 1H), 7.15-7.20 (m, 2H), 7.10-7.14 (m, 1H), 7.08 (d, J=7.3 Hz, 1H), 6.93 (d, J=3.8 Hz, 1H), 6.77 (s, 1H), 6.66 (br s, 1H), 6.55 (br d, J=8.8 Hz, 1H), 6.52 (br s, 1H), 6.49 (br dd, J=14.5, 1.6 Hz, 1H), 5.23 (br s, 1H), 4.96 (q, J=6.7 Hz, 1H), 4.55 (br dd, J=12.3, 3.8 Hz, 1H), 3.60 (dd, J=11.5, 4.6 Hz, 1H), 3.41-3.51 (m, 2H), 3.33-3.41 (m, 1H), 3.22-3.30 (m, 1H), 2.83-3.06 (m, 3H), 2.19-2.29 (m, 1H), 2.06-2.13 (m, 1H), 1.55 (d, J=6.6 Hz, 3H), 1.30-1.37 (m, 2H), 1.21-1.30 (m, 2H).

Compound 78

Major Rotamer (65%)
¹H NMR (500 MHz, DMSO-d₆) δ ppm 8.01 (t, J=8.8 Hz, 1H), 7.32 (d, J=7.3 Hz, 1H), 7.21-7.25 (m, 1H), 7.15-7.21 (m, 2H), 6.94 (d, J=3.5 Hz, 1H), 6.81 (s, 1H), 6.66 (br s, 1H), 6.54 (br d, J=8.8 Hz, 1H), 6.52 (br s, 1H), 6.49 (br d, J=14.8 Hz, 1H), 5.59 (q, J=6.5 Hz, 1H), 5.23 (br s, 1H), 3.81 (br dd, J=14.3, 4.3 Hz, 1H), 3.60 (dd, J=11.5, 4.6 Hz, 1H), 3.33-3.50 (m, 4H), 2.82-3.06 (m, 2H), 2.72 (br d, J=16.4 Hz, 1H), 2.19-2.29 (m, 1H), 2.05-2.14 (m, 1H), 1.52 (d, J=6.6 Hz, 3H), 1.30-1.37 (m, 2H), 1.21-1.29 (m, 2H).
Minor Rotamer (35%)
¹H NMR (500 MHz, DMSO-d₆) δ ppm 8.01 (t, J=8.8 Hz, 1H), 7.15-7.21 (m, 2H), 7.10-7.15 (m, 1H), 7.08 (d, J=7.3 Hz, 1H), 6.93 (d, J=3.8 Hz, 1H), 6.77 (s, 1H), 6.66 (br s, 1H), 6.54 (br d, J=8.8 Hz, 1H), 6.52 (br s, 1H), 6.49 (br d, J=14.8 Hz, 1H), 5.23 (br s, 1H), 4.96 (q, J=6.8 Hz, 1H), 4.51-4.58 (m, 1H), 3.60 (dd, J=11.5, 4.6 Hz, 1H), 3.33-3.50 (m, 3H), 3.23-3.30 (m, 1H), 2.82-3.06 (m, 3H), 2.19-2.29 (m, 1H), 2.05-2.14 (m, 1H), 1.55 (d, J=6.6 Hz, 3H), 1.30-1.37 (m, 2H), 1.21-1.29 (m, 2H).

Compound 79

Major Rotamer (65%)
¹H NMR (400 MHz, DMSO-d₆) δ ppm 8.00 (br t, J=8.7 Hz, 1H), 7.38 (br s, 1H), 7.32 (br d, J=7.3 Hz, 1H), 7.10-7.26 (m, 3H), 6.98-7.03 (m, 1H), 6.93 (br d, J=8.6 Hz, 1H), 6.84-6.90 (m, 2H), 5.59 (q, J=6.8 Hz, 1H), 3.91-4.01 (m, 1H), 3.77-3.86 (m, 1H), 3.42-3.52 (m, 1H), 3.17-3.32 (m, 4H), 2.68-3.15 (m, 6H), 2.02-2.21 (m, 2H), 1.52 (d, J=6.7 Hz, 3H), 1.31-1.39 (m, 2H), 1.21-1.30 (m, 2H).

Minor Rotamer (35%)

¹H NMR (400 MHz, DMSO-d₆) δ ppm 8.00 (br t, J=8.7 Hz, 1H), 7.38 (br s, 1H), 7.10-7.26 (m, 3H), 7.08 (br d, J=7.2 Hz, 1H), 6.98-7.03 (m, 1H), 6.93 (br d, J=8.6 Hz, 1H), 6.84-6.90 (m, 1H), 6.84-6.91 (m, 1H), 6.82 (s, 1H), 4.96 (q, J=6.4 Hz, 1H), 4.52-4.59 (m, 1H), 3.91-4.01 (m, 1H), 3.17-3.32 (m, 4H), 2.68-3.15 (m, 7H), 2.02-2.21 (m, 2H), 1.55 (br d, J=6.6 Hz, 3H), 1.31-1.39 (m, 2H), 1.21-1.30 (m, 2H).

Compound 80

Major Rotamer (65%)

¹H NMR (500 MHz, DMSO-d₆) δ ppm 8.00 (t, J=8.8 Hz, 1H), 7.41 (s, 1H), 7.32 (d, J=7.3 Hz, 1H), 7.14-7.25 (m, 3H), 7.04 (s, 1H), 6.93 (d, J=3.8 Hz, 1H), 6.80 (s, 1H), 6.54 (dd, J=8.8, 2.2 Hz, 1H), 6.43 (dd, J=14.8, 1.9 Hz, 1H), 5.59 (q, J=6.8 Hz, 1H), 4.20 (quin, J=6.5 Hz, 1H), 3.82 (ddd, J=9.8, 5.4, 1.3 Hz, 1H), 3.41-3.50 (m, 2H), 3.17-3.25 (m, 1H), 2.86-3.08 (m, 3H), 2.72 (br d, J=16.1 Hz, 1H), 2.27-2.35 (m, 1H), 1.96-2.04 (m, 1H), 1.52 (d, J=6.6 Hz, 3H), 1.30-1.37 (m, 2H), 1.21-1.30 (m, 2H), 1.02 (d, J=6.3 Hz, 3H).

Minor Rotamer (35%)

¹H NMR (500 MHz, DMSO-d₆) δ ppm 8.00 (t, J=8.8 Hz, 1H), 7.41 (s, 1H), 7.14-7.25 (m, 2H), 7.10-7.15 (m, 1H), 7.06-7.09 (m, 1H), 7.04 (s, 1H), 6.92 (d, J=3.8 Hz, 1H), 6.77 (s, 1H), 6.54 (dd, J=8.8, 2.2 Hz, 1H), 6.43 (dd, J=14.8, 1.9 Hz, 1H), 4.96 (q, J=6.5 Hz, 1H), 4.55 (ddd, J=12.9, 5.7, 1.9 Hz, 1H), 4.20 (quin, J=6.5 Hz, 1H), 3.41-3.50 (m, 1H), 3.25-3.29 (m, 1H), 3.17-3.25 (m, 1H), 2.86-3.08 (m, 4H), 2.27-2.35 (m, 1H), 1.96-2.04 (m, 1H), 1.55 (d, J=6.6 Hz, 3H), 1.30-1.37 (m, 2H), 1.21-1.30 (m, 2H), 1.02 (d, J=6.3 Hz, 3H).

Compound 81

Major Rotamer (65%)

¹H NMR (500 MHz, DMSO-d₆) δ ppm 7.98 (t, J=8.8 Hz, 1H), 7.47 (br s, 1H), 7.32 (d, J=7.6 Hz, 1H), 7.06-7.25 (m, 3H), 6.87-6.98 (m, 2H), 6.80 (s, 1H), 6.53 (dd, J=9.0, 1.7 Hz, 1H), 6.44 (br d, J=14.8 Hz, 1H), 5.59 (q, J=6.9 Hz, 1H), 4.01-4.08 (m, 1H), 3.82 (br dd, J=13.2, 4.1 Hz, 1H), 3.35-3.50 (m, 2H), 3.21-3.30 (m, 1H), 2.82-3.05 (m, 2H), 2.68-2.75 (m, 2H), 2.20-2.29 (m, 1H), 2.06-2.15 (m, 1H), 1.52 (d, J=6.9 Hz, 3H), 1.29-1.37 (m, 2H), 1.25-1.29 (m, 2H), 1.22 (br d, J=6.3 Hz, 3H).

Minor Rotamer (35%)

¹H NMR (500 MHz, DMSO-d₆) δ ppm 7.98 (t, J=8.8 Hz, 1H), 7.47 (br s, 1H), 7.06-7.25 (m, 4H), 6.87-6.98 (m, 2H), 6.76 (s, 1H), 6.53 (dd, J=9.0, 1.7 Hz, 1H), 6.44 (br d, J=14.8 Hz, 1H), 4.97 (q, J=7.1 Hz, 1H), 4.55 (br dd, J=12.6, 3.8 Hz, 1H), 4.01-4.08 (m, 1H), 3.35-3.50 (m, 2H), 3.22-3.30 (m, 1H), 2.82-3.05 (m, 3H), 2.68-2.75 (m, 1H), 2.20-2.29 (m, 1H), 2.06-2.15 (m, 1H), 1.55 (d, J=6.6 Hz, 3H), 1.29-1.37 (m, 2H), 1.25-1.29 (m, 2H), 1.22 (br d, J=6.3 Hz, 3H).

Compound 82

Major Rotamer (65%)

¹H NMR (500 MHz, DMSO-d₆) δ ppm 7.98 (t, J=8.8 Hz, 1H), 7.47 (br s, 1H), 7.32 (d, J=7.3 Hz, 1H), 7.21-7.25 (m, 1H), 7.15-7.21 (m, 2H), 6.87-6.96 (m, 2H), 6.80 (s, 1H), 6.53 (br d, J=8.8 Hz, 1H), 6.44 (dd, J=15.0, 1.7 Hz, 1H), 5.58 (q, J=6.5 Hz, 1H), 4.00-4.08 (m, 1H), 3.82 (br dd, J=13.9, 3.8 Hz, 1H), 3.40-3.50 (m, 2H), 3.28-3.35 (m, 1H obscured by H₂O peak), 2.82-3.06 (m, 2H), 2.68-2.76 (m, 2H), 2.19-2.29 (m, 1H), 2.06-2.14 (m, 1H), 1.52 (d, J=6.6 Hz, 3H), 1.30-1.38 (m, 2H), 1.25-1.30 (m, 2H), 1.22 (d, J=6.3 Hz, 3H).

Minor Rotamer (35%)

¹H NMR (500 MHz, DMSO-d₆) δ ppm 7.98 (t, J=8.8 Hz, 1H), 7.47 (br s, 1H), 7.15-7.21 (m, 2H), 7.10-7.14 (m, 1H), 7.06-7.10 (m, 1H), 6.87-6.96 (m, 2H), 6.76 (s, 1H), 6.53 (br d, J=8.8 Hz, 1H), 6.44 (dd, J=15.0, 1.7 Hz, 1H), 4.97 (q, J=6.5 Hz, 1H), 4.55 (br dd, J=12.8, 3.6 Hz, 1H), 4.00-4.08 (m, 1H), 3.40-3.50 (m, 1H), 3.28-3.35 (m, 1H obscured by H₂O peak), 3.21-3.27 (m, 1H), 2.82-3.06 (m, 3H), 2.68-2.76 (m, 1H), 2.19-2.29 (m, 1H), 2.06-2.14 (m, 1H), 1.55 (d, J=6.6 Hz, 3H), 1.30-1.38 (m, 2H), 1.25-1.30 (m, 2H), 1.22 (d, J=6.3 Hz, 3H).

Compound 83

Major Rotamer (65%)

¹H NMR (500 MHz, DMSO-d₆) δ ppm 8.00 (t, J=8.8 Hz, 1H), 7.41 (s, 1H), 7.32 (d, J=7.3 Hz, 1H), 7.15-7.26 (m, 3H), 7.04 (s, 1H), 6.93 (d, J=3.5 Hz, 1H), 6.80 (s, 1H), 6.54 (br d, J=8.8 Hz, 1H), 6.43 (dd, J=14.8, 1.6 Hz, 1H), 5.59 (q, J=6.6 Hz, 1H), 4.20 (quin, J=6.5 Hz, 1H), 3.82 (br dd, J=13.6, 3.8 Hz, 1H), 3.41-3.50 (m, 2H), 3.17-3.25 (m, 1H), 2.86-3.07 (m, 3H), 2.72 (br d, J=16.1 Hz, 1H), 2.27-2.35 (m, 1H), 2.00 (dt, J=12.6, 6.6 Hz, 1H), 1.52 (d, J=6.6 Hz, 3H), 1.30-1.37 (m, 2H), 1.21-1.29 (m, 2H), 1.02 (d, J=6.3 Hz, 3H).

Minor Rotamer (35%)

¹H NMR (500 MHz, DMSO-d₆) δ ppm 8.00 (t, J=8.8 Hz, 1H), 7.41 (s, 1H), 7.15-7.26 (m, 2H), 7.10-7.15 (m, 1H), 7.06-7.09 (m, 1H), 7.04 (s, 1H), 6.92 (d, J=3.8 Hz, 1H), 6.77 (s, 1H), 6.54 (br d, J=8.8 Hz, 1H), 6.43 (dd, J=14.8, 1.6 Hz, 1H), 4.97 (q, J=6.6 Hz, 1H), 4.55 (br dd, J=12.9, 3.2 Hz, 1H), 4.20 (quin, J=6.5 Hz, 1H), 3.41-3.50 (m, 1H), 3.25-3.29 (m, 1H), 3.17-3.25 (m, 1H), 2.86-3.07 (m, 4H), 2.27-2.35 (m, 1H), 2.00 (dt, J=12.6, 6.6 Hz, 1H), 1.55 (d, J=6.9 Hz, 3H), 1.30-1.37 (m, 2H), 1.21-1.29 (m, 2H), 1.02 (d, J=6.3 Hz, 3H).

Compound 84

Major Rotamer (65%)

¹H NMR (400 MHz, DMSO-d₆) δ ppm 9.31 (d, J=7.8 Hz, 1H), 8.89 (d, J=4.0 Hz, 1H), 8.15-8.23 (m, 1H), 8.05 (t, J=8.8 Hz, 1H), 7.91 (s, 1H), 7.65-7.72 (m, 1H), 7.52 (br s, 1H), 7.34 (d, J=7.2 Hz, 1H), 7.06-7.27 (m, 4H), 7.02 (br s, 1H), 6.55 (dd, J=8.9, 1.8 Hz, 1H), 6.48 (dd, J=14.6, 1.7 Hz, 1H), 5.64 (q, J=6.5 Hz, 1H), 4.07 (br dd, J=13.0, 4.2 Hz, 1H), 3.48-3.54 (m, 2H), 3.34-3.47 (m, 3H), 3.00-3.14 (m, 2H), 2.77 (br d, J=16.6 Hz, 1H), 2.16-2.26 (m, 1H), 2.07-2.16 (m, 1H), 1.56 (d, J=6.7 Hz, 3H).

Minor Rotamer (35%)

¹H NMR (400 MHz, DMSO-d₆) δ ppm 9.30 (d, J=8.3 Hz, 1H), 8.86 (br d, J=4.3 Hz, 1H), 8.15-8.23 (m, 1H), 8.05 (t, J=8.8 Hz, 1H), 7.86 (s, 1H), 7.65-7.72 (m, 1H), 7.52 (br s, 1H), 7.06-7.27 (m, 5H), 7.02 (br s, 1H), 6.55 (dd, J=8.9, 1.8 Hz, 1H), 6.48 (dd, J=14.6, 1.7 Hz, 1H), 5.17 (q, J=7.0 Hz, 1H), 4.57-4.64 (m, 1H), 3.55-3.59 (m, 1H), 3.34-3.47 (m, 3H), 3.27-3.31 (m, 1H), 3.00-3.14 (m, 1H), 2.93-3.00 (m, 1H), 2.84-2.91 (m, 1H), 2.16-2.26 (m, 1H), 2.07-2.16 (m, 1H), 1.61 (d, J=6.8 Hz, 3H).

Compound 85

Major Rotamer (65%)

$^1$H NMR (400 MHz, DMSO-$d_6$) δ ppm 8.38 (br t, J=9.3 Hz, 1H), 7.32 (br d, J=7.5 Hz, 1H), 7.15-7.26 (m, 3H), 6.93-6.97 (m, 1H), 6.83 (s, 1H), 6.58 (br d, J=8.3 Hz, 1H), 6.46-6.72 (m, 2H), 5.58 (q, J=7.0 Hz, 1H), 5.21 (br s, 1H), 3.76-3.85 (m, 1H), 3.60-3.71 (m, 2H), 3.52-3.59 (m, 1H), 3.41-3.52 (m, 2H), 2.81-3.07 (m, 2H), 2.72 (br d, J=16.5 Hz, 1H), 2.18-2.29 (m, 1H), 2.06-2.15 (m, 1H), 1.52 (br d, J=6.7 Hz, 3H), 1.30-1.39 (m, 2H), 1.21-1.30 (m, 2H).

Minor Rotamer (35%)

$^1$H NMR (400 MHz, DMSO-$d_6$) δ ppm 8.38 (br t, J=9.3 Hz, 1H), 7.15-7.26 (m, 2H), 7.09-7.15 (m, 1H), 7.08 (br d, J=7.6 Hz, 1H), 6.93-6.97 (m, 1H), 6.80 (s, 1H), 6.58 (br d, J=8.3 Hz, 1H), 6.46-6.72 (m, 2H), 5.21 (br s, 1H), 4.96 (q, J=7.0 Hz, 1H), 4.51-4.58 (m, 1H), 3.60-3.71 (m, 2H), 3.52-3.59 (m, 1H), 3.41-3.52 (m, 2H), 2.81-3.07 (m, 3H), 2.18-2.29 (m, 1H), 2.06-2.15 (m, 1H), 1.55 (br d, J=6.8 Hz, 3H), 1.30-1.39 (m, 2H), 1.21-1.30 (m, 2H).

Compound 86

Major Rotamer (65%)

$^1$H NMR (500 MHz, DMSO-$d_6$) δ ppm 7.52 (br s, 1H), 7.32 (d, J=7.6 Hz, 1H), 7.09-7.25 (m, 3H), 7.01 (br s, 1H), 6.82 (d, J=12.0 Hz, 2H), 6.00 (s, 1H), 5.59 (q, J=6.6 Hz, 1H), 3.89 (s, 3H), 3.82 (br dd, J=13.7, 3.6 Hz, 1H), 3.62-3.70 (m, 1H), 3.54-3.62 (m, 1H), 3.48-3.54 (m, 1H), 3.44-3.48 (m, 1H), 3.39-3.44 (m, 1H), 3.07 (quin, J=7.6 Hz, 1H), 2.81-2.95 (m, 2H), 2.71 (br d, J=16.4 Hz, 1H), 2.14-2.23 (m, 1H), 2.04-2.14 (m, 1H), 1.52 (d, J=6.9 Hz, 3H), 1.22-1.35 (m, 4H).

Minor Rotamer (35%)

$^1$H NMR (500 MHz, DMSO-$d_6$) δ ppm 7.52 (br s, 1H), 7.09-7.21 (m, 4H), 7.01 (br s, 1H), 6.80 (d, J=22.1 Hz, 2H), 6.00 (s, 1H), 4.96 (q, J=6.7 Hz, 1H), 4.55 (br dd, J=13.1, 3.0 Hz, 1H), 3.89 (s, 3H), 3.62-3.70 (m, 1H), 3.54-3.62 (m, 1H), 3.48-3.54 (m, 1H), 3.39-3.44 (m, 1H), 3.21-3.30 (m, 1H), 3.07 (quin, J=7.6 Hz, 1H), 2.96-3.04 (m, 2H), 2.81-2.95 (m, 1H), 2.14-2.23 (m, 1H), 2.04-2.14 (m, 1H), 1.54 (d, J=6.6 Hz, 3H), 1.22-1.35 (m, 4H).

Compound 87

Major Rotamer (65%)

$^1$H NMR (500 MHz, DMSO-$d_6$) δ ppm 7.50 (br s, 1H), 7.32 (d, J=7.6 Hz, 1H), 7.07-7.25 (m, 3H), 7.00 (br s, 1H), 6.92 (s, 1H), 6.80 (s, 1H), 6.02 (s, 1H), 5.58 (q, J=6.8 Hz, 1H), 4.26-4.33 (m, 2H), 3.80 (br dd, J=13.9, 3.8 Hz, 1H), 3.67-3.72 (m, 2H), 3.64 (br t, J=9.1 Hz, 1H), 3.53-3.61 (m, 1H), 3.50 (dd, J=10.4, 6.9 Hz, 1H), 3.37-3.48 (m, 2H), 3.29 (s, 3H), 3.03-3.10 (m, 1H), 2.82-2.96 (m, 2H), 2.71 (br d, J=16.1 Hz, 1H), 2.14-2.22 (m, 1H), 2.04-2.13 (m, 1H), 1.52 (d, J=6.9 Hz, 3H), 1.23-1.34 (m, 4H).

Minor Rotamer (35%)

$^1$H NMR (500 MHz, DMSO-$d_6$) δ ppm 7.50 (br s, 1H), 7.07-7.25 (m, 4H), 7.00 (br s, 1H), 6.92 (s, 1H), 6.77 (s, 1H), 6.02 (s, 1H), 4.96 (q, J=6.1 Hz, 1H), 4.55 (br dd, J=11.7, 4.4 Hz, 1H), 4.26-4.33 (m, 2H), 3.67-3.72 (m, 2H), 3.64 (br t, J=9.1 Hz, 1H), 3.53-3.61 (m, 1H), 3.50 (dd, J=10.4, 6.9 Hz, 1H), 3.37-3.48 (m, 1H), 3.28 (s, 3H), 3.23-3.28 (m, 1H), 3.03-3.10 (m, 1H), 2.96-3.03 (m, 2H), 2.82-2.96 (m, 1H), 2.14-2.22 (m, 1H), 2.04-2.13 (m, 1H), 1.54 (d, J=6.6 Hz, 3H), 1.23-1.34 (m, 4H).

Compound 88

Major Rotamer (65%)

$^1$H NMR (500 MHz, DMSO-$d_6$) δ ppm 8.08 (d, J=5.7 Hz, 1H), 7.53 (br s, 1H), 7.32 (d, J=7.6 Hz, 1H), 7.04-7.26 (m, 4H), 7.01 (br s, 1H), 6.84 (s, 1H), 5.59 (q, J=6.9 Hz, 1H), 3.80 (br dd, J=13.9, 3.5 Hz, 1H), 3.74 (dd, J=10.7, 7.9 Hz, 1H), 3.58-3.69 (m, 2H), 3.43-3.57 (m, 2H), 3.08-3.15 (m, 1H), 2.83-3.05 (m, 2H), 2.72 (br d, J=16.1 Hz, 1H), 2.19-2.28 (m, 1H), 2.09-2.17 (m, 1H), 1.52 (d, J=6.9 Hz, 3H), 1.31-1.38 (m, 2H), 1.22-1.30 (m, 2H).

Minor Rotamer (35%)

$^1$H NMR (500 MHz, DMSO-$d_6$) δ ppm 8.08 (d, J=5.7 Hz, 1H), 7.53 (br s, 1H), 7.04-7.26 (m, 5H), 7.01 (br s, 1H), 6.80 (s, 1H), 4.96 (q, J=7.0 Hz, 1H), 4.55 (br dd, J=12.9, 3.2 Hz, 1H), 3.74 (dd, J=10.7, 7.9 Hz, 1H), 3.58-3.69 (m, 2H), 3.43-3.57 (m, 2H), 3.08-3.15 (m, 1H), 2.83-3.05 (m, 3H), 2.19-2.28 (m, 1H), 2.09-2.17 (m, 1H), 1.54 (d, J=6.6 Hz, 3H), 1.31-1.38 (m, 2H), 1.22-1.30 (m, 2H).

Compound 89

Major Rotamer (65%)

$^1$H NMR (500 MHz, DMSO-$d_6$) δ ppm 7.50 (br s, 1H), 7.32 (d, J=7.6 Hz, 1H), 7.10-7.25 (m, 3H), 6.99 (s, 1H), 6.84 (s, 1H), 6.81 (d, J=2.2 Hz, 1H), 6.36 (br s, 1H), 6.30 (dd, J=13.6, 1.9 Hz, 1H), 5.59 (q, J=6.6 Hz, 1H), 3.84 (br dd, J=13.9, 3.8 Hz, 1H), 3.44-3.51 (m, 2H), 3.34-3.42 (m, 2H), 3.23-3.31 (m, 1H), 3.07 (quin, J=7.8 Hz, 1H), 2.82-2.96 (m, 2H), 2.72 (br d, J=16.4 Hz, 1H), 2.37 (s, 3H), 2.15-2.23 (m, 1H), 2.05-2.14 (m, 1H), 1.52 (d, J=6.9 Hz, 3H), 1.22-1.34 (m, 4H).

Minor Rotamer (35%)

$^1$H NMR (500 MHz, DMSO-$d_6$) δ ppm 7.50 (br s, 1H), 7.10-7.25 (m, 4H), 6.99 (s, 1H), 6.81 (s, 1H), 6.81 (d, J=2.2 Hz, 1H), 6.36 (br s, 1H), 6.30 (dd, J=13.6, 1.9 Hz, 1H), 4.99 (q, J=6.6 Hz, 1H), 4.56 (br dd, J=12.8, 3.3 Hz, 1H), 3.44-3.51 (m, 1H), 3.34-3.42 (m, 2H), 3.23-3.31 (m, 2H), 3.07 (quin, J=7.8 Hz, 1H), 2.96-3.04 (m, 2H), 2.82-2.96 (m, 1H), 2.37 (s, 3H), 2.15-2.23 (m, 1H), 2.05-2.14 (m, 1H), 1.55 (d, J=6.6 Hz, 3H), 1.22-1.34 (m, 4H).

Compound 90

Major Rotamer (65%)

$^1$H NMR (500 MHz, DMSO-$d_6$) δ ppm 9.35 (s, 1H), 8.85 (d, J=2.5 Hz, 1H), 8.68-8.73 (m, 1H), 7.90 (t, J=8.8 Hz, 1H), 7.62 (s, 1H), 7.51 (br s, 1H), 7.34 (d, J=7.3 Hz, 1H), 7.06-7.27 (m, 4H), 7.00 (br s, 1H), 6.53 (br d, J=8.8 Hz, 1H), 6.46 (dd, J=14.8, 1.9 Hz, 1H), 5.64 (q, J=6.8 Hz, 1H), 3.96 (br dd, J=13.9, 4.7 Hz, 1H), 3.51-3.58 (m, 1H), 3.46-3.51 (m, 1H), 3.29-3.45 (m, 3H partially obscured by H$_2$O peak), 3.03-3.12 (m, 2H), 2.76 (br d, J=16.4 Hz, 1H), 2.16-2.24 (m, 1H), 2.05-2.14 (m, 1H), 1.56 (d, J=6.6 Hz, 3H).

Minor Rotamer (35%)

$^1$H NMR (500 MHz, DMSO-$d_6$) δ ppm 9.31 (s, 1H), 8.84 (d, J=2.8 Hz, 1H), 8.65-8.70 (m, 1H), 7.90 (t, J=8.8 Hz, 1H), 7.58 (s, 1H), 7.51 (br s, 1H), 7.06-7.27 (m, 5H), 7.00 (br s, 1H), 6.53 (br d, J=8.8 Hz, 1H), 6.46 (dd, J=14.8, 1.9 Hz, 1H), 5.12 (q, J=6.8 Hz, 1H), 4.56-4.63 (m, 1H), 3.46-3.51 (m, 1H), 3.29-3.45 (m, 4H partially obscured by H$_2$O peak), 3.03-3.12 (m, 1H), 2.84-2.99 (m, 2H), 2.16-2.24 (m, 1H), 2.05-2.14 (m, 1H), 1.62 (d, J=6.6 Hz, 3H).

Compound 91

Major Rotamer (65%)

$^1$H NMR (500 MHz, DMSO-$d_6$) δ ppm 8.00 (t, J=8.5 Hz, 1H), 7.51 (br s, 1H), 7.32 (d, J=7.6 Hz, 1H), 7.14-7.25 (m, 3H), 7.03-7.09 (m, 1H), 6.95 (d, J=3.5 Hz, 1H), 6.82 (s, 1H), 6.36-6.43 (m, 2H), 5.58 (q, J=6.6 Hz, 1H), 4.05 (t, J=8.0 Hz, 2H), 3.91 (t, J=6.8 Hz, 2H), 3.81 (br dd, J=13.7, 3.9 Hz, 1H), 3.43-3.51 (m, 2H), 2.83-3.05 (m, 2H), 2.72 (br d, J=16.1 Hz, 1H), 1.52 (d, J=6.9 Hz, 3H), 1.30-1.37 (m, 2H), 1.22-1.30 (m, 2H).

Minor Rotamer (35%)

$^1$H NMR (500 MHz, DMSO-d$_6$) δ ppm 8.00 (t, J=8.5 Hz, 1H), 7.51 (br s, 1H), 7.14-7.25 (m, 2H), 7.10-7.14 (m, 1H), 7.03-7.09 (m, 2H), 6.94 (d, J=3.8 Hz, 1H), 6.78 (s, 1H), 6.36-6.43 (m, 2H), 4.96 (m, 1H), 4.52-4.58 (m, 1H), 4.05 (t, J=8.0 Hz, 2H), 3.91 (t, J=6.8 Hz, 2H), 3.43-3.51 (m, 2H), 3.23-3.30 (m, 1H), 2.83-3.05 (m, 3H), 1.55 (d, J=6.6 Hz, 3H), 1.30-1.37 (m, 2H), 1.22-1.30 (m, 2H).

Compound 92

Major Rotamer (65%)

$^1$H NMR (400 MHz, DMSO-d$_6$) δ ppm 8.35 (t, J=9.1 Hz, 1H), 7.38 (br s, 1H), 7.32 (br d, J=7.1 Hz, 1H), 7.05-7.26 (m, 3H), 6.92-6.96 (m, 1H), 6.87 (br s, 1H), 6.84 (s, 1H), 6.41 (br d, J=7.8 Hz, 1H), 5.58 (q, J=6.7 Hz, 1H), 4.16 (t, J=8.3 Hz, 2H), 3.80 (br dd, J=13.8, 3.8 Hz, 1H), 3.73 (dd, J=8.4, 5.8 Hz, 2H), 3.41-3.51 (m, 1H), 2.85-3.07 (m, 3H), 2.71 (br d, J=16.6 Hz, 1H), 2.43-2.47 (m, 2H partially obscured by DMSO peak), 1.52 (d, J=6.8 Hz, 3H), 1.30-1.38 (m, 2H), 1.20-1.29 (m, 2H).

Minor Rotamer (35%)

$^1$H NMR (400 MHz, DMSO-d$_6$) δ ppm 8.35 (t, J=9.1 Hz, 1H), 7.38 (br s, 1H), 7.05-7.26 (m, 4H), 6.92-6.96 (m, 1H), 6.87 (br s, 1H), 6.80 (s, 1H), 6.41 (br d, J=7.8 Hz, 1H), 4.95 (q, J=6.8 Hz, 1H), 4.51-4.59 (m, 1H), 4.16 (t, J=8.3 Hz, 2H), 3.73 (dd, J=8.4, 5.8 Hz, 2H), 3.22-3.31 (m, 1H), 2.85-3.07 (m, 4H), 2.43-2.47 (m, 2H partially obscured by DMSO peak), 1.55 (br d, J=6.7 Hz, 3H), 1.30-1.38 (m, 2H), 1.20-1.29 (m, 2H).

Compound 93

Major Rotamer (65%)

$^1$H NMR (400 MHz, DMSO-d$_6$) δ ppm 7.99 (t, J=8.6 Hz, 1H), 7.32 (br d, J=7.3 Hz, 1H), 7.10-7.28 (m, 3H), 6.89-6.98 (m, 1H), 6.80 (s, 1H), 6.49 (br d, J=9.4 Hz, 1H), 6.40 (br d, J=14.7 Hz, 1H), 5.54-5.63 (m, 1H), 3.75-3.86 (m, 1H), 3.19-3.66 (m, 6H), 2.68-3.06 (m, 4H), 2.01-2.16 (m, 2H), 1.72-1.80 (m, 1H), 1.46-1.59 (m, 3H), 1.19-1.39 (m, 4H).

Minor Rotamer (35%)

$^1$H NMR (400 MHz, DMSO-d$_6$) δ ppm 7.99 (t, J=8.6 Hz, 1H), 7.10-7.28 (m, 3H), 7.07 (br d, J=7.5 Hz, 1H), 6.89-6.98 (m, 1H), 6.77 (s, 1H), 6.49 (br d, J=9.4 Hz, 1H), 6.40 (br d, J=14.7 Hz, 1H), 4.91-5.00 (m, 1H), 4.50-4.60 (m, 1H), 3.19-3.66 (m, 6H), 2.68-3.06 (m, 4H), 2.01-2.16 (m, 2H), 1.72-1.80 (m, 1H), 1.46-1.59 (m, 3H), 1.19-1.39 (m, 4H).

Compound 94

Major Rotamer (65%)

$^1$H NMR (400 MHz, DMSO-d$_6$) δ ppm 8.00 (t, J=8.8 Hz, 1H), 7.32 (d, J=7.6 Hz, 1H), 7.10-7.26 (m, 3H), 6.87-7.00 (m, 1H), 6.80 (s, 1H), 6.50 (br d, J=8.7 Hz, 1H), 6.43 (br d, J=14.9 Hz, 1H), 5.59 (q, J=6.8 Hz, 1H), 3.81 (br dd, J=14.0, 4.2 Hz, 1H), 3.31-3.60 (m, 7H), 3.06-3.15 (m, 1H), 2.68-3.14 (m, 4H), 2.03-2.21 (m, 1H), 1.78-1.95 (m, 1H), 1.45-1.60 (m, 3H), 1.17-1.43 (m, 4H).

Minor Rotamer (35%)

$^1$H NMR (400 MHz, DMSO-d$_6$) δ ppm 8.00 (t, J=8.8 Hz, 1H), 7.10-7.26 (m, 3H), 7.08 (d, J=7.5 Hz, 1H), 6.87-7.00 (m, 1H), 6.77 (s, 1H), 6.50 (br d, J=8.7 Hz, 1H), 6.43 (br d, J=14.9 Hz, 1H), 4.96 (d, J=6.6 Hz, 1H), 4.50-4.60 (m, 1H), 3.31-3.60 (m, 7H), 3.06-3.15 (m, 1H), 2.68-3.14 (m, 4H), 2.03-2.21 (m, 1H), 1.78-1.95 (m, 1H), 1.45-1.60 (m, 3H), 1.17-1.43 (m, 4H).

Compound 95

Major Rotamer (65%)

$^1$H NMR (500 MHz, DMSO-d$_6$) δ ppm 7.99 (t, J=8.8 Hz, 1H) 7.31 (br d, J=7.6 Hz, 1H) 7.04-7.27 (m, 3H) 6.90-6.97 (m, 1H) 6.70-6.88 (m, 1H) 6.48 (br d, J=8.8 Hz, 1H) 6.40 (dd, J=14.7, 1.4 Hz, 1H) 5.59 (q, J=6.5 Hz, 1H) 4.89-5.01 (m, 2H) 4.18 (br d, J=3.5 Hz, 2H) 3.82 (br dd, J=13.4, 3.9 Hz, 1H) 3.40-3.55 (m, 3H) 3.18 (br dd, J=9.8, 3.8 Hz, 2H) 2.81-3.05 (m, 2H) 2.65-2.78 (m, 1H) 1.48-1.58 (m, 3H) 1.19-1.39 (m, 4H).

Minor Rotamer (35%)

$^1$H NMR (500 MHz, DMSO-d$_6$) δ ppm 7.99 (t, J=8.8 Hz, 1H) 7.04-7.27 (m, 4H) 6.90-6.97 (m, 1H) 6.70-6.88 (m, 1H) 6.48 (br d, J=8.8 Hz, 1H) 6.40 (dd, J=14.7, 1.4 Hz, 1H) 4.89-5.01 (m, 3H) 4.55 (br dd, J=12.9, 3.2 Hz, 1H) 4.18 (br d, J=3.5 Hz, 2H) 3.40-3.55 (m, 2H) 3.23-3.28 (m, 1H) 3.18 (br dd, J=9.8, 3.8 Hz, 2H) 2.81-3.05 (m, 3H) 1.48-1.58 (m, 3H) 1.19-1.39 (m, 4H).

Compound 96

Major Rotamer (65%)

$^1$H NMR (500 MHz, DMSO-d$_6$) δ ppm 7.99 (t, J=8.5 Hz, 1H) 7.32 (d, J=7.3 Hz, 1H) 7.07-7.25 (m, 3H) 6.91-6.95 (m, 1H) 6.76-6.82 (m, 1H) 6.52 (dd, J=8.8, 1.9 Hz, 1H) 6.45 (dd, J=14.7, 2.0 Hz, 1H) 5.59 (q, J=6.8 Hz, 1H) 5.31 (d, J=3.8 Hz, 1H) 4.26 (br s, 1H) 3.78-3.85 (m, 2H) 3.43-3.55 (m, 3H) 3.26-3.41 (m, 4H) 3.20 (d, J=10.7 Hz, 1H) 2.84-3.05 (m, 2H) 2.72 (br d, J=16.4 Hz, 1H) 1.48-1.58 (m, 3H) 1.21-1.37 (m, 4H).

Minor Rotamer (35%)

$^1$H NMR (500 MHz, DMSO-d$_6$) δ ppm 7.99 (t, J=8.5 Hz, 1H) 7.07-7.25 (m, 4H) 6.91-6.95 (m, 1H) 6.76-6.82 (m, 1H) 6.52 (dd, J=8.8, 1.9 Hz, 1H) 6.45 (dd, J=14.7, 2.0 Hz, 1H) 5.31 (d, J=3.8 Hz, 1H) 4.96 (d, J=6.9 Hz, 1H) 4.52-4.58 (m, 1H) 4.26 (br s, 1H) 3.78-3.85 (m, 1H) 3.43-3.55 (m, 2H) 3.26-3.41 (m, 5H) 3.20 (d, J=10.7 Hz, 1H) 2.84-3.05 (m, 3H) 1.48-1.58 (m, 3H) 1.21-1.37 (m, 4H).

Compound 97

Major Rotamer (65%)

$^1$H NMR (500 MHz, DMSO-d$_6$) δ ppm 8.03 (t, J=8.4 Hz, 1H) 7.32 (d, J=7.6 Hz, 1H) 7.06-7.24 (m, 3H) 6.95-6.98 (m, 1H) 6.78-6.83 (m, 1H) 6.55-6.60 (m, 2H) 6.15 (d, J=5.4 Hz, 1H) 5.59 (q, J=6.6 Hz, 1H) 4.36-4.43 (m, 1H) 3.71-3.84 (m, 4H) 3.43-3.50 (m, 1H) 3.31-3.38 (m, 1H) 2.84-3.05 (m, 2H) 2.72 (br d, J=16.1 Hz, 1H) 1.49-1.57 (m, 3H) 1.22-1.38 (m, 4H).

Minor Rotamer (35%)

$^1$H NMR (500 MHz, DMSO-d$_6$) δ ppm 8.03 (t, J=8.4 Hz, 1H) 7.06-7.24 (m, 4H) 6.95-6.98 (m, 1H) 6.78-6.83 (m, 1H) 6.55-6.60 (m, 2H) 6.15 (d, J=5.4 Hz, 1H) 4.97 (q, J=6.6 Hz, 1H) 4.52-4.58 (m, 1H) 4.36-4.43 (m, 1H) 3.71-3.84 (m, 3H) 3.31-3.38 (m, 1H) 3.23-3.28 (m, 1H) 2.84-3.05 (m, 3H) 1.49-1.57 (m, 3H) 1.22-1.38 (m, 4H).

Compound 98

Major Rotamer (65%)

$^1$H NMR (500 MHz, DMSO-$d_6$) δ ppm 7.98 (t, J=8.8 Hz, 1H) 7.31 (d, J=7.3 Hz, 1H) 7.07-7.24 (m, 3H) 6.91-6.95 (m, 1H) 6.75-6.81 (m, 1H) 6.55 (dd, J=8.8, 1.9 Hz, 1H) 6.49 (dd, J=14.8, 1.9 Hz, 1H) 5.59 (q, J=6.8 Hz, 1H) 4.87-4.93 (m, 2H) 4.83 (d, J=3.8 Hz, 1H) 4.35-4.41 (m, 1H) 4.06 (t, J=3.9 Hz, 1H) 3.82 (br dd, J=13.6, 3.8 Hz, 1H) 3.43-3.61 (m, 4H) 3.38 (dt, J=11.7, 6.7 Hz, 1H) 2.84-3.07 (m, 3H) 2.72 (br d, J=16.4 Hz, 1H) 1.49-1.57 (m, 3H) 1.22-1.38 (m, 4H).

Minor Rotamer (35%)

$^1$H NMR (500 MHz, DMSO-$d_6$) δ ppm 7.98 (t, J=8.8 Hz, 1H) 7.31 (d, J=7.3 Hz, 1H) 7.07-7.24 (m, 3H) 6.91-6.95 (m, 1H) 6.75-6.81 (m, 1H) 6.55 (dd, J=8.8, 1.9 Hz, 1H) 6.49 (dd, J=14.8, 1.9 Hz, 1H) 4.98 (br d, J=6.6 Hz, 1H) 4.87-4.93 (m, 2H) 4.83 (d, J=3.8 Hz, 1H) 4.52-4.57 (m, 1H) 4.35-4.41 (m, 1H) 4.06 (t, J=3.9 Hz, 1H) 3.43-3.61 (m, 3H) 3.38 (dt, J=11.7, 6.7 Hz, 1H) 3.23-3.26 (m, 1H) 2.84-3.07 (m, 4H) 1.49-1.57 (m, 3H) 1.22-1.38 (m, 4H).

Compound 99

Major Rotamer (65%)

$^1$H NMR (400 MHz, DMSO-$d_6$) δ ppm 7.99 (t, J=8.8 Hz, 1H) 7.03-7.36 (m, 4H) 6.87-6.99 (m, 1H) 6.80 (s, 1H) 6.49 (br d, J=8.8 Hz, 1H) 6.41 (br d, J=14.6 Hz, 1H) 5.59 (q, J=6.6 Hz, 1H) 5.16 (d, J=4.5 Hz, 1H) 3.94 (quin, J=4.9 Hz, 1H) 3.81 (br dd, J=13.8, 3.7 Hz, 1H) 3.50-3.63 (m, 2H) 3.40-3.50 (m, 1H) 2.65-3.16 (m, 5H) 2.13-2.23 (m, 1H) 1.45-1.61 (m, 3H) 1.19-1.41 (m, 4H) 1.02 (d, J=6.8 Hz, 3H).

Minor Rotamer (35%)

$^1$H NMR (400 MHz, DMSO-$d_6$) δ ppm 7.99 (t, J=8.8 Hz, 1H) 7.03-7.36 (m, 4H) 6.87-6.99 (m, 1H) 6.76 (s, 1H) 6.49 (br d, J=8.8 Hz, 1H) 6.41 (br d, J=14.6 Hz, 1H) 5.16 (d, J=4.5 Hz, 1H) 4.96 (q, J=6.4 Hz, 1H) 4.49-4.61 (m, 1H) 3.94 (quin, J=4.9 Hz, 1H) 3.50-3.63 (m, 2H) 3.20-3.29 (m, 1H) 2.65-3.16 (m, 5H) 2.13-2.23 (m, 1H) 1.45-1.61 (m, 3H) 1.19-1.41 (m, 4H) 1.02 (d, J=6.8 Hz, 3H).

Compound 100

Major Rotamer (65%)

$^1$H NMR (500 MHz, DMSO-$d_6$) δ ppm 7.99 (t, J=8.8, 1H), 7.32 (d, J=7.6 Hz, 1H), 7.09-7.26 (m, 3H), 6.90-6.96 (m, 1H), 6.80 (s, 1H), 6.50 (dd, J=8.7, 1.7 Hz, 1H), 6.42 (dd, J=14.7, 1.7 Hz, 1H), 5.55-5.62 (m, 1H), 5.17 (d, J=3.2 Hz, 2H), 4.07 (br s, 2H), 3.82 (br dd, J=13.7, 3.6 Hz, 1H), 3.53 (br dd, J=10.2, 3.6 Hz, 2H), 3.43-3.50 (m, 1H), 3.17 (d, J=10.4 Hz, 2H), 2.68-3.06 (m, 3H), 1.48-1.58 (m, 3H) 1.21-1.38 (m, 4H).

Minor Rotamer (35%)

$^1$H NMR (500 MHz, DMSO-$d_6$) δ ppm 7.99 (t, J=8.8, 1H), 7.09-7.26 (m, 3H), 7.07 (d, J=7.6 Hz, 1H), 6.90-6.96 (m, 1H), 6.76 (s, 1H), 6.50 (dd, J=8.7, 1.7 Hz, 1H), 6.42 (dd, J=14.7, 1.7 Hz, 1H), 5.17 (d, J=3.2 Hz, 2H), 4.93-5.00 (m, 1H), 4.55 (br dd, J=12.9, 3.2 Hz, 1H), 4.07 (br s, 2H), 3.53 (br dd, J=10.2, 3.6 Hz, 2H), 3.22-3.29 (m, 1H), 3.17 (d, J=10.4 Hz, 2H), 2.68-3.06 (m, 3H), 1.48-1.58 (m, 3H) 1.21-1.38 (m, 4H).

Compound 101

Major Rotamer (65%)

$^1$H NMR (400 MHz, DMSO-$d_6$) δ ppm 9.64 (br s, 1H) 9.40 (br s, 1H) 8.00 (t, J=8.7 Hz, 1H) 7.03-7.40 (m, 4H) 6.88-7.01 (m, 1H) 6.81 (s, 1H) 6.37-6.59 (m, 2H) 5.59 (q, J=6.7 Hz, 1H) 3.81 (br dd, J=13.9, 4.1 Hz, 1H) 3.21-3.67 (m, 6H) 2.71-3.12 (m, 3H) 2.25 (br d, J=6.1 Hz, 2H) 1.48-1.60 (m, 3H) 1.20-1.40 (m, 4H).

Minor Rotamer (35%)

$^1$H NMR (400 MHz, DMSO-$d_6$) δ ppm 9.64 (br s, 1H) 9.40 (br s, 1H) 8.00 (t, J=8.7 Hz, 1H) 7.03-7.40 (m, 4H) 6.88-7.01 (m, 1H) 6.77 (s, 1H) 6.37-6.59 (m, 2H) 4.96 (q, J=6.8 Hz, 1H) 4.55 (br d, J=11.2 Hz, 1H) 3.21-3.67 (m, 6H) 2.71-3.12 (m, 3H) 2.25 (br d, J=6.1 Hz, 2H) 1.48-1.60 (m, 3H) 1.20-1.40 (m, 4H).

Compound 102

Major Rotamer (65%)

$^1$H NMR (500 MHz, DMSO-$d_6$) δ ppm 7.99 (br t, J=8.7 Hz, 1H) 7.03-7.34 (m, 4H) 6.93 (m, 1H) 6.79 (s, 1H) 6.50 (d, J=8.2 Hz, 1H) 6.42 (d, J=14.8 Hz, 1H) 5.59 (q, J=6.2 Hz, 1H) 5.16 (br s, 2H) 4.08 (br s, 2H) 3.82 (br dd, J=13.6, 4.1 Hz, 1H) 3.51-3.57 (m, 2H) 3.42-3.51 (m, 1H) 3.17 (d, J=10.4 Hz, 2H) 2.69-3.08 (m, 3H) 1.47-1.59 (m, 3H) 1.22-1.40 (m, 4H).

Minor Rotamer (35%)

$^1$H NMR (500 MHz, DMSO-$d_6$) δ ppm 7.99 (br t, J=8.7 Hz, 1H) 7.03-7.34 (m, 4H) 6.93 (m, 1H) 6.75 (s, 1H) 6.50 (d, J=8.2 Hz, 1H) 6.42 (d, J=14.8 Hz, 1H) 5.16 (br s, 2H) 4.92-5.02 (m, 1H) 4.48-4.61 (m, 1H) 4.08 (br s, 2H) 3.51-3.57 (m, 2H) 3.22-3.27 (m, 1H) 3.17 (d, J=10.4 Hz, 2H) 2.69-3.08 (m, 3H) 1.47-1.59 (m, 3H) 1.22-1.40 (m, 4H).

Compound 103

Major Rotamer (65%)

$^1$H NMR (400 MHz, DMSO-$d_6$) δ ppm 8.00 (t, J=8.8 Hz, 1H), 7.32 (d, J=7.7 Hz, 1H), 7.09-7.27 (m, 3H), 6.89-6.96 (m, 1H), 6.80 (s, 1H), 6.44-6.55 (m, 1H), 6.31-6.44 (m, 1H), 5.52-5.64 (m, 1H), 4.91 (t, J=5.6 Hz, 1H), 4.85 (s, 1H), 3.77-3.87 (m, 1H), 3.36-3.56 (m, 6H), 3.12 (br d, J=10.3 Hz, 1H), 2.68-3.08 (m, 3H), 2.02-2.17 (m, 1H), 1.75-1.87 (m, 1H), 1.40-1.60 (m, 3H), 1.19-1.39 (m, 4H).

Minor Rotamer (35%)

$^1$H NMR (400 MHz, DMSO-$d_6$) δ ppm 8.00 (t, J=8.8 Hz, 1H), 7.09-7.27 (m, 3H), 7.08 (d, J=7.1 Hz, 1H), 6.89-6.96 (m, 1H), 6.76 (s, 1H), 6.44-6.55 (m, 1H), 6.31-6.44 (m, 1H), 4.88-5.00 (m, 2H), 4.85 (s, 1H), 4.50-4.60 (m, 1H), 3.36-3.56 (m, 5H) 3.19-3.29 (m, 1H), 3.12 (br d, J=10.3 Hz, 1H), 2.68-3.08 (m, 3H), 2.02-2.17 (m, 1H), 1.75-1.87 (m, 1H), 1.40-1.60 (m, 3H), 1.19-1.39 (m, 4H).

Compound 104

Major Rotamer (65%)

$^1$H NMR (400 MHz, DMSO-$d_6$) δ ppm 8.00 (t, J=8.9 Hz, 1H), 7.32 (d, J=7.4 Hz, 1H), 7.09-7.27 (m, 3H), 6.89-6.96 (m, 1H), 6.80 (s, 1H), 6.44-6.55 (m, 1H), 6.34-6.44 (m, 1H), 5.54-5.64 (m, 1H), 4.91 (t, J=5.6 Hz, 1H), 4.85 (s, 1H), 3.76-3.87 (m, 1H), 3.36-3.53 (m, 6H), 3.12 (br d, J=10.3 Hz, 1H), 2.68-3.08 (m, 3H), 2.02-2.17 (m, 1H), 1.75-1.87 (m, 1H), 1.46-1.60 (m, 3H), 1.18-1.40 (m, 4H).

Minor Rotamer (35%)

$^1$H NMR (400 MHz, DMSO-$d_6$) δ ppm 8.00 (t, J=8.9 Hz, 1H), 7.09-7.27 (m, 3H), 7.08 (d, J=7.1 Hz, 1H), 6.89-6.96 (m, 1H), 6.76 (s, 1H), 6.44-6.55 (m, 1H), 6.34-6.44 (m, 1H), 4.88-5.00 (m, 2H), 4.85 (s, 1H), 4.50-4.60 (m, 1H), 3.36-3.53 (m, 5H) 3.21-3.29 (m, 1H), 3.12 (br d, J=10.3 Hz, 1H), 2.68-3.08 (m, 3H), 2.02-2.17 (m, 1H), 1.75-1.87 (m, 1H), 1.46-1.60 (m, 3H), 1.18-1.40 (m, 4H).

Compound 105

Major Rotamer (65%)
 $^1$H NMR (400 MHz, DMSO-d$_6$) δ ppm 11.22 (s, 1H) 7.52 (br s, 1H) 7.05-7.35 (m, 4H) 7.02 (br s, 1H) 6.93-6.98 (m, 1H) 6.92 (s, 1H) 6.09 (br d, J=14.7 Hz, 1H) 5.96 (s, 1H) 5.59 (q, J=6.5 Hz, 1H) 3.80 (br dd, J=13.9, 3.9 Hz, 1H) 3.23-3.51 (m, 5H) 2.71-3.11 (m, 4H) 2.05-2.23 (m, 2H) 1.49-1.61 (m, 3H) 1.22-1.37 (m, 4H).

Minor Rotamer (35%)
 $^1$H NMR (400 MHz, DMSO-d$_6$) δ ppm 11.21 (s, 1H) 7.52 (br s, 1H) 7.05-7.35 (m, 4H) 7.02 (br s, 1H) 6.93-6.98 (m, 1H) 6.88 (s, 1H) 6.09 (br d, J=14.7 Hz, 1H) 5.96 (s, 1H) 4.94 (q, J=6.6 Hz, 1H) 4.51-4.60 (m, 1H) 3.23-3.51 (m, 5H) 2.71-3.11 (m, 4H) 2.05-2.23 (m, 2H) 1.49-1.61 (m, 3H) 1.22-1.37 (m, 4H).

Compound 106

Major Rotamer (65%)
 $^1$H NMR (400 MHz, DMSO-d$_6$) δ ppm 7.51 (br s, 1H) 7.09-7.36 (m, 4H) 6.95-7.05 (m, 2H) 6.79 (s, 1H) 6.00-6.14 (m, 2H) 5.59 (q, J=6.8 Hz, 1H) 4.82-4.91 (m, 1H) 4.08-4.20 (m, 2H) 3.77-3.90 (m, 1H) 3.66-3.75 (m, 2H) 3.19-3.58 (m, 5H) 2.69-3.14 (m, 4H) 2.03-2.27 (m, 2H) 1.46-1.61 (m, 3H) 1.21-1.34 (m, 4H).

Minor Rotamer (35%)
 $^1$H NMR (400 MHz, DMSO-d$_6$) δ ppm 7.51 (br s, 1H) 7.09-7.36 (m, 4H) 6.95-7.05 (m, 2H) 6.76 (s, 1H) 6.00-6.14 (m, 2H) 4.95 (q, J=6.7 Hz, 1H) 4.82-4.91 (m, 1H) 4.55 (br d, J=15.5 Hz, 1H) 4.08-4.20 (m, 2H) 3.66-3.75 (m, 2H) 3.19-3.58 (m, 5H) 2.69-3.14 (m, 4H) 2.03-2.27 (m, 2H) 1.46-1.61 (m, 3H) 1.21-1.34 (m, 4H).

Compound 107

Major Diastereomer (65%)
 $^1$H NMR (400 MHz, DMSO-d$_6$) δ ppm 8.01 (t, J=8.9 Hz, 1H) 7.29-7.35 (m, 1H) 7.03-7.28 (m, 3H) 6.89-7.02 (m, 1H) 6.81 (s, 1H) 6.54 (dd, J=9.0, 2.0 Hz, 1H) 6.49 (dd, J=14.8, 2.0 Hz, 1H) 5.47-5.65 (m, 2H) 5.13 (dt, J=55.9, 2.0 Hz, 1H) 4.26-4.49 (m, 1H) 3.81 (br dd, J=13.7, 3.7 Hz, 1H) 3.40-3.70 (m, 4H) 3.16 (t, J=8.7 Hz, 1H) 2.83-3.08 (m, 2H) 2.72 (br d, J=16.1 Hz, 1H) 1.52 (d, J=6.9 Hz, 3H) 1.17-1.43 (m, 4H).

Minor Diastereomer (35%)
 $^1$H NMR (400 MHz, DMSO-d$_6$) δ ppm 8.01 (t, J=8.9 Hz, 1H) 7.03-7.28 (m, 4H) 6.89-7.02 (m, 1H) 6.77 (s, 1H) 6.54 (dd, J=9.0, 2.0 Hz, 1H) 6.49 (dd, J=14.8, 2.0 Hz, 1H) 5.47-5.65 (m, 1H) 5.13 (dt, J=55.9, 2.0 Hz, 1H) 4.96 (q, J=7.0 Hz, 1H) 4.49-4.63 (m, 1H) 4.26-4.49 (m, 1H) 3.40-3.70 (m, 3H) 3.22-3.28 (m, 1H) 3.16 (t, J=8.7 Hz, 1H) 2.83-3.08 (m, 3H) 1.55 (d, J=6.9 Hz 3H) 1.17-1.43 (m, 4H).

Melting Points

For a number of compounds, melting points (m.p.) were determined with a differential scanning calorimeter DSC 1 (Mettler Toledo). Melting points were measured with a temperature gradient of 10° C./minute from 25° C. to 350° C. The reported values are peak values. Values are obtained with experimental uncertainties that are commonly associated with this analytical method.

| Co. No. | m.p. |
|---|---|
| 5 | 220.25° C. |
| 7 | 189.00° C. |
| 11 | 159.35° C. |
| 17 | 258.48° C. |
| 19 | 308.63° C. |
| 32 | 297.57° C. |
| 33 | 292.70° C. |
| 34 | 289.10° C. |
| 35 | 174.2° C. |
| 36 | 237.70° C. |
| 37 | 123.18° C. |
| 42 | 206.84° C. |
| 43 | 214.36° C. |
| 46 | 270.00° C. |
| 47 | 245.69° C. |
| 49 | 239.19° C. |
| 52 | 246.17° C. |
| 53 | 228.33° C. |
| 54 | 254.46° C. |
| 55 | 253.3° C. |
| 57 | 216.34° C. |
| 62 | 173.36° C. |
| 65 | 211.64° C. |
| 66 | 143.13° C. |
| 67 | 205.81° C. |
| 72 | 252.4° C. |
| 74 | 144.01° C. |
| 75 | 197.51° C. |
| 76 | 221.20° C. |
| 78 | 283.43° C. |
| 79 | 285.54° C. |
| 80 | 182.93° C. |
| 81 | 271.19° C. |
| 82 | 294.89° C. |
| 83 | 235.56° C. |
| 84 | 252.18° C. |
| 85 | 277.22° C. |
| 87 | 152.28° C. |
| 90 | 269.08° C. |
| 91 | 236.01° C. |

Optical Rotation

The optical rotation was measured using a polarimeter with light at the wavelength of the D-line of sodium (589 nm) at a temperature of 20° C. in DMF as solvent. Compound (45) and compound (84) were measured at 546 nm.

| Co. No. | $[α]_D^{20}$ | c (w/v %) |
|---|---|---|
| 2 | −71.71° | 0.2301 |
| 3 | +16.14° | 0.2478 |
| 4 | +20.58° | 0.2478 |
| 5 | −33.57° | 0.28 |
| 6 | −26° | 0.25 |
| 7 | −43.31° | 0.254 |
| 8 | −17.93° | 0.29 |
| 9 | −33.9° | 0.2566 |
| 10 | −22.37° | 0.2637 |
| 11 | −38.13° | 0.278 |
| 12 | −17.67° | 0.3 |
| 13 | −19.36° | 0.2583 |
| 14 | −14.7° | 0.2177 |
| 15 | −59.7° | 0.2345 |
| 16 | +9.48° | 0.2531 |
| 17 | −5.25° | 0.2478 |
| 18 | −9.69° | 0.3097 |
| 26 | −26.64° | 0.289 |
| 30 | −52.69° | 0.26 |
| 31 | −3.7° | 0.27 |
| 32 | −53.33° | 0.3 |
| 33 | −59.38° | 0.32 |
| 36 | −17.69° | 0.26 |
| 37 | −24.1° | 0.278 |
| 38 | −13.23° | 0.257 |
| 39 | +16.45° | 0.304 |
| 40 | −23.33° | 0.27 |
| 41 | −28.71° | 0.31 |

-continued

| Co. No. | $[\alpha]_D^{20}$ | c (w/v %) |
|---|---|---|
| 42 | −18.8° | 0.266 |
| 43 | −48.52° | 0.27 |
| 44 | −79.23° | 0.26 |
| 45 | +4.69° | 0.32 |
| 46 | −25.65° | 0.269 |
| 47 | −19.49° | 0.272 |
| 48 | −265.35° | 0.254 |
| 49 | −40.77° | 0.26 |
| 50 | −35.58° | 0.2867 |
| 51 | −27.51° | 0.269 |
| 52 | −35.03° | 0.294 |
| 53 | −40.42° | 0.2301 |
| 54 | −20.06° | 0.324 |
| 55 | −9.33° | 0.3 |
| 56 | −14.65° | 0.2389 |
| 57 | −14.84° | 0.256 |
| 58 | −14.56° | 0.261 |
| 59 | −17.81° | 0.219 |
| 60 | −16.33° | 0.245 |
| 62 | −15.91° | 0.2389 |
| 63 | −7.22° | 0.263 |
| 64 | −14.6° | 0.274 |
| 65 | −33.21° | 0.271 |
| 66 | −29.77° | 0.262 |
| 67 | −34.97 | 0.306 |
| 68 | −32.74° | 0.281 |
| 70 | −30.09° | 0.216 |
| 72 | −30.0° | 0.25 |
| 74 | −33.22° | 0.292 |
| 76 | −16° | 0.25 |
| 77 | −55.36° | 0.28 |
| 78 | −6.88° | 0.32 |
| 80 | −12.58° | 0.302 |
| 81 | −46.29° | 0.283 |
| 82 | −9.12° | 0.296 |
| 83 | −47.3° | 0.315 |
| 84 | +5.37° | 0.298 |
| 85 | −79.09° | 0.33 |
| 86 | −39.12° | 0.294 |
| 87 | −30.74° | 0.27 |
| 88 | −33.33° | 0.21 |
| 89 | −36.49° | 0.285 |
| 90 | −14° | 0.25 |
| 91 | −32.08° | 0.265 |
| 92 | −29.01° | 0.262 |
| 93 | −30.94 | 0.32 |
| 94 | −8.93 | 0.28 |
| 95 | −31 | 0.3 |
| 96 | −29.23 | 0.26 |
| 97 | −18.13 | 0.32 |
| 98 | −70.35 | 0.317 |
| 100 | −49.64 | 0.28 |
| 101 | +33.93 | 0.28 |
| 102 | −9.29 | 0.28 |
| 103 | −31.2 | 0.25 |
| 104 | +28.57 | 0.28 |
| 105 | −17.59 | 0.29 |
| 106 | −38.21 | 0.28 |

E. PHARMACOLOGICAL EXAMPLES

E.1 Antiviral Activity

Black 384-well clear-bottom microtiter plates (Corning, Amsterdam, The Netherlands) were filled via acoustic drop ejection using the echo liquid handler (Labcyte, Sunnyvale, Calif.). 200 nL of compound stock solutions (100% DMSO) were transferred to the assay plates. 9 serial 4-fold dilutions of compound were made, creating per quadrant the same compound concentration. The assay was initiated by adding 10 µL of culture medium to each well (RPMI medium without phenol red, 10% FBS-heat inactivated, 0.04% gentamycin (50 mg/mL). All addition steps are done by using a multidrop dispenser (Thermo Scientific, Erembodegem, Belgium). Next, rgRSV224 virus (MOI=1) diluted in culture medium was added to the plates. rgRSV224 virus is an engineered virus that includes an additional GFP gene (Hallak L K, Spillmann D, Collins P L, Peeples M E. Glycosaminoglycan sulfation requirements for respiratory syncytial virus infection; Journal of virology (2000), 74(22), 10508-13) and was in-licensed from the NIH (Bethesda, Md., USA). Finally, 20 µL of a HeLa cell suspension (3,000 cells/well) were plated. Medium, virus- and mock-infected controls were included in each test. The wells contain 0.05% DMSO per volume. Cells were incubated at 37° C. in a 5% $CO_2$ atmosphere. Three days post-virus exposure, viral replication was quantified by measuring GFP expression in the cells by an in house developed MSM laser microscope (Tibotec, Beerse, Belgium). The EC50 was defined as the 50% inhibitory concentration for GFP expression. In parallel, compounds were incubated for three days in a set of white 384-well microtiter plates (Corning) and the cytotoxicity of compounds in HeLa cells was determined by measuring the ATP content of the cells using the ATPlite kit (Perkin Elmer, Zaventem, Belgium) according to the manufacturer's instructions. The CC50 was defined as the 50% concentration for cytotoxicity.

TABLE antiviral data

| Co. No. | RSV HELA EC50 (µM) | TOX HELA CC50 (µM) |
|---|---|---|
| 1 | 0.085 | >100 |
| 2 | 0.056 | 38.7 |
| 3 | 0.063 | 43.0 |
| 4 | 0.049 | 23.0 |
| 5 | 0.118 | >25 |
| 6 | 0.098 | >100 |
| 7 | 0.037 | 71.5 |
| 8 | 0.041 | 51.5 |
| 9 | 0.108 | >100 |
| 10 | 0.070 | >100 |
| 11 | 0.044 | >100 |
| 12 | 0.041 | >100 |
| 13 | 0.058 | 80.5 |
| 14 | 0.039 | 81.2 |
| 15 | 0.100 | >100 |
| 16 | 0.110 | >100 |
| 17 | 0.050 | >100 |
| 18 | 0.044 | >100 |
| 19 | 0.041 | 72.3 |
| 20 | 0.052 | 55.9 |
| 21 | 0.045 | >100 |
| 22 | 0.145 | >100 |
| 23 | 0.032 | 30.3 |
| 24 | 0.030 | 26.4 |
| 25 | 0.023 | 29.6 |
| 26 | 0.020 | 29.6 |
| 27 | 0.089 | 34.4 |
| 28 | 0.072 | 32.2 |
| 29 | 0.045 | 43.7 |
| 30 | 0.036 | 33.9 |
| 31 | 0.036 | 39.1 |
| 32 | 0.060 | 32.1 |
| 33 | 0.043 | 34.5 |
| 34 | 0.037 | 23.1 |
| 35 | 0.033 | 25.5 |
| 36 | 0.012 | 29.3 |
| 37 | 0.019 | 62.0 |
| 38 | 0.043 | >100 |
| 39 | 0.291 | 53.1 |
| 40 | 0.061 | 52.3 |
| 41 | 0.036 | 51.1 |
| 42 | 0.025 | 28.9 |
| 43 | 0.017 | 29.8 |
| 44 | 0.019 | 45.2 |
| 45 | 0.020 | 31.4 |
| 46 | 0.007 | 31.3 |

TABLE-continued antiviral data

| Co. No. | RSV HELA EC50 (µM) | TOX HELA CC50 (µM) |
|---|---|---|
| 47 | 0.009 | 41.5 |
| 49 | 0.024 | 32.3 |
| 50 | 0.031 | 35.1 |
| 51 | 0.131 | 67.9 |
| 52 | 0.014 | 41.3 |
| 53 | 0.035 | >100 |
| 54 | 0.192 | 77.4 |
| 55 | 0.016 | >100 |
| 56 | 0.032 | 58.9 |
| 57 | 0.023 | >100 |
| 58 | 0.036 | >100 |
| 59 | 0.047 | N.A. |
| 60 | 0.029 | 41.3 |
| 61 | 0.193 | >100 |
| 62 | 0.043 | >100 |
| 63 | 0.011 | 27.2 |
| 64 | 0.029 | 8.9 |
| 65 | 0.048 | 39.1 |
| 66 | 0.040 | 36.4 |
| 67 | 0.030 | 36.5 |
| 68 | 0.058 | 26.6 |
| 69 | 0.059 | 33.2 |
| 70 | 0.104 | 28.2 |
| 71 | 0.105 | 29.8 |
| 72 | 0.087 | >100 |
| 73 | 0.101 | >100 |
| 74 | 0.076 | 48.1 |
| 75 | 0.076 | >100 |
| 76 | 0.246 | >100 |
| 77 | 0.082 | >100 |
| 78 | 0.055 | 47.3 |
| 79 | 0.476 | 13.3 |
| 80 | 0.091 | 35.9 |
| 81 | 0.099 | 38.4 |
| 82 | 0.033 | 33.1 |
| 83 | 0.044 | 42.4 |
| 84 | 0.006 | 19.0 |
| 85 | 0.152 | >100 |
| 86 | 0.161 | 49.5 |
| 87 | 0.215 | 47.4 |
| 88 | 0.017 | 47.6 |
| 89 | 0.165 | 33.4 |
| 90 | 0.046 | N.A. |
| 91 | 0.036 | 28.3 |
| 92 | 0.071 | 41.5 |
| 93 | 0.039 | 13.4 |
| 94 | 0.19 | >100 |
| 95 | 0.018 | 31.1 |
| 96 | 0.05 | 22.5 |
| 97 | 0.053 | 26.1 |
| 98 | 0.039 | 47.6 |
| 99 | 0.092 | >100 |
| 100 | 0.011 | 23.8 |
| 101 | 0.058 | 45.4 |
| 102 | 0.026 | 44.4 |
| 103 | 0.019 | 35.8 |
| 104 | 0.025 | 28.2 |
| 105 | 0.025 | 83.6 |
| 106 | 0.089 | 21 |
| 107 | 0.017 | 21.2 |

N.A.: not available

E.2 Pharmacokinetics after Single Intravenous Administration in the Fasted Male Beagle Dog The test compound was dissolved in a 20% (w/v) hydroxypropyl-β-cyclodextrin (HP-beta-CD) solution at a final concentration of 2 mg/mL for the intravenous formulation. NaOH was added to the formulations to facilitate dissolution and after total dissolution the pH was adjusted with HCl to 8.4. The intravenous (IV) formulation was made isotonic with mannitol. Prior to dosing, all formulations were stored at room temperature and protected from light. The IV formulation was dosed in a cephalic vein at 0.5 mL/kg to obtain a final dose of 1 mg/kg.

Three male Beagle dogs, with a mean weight of 10.9±1.1 kg, were used. A complete concentration time profile was obtained from each individual animal. Prior to dosing, animals were fasted overnight. Their standard dry diet was returned to them at 2 hours post dose. Tap water was available ad libitum.

From each individual animal, blood samples were taken at 7 and 20 minutes, 1, 2, 4, 7, 24 and 48 hours after intravenous dose administration. Blood was collected from a jugular vein into 2 mL BD Vacutainers™ K3E (Becton Dickinson). Samples were placed immediately on melting ice and plasma was obtained following centrifugation at 4° C. for 10 minutes at approximately 1900×g. All samples were shielded from daylight and stored at ≤−18° C. prior to analysis. Plasma samples were analysed using a qualified research LC-MS/MS method. The key analytical performance (linearity, upper and lower limit of quantification, accuracy and precision) of the method was reported together with the plasma concentrations. The lower limit of quantification (LLOQ) was 10.0 ng/mL.

Pharmacokinetic analysis was performed using Phoenix™ Professional (Version 6.3). A non-compartmental analysis using the linear/log trapezoidal rule with linear/log interpolation was used for all data.

The plasma concentration profile of Compound (37) and Compound (102) of the present invention has been reproduced in FIGS. 1 and 2.

The plasma concentration profile of Compound (W37) and Compound (W38) of WO-2016/174079 has been reproduced in FIGS. 3 and 4.

After intravenous administration at 1 mg/kg in dogs the compounds (W37) and (W38) of WO-2016/174079 show a rapid decline in plasma concentration in the first 8 hours after administration. The plasma concentration profile of Compound (37) and Compound (102) of the present invention does not show this rapid decline thereby indicating these compounds have improved metabolic stability properties and improved bio-availability.

DESCRIPTION OF THE DRAWINGS

FIG. 1: plasma concentration profile of Compound (102)
FIG. 2: plasma concentration profile of Compound (37)
FIG. 3: plasma concentration profile of compound (W37) of WO-2016/174079
FIG. 4: plasma concentration profile of compound (W38) of WO-2016/174079

F. PROPHETIC COMPOSITION EXAMPLES

"Active ingredient" as used throughout these examples relates to a final compound of Formula (I), the pharmaceutically acceptable salts thereof, the solvates and the stereochemically isomeric forms and the tautomers thereof.

Typical examples of recipes for the formulation of the invention are as follows:

F.1. Tablets

| Active ingredient | 5 to 50 mg |
|---|---|
| Di calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

F.2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

F.3. Injectable

A parenteral composition is prepared by stirring 1.5% by weight of active ingredient of the invention in 10% by volume propylene glycol in water.

F.4. Ointment

| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of Formula (I), including any stereochemically isomeric form thereof:

(I)

wherein:
A is (a-1)

or (a-2)

;

n is 0 or 1 and m is 1; or n is 0 and m is 2;
for $X^1$, $X^2$, and $X^3$:
  $X^1$ is $CR^{11}$ and $X^2$ is $CR^{11}$ and $X^3$ is $CR^{11}$, or
  $X^1$ is N and $X^2$ is $CR^{11}$ and $X^3$ is $CR^{11}$, or
  $X^1$ is N and $X^2$ is $CR^{11}$ and $X^3$ is N;
  wherein each $R^{11}$ is independently selected from hydrogen, halo, hydroxy, —$NH_2$, $C_{1-4}$alkyl, $C_{1-4}$alkyloxy, $C_{1-4}$alkyloxy$C_{1-4}$alkyloxy, and hydroxy$C_{1-4}$alkyloxy;
$R^1$ is $CH_3$;
$R^2$ is hydrogen or fluoro;
$R^3$ is halo;
$R^4$ is cyclopropyl; phenyl; phenyl substituted with halo, hydroxy, cyano, $C_{1-4}$alkyl, polyhalo$C_{1-4}$alkyl, or $C_{1-4}$alkyloxy; or Heteroaryl;
$R^5$ is hydrogen, $C_{1-4}$alkyl, or hydroxy$C_{1-4}$alkyl;
each $R^6$ is independently selected from hydrogen, $C_{1-4}$alkyl, hydroxy, halo, and $C_{1-4}$alkyloxy;
each $R^{6a}$ is independently selected from hydrogen and halo;
$R^7$ is hydrogen, $C_{1-4}$alkyl, or hydroxy$C_{1-4}$alkyl;
$R^8$ is —OH, —CN, —O—(CO)—$NR^{12}R^{13}$, —$C_{1-4}$alkyl-(CO)—$NR^{12}R^{13}$, —(CO)—$NR^{12}R^{13}$, —(CS)—$NR^{12}R^{13}$, —(CO)—$NR^{12}$—CN, —(CO)—$NR^{12}$—$SO_2$—$R^{14}$, —$NR^{12}$—(CO)—$R^{14}$, —$NR^{12}$—(CO)—O—$R^{14}$, —$NR^{12}$—$SO_2$—$R^{14}$, —$NH_2$, —$NR^{12}$—$R^{15}$, —$SO_2$—$R^{14}$, —$SO_2$—$NR^{12}R^{13}$, —$SO_2$—$NR^{12}$—(CO)—$R^{14}$, or —SO(=NH)(—$R^{14}$), or Heteroaryl$^1$;
  wherein $R^{12}$ and $R^{13}$ are each independently selected from hydrogen and $C_{1-4}$alkyl;
  $R^{14}$ is $C_{1-4}$alkyl, or polyhalo$C_{1-4}$alkyl; and
  $R^{15}$ is di($C_{1-4}$alkyl)-(P=O)— or polyhalo$C_{1-4}$alkyl;
or $R^7$ and $R^8$ may be taken together to form —$CH_2$—($SO_2$)—$CH_2$— or —$CH_2$—O—$CH_2$—;
each $R^9$ is independently selected from hydrogen and $C_{1-4}$alkyl;
$R^{10}$ is hydrogen, halo, or $C_{1-6}$alkyl;
when n=1 and m=1, $R^8$ and $R^9$ may be taken together to form —$CH_2$—;
when n=1 and m=1, $R^8$ and $R^9$ may be taken together to form —$CH_2$—(CO)—O—;
Heteroaryl is pyridinyl or pyrimidinyl, wherein each Heteroaryl is optionally substituted with $C_{1-4}$alkyl, halo, amino, or aminocarbonyl; and
Heteroaryl$^1$ is tetrazolyl or 5-oxo-4,5-dihydro-1,2,4-oxadiazolyl;
or a pharmaceutically acceptable acid addition salt thereof.

2. The compound according to claim 1, wherein:
n is 0 or 1 and m is 1; or n is 0 and m is 2;
for $X^1$, $X^2$, and $X^3$:
  $X^1$ is $CR^{11}$ and $X^2$ is $CR^{11}$ and $X^3$ is $CR^{11}$, or
  $X^1$ is N and $X^2$ is $CR^{11}$ and $X^3$ is $CR^{11}$, or
  $X^1$ is N and $X^2$ is $CR^{11}$ and $X^3$ is N;
  wherein each $R^{11}$ is independently selected from hydrogen, halo, hydroxy, $C_{1-4}$alkyl, $C_{1-4}$alkyloxy, $C_{1-4}$alkyloxy$C_{1-4}$alkyloxy, and hydroxy$C_{1-4}$alkyloxy;
$R^1$ is $CH_3$;
$R^2$ is hydrogen;
$R^3$ is halo;
$R^4$ is cyclopropyl; phenyl; phenyl substituted with halo, cyano, $C_{1-4}$alkyl, polyhalo$C_{1-4}$alkyl, or $C_{1-4}$alkyloxy; or Heteroaryl;
$R^5$ is hydrogen;
each $R^6$ is independently selected from hydrogen, $C_{1-4}$alkyl, hydroxy, halo, and $C_{1-4}$alkyloxy;
each $R^{6a}$ is independently selected from hydrogen and halo;

R$^7$ is hydrogen, C$_{1-4}$alkyl, or hydroxyC$_{1-4}$alkyl;
R$^8$ is —OH, —CN, —O—(CO)—NR$^{12}$R$^{13}$, —C$_{1-4}$alkyl-(CO)—NR$^{12}$R$^{13}$, —(CO)—NR$^{12}$R$^{13}$, —(CS)—NR$^{12}$R$^{13}$, —(CO)—NR$^{12}$—CN, —(CO)—NR$^{12}$—SO$_2$—R$^{14}$, —NR$^{12}$—(CO)—R$^{14}$, —NR$^{12}$—(CO)—O—R$^{14}$, —NR$^{12}$—SO$_2$—R$^{14}$, —NH$_2$, —NR$^{12}$—R$^{15}$, —SO$_2$—R$^{14}$, —SO$_2$—NR$^{12}$R$^{13}$, —SO$_2$—NR$^{12}$—(CO)—R$^{14}$, or —SO(=NH)(—R$^{14}$), or Heteroaryl$^1$;
  wherein R$^{12}$ and R$^{13}$ are each independently selected from hydrogen and C$_{1-4}$alkyl;
R$^{14}$ is C$_{1-4}$alkyl or polyhaloC$_{1-4}$alkyl; and
R$^{15}$ is di(C$_{1-4}$alkyl)-(P=O)— or polyhaloC$_{1-4}$alkyl;
or R$^7$ and R$^8$ may be taken together to form —CH$_2$—(SO$_2$)—CH$_2$— or —CH$_2$—O—CH$_2$—;
each R$^9$ is independently selected from the group consisting of hydrogen and C$_{1-4}$alkyl;
R$^{10}$ is hydrogen;
when n=1 and m=1, R$^8$ and R$^9$ may be taken together to form —CH$_2$—(CO)—O—;
Heteroaryl is pyridinyl or pyrimidinyl, wherein each Heteroaryl is optionally substituted with halo; and
Heteroaryl$^1$ is tetrazolyl or 5-oxo-4,5-dihydro-1,2,4-oxadiazolyl.

3. The compound according to claim 1, wherein X$^1$ is CR$^{11}$ and X$^2$ is CR$^{11}$ and X$^3$ is CR$^{11}$.

4. The compound according to claim 1, wherein X$^1$ is N and X$^2$ is CR$^{11}$ and X$^3$ is CR$^{11}$; or X$^1$ is N and X$^2$ is CR$^{11}$ and X$^3$ is N.

5. The compound according to claim 1, wherein radical A is of formula (a-1).

6. The compound according to claim 1, wherein n is 0 and m is 1.

7. The compound according to claim 1, wherein n is 1 and m is 1.

8. The compound according to claim 1, wherein:
A is

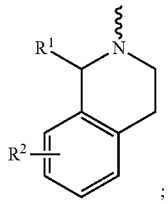

;

n is 0 or 1;
m is 1;
X$^1$ is CR$^{11}$ and X$^2$ is CR$^{11}$ and X$^3$ is CR$^{11}$;
  wherein each R$^{11}$ is hydrogen;
R$^1$ is CH$_3$;
R$^2$ is hydrogen;
R$^3$ is halo;
R$^4$ is cyclopropyl or Heteroaryl;
R$^5$ is hydrogen;
each R$^6$ is independently selected from hydrogen, hydroxy, and halo;
each R$^{6a}$ is hydrogen;
R$^7$ is hydrogen or hydroxyC$_{1-4}$alkyl;
R$^8$ is —OH, —C$_{1-4}$alkyl-(CO)—NR$^{12}$R$^{13}$, or —(CO)—NR$^{12}$R$^{13}$;
  wherein R$^{12}$ and R$^{13}$ are each independently selected from hydrogen and C$_{1-4}$alkyl;
R$^{10}$ is hydrogen; and
Heteroaryl is pyridinyl.

9. The compound according to claim 1, wherein:
A is

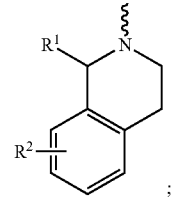

;

n is 1;
m is 1;
X$^1$ is CR$^{11}$ and X$^2$ is CR$^{11}$ and X$^3$ is CR$^{11}$;
  wherein each R$^{11}$ is hydrogen;
R$^1$ is CH$_3$;
R$^2$ is hydrogen;
R$^3$ is halo;
R$^4$ is cyclopropyl;
R$^5$ is hydrogen;
each R$^6$ is independently selected from hydrogen, hydroxy, and halo;
each R$^{6a}$ is hydrogen;
R$^7$ is hydrogen or hydroxyC$_{1-4}$alkyl;
R$^8$ is —OH or —(CO)—NR$^{12}$R$^{13}$;
  wherein R$^{12}$ and R$^{13}$ are each independently selected from hydrogen and C$_{1-4}$alkyl; and
R$^{10}$ is hydrogen.

10. The compound according to claim 1, wherein:
A is

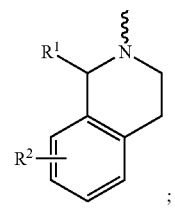

;

n is 1;
m is 1;
X$^1$ is CR$^{11}$ and X$^2$ is CR$^{11}$ and X$^3$ is CR$^{11}$;
  wherein each R$^H$ is hydrogen;
R$^1$ is CH$_3$;
R$^2$ is hydrogen;
R$^3$ is halo;
R$^4$ is cyclopropyl;
R$^5$ is hydrogen;
each R$^6$ is independently selected from hydrogen and hydroxy;
each R$^{6a}$ is hydrogen;
R$^7$ is hydrogen;
R$^8$ is —OH or —(CO)—NR$^{12}$R$^{13}$;
  wherein R$^{12}$ and R$^{13}$ are each independently selected from hydrogen and C$_{1-4}$alkyl, and
R$^{10}$ is hydrogen.

11. The compound according to claim 1, wherein the compound is selected from:

13
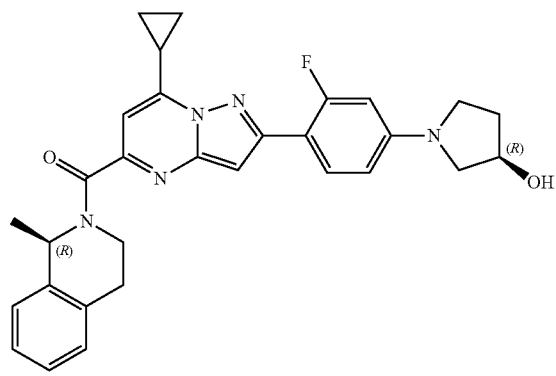
14
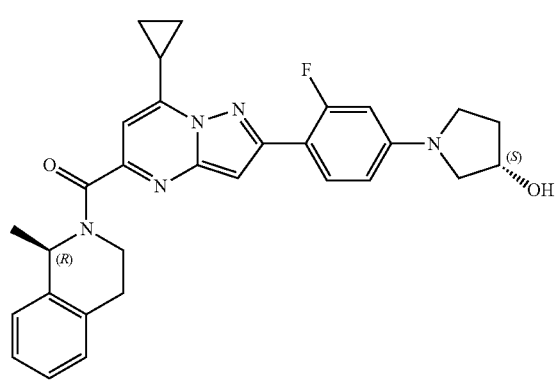
36
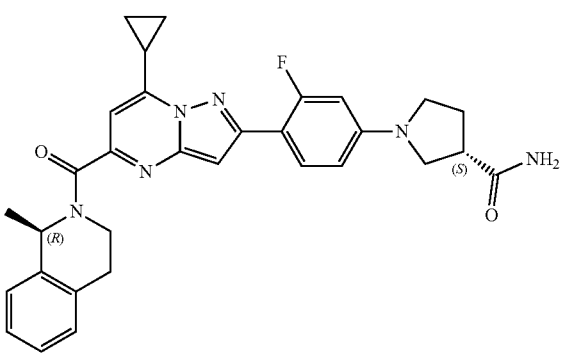
37
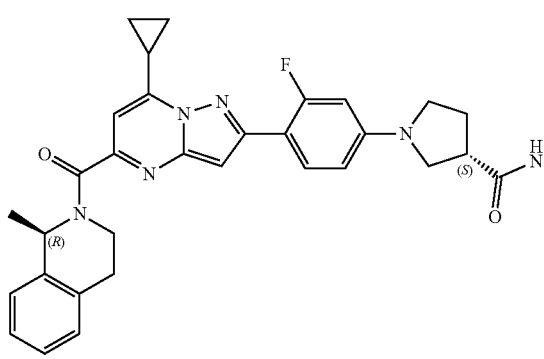
-continued
66
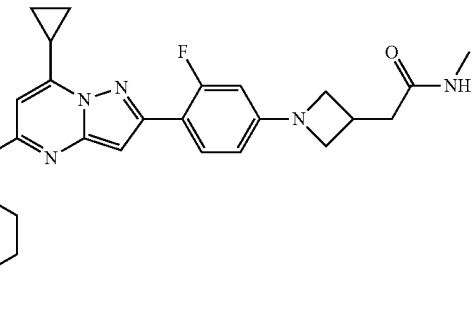
84
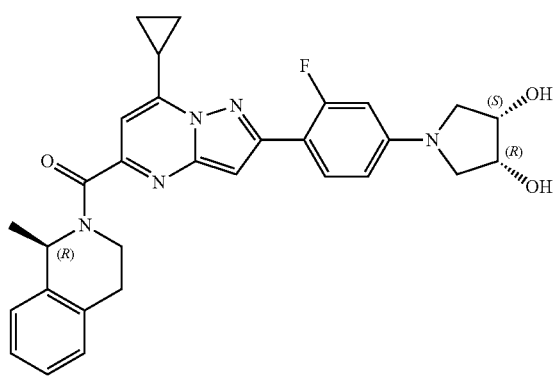
95
100
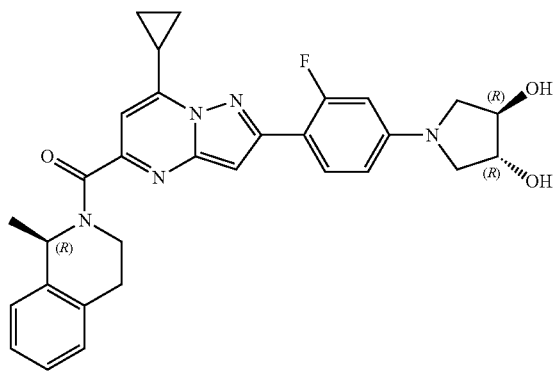

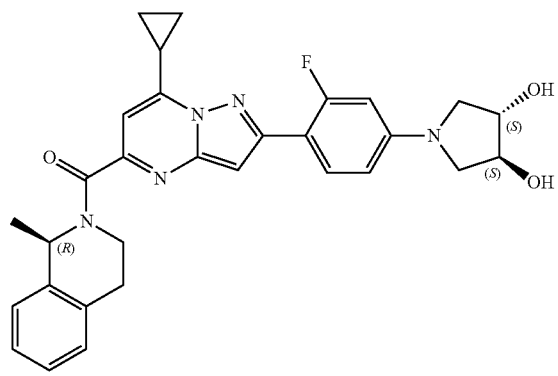
102
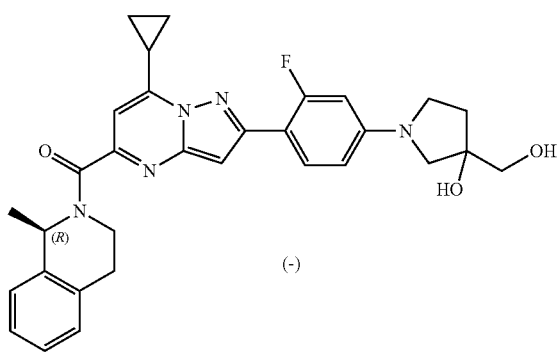
103
(-)
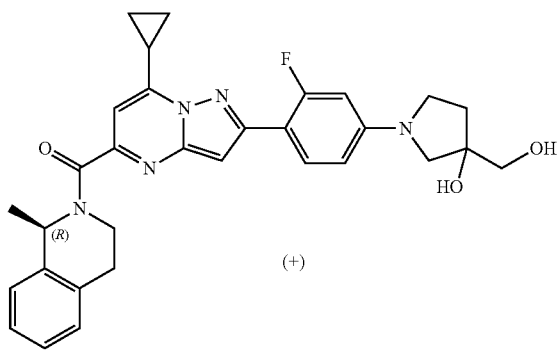
104
(+)
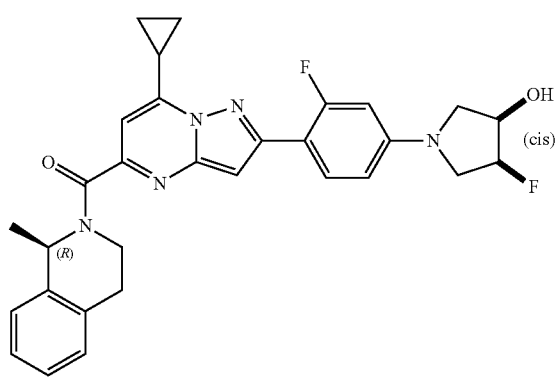
107
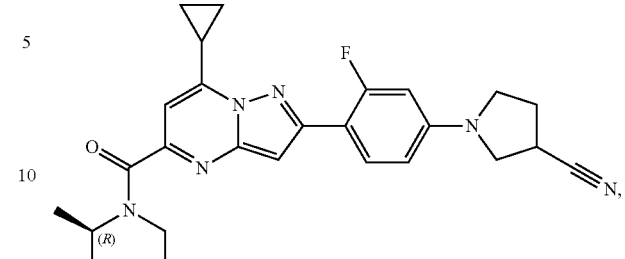
1
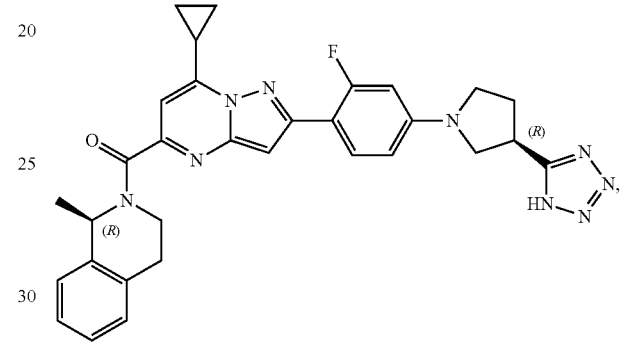
2
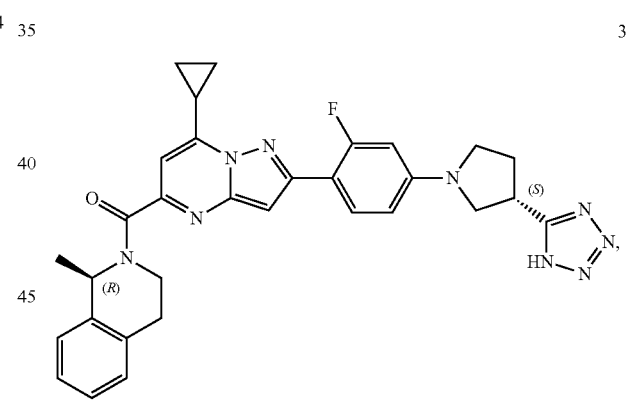
3
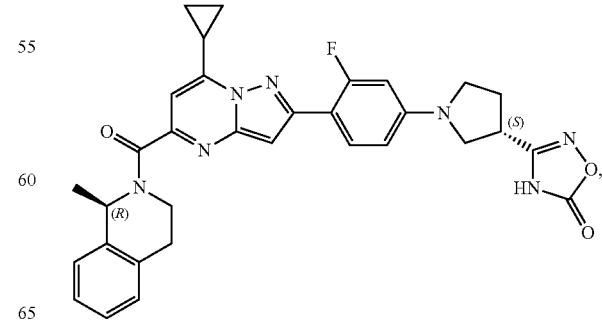
4

371
-continued
5
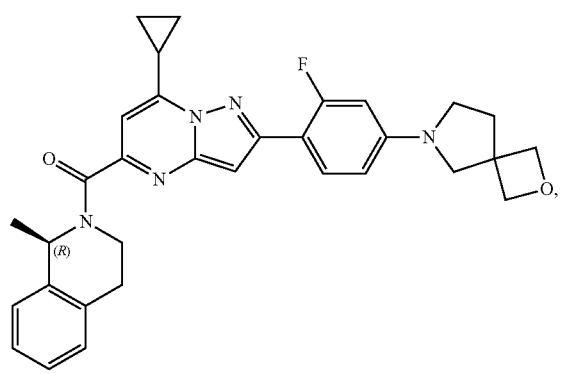
6
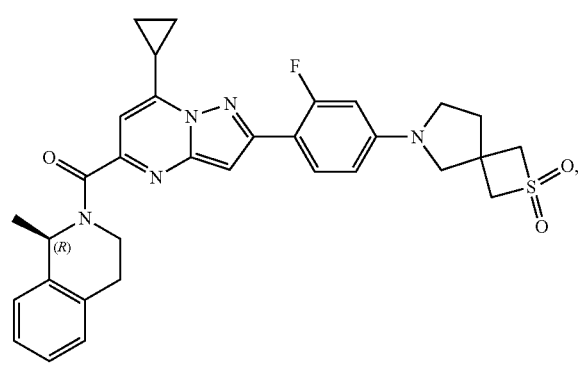
7
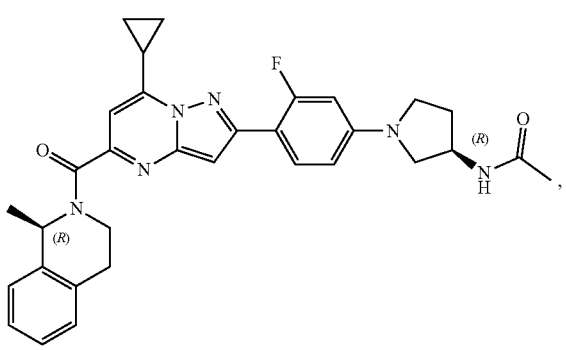
8
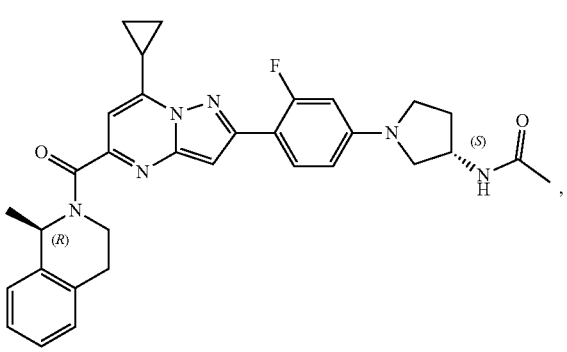
372
-continued
9
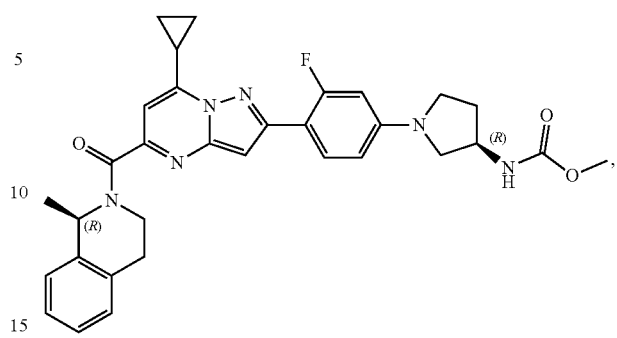
10
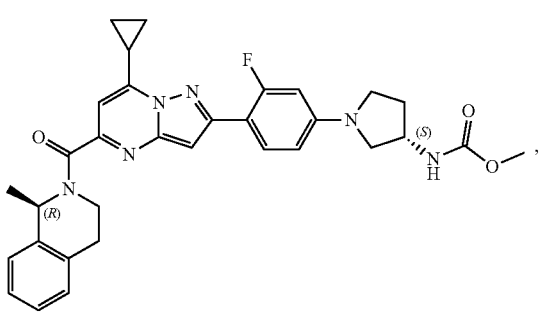
11
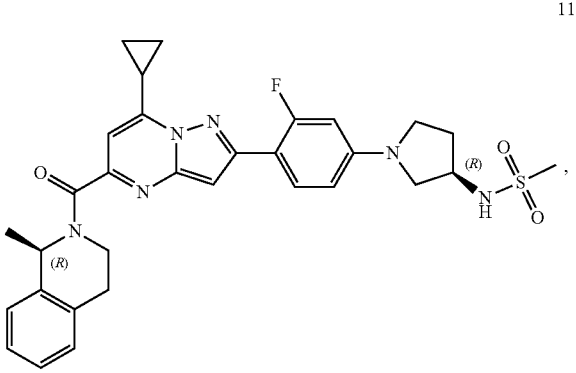
12
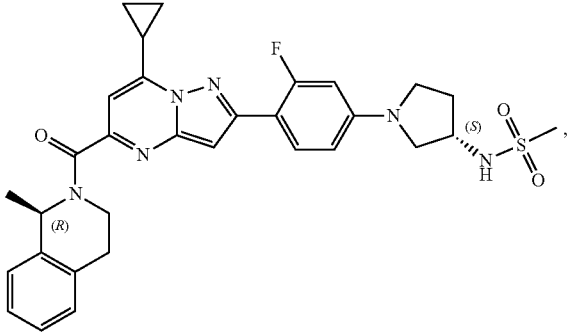

15
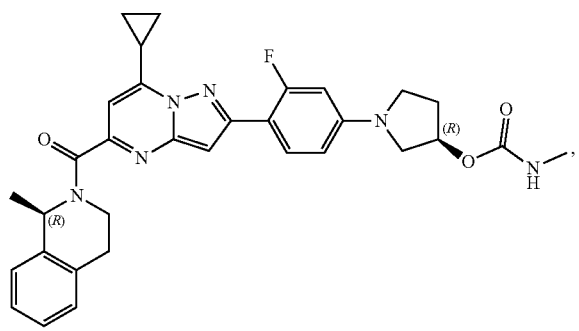
16
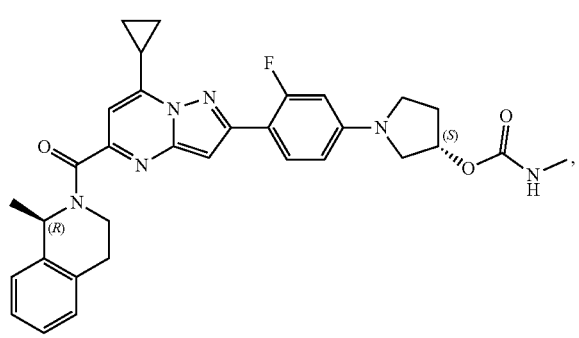
17
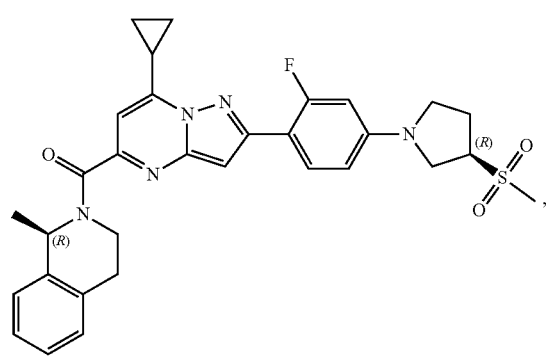
18
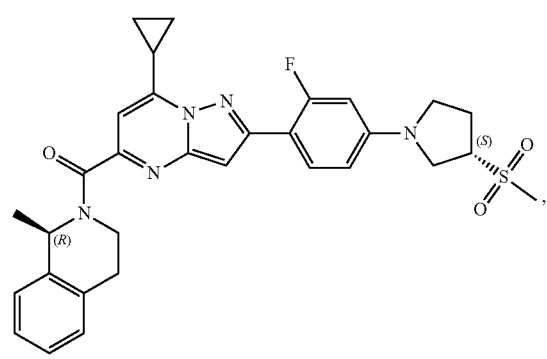
19
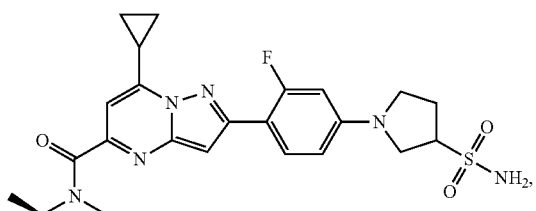
20
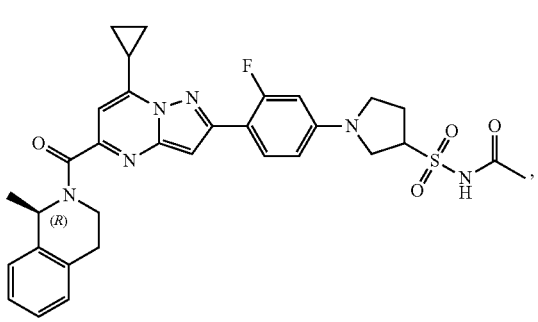
21
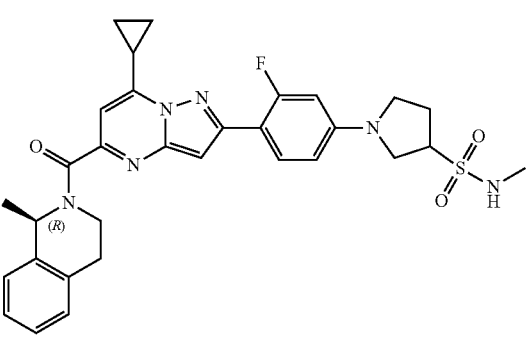
22
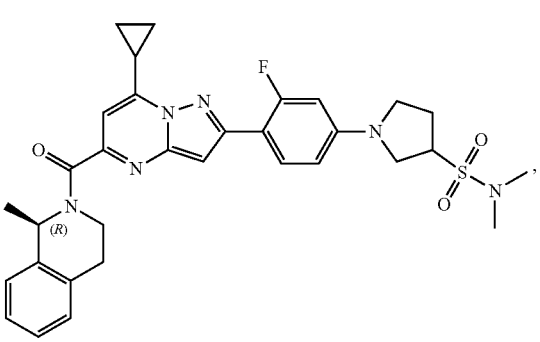
23
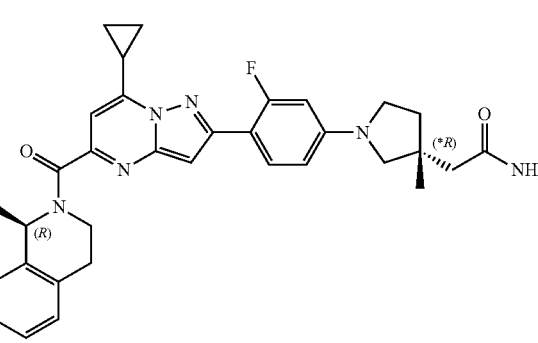

-continued
24
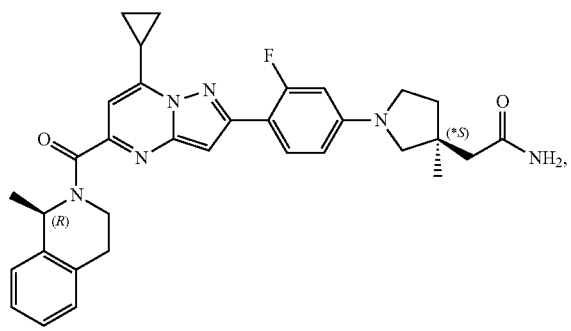
25
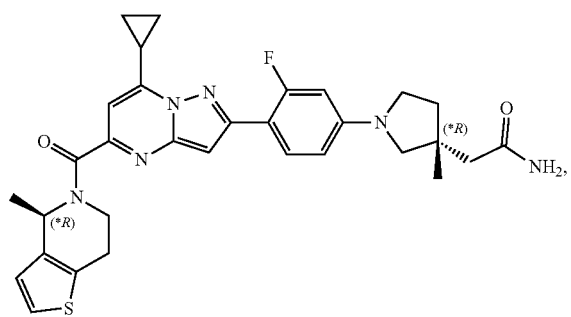
26
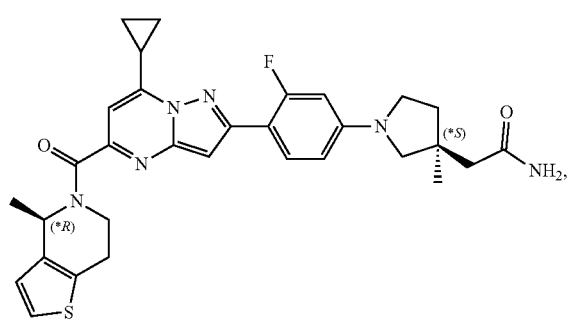
27
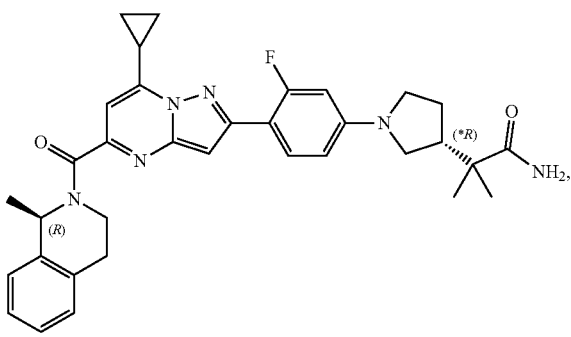
-continued
28
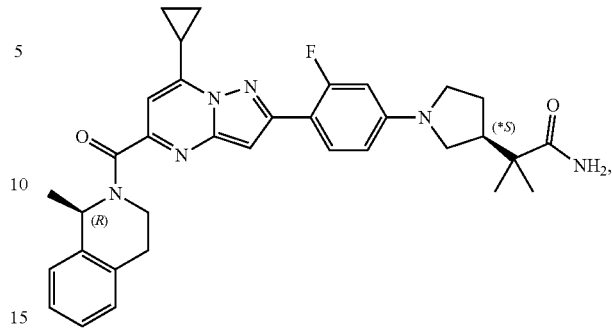
29
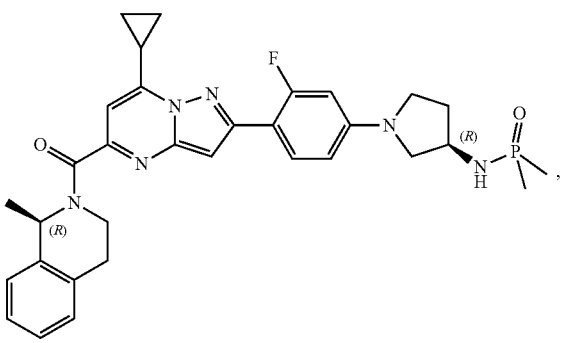
30
31
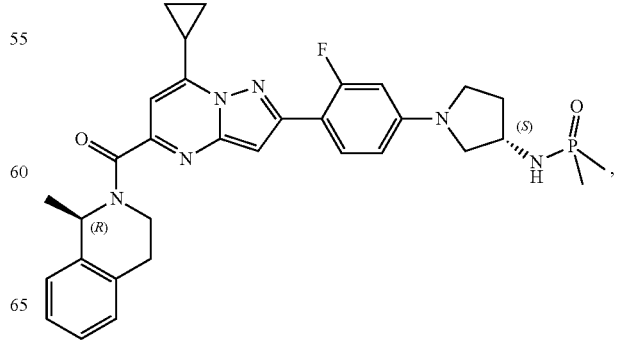

32
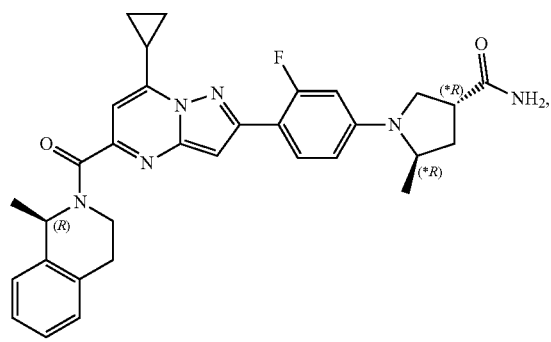
33
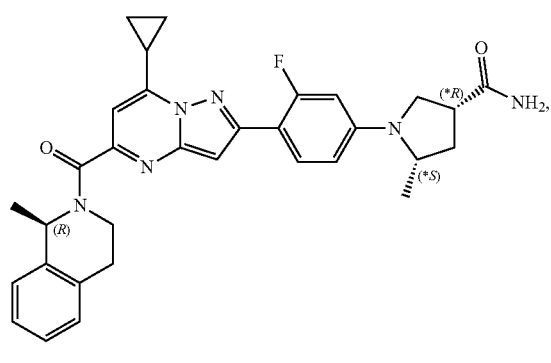
34
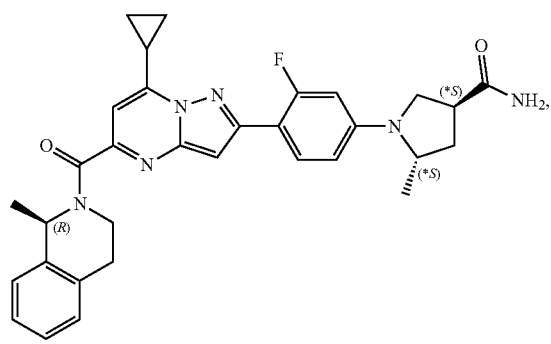
35
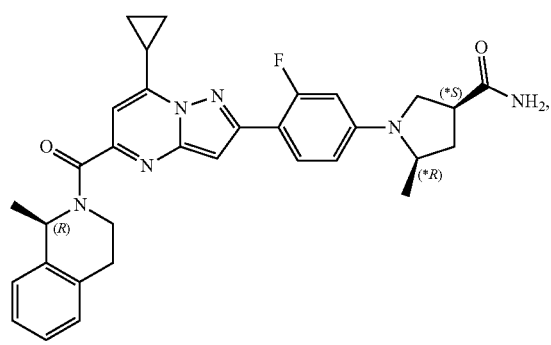
38
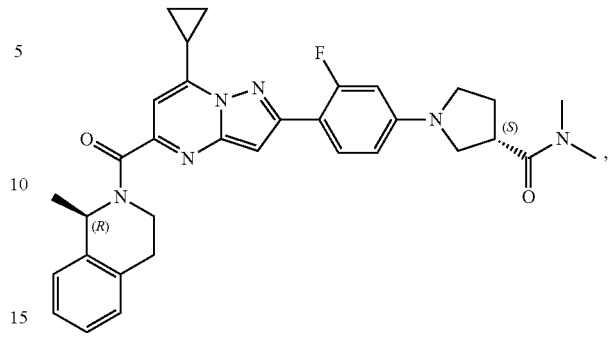
39
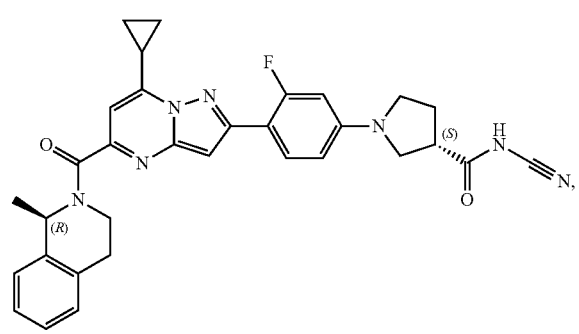
40
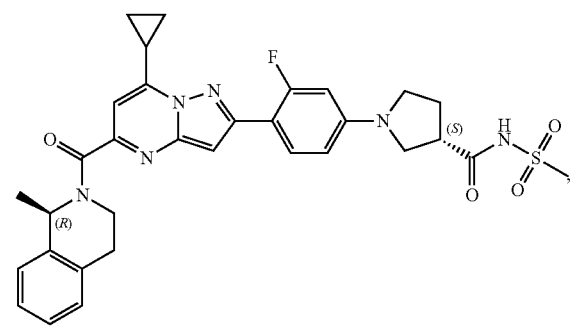
41
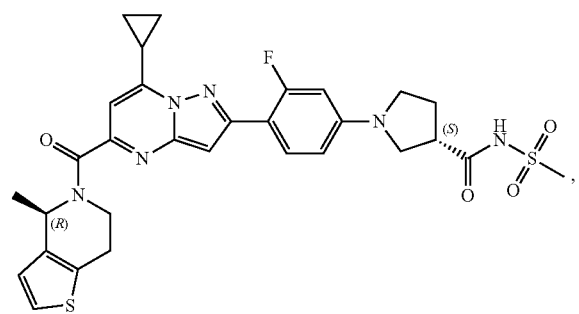

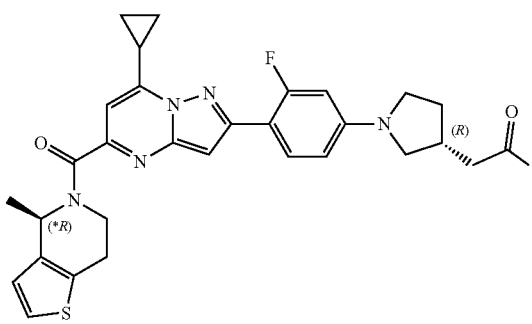
42
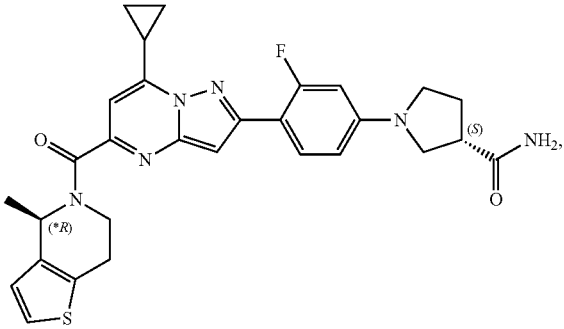
46
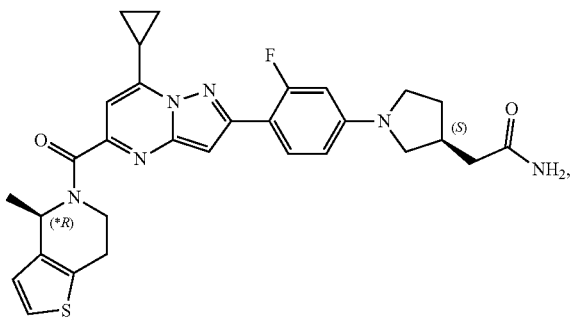
43
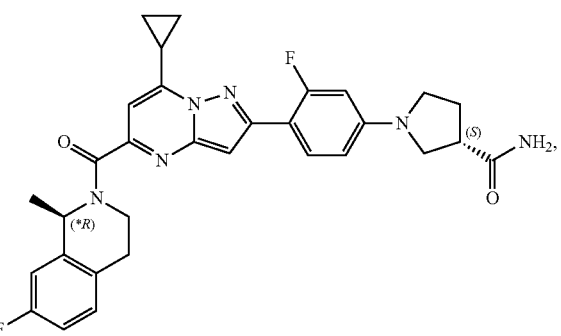
47
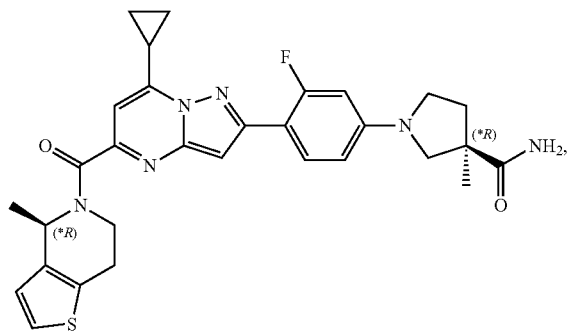
44
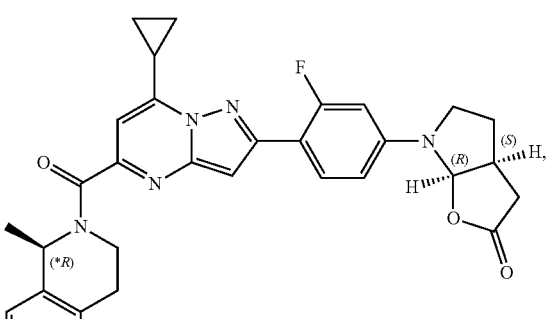
48
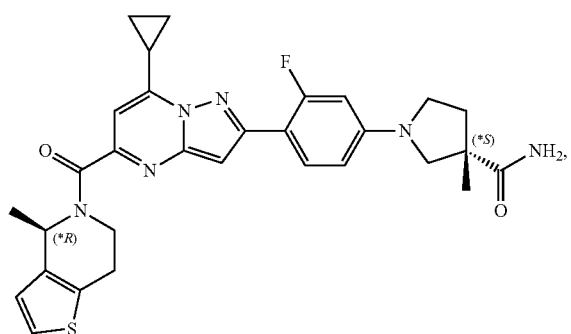
45
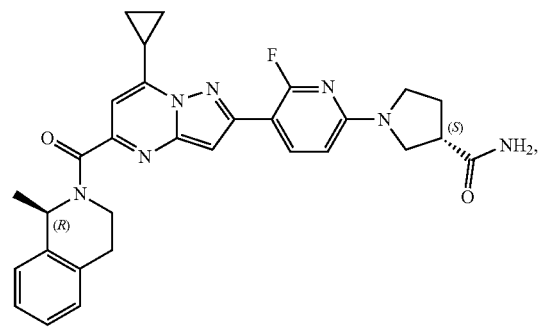
49

| 381 -continued | 382 -continued |
|---|---|
| 50<br>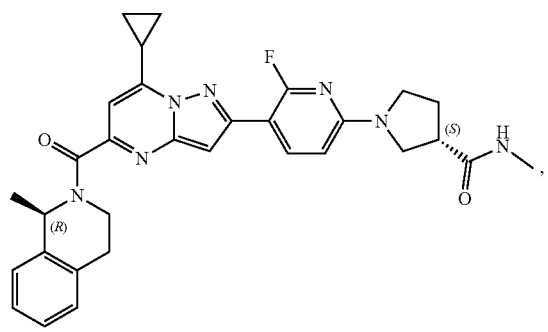 | 54<br>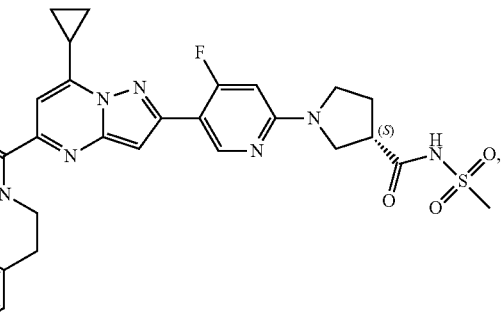 |
| 51<br>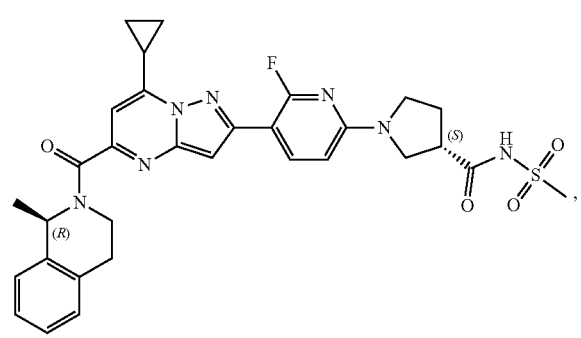 | 55<br>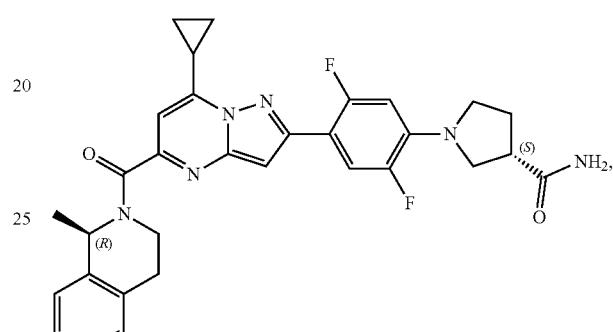 |
| 52<br>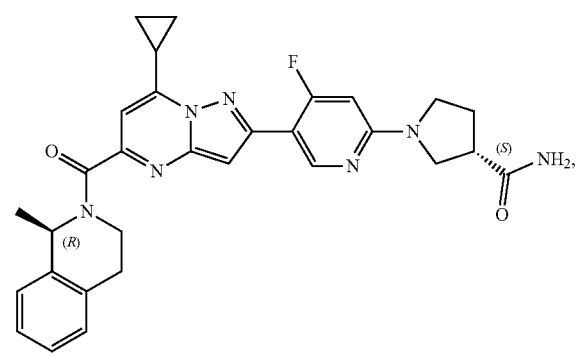 | 56<br>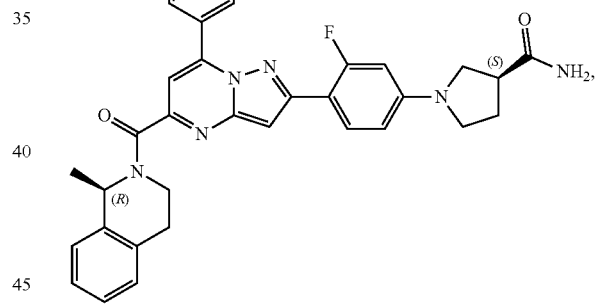 |
| 53<br>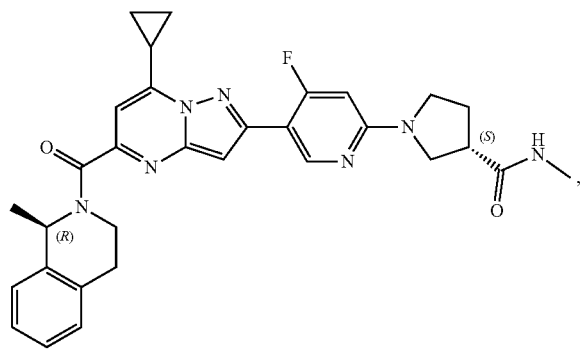 | 57<br>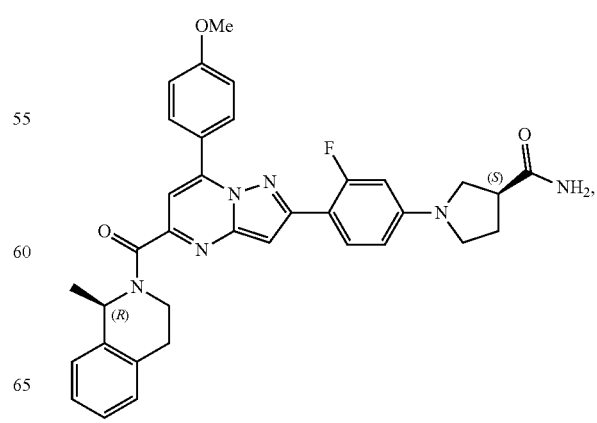 |

383
-continued
58
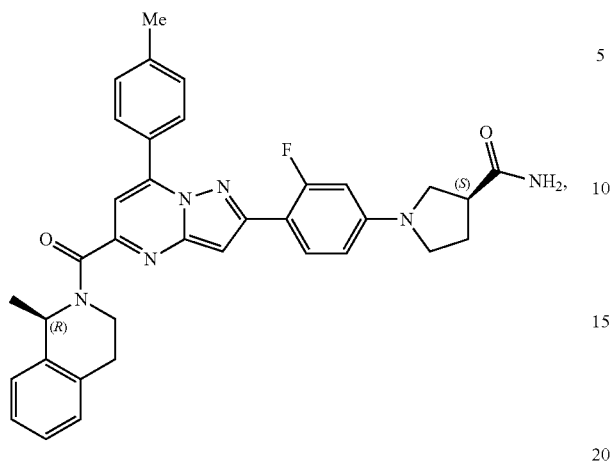
59
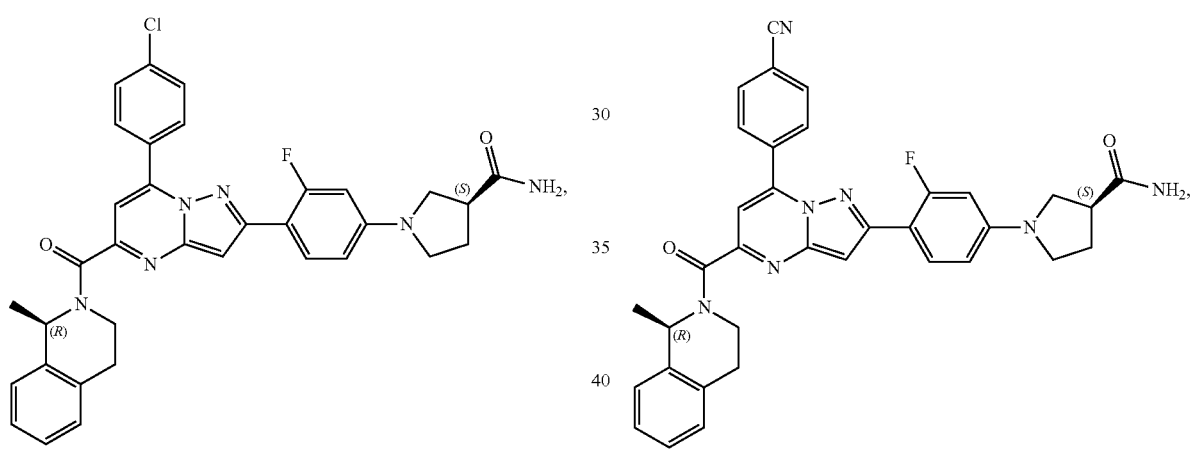
60
384
-continued
61
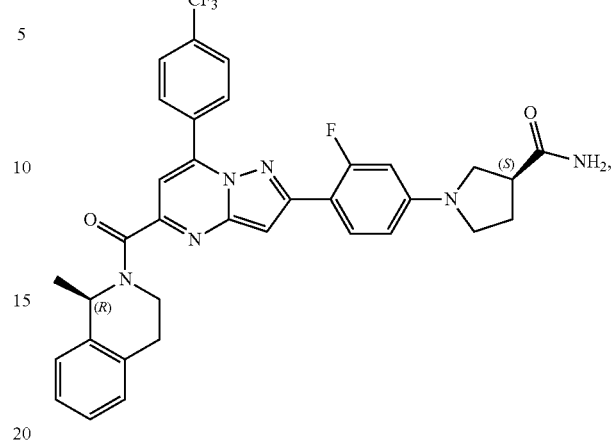
62
63
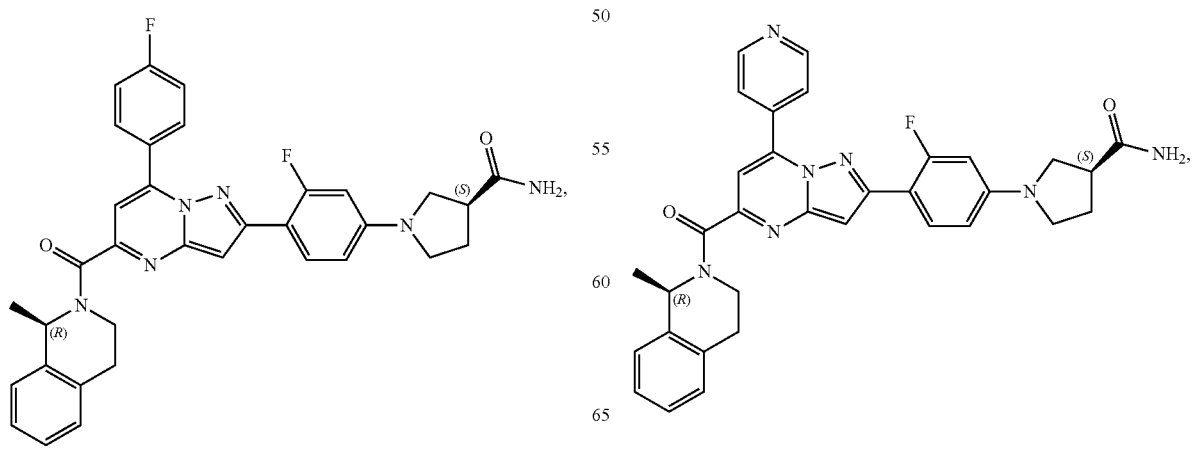

64
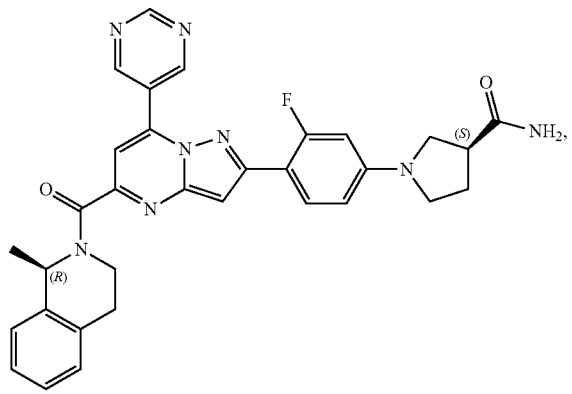
65
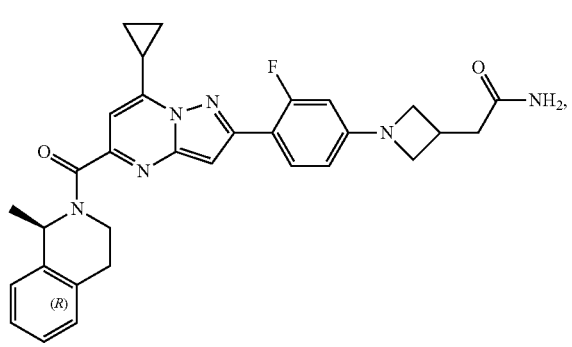
67
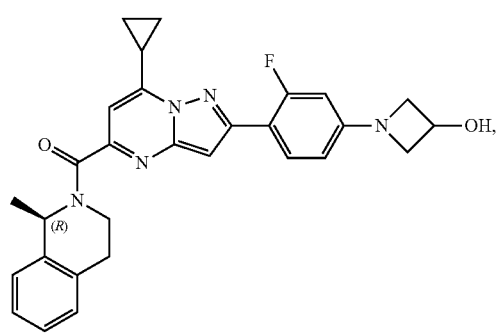
68
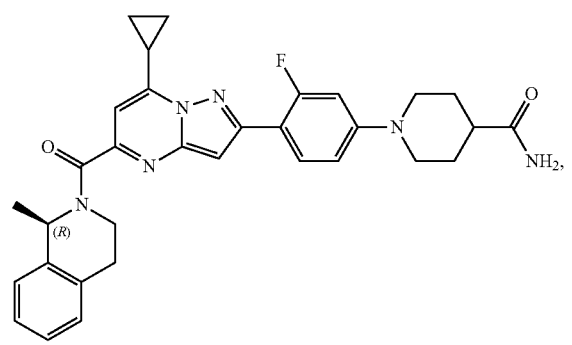
69
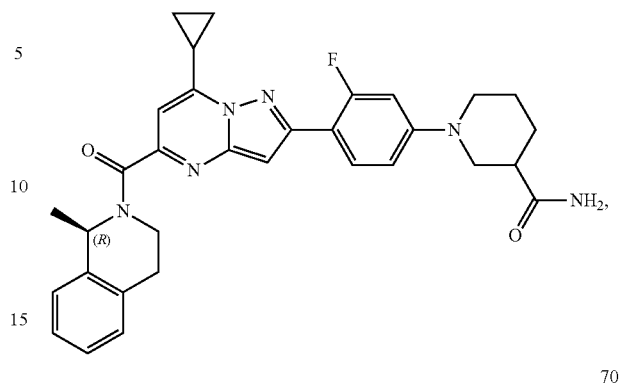
70
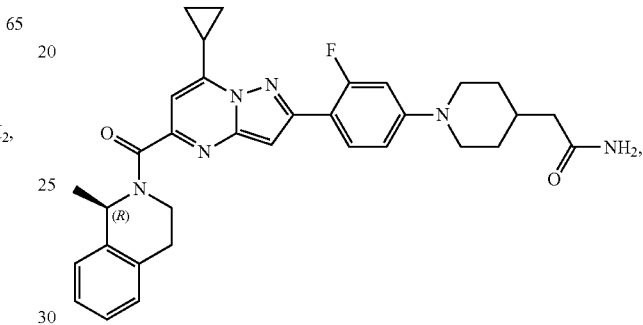
71
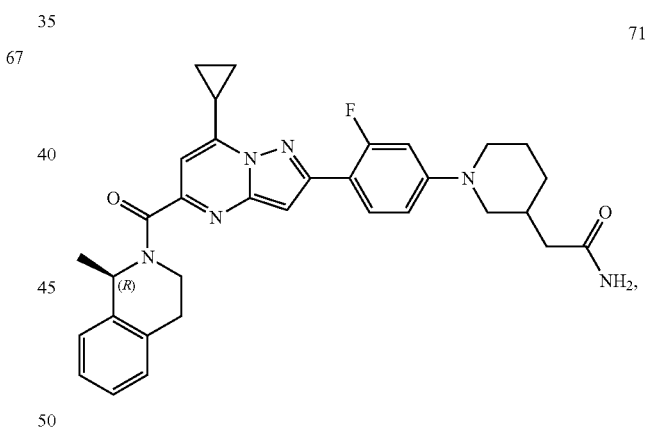
72
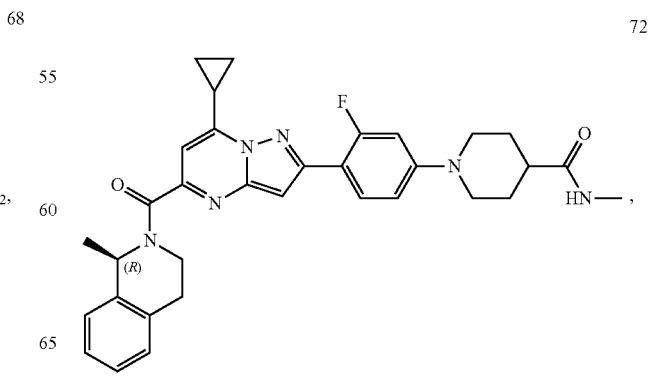

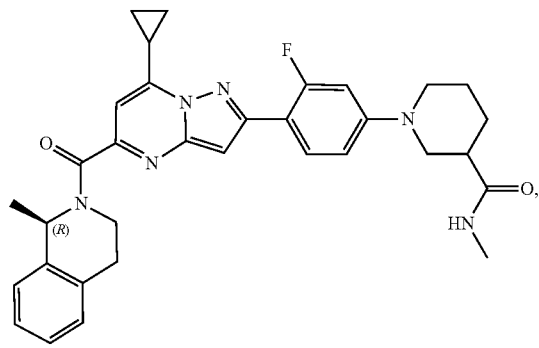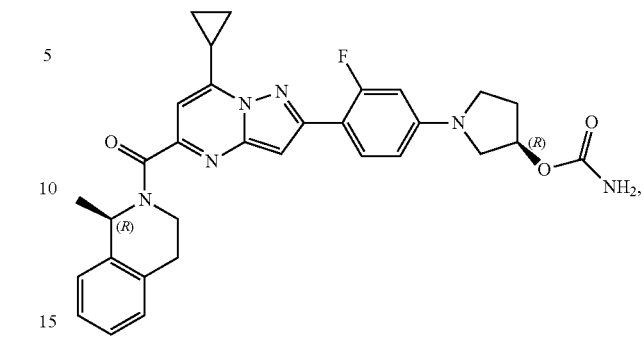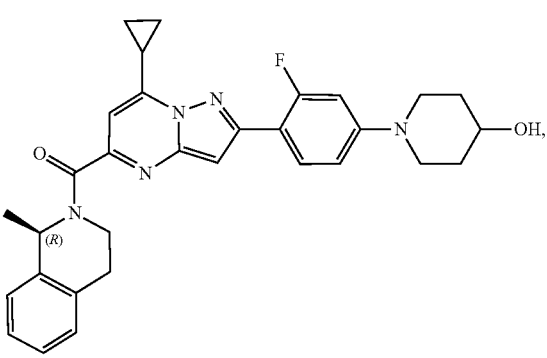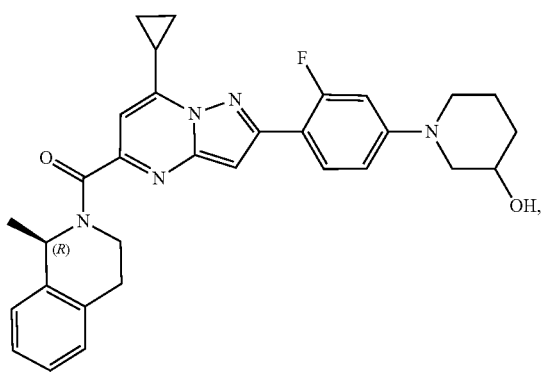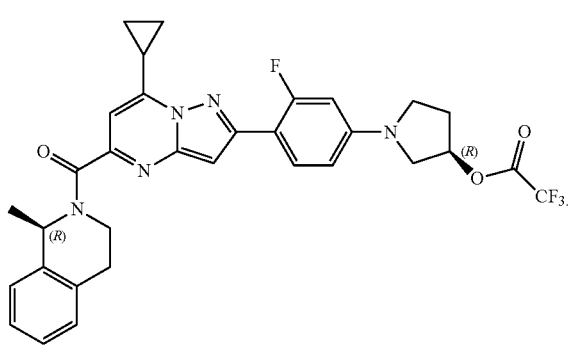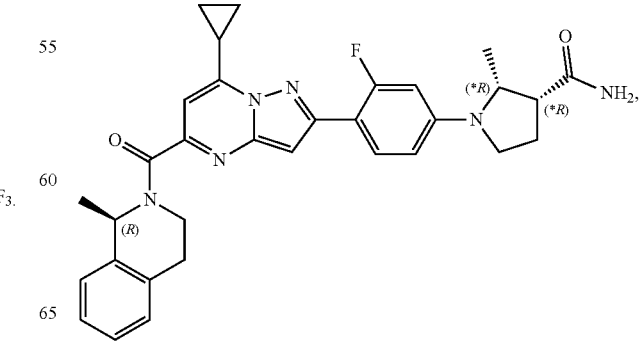

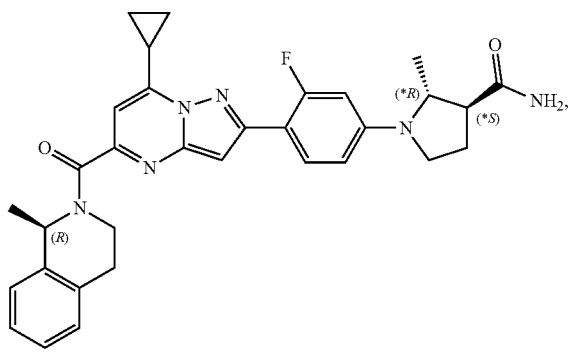
81
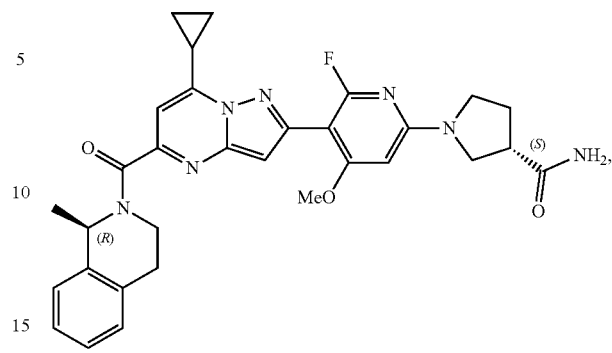
86
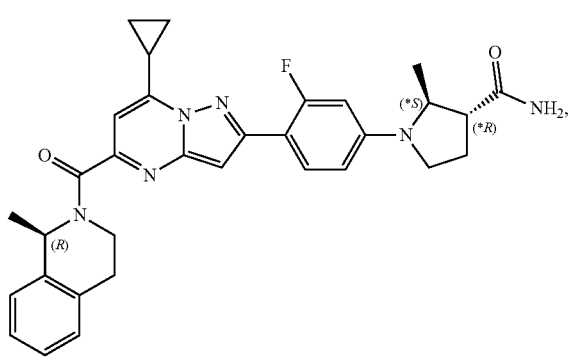
82
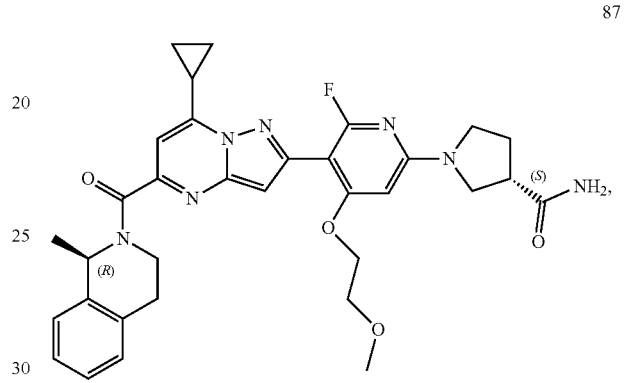
87
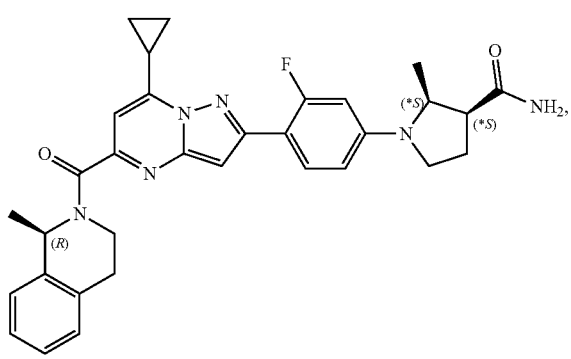
83
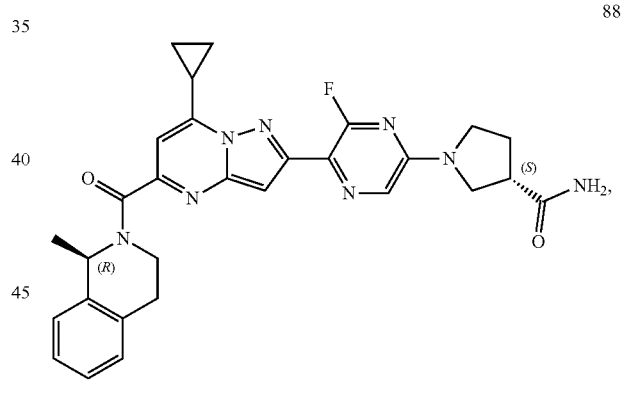
88
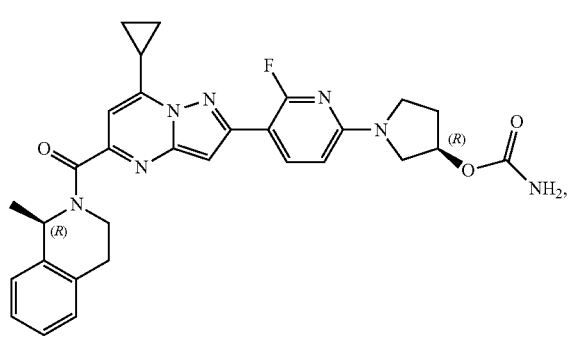
85
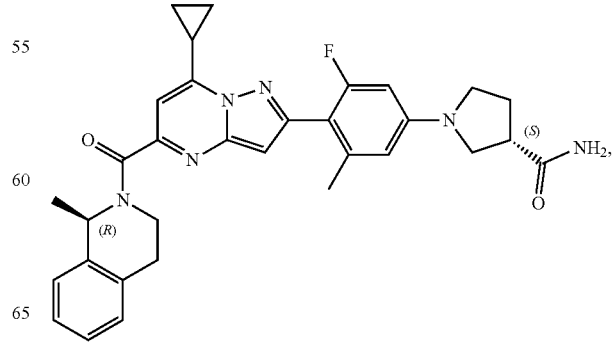
89

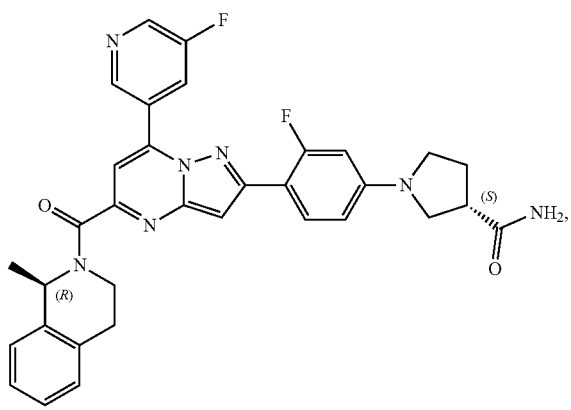
90
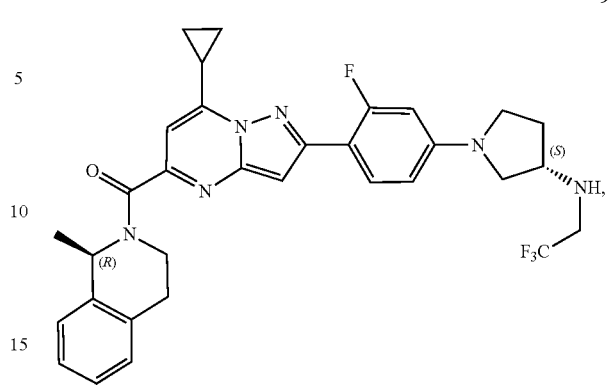
94
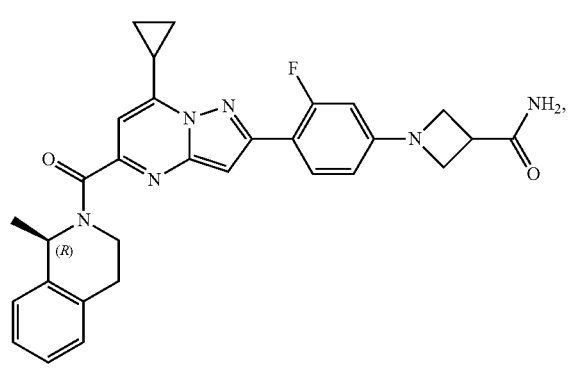
91
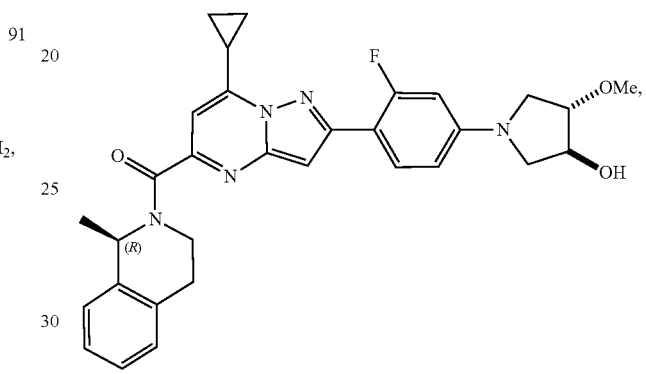
96
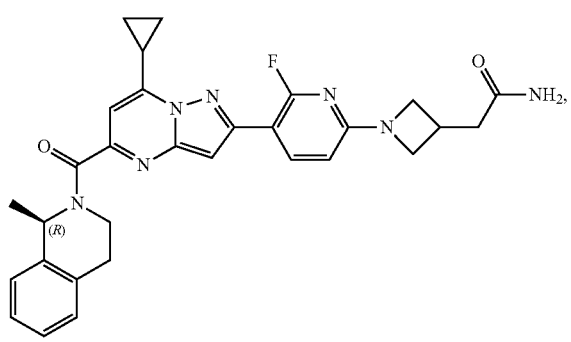
92
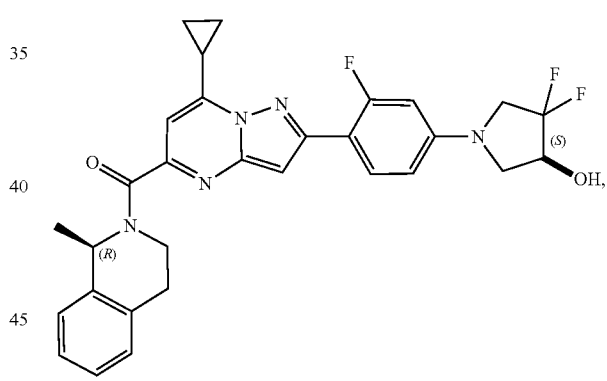
97
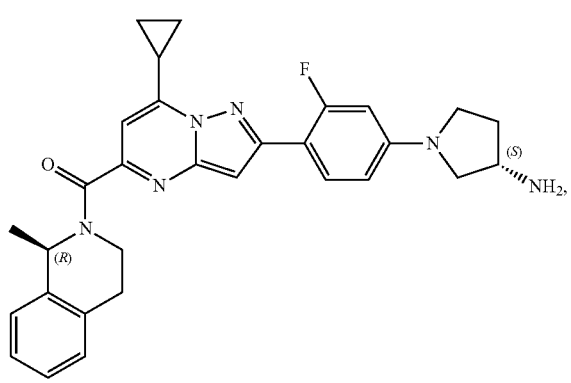
93
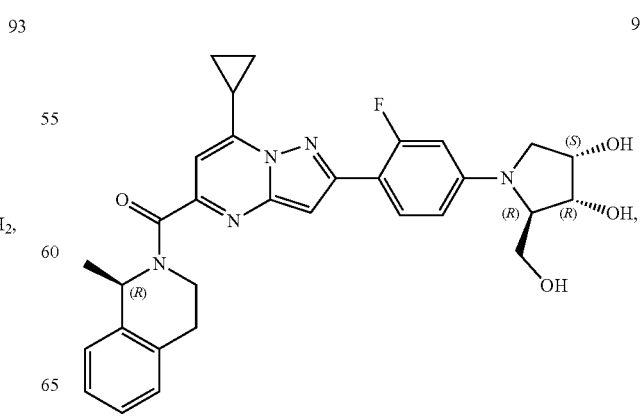
98

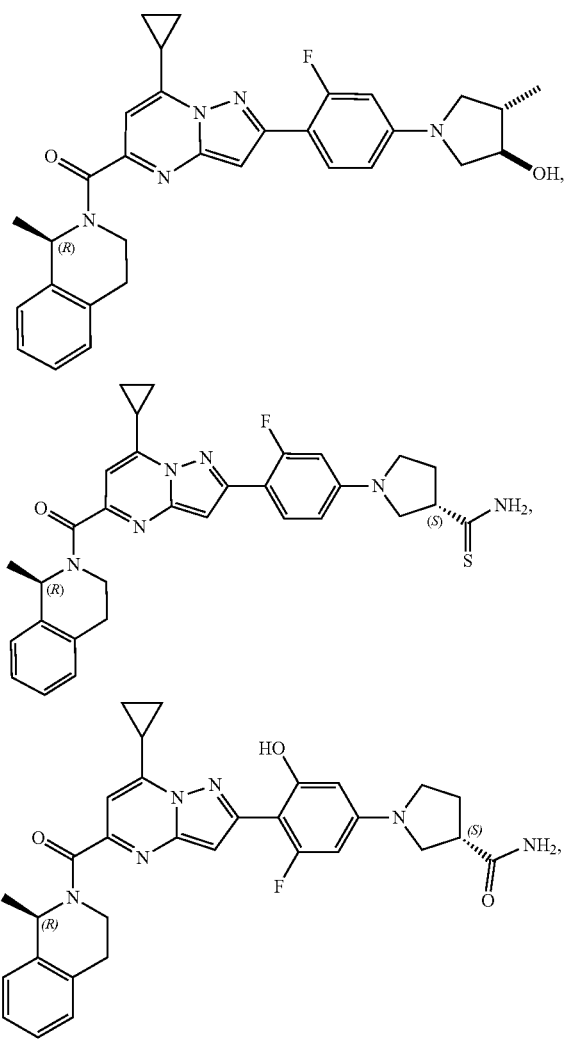

and pharmaceutically acceptable acid addition salts thereof.

12. A pharmaceutical composition comprising a pharmaceutically acceptable carrier and a therapeutically active amount of the compound according to claim 1 or a pharmaceutically acceptable acid addition salt thereof.

13. The pharmaceutical composition according to claim 12, further comprising another antiviral agent.

14. The pharmaceutical composition according to claim 13, wherein the other antiviral agent is a respiratory syncytial virus (RSV) inhibiting compound.

15. A process for preparing a pharmaceutical composition according to claim 12, wherein a therapeutically active amount of a compound according to claim 1 or a pharmaceutically acceptable acid addition salt thereof is intimately mixed with a pharmaceutically acceptable carrier.

16. A method of treating respiratory syncytial virus (RSV) in a subject in need thereof comprising administering to the subject an anti-virally effective amount of a compound according to claim 1 or a pharmaceutically acceptable acid addition salt thereof or an anti-virally effective amount of a pharmaceutical composition according to claim 12.

* * * * *